US009139589B2

(12) United States Patent
Hirose et al.

(10) Patent No.: US 9,139,589 B2
(45) Date of Patent: Sep. 22, 2015

(54) HETEROARYLS AND USES THEREOF

(75) Inventors: Masaaki Hirose, Cambridge, MA (US); Steven P. Langston, North Andover, MA (US); Hirotake Mizutani, Cambridge, MA (US); Stepan Vyskocil, Arlington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 147 days.

(21) Appl. No.: 12/657,853

(22) Filed: Jan. 28, 2010

(65) Prior Publication Data

US 2011/0003806 A1 Jan. 6, 2011

Related U.S. Application Data

(60) Provisional application No. 61/229,399, filed on Jul. 29, 2009, provisional application No. 61/206,417, filed on Jan. 30, 2009, provisional application No. 61/148,533, filed on Jan. 30, 2009.

(51) Int. Cl.

| | |
|---|---|
| ***C07D 345/00*** | (2006.01) |
| ***C07D 517/00*** | (2006.01) |
| ***C07D 487/04*** | (2006.01) |
| ***C07D 417/04*** | (2006.01) |
| ***C07D 419/14*** | (2006.01) |
| ***C07D 471/04*** | (2006.01) |
| ***C07D 513/04*** | (2006.01) |

(52) U.S. Cl.

CPC ............ *C07D 487/04* (2013.01); *C07D 417/04* (2013.01); *C07D 419/14* (2013.01); *C07D 471/04* (2013.01); *C07D 513/04* (2013.01)

(58) Field of Classification Search

USPC .............. 514/233.2, 236.2, 248, 255.05, 256, 514/260.1, 263.23, 265.1, 275, 300, 301, 514/302, 307, 333, 336, 340, 341, 342, 365, 514/368; 544/127, 131, 133, 236, 255, 264, 544/280, 327, 331, 362, 405; 548/154, 155, 548/202

See application file for complete search history.

(56) References Cited

U.S. PATENT DOCUMENTS

| | | | | |
|---|---|---|---|---|
| 3,257,203 | A | 6/1966 | Sus et al. | |
| 3,821,384 | A | 6/1974 | Ariyan et al. | |
| 3,852,293 | A | 12/1974 | Ariyan et al. | |
| 4,371,607 | A | 2/1983 | Donges | |
| 5,134,142 | A | 7/1992 | Matsuo et al. | |
| 6,015,826 | A | 1/2000 | Pechacek et al. | |
| 6,555,501 | B1 | 4/2003 | Bastiaans et al. | |
| 6,608,087 | B1 | 8/2003 | Charifson et al. | |
| 6,984,652 | B2 | 1/2006 | Yager et al. | |
| 7,074,801 | B1 | 7/2006 | Yoshida et al. | |
| 7,405,235 | B2 | 7/2008 | Levy et al. | |
| 7,504,513 | B2 | 3/2009 | Boylan et al. | |
| 7,511,041 | B2 | 3/2009 | Shimada et al. | |
| 7,560,568 | B2 | 7/2009 | Emmitte | |
| 7,741,348 | B2 | 6/2010 | Nan et al. | |
| 8,183,240 | B2 | 5/2012 | Cardin et al. | |
| 8,440,664 | B2 | 5/2013 | Cardin et al. | |
| 8,586,582 | B2 | 11/2013 | Liang et al. | |
| 8,765,746 | B2 | 7/2014 | Freeze et al. | |
| 8,796,268 | B2 | 8/2014 | Freeze et al. | |
| 8,796,271 | B2 | 8/2014 | Hirose et al. | |
| 2002/0022729 | A1 | 2/2002 | Kawai et al. | |
| 2003/0096816 | A1* | 5/2003 | Cao et al. | 514/242 |
| 2004/0116425 | A1 | 6/2004 | Li et al. | |
| 2004/0198773 | A1 | 10/2004 | Hart et al. | |
| 2004/0248896 | A1 | 12/2004 | Dean et al. | |
| 2004/0266751 | A1 | 12/2004 | King | |

(Continued)

FOREIGN PATENT DOCUMENTS

| | | | |
|---|---|---|---|
| CN | 1816549 | A | 8/2006 |
| DE | 275870 | A1 | 2/1990 |

(Continued)

OTHER PUBLICATIONS

International Search Report and Written Opinion dated Jan. 6, 2010 from International Application No. PCT/US2010/000234, which relates to U.S. Appl. No. 12/657,853.

U.S. Appl. No. 14/318,223, filed Jun. 27, 2014, Freeze et al.

U.S. Appl. No. 14/445,373, filed Jul. 29, 2014, Hirose et al.

U.S. Appl. No. 14/445,376, filed Jul. 29, 2014, Freeze et al.

(Continued)

*Primary Examiner* — Jennifer M Kim
*Assistant Examiner* — Jean Cornet
(74) *Attorney, Agent, or Firm* — Choate, Hall & Stewart LLP; Andrea L. C. Reid

(57) ABSTRACT

This invention provides compounds of formula IA or IB:

IA

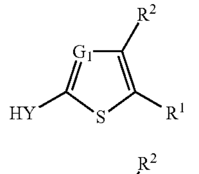

IB

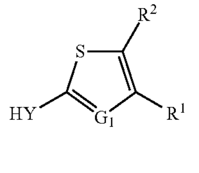

wherein $R^1$, $R^2$, $G_1$ and HY are as described in the specification. The compounds are inhibitors of PI3K and/or mTor and are thus useful for treating proliferative, inflammatory, or cardiovascular disorders.

28 Claims, No Drawings

(56) References Cited

U.S. PATENT DOCUMENTS

| | | | |
|---|---|---|---|
| 2005/0004122 | A1 | 1/2005 | Brown et al. |
| 2005/0054697 | A1 | 3/2005 | Yager et al. |
| 2005/0124678 | A1 | 6/2005 | Levy et al. |
| 2006/0041006 | A1 | 2/2006 | Ibrahim et al. |
| 2006/0074119 | A1 | 4/2006 | Andrews et al. |
| 2006/0128732 | A1 | 6/2006 | Shimada et al. |
| 2006/0199804 | A1 | 9/2006 | Hummersone et al. |
| 2007/0066666 | A1 | 3/2007 | Emmitte |
| 2007/0142415 | A1 | 6/2007 | Vanotti et al. |
| 2007/0203210 | A1 | 8/2007 | Boylan et al. |
| 2008/0021217 | A1 | 1/2008 | Borchardt et al. |
| 2008/0045570 | A1 | 2/2008 | Brenchley et al. |
| 2008/0132546 | A1 | 6/2008 | Basarab et al. |
| 2008/0255120 | A1 | 10/2008 | Lin et al. |
| 2008/0293716 | A1 | 11/2008 | Drewry et al. |
| 2008/0306060 | A1 | 12/2008 | Alexander et al. |
| 2008/0306121 | A1 | 12/2008 | Nan et al. |
| 2009/0012031 | A1 | 1/2009 | Chinnaiyan et al. |
| 2009/0030016 | A1 | 1/2009 | Gandhi et al. |
| 2009/0036435 | A1 | 2/2009 | Curry et al. |
| 2009/0247567 | A1 | 10/2009 | Do et al. |
| 2009/0325925 | A1 | 12/2009 | Renou et al. |
| 2010/0075951 | A1 | 3/2010 | Cardin et al. |
| 2010/0130473 | A1 | 5/2010 | Hummersone et al. |
| 2010/0256172 | A1 | 10/2010 | Shi et al. |
| 2010/0267759 | A1 | 10/2010 | Seefeld et al. |
| 2011/0003807 | A1 | 1/2011 | Banno et al. |
| 2011/0021531 | A1 | 1/2011 | Chobanian et al. |
| 2012/0142732 | A1 | 6/2012 | Cullis et al. |
| 2012/0172345 | A1 | 7/2012 | Freeze et al. |
| 2012/0178723 | A1 | 7/2012 | Hirose et al. |
| 2012/0214794 | A1 | 8/2012 | Freeze et al. |
| 2013/0165464 | A1 | 6/2013 | Chau et al. |
| 2013/0165472 | A1 | 6/2013 | Chau et al. |
| 2013/0165483 | A1 | 6/2013 | Chau et al. |
| 2013/0217689 | A1 | 8/2013 | Cardin et al. |
| 2013/0267563 | A1 | 10/2013 | Hirose et al. |

FOREIGN PATENT DOCUMENTS

| | | | |
|---|---|---|---|
| EP | 0853083 A1 | | 7/1998 |
| EP | 2313399 B1 | | 5/2014 |
| GB | 874634 A | | 8/1961 |
| JP | 10087490 A | | 4/1998 |
| JP | 2006-508063 A | | 3/2006 |
| JP | 2006-525266 A | | 11/2006 |
| JP | 2007-519720 A | | 7/2007 |
| JP | 2007-197324 A | | 8/2007 |
| JP | 2008-531537 A | | 8/2008 |
| WO | WO-97/12615 A1 | | 4/1997 |
| WO | WO-98/08845 A1 | | 3/1998 |
| WO | WO-98/47894 A1 | | 10/1998 |
| WO | WO-00/02871 A1 | | 1/2000 |
| WO | WO-00/35912 A1 | | 6/2000 |
| WO | WO-00/63204 A2 | | 10/2000 |
| WO | WO-02/088107 A1 | | 11/2002 |
| WO | WO-03/015776 A1 | | 2/2003 |
| WO | WO-03/027085 A2 | | 4/2003 |
| WO | WO-03/027107 A1 | | 4/2003 |
| WO | WO-03/040096 A2 | | 5/2003 |
| WO | WO-2004/016592 A1 | | 2/2004 |
| WO | WO-2004/016741 A2 | | 2/2004 |
| WO | WO 2004/096797 | | 11/2004 |
| WO | WO-2006/046031 A1 | | 5/2006 |
| WO | WO-2006/068933 A2 | | 6/2006 |
| WO | WO-2006/069063 A1 | | 6/2006 |
| WO | WO-2006/078287 A2 | | 7/2006 |
| WO | WO-2006/097030 A1 | | 9/2006 |
| WO | WO 2006102194 A1 | * | 9/2006 |
| WO | WO-2006/114313 A1 | | 11/2006 |
| WO | WO-2007/002559 A1 | | 1/2007 |
| WO | WO-2007/043400 A1 | | 4/2007 |
| WO | WO-2007/087488 A2 | | 8/2007 |
| WO | WO 2007096315 A1 | * | 8/2007 |
| WO | WO 2007/129044 | | 11/2007 |
| WO | WO-2007/129161 A2 | | 11/2007 |
| WO | WO-2007/138110 A2 | | 12/2007 |
| WO | WO-2008/014238 A2 | | 1/2008 |
| WO | WO-2008/021235 A2 | | 2/2008 |
| WO | WO-2008/023159 A1 | | 2/2008 |
| WO | WO-2008/024980 A2 | | 2/2008 |
| WO | WO-2008/036541 A1 | | 3/2008 |
| WO | WO-2008/047109 A1 | | 4/2008 |
| WO | WO-2008/083070 A1 | | 7/2008 |
| WO | WO-2008/090382 A1 | | 7/2008 |
| WO | WO-2008/097835 A2 | | 8/2008 |
| WO | WO-2008/098105 A1 | | 8/2008 |
| WO | WO-2008/134679 A1 | | 11/2008 |
| WO | WO-2008/139161 A1 | | 11/2008 |
| WO | WO-2008/157273 A1 | | 12/2008 |
| WO | WO-2009/040730 A2 | | 4/2009 |
| WO | WO-2009/042607 A1 | | 4/2009 |
| WO | WO-2009/049028 A1 | | 4/2009 |
| WO | WO-2009/094224 A1 | | 7/2009 |
| WO | WO-2009/106885 A1 | | 9/2009 |
| WO | WO-2009/122148 A1 | | 10/2009 |
| WO | WO-2009/154741 A1 | | 12/2009 |
| WO | WO-2009/158374 A2 | | 12/2009 |
| WO | WO-2010/001126 A1 | | 1/2010 |
| WO | WO-2010/005841 A1 | | 1/2010 |
| WO | WO-2010/017079 A1 | | 2/2010 |
| WO | WO-2010/055304 A2 | | 5/2010 |
| WO | WO-2010/071741 A1 | | 6/2010 |
| WO | WO-2010/080873 A1 | | 7/2010 |
| WO | WO-2010/090716 A1 | | 8/2010 |
| WO | WO-2010/121675 A2 | | 10/2010 |
| WO | WO-2010/132598 A1 | | 11/2010 |
| WO | WO-2011/043371 A1 | | 4/2011 |

OTHER PUBLICATIONS 1,2,4-Oxadiazole, 5-[5-(1 H-imidazol-2-yl)-2-thienyl]-3-(methoxymethyl)-(CA Index Name), CAS Registry No. 1069660-66-7, entered Nov. 2, 2008.

1,2,4-Oxadiazole-3-ethanamine, 5-[5-(1H-imidazol-2-yl)-2-thienyl]-N,N-dimethyl- (CA Index Name), CAS Registry No. 1066888-52-5, entered Oct. 27, 2008.

1H-Pyrazole-1-carboxylic acid, 5-[2,2'-bithiophen]-5-yl-, ethyl ester (CA Index Name), CAS Registry No. 957595-63-0, entered Dec. 12, 2007.

2,7-Naphthyridine, 1,2,3,4-tetrahydro-5-[5-[5-(1H-imidazol-2-yl)-2-thienyl]-1,2,4-oxadiazol-3-yl]-6-methyl- (CA Index Name), CAS Registry No. 1069717-72-1, entered Nov. 2, 2008.

2-Thiazolamine, 4-[5-(2H-tetrazol-5-yl)-2-thienyl]- (CA Index Name), CAS Registry No. 937625-84-8, entered Jun. 17, 2007.

2-Thiophenecarboxylic acid, 3-(4-chlorophenyl)-4-cyano-5(4-morpholinyl)-(CA Index Name), CAS Registry No. 883097-33-4, entered May 5, 2006.

2-Thiophenecarboxylic acid, 3-(4-chlorophenyl)-4-cyano-5(4-morpholinyl)-, methyl ester (CA Index Name), CAS Registry No. 882283-38-7, entered Apr. 30, 2006.

3H-1,2,4-Triazole-3-thione, 2,4-dihydro-4-methyl-5-[4-methyl-2-(5-methyl-3-isoxazolyl)-5-thiazolyl]-(CA Index Name), CAS Registry No. 264616-86-6, entered May 12, 2000.

4-Oxazolecarboxylic acid, 5-[(ethoxymethylene)amino]-2-(4-pyridinyl)-, ethyl ester- (CA Index Name), CAS Registry No. 885901-22-4, entered May 29, 2006.

4-Thiazolecarboxamide, 2-(4-acetyl-5-methyl-1H-1,2,3-triazol-1-yl)-N,N-diethyl-5-phenyl- (CA Index Name), CAS Registry No. 709639-21-4, entered Jul. 14, 2004.

Abdelrazek et al., Heterocyclic Synthesis with Nitriles: Synthesis of Some Novel Thiophene and Thieno[2,3-d]Pyrimidine Derivatives, Phosphorus, Sulfur, and Silicons, 71:93-97 (1992).

Acetamide, N-(3,5-dichlorophenyl)-2-[[4-methyl-5-[4-methyl-2-(5-methyl-3-isoxazolyl)-5-thiazolyl]-4H-1,2,4-triazol-3-yl]thio]-(CA Index Name), CAS Registry No. 264626-19-9, entered May 12, 2000.

Acetamide, N-(4-chlorophenyl)-2-[[4-methyl-5-[4-methyl-2-(5-methyl-3-isoxazolyl)-5-thiazolyl]-4H-1,2,4-triazol-3-yl]thio]-(CA Index Name), CAS Registry No. 264626-21-3, entered May 12, 2000.

(56) References Cited

OTHER PUBLICATIONS

Adib, M. et al., Facile One-Pot Three-Component Synthesis of Functionalized Pyridylfuran-2-amines, Helvetica Chimica Acta, 89(2):299-303 (2006).
Al-Azawe et al., Synthesis of 2, 5-Disubstituted Thiazoles and Their Reactions with Grignard Reagents, Journal of the Iraqi Chemical Society, 13(1): 1-13 (1988).
Amer, A. et al, Ring Closure Reactions involving 1-Hydrazinophthalazine [1]. Reactions with 1,2,4-Tricarbonyl and 1,3-Dicarbonyl Compounds, Journal of Heterocclic Chemistry, 20: 1231-1238 (1983).
Amer, A., et al., Factors Influencing the Pathway of Reactions of 1-Hydra-zinophthalazine With Di- and Tricarbonyl Compounds, Hetercycles, 26(7): 1853-1862 (1987).
Annis, D. A., et al., Inhibitors of the Lipid Phosphatase SHIP2 Discovered by High Throughput Affinity Selection-Mass Spectrometry Screening of Combinatorial Libraries, Combinatorial Chemistry & High Throughput Screening, 12:760-771 (2009).
Batista et al., Synthesis and characterization of new thienylpyrrolyl-benzothiazoles as efficient and thermally stable nonlinear optical chromophores, Tetrahedron, 63(20):4258-4265 (2007).
Batista et al., Synthesis and Second-Order Nonlinear Optical Properties of New Chromophores Containing Benzimidazole, Thiophene, and Pyrrole Heterocycles, Tetrahedron, 63(39): 9842-9849 (2007).
Benzamide, N,N'-(4,4'-di-2-thienyl[2,2'-bithiazole]-5,5'-diyl)bis-(CA Index Name) CAS Registry No. 691381-57-4, entered Jun. 10, 2004.
Benzamide, N,N'-[4,4'-bis(4-fluorophenyl)[2,2'-bithiazole]-5,5'-diyl]bis[4-methyl- (CA Index Name) CAS Registry No. 691381-60-9, entered Jun. 10, 2004.
Benzamide, N-(4'-amino-2',3'-dihydro-3',4-diphenyl-2'-thioxo[2,5'-bithiazol]-5-yl)- (CA Index Name)CAS Registry No. 879910-33-5, entered Apr. 10, 2006.
Benzamide, N-[2-(5-amino-1-phenyl-1H-pyrazol-4-yl)-4-phenyl-5-thiazolyl]-4-methyl- (CA Index Name), CAS Registry No. 1017527-68-2, entered Apr. 27, 2008.
Berndt, A. et al., The p100σ crystal structure uncovers mechanisms for selectivity and potency of novel PI3K inhibitors, Nature Chemical Biology, 6(2):117-124 (2010).
Boppana, K. et al., Knowledge based identification of MAO-B selective inhibitors using pharmacophore and structure based virtual screening models, European Journal of Medicinal Chemistry, 44:3584-3590 (2009).
Caballero, J., et al., Investigation of the Differences in Activity between Hydroxycycloalkyl N1 Substituted Pyrazole Derivatives As Inhibitors of B-Raf Kinase by Using Docking, Molecular Dynamics, QM/MM, and Fragment-Based De Novo Design: Study of Binding Mode of Diastereomer Compounds, Journal of Chemical Information and Modeling, 51: 2920-2931 (2011).
Carbamic acid, N,N'-(4,4'-di-2-thienyl[2,2'-bithiazole]-5,5'-diyl)bis-,C,C'-dimethyl ester (CA Index Name) CAS Registry No. 691381-58-5, entered Jun. 10, 2004.
Carbamic acid,4,4'-diphenyl[2,2'-bithiazole]-5,5'-diyl)bis-, dimethyl ester (9CI)(CA Index Name), CAS Registry No. 505060-78-6, entered Apr. 25, 2003.
Chattopadhyay, S. K. et al., Efficient Construction of the Carbon Skeleton of the Novel Polyoxazole-Based Cyclopeptide IB-01211 via a Biomimetic Macrocyclisation, SYNLETT, 4:555-558 (2010).
Choi, W. et al., Synthesis and Antiproliferative Activities of 1-Substituted-3-(3-chloro-5-methoxy phenyl)-4-pyridinylpyrazole Derivatives Against Melanoma Cell Line, Bulletin of the Korean Chemical Society, 30(9):2027-2031 (2009).
Cudworth et al., Structure- Activity Relationship Development of Dihaloaryl Triazole Compounds as Insecticides and Acaricides. 1. Phenyl Thiophen-2-yl Triazoles, Journal of Agricultural and Food Chemistry, 55(18): 7517-7526 (2007).
Database CAS Registry (Columbus, Ohio), RN 893689-50-4 (Entered Jul. 17, 2006).
Database CAS Registry (Columbus, Ohio), RN 893692-42-7 (Entered Jul. 17, 2006).
Database CAS Registry (Columbus, Ohio), RN 893704-20-6 (Entered Jul. 17, 2006).
Database CAS Registry (Columbus, Ohio), RN 893705-40-3 (Entered Jul. 17, 2006).
Database CAS Registry (Columbus, Ohio), RN 898517-78-7 (Entered Aug. 3, 2006).
Database CHEMCATS, Chemical Abstracts Service, Columbus, Ohio, US, XP002545555, order No. T5337328.
Datta et al., A Novel Route to Methyl 3-3(3,4-Disubstituted 5-alkylthio/amino-2-thienyl) propenoates, Synthesis, 7:556-567 (1988).
Di Fabio, R. et al., Dihydropyrrole[2,3-D]Pyridine Derivatives As Novel Corticotropin-Releasing Factor-1 Antagonists: Mapping of the Receptor Binding Pocket by in Silico Docking Studies, Journal of Medicinal Chemistry, 51(22): 7273-7286 (2008).
Dzvinchuk, I.B. et al., Selective Recyclization of 2-Aroylmethyl-1h-Benzimidazole Hydrazones by Condensation with Dimethylformamide, Chemistry of Heterocyclic Compounds, 37(9): 1096-1101 (2001).
Dzvinchuk, I.B. et al., Synthesis and Tautomerism of 2-[3(5)-Aryl(Methyl)Pyrazol-4-YI]-1-Benzimidazoles, Chemistry of Heterocyclic Compounds, 42(9): 1190-1196 (2006).
Emmitte et al., Discovery of Thiophene Inhibitors of Polo-like Kinase, Bioorganic & Medicinal Chemistry Letters, 19(3): 1018-1021 (2009).
Fletcher, A. N. et al., Laser Dye Stability, Part 12. The Pyridinium Salts, Applied Physics, B43:155-160 (1987).
Fridman et al., Spectroscopy, Photophysical and Photochemical Properties of Bisimidazole, Derivatives, Journal of Photochemistry and Photobiology, A: Chemistry, 188(1): 25-33 (2007).
Ge, M. et al., A General Method for the Preparation of 3-ACYL-4-CYANO-5-AMINO-PYRAZOLES, Tetrahedron Letters, 47: 5797-5799 (2006).
Golub, T.R. et al., Molecular classification of cancer: class discovery and class prediction by gene expression monitoring, Science, 286(5439):531-7 (1999).
Green et al., Parallel Synthesis of 2-aryl-4-aminobenzimidazoles and their Evaluation as Gonadotropin Releasing Hormone Antagonists, Journal of Combinatorial Chemistry, 11(1): 117-125 (2009).
Hernandez, D. et al., Synthesis and Antitumor Activity of Mechercharmycin A Analogues, Journal of Medicinal Chemistry, 51: 5722-5730 (2008).
Hernandez, D. et al., Synthesis of Natural Product Derivatives Containing 2,4-Concatenated Oxazoles, European Journal of Organic Chemistry, (19): 3389-3396 (2008).
Heyde et al., A Simple Route to N,N-Dialkyl Derivatives of 2-Amino-5-thiophenecarboxylates, Eur. J. Org. Chem.: 3273-3278 (2000).
Hirai et al., Heterocyclic Cation Systems. 14. Synthesis of Thieno[3,2-e][1,4]diazepine, Thiazolo[4,5-e][1,4]diazepine, and s-Triazolo[3,4-c]thiazolo[4,5-e][1,4]diazepine Derivatives, Journal of Organic Chemistry, 45:253-260 (1980).
Hirai et al., Novel Synthesis of Thiophene Derivatives from 1,3-Oxathil-2-ylideneimmonium Salt, Chemical & Pharmaceutical Bulletin, 19(10): 2194-2197 (1971).
Imidazo[1,2-a]pyridine, 6-[3-[5-(2H-tetrazol-5-yl)-2-thienyl]-1 H-pyrazol-4-yl]-3-(2-thiazolyl)-(CA Index Name) CAS Registry No. 732241-18-8, entered Aug. 25, 2004).
International Search Report for PCT/US09/00513, 3 pages (Jun. 10, 2009).
International Search Report for PCT/US09/03607, 4 pages (Sep. 23, 2009).
International Search Report for PCT/US11/47245, 2 pages (Dec. 22, 2011).
International Search Report for PCT/US11/47407, 2 pages (Dec. 22, 2011).
International Search Report for PCT/US11/56135, 4 pages (May 31, 2012).
International Search Report for PCT/US2011/047241, 3 pages (Jan. 6, 2012).
Laszlo et al., Pyrroles and Other Heterocycles as Inhibitors of P38 Kinase, Bioorganic and Medical Chemistry Letters, 8: 2689-2694 (1998).

(56) References Cited

OTHER PUBLICATIONS

Lethu et al., Discovery of a New Class of Protein Farnesyltransferase Inhibitors in the Arylthiophene Series, J. Med. Chem., 52: 6205-6208 (2009).
Liang, J. et al., Crystal Structure of P13K [sic] SH3 Domain at 2.0 A Resolution, Journal of Molecular Biology, 257:632-643 (1996).
Lima, L. and Barreiro, E., Bioisosterism: A Useful Strategy for Molecular Modification and Drug Design, Current Medicinal Chemistry, 12: 23-49 (2005).
Liu et al., Highly Selective and Potent Thiophenes as PI3K Inhibitors with Oral Antitumor Activity, Med. Chem. Lett., 2:809-813 (2011).
Lucchesini, A Simple Way to Sequentially Connected Polycycles Containing Terminal Pyrrole Rings: Synthesis of Possible Precursors of Materials for Nonlinear Optics, Tetrahedron, 48(45): 9951-9966 (1992).
Mamedov et al., Synthesis and Some Properties of the Methyl Ester and N,N-diethylamide of 2-Azido-5-Phyenyl-4-Thiazolecarboxylic Acid, Chemistry of Heterocyclic Compounds, 29(5): 607-611 (1993).
Matschke et al., Quinomethides Versus Unsymmetric Hybrids: Two Variations of Non-Radicaloid SEM-States in Four-Electron Redox Systems of bis-4H-imidazoles, Structural Chemistry, 19(3):399-405 (2008).
Menear, K. A. et al., Identification and optimisation of novel and selective small molecular weight kinase inhibitors of mTOR, Bioorganic & Medicinal Chemistry Letters, 19:5898-5901 (2009).
Moorthy et al., In Silico-Based Structural Analysis of Arylthiophene Derivatives for Ftase Inhibitory Activity, hERG, and Other Toxic Effects, Journal of Biomolecular Screening, 16(9):1037-1046 (2011).
Morpholine, 4-(5-(4,5-diphenyl-1H-imidazol-2-yl)-2-thienyl]-, Ryan Scientific Screening Library, Publication date: Jan. 25, 2008, CAS Registry No. 851954-74-0.
Nagasaki et al., CASREACT 139:52925 (2003).
Nagasaki et al., Useful Synthesis of Various Thiazole and Polythiazolyl Derivatives from Thiocarboxamide and -Bromacyl Compound, Heterocycles, 60(2): 321-335 (2003).
Pinto et al., The Synthesis of 5-alkoxy and 5-amino Substituted Thiophenes, Tetrahedron Letters, 41(10): 1597-1600 (2000).
Pyrazolo[1,5-a]pyrimidin-7(4H)-one,3-ethyl-5-[5-(1H-imidazol-2-yl)-2-thienyl]- (CA Index Name), CAS Registry No. 1087437-07-7, entered Dec. 21, 2008.
RAAP, Some Synthesis with Dimethyl Monothionemalonate, Canadian Journal of Chemistry, 46:13, 2255-2261 (1968).
Rehwald et al., New Synthesis of 2,4-Diaminothiophenes- Use of (1,3-oxathiol-2-ylidene)Malononitrile, Heterocycles, 45(3): 493-500 (1997).
Revesz, L. et al., SAR of 2,6-Diamino-3,5-difluoropyridinyl Substituted Heterocycles as Novel p38 MAP Kinase Inhibitors, Bioorganic & Medicinal Chemistry Letters, 12(16):2109-2112 (2002).
Sheridan, The Most Common Chemical Replacements in Drug-Like Compounds, J. Chem. Inf. Comput. Sci., 42:103-108 (2002).
Thompson, M. J. et al., Development of a Diversity-Oriented Approach to Oxazole-5-amide Libraries, Journal of Organic Chemistry, 74(10):3856-3865 (2009).
Tsuge, O., and Torii, A., Compounds Related to Acridine. VIII.[1)] Reaction of 9-Vinylacridine with p-Substituted Nitrosobenzenes, Bulletin of the Chemical Society of Japan, 45: 3187-3191 (1972).
Wang, Q. et al., Copper-Mediated Amidation of Heterocyclic and Aromatic C-H Bonds, Organic Letters, 11( 22): 5178-5180 (2009).
Welker et al., Recent Syntheses of PI3K/Akt/mTOR signaling pathway inhibitors, Bioorganic & Medicinal Chemistry, 21(14): 4063-4091 (2013).
Written Opinion for PCT/US09/00513, 5 pages (Jun. 10, 2009).
Written Opinion for PCT/US09/03607, 5 pages (Sep. 23, 2009).
Written Opinion for PCT/US11/47245, 5 pages (Dec. 22, 2011).
Written Opinion for PCT/US11/47407, 7 pages (Jun. 10, 2009).
Written Opinion for PCT/US11/56135, 13 pages (May 31, 2012).
Written Opinion for PCT/US2011/047241, 9 pages (Jan. 6, 2012).
Ye, L., et al., Pyrazolylthiazole as ΔF508-Cystic Fibrosis Transmembrane Conductance Regulator Correctors with Improved Hydrophilicity Compared to Bithiazoles, Journal of Medicinal Chemistry, 53:3772-3781 (2010).
Zhang, F. et al., Decarboxylative C-H Cross-Coupling of Azoles, Angew. Chem. Int. Ed., 49(15): 2768-2771 (2010).
Zhou et al., Selenium-Containing Heterocycles from Isoselenocyanates: Synthesis of 1,3-Selenazoles from N-Phenylimidoyl Isoselenocyanates, Helvetica Chimica Acta, 83: 1576-1598 (2000).

* cited by examiner

HETEROARYLS AND USES THEREOF

The present application claims the benefit of U.S. Provisional Application Ser. No. 61/229,399, filed Jul. 29, 2009, U.S. Provisional Application Ser. No. 61/206,417, filed Jan. 30, 2009 and U.S. Provisional Application Ser. No. 61/148,533, filed Jan. 30, 2009. The entire contents of each of the above-referenced patent applications are incorporated herein by this reference.

BACKGROUND OF THE INVENTION

Phosphatidylinositol 3-kinase (PI3K) is a family of lipid kinases that phosphorylate phosphatidylinositol at the 3' position of the inositol ring. PI3K is comprised of several classes of genes, including Class IA, IB, II and III and some of these classes contain several isoforms (reviewed in Engelman et al., Nature Review Genetics 7:606-619 (2006)). Adding to the complexity of this family is the fact that PI3Ks function as heterodimers, comprising a catalytic domain and a regulatory domain. The PI3K family is structurally related to a larger group of lipid and serine/threonine protein kinases known as the phosphatidylinositol 3-kinase like kinases (PIKKs), which also includes DNA-PK, ATM, ATR, mTOR, TRRAP and SMG1.

PI3K is activated downstream of various mitogenic signals mediated through receptor tyrosine kinases, and subsequently stimulates a variety of biological outcomes; including increased cell survival, cell cycle progression, cell growth, cell metabolism, cell migration and angiogenesis (reviewed in Cantley, Science 296:1655-57 (2002); Hennessy et al., Nature Reviews Drug Discovery 4:988-1004 (2005); Engelman et al., Nature Review Genetics 7:606-619 (2006)). Thus, PI3K hyper-activation is associated with a number of hyper-proliferative, inflammatory, or cardiovascular disorders; including cancer, inflammation, and cardiovascular disease.

There are a number of genetic aberrations that lead to constitutive PI3K signaling; including activating mutations in PI3K itself (Hennessy et al., Nature Reviews Drug Discovery 4:988-1004 (2005); reviewed in Bader et al., Nature Reviews Cancer 5:921-9 (2005)); RAS (reviewed in Downward Nature Reviews Cancer 3:11-22 (2003)) and upstream receptor tyrosine kinases (reviewed in Zwick et al., Trends in Molecular Medicine 8:17-23 (2002)) as well as inactivating mutations in the tumor suppressor PTEN (reviewed in Cully et al., Nature Reviews Cancer 6:184-92 (2006)). Mutations in each of these gene classes have proven to be oncogenic and are commonly found in a variety of cancers.

The molecules defined within this invention inhibit the activity of PI3K, and therefore may be useful for the treatment of proliferative, inflammatory, or cardiovascular disorders. Cases where PI3K pathway mutations have been linked to proliferative disorders where the molecules defined within this invention may have a therapeutic benefit include benign and malignant tumors and cancers from diverse lineage, including but not limited to those derived from colon (Samuels et al., Science 304:554 (2004); reviewed in Karakas et al., British Journal of Cancer 94: 455-59 (2006)), liver (reviewed in Karakas et al., British Journal of Cancer 94: 455-59 (2006)), intestine (reviewed in Hennessy et al., Nature Reviews Drug Discovery 4:988-1004 (2005)), stomach (Samuels et al., Science 304:554 (2004); reviewed in Karakas et al., British Journal of Cancer 94: 455-59 (2006)), esophagus (Phillips et al., International Journal of Cancer 118:2644-6 (2006)); pancreas (reviewed in Downward Nature Reviews Cancer 3:11-22 (2003)); skin (reviewed in Hennessy et al., Nature Reviews Drug Discovery 4:988-1004 (2005)), prostate (reviewed in Hennessy et al., Nature Reviews Drug Discovery 4:988-1004 (2005)), lung (Samuels et al., Science 304:554 (2004); reviewed in Karakas et al., British Journal of Cancer 94: 455-59 (2006)), breast (Samuels et al., Science 304:554 (2004); Isakoff et al., Can Res 65:10992-1000 (2005); reviewed in Karakas et al., British Journal of Cancer 94: 455-59 (2006)), endometrium (Oda et al., Can Res 65:10669-73 (2005); reviewed in Hennessy et al., Nature Reviews Drug Discovery 4:988-1004 (2005)), cervix (reviewed in Hennessy et al., Nature Reviews Drug Discovery 4:988-1004 (2005)); ovary (Shayesteh et al., Nature Genetics 21:99-102 (1999); reviewed in Karakas et al., British Journal of Cancer 94: 455-59 (2006)), testes (Moul et al., Genes Chromosomes Cancer 5:109-18 (1992); Di Vizio et al., Oncogene 24:1882-94 (2005)), hematological cells (reviewed in Karakas et al., British Journal of Cancer 94: 455-59 (2006); Hennessy et al., Nature Reviews Drug Discovery 4:988-1004 (2005)), pancreas (reviewed in Downward Nature Reviews Cancer 3:11-22 (2003)), thyroid (reviewed in Downward Nature Reviews Cancer 3:11-22 (2003); reviewed in Hennessy et al., Nature Reviews Drug Discovery 4:988-1004 (2005)); brain (Samuels et al., Science 304:554 (2004); reviewed in Karakas et al., British Journal of Cancer 94: 455-59 (2006)), bladder (Lopez-Knowles et al., Cancer Research 66:7401-7404 (2006); Hennessy et al., Nature Reviews Drug Discovery 4:988-1004 (2005)); kidney (reviewed in Downward Nature Reviews Cancer 3:11-22 (2003)) and Head and Neck (reviewed in Engelman et al., Nature Reviews Genetics 7:606-619 (2006)).

Other classes of disorders with aberrant PI3K pathway signaling where the molecules defined within this invention may have a therapeutic benefit include inflammatory and cardiovascular diseases, including but not limited to allergies/anaphylaxis (reviewed in Rommel et al., Nature Reviews Immunology 7:191-201 (2007)), acute and chronic inflammation (reviewed in Ruckle et al., Nature Reviews Drug Discovery 5:903-12 (2006); reviewed in Rommel et al., Nature Reviews Immunology 7:191-201 (2007)), rheumatoid arthritis (reviewed in Rommel et al., Nature Reviews Immunology 7:191-201 (2007)); autoimmunity disorders (reviewed in Ruckle et al., Nature Reviews Drug Discovery 5:903-12 (2006)), thrombosis (Jackson et al., Nature Medicine 11:507-14 (2005); reviewed in Ruckle et al., Nature Reviews Drug Discovery 5:903-12 (2006)), hypertension (reviewed in Ruckle et al., Nature Reviews Drug Discovery 5:903-12 (2006)), cardiac hypertrophy (reviewed in Proud et al., Cardiovascular Research 63:403-13 (2004)), and heart failure (reviewed in Mocanu et al., British Journal of Pharmacology 150:833-8 (2007)).

Clearly, it would be beneficial to provide novel PI3K inhibitors that possess good therapeutic properties, especially for the treatment of proliferative, inflammatory, or cardiovascular disorders.

1. General Description of Compounds of the Invention:

This invention provides compounds that are inhibitors of PI3K and/or mTOR, and accordingly are useful for the treatment of proliferative, inflammatory, or cardiovascular disorders. The compounds of this invention are [1] represented by formula I-A and I-B:

IA

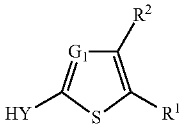

IB

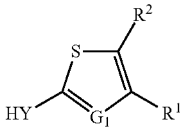

or a pharmaceutically acceptable salt thereof, wherein:

$G_1$ is N or $CR^3$, wherein $R^3$ is H, —CN, halogen, —Z—$R^5$, $C_{1-6}$ aliphatic, or 3-10-membered cycloaliphatic, wherein:

Z is selected from an optionally substituted $C_{1-3}$ alkylene chain, —O—, —$N(R^{3a})$—, —S—, —S(O)—, —$S(O)_2$—, —C(O)—, —$CO_2$—, —$C(O)NR^{3a}$—, —$N(R^{3a})C(O)$—, —$N(R^{3a})CO_2$—, —$S(O)_2NR^{3a}$—, —$N(R^{3a})S(O)_2$—, —$OC(O)N(R^{3a})$—, —$N(R^{3a})C(O)NR^{3a}$—, —$N(R^{3a})S(O)_2N(R^{3a})$—, or —OC(O)—;

$R^{3a}$ is hydrogen or an optionally substituted $C_{1-4}$ aliphatic, and $R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$R^1$ is CY, —$CON(R^4)_2$, —$NHCOR^4$, —$NHSO_2R^4$, —$NHCON(R^4)_2$, —$NHCOOR^4$, —$NHSO_2N(R^4)_2$, or —$NHSO_2OR^4$, wherein:

CY is

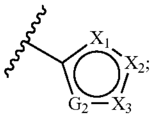

wherein:

$X_1$, $X_2$, and $X_3$, are each independently N, O, S, or $CR^7$, provided that only one of $X_1$, $X_2$, or $X_3$ may be O or S, $G_2$ is —N═ or —$NR^{4'}$—, wherein:

each occurrence of $R^4$ and R4' is independently H, —$Z_2$—$R^6$, optionally substituted $C_{1-6}$ aliphatic, or optionally substituted 3-10-membered cycloaliphatic, wherein:

$Z_2$ is selected from an optionally substituted $C_{1-3}$ alkylene chain, —S(O)—, —$S(O)_2$—, —C(O)—, —$CO_2$—, —$C(O)NR^{4a}$—, or —$S(O)_2NR^{4a}$—.

$R^{4a}$ is hydrogen or an optionally substituted $C_{1-4}$ aliphatic, and $R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4a}$ is independently hydrogen, —CN, halogen, —$Z_3$—$R^8$, $C_{1-6}$ aliphatic, or 3-10-membered cycloaliphatic, wherein:

$Z_3$ is selected from an optionally substituted $C_{1-3}$ alkylene chain, —O—, —$N(R^{7a})$—, —S—, —S(O)—, —$S(O)_2$—, —C(O)—, —$CO_2$—, —$C(O)NR^{7a}$—, —$N(R^{7a})C(O)$—, —$N(R^{7a})CO_2$—, —$S(O)_2NR^{7a}$—, —$N(R^{7a})S(O)_2$—, —$OC(O)N(R^{7a})$—, —$N(R^{7a})C(O)NR^{7a}$—, —$N(R^{7a})S(O)_2N(R^{7a})$—, or —OC(O)—.

$R^{7a}$ is hydrogen or an optionally substituted $C_{1-4}$ aliphatic, and $R^8$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, $R^2$ is halogen, —W—$R^9$, or —$R^9$, wherein:

W is selected from an optionally substituted $C_{1-3}$ alkylene chain, —O—, —$N(R^{2a})$—, —S—, —S(O)—, —$S(O)_2$—, —C(O)—, —$CO_2$—, —$C(O)NR^{2a}$—, —$N(R^{2a})C(O)$—, —$N(R^{2a})CO_2$—, —$S(O)_2NR^{2a}$—, —$N(R^{2a})S(O)_2$—, —$OC(O)N(R^{2a})$—, —$N(R^{2a})C(O)NR^{2a}$—, —$N(R^{2a})S(O)_2N(R^{2a})$—, or —OC(O)—.

$R^{2a}$ is hydrogen or an optionally substituted $C_{1-4}$ aliphatic, and $R^9$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is an optionally substituted nitrogen-containing heteroaryl group, provided that the optionally substituted nitrogen-containing heteroaryl group is a group other than a 3-isoxazolyl, a 2-pyridyl, a 3-pyridyl, a 5-pyrimidinyl, a 2-pyrimidinyl, a 5,6-dimethoxy-1H-benzimidazole group, or a pyrazinyl group, provided that:

i) for compounds of formula I-A, the compound is other than those compounds where:

$G_1$ is $CR^3$; $R^1$ is —$CONHR^4$, or

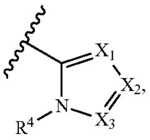

where $X_1$, $X_2$, and $X_3$ are each independently N or $CR^7$; and HY is an optionally substituted 6-membered nitrogen-containing heteroaryl group;

ii) for compounds of formula I-A or I-B, the compound is other than those compounds where:

$G_1$ is N; $R^1$ is

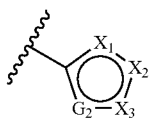

or $CON(R^4)_2$; and HY is an optionally substituted nitrogen-containing aromatic heterocyclic group;

and further provided that:

iii) for compounds of formula I-A when $R^1$ is —CON$(R^4)_2$, then $R^2$ is an optionally substituted group selected from 6-10-membered aryl, or 5-10-membered heteroaryl having 1-5 heteroatoms independently selected from nitrogen, oxygen, or sulfur, provided that compounds are other than: 2-thiophenecarboxamide, 5-dibenz[b,f][1,4]oxazepin-11-yl-N-hydroxy-3-phenyl-; 5-Thiazolecarboxamide, 2-(3,4-dihydro-1(2H)-quinolinyl)-N-hydroxy-4-phenyl-; 5-Thiazolecarboxamide, N-hydroxy-4-phenyl-2-(4-pyridinyl)-; 5-Thiazolecarboxamide, N-[2'-(aminosulfonyl)[1,1'-biphenyl]-2-yl]-4-(4-methoxyphenyl)-2-(1H-pyrrol-1-yl)-; 5-Thiazolecarboxamide, 4-(4-nitrophenyl)-2-(4-pyridinyl)-N-(3-trifluoromethyl)phenyl]-; 5-Thiazolecarboxamide, 4-(4-bromophenyl)-N-(1-methylethyl)-2-(2-propyl-4-pyridinyl)-; 5-Thiazolecarboxamide, 2-(2,3-dihydro-1H-indol-1-yl)-4-phenyl-N-(phenylmethyl)-; 5-Thiazolecarboxamide, 2-(2,3-dihydro-4H-1,4-benzoxazin-4-yl)-4-phenyl-N-(phenylmethyl)-; 5-Thiazolecarboxamide, 4-phenyl-N-[(1S,2S)-2-(phenylmethoxy)cyclopentyl]-2-(1H-pyrazol-1-yl)-; 5-Thiazolecarboxamide, 4-phenyl-N-(phenylmethyl)-2-(1H-pyrazol-1-yl)-; 5-Thiazolecarboxamide, N-[(4-chlorophenyl)methyl]-2-(3-methoxy-1H-pyrazol-1-yl)-4-phenyl-; 5-Thiazolecarboxamide, 4-phenyl-N-[1-(phenylmethyl)-3-pyrrolidinyl]-2-(1H-pyrazol-1-yl)-; 5-Thiazolecarboxamide, 2-(1H-benzimidazol-1-yl)-4-phenyl-; 5-Thiazolecarboxamide, N-[(1S,2R)-1-[(3,5-difluorophenyl)methyl]-3-[1-(3-ethynylphenyl)cyclopropyl]amino]-2-hydroxypropyl]-4-phenyl-2-(1H-pyrrol-1-yl)-; 4-Thiazolecarboxamide, 2-(4-acetyl)-5-methyl-1H-1,2,3-triazol-1-yl)-N,N-diethyl-5-phenyl-; 3-Thiophenecarboxamide, N-[1-(aminoethyl)-2-phenylethyl]-2-(3-furanyl)-5-(1-methyl-1H-pyrazol-5-yl)-, hydrochloride; 3-Thiophenecarboxamide, N-[1-(aminoethyl)-2-phenylethyl]-2-(3-furanyl)-5-(1-methyl-1H-pyrazol-5-yl)-; Carbamic acid, N-[2-[[[2-(3-furanyl)-5-(1-methyl-1H-pyrazol-5-yl)-3-thienyl]carbonyl] amino-3-phenylpropyl]-, 1,1-dimethylethylester; 3-Thiophenecarboxamide, N-methyl,2,5-di-4-pyridinyl-; 3-Thiophenecarboxamide, 2,5-di-4-pyridinyl-; 1H-1,2,3-triazole-4-acetic acid, 1-[4-[(diethylamino) carbonyl]-5-phenyl-2-thiazolyl]-5-methyl-a-oxo-, ethyl ester; 4-Thiazolecarboxamide, 2-[4-(1,2-dioxopropyl)-5-methyl-1H-1,2,3-triazol-1-yl]-N,N-diethyl-5-phenyl-; and for compounds of formula I-B, when $G_1$ is N, $R^2$ is substituted or unsubstituted phenyl or pyridyl, and HY is substituted or unsubstituted 1H-indazol-3-yl, then $R^1$ is other than $CON(R^4)_2$;

for compounds for formula I-A or I-B compounds are other than: 3-thiophenecarboxylic acid-2-(acetylamino)-5-[7-(4-chlorophenyl)-1,7-dihydro-2-(trifluoromethyl) [1,2,4]triazolo[1,5-a]pyrimidin-5-yl]-4-methyl-ethyl ester; 3-thiophenecarboxylic acid-2-(acetylamino)-5-[7-(4-chlorophenyl)-1,7-dihydro-2-(trifluoromethyl) [1,2,4]triazolo[1,5-a]pyrimidin-5-yl]-4-methyl-, ethyl ester; 5-Thiazoleacetamide, N-[[(2S)-4-[(3,4-difluorophenyl)methyl]-2-morpholinyl]methyl]-4-methyl-2-(5-methyl-3-isoxazolyl)-; 5-Thiazoleacetamide, N-[[(2S)-4-[(3,4-dichlorophenyl)methyl]-2-morpholinyl]methyl]-4-methyl-2-(5-methyl-3-isoxazolyl)-; Benzenecarboximidamide, 4-chloro-N-[[[[4-methyl-2-(2-thienyl)-5-thiazolyl]amino]carbonyl]oxy]-; Benzenecarboximidamide, N-[[[[4-methyl-2-(2-thienyl)-5-thiazolyl]amino]carbonyl]oxy]-4-(trifluoromethyl)-; Benzenecarboximidamide, 4-(1,1-dimethylethyl)-N-[[[[4-methyl-2-(2-thienyl)-5-thiazolyl]amino]carbonyl]oxy]-; Urea, N-(4-chlorophenyl)-N'-[4-methyl-2-(2-thienyl)-5-thiazolyl]-; or Urea, N-[4-(1-methylethyl)phenyl]-N'-[4-methyl-2-(2-thienyl)-5-thiazolyl]-;

iv) for compounds of formula I-A or I-B:

a) when $R^1$ is $NHCO(R^4)_2$, $G_1$ is $CR^3$, and $R^2$ or $R^3$ is Br, then HY is other than an optionally substituted 1H-pyrrolo[2,3-b]pyridin-4-yl group;

b) when $G_1$ is $CR^3$, $R^1$ is —$NHCOR^4$, and $R^2$ or $R^3$ is $CONH_2$, then HY is other than an optionally substituted 4,5,6,7-tetrahydro-1H-indol-1-yl or 4,5,6,7-tetrahydro-1H-indazol-1-yl group;

c) when $R^1$ is $NHCOR^4$, $G_1$ is $CR^3$, and $R^2$ or $R^3$ is Me, then HY is other than an optionally substituted group selected from:

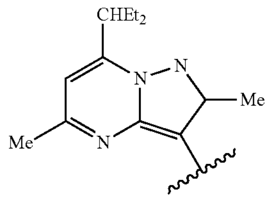

or

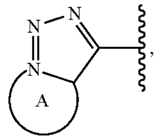

, wherein ring A is an optionally substituted fused thiadiazin-3-yl, thiadiazol-3-yl, or benzo group;

d) compounds are other than those compounds where $R^1$ or $R^2$ is Br, $R^1$ is —$NHCOR^4$, and HY is optionally substituted 1H-pyrrolo[2,3-b]pyridine-4-yl;

e) compounds are other than 1H-Benzimidazole, 2,2'-[benzo[1,2-b:5,4-b']dithiophene-2,6-diylbis(4-hexyl-5,2-thiophenediyl)]bis-; Imidazo[1,2-b]pyridazine, 8-(1-ethylpropyl)-2,6-dimethyl-3-[3-methyl-5-(2H-tetrazol-5-yl)-2-thienyl];

f) compounds are other than those compounds where $R^1$ is —$NHCON(R^4)_2$, —$NHCOR^4$, or $NHCOOR^4$, and $R^2$ is —CN, —$COOR^9$, $OR^9$, or —$CONR^{2a}R^9$;

g) compounds are other than: Acetamide, N-[5-(1H-benzotriazol-1-yl)-3-cyano-4-methyl-2-thienyl]- h) compounds are other than: 2-Butenoic acid, 4-[[4-amino-5-(2-benzothiazolyl)-3-cyano-2-thienyl] amino]-4-oxo-; or 3-Thiophenecarboxylic acid, 4-amino-5-(2-benzothiazolyl)-2-[(3-carboxy-1-oxo-2-propen-1-yl)amino]-, 3-ethyl ester; 2-Butenoic acid, 4-[[4-amino-5-(2-benzothiazolyl)-3-cyano-2-thienyl]amino]-4-oxo-; 3-Thiophenecarboxylic acid, 4-amino-5-(2-benzothiazolyl)-2-[(3-carboxy-1-oxo-2-propen-1-yl)amino]-, 3-ethyl ester i) compounds are other than: -Benzimidazole, 2,2'-(3,4-dimethyl-2,5-thiophenediyl)bis[5-butoxy-4,6-dichloro-; 1H-Benzimidazole-6-carbonitrile, 2-[5-(6-dodecyl-1H-benzimidazol-2-yl)-3,4-diethoxy-2- thienyl]-; or 1H-Benzimidazole, 2,2'-[3,4-bis(phenylmethyl)-2,5-thiophenediyl]bis[5-(phenylmethyl)- j) compounds are other than 7H-Pyrrolo[2,3-d]pyrimidin-2-amine, 4-[4-methyl-5-(2H-tetrazol-5-yl)-2-thienyl]-N-[4-[2-(1-pyrrolidinyl)ethoxy]phenyl]- k) compounds are other than: Thiophene, 2,5-bis(2-benzimidazolyl)-3,4-dibromo-;

l) compounds are other than: Tricyclo[3.3.1.13,7]decane-1-carboxamide, N-[3-[2-(dimethylamino)-1-hydroxyethyl]-5-(8-quinolinyl)-2-thienyl]-; or Tricyclo[3.3.1.13,7]decane-1-carboxamide, N-[3-[2-(dimethylamino)acetyl]-5-(8-quinolinyl)-2-thienyl]-; and m) compounds are other than Thiophene, 2,5-bis(2-benzimidazolyl)-3,4-dibromo-;

n) compounds are other than: Acetemide, N-[5-(4-acetyl-5-[4-[(2,4-dichlorophenyl)methoxy]-3-methoxyphenyl]-4,5-dihydro-1,3,4-oxadiazol-2-yl]-3-cyano-4-methyl-2-thienyl]-; Butanamide, N-[3-cyano-5-[3-[(2,4-dichlorophenyl)methyl]-1,2,4-oxadiazol-5-yl]-4-methyl-2-thienyl]-2-ethyl-; Acetamide, 2-bromo-N-[3-(2-chlorobenzoyl)-5-(4,5-dihydro-4,4-dimethyl-2-oxazolyl)-2-thienyl; and Acetamide, 2-amino-N-[3-(2-chlorobenzoyl)-5-(4,5-dihydro-4,4-dimethyl-2-oxazolyl)-2-thienyl]-

The invention also provides [2] compounds of [1] wherein $R^1$ is CY, and CY is

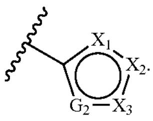

The invention also provides [3], compounds of [1] wherein $R^1$ is —$CON(R^4)_2$, —$NHCOR^4$, —$NHSO_2R^4$, —$NHCON(R^4)_2$, —$NHCOOR^4$, —$NHSO_2N(R^4)_2$, or —$NHSO_2OR^4$.

Also provided is [4], compounds of [1] or [2], wherein HY is selected from:

A

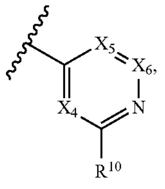

B

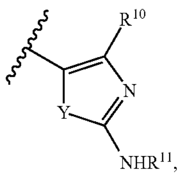

C

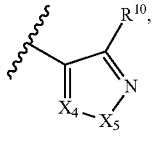

or

-continued

D

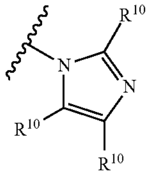

wherein $R^{10}$ is —$R^{10b}$, —$V_1$—$R^{10c}$, -$T_1$-$R^{10b}$, or —$V_1$-$T_1$-$R^{10b}$ wherein:

$V_1$ is —$NR^{10a}$—, —$NR^{10a}$—C(S)—, —$NR^{10a}$—C($NR^{10a}$)—, $NR^{10a}C(O)OR^{10a}$—, $NR^{10a}C(O)NR^{10a}$—, $NR^{1a}C(O)SR^{10a}$—, $NR^{1a}C(S)OR^{10a}$—, $NR^{10a}C(S)NR^{10a}$—, $NR^{10a}C(S)SR^{10a}$—, —$NR^{10a}C(NR^{10a})OR^{10a}$—, —$NR^{10a}C(NR^{10a})NR^{10a}$—, —$NR^{10a}S(O)_2$—, —$NR^{10a}S(O)_2NR^{10a}$—, —C(O)—, —$CO_2$—, —$C(O)NR^{10a}$—, $C(O)NR^{10a}O$—, —$SO_2$—, or —$SO_2NR^{10a}$—;

each occurrence of $R^{10a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$ alkylene chain wherein the alkylene chain optionally is interrupted by —$N(R^{10a})$—, —O—, —S—, —S(O)—, —$S(O)_2$—, —C(O)—, —C(O)O—, —$C(O)N(R^{10a})$—, —$S(O)_2N(R^{10a})$—, —$OC(O)N(R^{10a})$—, —$N(R^{10a})C(O)$—, —$N(R^{10a})SO_2$—, —$N(R^{10a})C(O)O$—, —$NR^{10a}C(O)N(R^{10a})$—, —$N(R^{10a})S(O)_2N(R^{10a})$—, —OC(O)—, or —$C(O)N(R^{10a})$—O— or wherein $T_1$ forms part of an optionally substituted 3-7 membered cycloaliphatic or heterocyclyl ring;

each occurrence of $R^{10b}$ is independently hydrogen, halogen, —CN, —$NO_2$, —$N(R^{10a})_2$, —$OR^{10a}$, —$SR^{10a}$, —$S(O)_2R^{10a}$, —$C(O)R^{10a}$, —$C(O)OR^{10a}$, —$C(O)N(R^{10a})_2$, —$S(O)_2N(R^{10a})_2$, —$OC(O)N(R^{10a})_2$, —$N(R^{10a})C(O)R^{10a}$, —$N(R^{10a})SO_2R^{10a}$, —$N(R^{10a})C(O)OR^{10a}$, —$N(R^{10a})C(O)N(R^{10a})_2$, or —$N(R^{10a})SO_2N(R^{10a})_2$, or an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^{10a}$ and $R^{10c}$ taken together with a nitrogen atom to which they are bound form an optionally substituted 4-7-membered heterocyclyl ring having 0-1 additional heteroatoms independently selected from nitrogen, oxygen, or sulfur, wherein each occurrence of $X_4$, $X_5$, and $X_6$ is independently N or $CR^{10}$, or two adjacent groups selected from Y, $R^{11}$, $R^{10}$, $X_4$, $X_5$, and $X_6$, taken together, form an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, and each occurrence of $R^{11}$ is independently hydrogen, —C(O)$R^{11a}$—, —$CO_2R^{11a}$—, —C(O)$NR^{11a}$—, C(O)$NR^{11a}$O—, —$SO_2R^{11a}$—, —$SO_2NR^{11a}$—, or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{11a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and Y is N or $CR^{10}$.

The invention also provides [5] compounds of [4], wherein HY is selected from:

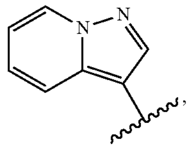
i

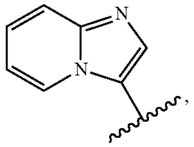
ii

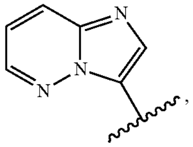
iii

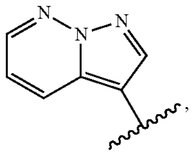
iv

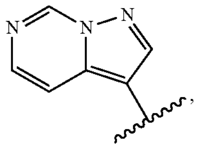
v

-continued

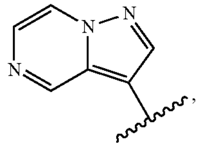
vi

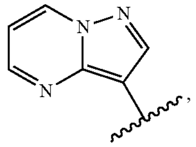
vii

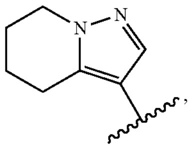
viii

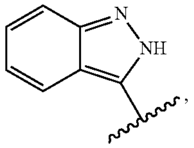
ix

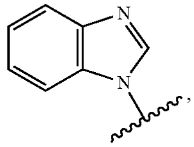
x

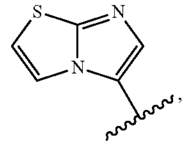
xi

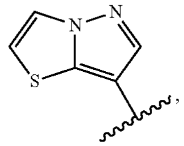
xii

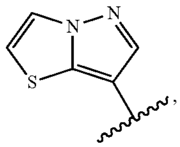
xiii

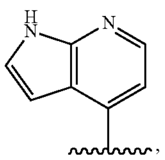
xiv

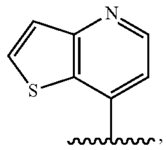
xv

-continued
xvi
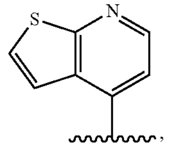
xvii
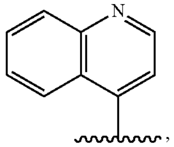
xviii
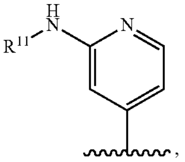
xix
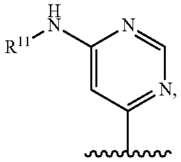
xx
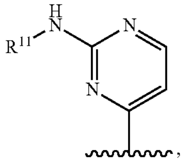
xxi
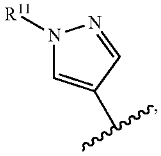
xxii
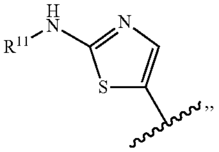
xxiii
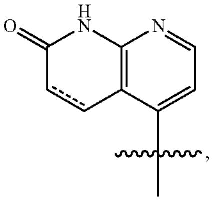
xxiv
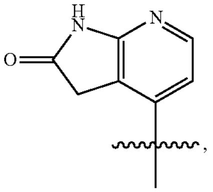
-continued
xxv
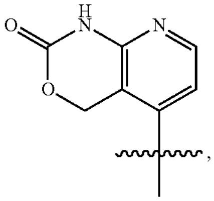
xxvi
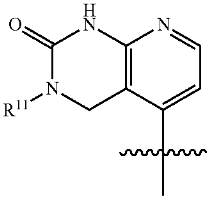
xxvii
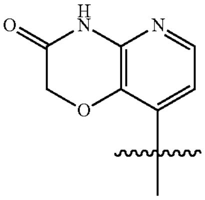
xxviii
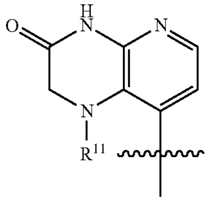
xxix
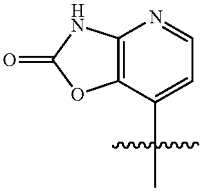
xxx
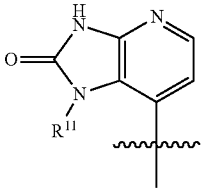
xxxi
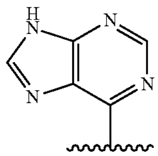
xxxii
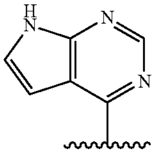

-continued xxxiii

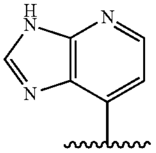

xxxiv

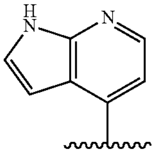

xxxv

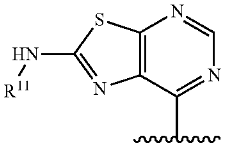

or xxxvi

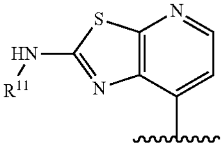

wherein each HY group is optionally additionally substituted with one or more occurrences of $R^{10}$.

The invention also provides [6] compounds of [5], wherein HY is selected from:

i

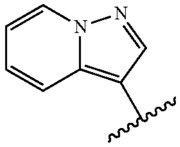

, v

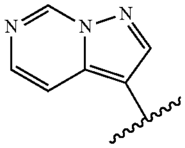

, x

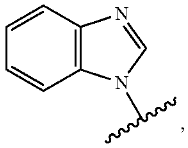

, xiv

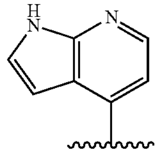

, xvii

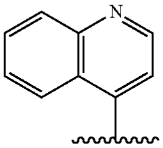

,

-continued xviii

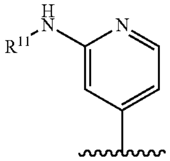

, xxiii

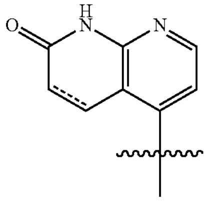

, xxix

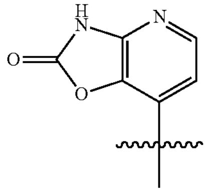

, xxxi

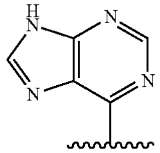

, xxxii

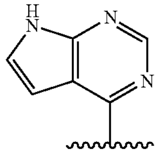

or xxxv

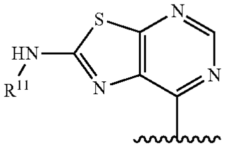

wherein each HY group is optionally additionally substituted with one or more occurrences of $R^{10}$.

The invention also provides [7] compounds of [5], wherein HY is selected from:

i

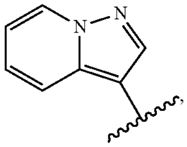

, ii

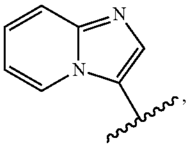

,

-continued
iii
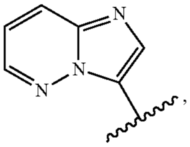
iv
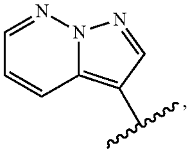
v
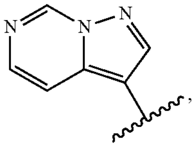
vi
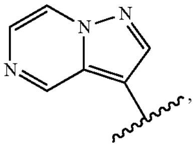
vii
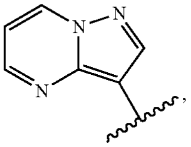
viii
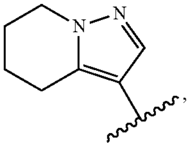
ix
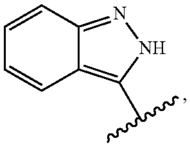
x
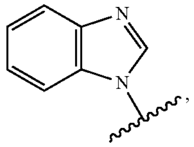
xi
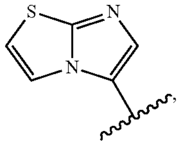
xii
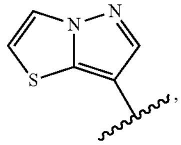
-continued
xiii
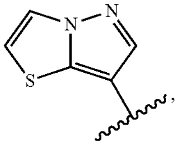
xiv
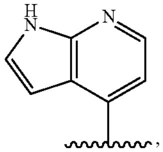
xv
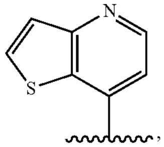
xvi
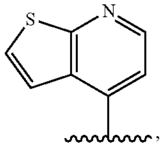
xvii
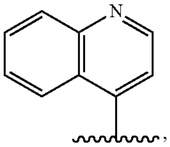
xxiii
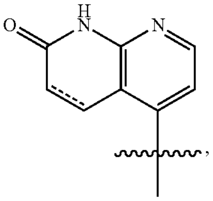
xxiv
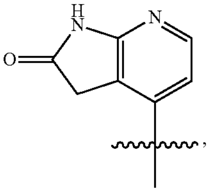
xxv
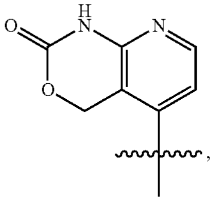

-continued
xxvi
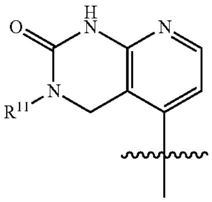
xxvii
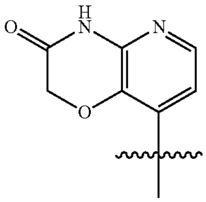
xxviii
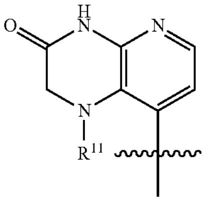
xxix
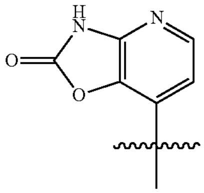
xxx
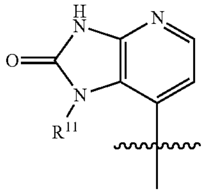
xxxi
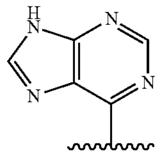
xxxii
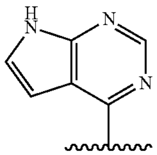
xxxiii
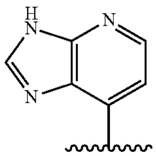
-continued
xxxiv
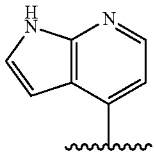
xxxv
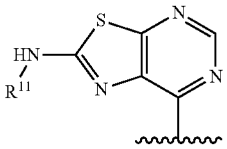
or
xxxvi
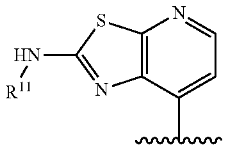
wherein each HY group is optionally additionally substituted with one or more occurrences of $R^{10}$.
The invention also provides [8] compounds of [7], wherein HY is selected from:
i
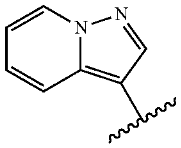
,
v
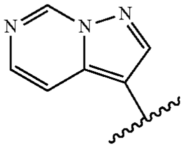
,
x
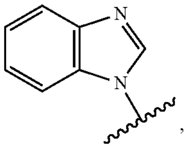
,
xiv
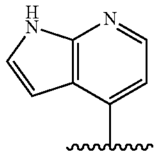
,
xvii
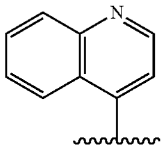
, -continued xxiii

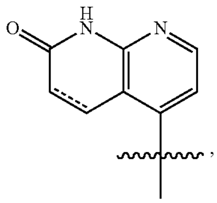

, xxix

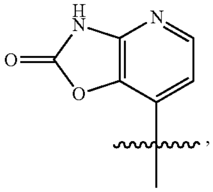

, xxxi

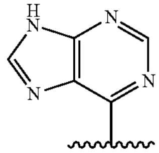

, xxxii

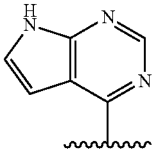

or xxxv

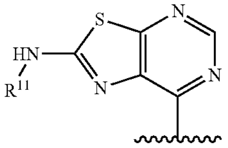

wherein each HY group is optionally additionally substituted with one or more occurrences of $R^{10}$.

The invention also provides [9] compounds of [1] or [2], wherein HY is selected from:

xxiii

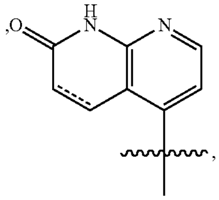

, xxiv

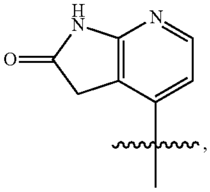

,

-continued xxv

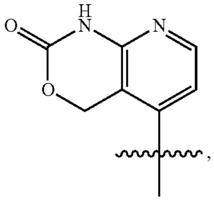

, xxvi

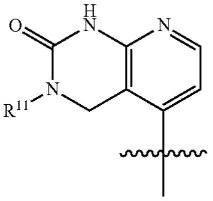

xxvii

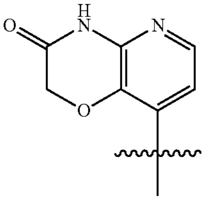

xxviii

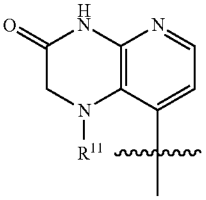

xxix

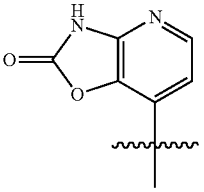

xxx

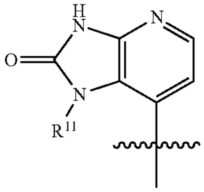

wherein each HY group is optionally additionally substituted with one or more occurrences of $R^{10}$.

The invention also provides [10] compounds of [9], wherein HY is selected from:

xxiii

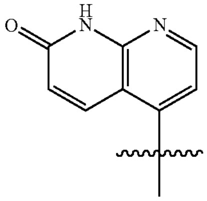

or

-continued xxix

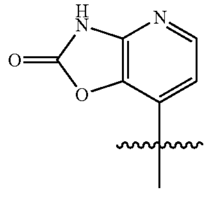

The invention also provides [11] compounds of [1] or [2], wherein $G_1$ is $CR^3$.

The invention also provides [12] compounds of [11], wherein $G_1$ is CH.

The invention also provides [13] compounds of [1] or [2], wherein $G_1$ is N.

The invention also provides [14] compounds of [1] or [2], wherein $R^2$ is a 3-10-membered cycloaliphatic, 4-10-membered heterocyclyl having 1-5 heteroatoms independently selected from nitrogen, oxygen, or sulfur 6-10-membered aryl, or 5-10-membered heteroaryl having 1-5 heteroatoms independently selected from nitrogen, oxygen, or sulfur, optionally substituted with 1-4 independent occurrences of $R^{12}$, wherein $R^{12}$ is —$R^{12a}$, -$T_2$-$R^{12d}$, or —$V_2$-$T_2$-$R^{12d}$, and:

each occurrence of $R^{9a}$ is independently halogen, —CN, —$NO_2$, —$R^{12c}$, —$N(R^{12b})_2$, $OR^{12b}$, —$SR^{12c}$, —$S(O)_2R^{12c}$, —$C(O)R^{12b}$, —$C(O)OR^{12b}$, —$C(O)N(R^{12b})_2$, —$S(O)_2N(R^{12b})_2$, —$OC(O)N(R^{12b})_2$, —$N(R^{12e})C(O)R^{12b}$, —$N(R^{12e})SO_2R^{12c}$, —$N(R^{12e})C(O)OR^{12b}$, —$N(R^{12e})C(O)N(R^{12b})_2$, or —$N(R^{12e})SO_2N(R^{12b})_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —$N(R^{12e})$—, —O—, —S—, —S(O)—, —$S(O)_2$—, —C(O)—, —C(O)O—, —$C(O)N(R^{12e})$—, —$S(O)_2N(R^{12e})$—, —$OC(O)N(R^{12e})$—, —$N(R^{12e})C(O)$—, —$N(R^{12e})SO_2$—, —$N(R^{12e})C(O)O$—, —$NR^{12e}C(O)N(R^{12e})$—, —$N(R)SO_2N(R^{12e})$—, —OC(O)—, or —$C(O)N(R^{12e})$—O—; and $T_2$ is an optionally substituted $C_1$-$C_6$ alkylene chain wherein the alkylene chain optionally is interrupted by —$N(R^{13})$—, —O—, —S—, —S(O)—, —$S(O)_2$—, —C(O)—, —C(O)O—, —$C(O)N(R^{13})$—, —$S(O)_2N(R^{13})$—, —$OC(O)N(R^{13})$—, —$N(R^{13})C(O)$—, —$N(R^{13})SO_2$—, —$N(R^{13})C(O)O$—, —$NR^{13}C(O)N(R^{13})$—, —$N(R^{13})S(O)_2N(R^{13})$—, —OC(O)—, or —$C(O)N(R^{13})$—O— or wherein $T_3$ or a portion thereof optionally forms part of an optionally substituted 3-7 membered cycloaliphatic or heterocyclyl ring, wherein $R^{13}$ is hydrogen or an optionally substituted $C_{1-4}$aliphatic group.

The invention also provides [15] compounds of [14] wherein $R^2$ is an optionally substituted 6-10-membered aryl or 5-10-membered heteroaryl having 1-5 heteroatoms independently selected from nitrogen, oxygen, or sulfur.

The invention also provides [16] compounds of [15] wherein $R^2$ is a phenyl group substituted with 1-3 independent occurrences of halogen, $C_{1-3}$ alkyl, CN, $C_{1-3}$haloalkyl, —$OC_{1-3}$ alkyl, —$OC_{1-3}$ haloalkyl, —$NHC(O)C_{1-3}$ alkyl, —$NHC(O)NHC_{1-3}$ alkyl, $NHS(O)_2C_{1-3}$ alkyl, or —C(O)H.

The invention also provides [17], compounds of [16] wherein $R^2$ is halogen.

The invention also provides [18], compounds of [1] or [2] wherein when $R^1$ is CY, $X_1$ is N, $G_2$ is $NR^{4'}$, and $X_2$ and $X_3$ are $CR^7$.

The invention also provides [19], compounds of [18], wherein $X_3$ is CH.

The invention also provides [20], compounds of [1] or [2], wherein when $R^1$ is CY, $X_1$ and $X_2$ are N, $O_2$ is $NR^{4'}$ and $X_3$ is $CR^7$.

The invention also provides [21], compounds of [20] wherein $R^7$ is H or $NH_2$.

The invention also provides [22], compounds of [1], wherein one or more, or all, of $R^1$, $R^2$ and HY are selected from:

a. $R^1$ is CY, and CY is

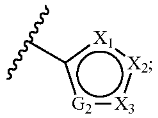

b. $R^2$ is a 3-10-membered cycloaliphatic, 4-10-membered heterocyclyl having 1-5 heteroatoms independently selected from nitrogen, oxygen, or sulfur 6-10-membered aryl, or 5-10-membered heteroaryl having 1-5 heteroatoms independently selected from nitrogen, oxygen, or sulfur, optionally substituted with 1-4 independent occurrences of $R^{12}$, wherein $R^{12}$ is —$R^{12a}$, -$T_2$-$R^{12d}$, or —$V_2$-$T_2$-$R^{12d}$, and:

each occurrence of $R^{9a}$ is independently halogen, —CN, —$NO_2$, —$R^{12c}$, —$N(R^{12b})_2$, —$OR^{12b}$, —$SR^{12c}$, —$S(O)_2R^{12c}$, —$C(O)R^{12b}$, —$C(O)OR^{12c}$, —$C(O)N(R^{12})_2$, —$S(O)_2N(R^{12b})_2$, —$OC(O)N(R^{12b})_2$, —$N(R^{12e})C(O)R^{12b}$, —$N(R^{12e})SO_2R^{12c}$, —$N(R^{12e})C(O)OR^{12b}$, —$N(R^{12e})C(O)N(R^{12b})_2$, or —$N(R^{12e})SO_2N(R^{12b})_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 0.1-5 heteroatoms independently selected from nitrogen, oxygen, or sulfur;

each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —$N(R^{12e})$—, —O—, —S—, —S(O)—, —$S(O)_2$—, —C(O)—, —C(O)O—, —$C(O)N(R^{12e})$—, $S(O)_2N(R^{12e})$—, —$OC(O)N(R^{12e})$—, —$N(R^{12e})C(O)$—, —$N(R^{12e})SO_2$—, —$N(R^{12e})C(O)O$—, —$NR^{12e}C(O)N(R^{12e})$—, —$N(R^{12e})SO_2N(R^{12e})$—, —OC(O)—, or —$C(O)N(R^{12e})$—O—; and $T_2$ is an optionally substituted $C_1$-$C_6$ alkylene chain wherein the alkylene chain optionally is interrupted by —$N(R^{13})$—, —O—, —S—, —S(O)—, —$S(O)_2$—, —C(O)—, —C(O)O—, —$C(O)N(R^{13})$—, —$S(O)_2N(R^{13})$—, —$OC(O)N(R^{13})$—, —$N(R^{13})C(O)$—, —$N(R^{13})SO_2$—, —$N(R^{13})C(O)O$—, —$NR^{13}C(O)N(R^{13})$—, —$N(R^{13})S(O)_2N(R^{13})$—, —OC(O)—, or —$C(O)N(R^{13})$—O— or wherein $T_3$ or a portion thereof optionally forms part of an optionally substituted 3-7 membered cycloaliphatic or heterocyclyl ring, wherein $R^{13}$ is hydrogen or an optionally substituted $C_{1-4}$aliphatic group; and c. HY is selected from:

A

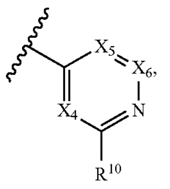

B

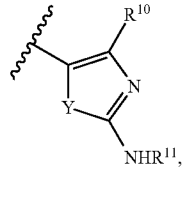

-continued

C

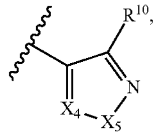

or

D

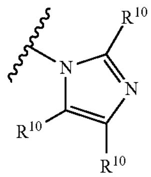

wherein $R^{10}$ is —$R^{10b}$, —$V_1$—$R^{10c}$, -$T_1$-$R^{10b}$ or —$V_1$-$T_1$-$R^{10b}$ wherein:

$V_1$ is —$NR^{10a}$, —$NR^{10a}$—C(O)—, —$NR^{10a}$—C(S)—, —$NR^{10a}$—$C(NR^{10a})$—, $NR^{10a}C(O)OR^{10a}$—, $NR^{10a}C(O)NR^{10a}$—, $NR^{1a}C(O)SR^{10a}$—, $NR^{1a}C(S)OR^{10a}$—, $NR^{10a}C(S)NR^{10a}$—, $NR^{10a}C(S)SR^{10a}$—, —$NR^{10a}C(NR^{10a})OR^{10a}$—, —$NR^{10a}C(NR^{10a})NR^{10a}$—, —$NR^{10a}S(O)_2$—, —$NR^{10a}S(O)_2NR^{10a}$—, —C(O)—, —$CO_2$—, —$C(O)NR^{10a}$—, $C(O)NR^{10a}$—, —$SO_2$—, or —$SO_2NR^{10a}$—;

each occurrence of $R^{10a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$ alkylene chain wherein the alkylene chain optionally is interrupted by —$N(R^{10a})$—, —O—, —S—, —S(O)—, —$S(O)_2$—, —C(O)—, —C(O)O—, —$C(O)N(R^{10a})$—, —$S(O)_2N(R^{10a})$—, —$OC(O)N(R^{10a})$—, —$N(R^{10a})C(O)$—, —$N(R^{10a})SO_2$—, —$N(R^{10a})C(O)O$—, —$NR^{10a}C(O)N(R^{10a})$—, —$N(R^{10a})S(O)_2N(R^{10a})$—, —OC(O)—, or —$C(O)N(R^{10a})$—O— or wherein $T_1$ forms part of an optionally substituted 3-7 membered cycloaliphatic or heterocyclyl ring;

each occurrence of $R^{10b}$ is independently hydrogen, halogen, —CN, —$NO_2$, —$N(R^{10a})_2$, —$OR^{10a}$, —$SR^{10a}$, —$S(O)_2R^{10a}$, —$C(O)R^{10a}$, —$C(O)OR^{10a}$, —$C(O)N(R^{10a})_2$, —$S(O)_2N(R^{10a})_2$, —$OC(O)N(R^{10a})_2$, —$N(R^{10a})C(O)R^{10a}$, —$N(R^{10a})SO_2R^{10a}$, —$N(R^{10a}C(O)OR^{10a}$, —$N(R^{10a})C(O)N(R^{10a})_2$, or —$N(R^{10a})SO_2N(R^{10a})_2$, or an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^{10a}$ and $R^{10c}$ taken together with a nitrogen atom to which they are bound form an optionally substituted 4-7-membered heterocyclyl ring having 0-1 additional heteroatoms independently selected from nitrogen, oxygen, or sulfur, wherein each occurrence of $X_4$, $X_5$, and $X_6$ is independently N or $CR^{10}$, or two adjacent groups selected from Y, $R^{11}$, $R^{10}$, $X_4$, $X_5$, and $X_6$, taken together, form an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, and each occurrence of $R^{11}$ is independently hydrogen, —$C(O)R^{11a}$—, —$CO_2R^{11a}$—, —$C(O)NR^{11a}$—, $C(O)NR^{11a}O$—, —$SO_2R^{11a}$—, —$SO_2NR^{11a}$—, or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{11a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen; oxygen, or sulfur; and Y is N or $CR^{10}$.

The invention also provides [23], compounds of [22], wherein HY is selected from:

i

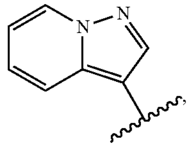

ii

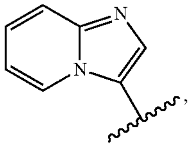

iii

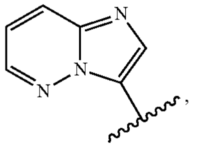

iv

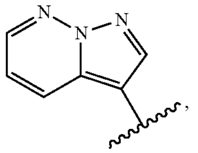

-continued v

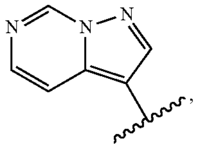

vi

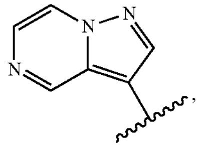

vii

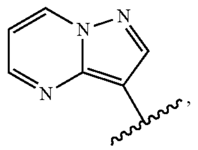

viii

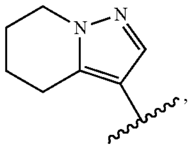

ix

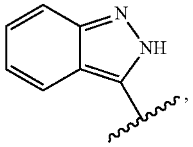

x

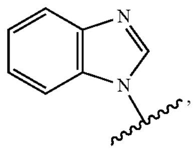

xi

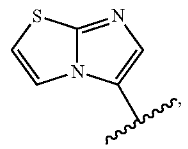

xii

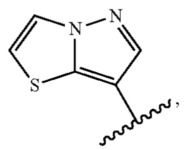

xiii

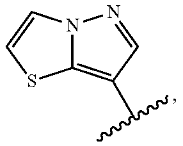

xiv

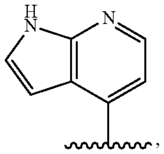

-continued
xv
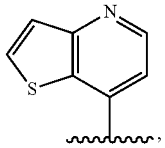
xvi
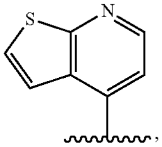
xvii
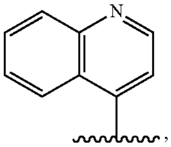
xviii
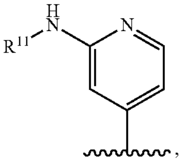
xix
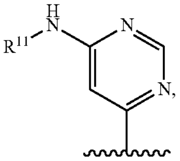
xx
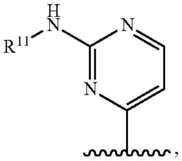
xxi
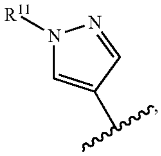
xxii
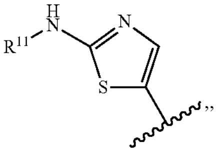
xxiii
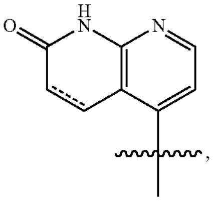
-continued
xxiv
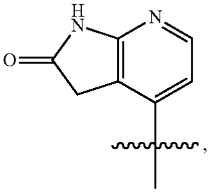
xxv
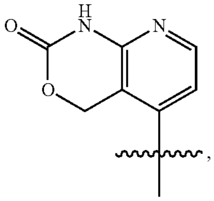
xxvi
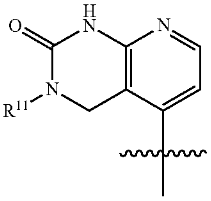
xxvii
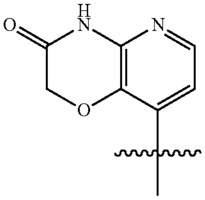
xxviii
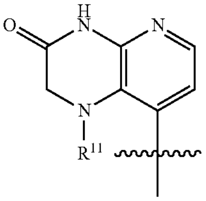
xxix
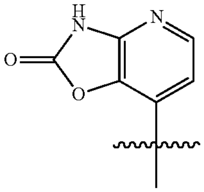
xxx
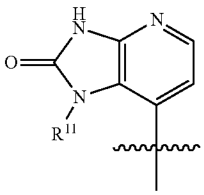
xxxi
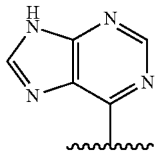

-continued xxxii

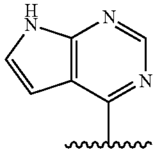

xxxiii

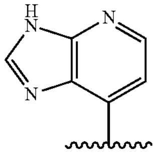

xxxiv

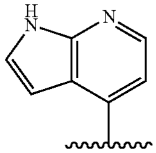

xxxv

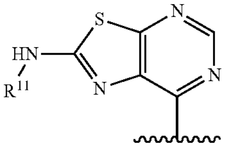

or xxxvi

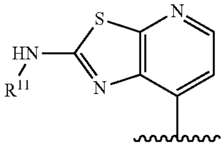

wherein each HY group is optionally additionally substituted with one or more occurrences of $R^{10}$.

The invention also provides [24], compounds of [23], wherein HY is selected from:

i

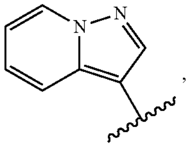

v

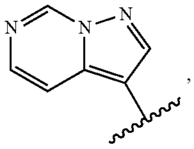

x

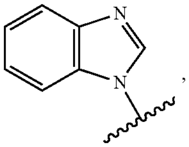

xiv

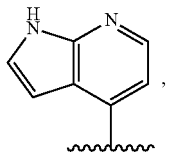

-continued xvii

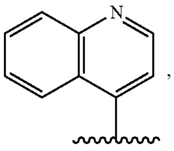

xviii

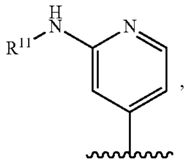

xxiii

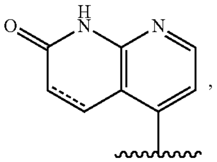

xxix

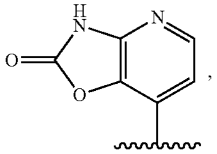

xxxi

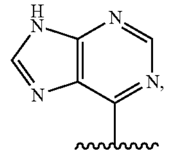

xxxii

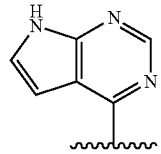

or xxxv

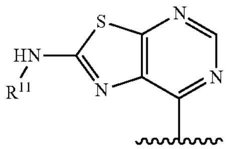

wherein each HY group is optionally additionally substituted with one or more occurrences of $R^{10}$ The invention also provides [25], compounds of [24], wherein HY is selected from:

i

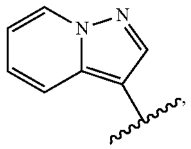

-continued
ii
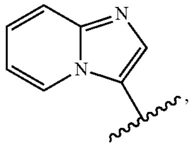,
iii
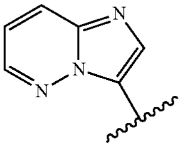,
iv
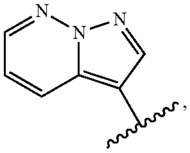,
v
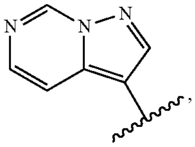,
vi
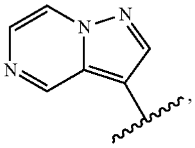,
vii
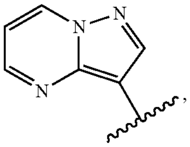,
viii
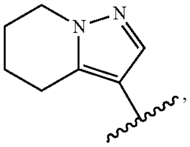,
ix
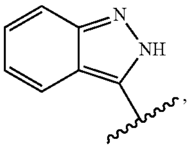,
x
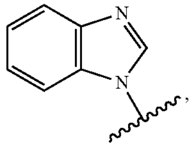,
xi
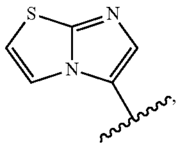,
-continued
xii
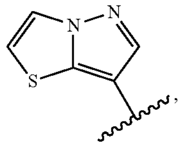,
xiii
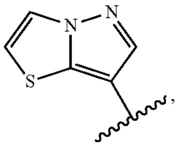,
xiv
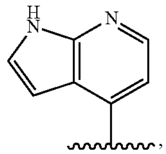,
xv
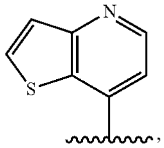,
xvi
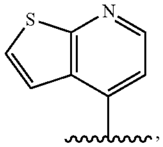,
xvii
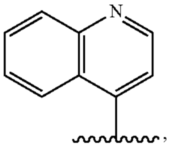,
xxiii
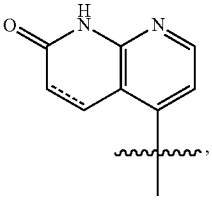,
xxiv
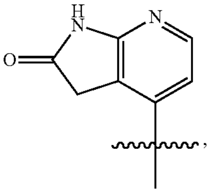,
xxv
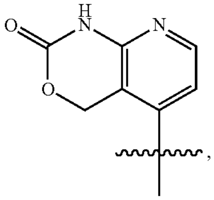, -continued
xxvi
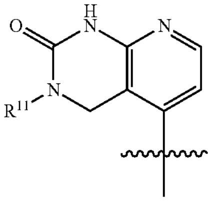
xxvii
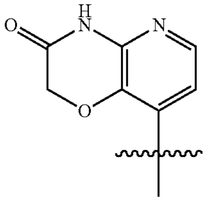
xxviii
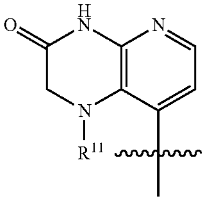
xxix
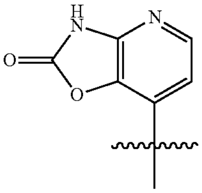
xxx
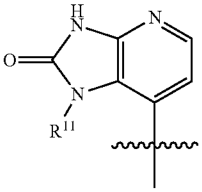
xxxi
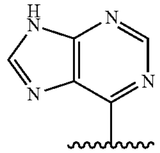
xxxii
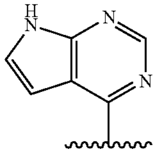
xxxiii
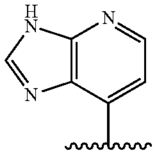
-continued
xxxiv
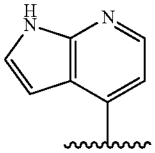
xxxv
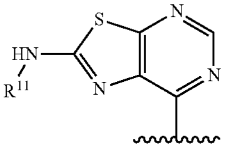
or
xxxvi
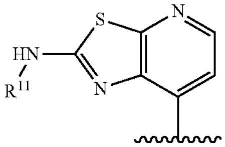
wherein each HY group is optionally additionally substituted with one or more occurrences of $R^{10}$.
The invention also provides [26], compounds of [25], wherein HY is selected from:
i
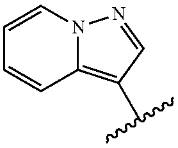
,
v
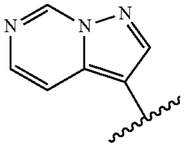
,
x
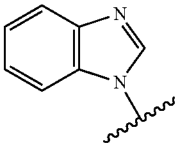
,
xiv
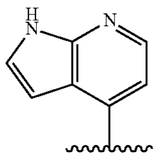
,
xvii
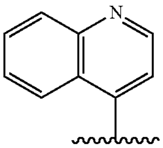
, -continued xxiii

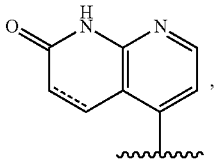

xxix

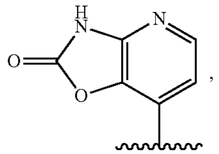

xxxi

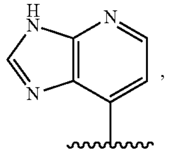

xxxii

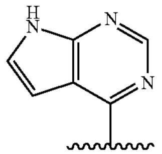

or xxxv

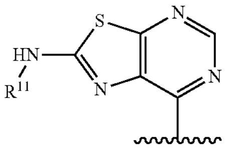

wherein each HY group is optionally additionally substituted with one or more occurrences of $R^{10}$.

The invention also provides [27], compounds of [22], [23], [24], [25], or [26], wherein $R^2$ is an optionally substituted 6-10-membered aryl or 5-10-membered heteroaryl having 1-5 heteroatoms independently selected from nitrogen, oxygen, or sulfur.

The invention also provides [28], compounds of [22], [23], [24], [25], or [26], wherein $R^2$ is a phenyl group substituted with 1-3 independent occurrences of halo, $C_{1-3}$ alkyl, CN, —$OC_{1-3}$ alkyl, —$OC_{1-3}$haloalkyl, —NHC(O)$C_{1-3}$ alkyl, —NHC(O)NH$C_{1-3}$ alkyl, NHS$(O)_2C_{1-3}$ alkyl, or —C(O)H.

The invention also provides [29], compounds of [1], for compounds of I-A, wherein $G_1$ is $CR^3$, HY is an optionally substituted 6-membered nitrogen-containing heteroaryl group, and $R^1$ is —$NHCOR^4$, —$NHSO_2R^4$, —$NHCON(R^4)_2$, —$NHCOOR^4$, —$NHSO_2N(R^4)_2$, or —$NHSO_2OR^4$.

The invention also provides [30], compounds of [29], wherein:

$G_1$ is CH:

HY is xviii

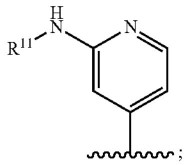

$R^1$ is —$NHCOR^4$, —$NHSO_2R^4$, —$NHCON(R^4)_2$, —$NHCOOR^4$, —$NHSO_2N(R^4)_2$, or —$NHSO_2OR^4$, $R^4$ is $C_{1-6}$ alkyl, and $R^2$ is a $C_{6-18}$ aryl group which is optionally substituted by halogen.

The invention also provides [31], compounds of [30], wherein:

$G_1$ is CH;

HY is xviii

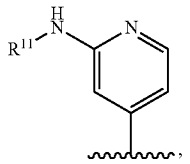

$R_{11}$ is $C_{1-6}$arkylcarbonyl, $R^1$ is —$NHCOR^4$, $R^4$ is $C_{1-6}$ alkyl and $R^2$ is a $C_{6-18}$ aryl group which is optionally substituted by halogen.

The invention also provides [32], compounds of [1], for compounds of formula I-A, wherein $G^1$ is $CR^3$, HY is an optionally substituted bicyclic or polycyclic nitrogen-containing heteroaryl group, and $R^1$ is CY, —$CON(R^4)_2$, —$NHCOR^4$, —$NHSO_2R^4$, —$NHCON(R^4)_2$, —$NHCOOR^4$, —$NHSO_2N(R^4)_2$, or —$NHSO_2OR^4$.

The invention also provides [33], compounds of [32], wherein HY is selected from:

i

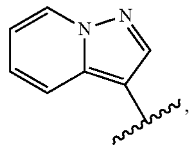

ii

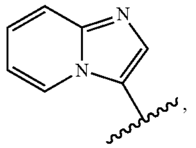

iii

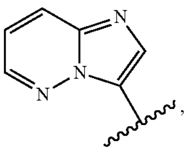

-continued
iv
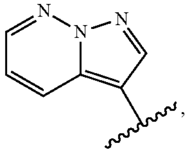
v
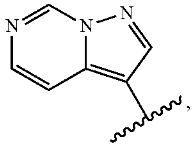
vi
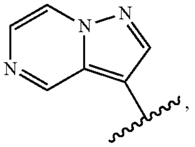
vii
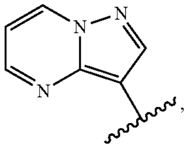
viii
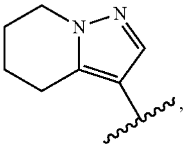
ix
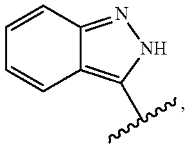
x
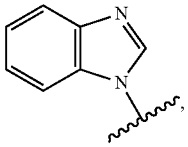
xi
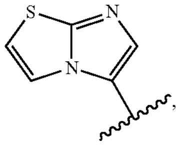
xii
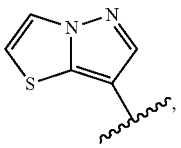
xiii
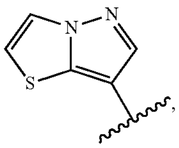
-continued
xiv
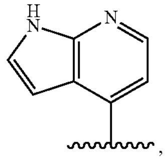
xv
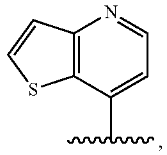
xvi
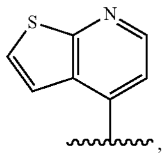
xvii
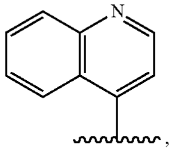
xxiii
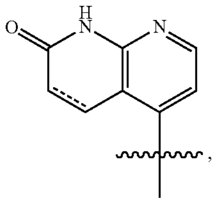
xxiv
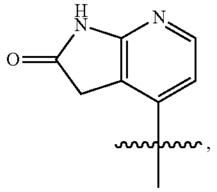
xxv
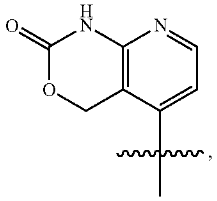
xxvi
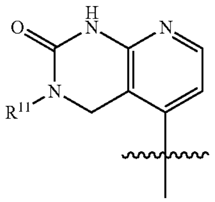

-continued
xxvii
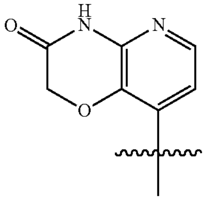
xxviii
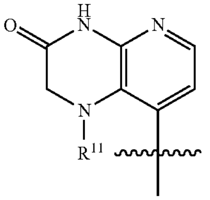
xxix
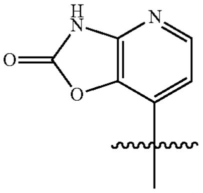
xxx
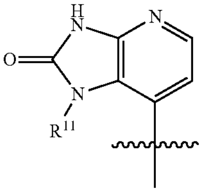
xxxi
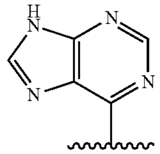
xxxii
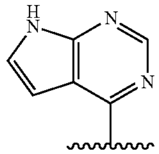
xxxiii
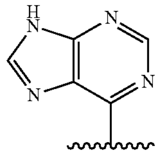
xxxiv
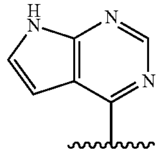
-continued
xxxv
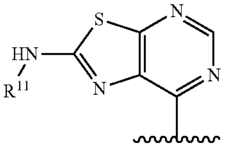
or
xxxvi
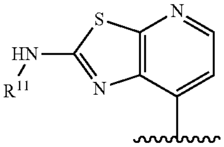
wherein each HY group is optionally additionally substituted with one or more occurrences of $R^{10}$.
The invention also provides [34], compounds of [33], wherein HY is selected from:
i
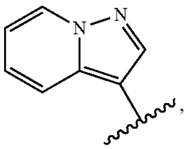
v
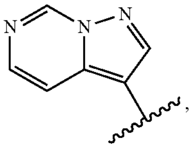
x
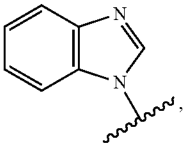
xiv
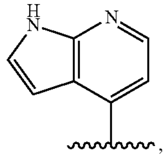
xvii
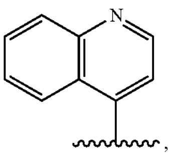
xxiii
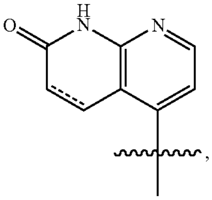

-continued xxix

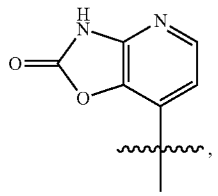

xxxi

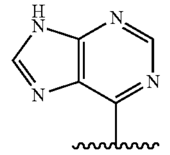

xxxv

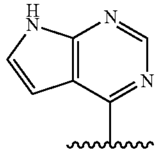

or xxxvi

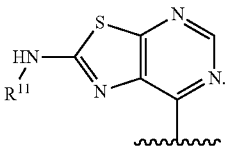

wherein each HY group is optionally additionally substituted with one or more occurrences of $R^{10}$.

The invention also provides [35], compounds of [34], wherein $R^1$ is CY, and CY is

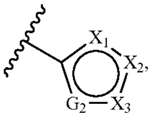

$R^2$ is an optionally substituted 6-10-membered aryl or 5-10-membered heteroaryl having 1-5 heteroatoms independently selected from nitrogen, oxygen, or sulfur.

The invention also provides [36], compounds of [35], wherein $R^2$ is a phenyl group substituted with 1-3 independent occurrences of halo, $C_{1-3}$ alkyl, CN, $C_{1-3}$haloalkyl, —$OC_{1-3}$ alkyl, —$OC_{1-3}$ haloalkyl, —NHC(O)$C_{1-3}$ alkyl, —NHC(O)NH$C_{1-3}$ alkyl, $NHS(O)_2C_{1-3}$alkyl, or —C(O)H.

The invention also provides [37], compounds of [35], wherein $X_1$ is N and $X_2$ and $X_3$ are CH.

The invention also provides [38], compounds of [35], wherein $X_1$ and $X_2$ are N, and $X_3$ is CH.

The invention also provides [39], compounds of [1], for compounds of formula I-A, wherein $G^1$ is N, HY is an optionally substituted nitrogen-containing heteroaryl group, and $R^1$ is —$CON(R^4)_2$, —$NHCOR^4$, —$NHSO_2R^4$, —$NHCON(R^4)_2$, —$NHCOOR^4$, —$NHSO_2N(R^4)_2$, or —$NHSO_2OR^4$.

The invention also provides [40], compounds of [39], wherein $R^1$ is —$NHSO_2R^4$, and $R^4$ is $C_{1-6}$alkyl.

The invention also provides [41], compounds of [40], wherein $R^1$ is CY, and CY is

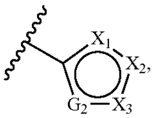

$R^2$ is an optionally substituted 6-10-membered aryl or 5-10-membered heteroaryl having 1-5 heteroatoms independently selected from nitrogen, oxygen, or sulfur.

The invention also provides [42], compounds of [40], wherein $R^2$ is a phenyl group substituted with 1-3 independent occurrences of halo, $C_{1-3}$ alkyl, CN, $C_{1-3}$haloalkyl, —$OC_{1-3}$ alkyl, —$OC_{1-3}$ haloalkyl, —NHC(O)$C_{1-3}$ alkyl, —NHC(O)NH$C_{1-3}$ alkyl, $NHS(O)_2C_{1-3}$alkyl, or —C(O)H.

The invention also provides [43], compounds of [42], wherein $X_1$ is N and $X_2$ and $X_3$ are CH.

The invention also provides [44], compounds of [42], wherein $X_1$ and $X_2$ are N, and $X_3$ is CH.

The invention also provides [45], compounds of [1], wherein compounds are represented by formula I-B.

The invention also provides [46], compounds of [45] wherein $G_1$ is CH.

The invention also provides [47], compounds of [1] having formula III:

III

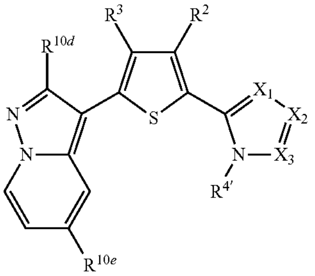

wherein $R^{10d}$ is hydrogen or optionally substituted $C_{1-4}$alkyl, and $R^{10e}$ is $R^{10}$.

The invention also provides [48], compounds of [47]: wherein $R^{10e}$ is —$V_1$—$R^{10c}$, or halogen.

The invention also provides [49], compounds of [47], wherein $R^{10d}$ is hydrogen or $C_{1-6}$ alkyl such as methyl, $R^{10e}$ is H, hydroxy, $C_{1-6}$alkyl, $C_{1-6}$ alkoxy optionally substituted by a group selected from hydroxy, $C_{1-6}$ alkyl-carbonylamino and amino-$C_{1-6}$ alkyl-carbonylamino, $C_{6-18}$ aryl-$C_{1-4}$alkyl-oxy, 4- to 7-membered monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom optionally substituted by $C_{1-6}$ alkyl optionally substituted by halogen and 4- to 7-membered monocyclic non-aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom optionally substituted by a group selected from halogen, $C_{1-6}$ alkyl, $C_{1-6}$ alkylsulfonyloxy and $C_{1-6}$ alkyl-carbonyl optionally substituted by hydroxyl, $R^3$ is H, and $R^{4'}$ is H.

The invention also provides [50], compounds of [47], [48], or [49], wherein $X_1$ is N and $X_2$ and $X_3$ are H.

The invention also provides [51], compounds of [47], [48], or [49], wherein $X_1$ and $X_2$ are N, and $X_3$ is H.

The invention also provides [52], compounds of [47], [48], or [49], wherein $R^2$ is an optionally substituted 6-10-membered aryl or 5-10-membered heteroaryl having 1-5 heteroatoms independently selected from nitrogen, oxygen, or sulfur.

The invention also provides [53], compounds of [47], [48], or [49], wherein: $R^2$ is a phenyl group substituted with 1-3 independent occurrences of halo, $C_{1-3}$ alkyl, CN, $C_{1-3}$haloalkyl, —$OC_{1-3}$ alkyl, —$OC_{1-3}$haloalkyl, —NHC(O)$C_{1-3}$ alkyl, —NHC(O)NH$C_{1-3}$alkyl, NHS$(O)_2C_{1-3}$alkyl, or —C(O)H.

The invention also provides [54], compounds of [1],

IA

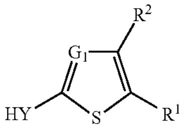

IB

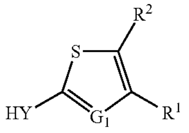

or a pharmaceutically acceptable salt thereof, wherein:

$G_1$ is N or $CR^3$, wherein $R^3$ is H, —CN, halogen, —Z—$R^5$, $C_{1-6}$ aliphatic, or 3-10-membered cycloaliphatic, wherein:

Z is selected from an optionally substituted $C_{1-3}$ alkylene chain, —O—, —N($R^{3a}$)—, —S—, —S(O)—, —$S(O)_2$—, —C(O)—, —$CO_2$—, —C(O)N$R^{3a}$—, —N($R^{3a}$)C(O)—, —N($R^{3a}$)$CO_2$—, —$S(O)_2NR^{3a}$—, —N($R^{3a}$)$S(O)_2$—, —OC(O)N($R^{3a}$)—, —N($R^{3a}$)C(O)N$R^{3a}$—, —N($R^{3a}$)$S(O)_2$N($R^{3a}$)—, or —OC(O)—;

$R^{3a}$ is hydrogen or an optionally substituted $C_{1-4}$ aliphatic, and $R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$R^1$ is CY, —CON$(R^4)_2$, —NHCO$R^4$, —NHSO$_2R^4$, —NHCON$(R^4)_2$, —NHCOO$R^4$, —NHSO$_2$N$(R^4)_2$, or —NHSO$_2$O$R^4$, wherein:

CY is

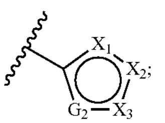

wherein:

$X_1$, $X_2$, and $X_3$, are each independently N, O, S, or $CR^7$, provided that only one of $X_1$, $X_2$, or $X_3$ may be O or S, $G_2$ is —N═ or —N$R^{4'}$—, wherein:

each occurrence of $R^4$ and $R^{4'}$ is independently H, —$Z_2$—$R^6$, optionally substituted $C_{1-6}$ aliphatic, or optionally substituted 3-10-membered cycloaliphatic, wherein:

$Z_2$ is selected from an optionally substituted $C_{1-3}$ alkylene chain, —S(O)—, —$S(O)_2$—, —C(O)—, —C(O)N$R^{4a}$—, or —$S(O)_2$N$R^{4a}$—.

$R^{4a}$ is hydrogen or an optionally substituted $C_{1-4}$ aliphatic, and $R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^7$ is independently hydrogen, —CN, halogen, —$Z_3$—$R^8$, $C_{1-6}$ aliphatic, or 3-10-membered cycloaliphatic, wherein:

$Z_3$ is selected from an optionally substituted $C_{1-3}$ alkylene chain, —O—, —N($R^{7a}$)—, —S—, —S(O)—, —$S(O)_2$—, —C(O)—, —C(O)N$R^{7a}$—, —N($R^{7a}$)C(O)—, —N($R^{7a}$)$CO_2$—, —$S(O)_2$N$R^{7a}$—, —N($R^{7a}$)$S(O)_2$—, —OC(O)N($R^{7a}$)—, —N($R^{7a}$)C(O)N$R^{7a}$—, —N($R^{7a}$)$S(O)_2$N($R^{7a}$)—, or —OC(O)—.

$R^{7a}$ is hydrogen or an optionally substituted $C_{1-4}$ aliphatic, and $R^8$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, $R^2$ is halogen, —W—$R^9$, or —$R^9$, wherein:

W is selected from an optionally substituted $C_{1-3}$ alkylene chain, —O—, —N($R^{2a}$)—, —S—, —S(O)—, —$S(O)_2$—, —C(O)—, —N($R^{2a}$)C(O)—, —C(O)N$R^{2a}$—, —N($R^{2a}$)$CO_2$—, —$S(O)_2$N$R^{2a}$—, —N($R^{2a}$)$S(O)_2$—, —OC(O)N($R^{2a}$)—, —N($R^{2a}$)C(O)N$R^{2a}$—, —N($R^{2a}$)$S(O)_2$N($R^{2a}$)—, or —OC(O)—.

$R^{2a}$ is hydrogen or an optionally substituted $C_{1-4}$ aliphatic, and $R^9$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is selected from:

xxiii

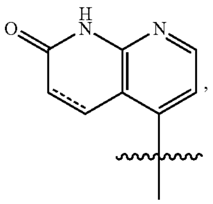

-continued xxiv

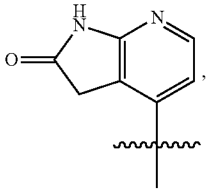

, xxv

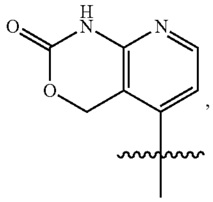

, xxvi

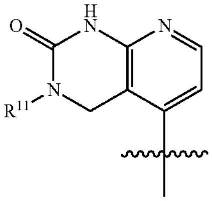

xxvii

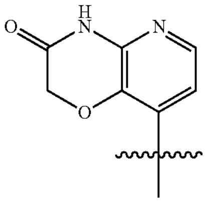

xxviii

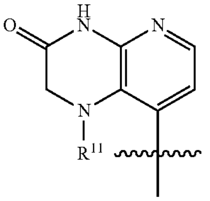

xxix

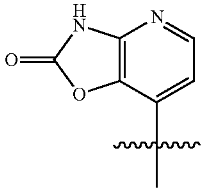

or xxx

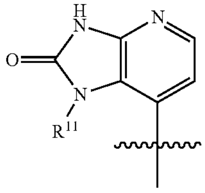

wherein each HY group is optionally additionally substituted with one or more occurrences of $R^{10}$.

The invention also provides [55], compounds of [54], wherein HY is selected from:

xxiii

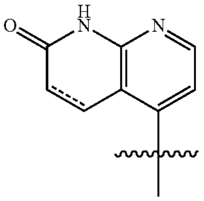

or xxix

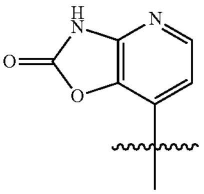

wherein each HY group is optionally additionally substituted with one or more occurrences of $R^{10}$.

The invention also provides [56], compounds of [54], wherein $R^1$ is CY, and CY is

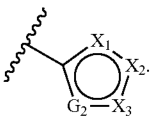

The invention also provides [57], compounds of [54], wherein $R^1$ is —$CON(R^4)_2$, —$NHCOR^4$, —$NHSO_2R^4$, —$NHCON(R^4)_2$, —$NHCOOR^4$, —$NHSO_2N(R^4)_2$, or —$NHSO_2OR^4$.

The invention also provides [58], compounds of [54], [55], [56], or [57], wherein $G_1$ is $CR^3$.

The invention also provides [59], compounds of [54], [55], [56], or [57], wherein $G_1$ is N.

The invention also provides [60], compounds of [54], [55], [56], or [57], wherein $R^2$ is a 3-10-membered cycloaliphatic, 4-10-membered heterocyclyl having 1-5 heteroatoms independently selected from nitrogen, oxygen, or sulfur 6-10-membered aryl, or 5-10-membered heteroaryl having 1-5 heteroatoms independently selected from nitrogen, oxygen, or sulfur, optionally substituted with 1-4 independent occurrences of $R^{12}$, wherein $R^{12}$ is —$R^{12a}$, -$T_2$-$R^{12d}$, or —$V_2$-$T_2$-$R^{12d}$, and:

each occurrence of $R^{9a}$ is independently halogen, —CN, —$NO_2$, —$R^{12c}$, —$N(R^{12b})_2$, —$OR^{12b}$, —$SR^{12c}$, —$S(O)_2R^{12c}$, —$C(O)R^{12b}$, —$C(O)OR^{12b}$, —$C(O)N(R^{12b})_2$, —$S(O)_2N(R^{12})_2$, —$OC(O)N(R^{12b})_2$, —$N(R^{12e})C(O)R^{12b}$, —$N(R^{12e})SO_2R^{12c}$, —$N(R^{12e})C(O)OR^{12b}$, —$N(R^{12e})C(O)N(R^{12b})_2$, or —$N(R^{12e})SO_2N(R^{12b})_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N$R^{12e}$C(O)N($R^{12e}$)—, —N($R^{12e}$)SO$_2$N($R^{12e}$)—, —OC(O)—, or —C(O)N($R^{12e}$)—O—; and $T_2$ is an optionally substituted $C_1$-$C_6$ alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)SO$_2$—, —N($R^{13}$)C(O)O—, —N$R^{13}$C(O)N($R^{13}$)—, —N($R^{13}$)S(O)$_2$N($R^{13}$)—, —OC(O)—, or —C(O)N($R^{13}$)—O— or wherein $T_3$ or a portion thereof optionally forms part of an optionally substituted 3-7 membered cycloaliphatic or heterocyclyl ring, wherein $R^{13}$ is hydrogen or an optionally substituted $C_{1-4}$aliphatic group.

The invention also provides [61], compounds of [54], [55], [56], or [57], wherein $R^2$ is an optionally substituted 6-10-membered aryl or 5-10-membered heteroaryl having 1-5 heteroatoms independently selected from nitrogen, oxygen, or sulfur.

The invention also provides [62], compounds of [54] wherein: $R^2$ is a phenyl group substituted with 1-3 independent occurrences of halogen, $C_{1-3}$ alkyl, CN, $C_{1-3}$haloalkyl, —O$C_{1-3}$ alkyl, —O$C_{1-3}$haloalkyl, —NHC(O)$C_{1-3}$ alkyl, —NHC(O)NH$C_{1-3}$ alkyl, NHS(O)$_2C_{1-3}$ alkyl, or —C(O)H.

The invention also provides [63], compounds of [62], wherein $R^2$ is halogen.

The invention also provides [64], compounds of [54] wherein when $R^1$ is CY, $X_1$ is N, $G_2$ is $NR^{4'}$, and $X_2$ and $X_3$ are $CR^7$.

The invention also provides [65], compounds of [54], wherein when $R^1$ is CY, $X_1$ and $X_2$ are N, $G_2$ is $NR^4$ and $X_3$ is $CR^7$.

The invention also provides [66], compounds of [65], wherein $R^7$ is H or $NH_2$.

The invention also provides [67] a composition comprising compounds [1], [2], [29], [31], [37], [41], [43], or [52], and a pharmaceutically acceptable carrier.

The invention also provides [68] a method of treating a proliferative disorder in a patient comprising administering to said patient a therapeutically effective amount of compounds [1], [2], [29], [31], [37], [41], [43], or [52].

The invention also provides [69] the method of claim [68], wherein the proliferative disorder is breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

The invention also provides [70] a method of treating an inflammatory or cardiovascular disorder in a patient comprising administering to said patient a therapeutically effective amount of compounds [1], [2], [29], [31], [37], [41], [43], or [52].

The invention also provides [71], wherein the inflammatory or cardiovascular disorder is selected from allergies/anaphylaxis, acute and chronic inflammation, rheumatoid arthritis; autoimmunity disorders, thrombosis, hypertension, cardiac hypertrophy, and heart failure.

The invention also provides [72], a method for inhibiting PI3K or mTor activity in a patient comprising administering a composition comprising an amount of compounds [1], [2], [29], [31], [37], [41], [43], or [52], effective to inhibit PI3K or mTor activity in the patient.

2. Detailed Description of Compounds of the Invention:

Compounds of this invention include those described generally for formula I-A and I-B above, and are further illustrated by the classes, subclasses, and species disclosed herein. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound. As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-10, 3-8, 3-7, or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$aromatic hydrocarbon moiety comprising one to three aromatic rings. Preferably, the aryl group is a $C_{6-10}$aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-4}$alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5-10, more preferably 5, 6, 9, or 10 ring atoms; having 6, 10, or 14 $\pi$ electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a 3- to 10-, preferably 3- to 7-, 4- to 7-, or 4- to 10-membered heterocycle such as a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $NR^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring, moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., $—(CH_2)_n—$, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, $—NO_2$, —CN, $—R^+$, $—C(R^+)═C(R^+)_2$, $—C≡C—R^+$, $—OR^+$, $—SR^o$, $—S(O)R^o$, $—SO_2R^o$, $—SO_3R^+$, $—SO_2N(R^+)_2$, $—N(R^+)_2$, $—NR^+C(O)R^+$, $—NR^+C(S)R^+$, $—NR^+C(O)N(R^+)_2$, $—NR^+C(S)N(R^+)_2$, $—N(R^+)C(═NR^+)—N(R^+)_2$, $—N(R^+)C(═NR^+)—R^o$, $—NR^+CO_2R^+$, $—NR^+SO_2R^o$, $—NR^+SO_2N(R^+)_2$, $—O—C(O)R^+$, $—O—CO_2R^+$, $—OC(O)N(R^+)_2$, $—C(O)R^+$, $—C(S)R^o$, $—CO_2R^+$, $—C(O)—C(O)R^+$, $—C(O)N(R^+)_2$, $—C(S)N(R^+)_2$, $—C(O)N(R^+)—OR^+$, $—C(O)N(R^+)C(═NR^+)—N(R^+)_2$, $—N(R^+)C(═NR^+)—N(R^+)—C(O)R^+$, $—C(═NR)—N(R^+)_2$, $—C(═NR^+)—OR^+$, $—N(R^+)—N(R^+)_2$, $—C(═NR^+)—N(R^+)—OR^+$, $—C(R^o)═N—OR^+$, $—P(O)(R^+)_2$, $—P(O)(OR^+)_2$, $—O—P(O)—OR^+$, and $—P(O)(NR^+)—N(R^+)_2$, wherein $R^+$, independently, is hydrogen or an optionally substituted aliphatic, aryl, heteroaryl, cycloaliphatic, or heterocyclyl group, or two independent occurrences of $R^+$ are taken together with their intervening atom(s) to form an optionally substituted 5-7-membered aryl, heteroaryl, cycloaliphatic, or heterocyclyl ring. Each $R^o$ is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: ═O, ═S, $═C(R^*)_2$, $═N—N(R^*)_2$, $═N—OR^*$, $═N—NHC(O)R^*$, $═N—NHCO_2R^o═N—NHSO_2R^o$ or $═N—R^*$ where $R^o$ is defined above, and each $R^*$ is independently selected from hydrogen or an optionally substituted $C_{1-6}$ aliphatic group.

In addition to the substituents defined above and herein, optional substituents on the nitrogen of a non-aromatic heterocyclic ring also include and are generally selected from $—R^+$, $—N(R^+)_2$, $—C(O)R^+$, $—C(O)OR^+$, $—C(O)C(O)R^+$, $—C(O)CH_2C(O)R^+$, $—S(O)_2R^+$, $—S(O)_2N(R^+)_2$, $—C(S)N(R^+)_2$, $—C(═NH)—N(R^+)_2$, or $—N(R^+)S(O)_2R^+$; wherein each $R^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of $R^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of $R^+$ (or any other variable similarly defined in the specification and claims herein), are taken together with their intervening atom(s) include, but are not limited to the following: a) two independent occurrences of $R^+$ (or any other variable similarly defined in the specification or claims herein) that are bound to the same atom and are taken together with that atom to form a ring, for example, $N(R^+)_2$, where both occurrences of $R^+$ are taken together with the nitrogen atom to form a piperidin-1-yl, piperazin-1-yl, or morpholin-4-yl group; and b) two independent occurrences of $R^+$ (or any other variable similarly defined in the specification or claims herein) that are bound to different atoms and are taken together with both of those atoms to form a ring, for example where a phenyl group is substituted with two occurrences of

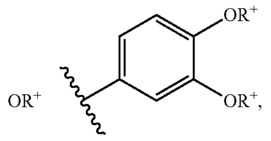

these two occurrences of $R^+$ are taken together with the oxygen atoms to which they are bound to form a fused 6-membered oxygen containing ring:

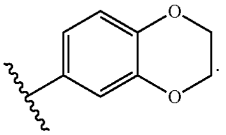 [SMILES: *c1ccc2c(c1)OCCO2]

It will be appreciated that a variety of other rings (e.g., spiro and bridged rings) can be formed when two independent occurrences of $R^+$ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diasteromeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

In general, compounds of the invention are represented by formula (I-A) or (I-B):

IA

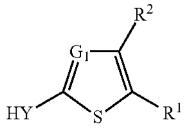

IB

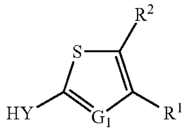

or a pharmaceutically acceptable salt thereof, wherein:

- $G_1$ is N or $CR^3$, wherein $R^3$ is H, —CN, halogen, $C_{1-6}$ aliphatic, or 3-10-membered cycloaliphatic, wherein:
  - Z is selected from an optionally substituted $C_{1-3}$ alkylene chain, —O—, —$N(R^{3a})$—, —S—, —S(O)—, —$S(O)_2$—, —C(O)—, —$CO_2$—, —$C(O)NR^{3a}$—, —$N(R^{3a})C(O)$—, —$N(R^{3a})CO_2$—, —$S(O)_2NR^{3a}$—, —$N(R^{3a})S(O)_2$—, —$OC(O)N(R^{3a})$—, —$N(R^{3a})C(O)NR^{3a}$—, —$N(R^{3a})S(O)_2N(R^{3a})$—, or —OC(O)—;
  - $R^{3a}$ is hydrogen or an optionally substituted $C_{1-4}$ aliphatic, and
  - $R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
- $R^1$ is CY, —$CON(R^4)_2$, —$NHCOR^4$, —$NHSO_2R^4$, —$NHCON(R^4)_2$, —$NHCOOR^4$, —$NHSO_2N(R^4)_2$, or —$NHSO_2OR^4$, wherein:

CY is

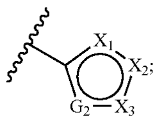

wherein:

$X_1$, $X_2$, and $X_3$, are each independently N, O, S, or $CR^7$, provided that only one of $X_1$, $X_2$, or $X_3$ may be O or S, $G_2$ is —N= or —$NR^{4'}$—, wherein:

each occurrence of $R^4$ or $R^{4'}$ is independently H, —$Z_2$—$R^6$, optionally substituted $C_{1-6}$ aliphatic, or optionally substituted 3-10-membered cycloaliphatic, wherein:

$Z_2$ is selected from an optionally substituted $C_{1-3}$ alkylene chain, —S(O)—, —$S(O)_2$—, —C(O)—, —$CO_2$—, —$C(O)NR^{4a}$—, or —$S(O)_2NR^{4a}$—.

$R^{4a}$ is hydrogen or an optionally substituted $C_{1-4}$ aliphatic, and $R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^7$ is independently hydrogen, —CN, halogen, —$Z_3$—$R^8$, $C_{1-6}$ aliphatic, or 3-10-membered cycloaliphatic, wherein:

$Z_3$ is selected from an optionally substituted $C_{1-3}$ alkylene chain, —O—, —$N(R^{7a})$—, —S—, —S(O)—, —$S(O)_2$—, —C(O)—, —$CO_2$—, —$C(O)NR^{2a}$—, —$N(R^{2a})C(O)$—, —$N(R^{7a})CO_2$—, —$S(O)_2NR^{7a}$—, —$N(R^{7a})S(O)_2$—, —$OC(O)N(R^{7a})$—, —$N(R^{2a})C(O)NR^{7a}$—, —$N(R^{7a})S(O)_2N(R^{7a})$—, or —OC(O)—.

$R^{7a}$ is hydrogen or an optionally substituted $C_{1-4}$ aliphatic, and $R^8$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, $R^2$ is halogen, —W—$R^9$, or —$R^9$, wherein:

W is selected from an optionally substituted $C_{1-3}$ alkylene chain, —O—, —$N(R^{2a})$—, —S—, —S(O)—, —$S(O)_2$—, —C(O)—, —$CO_2$—, —$C(O)NR^{2a}$—, —$N(R^{2a})C(O)$—, —$N(R^{2a})CO_2$—, —$S(O)_2NR^{2a}$—, —$N(R^{2a})S(O)_2$—, —$OC(O)N(R^{2a})$—, —$N(R^{2a})C(O)NR^{2a}$—, —$N(R^{2a})S(O)_2N(R^{2a})$—, or —OC(O)—.

$R^{2a}$ is hydrogen or an optionally substituted $C_{1-4}$ aliphatic, and $R^9$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is an optionally substituted nitrogen-containing heteroaryl group, provided that the optionally substituted nitrogen-containing heteroaryl group is a group other than a 3-isoxazolyl, a 2-pyridyl, a 3-pyridyl, a 5-pyrimidinyl, a 2-pyrimidinyl, a 5,6-dimethoxy-1H-benzimidazole group, or a pyrazinyl group, provided that:

i) when $R^1$ is an optionally substituted thiazolyl group and HY is an optionally substituted thiazolyl group, then the optionally substituted thiazolyl group for HY is a group represented by

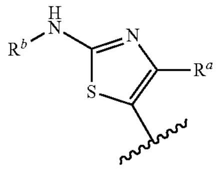

wherein $R^a$ is a hydrogen atom, an alkyl group or a halogen atom, $R^b$ is (i) a hydrogen atom, (ii) an optionally substituted hydrocarbon-carbonyl group, (iii) an optionally substituted heterocyclyl-carbonyl group, (iv) an optionally substituted carbamoyl group, (v) an optionally substituted alkoxycarbonyl group, (vi) an optionally substituted hydrocarbon-sulfonyl group, (vii) an optionally substituted heterocyclyl-sulfonyl group, (viii) an optionally substituted sulfamoyl group, (ix) an optionally substituted hydrocarbon group or (x) an optionally substituted heterocyclic group, or a salt thereof (excluding

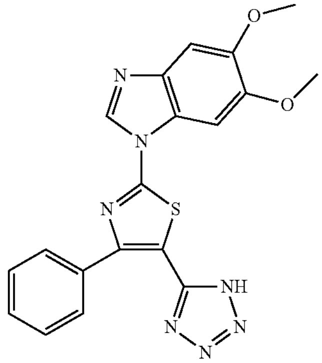

,

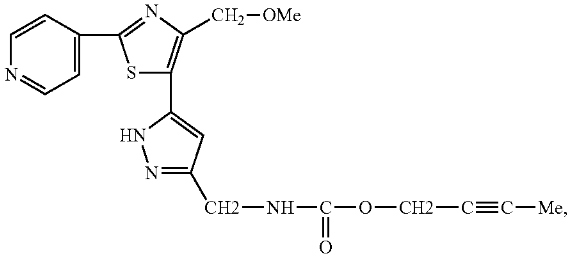

-continued

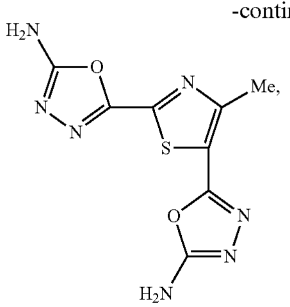

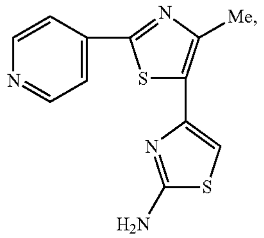

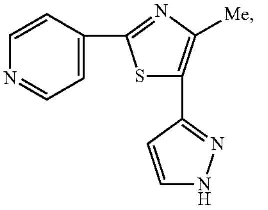

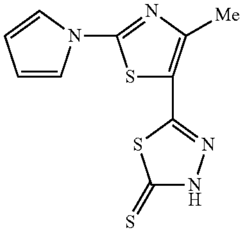

and

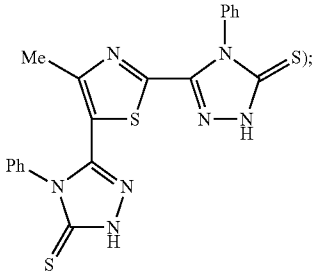

);

ii) for compounds of formula I-B the compound is other than: 4-Thiazolecarboxamide, 2-(4-acetyl-5-methyl-1H-1,2,3-triazol-1-yl)-N,N-diethyl-5-phenyl-; 1H-1,2,3-Triazole-4-acetic acid, 1-[4-[(diethylamino)carbonyl]-5-phenyl-2-thiazolyl]-5-methyl-a-oxo-, ethyl ester; 4-Thiazolecarboxamide, 2-[4-(1,2-dioxopropyl)-5-methyl-1H-1,2,3-triazol-1-yl]-N,N-diethyl-5-phenyl-; and provided that for compounds of formula I-B, when $G_1$ is N, $R^1$ is optionally substituted 1H-indazol-3-yl and $R^3$ is $CON(R^4)_2$, then $R^2$ is a group other than unsubstituted phenyl or 3-pyridyl;

iii) for compounds of formula I-A, where $G_1$ is $CR^4$, a) when $R^1$ is $—CON(R^4)_2$, then $R^2$ is an optionally substituted group selected from 6-10-membered aryl, or 5-10-membered heteroaryl having 1-5 heteroatoms independently selected from nitrogen, oxygen, or sulfur; and b) the compound is other than 4-[5-[3-(2-chloro-6-fluorophenyl)-1-methyl-1H-1,2,4-triazol-5-yl]-4-methyl-2-thienyl]-pyridine; or 4-[5-(2H-tetrazol-5-yl)-2-thienyl]-pyridine;

i. for compounds of formula I-A when $R^1$ is $—CON(R^4)_2$, then $R^2$ is an optionally substituted group selected from 6-10-membered aryl, or 5-10-membered heteroaryl having 1-5 heteroatoms independently selected from nitrogen, oxygen, or sulfur, provided that compounds are other than: 2-thiophenecarboxamide, 5-dibenz[b,f][1,4]oxazepin-11-yl-N-hydroxy-3-phenyl-; 5-Thiazolecarboxamide, 2-(3,4-dihydro-1(2H)-quinolinyl)-N-hydroxy-4-phenyl-; 5-Thiazolecarboxamide, N-hydroxy-4-phenyl-2-(4-pyridinyl)-; 5-Thiazolecarboxamide, N-[2'-(aminosulfonyl)[1,1'-biphenyl]-2-yl]-4-(4-methoxyphenyl)-2-(1H-pyrrol-1-yl)-; 5-Thiazolecarboxamide, 4-(4-nitrophenyl)-2-(4-pyridinyl)-N-(3-trifluoromethyl)phenyl]-; 5-Thiazolecarboxamide, 4-(4-bromophenyl)-N-(1-methylethyl)-2-(2-propyl-4-pyridinyl)-; 5-Thiazolecarboxamide, 2-(2,3-dihydro-1H-indol-1-yl)-4-phenyl-N-(phenylmethyl)-; 5-Thiazolecarboxamide, 2-(2,3-dihydro-4H-1,4-benzoxazin-4-yl)-4-phenyl-N-(phenylmethyl)-; 5-Thiazolecarboxamide, 4-phenyl-N-[(1S,2S)-2-(phenylmethoxy)cyclopentyl]-2-(1H-pyrazol-1-yl)-; 5-Thiazolecarboxamide, 4-phenyl-N-(phenylmethyl)-2-(1H-pyrazol-1-yl)-; 5-Thiazolecarboxamide, N-[(4-chlorophenyl)methyl]-2-(3-methoxy-1H-pyrazol-1-yl)-4-phenyl-; 5-Thiazolecarboxamide, 4-phenyl-N-[1-(phenylmethyl)-3-pyrrolidinyl]-2-(1H-pyrazol-1-yl)-; 5-Thiazolecarboxamide, 2-(1H-benzimidazol-1-yl)-4-phenyl-; 5-Thiazolecarboxamide, N-[(1S,2R)-1-[(3,5-difluorophenyl)methyl]-3-[1-(3-ethynylphenyl)cyclopropyl]amino]-2-hydroxypropyl]-4-phenyl-2-(1H-pyrrol-1-yl)-; 4-Thiazolecarboxamide, 2-(4-acetyl)-5-methyl-1H-1,2,3-triazol-1-yl)-N,N-diethyl-5-phenyl-; 3-Thiophenecarboxamide, N-[1-(aminoethyl)-2-phenylethyl]-2-(3-furanyl)-5-(1-methyl-1H-pyrazol-5-yl)-, hydrochloride; 3-Thiophenecarboxamide, N-[1-(aminoethyl)-2-phenylethyl]-2-(3-furanyl)-5-(1-methyl-1H-pyrazol-5-yl)-; Carbamic acid, N-[2-[[[2-(3-furanyl)-5-(1-methyl-1H-pyrazol-5-yl)-3-thienyl]carbonyl]amino-3-phenylpropyl]-, 1,1-dimethylethylester; 3-Thiophenecarboxamide, N-methyl,2,5-di-4-pyridinyl-; 3-Thiophenecarboxamide, 2,5-di-4-pyridinyl-; 1H-1,2,3-triazole-4-acetic acid, 1-[4-[(diethylamino)carbonyl]-5-phenyl-2-thiazolyl]-5-methyl-a-oxo-, ethyl ester; 4-Thiazolecarboxamide, 2-[4-(1,2-dioxopropyl)-5-methyl-1H-1,2,3-triazol-1-yl]-N,N-diethyl-5-phenyl-; and for compounds of formula I-B, when $G_1$ is N, $R^2$ is substituted or unsubstituted phenyl or pyridyl, and HY is substituted or unsubstituted 1H-indazol-3-yl, then $R^1$ is other than $CON(R^4)_2$;

for compounds of formula I-A or I-B compounds are other than: 3-thiophenecarboxylic acid-2-(acetylamino)-5-[7-(4-chlorophenyl)-1,7-dihydro-2-(trifluoromethyl)[1,2,4]triazolo[1,5-a]pyrimidin-5-yl]-4-methyl-ethyl ester; 3-thiophenecarboxylic acid-2-(acetylamino)-5-[7-(4-chlorophenyl)-1,7-dihydro-2-(trifluoromethyl)[1,2,4]triazolo[1,5-a]pyrimidin-5-yl]-4-methyl-, ethyl ester; 5-Thiazoleacetamide, N-[[(2S)-4-[(3,4-difluorophenyl)methyl]-2-morpholinyl]methyl]-4-methyl-2-(5-methyl-3-isoxazolyl)-; 5-Thiazoleacetamide, N-[[(2S)-4-[(3,4-dichlorophenyl)methyl]-2-morpholinyl]methyl]-4-methyl-2-(5-methyl-3-isoxazolyl)-; Benzenecarboximidamide, 4-chloro-N-[[[[4-methyl-2-(2-thienyl)-5-thiazolyl]amino]carbonyl]oxy]-; Benzenecarboximidamide, N-[[[[4-methyl-2-(2-thienyl)-5-thiazolyl]amino]carbonyl]oxy]-4-(trifluoromethyl)-; Benzenecarboximidamide, dimethylethyl)-N-[[[[4-methyl-2-(2-thienyl)-5-thiazolyl]amino]carbonyl]oxy]-; Urea, N-(4-chlorophenyl)-N'-[4-methyl-2-(2-thienyl)-5-thiazolyl]-; or Urea, N-[4-(1-methylethyl)phenyl]-N'-[4-methyl-2-(2-thienyl)-5-thiazolyl]-;

v) for compounds of formula I-A or I-B:

a) when $R^1$ is $NHCOR^4$, $G_1$ is $CR^3$, and $R^2$ or $R^3$ is Br, then HY is other than an optionally substituted 1H-pyrrolo[2,3-b]pyridin-4-yl group; when $G_1$ is $CR^3$, $R^1$ is $—NHCOR^4$, and $R^2$ or $R^3$ is $CONH_2$, then HY is other than an optionally substituted 4,5,6,7-tetrahydro-1H-indol-1-yl or 4,5,6,7-tetrahydro-1H-indazol-1-yl group when $R^1$ is $NHCOR^4$, $G_1$ is $CR^3$, and $R^2$ or $R^3$ is Me, then HY is other than an optionally substituted group selected from:

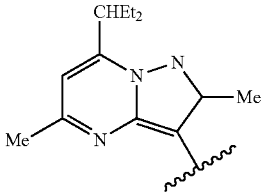
or
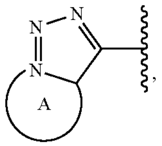
, wherein ring A is an optionally substituted fused thiadiazin-3-yl, thiadiazol-3-yl, or benzo group;

b) compounds are other than those compounds where $R^1$ or $R^2$ is Br, $R^1$ is —$NHCOR^4$, and HY is optionally substituted 1H-pyrrolo[2,3-b]pyridine-4-yl;

c) compounds are other than 1H-Benzimidazole, 2,2'-[benzo[1,2-b:5,4-b]dithiophene-2,6-diylbis(4-hexyl-5,2-thiophenediyl)]bis-; Imidazo[1,2-b]pyridazine, 8-(1-ethylpropyl)-2,6-dimethyl-3-[3-methyl-5-(2H-tetrazol-5-yl)-2-thienyl;

d) compounds are other than those compounds where $R^1$ is —$NHCON(R^4)_2$, —$NHCOR^4$, or $NHCOOR^4$, and $R^2$ is —CN, —$COOR^9$, $OR^9$, or —$CONR^{2a}R^9$;

e) compounds are other than: Acetamide, N-[5-(1H-benzotriazol-1-yl)-3-cyano-4-methyl-2-thienyl]-;

f) compounds are other than: 2-Butenoic acid, 4-[[4-amino-5-(2-benzothiazolyl)-3-cyano-2-thienyl] amino]-4-oxo-; or 3-Thiophenecarboxylic acid, 4-amino-5-(2-benzothiazolyl)-2-[(3-carboxy-1-oxo-2-propen-1-yl)amino]-, 3-ethyl ester; 2-Butenoic acid, 4-[[4-amino-5-(2-benzothiazolyl)-3-cyano-2-thienyl]amino]-4-oxo-; 3-Thiophenecarboxylic acid, 4-amino-5-(2-benzothiazolyl)-2-[(3-carboxy-1-oxo-2-propen-1-yl)amino]-, 3-ethyl ester;

g) compounds are other than: -Benzimidazole, 2,2'-(3,4-dimethyl-2,5-thiophenediyl)bis[5-butoxy-4,6-dichloro-; 1H-Benzimidazole-6-carbonitrile, 2-[5-(6-dodecyl-1H-benzimidazol-2-yl)-3,4-diethoxy-2-thienyl]-; or 1H-Benzimidazole, 2,2'-[3,4-bis(phenylmethyl)-2,5-thiophenediyl]bis[5-(phenylmethyl)-;

h) compounds are other than 7H-Pyrrolo[2,3-d]pyrimidin-2-amine, 4-[4-methyl-5-(2H-tetrazol-5-yl)-2-thienyl]-N-[4-[2-(1-pyrrolidinyl)ethoxy]phenyl]-;

i) compounds are other than: Thiophene, 2,5-bis(2-benzimidazolyl)-3,4-dibromo-;

j) compounds are other than: Tricyclo[3.3.1.13,7]decane-1-carboxamide, N-[3-[2-(dimethylamino)-1-hydroxyethyl]-5-(8-quinolinyl)-2-thienyl]-; or Tricyclo[3.3.1.13,7]decane-1-carboxamide, N-[3-[2-(dimethylamino)acetyl]-5-(8-quinolinyl)-2-thienyl]-;

k) Thiophene, 2,5-bis(2-benzimidazolyl)-3,4-dibromo-; and l) compounds are other than: Acetemide, N-[5-(4-acetyl-5-[4-[(2,4-dichlorophenyl)methoxy]-3-methoxyphenyl]-4,5-dihydro-1,3,4-oxadiazol-2-yl]-3-cyano-4-methyl-2-thienyl]-; Butanamide, N-[3-cyano-5-[3-[(2,4-dichlorophenyl)methyl]-1,2,4-oxadiazol-5-yl]-4-methyl-2-thienyl]-2-ethyl-; Acetamide, 2-bromo-N-[3-(2-chlorobenzoyl)-5-(4,5-dihydro-4,4-dimethyl-2-oxazolyl)-2-thienyl; and Acetamide, 2-amino-N-[3-(2-chlorobenzoyl)-5-(4,5-dihydro-4,4-dimethyl-2-oxazolyl)-2-thienyl]-.

In some embodiments of the invention, for compounds (I-A) or (I-B) or subsets thereof, $R^1$ is CY, and CY is

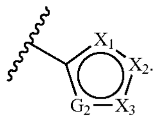

In other embodiments, $R^1$ is —$CON(R^4)_2$, —$NHCOR^4$, —$NHSO_2R^4$, —$NHCON(R^4)_2$, —$NHCOOR^4$, —$NHSO_2N(R^4)_2$, or —$NHSO_2OR^4$.

In some embodiments, for compounds (I-A) or (I-B), or subsets thereof, HY is selected from:

A

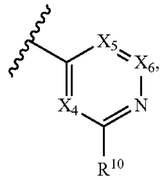

B

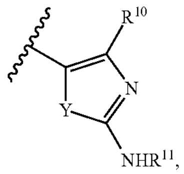

C

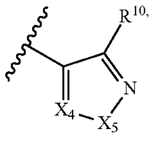
or

D

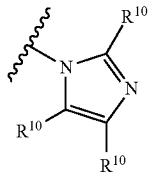

wherein $R^{10}$ is $R^{10b}$, —$V_1$—$R^{10c}$, -$T_1$-$R^{10b}$, or —$V_1$-$T_1$-$R^{10b}$ wherein:

$V_1$ is —$NR^{10a}$—, —$NR^{10a}$—C(O)—, —$NR^{10a}$—C(S)—, —$NR^{10a}$—$C(NR^{10a})$—, $NR^{10a}C(O)OR^{10a}$—, $NR^{10a}C(O)NR^{10a}$—, $NR^{1a}C(O)R^{10a}$—, $NR^{1a}C(S)OR^{10a}$—, $NR^{10a}C(S)NR^{10a}$—, $NR^{10a}C(S)R^{10a}$—, —$NR^{10a}C(NR^{10a})OR^{10a}$—, —$NR^{10a}C(NR^{10a})NR^{10a}$—, —$NR^{10a}S(O)_2$, —$NR^{10a}S(O)_2NR^{10a}$—, —C(O)—, —$CO_2$—, —$C(O)NR^{10a}$—, $C(O)NR^{10a}O$—, —$SO_2$—, or —$SO_2N^{10a}$—;

each occurrence of $R^{10a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$ alkylene chain wherein the alkylene chain optionally is interrupted by —N($R^{10a}$)—, —O—, —S—, —S(O)—, —$S(O)_2$—, —C(O)—, —C(O)O—, —C(O)N($R^{10a}$)—, —$S(O)_2N$($R^{10a}$)—, —OC(O)N($R^{10a}$)—, —N($R^{10a}$)C(O)—, —N($R^{10a}$)$SO_2$—, —N($R^{10a}$)C(O)—, —$NR^{10a}$C(O)N($R^{10a}$)—, —N($R^{10a}$)$S(O)_2N$($R^{10a}$)—, —OC(O)—, or —C(O)N($R^{10a}$)—O— or wherein $T_1$ forms part of an optionally substituted 3-7 membered cycloaliphatic or heterocyclyl ring;

each occurrence of $R^{10b}$ is independently hydrogen, halogen, —CN, —$NO_2$, —N($R^{10a}$)$_2$, —$OR^{10a}$, —$SR^{10a}$, —$S(O)_2R^{10a}$, —C(O)$OR^{10a}$, —C(O)N($R^{10a}$)$_2$, —$S(O)_2N$($R^{10a}$)$_2$, —OC(O)N($R^{10a}$)$_2$, —N($R^{10a}$)C(O)$R^{10a}$, —N($R^{10a}$)$SO_2R^{10a}$, —N($R^{10a}$)C(O)$OR^{10a}$, —N($R^{10a}$)C(O)N($R^{10a}$)$_2$, or —N($R^{10a}$)$SO_2N$($R^{10a}$)$_2$, or an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^{10a}$ and $R^{10c}$ taken together with a nitrogen atom to which they are bound form an optionally substituted 4-7-membered heterocyclyl ring having 0-1 additional heteroatoms independently selected from nitrogen, oxygen, or sulfur, wherein each occurrence of $X_4$, $X_5$, and $X_6$ is independently N or $CR^{10}$, or two adjacent groups selected from Y, $R^{11}$, $R^{10}$, $X_4$, $X_5$, and $X_6$, taken together, form an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, and each occurrence of $R^{11}$ is independently hydrogen, —C(O)$R^{11a}$—, —$CO_2R^{11a}$—, —C(O)$NR^{11a}$—, C(O)$NR^{11a}$O—, —$SO_2R^{11a}$—, —$SO_2NR^{11a}$—, or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{11a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and Y is N or $CR^{10}$.

In other embodiments, for compounds (I-A) or (I-B), or subsets thereof, HY is selected from:

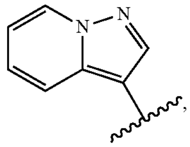

i

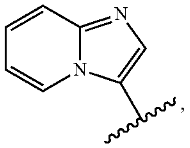

ii

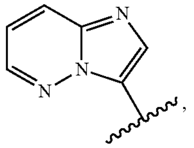

iii

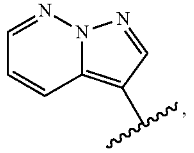

iv

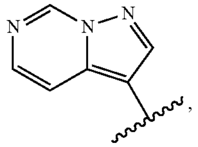

v

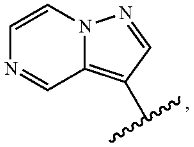

vi

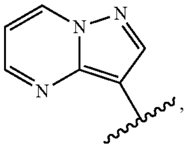

vii

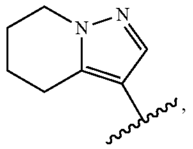

viii

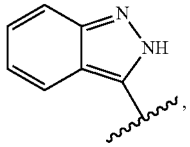

ix

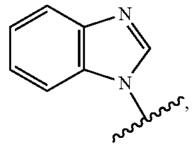

x

-continued
xi
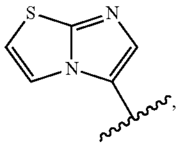,
xii
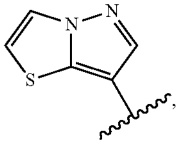,
xiii
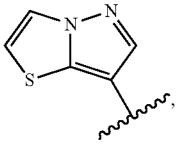,
xiv
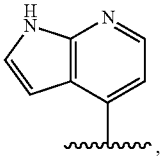,
xv
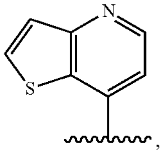,
xvi
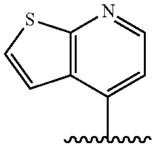,
xvii
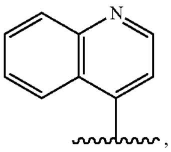,
xviii
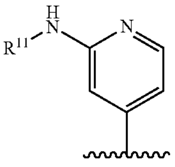,
xix
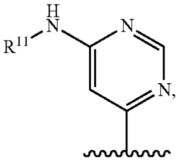
-continued
xx
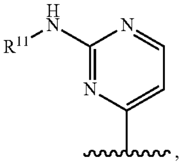,
xxi
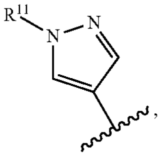,
xxii
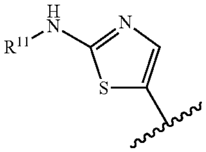,
xxiii
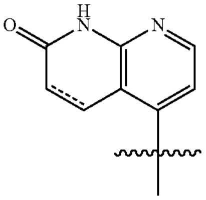,
xxiv
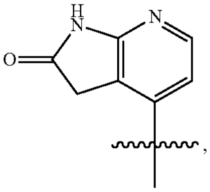,
xxv
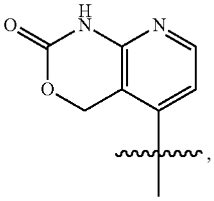,
xxvi
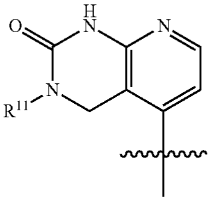
xxvii
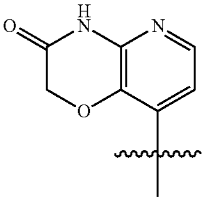

-continued
xxviii
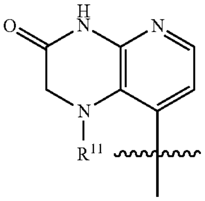
xxix
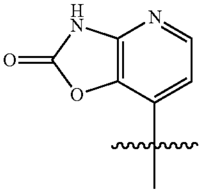
xxx
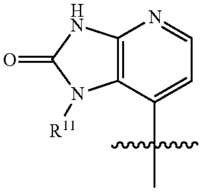
xxxi
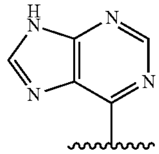
xxxii
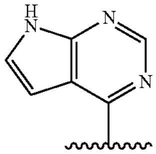
xxxiii
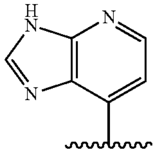
xxxiv
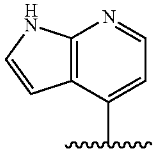
xxxv
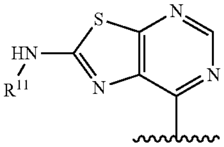
or
xxxvi
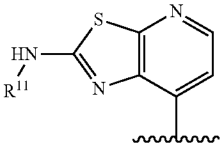
wherein each HY group is optionally additionally substituted with one or more occurrences of $R^{10}$.
In still other embodiments, for compounds (I-A) or (I-B), or subsets thereof, HY is selected from:
i
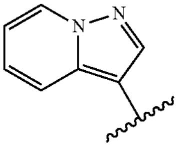
,
v
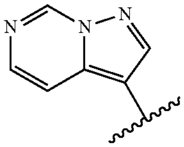
,
x
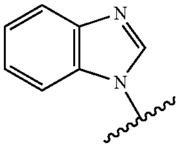
,
xiv
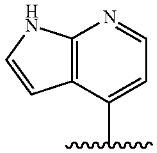
,
xvii
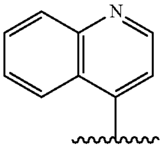
,
xviii
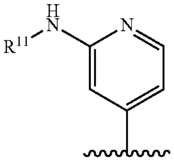
,
xxiii
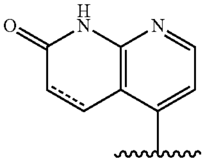
,
xxix
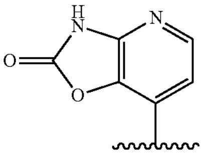
,
xxxi
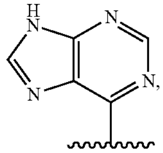

-continued
xxxii
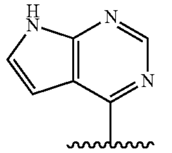
or
xxxv
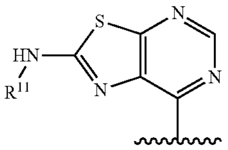
wherein each HY group is optionally additionally substituted with one or more occurrences of $R^{10}$
In still other embodiments, for compounds (I-A) or (I-B), or subsets thereof, HY is selected from:
i
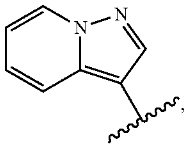
ii
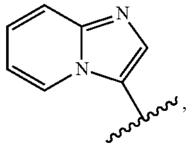
iii
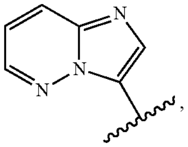
iv
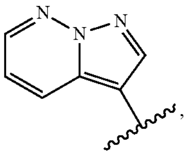
v
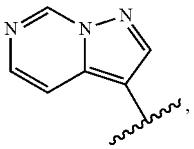
vi
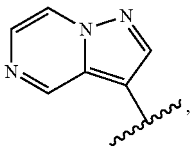
vii
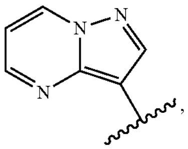
-continued
viii
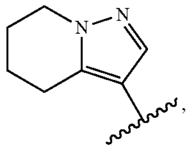
ix
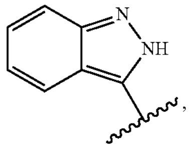
x
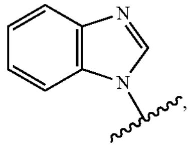
xi
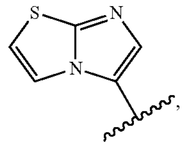
xii
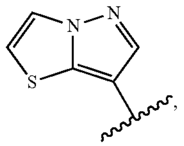
xiii
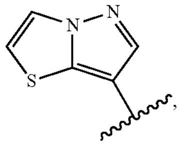
xiv
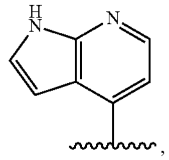
xv
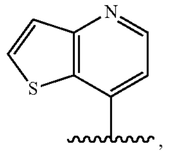
xvi
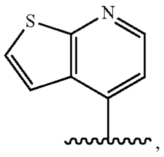
xvii
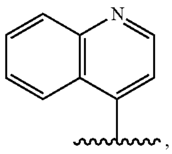

-continued
xxiii
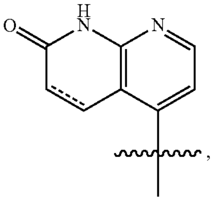
xxiv
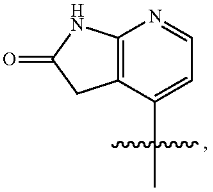
xxv
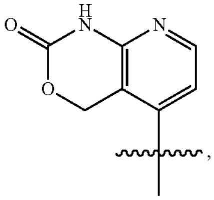
xxvi
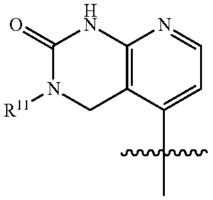
xxvii
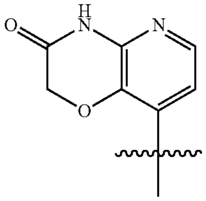
xxviii
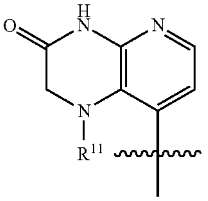
xxix
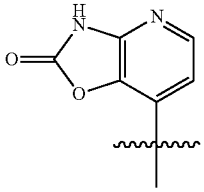
-continued
xxx
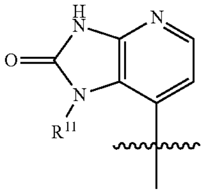
xxxi
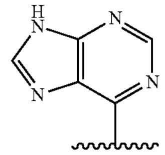
xxxii
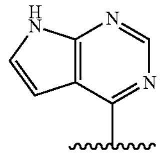
xxxiii
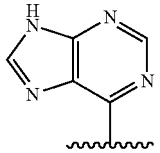
xxxiv
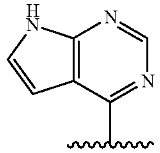
xxxv
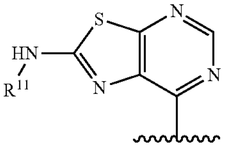
or
xxxvi
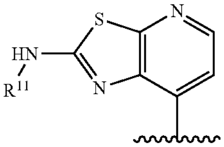
wherein each HY group is optionally additionally substituted with one or more occurrences of $R^{10}$.
In yet other embodiments, for compounds (I-A) or (I-B), or subsets thereof, HY is selected from:
i
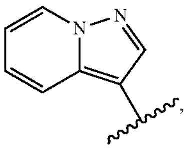

-continued
v
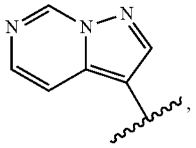
x
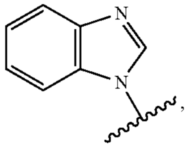
xiv
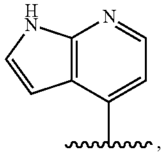
xvii
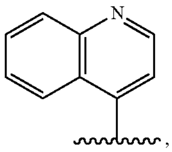
xxiii
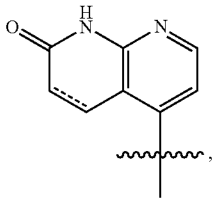
xxix
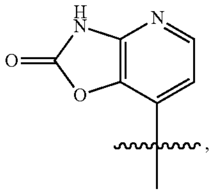
xxxi
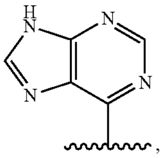
xxxii
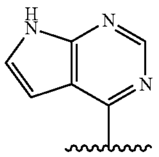
or
xxxv
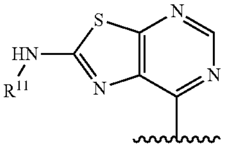
wherein each HY group is optionally additionally substituted with one or more occurrences of $R^{10}$.
In yet other embodiments, for compounds (I-A) or (I-B), or subsets thereof, HY is selected from:
xxiii
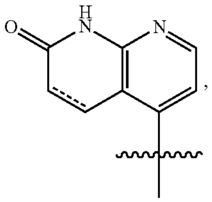
xxiv
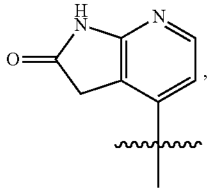
xxv
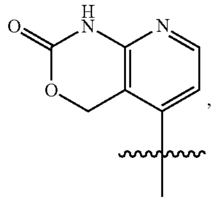
xxvi
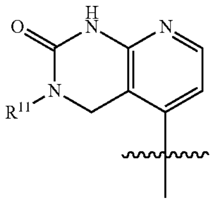
xxvii
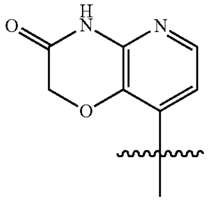
xxviii
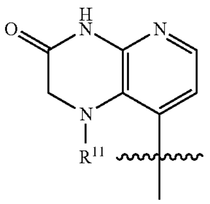
xxix
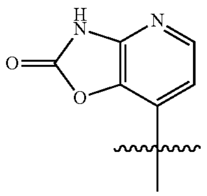
or -continued xxx

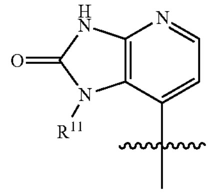

wherein each HY group is optionally additionally substituted with one or more occurrences of $R^{10}$.

In yet other embodiments, for compounds (I-A) or (I-B), or subsets thereof, HY is selected from:

xxiii

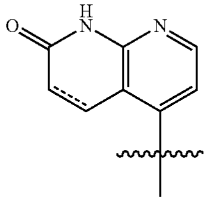

or xxix

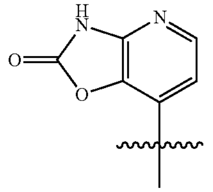

wherein each HY group is optionally additionally substituted with one or more occurrences of $R^{10}$.

In some embodiments, for compounds (I-A) or (I-B), or subsets thereof, $G_1$ is $CR^3$. In certain embodiments, $G^1$ is CH.

In other embodiments, for compounds (I-A) or (I-B), or subsets thereof, $G_1$ is N.

In still other embodiments, for compounds (I-A) or (I-B), or subsets thereof, $R^2$ is a 3-10-membered cycloaliphatic, 4-10-membered heterocyclyl having 1-5 heteroatoms independently selected from nitrogen, oxygen, or sulfur 6-10-membered aryl, or 5-10-membered heteroaryl having 1-5 heteroatoms independently selected from nitrogen, oxygen, or sulfur, optionally substituted with 1-4 independent occurrences of $R^{12}$, wherein $R^{12}$ is $—R^{12a}$, $-T_2-R^{12d}$, or $—V_2-T_2-R^{12d}$, and:

each occurrence of $R^{9a}$ is independently halogen, —CN, $—NO_2$, $—R^{12c}$, $—N(R^{12b})_2$, $—OR^{12b}$, $—SR^{12c}$, $—S(O)_2R^{12c}$, $—C(O)R^{12b}$, $—C(O)OR^{12b}$, $—C(O)N(R^{12b})_2$, $—S(O)_2N(R^{12b})_2$, $—OC(O)N(R^{12b})_2$, $—N(R^{12e})C(O)R^{12b}$, $—N(R^{12e})SO_2R^{12c}$, $—N(R^{12e})C(O)OR^{12b}$, $—N(R^{12e})C(O)N(R^{12})_2$, or $—N(R^{12e})SO_2N(R^{12b})_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$ aliphatic, 3-10-membered cycloaliphatic, 4-10-mem bered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently $—N(R^{12e})—$, —O—, —S—, —S(O)—, $—S(O)_2—$, —C(O)—, —C(O)O—, $—C(O)N(R^{12e})—$, $—S(O)_2N(R^{12e})—$, $—OC(O)N(R^{12e})—$, $—N(R^{12e})C(O)—$, $—N(R^{12e})SO_2—$, $—N(R^{12e})C(O)O—$, $—NR^{12e}C(O)N(R^{12e})—$, $—N(R^{12e})SO_2N(R^{12e})—$, —OC(O)—, or $—C(O)N(R^{12e})—O—$; and $T_2$ is an optionally substituted $C_1$-$C_6$ alkylene chain wherein the alkylene chain optionally is interrupted by $—N(R^{13})—$, —O—, —S—, —S(O)—, $—S(O)_2—$, —C(O)—, —C(O)O—, $—C(O)N(R^{13})—$, $—S(O)_2N(R^{13})—$, $—OC(O)N(R^{13})—$, $—N(R^{13})C(O)—$, $—N(R^{13})SO_2—$, $—N(R^{13})C(O)O—$, $—NR^{13}C(O)N(R^{13})—$, $—N(R^{13})S(O)_2N(R^{13})—$, —OC(O)—, or $—C(O)N(R^{13})—O—$ or wherein $T_3$ or a portion thereof optionally forms part of an optionally substituted 3-7 membered cycloaliphatic or heterocyclyl ring, wherein $R^{13}$ is hydrogen or an optionally substituted $C_{1-4}$aliphatic group.

In still other embodiments, for compounds (I-A) or (I-B), or subsets thereof, $R^2$ is an optionally substituted 6-10-membered aryl or 5-10-membered heteroaryl having 1-5 heteroatoms independently selected from nitrogen, oxygen, or sulfur.

In still other embodiments, for compounds (I-A) or (I-B), or subsets thereof, $R^2$ is a phenyl group substituted with 1-3 independent occurrences of halo, $C_{1-3}$ alkyl, CN, $C_{1-3}$haloalkyl, $—OC_{1-3}$ alkyl, $—OC_{1-3}$ haloalkyl, $—NHC(O)C_{1-3}$ alkyl, $—NHC(O)NHC_{1-3}$ alkyl, $NHS(O)_2C_{1-3}$ alkyl, or —C(O)H. In certain embodiments, $R^2$ is a phenyl group substituted with a halogen.

In yet other embodiments, for compounds (I-A) or (I-B), or subsets thereof, $R^1$ is CY, $X_1$ is N, $G_2$ is $NR^{4'}$, and $X_2$ and $X_3$ are $CR^7$. In certain embodiments, $X_3$ is CH.

In still other embodiments, for compounds (I-A) or (I-B), or subsets thereof, $R^1$ is CY, $X_1$ and $X_2$ are N, $G_2$ is $NR^{4'}$ and $X_3$ is $CR^7$. In certain embodiments, $R^1$ is H or $NH^2$.

In yet other embodiments, for compounds (I-A) or (I-B), or subsets thereof, wherein one or more, or all, of $R^1$, $R^2$ and HY are selected from:

a. $R^1$ is CY, and CY is

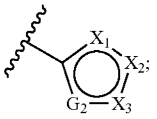

b. $R^2$ is a 3-10-membered cycloaliphatic, 4-10-membered heterocyclyl having 1-5 heteroatoms independently selected from nitrogen, oxygen, or sulfur 6-10-membered aryl, or 5-10-membered heteroaryl having 1-5 heteroatoms independently selected from nitrogen, oxygen, or sulfur, optionally substituted with 1-4 independent occurrences of $R^{12}$, wherein $R^{12}$ is —$R^{12a}$, -$T_2$-$R^{12d}$, or —$V_2$-$T_2$-$R^{12d}$, and:

each occurrence of $R^{9a}$ is independently halogen, —CN, —$NO_2$, —$R^{12c}$, —$N(R^{12b})_2$, —$OR^{12b}$, —$SR^{12c}$, —$S(O)_2R^{12c}$, —$C(O)R^{12b}$, —$C(O)OR^{12b}$, —$C(O)N(R^{12})_2$, —$S(O)_2N(R^{12})_2$, —$OC(O)N(R^{12})_2$, —$N(R^{12e})C(O)R^{12b}$, —$N(R^{12e})SO_2R^{12c}$, —$N(R^{12e})C(O)OR^{12b}$, —$N(R^{12e})C(O)N(R^{12})_2$, or —$N(R^{12e})SO_2N(R^{12b})_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —$N(R^{12e})$—, —O—, —S—, —S(O)—, —$S(O)_2$—, —C(O)—, —C(O)O—, —$C(O)N(R^{12e})$—, —$S(O)_2N(R^{12e})$—, —$OC(O)N(R^{12e})$—, —$N(R^{12e})C(O)$—, —$N(R^{12e})SO_2$—, —$N(R^{12e})C(O)O$—, —$NR^{12e}C(O)N(R^{12e})$—, —$N(R^{12e})SO_2N(R^{12e})$—, —OC(O)—, or —$C(O)N(R^{12e})$—O—; and $T_2$ is an optionally substituted $C_1$-$C_6$ alkylene chain wherein the alkylene chain optionally is interrupted by —$N(R^{13})$—, —O—, —S—, —S(O)—, —$S(O)_2$—, —C(O)—, —C(O)O—, —$C(O)N(R^{13})$—, —$S(O)_2N(R^{13})$—, —$OC(O)N(R^{13})$—, —$N(R^{13})C(O)$—, —$N(R^{13})SO_2$—, —$N(R^{13})C(O)O$—, —$NR^{13}C(O)N(R^{13})$—, —$N(R^{13})S(O)_2N(R^{13})$—, —OC(O)—, or —$C(O)N(R^{13})$—O— or wherein $T_3$ or a portion thereof optionally forms part of an optionally substituted 3-7 membered cycloaliphatic or heterocyclyl ring, wherein $R^{13}$ is hydrogen or an optionally substituted $C_{1-4}$aliphatic group; and c. HY is selected from:

A

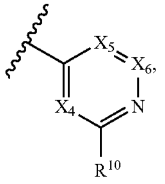

B

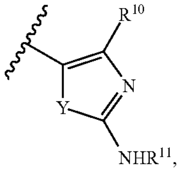

C

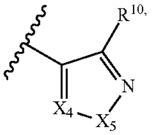

or

D

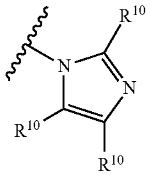

wherein $R^{10}$ is —$R^{10b}$, —$V_1$—$R^{10c}$, -$T_1$-$R^{10b}$, or —$V_1$-$T_1$-$R^{10b}$ wherein:

$V_1$ is —$NR^{10a}$—, —$NR^{10a}$—C(O)—, —$NR^{10a}$—C(S)—, —$NR^{10a}$—$C(NR^{10a})$—, $NR^{10a}C(O)OR^{10a}$—, $NR^{10a}C(O)NR^{10a}$—, $NR^{1a}C(O)SR^{10a}$—, $NR^{1a}C(S)OR^{10a}$—, $NR^{10a}C(S)NR^{10a}$—, $NR^{10a}C(S)SR^{10a}$—, —$NR^{10a}C(NR^{10a})OR^{10a}$—, —$NR^{10a}C(NR^{10a})NR^{10a}$—, —$NR^{10a}S(O)_2$—, —$NR^{10a}S(O)_2NR^{10a}$—, —C(O)—, —$CO_2$—, —$C(O)NR^{10a}$—, $C(O)NR^{10a}O$—, —$SO_2$—, or —$SO_2NR^{10a}$—;

each occurrence of $R^{10a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$ alkylene chain wherein the alkylene chain optionally is interrupted by —$N(R^{10a})$—, —O—, —S—, —S(O)—, —$S(O)_2$—, —C(O)—, —C(O)O—, —$C(O)N(R^{10a})$—, —$S(O)_2N(R^{10a})$—, —$OC(O)N(R^{10a})$—, —$N(R^{10a})C(O)$—, —$N(R^{10a})SO_2$—, —$N(R^{10a})C(O)O$—, —$NR^{10a}C(O)N(R^{10a})$—, —$N(R^{10a})S(O)_2N(R^{10a})$—, —OC(O)—, or —$C(O)N(R^{10a})$—O— or wherein $T_1$ forms part of an optionally substituted 3-7 membered cycloaliphatic or heterocyclyl ring;

each occurrence of $R^{10b}$ is independently hydrogen, halogen, —CN, —$NO_2$, —$N(R^{10a})_2$, —$SR^{10a}$, —$S(O)_2R^{10a}$, —$C(O)R^{10a}$, —$C(O)OR^{10a}$, —$C(O)N(R^{10a})_2$, —$S(O)_2N(R^{10a})_2$, —$OC(O)N(R^{10a})_2$, —$N(R^{10a})C(O)R^{10a}$, —$N(R^{10a})SO_2R^{10a}$, —$N(R^{10a})C(O)OR^{10a}$, —$N(R^{10a})C(O)N(R^{10a})_2$, or —$N(R^{10a})SO_2N(R^{10a})_2$, or an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^{10a}$ and $R^{10c}$ taken together with a nitrogen atom to which they are bound form an optionally substituted 4-7-membered heterocyclyl ring having 0-1 additional heteroatoms independently selected from nitrogen, oxygen, or sulfur, wherein each occurrence of $X_4$, $X_5$, and $X_6$ is independently N or $CR^{10}$, or two adjacent groups selected from Y, $R^{11}$, $R^{10}$, $X_4$, $X_5$, and $X_6$, taken together, form an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, and each occurrence of $R^{11}$ is independently hydrogen, —$C(O)R^{11a}$—, —$CO_2R^{11a}$—, —$C(O)NR^{11a}$—, $C(O)NR^{11a}O$—, —$SO_2R^{11a}$—, —$SO_2NR^{11a}$—, or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{11a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and Y is N or $CR^{10}$.

In yet other embodiments, for compounds (I-A), or subsets thereof, $G_1$ is $CR^3$, HY is an optionally substituted 6-membered nitrogen-containing heteroaryl group, and $R^1$ is —$NHCOR^4$, —$NHSO_2R^4$, —$NHCON(R^4)_2$, —$NHCOOR^4$, —$NHSO_2N(R^4)_2$, or —$NHSO_2OR^4$.

In certain embodiments, $G_1$ is CH;

HY is

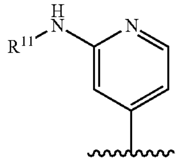

xviii;

$R^1$ is —$NHCOR^4$, —$NHSO_2R^4$, —$NHCON(R^4)_2$, —$NHCOOR^4$, —$NHSO_2N(R^4)_2$, or —$NHSO_2OR^4$, $R^4$ is $C_{1-6}$ alkyl, and $R^2$ is a $C_{6-18}$ aryl group which is optionally substituted by halogen.

In other embodiments:

$G_1$ is CH;

HY is

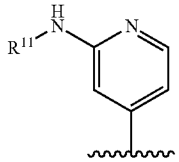

xviii, wherein $R_{11}$ is $C_{1-6}$ arkylcarbonyl, $R^1$ is —$NHCOR^4$, $R^4$ is $C_{1-6}$ alkyl and $R^2$ is a $C_{6-18}$ aryl group which is optionally substituted by halogen.

In still other embodiments, for compounds (I-A) or (I-B), or subsets thereof $G^1$ is $CR^3$, HY is an optionally substituted bicyclic or polycyclic nitrogen-containing heteroaryl group, and $R^1$ is CY, —$CON(R^4)_2$, —$NHCOR^4$, —$NHSO_2R^4$, —$NHCON(R^4)_2$, —$NHCOOR^4$, —$NHSO_2N(R^4)_2$, or —$NHSO_2OR^4$.

In yet other embodiments, for compounds of formula (I-A) or (I-B), wherein $G^1$ is N, HY is an optionally substituted nitrogen-containing heteroaryl group, and $R^1$ is, —$NHCOR^4$, —$NHSO_2R^4$, —$NHCON(R^4)_2$, —$NHCOOR^4$, —$NHSO_2N(R^4)_2$, or —$NHSO_2OR^4$.

In other embodiments, compounds of formula (I-B) are provided where $G_1$ is CH.

In certain other embodiments, $R^1$ is CY, and CY is

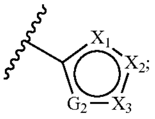

$R^2$ is an optionally substituted 6-10-membered aryl or 5-10-membered heteroaryl having 1-5 heteroatoms independently selected from nitrogen, oxygen, or sulfur.

In yet other embodiments, $R^2$ is a phenyl group substituted with 1-3 independent occurrences of halo, $C_{1-3}$ alkyl, CN, $C_{1-3}$haloalkyl, —$OC_{1-3}$ alkyl, —$OC_{1-3}$ haloalkyl, —NHC(O)$C_{1-3}$ alkyl, —NHC(O)NH$C_{1-3}$ alkyl, $NHS(O)_2C_{1-3}$ alkyl, or —C(O)H.

In still other embodiments, $X_1$ is N and $X_2$ and $X_3$ are CH.

In yet other embodiments, $X_1$ and $X_2$ are N, and $X_3$ is CH.

In still other embodiments, a compound of formula II-A-I is provided:

II-A-i

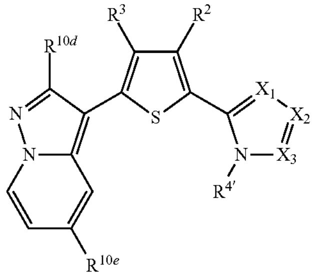

wherein $R^{10d}$ is hydrogen or optionally substituted $C_{1-4}$alkyl, and $R^{10e}$ is $R^{10}$.

In some embodiments, for compound II-A-i, $R^{10e}$ is —$V_1$—$R^{10c}$, or halogen. In other embodiments, for compound II-A-i, $X_1$ is N and $X_2$ and $X_3$ are H. In other embodiments, $X_1$ and $X_2$ are N, and $X_3$ is H.

In still other embodiments for compound II-A-i, $R^2$ is an optionally substituted 6-10-membered aryl or 5-10-membered heteroaryl having 1-5 heteroatoms independently selected from nitrogen, oxygen, or sulfur.

In yet other embodiments, for compound II-A-i, $R^2$ is a phenyl group substituted with 1-3 independent occurrences of halo, $C_{1-3}$ alkyl, CN, $C_{1-3}$haloalkyl, —$OC_{1-3}$ alkyl, —$OC_{1-3}$ haloalkyl, —NHC(O)$C_{1-3}$ alkyl, —NHC(O)NH$C_{1-3}$ alkyl, NHS(O)$_2$$C_{1-3}$ alkyl, or —C(O)H.

In yet other embodiments, a compound of formula IA or IB is provided:

IA

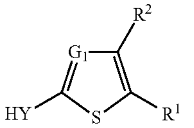

IB

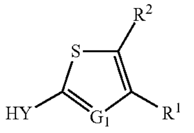

or a pharmaceutically acceptable salt thereof, wherein:

$G_1$ is N or $CR^3$, wherein $R^3$ is H, —CN, halogen, —Z—$R^5$, $C_{1-6}$ aliphatic, or 3-10-membered cycloaliphatic, wherein:

Z is selected from an optionally substituted $C_{1-3}$ alkylene chain, —O—, —N($R^{3a}$)—, —S—, —S(O)—, —S(O)$_2$—, —C(O)—, —$CO_2$—, —C(O)N$R^{3a}$—, —N($R^{3a}$)C(O)—, —N($R^{3a}$)$CO_2$—, —S(O)$_2$N$R^{3a}$—, —N($R^{3a}$)S(O)$_2$—, —OC(O)N($R^{3a}$)—, —N($R^{3a}$)C(O)N$R^{3a}$—, —N($R^{3a}$)S(O)$_2$N($R^{3a}$)—, or —OC(O)—;

$R^{3a}$ is hydrogen or an optionally substituted $C_{1-4}$ aliphatic, and $R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$R^1$ is CY, —CON($R^4$)$_2$, —NHCO$R^4$, —NHSO$_2$$R^4$, —NHCON($R^4$)$_2$, —NHCOO$R^4$, —NHSO$_2$N($R^4$)$_2$, or —NHSO$_2$O$R^4$, wherein:

CY is

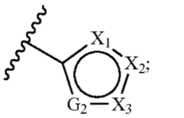

wherein:

$X_1$, $X_2$, and $X_3$, are each independently N, O, S, or $CR^7$, provided that only one of $X_1$, $X_2$, or $X_3$ may be O or S, $G_2$ is —N= or —N$R^{4'}$—, wherein:

each occurrence of $R^4$ and R4' is independently H, —$Z_2$—$R^6$, optionally substituted $C_{1-6}$ aliphatic, or optionally substituted 3-10-membered cycloaliphatic, wherein:

$Z_2$ is selected from an optionally substituted $C_{1-3}$ alkylene chain, —S(O)—, —S(O)$_2$—, —C(O)—, —$CO_2$—, —C(O)N$R^{4a}$—, or —S(O)$_2$N$R^{4a}$—.

$R^{4a}$ is hydrogen or an optionally substituted $C_{1-4}$ aliphatic, and $R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^7$ is independently hydrogen, —CN, halogen, —$Z_3$—$R^8$, $C_{1-6}$ aliphatic, or 3-10-membered cycloaliphatic, wherein:

$Z_3$ is selected from an optionally substituted $C_{1-3}$ alkylene chain, —O—, —N($R^{7a}$)—, —S—, —S(O)—, —S(O)$_2$—, —C(O)—, —$CO_2$—, —C(O)N$R^{7a}$—, —N($R^{7a}$)C(O)—, —N($R^{7a}$)$CO_2$—, —S(O)$_2$N$R^{7a}$—, —N($R^{7a}$)S(O)$_2$—, —OC(O)N($R^{7a}$)—, —N($R^{7a}$)C(O)N$R^{7a}$—, —N($R^{7a}$)S(O)$_2$N($R^{7a}$)—, or —OC(O)—.

$R^{7a}$ is hydrogen or an optionally substituted $C_{1-4}$ aliphatic, and $R^8$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, $R^2$ is halogen, —W—$R^9$, or —$R^9$, wherein:

W is selected from an optionally substituted $C_{1-3}$ alkylene chain, —O—, —N($R^{2a}$)—, —S—, —S(O)—, —S(O)$_2$—, —C(O)—, —$CO_2$—, —C(O)N$R^{2a}$—, —N($R^{2a}$)C(O)—, —N($R^{2a}$)$CO_2$—, —S(O)$_2$N$R^{2a}$—, —N($R^{2a}$)S(O)$_2$—, —OC(O)N($R^{2a}$)—, —N($R^{2a}$)C(O)N$R^{2a}$—, —N($R^{2a}$)S(O)$_2$N($R^{2a}$)—, or —OC(O)—.

$R^{2a}$ is hydrogen or an optionally substituted $C_{1-4}$ aliphatic, and $R^9$ is an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is selected from:

xxiii

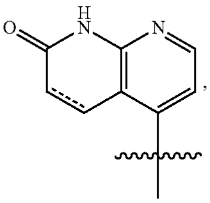
, xxiv

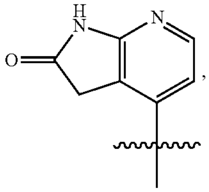
, xxv

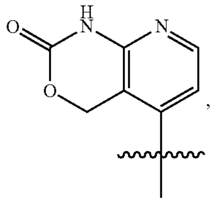
, xxvi

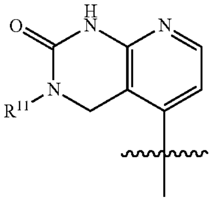

xxvii

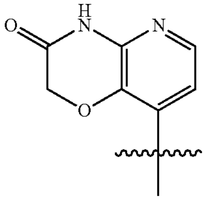

xxviii

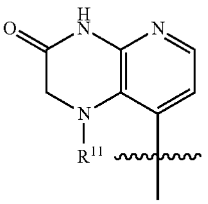

xxix

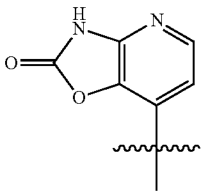
or

-continued xxx

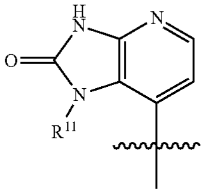

wherein each HY group is optionally additionally substituted with one or more occurrences of $R^{10}$.

In some embodiments, $R^1$ is CY, and CY is

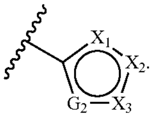

In other embodiments, $R^1$ is $—CON(R^4)_2$, $—NHCOR^4$, $—NHSO_2R^4$, $—NHCON(R^4)_2$, $—NHCOOR^4$, $—NHSO_2N(R^4)_2$, or $—NHSO_2OR^4$. In yet other embodiments, $G_1$ is $CR^3$. In still other embodiments, $G_1$ is N.

In yet other embodiments, $R^2$ is a 3-10-membered cycloaliphatic, 4-10-membered heterocyclyl having 1-5 heteroatoms independently selected from nitrogen, oxygen, or sulfur 6-10-membered aryl, or 5-10-membered heteroaryl having 1-5 heteroatoms independently selected from nitrogen, oxygen, or sulfur, optionally substituted with 1-4 independent occurrences of $R^{12}$, wherein $R^{12}$ is $—R^{12a}$, $-T_2-R^{12d}$, or $—V_2-T_2-R^{12d}$, and:

each occurrence of $R^{9a}$ is independently halogen, —CN, $—NO_2$, $—R^{12c}$, $—N(R^{12b})_2$, $—OR^{12b}$, $—SR^{12c}$, $—S(O)_2R^{12c}$, $—C(O)R^{12b}$, $—C(O)OR^{12b}$, $—C(O)N(R^{12b})_2$, $—S(O)_2N(R^{12})_2$, $—OC(O)N(R^{12})_2$, $—N(R^{12e})C(O)R^{12b}$, $—N(R^{12e})SO_2R^{12c}$, $—N(R^{12e})C(O)OR^{12b}$, $—N(R^{12e})C(O)N(R^{12b})_2$, or $—N(R^{12e})SO_2N(R^{12b})_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur; each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —$N(R^{12e})$—, —O—, —S—, —S(O)—, —$S(O)_2$—, —C(O)—, —C(O)O—, —$C(O)N(R^{12e})$—, —$S(O)_2N(R^{12e})$—, —$OC(O)N(R^{12e})$—, —$N(R^{12e})C(O)$—, —$N(R^{12e})SO_2$—, —$N(R^{12e})C(O)O$—, —$NR^{12e}C(O)N(R^{12e})$—, —$N(R^{12e})SO_2N(R^{12e})$—, —OC(O)—, or —$C(O)N(R^{12e})$—O—; and $T_2$ is an optionally substituted $C_1$-$C_6$ alkylene chain wherein the alkylene chain optionally is interrupted by —$N(R^{13})$—, —O—, —S—, —S(O)—, —$S(O)_2$—, —C(O)—, —C(O)O—, —$C(O)N(R^{13})$—, —$S(O)_2N(R^{13})$—, —$OC(O)N(R^{13})$—, —$N(R^{13})C(O)$—, —$N(R^{13})SO_2$—, —$N(R^{13})C(O)O$—, —$NR^{13}C(O)N(R^{13})$—, —$N(R^{13})S(O)_2N(R^{13})$—, —OC(O)—, or —$C(O)N(R^{13})$—O— or wherein $T_3$ or a portion thereof optionally forms part of an optionally substituted 3-7 membered cycloaliphatic or heterocyclyl ring, wherein $R^{13}$ is hydrogen or an optionally substituted $C_{1-4}$aliphatic group.

In still other embodiments, $R^2$ is an optionally substituted 6-10-membered aryl or 5-10-membered heteroaryl having 1-5 heteroatoms independently selected from nitrogen, oxygen, or sulfur. In yet other embodiments, $R^2$ is a phenyl group substituted with 1-3 independent occurrences of halo, $C_{1-3}$ alkyl, CN, $C_{1-3}$haloalkyl, —$OC_{1-3}$ alkyl, —$OC_{1-3}$ haloalkyl, —$NHC(O)C_{1-3}$ alkyl, —$NHC(O)NHC_{1-3}$ alkyl, $NHS(O)_2C_{1-3}$ alkyl, or —C(O)H.

As described in the general description above, in certain embodiments, compounds of formula II-A are provided:

II-A

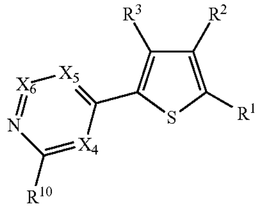

or a pharmaceutically acceptable salt thereof, wherein:

$R^1$ is CY is

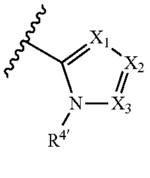
or
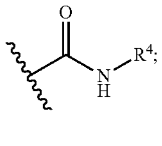

$R^2$ is H, halogen, —W—$R^9$, or —$R^9$, wherein:

W is selected from an optionally substituted $C_{1-3}$ alkylene chain, —O—, —$N(R^{2a})$—, —S—, —S(O)—, —$S(O)_2$—, —C(O)—, —$CO_2$—, —$C(O)NR^{2a}$—, —$N(R^{2a})C(O)$—, —$N(R^{2a})CO_2$—, —$S(O)_2NR^{2a}$—, —$N(R^{2a})S(O)_2$—, —$OC(O)N(R^{2a})$—, —$N(R^{2a})C(O)NR^{2a}$—, —$N(R^{2a})S(O)_2N(R^{2a})$—, or —OC(O)—.

$R^{2a}$ is hydrogen or an optionally substituted $C_{1-4}$ aliphatic, and $R^9$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$R^3$ is H, —CN, halogen, —Z—$R^5$, $C_{1-6}$ aliphatic, or 3-10-membered cycloaliphatic, wherein:

Z is selected from an optionally substituted $C_{1-3}$ alkylene chain, —O—, —$N(R^{3a})$—, —S—, —S(O)—, —$S(O)_2$—, —C(O)—, —$CO_2$—, —$C(O)NR^{3a}$—, —$N(R^{3a})C(O)$—, —$N(R^{3a})CO_2$—, —$S(O)_2NR^{3a}$—, —$N(R^{3a})S(O)_2$—, —$OC(O)N(R^{3a})$—, —$N(R^{34})C(O)NR^{3a}$—, —$N(R^{3a})S(O)_2N(R^{3a})$—, or —OC(O)—;

$R^{3a}$ is hydrogen or an optionally substituted $C_{1-4}$ aliphatic, and $R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^4$ and $R^{4'}$ is independently H, —Z—$R^6$, $C_{1-6}$ aliphatic, or 3-10-membered cycloaliphatic, wherein:

Z is selected from an optionally substituted $C_{1-3}$ alkylene chain, —O—, —$N(R^{4a})$—, —S(O)—, —$S(O)_2$—, —C(O)—, —$CO_2$—, —$C(O)NR^{4a}$—, —$N(R^{4a})C(O)$—, —$N(R^{4a})CO_2$—, —$S(O)_2NR^{4a}$—, —$N(R^{4a})S(O)_2$—, —$OC(O)N(R^{4a})$—, —$N(R^{4a})C(O)NR^{4a}$—, —$N(R^{4a})S(O)_2N(R^{4a})$—, or —OC(O)—.

$R^{4a}$ is hydrogen or an optionally substituted $C_{1-4}$ aliphatic, and $R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and $X_1$, $X_2$, and $X_3$, are each independently N or $CR^7$, wherein each occurrence of $R^7$ is independently hydrogen, —CN, halogen, —$Z_3$—$R^8$, optionally substituted $C_{1-6}$ aliphatic, or optionally substituted 3-10-membered cycloaliphatic, wherein:

$Z_3$ is selected from an optionally substituted $C_{1-3}$ alkylene chain, —O—, —$N(R^{7a})$—, —S—, —S(O)—, —$S(O)_2$—, —C(O)—, —$CO_2$—, —$C(O)NR^{7a}$—, —$N(R^{7a})C(O)$—, —$N(R^{7a})CO_2$—, —$S(O)_2NR^{7a}$—, —$N(R^{7a})S(O)_2$—, —$OC(O)N(R^{74})$—, —$N(R^{7a})C(O)NR^{7a}$—, —$N(R^{7a})S(O)_2N(R^{7a})$—, or —OC(O)—;

$R^{7a}$ is hydrogen or an optionally substituted $C_{1-4}$ aliphatic, and $R^8$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, and $X_4$, $X_5$ and $X_6$ are each independently $R^{10}$, wherein:

$R^{10}$ is —$R^{10b}$, or —$V_1$—$R^{10c}$, -$T_1$-$R^{10b}$, or —$V_1$-$T_1$-$R^{10b}$ wherein:

$V_1$ is —$NR^{10a}$—, —$NR^{10a}$—C(O)—, —$NR^{10a}$—C(S)—, —$NR^{10a}$—C($NR^{10a}$)—, $NR^{10a}$C(O)O—, $NR^{10a}$C(O)$NR^{10a}$—, $NR^{10a}$C(O)$S^{a}$—, $NR^{10a}$C(S)O—, $NR^{10a}$C(S)$NR^{10a}$—, $NR^{10a}$C(S)S—, —$NR^{10a}$C($NR^{10a}$)O—, —$NR^{10a}$C($NR^{10a}$)$NR^{10a}$—, —$NR^{10a}S(O)_2$—, —$NR^{10a}S(O)_2NR^{10a}$—, —C(O)—, —$CO_2$—, C(O)$NR^{10a}$—, —C(O)$NR^{10a}$O—, —$SO_2$—, or —$SO_2NR^{10a}$—;

each occurrence of $R^{10a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$ alkylene chain wherein the alkylene chain optionally is interrupted by —N($R^{10a}$)—, —O—, —S—, —S(O)—, —$S(O)_2$—, —C(O)—, —C(O)O—, —C(O)N($R^{10a}$)—, —$S(O)_2$N($R^{10a}$)—, —OC(O)N($R^{10a}$)—, —N($R^{10a}$)C(O)—, —N($R^{10a}$)$SO_2$—, —N($R^{10a}$)C(O)O—, —$NR^{10a}$C(O)N($R^{10a}$)—, —N($R^{10a}$)$S(O)_2$N($R^{10a}$)—, —OC(O)—, or —C(O)N($R^{10a}$)—O— or wherein $T_1$ forms part of an optionally substituted 3-7 membered cycloaliphatic or heterocyclyl ring;

each occurrence of $R^{10b}$ is independently hydrogen, halogen, —CN, —$NO_2$, —N($R^{10a}$)$_2$, —$SR^{10a}$, —$S(O)_2R^{10a}$, —C(O)$R^{10a}$, —C(O)$OR^{10a}$, —C(O)N($R^{10a}$)$_2$, —$S(O)_2$N($R^{10a}$)$_2$, —OC(O)N($R^{10a}$)$_2$, —N($R^{10a}$)C(O)$R^{10a}$, —N($R^{10a}$)$SO_2R^{10a}$, —N($R^{10a}$)C(O)$OR^{10a}$, —N($R^{10a}$)C(O)N($R^{10a}$)$_2$, or —N($R^{10a}$)$SO_2$N($R^{10a}$)$_2$, or an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^{10a}$ and $R^{10c}$ taken together with a nitrogen atom to which they are bound form an optionally substituted 4-7-membered heterocyclyl ring having 0-1 additional heteroatoms independently selected from nitrogen, oxygen, or sulfur;

provided that:

a) when $R^1$ is —$CONHR^4$, then $R^2$ is an optionally substituted group selected from 6-10-membered aryl, or 5-10-membered heteroaryl having 1-5 heteroatoms independently selected from nitrogen, oxygen, or sulfur; and b) the compound of formula I is other than 4-[5-[3-(2-chloro-6-fluorophenyl)-1-methyl-1H-1,2,4-triazol-5-yl]-4-methyl-2-thienyl]-pyridine; or 4-[5-(2H-tetrazol-5-yl)-2-thienyl]-pyridine.

In certain embodiments, for compounds of general formula II-A, one or more substituents are selected from:

(a) $R^2$ is an optionally substituted 6-10-membered aryl, or 5-10-membered heteroaryl having 1-5 heteroatoms independently selected from nitrogen, oxygen, or sulfur; or (b) $R^{10}$ is —$V_1$—$R^{10c}$.

In other embodiments, for compounds of general formula II-A, compounds are represented by:

II-A-a

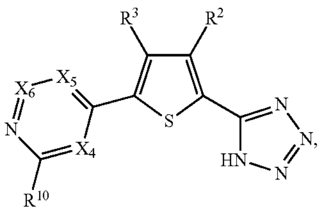

II-A-b

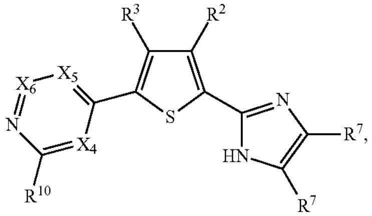

II-A-c

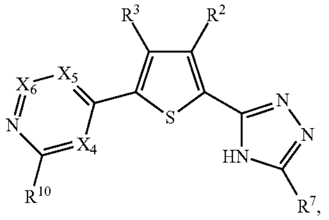

II-A-d

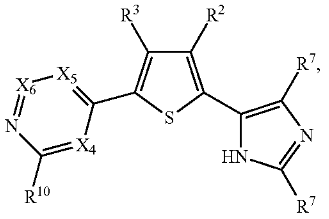

II-A-e

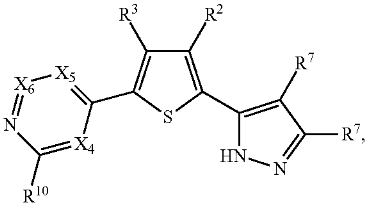

or

II-A-f

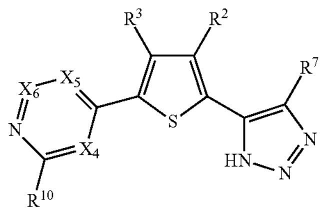

In still other embodiments, for compounds of general formulas II-A, II-A-a, II-A-b, II-A-c, II-A-d, II-A-e, or II-A-f, $X_5$ is N, and $X_4$ and $X_6$ are each $CR^{10}$. In yet other embodiments, $X_4$ is N, and $X_5$ and $X_6$ are each $CR^{10}$. In still other embodiments, $X_4$, $X_5$ and $X_6$ are each $CR^{10}$. In further embodiments, $R^{10}$ is hydrogen, halogen or a $C_{1-6}$ alkyl group.

In other embodiments, for compounds of general formulas II-A, II-A-a, II-A-b, II-A-c, II-A-d, II-A-e, or II-A-f, $R^{10}$ is —$V_1$—$R^{10c}$ or —$V_1$-$T_1$-$R^{10b}$ wherein:

$V_1$ is —$NR^{10a}$—, —$NR^{10a}C(O)$—, —$NR^{10a}$—$C(NR^{10a})$—, $NR^{10a}C(O)O$—, or —$NR^{10a}S(O)_2$—;

each occurrence of $R^{10a}$ is independently hydrogen, $C_{1-6}$alkyl group, or 3-10-membered cycloalkyl group;

$T_1$ is $C_1$-$C_6$ alkylene chain wherein the alkylene chain optionally is interrupted by —$N(R^{10a})$—, or —O—;

each occurrence of $R^{10b}$ is independently hydrogen, halogen, —$N(R^{10a})_2$, —$N(R^{10a})C(O)R^{10a}$;

each occurrence of $R^{10c}$ is independently hydrogen, a $C_{1-6}$ alkyl group optionally substituted by halogen or hydroxyl, or a 6-10-membered aryl group optionally substituted by $C_{1-6}$ alkyl or $C_{1-6}$ alkyloxy.

In other embodiments, for compounds of general formula II-A, II-A-a, II-A-b, II-A-c, II-A-d, II-A-e, or II-A-f, $R^2$ is a 3-10-membered cycloaliphatic, 4-10-membered heterocyclyl having 1-5 heteroatoms independently selected from nitrogen, oxygen, or sulfur 6-10-membered aryl, or 5-10-membered heteroaryl having 1-5 heteroatoms independently selected from nitrogen, oxygen, or sulfur, optionally substituted with 1-4 independent occurrences of $R^9$, wherein $R^9$ is —$R^{9a}$, -$T_2$-$R^{9d}$, or —$V_2$-$T_2$-$R^{9d}$, and:

each occurrence of $R^{9a}$ is independently halogen, —CN, —$NO_2$, —$R^{9c}$, —$N(R^{9b})_2$, —$OR^{9b}$, —$SR^{9c}$, —$S(O)_2R^{9c}$, —$C(O)R^{9b}$, —$C(O)OR^{9b}$, —$C(O)N(R^{9b})_2$, —$S(O)_2N(R^{9b})_2$, —$OC(O)N(R^{9b})_2$, —$N(R^{9e})C(O)R^{9b}$, —$N(R^{9e})SO_2R^{9c}$, —$N(R^{9e})C(O)OR^{9b}$, —$N(R^{9e})C(O)N(R^{9b})_2$, or —$N(R^{9e})SO_2N(R^{9b})_2$, or two occurrences of $R^{9b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{9b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9e}$ is independently hydrogen or an optionally substituted $C_{1-6}$ aliphatic group;

each occurrence of $V_2$ is independently —$N(R^{9e})$—, —O—, —S—, —S(O)—, —$S(O)_2$—, —C(O)—, —C(O)O—, —$C(O)N(R^{9e})$—, —$S(O)_2N(R^{9e})$—, —$OC(O)N(R^{9e})$—, —$N(R^{9e})C(O)$—, —$N(R^{9e})SO_2$—, —$N(R^{9e})C(O)O$—, —$NR^{9e}C(O)N(R^{9e})$—, —$N(R^{9e})SO_2N(R^{9e})$—, —OC(O)—, or —$C(O)N(R^{9e})$—O—; and $T_2$ is an optionally substituted $C_1$-$C_6$ alkylene chain wherein the alkylene chain optionally is interrupted by —$N(R^{7a})$—, —O—, —S—, —S(O)—, —$S(O)_2$—, —C(O)—, —C(O)O—, —$C(O)N(R^{7a})$—, —$S(O)_2N(R^{7a})$—, —$OC(O)N(R^{7a})$—, —$N(R^{7a})C(O)$—, —$N(R^{7a})SO_2$—, —$N(R^{7a})C(O)O$—, —$NR^{7a}C(O)N(R^{7a})$—, —$N(R^{7a})S(O)_2N(R^{7a})$—, —OC(O)—, or —$C(O)N(R^{7a})$—O— or wherein $T_3$ or a portion thereof optionally forms part of an optionally substituted 3-7 membered cycloaliphatic or heterocyclyl ring.

In still other embodiments for compounds of general formula II-A, II-A-a, II-A-b, II-A-c, II-A-d, II-A-e, or II-A-f, $R^2$ is a phenyl group substituted with 1-3 independent occurrences of halo, $C_{1-3}$ alkyl, CN, $C_{1-3}$haloalkyl, —$OC_{1-3}$ alkyl, —$OC_{1-3}$ haloalkyl, —$NHC(O)C_{1-3}$ alkyl, —$NHC(O)NHC_{1-3}$ alkyl, $NHS(O)_2C_{1-3}$ alkyl, or —C(O)H. In further other embodiments for compounds of general formula II-A, II-A-a, II-A-b, II-A-c, II-A-d, II-A-e, or II-A-f, $R^2$ is a phenyl group substituted with 1-3 independent occurrences of halo.

In yet other embodiments, for compounds of general formula II-A, II-A-a, II-A-b, II-A-c, II-A-d, II-A-e, or II-A-f, and subsets thereof, $R^3$ is H or CN.

In other embodiments, for compounds of general formula II-A, II-A-a, II-A-b, II-A-c, II-A-d, II-A-e, or II-A-f, $R^4$ is H, or —Z—$R^6$, wherein: Z is $C_{1-3}$ alkylene chain, and $R^6$ is a 6-10-membered aryl group.

In other embodiments, for compounds of general formula II-A, II-A-a, II-A-b, II-A-c, II-A-d, II-A-e, or II-A-f, $R^7$ is independently hydrogen, halogen, or a $C_{1-6}$ alkyl group, or —$Z_3$—$R^8$ wherein:

$Z_3$ is selected from $C_{1-3}$ alkylene chain, or —$CO_2$—, and $R^8$ is a $C_{1-6}$ alkyl group, a 4-10-membered heterocyclyl group having 1-5 heteroatoms independently selected from nitrogen, oxygen, or sulfur, or a 6-10-membered aryl group each of which is optionally substituted by halogen.

In other embodiments, the compound has the structure of formula I-A-iii:

I-A-iii

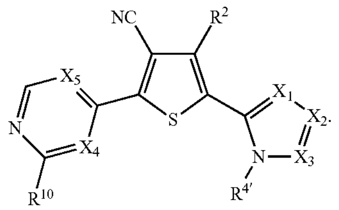

In some embodiments, for compounds of formula II-A, II-A-a, II-A-b, II-A-c, II-A-d, II-A-e, or II-A-f:

$R^{10}$ is —$V_1$—$R^{10c}$, where $V_1$ is —$NR^{10a}CO$—, —$N(R^{10a})_2$ or —$NR^{10a}C(NR^{10a})NR^{10a}$— and $R^2$ is a phenyl group substituted with 1-3 independent occurrences of halo, $C_{1-3}$ alkyl, —CN, $C_{1-3}$haloalkyl, —$OC_{1-3}$ alkyl, —$OC_{1-3}$ haloalkyl, —$NHC(O)C_{1-3}$ alkyl, —$NHC(O)NHC_{1-3}$ alkyl, $NHS(O)_2C_{1-3}$ alkyl, or —C(O)H.

Preferred $R^{10a}$ is independently hydrogen, a $C_{1-6}$alkyl group, or a 3-10-membered cycloalkyl group, particularly hydrogen and preferred $R^{10c}$ is independently hydrogen, a $C_{1-6}$ alkyl group optionally substituted by halogen or hydroxyl, or a 6-10-membered aryl group optionally substituted by $C_{1-6}$ alkyl or $C_{1-6}$ alkyloxy.

Preferred $R^2$ is a phenyl group optionally substituted with 1-3 independent occurrences of halo.

In some embodiments for compounds of formulas II-A, II-A-a, II-A-b, II-A-c, II-A-d, II-A-e, or II-A-f, $X_4$ is N and $X_5$ and $X_6$ are each $CR^{10}$.

In other embodiments, for compounds of formulas II-A, II-A-a, II-A-b, II-A-c, II-A-d, II-A-e, or II-A-f, $X_4$ is N, $X_5$ is N, and $X_6$ is $CR^{10}$.

In other embodiments, for compounds of formulas II-A, II-A-a, II-A-b, II-A-c, II-A-d, II-A-e, or II-A-f, $R^{10}$ is hydrogen, halogen or a $C_{1-6}$ alkyl group.

In other embodiments, for compounds of formulas II-A, II-A-a, II-A-b, II-A-c, II-A-d, II-A-e, or II-A-f, any combination of preferable group of each symbol mentioned above is used.

In still other embodiments, as described in the general description above, the present invention provides compounds represented by the formulas (I-A-i), (I-A-ii), (II-A-ii), (I-B-i) and additional description for these compounds is provided directly below.

As the "optionally substituted group bonded via a carbon atom" in the present specification, cyano, an optionally substituted alkyl group (preferably $C_{1-20}$ alkyl group, particularly preferably $C_{1-8}$ alkyl group), an optionally substituted alkenyl group (preferably $C_{2-8}$ alkenyl group), an optionally substituted alkynyl group (preferably $C_{2-8}$ alkynyl group), an optionally substituted $C_{1-8}$ alkyl-carbonyl group, an optionally substituted $C_{3-8}$ cycloalkyl group, an optionally substituted aryl group (preferably $C_{6-18}$ aryl group), an optionally substituted $C_{6-18}$ aryl-$C_{1-4}$ alkyl group, an optionally substituted $C_{6-18}$ aryl-carbonyl group, an optionally substituted $C_{6-18}$ aryl-$C_{1-4}$ alkyl-carbonyl group, an optionally substituted heterocyclic group (heterocyclic group bonded via a carbon atom), an optionally substituted heterocyclyl-$C_{1-4}$ alkyl group, an optionally substituted heterocyclyl-carbonyl group, an optionally substituted heterocyclyl-$C_{1-4}$ alkyl-carbonyl group, an optionally substituted carbamoyl group and the like can be used.

Examples of the "$C_{1-20}$ alkyl group" of the above-mentioned "optionally substituted $C_{1-20}$ alkyl group" include $C_{1-8}$ alkyl such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl etc., and the like.

The "alkyl group" of the above-mentioned "optionally substituted alkyl group" may have not less than 1 (preferably 1 to 5, more preferably 1 to 3) substituents at substitutable position(s). Such substituent(s) may be one to an acceptable maximum number of substituents at any substitutable position(s), which is/are selected from a substituent group consisting of (1) a halogen atom (e.g., fluorine, chlorine, bromine, iodine);

(2) cyano;

(3) nitro;

(4) hydroxy;

(5) $C_{1-6}$ alkoxy (e.g., methoxy, ethoxy, propoxy, isopropoxy, butoxy, isobutoxy, tert-butoxy etc.) optionally having 1 to 3 substituents selected from a halogen atom (e.g., fluorine, chlorine, bromine, iodine) and $C_{1-6}$ alkoxy (e.g., methoxy, ethoxy, propoxy, isopropoxy, butoxy, isobutoxy, tert-butoxy etc.);

(6) $C_{2-6}$ alkenyloxy (e.g., ethenyloxy, propenyloxy, butenyloxy, pentenyloxy, hexenyloxy etc.) optionally having 1 to 3 halogen atoms (e.g., fluorine, chlorine, bromine, iodine);

(7) $C_{2-6}$ alkynyloxy (e.g., ethynyloxy, propynyloxy, butynyloxy, pentynyloxy, hexynyloxy etc.) optionally having 1 to 3 halogen atoms (e.g., fluorine, chlorine, bromine, iodine);

(8) $C_{3-8}$ cycloalkyloxy (e.g., cyclopropyloxy, cyclobutyloxy, cyclopentyloxy, cyclohexyloxy) optionally having 1 to 3 halogen atoms (e.g., fluorine, chlorine, bromine, iodine);

(9) $C_{3-8}$ cycloalkenyloxy (e.g., cyclopropenyloxy, cyclobutenyloxy, cyclopentenyloxy, cyclohexenyloxy etc.) optionally having 1 to 3 halogen atoms (e.g., fluorine, chlorine, bromine, iodine);

(10) $C_{6-14}$ aryloxy (e.g., phenyloxy, 1-naphthyloxy, 2-naphthyloxy etc.) optionally having 1 to 3 halogen atoms (e.g., fluorine, chlorine, bromine, iodine);

(11) $C_{3-8}$ cycloalkyl-$C_{1-6}$ alkoxy (e.g., cyclopropylmethyloxy, cyclopropylethyloxy, cyclobutylmethyloxy, cyclopentylmethyloxy, cyclohexylmethyloxy, cyclohexylethyloxy etc.) optionally having 1 to 3 halogen atoms (e.g., fluorine, chlorine, bromine, iodine);

(12) $C_{3-8}$cycloalkenyl-$C_{1-6}$ alkoxy (e.g., cyclopentenylmethyloxy, cyclohexenylmethyloxy, cyclohexenylethyloxy, cyclohexenylpropyloxy etc.) optionally having 1 to 3 halogen atoms (e.g., fluorine, chlorine, bromine, iodine);

(13) $C_{6-14}$ aryl-$C_{1-6}$alkoxy (e.g., phenylmethyloxy, phenylethyloxy etc.) optionally having 1 to 3 halogen atoms (e.g., fluorine, chlorine, bromine, iodine);

(14) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom;

(15) 4- to 7-membered (preferably 5- or 6-membered) monocyclic non-aromatic heterocyclyl-$C_{1-4}$ alkyl-oxy (e.g., morpholinylethyloxy, piperidinylethyloxy etc.) containing, as a ring constituting atom besides carbon atom, 1 to 4 heteroatoms selected from an oxygen atom, a sulfur atom and a nitrogen atom;

(16) $C_{1-6}$ alkyl-aminosulfonyl (e.g., methylaminosulfonyl, ethylaminosulfonyl, propylaminosulfonyl etc.);

(17) di-$C_{1-6}$ alkyl-aminosulfonyl (e.g., dimethylaminosulfonyl, diethylaminosulfonyl, dipropylaminosulfonyl etc.);

(18) $C_{1-6}$ alkyl-aminocarbonyl (e.g., methylaminocarbonyl, ethylaminocarbonyl, propylaminocarbonyl etc.);

(19) di-$C_{1-6}$ alkyl-aminocarbonyl (e.g., dimethylaminocarbonyl, diethylaminocarbonyl, dipropylaminocarbonyl etc.);

(20) formyl;

(21) $C_{1-6}$ alkyl-carbonyl (e.g., acetyl, ethylcarbonyl, propylcarbonyl, isopropylcarbonyl etc.);

(22) $C_{2-6}$ alkenyl-carbonyl (e.g., ethenylcarbonyl, propenylcarbonyl, butenylcarbonyl, pentenylcarbonyl, hexenylcarbonyl etc.);

(23) $C_{2-6}$ alkynyl-carbonyl (e.g., ethynylcarbonyl, propynylcarbonyl, butynylcarbonyl, pentynylcarbonyl, hexynylcarbonyl etc.);

(24) $C_{3-8}$ cycloalkyl-carbonyl (e.g., cyclopropylcarbonyl, cyclobutylcarbonyl, cyclopentylcarbonyl, cyclohexylcarbonyl etc.);

(25) $C_{3-6}$cycloalkenyl-carbonyl (e.g., cyclopropenylcarbonyl, cyclobutenylcarbonyl, cyclopentenylcarbonyl, cyclohexenylcarbonyl etc.);

(26) $C_{6-14}$ aryl-carbonyl (e.g., benzoyl, 1-naphthylcarbonyl, 2-naphthylcarbonyl etc.);

(27) $C_{3-8}$ cycloalkyl-$C_{1-6}$alkyl-carbonyl (e.g., cyclopropylmethylcarbonyl, cyclopropylethylcarbonyl, cyclobutylmethylcarbonyl, cyclopentylmethylcarbonyl, cyclohexylmethylcarbonyl, cyclohexylethylcarbonyl etc.);

(28) $C_{3-6}$cycloalkenyl-$C_{1-6}$alkyl-carbonyl (e.g., cyclopentenylmethylcarbonyl, cyclohexenylmethylcarbonyl, cyclohexenylethylcarbonyl, cyclohexenylpropylcarbonyl etc.);

(29) $C_{6-14}$aryl-$C_{1-6}$alkyl-carbonyl (e.g., benzylcarbonyl, phenylethylcarbonyl etc.);

(30) 4- to 7-membered (preferably 5- or 6-membered) monocyclic aromatic heterocyclyl-carbonyl (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl etc.)

containing, as a ring constituting atom besides carbon atom, 1 to 4 heteroatoms selected from a nitrogen atom, an oxygen atom and a sulfur atom;

(31) 8- to 12-membered fused aromatic heterocyclyl-carbonyl (e.g., benzofurylcarbonyl, isobenzofurylcarbonyl, benzothienylcarbonyl, isobenzothienylcarbonyl, indolylcarbonyl, isoindolylcarbonyl, 1H-indazolylcarbonyl, benzimidazolylcarbonyl, benzoxazolylcarbonyl etc.) containing, as a ring constituting atom besides carbon atom, 1 to 4 heteroatoms selected from a nitrogen atom, an oxygen atom and a sulfur atom;

(32) 4- to 7-membered (preferably 5- or 6-membered) non-aromatic heterocyclyl-carbonyl (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidinylcarbonyl etc.) containing, as a ring constituting atom besides carbon atom, 1 to 4 heteroatoms selected from a nitrogen atom, an oxygen atom and a sulfur atom;

(33) $C_{1-6}$alkylsulfonyl (e.g., methylsulfonyl, ethylsulfonyl etc.);

(34) $C_{2-6}$alkenylsulfonyl (e.g., ethenylsulfonyl, propenylsulfonyl etc.);

(35) $C_{2-6}$ alkynylsulfonyl (e.g., ethynylsulfonyl, propynylsulfonyl, butynylsulfonyl, pentynylsulfonyl, hexynylsulfonyl etc.);

(36) $C_{3-8}$cycloalkylsulfonyl (e.g., cyclopropylsulfonyl, cyclobutylsulfonyl etc.);

(37) $C_{3-6}$cycloalkenylsulfonyl (e.g., cyclopropenylsulfonyl, cyclobutenylsulfonyl etc.);

(38) $C_{6-10}$ arylsulfonyl (e.g., phenylsulfonyl etc.);

(39) $C_{3-8}$ cycloalkyl-$C_{1-6}$alkyl-sulfonyl (e.g., cyclopropylmethylsulfonyl etc.);

(40) $C_{3-6}$ cycloalkenyl-$C_{1-6}$alkyl-sulfonyl (e.g., cyclopentenylmethylsulfonyl etc.);

(41) $C_{6-14}$ aryl-$C_{1-6}$ alkyl-sulfonyl (e.g., benzylsulfonyl etc.);

(42) 4- to 7-membered (preferably 5- or 6-membered) monocyclic aromatic heterocyclyl-sulfonyl (e.g., furylsulfonyl, thienylsulfonyl, pyridylsulfonyl etc.) containing, as a ring constituting atom besides carbon atom, 1 to 4 heteroatoms selected from a nitrogen atom, an oxygen atom and a sulfur atom;

(43) 8- to 12-membered fused aromatic heterocyclyl-sulfonyl (e.g., benzofurylsulfonyl, isobenzofurylsulfonyl etc.) containing, as a ring constituting atom besides carbon atom, 1 to 4 heteroatoms selected from a nitrogen atom, an oxygen atom and a sulfur atom;

(44) 4- to 7-membered (preferably 5- or 6-membered) non-aromatic heterocyclyl-sulfonyl (e.g., oxiranylsulfonyl, azetidinylsulfonyl etc.) containing, as a ring constituting atom besides carbon atom, 1 to 4 heteroatoms selected from a nitrogen atom, an oxygen atom and a sulfur atom;

(45) amino;

(46) mono-$C_{1-6}$alkylamino (e.g., methylamino, ethylamino, propylamino, isopropylamino, butylamino, isobutylamino, tert-butylamino etc.);

(47) di-$C_{1-6}$ alkylamino (e.g., dimethylamino, diethylamino, dipropylamino, diisopropylamino, dibutylamino, diisobutylamino, di-tert-butylamino etc.);

(48) mono($C_{1-6}$ alkyl-carbonyl)amino (e.g., acetylamino, ethylcarbonylamino, propylcarbonylamino, tert-butylcarbonylamino etc.) optionally having 1 to 3 halogen atoms (e.g., fluorine, chlorine, bromine, iodine);

(49) mono($C_{6-14}$ arylthio (e.g., phenylthio)-$C_{1-6}$ alkyl-carbonyl)amino (e.g., $C_{1-6}$ alkyl-carbonylamino group such as acetylamino, ethylcarbonylamino etc.; phenylthioethylcarbonylamino etc.);

(50) mono(heterocyclyl-$C_{1-8}$ alkyl-carbonyl)amino (the heterocyclyl is 4- to 7-membered (preferably 5- or 6-membered) monocyclic aromatic heterocycle or monocyclic non-aromatic heterocycle (e.g., morpholinyl) containing, as a ring constituting atom besides carbon atom, 1 to 4 heteroatoms selected from an oxygen atom, a sulfur atom and a nitrogen atom) (e.g., morpholinylethylcarbonylamino etc.);

(51) mono($C_{3-6}$ cycloalkyl-carbonyl)amino (e.g., cyclopropylcarbonylamino, cyclobutylcarbonylamino, cyclopentylcarbonylamino, cyclohexylcarbonylamino etc.);

(52) mono($C_{6-14}$aryl-carbonyl)amino (e.g., benzoylamino etc.) optionally having 1 to 3 halogen atoms (e.g., fluorine, chlorine, bromine, iodine);

(53) mono(5- to 7-membered monocyclic aromatic heterocyclyl-carbonyl)amino (which 5- to 7-membered monocyclic aromatic heterocyclyl contains, as a ring constituting atom besides carbon atom, 1 to 4 heteroatoms selected from a nitrogen atom, an oxygen atom and a sulfur atom) (e.g., furylcarbonylamino, thienylcarbonylamino, pyrrolylcarbonylamino, oxazolylcarbonylamino, isoxazolylcarbonylamino, thiazolylcarbonylamino, isothiazolylcarbonylamino, imidazolylcarbonylamino, pyridylcarbonylamino, pyrazolylcarbonylamino etc.);

(54) mono(8- to 12-membered fused aromatic heterocyclyl-carbonyl)amino (which 8- to 12-membered fused aromatic heterocyclyl contains, as a ring constituting atom besides carbon atom, 1 to 4 heteroatoms selected from a nitrogen atom, an oxygen atom and a sulfur atom) (e.g., benzofurylcarbonylamino, isobenzofurylcarbonylamino, benzothienylcarbonylamino, isobenzothienylcarbonylamino etc.);

(55) mono(non-aromatic heterocyclyl-carbonyl)amino (which non-aromatic heterocyclyl is 4- to 7-membered (preferably 5- or 6-membered) non-aromatic heterocycle containing, as a ring constituting atom besides carbon atom, 1 to 4 heteroatoms selected from a nitrogen atom, an oxygen atom and a sulfur atom) (e.g., oxiranylcarbonylamino, azetidinylcarbonylamino, oxetanylcarbonylamino etc.);

(56) thiol;

(57) $C_{1-6}$ alkylsulfanyl (e.g., methylsulfanyl, ethylsulfanyl etc.);

(58) $C_{2-6}$ alkenylsulfanyl (e.g., ethenylsulfanyl, propenylsulfanyl etc.);

(59) $C_{2-6}$ alkynylsulfanyl (e.g., ethynylsulfanyl, propynylsulfanyl, butynylsulfanyl, pentynylsulfanyl, hexynylsulfanyl etc.);

(60) $C_{3-8}$ cycloalkylsulfanyl (e.g., cyclopropylsulfanyl, cyclobutylsulfanyl etc.);

(61) $C_{3-6}$ cycloalkenylsulfanyl (e.g., cyclopropenylsulfanyl, cyclobutenylsulfanyl etc.);

(62) $C_{6-14}$ arylsulfanyl (e.g., phenylsulfanyl etc.);

(63) $C_{3-8}$ cycloalkyl-$C_{1-6}$ alkyl-sulfanyl (e.g., cyclopropylmethylsulfanyl etc.);

(64) $C_{3-6}$ cycloalkenyl-$C_{1-6}$ alkyl-sulfanyl (e.g., cyclopentenylmethylsulfanyl etc.);

(65) a 4- to 7-membered (preferably 5- or 6-membered) monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.) optionally having 1 to 3 $C_{1-4}$ alkyl (e.g., methyl, ethyl etc.), containing, as a ring constituting atom besides carbon atom, 1 to 4 heteroatoms selected from a nitrogen atom, an oxygen atom and a sulfur atom;

(66) an 8- to 12-membered fused aromatic heterocyclic group (e.g., benzofuryl, isobenzofuryl, benzothienyl, isobenzothienyl, indolyl, isoindolyl, 1H-indazolyl, benzimidazolyl, benzoxazolyl etc.) containing, as a ring constituting atom besides carbon atom, 1 to 4 heteroatoms selected from a nitrogen atom, an oxygen atom and a sulfur atom;

(67) a 4- to 7-membered (preferably 5- or 6-membered) non-aromatic heterocyclic group (e.g., oxiranyl, azetidinyl, oxetanyl, thietanyl, pyrrolidinyl, tetrahydrofuryl, thiolanyl, piperidinyl etc.) containing, as a ring constituting atom besides carbon atom, 1 to 4 heteroatoms selected from a nitrogen atom, an oxygen atom and a sulfur atom;
(68) 4- to 7-membered (preferably 5- or 6-membered) monocyclic aromatic heterocyclyl-oxy (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy etc.) containing, as a ring constituting atom besides carbon atom, 1 to 4 heteroatoms selected from a nitrogen atom, an oxygen atom and a sulfur atom;
(69) 8- to 12-membered fused aromatic heterocyclyl-oxy (e.g., benzofuryloxy, isobenzofuryloxy, benzothienyloxy, isobenzothienyloxy, indolyloxy, isoindolyloxy, 1H-indazolyloxy, benzimidazolyloxy, benzoxazolyloxy etc.) containing, as a ring constituting atom besides carbon atom, 1 to 4 heteroatoms selected from a nitrogen atom, an oxygen atom and a sulfur atom;
(70) 5 or 7-membered non-aromatic heterocyclyl-oxy (e.g., oxiranyloxy, azetidinyloxy, oxetanyloxy, thietanyloxy, pyrrolidinyloxy, tetrahydrofuryloxy, thiolanyloxy, piperidinyloxy etc.) containing, as a ring constituting atom besides carbon atom, 1 to 4 heteroatoms selected from a nitrogen atom, an oxygen atom and a sulfur atom;
(71) oxo;
(72) $C_{1-6}$ alkylsulfinyl (e.g., methylsulfinyl, ethylsulfinyl etc.);
(73) $C_{2-6}$ alkenylsulfinyl (e.g., ethenylsulfinyl, propenylsulfinyl etc.);
(74) $C_{2-6}$ alkynylsulfinyl (e.g., ethynylsulfinyl, propynylsulfinyl, butynylsulfinyl, pentynylsulfinyl, hexynylsulfinyl etc.);
(75) $C_{3-8}$ cycloalkylsulfinyl (e.g., cyclopropylsulfinyl, cyclobutylsulfinyl etc.);
(76) $C_{3-6}$ cycloalkenylsulfinyl (e.g., cyclopropenylsulfinyl, cyclobutenylsulfinyl etc.);
(77) $C_{6-14}$ arylsulfinyl (e.g., phenylsulfinyl etc.);
(78) $C_{3-8}$ cycloalkyl-$C_{1-6}$ alkyl-sulfinyl (e.g., cyclopropylmethylsulfinyl etc.);
(79) $C_{3-6}$ cycloalkenyl-$C_{1-6}$alkyl-sulfinyl (e.g., cyclopentenylmethylsulfinyl etc.);
(80) aminothiocarbonyl substituted by $C_{1-6}$ alkyl or $C_{6-14}$ aryl-$C_{1-4}$ alkyl-carbonyl (e.g., methylaminothiocarbonyl, ethylaminothiocarbonyl, propylaminothiocarbonyl, benzylcarbonylaminothiocarbonyl etc.);
(81) di-$C_{1-6}$ alkyl-aminothiocarbonyl (e.g., dimethylaminothiocarbonyl, diethylaminothiocarbonyl, dipropylaminothiocarbonyl etc.);
(82) carboxy;
(83) $C_{1-6}$alkoxycarbonyl (e.g., methoxycarbonyl, ethoxycarbonyl, propoxycarbonyl, isopropoxycarbonyl, butoxycarbonyl, isobutoxycarbonyl, tert-butoxycarbonyl etc.);
(84) $C_{2-6}$ alkenyloxy-carbonyl (e.g., ethenyloxycarbonyl, propenyloxycarbonyl, butenyloxycarbonyl, pentenyloxycarbonyl, hexenyloxycarbonyl etc.);
(85) $C_{2-6}$ alkynyloxy-carbonyl (e.g., ethynyloxycarbonyl, propynyloxycarbonyl, butynyloxycarbonyl, pentynyloxycarbonyl, hexynyloxycarbonyl etc.);
(86) $C_{3-8}$ cycloalkyl-oxy-carbonyl (e.g., cyclopropyloxycarbonyl, cyclobutyloxycarbonyl, cyclopentyloxycarbonyl, cyclohexyloxycarbonyl etc.);
(87) $C_{3-6}$ cycloalkenyloxy-carbonyl (e.g., cyclopropenyloxycarbonyl, cyclobutenyloxycarbonyl, cyclopentenyloxycarbonyl, cyclohexenyloxycarbonyl etc.);
(88) $C_{6-14}$ aryloxy-carbonyl (e.g., phenyloxycarbonyl, 1-naphthyloxycarbonyl, 2-naphthyloxycarbonyl etc.);
(89) $C_{3-8}$ cycloalkyl-$C_{1-6}$alkoxy-carbonyl (e.g., cyclopropylmethyloxycarbonyl, cyclopropylethyloxycarbonyl, cyclobutylmethyloxycarbonyl, cyclopentylmethyloxycarbonyl, cyclohexylthethyloxycarbonyl, cyclohexylethyloxycarbonyl etc.);
(90) $C_{3-6}$cycloalkenyl-$C_{1-6}$alkoxy-carbonyl (e.g., cyclopentenylmethyloxycarbonyl, cyclohexenylmethyloxycarbonyl, cyclohexenylethyloxycarbonyl, cyclohexenylpropyloxycarbonyl etc.); and
(91) $C_{6-14}$ aryl-$C_{1-6}$alkoxy-carbonyl (e.g., phenylmethyloxycarbonyl, phenylethyloxycarbonyl etc.) (hereinafter to be abbreviated as substituent group X). When two or more substituents are present, they may be the same or different, and preferable number of substituents is 1 to 5, more preferably 1 to 3.

Examples of the "$C_{2-8}$ alkenyl group" of the above-mentioned "optionally substituted $C_{2-8}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

Examples of the "alkenyl group" of the above-mentioned "optionally substituted alkenyl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "$C_{2-8}$ alkynyl group" of the above-mentioned "optionally substituted $C_{2-8}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like.

The "alkynyl group" of the above-mentioned "optionally substituted alkynyl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "$C_{1-8}$ alkyl-carbonyl group" of the above-mentioned "optionally substituted C1-8 alkyl-carbonyl group" include acetyl, ethylcarbonyl, propylcarbonyl, isopropylcarbonyl, butylcarbonyl, isobutylcarbonyl, sec-butylcarbonyl, tert-butylcarbonyl, pentylcarbonyl, isopentylcarbonyl, neopentylcarbonyl, 1-ethylpropylcarbonyl, hexylcarbonyl, isohexylcarbonyl, 1,1-dimethylbutylcarbonyl, 2,2-dimethylbutylcarbonyl, 3,3-dimethylbutylcarbonyl, 2-ethylbutylcarbonyl, heptylcarbonyl, octylcarbonyl and the like.

The "$C_{1-8}$ alkyl-carbonyl group" of the above-mentioned "optionally substituted $C_{1-8}$ alkyl-carbonyl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "$C_{3-8}$ cycloalkyl group" of the above-mentioned "optionally substituted $C_{3-8}$ cycloalkyl group" include cyclopropyl, cyclobutyl, cyclopentyl, cyclohexyl, cycloheptyl, cyclooctyl and the like.

The "$C_{3-8}$ cycloalkyl group" of the above-mentioned "optionally substituted $C_{3-8}$ cycloalkyl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "$C_{6-18}$ aryl group" of the above-mentioned "optionally substituted $C_{6-18}$ aryl group" include phenyl, naphthyl, anthryl, phenanthryl, acenaphthylenyl, biphenylyl and the like, and phenyl is preferable.

The "aryl group" of the above-mentioned "optionally substituted aryl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "$C_{6-18}$ aryl-$C_{1-4}$ alkyl group" of the above-mentioned "optionally substituted $C_{6-18}$ aryl-$C_{1-4}$ alkyl group" include benzyl, phenethyl, phenylpropyl, naphthylmethyl, biphenylylmethyl and the like.

The "$C_{6-18}$ aryl-$C_{1-4}$ alkyl group" of the above-mentioned "optionally substituted $C_{6-18}$ aryl-$C_{1-4}$ alkyl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "$C_{6-18}$ aryl-carbonyl group" of the above-mentioned "optionally substituted $C_{6-18}$ aryl-carbonyl group" include phenylcarbonyl, naphthylcarbonyl, anthrylcarbonyl, phenanthrylcarbonyl, acenaphthylenylcarbonyl, biphenylylcarbonyl and the like.

The "$C_{6-18}$ aryl-carbonyl group" of the above-mentioned "optionally substituted $C_{6-18}$ aryl-carbonyl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "$C_{6-18}$ aryl-$C_{1-4}$ alkyl-carbonyl group" of the above-mentioned "optionally substituted $C_{6-18}$ aryl-$C_{1-4}$ alkyl-carbonyl group" include benzylcarbonyl, phenethylcarbonyl, phenylpropylcarbonyl, naphthylmethylcarbonyl, biphenylylmethylcarbonyl and the like.

The "$C_{6-18}$ aryl-$C_{1-4}$ alkyl-carbonyl group" of the above-mentioned "optionally substituted $C_{6-18}$ aryl-$C_{1-4}$ alkyl-carbonyl group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the "heterocyclic group" of the above-mentioned "optionally substituted heterocyclic group" include an aromatic heterocyclic group and a non-aromatic heterocyclic group.

Examples of the aromatic heterocyclic group include a 4- to 7-membered (preferably 5- or 6-membered) monocyclic aromatic heterocyclic group containing, as a ring constituting atom besides carbon atom, 1 to 4 heteroatoms selected from an oxygen atom, a sulfur atom and a nitrogen atom, and a 8- to 12-membered fused aromatic heterocyclic group. Examples of the fused aromatic heterocyclic group include a group derived from a fused ring wherein a ring corresponding to such 4- to 7-membered monocyclic aromatic heterocyclic group, and 1 or 2 rings selected from a 5- or 6-membered aromatic heterocycle containing 1 or 2 nitrogen atoms, a 5-membered aromatic heterocycle containing one sulfur atom and a benzene ring are condensed, and the like.

Preferable examples of the aromatic heterocyclic group include a monocyclic aromatic heterocyclic group such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like; a fused aromatic heterocyclic group such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuryl (e.g., 2-benzofuryl3-benzofuryl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), pyrrolopyrimidinyl (e.g., 1H-pyrrolo[2,3-d]pyrimidin-2-yl, 1H-pyrrolo[2,3-d]pyrimidin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

Examples of the non-aromatic heterocyclic group include a 4- to 7-membered (preferably 5- or 6-membered) monocyclic non-aromatic heterocyclic group containing, as a ring constituting atom besides carbon atom, 1 to 4 heteroatoms selected from an oxygen atom, a sulfur atom and a nitrogen atom, and a 8- to 12-membered fused non-aromatic heterocyclic group. Examples of the fused non-aromatic heterocyclic group include a group derived from a fused ring wherein a ring corresponding to such 4- to 7-membered monocyclic non-aromatic heterocyclic group, and 1 or 2 rings selected from a 5- or 6-membered heterocycle containing 1 or 2 nitrogen atoms, a 5-membered heterocycle containing one sulfur atom and a benzene ring are condensed, and the like.

Preferable examples of the non-aromatic heterocyclic group include a monocyclic non-aromatic heterocyclic group such as oxetanyl (e.g., 2-oxetanyl, 3-oxetanyl), pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), 2-thioxo-1,3-oxazolidin-5-yl, pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like; a fused non-aromatic heterocyclic group such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like.

The "heterocyclic group" of the above-mentioned "optionally substituted heterocyclic group" may have one or more (preferably 1 to 5, more preferably 1 to 3) substituents at substitutable position(s). Examples of such substituent include substituents selected from substituent group X. When the number of the substituents is two or more, the respective substituents may be the same or different.

Examples of the above-mentioned "optionally substituted heterocyclyl-$C_{1-4}$ alkyl group" include a group wherein $C_{1-4}$ alkyl (e.g., methyl, ethyl, propyl, isopropyl, butyl, isobutyl, sec-butyl, tert-butyl) is substituted by the above-mentioned "optionally substituted heterocyclic group".

Examples of the above-mentioned "optionally substituted heterocyclyl-carbonyl group" include a group wherein carbonyl is bonded to the above-mentioned "optionally substituted heterocyclic group".

Examples of the above-mentioned "optionally substituted heterocyclyl-$C_{1-4}$ alkyl-carbonyl group" include a group wherein carbonyl is bonded to the above-mentioned "optionally substituted heterocyclyl-$C_{1-4}$ alkyl group".

The "carbamoyl group" of the above-mentioned "optionally substituted carbamoyl group" may have 1 or 2 substituents. Examples of such substituent include the aforementioned optionally substituted $C_{1-8}$ alkyl group, optionally substituted $C_{2-8}$ alkenyl group, optionally substituted $C_{2-8}$ alkynyl group, optionally substituted $C_{1-8}$ alkyl-carbonyl group, optionally substituted $C_{3-8}$ cycloalkyl group, optionally substituted $C_{6-18}$ aryl group, optionally substituted $C_{6-18}$ aryl-$C_{1-4}$ alkyl group, optionally substituted $C_{6-18}$ aryl-carbonyl group, optionally substituted $C_{6-18}$ aryl-$C_{1-4}$ alkyl-carbonyl group, optionally substituted heterocyclic group (heterocyclic group bonded via a carbon atom), optionally substituted heterocyclyl-$C_{1-4}$ alkyl group, optionally substituted heterocyclyl-carbonyl group and optionally substituted heterocyclyl-$C_{1-4}$ alkyl-carbonyl group. When the number of the substituents is two or more, the respective substituents may be the same or different.

Examples of the "optionally substituted group bonded via a nitrogen atom" include (i) amino, (ii) amino monosubstituted by the above-mentioned "optionally substituted group bonded via a carbon atom", (iii) amino disubstituted by the above-mentioned "optionally substituted group bonded via a carbon atom", preferably $C_{1-6}$ alkyl (e.g., methyl, ethyl, propyl, isopropyl, butyl, isobutyl, sec-butyl, tert-butyl, pentyl, hexyl etc.), and (iv) the above-mentioned optionally substituted heterocyclic group (heterocyclic group bonded via a nitrogen atom) and the like.

Examples of the "optionally substituted group bonded via an oxygen atom" include hydroxy optionally substituted by the above-mentioned "optionally substituted group bonded via a carbon atom".

Examples of the "optionally substituted group bonded via a sulfur atom" include mercapto optionally substituted by the above-mentioned "optionally substituted group bonded via a carbon atom". The sulfur atom may be oxidized.

HY is an optionally substituted nitrogen-containing aromatic heterocyclic group (excluding 3-isoxazolyl group, 2-pyridyl group, 3-pyridyl group, 5-pyrimidyl group, 2-pyrimidyl group and pyrazinyl group).

Examples of the "nitrogen-containing aromatic heterocyclic group" include a 4- to 7-membered (preferably 5- or 6-membered) monocyclic nitrogen-containing aromatic heterocyclic group containing, as a ring constituting atom, carbon atom and 1 to 4 nitrogen atoms, and further, optionally containing 1 or 2 heteroatoms selected from an oxygen atom and a sulfur atom, and a 8- to 12-membered fused nitrogen-containing aromatic heterocyclic group. Examples of the fused nitrogen-containing aromatic heterocyclic group include a group derived from a fused ring wherein a ring corresponding to such 4- to 7-membered monocyclic nitrogen-containing aromatic heterocyclic group, and 1 or 2 rings selected from a 5- or 6-membered aromatic heterocycle containing 1 or 2 nitrogen atoms, a 5-membered aromatic heterocycle containing one sulfur atom and a benzene ring are fused, and the like.

Preferable examples of the nitrogen-containing aromatic heterocyclic group include a monocyclic nitrogen-containing aromatic heterocyclic group such as pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like; a fused nitrogen-containing aromatic heterocyclic group such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), pyrrolopyrimidinyl (e.g., 1H-pyrrolo[2,3-d]pyrimidin-2-yl, 1H-pyrrolo[2,3-d]pyrimidin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), tetrahydropyrazolopyridyl, pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

As preferable examples of the substituent of the "nitrogen-containing aromatic heterocyclic group", a group selected from a substituent group consisting of (1) a halogen atom (e.g., fluorine, chlorine, bromine, iodine);

(2) cyano;

(3) nitro;

(4) an optionally substituted hydrocarbon group;

(5) an optionally substituted heterocyclic group;

(6) a formyl group;

(7) an optionally substituted hydrocarbon-carbonyl group;

(8) an optionally substituted heterocyclyl-carbonyl group;

(9) an optionally substituted hydroxy group, specifically a hydroxy group optionally substituted by a group selected from an optionally substituted hydrocarbon group and an optionally substituted heterocyclic group;

(10) an optionally substituted amino group, specifically an amino group optionally substituted by 1 or 2 groups selected from an optionally substituted hydrocarbon group, an optionally substituted heterocyclic group, an optionally substituted hydrocarbon-carbonyl group and an optionally substituted heterocyclyl-carbonyl group;

(11) an optionally substituted carbamoyl group, specifically a carbamoyl group optionally substituted by 1 or 2 groups selected from an optionally substituted hydrocarbon group, an optionally substituted heterocyclic group, an optionally substituted hydrocarbon-carbonyl group and an optionally substituted heterocyclyl-carbonyl group;

(12) an optionally substituted sulfonyl group, specifically a sulfonyl group optionally substituted by a group selected from an optionally substituted hydrocarbon group and an optionally substituted heterocyclic group;

(13) an optionally substituted sulfamoyl group, specifically a sulfamoyl group optionally substituted by a group selected from an optionally substituted hydrocarbon group and an optionally substituted heterocyclic group; and

(14) an optionally esterified carboxyl group, specifically a carboxyl group optionally esterified by a group selected from an optionally substituted hydrocarbon group and an optionally substituted heterocyclic group, preferably an optionally substituted alkoxycarbonyl group, particularly preferably a carboxyl group optionally esterified by $C_{1-8}$alkyl (e.g., $C_{1-6}$ alkyl such as methyl, ethyl and the like) (hereinafter to be abbreviated as substituent group Y) can be used. Particularly, a group selected from the above-mentioned substituent group X can be used.

As the "optionally substituted hydrocarbon group" in the explanation of substituent group Y, an optionally substituted alkyl group (preferably $C_{1-20}$ alkyl group, particularly preferably $C_{1-8}$ alkyl group), an optionally substituted alkenyl group (preferably $C_{2-8}$ alkenyl group), an optionally substituted alkynyl group (preferably $C_{2-8}$ alkynyl group), an optionally substituted $C_{3-8}$ cycloalkyl group, an optionally substituted aryl group (preferably $C_{6-18}$ aryl group), an optionally substituted $C_{6-18}$ aryl-$C_{1-4}$ alkyl group and the like, which are exemplified as "optionally substituted group bonded via a carbon atom", can be used.

As the "optionally substituted heterocyclic group" in the explanation of substituent group Y, a group similar to the optionally substituted heterocyclic group exemplified as the "optionally substituted group bonded via a carbon atom" can be used.

As the "optionally substituted hydrocarbon" of the "optionally substituted hydrocarbon-carbonyl group" in the explanation of substituent group Y, a group similar to the above-mentioned "optionally substituted hydrocarbon group" can be used.

As the "optionally substituted heterocyclyl" of the "optionally substituted heterocyclyl-carbonyl group" in the explanation of substituent group Y, a group similar to the optionally substituted heterocyclic group exemplified as the "optionally substituted group bonded via a carbon atom" can be used.

As the "optionally substituted carbamoyl group" in the explanation of substituent group Y, a group similar to the optionally substituted carbamoyl group exemplified as the "optionally substituted group bonded via a carbon atom" can be used.

Among these, as the substituent of the "nitrogen-containing aromatic heterocyclic group", a halogen atom, an optionally substituted hydrocarbon group, an optionally substituted heterocyclic group, an optionally substituted hydroxy group, an optionally substituted amino group and the like are preferable. As the substituent of the monocyclic nitrogen-containing aromatic heterocyclic group (e.g., 4-pyridyl, pyrimidyl, pyrazolyl, particularly 4-pyridyl), particularly preferred are an optionally substituted amino group, particularly (1) $C_{1-8}$ alkyl-carbonylamino (e.g., $C_{1-6}$ alkyl-carbonylamino such as acetylamino, phenoxyacetylamino, ethylcarbonylamino, propylcarbonylamino, isopropylcarbonylamino, tert-butylcarbonylamino and the like; phenylthioethylcarbonylamino; thienylmethylcarbonyl, morpholinylethylcarbonylamino and the like) optionally substituted by substituent(s) selected from $C_{6-18}$ arylthio (e.g., phenylthio), $C_{6-18}$ aryloxy (e.g., phenoxy), a 4- to 7-membered (preferably 5- or 6-membered) monocyclic aromatic heterocyclic group (e.g., thienyl) containing, as a ring constituting atom besides carbon atom, 1 to 4 heteroatoms selected from an oxygen atom, a sulfur atom and a nitrogen atom and a monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, (2) $C_{3-8}$ cycloalkyl-carbonylamino (e.g., cyclopropylcarbonylamino, cyclopentyl, cyclohexylcarbonylamino), (3) $C_{6-18}$ aryl-carbonylamino (e.g., fluorophenylcarbonyl, chlorophenylcarbonyl, difluorophenylcarbonyl, methoxyphenylcarbonyl, dimethylaminophenylcarbonylamino) optionally substituted by a substituent(s) selected from a halogen atom, $C_{1-6}$ alkoxy, amino and mono- or di-$C_{1-6}$ alkylamino, (4) $C_{6-18}$ aryl-$C_{1-4}$ alkyl-carbonylamino (e.g., benzylcarbonylamino), (5) 4- to 7-membered (preferably 5- or 6-membered) monocyclic heterocyclyl (e.g., furyl, thienyl, isoxazolyl, pyridyl)-carbonylamino (e.g., furylcarbonylamino, methylisoxazolyl), said monocyclic heterocyclyl contains, as a ring constituting atom besides carbon atom, 1 to 4 heteroatoms selected from an oxygen atom, a sulfur atom and a nitrogen atom and is optionally substituted by $C_{1-6}$ alkyl.

More specifically, preferable examples of HY include (i) a group represented by

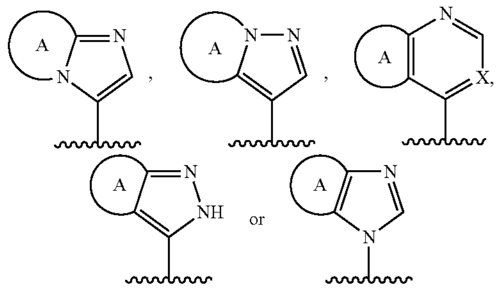

, , , or wherein A is a cyclic group and X is CH or N, optionally substituted by the above-mentioned substituent(s), particularly, (1) hydroxy, (2) $C_{1-6}$ alkyl such as methyl, ethyl and the like, (3) $C_{1-6}$ alkoxy optionally substituted by hydroxy, (4) $C_{6-18}$ aryl-$C_{1-4}$ alkyl-oxy (e.g., benzyloxy), (5) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom, (6) 4- to 7-membered (preferably 5- or 6-membered) monocyclic non-aromatic heterocyclyl-$C_{1-4}$ alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom, and the like, or (ii) a 4-pyridyl group, a pyrimidinyl group, a pyrazolyl group, a thiazolyl group, an oxazolyl group, an imidazolyl group, a triazolyl group, an isothiazolyl group or a pyridazinyl group, particularly a 4-pyridyl group and the like, which are optionally substituted by the above-mentioned substituent(s), particularly, (1) a halogen atom (e.g., chlorine atom), (2) $C_{1-6}$ alkyl (e.g., methyl, ethyl, propyl), (3) $C_{1-8}$ alkyl-carbonylamino (e.g., $C_{1-6}$alkyl-carbonylamino such as acetylamino, phenoxyacetylamino, ethylcarbonylamino, propylcarbonylamino, isopropylcarbonylamino, tert-butylcarbonylamino and the like; phenylthioethylcarbonylamino; thienylmethylcarbonyl, morpholinylethylcarbonylamino and the like) optionally substituted by substituent(s) selected from $C_{6-18}$ arylthio (e.g., phenylthio), $C_{6-18}$ aryloxy (e.g., phenoxy), and 4- to 7-membered (preferably 5- or 6-membered) monocyclic aromatic heterocyclic group (e.g., thienyl) or monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, (4) cycloalkyl-carbonylamino (e.g., cyclopropylcarbonylamino, cyclopentylcarbonylamino, cyclohexylcarbonylamino), (5) $C_{6-18}$ aryl-carbonylamino (e.g., fluorophenylcarbonylamino, chlorophenylcarbonylamino, difluorophenylcarbonylamino, methylphenylcarbonylamino, methoxyphenylcarbonylamino, dimethylaminophenylcarbonylamino) optionally substituted by a substituent(s) selected from a halogen atom, $C_{1-6}$ alkyl, $C_{1-6}$ alkoxy, amino and mono- or di-$C_{1-6}$ alkylamino, (6) $C_{6-18}$ aryl-$C_{1-4}$ alkyl-carbonylamino (e.g., benzylcarbonylamino) and (7) 4- to 7-membered (preferably 5- or 6-membered) monocyclic heterocyclyl (e.g., furyl, thienyl, isoxazolyl, pyridyl)-carbonylamino (e.g., furylcarbonylamino, methylisoxazolylcarbonylamino), said monocyclic heterocyclyl contains, as a ring constituting atom besides carbon atom, 1 to 4 heteroatoms selected from an oxygen atom, a sulfur atom and a nitrogen atom and is optionally substituted by $C_{1-6}$ alkyl.

As the cyclic group for A, cyclic hydrocarbon or heterocycle can be used.

As the cyclic hydrocarbon, $C_{6-18}$ cyclic hydrocarbon such as benzene, naphthalene and the like, $C_{3-8}$ cycloalkane such as cyclopentane, cyclohexane, cycloheptane, cyclooctane, etc. and the like are used.

As the heterocycle, a ring corresponding to the heterocyclic group exemplified as the group bonded via a carbon atom can be used.

As HY, a 4-pyridyl group, a 4-pyrimidyl group, a pyrazolyl group or a thiazolyl group, particularly a 4-pyridyl group, optionally substituted by substituent(s) selected from (1) $C_{1-8}$ alkyl-carbonylamino (e.g., $C_{1-6}$ alkyl-carbonylamino such as acetylamino, phenoxyacetylamino, ethylcarbonylamino, propylcarbonylamino, isopropylcarbonylamino, tert-butylcarbonylamino and the like; phenylthioethylcarbonylamino; thienylmethylcarbonyl, morpholinylethylcarbonylamino and the like) optionally substituted by substituent(s) selected from $C_{6-18}$ arylthio (e.g., phenylthio), $C_{6-18}$ aryloxy (e.g., phenoxy), and 4- to 7-membered (preferably 5- or 6-membered) monocyclic aromatic heterocyclic group (e.g., thienyl) or monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, (2) $C_{3-8}$ cycloalkyl-carbonylamino (e.g., cyclopropylcarbonylamino, cyclopentylcarbonylamino, cyclohexylcarbonylamino), (3) $C_{6-18}$ aryl-carbonylamino (e.g., fluorophenylcarbonylamino, chlorophenylcarbonylamino, difluorophenylcarbonylamino, methylphenylcarbonylamino, methoxyphenylcarbonylamino, dimethylaminophenylcarbonylamino) optionally substituted by substituent(s) selected from a halogen atom, $C_{1-6}$ alkyl, $C_{1-6}$ alkoxy, amino and mono- or di-$C_{1-6}$ alkylamino, (4) $C_{6-18}$ aryl-$C_{1-4}$ alkyl-carbonylamino (e.g., benzylcarbonylamino) and (5) 4- to 7-membered (preferably 5- or 6-membered) monocyclic heterocyclyl (e.g., furyl, thienyl, isoxazolyl, pyridyl)-carbonylamino (e.g., furylcarbonylamino, methyl isoxazolylcarbonylamino), said monocyclic heterocyclyl contains, as a ring constituting atom besides carbon atom, 1 to 4 heteroatoms selected from an oxygen atom, a sulfur atom and a nitrogen atom and is optionally substituted by $C_{1-6}$ alkyl, is preferable.

Particularly, as HY, (i) a group represented by

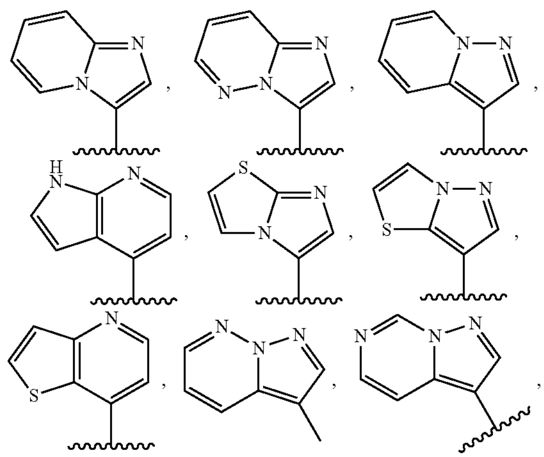

, , , , , , , , ,

-continued

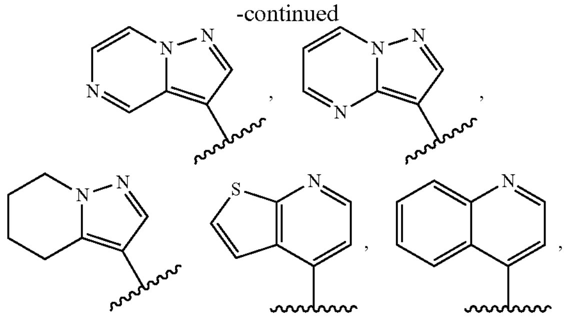

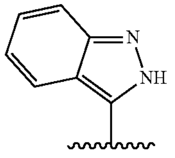

or

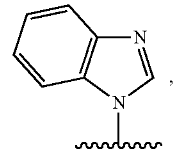

, particularly, a group represented by

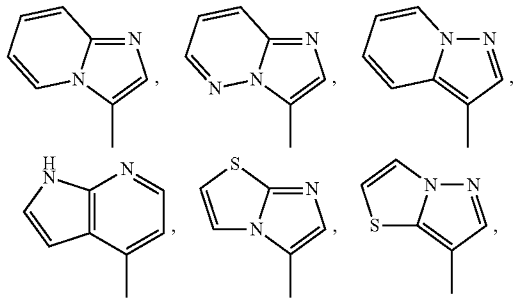

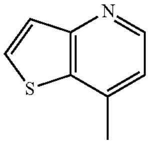

or

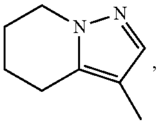

, optionally substituted by the above-mentioned substituent(s), particularly, (1) hydroxy, (2) $C_{1-6}$ alkyl such as methyl and the like which is optionally substituted by 4- to 7-membered (preferably 5- or 6-membered) monocyclic aromatic heterocyclyl-carbonyl-amino or $C_{1-6}$ alkylcarbonylamino optionally substituted by amino containing, as a ring constituting atom besides carbon atom, 1 to 4 heteroatoms selected from an oxygen atom, a sulfur atom and a nitrogen atom, (3) $C_{1-6}$ alkoxy optionally substituted by hydroxy, (4) $C_{6-18}$ aryl-$C_{1-4}$ alkyl-oxy (e.g., benzyloxy), (5) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom which is optionally substituted by $C_{1-6}$ alkyl optionally substituted by halogen, (6) 4- to 7-membered (preferably 5- or 6-membered) monocyclic non-aromatic heterocyclyl-$C_{1-4}$alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom and the like (e.g., hydroxy, $C_{1-6}$ alkyl such as methyl and the like) as well as (7) halogen, (8) $C_{2-6}$ alkenyl, (9)$C_{3-8}$ cycloalkyl, (10) $C_{6-18}$ aryl optionally substituted by $C_{1-6}$ alkoxy or halogen, (11) 4- to 7-membered (preferably 5- or 6-membered) monocyclic aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, (12) 4- to 7-membered (preferably 5- or 6-membered) monocyclic non-aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, (ii) a group represented by

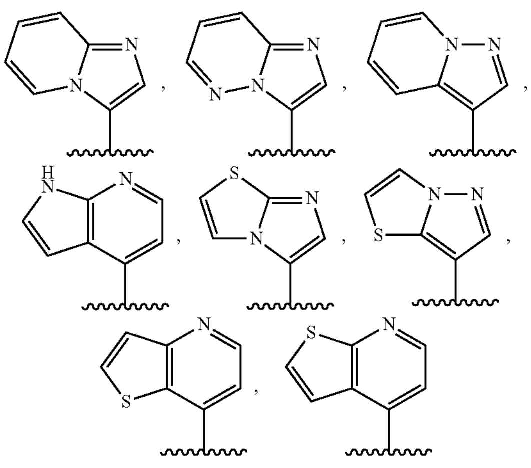

optionally substituted by the above-mentioned substituent(s), particularly, (1) hydroxy, (2) $C_{1-6}$ alkyl such as methyl and the like which is optionally substituted by 4- to 7-membered (preferably 5- or 6-membered) monocyclic aromatic heterocyclyl-carbonyl-amino or $C_{1-6}$ alkylcarbonylamino optionally substituted by amino containing, as a ring constituting atom besides carbon atom, 1 to 4 heteroatoms selected from an oxygen atom, a sulfur atom and a nitrogen atom, (3) $C_{1-6}$ alkoxy optionally substituted by hydroxy, (4) $C_{6-18}$ aryl-$C_{1-4}$alkyl-oxy (e.g., benzyloxy), (5) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom, which is optionally substituted by $C_{1-6}$ alkyl optionally substituted by halogen (6) 4- to 7-membered (preferably 5- or 6-membered) monocyclic non-aromatic heterocyclyl-$C_{1-4}$alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom and the like (e.g., hydroxy, $C_{1-6}$ alkyl such as methyl and the like) as well as (7) halogen, (8) $C_{2-6}$ alkenyl, (9)$C_{3-8}$ cycloalkyl, (10) $C_{6-18}$ aryl optionally substituted by $C_{1-6}$ alkoxy or halogen, (11) 4- to 7-membered (preferably 5- or 6-membered) monocyclic aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, (12) 4- to 7-membered (preferably 5- or 6-membered) monocyclic non-aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, or (iii) a group represented by

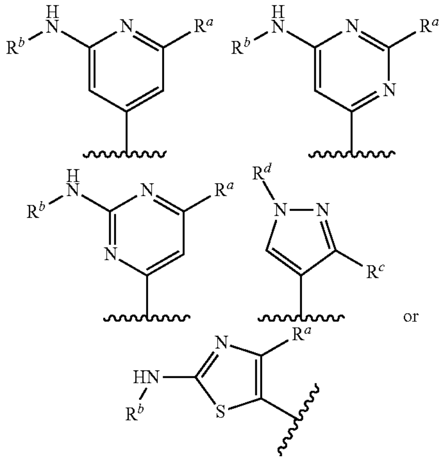

or wherein $R^a$ and $R^c$ are each a hydrogen atom, an alkyl group (for example, the aforementioned $C_{1-20}$ alkyl group, preferably the aforementioned $C_{1-6}$ alkyl group) or a halogen atom, $R_b$ is (i) a hydrogen atom, (ii) an optionally substituted hydrocarbon-carbonyl group, (iii) an optionally substituted heterocyclyl-carbonyl group, (iv) an optionally substituted carbamoyl group, (v) an optionally substituted alkoxycarbonyl group, (vi) an optionally substituted hydrocarbon-sulfonyl group, (vii) an optionally substituted heterocyclyl-sulfonyl group, (viii) an optionally substituted sulfamoyl group, (ix) an optionally substituted hydrocarbon group or (x) an optionally substituted heterocyclic group, and Rd is (i) a hydrogen atom, (ii) an optionally substituted hydrocarbon group or (iii) an optionally substituted heterocyclic group, particularly a group represented by

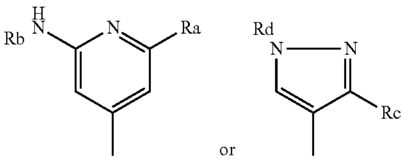

or and the like, is preferable.

As the alkyl group for $R^a$ or $R^c$, a $C_{1-20}$ alkyl group, preferably a $C_{1-8}$ alkyl group such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl and the like can be used. Of these, a $C_{1-6}$ alkyl group such as methyl, ethyl, propyl and the like are preferable.

As the halogen atom for $R^a$ or $R^c$, a fluorine atom, a chlorine atom, a bromine atom and an iodine atom can be used. Of these, a chlorine atom is preferable.

As the "optionally substituted hydrocarbon-carbonyl group" for $R^b$, a group similar to the "optionally substituted hydrocarbon-carbonyl group" of the aforementioned substituent group Y can be used.

As the "optionally substituted heterocyclyl-carbonyl group" for $R^b$, a group similar to the "optionally substituted heterocyclyl-carbonyl group" of the aforementioned substituent group Y can be used.

As the "optionally substituted carbamoyl group" for $R^b$, those similar to the "optionally substituted carbamoyl group" exemplified as the "optionally substituted group bonded via a carbon atom" can be used.

As the "optionally substituted alkoxycarbonyl group" for $R^b$, a $C_{1-8}$ alkoxycarbonyl group (e.g., methoxycarbonyl, ethoxycarbonyl, propoxycarbonyl and the like) optionally substituted by substituent(s) selected from the aforementioned substituent group X and the like can be used.

As the "optionally substituted hydrocarbon" of the "optionally substituted hydrocarbon-sulfonyl group" for $R^b$, a group similar to the "optionally substituted hydrocarbon group" of the aforementioned substituent group Y can be used.

As the "optionally substituted heterocyclyl" of the "optionally substituted heterocyclyl-sulfonyl group" for $R^b$, a group similar to the "optionally substituted heterocyclic group" of the aforementioned substituent group Y can be used.

As the "optionally substituted sulfamoyl group" for $R^b$, a group similar to the "optionally substituted sulfamoyl group" of the aforementioned substituent group Y can be used.

As the "optionally substituted hydrocarbon group" for $R^b$, a group similar to the "optionally substituted hydrocarbon group" of the aforementioned substituent group Y can be used.

As the "optionally substituted heterocyclic group" for $R^b$, a group similar to the "optionally substituted heterocyclic group" of the aforementioned substituent group Y can be used.

As the "optionally substituted hydrocarbon group" for $R^d$, a group similar to the "optionally substituted hydrocarbon group" of the aforementioned substituent group Y can be used.

As the "optionally substituted heterocyclic group" for $R^d$, a group similar to the "optionally substituted heterocyclic group" of the aforementioned substituent group Y can be used.

As $R^a$, a hydrogen atom, a halogen atom (e.g., chlorine atom), a $C_{1-6}$ alkyl group such as methyl, ethyl, propyl and the like are preferable.

As $R^b$, (1) a hydrogen atom, (2) a $C_{1-8}$ alkyl-carbonyl group (e.g., $C_{1-6}$ alkyl-carbonyl group such as acetyl, ethylcarbonyl and the like) optionally substituted by a substituent(s) selected from $C_{6-18}$ arylthio (e.g., phenylthio), 4- to 7-membered (preferably 5- or 6-membered) monocyclic aromatic heterocyclic group or monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, and the like, (3) a $C_{3-8}$ cycloalkyl-carbonyl group (e.g., cyclopropylcarbonyl) and the like are preferable.

As $R^c$ or $R^d$, a hydrogen atom, a $C_{1-6}$ alkyl group such as methyl, ethyl, propyl and the like, and the like are preferable.

In addition, preferable examples of HY include (i) a 8- to 10-membered nitrogen-containing aromatic fused heterocyclic group containing, besides carbon atom and nitrogen atom, 1 to 4 heteroatoms selected from an oxygen atom and a sulfur atom, which is optionally substituted by substituent(s) selected from (1) hydroxy, (2) $C_{1-6}$ alkyl such as methyl and the like, (3) $C_{1-6}$ alkoxy optionally substituted by hydroxy, (4) $C_{6-18}$ aryl-$C_{1-4}$ alkyl-oxy (e.g., benzyloxy), (5) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom and (6) 4- to 7-membered (preferably 5- or 6-membered) monocyclic non-aromatic heterocyclyl-$C_{1-4}$ alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom, (ii) a 4-pyridyl group or a pyrazolyl group, particularly a 4-pyridyl group, optionally substituted by substituent(s) selected from (1) a halogen atom (e.g., a chlorine atom), (2) C1-6 alkyl (e.g., methyl, ethyl, propyl), (3) $C_{1-8}$ alkyl-carbonylamino (e.g., $C_{1-6}$ alkyl-carbonylamino such as acetylamino, phenoxyacetylamino, ethylcarbonylamino, propylcarbonylamino, isopropylcarbonylamino, tert-butylcarbonylamino and the like; phenylthioethylcarbonylamino; thienylmethylcarbonyl, morpholinylethylcarbonylamino and the like) optionally substituted by substituent(s) selected from $C_{6-18}$ arylthio (e.g., phenylthio), $C_{6-18}$ aryloxy (e.g., phenoxy), and 4- to 7-membered (preferably 5- or 6-membered) monocyclic aromatic heterocyclic group (e.g., thienyl) or monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, (4) $C_{3-8}$ cycloalkyl-carbonylamino (e.g., cyclopropylcarbonylamino, cyclopentylcarbonylamino, cyclohexylcarbonylamino), (5) $C_{6-18}$ aryl-carbonylamino (e.g., fluorophenylcarbonylamino, chlorophenylcarbonylamino, difluorophenylcarbonylamino, methylphenylcarbonylamino, methoxyphenylcarbonylamino, dimethylaminophenylcarbonylamino) optionally substituted by substituent(s) selected from a halogen atom, $C_{1-6}$ alkyl, $C_{1-6}$ alkoxy, amino and mono- or di-$C_{1-6}$ alkylamino, (6) $C_{6-18}$ aryl-$C_{1-4}$ alkyl-carbonylamino (e.g., benzylcarbonylamino) and (7) 4- to 7-membered (preferably 5- or 6-membered) monocyclic heterocyclyl (e.g., furyl, thienyl, isoxazolyl, pyridyl)-carbonylamino (e.g., furylcarbonylamino, methylisoxazolylcarbonylamino), said monocyclic heterocyclyl contains, as a ring constituting atom besides carbon atom, 1 to 4 heteroatoms selected from an oxygen atom, a sulfur atom and a nitrogen atom and is optionally substituted by $C_{1-6}$ alkyl, and the like.

$R^2$ is a halogen atom, or the aforementioned optionally substituted group bonded via a carbon atom, a nitrogen atom, an oxygen atom or a sulfur atom. Particularly, (i) a halogen atom, (ii) an optionally substituted hydroxy group, (iii) an optionally substituted hydrocarbon group, (iv) an optionally substituted heterocyclic group, (v) an optionally substituted amino group, (vi) an optionally substituted thiol group or (vii) an acyl group is preferable.

As the halogen atom, a fluorine atom, a chlorine atom, a bromine atom or an iodine atom is used.

As the “optionally substituted hydroxy group”, a group similar to the “optionally substituted hydroxy group” for the aforementioned substituent group Y is used.

As the “optionally substituted hydrocarbon group”, a group similar to the “optionally substituted hydrocarbon group” for the aforementioned substituent group Y is used.

As the “optionally substituted heterocyclic group”, a group similar to the “optionally substituted heterocyclic group” for the aforementioned substituent group Y is used.

As the “optionally substituted amino group”, a group similar to the “optionally substituted amino group” for the aforementioned substituent group Y is used.

As the “optionally substituted thiol group”, a thiol group optionally substituted by the “optionally substituted hydrocarbon group” for the aforementioned substituent group Y or the “optionally substituted heterocyclic group” for the aforementioned substituent group Y is used.

As the “acyl group”, a “formyl group”, an “optionally substituted hydrocarbon-carbonyl group”, an “optionally substituted heterocyclyl-carbonyl group”, an “optionally substituted carbamoyl group”, an “optionally substituted sulfonyl group”, an “optionally substituted sulfamoyl group”, an “optionally esterified carboxyl group” and the like for the aforementioned substituent group Y are used.

As $R^2$, an optionally substituted hydrocarbon group, an optionally substituted heterocyclic group and the like are preferable. For example, (i) a $C_{1-8}$ alkyl group (preferably a $C_{1-6}$ alkyl group) (e.g., a tert-butyl group), (ii) a $C_{2-8}$ alkenyl group (e.g., a $C_{2-6}$ alkenyl group such as a propenyl group and the like), (iii) a $C_{3-8}$ cycloalkyl group (e.g., a cyclohexyl group), (iv) a hydroxy group (e.g., an ethyloxy group, a propyloxy group, a propenyloxy group, a benzyloxy group) optionally substituted by $C_{1-8}$ alkyl (preferably $C_{1-6}$ alkyl), $C_{2-8}$ alkenyl (preferably $C_{2-6}$ alkenyl) or $C_{6-18}$ aryl-$C_{1-4}$ alkyl (preferably phenyl-$C_{1-4}$ alkyl), (v) a $C_{6-18}$ aryl group (preferably a phenyl group) optionally substituted by a halogen atom, an optionally halogenated $C_{1-8}$ alkyl (preferably optionally halogenated $C_{1-6}$ alkyl) or $C_{1-8}$ alkoxy (preferably $C_{1-6}$ alkoxy) (e.g., a phenyl group, a trifluoromethylphenyl group, a fluorophenyl group, a difluorophenyl group, a methoxyphenyl group, a chlorophenyl group), (vi) a $C_{6-18}$ aryl-$C_{1-4}$ alkyl group (preferably a phenyl-$C_{1-4}$ alkyl group) (e.g., a benzyl group), (vii) a 4- to 7-membered (preferably 5- or 6-membered) aromatic monocyclic heterocyclic group (e.g., a thienyl group, a furyl group) containing, besides carbon atom, 1 to 3 heteroatoms selected from a nitrogen atom, an oxygen atom and a sulfur atom, (vii) a 4- to 7-membered (preferably 5- or 6-membered) non-aromatic heterocyclic group (e.g., a tetrahydropyranyl group) containing, besides carbon atom, 1 to 3 heteroatoms selected from a nitrogen atom, an oxygen atom and a sulfur atom and the like are preferably used. Among these, a $C_{6-18}$ aryl group (e.g., phenyl group, trifluoromethylphenyl group, fluorophenyl group, difluorophenyl group, methoxyphenyl group, chlorophenyl group) optionally substituted by a halogen atom, an optionally halogenated $C_{1-8}$ alkyl or $C_{1-8}$ alkoxy, and the like are preferable.

$R^1$ is (1) $CON(R^4)R^{4'}$, wherein $R^4$ and $R^{4'}$ are hydrogen or optionally substituted $C_1$-$C_6$ aliphatic, or (2) an optionally substituted 5-membered aromatic heterocyclic group containing 2 to 4 nitrogen atoms besides carbon atom, which is bonded via a carbon atom; (2) an optionally substituted 5-membered aromatic heterocyclic group containing 2 to 4 nitrogen atoms besides carbon atom, which is bonded via a carbon atom or (3) an optionally substituted 5-membered aromatic heterocyclic group containing 1 to 3 nitrogen atoms besides carbon atom and further containing one oxygen atom or sulfur atom, which is bonded via a carbon atom.

As $R^1$, (1) an optionally substituted 5-membered aromatic heterocyclic group containing 2 to 4 nitrogen atoms besides carbon atom, which is bonded via a carbon atom or (2) an optionally substituted 5-membered aromatic heterocyclic group containing 1 to 3 nitrogen atoms besides carbon atom and further containing one oxygen atom or sulfur atom, which is bonded via a carbon atom is preferable.

However, when $R^1$ is an optionally substituted thiazolyl group and HY is an optionally substituted thiazolyl group, the optionally substituted thiazolyl group for HY is a group represented by

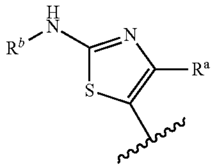

wherein $R^a$ is a hydrogen atom, an alkyl group or a halogen atom,
$R^b$ is (i) a hydrogen atom, (ii) an optionally substituted hydrocarbon-carbonyl group, (iii) an optionally substituted heterocyclyl-carbonyl group, (iv) an optionally substituted carbamoyl group, (v) an optionally substituted alkoxycarbonyl group, (vi) an optionally substituted hydrocarbon-sulfonyl group, (vii) an optionally substituted heterocyclyl-sulfonyl group, (viii) an optionally substituted sulfamoyl group, (ix) an optionally substituted hydrocarbon group or (x) an optionally substituted heterocyclic group.

Examples of the "5-membered aromatic heterocyclic group containing 2 to 4 nitrogen atoms besides carbon atom, which is bonded via a carbon atom" include imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl) and the like. Particularly, triazolyl (e.g., 1,2,4-triazol-1-yl, 1,2,4-triazol-3-yl, 1,2,3-triazol-1-yl, 1,2,3-triazol-2-yl, 1,2,3-triazol-4-yl) is preferable.

As the substituent of the "5-membered aromatic heterocyclic group containing 2 to 4 nitrogen atoms besides carbon atom, which is bonded via a carbon atom", a group selected from the aforementioned substituent group X is used. Particularly, $C_{1-8}$ alkyl (preferably, $C_{1-6}$ alkyl such as methyl and the like) and the like are preferable.

As the "5-membered aromatic heterocyclic group containing 1 to 3 nitrogen atoms besides carbon atom and further containing one oxygen atom or sulfur atom, which is bonded via a carbon atom", thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl) and the like are used.

As the substituent of the "5-membered aromatic heterocyclic group containing 1 to 3 nitrogen atoms besides carbon atom and further containing one oxygen atom or sulfur atom, which is bonded via a carbon atom", a group selected from the aforementioned substituent group X is used. Particularly, $C_{1-8}$ alkyl (preferably, $C_{1-6}$ alkyl such as methyl and the like) and the like are preferable.

As $R^1$, triazolyl (e.g., 1,2,4-triazol-1-yl, 1,2,4-triazol-3-yl, 1,2,3-triazol-1-yl, 1,2,3-triazol-2-yl, 1,2,3-triazol-4-yl) optionally substituted by $C_{1-8}$ alkyl (preferably, $C_{1-6}$ alkyl such as methyl and the like) and the like are preferable.

$R^4$ and $R^{4'}$ are respectively hydrogen, —$Z_1$—$R^5$, optionally substituted $C_{1-6}$ aliphatic, or optionally substituted 3-10-membered cycloaliphatic, wherein $Z_1$ is selected from an optionally substituted $C_{1-3}$ alkylene chain, —S(O)—, —$S(O)_2$—, —C(O)—, —$CO_2$—, —C(O)$NR^{4a}$—, or —$S(O)_2NR^{4a}$—, wherein $R^{4a}$ is hydrogen or an optionally substituted $C_{1-4}$ aliphatic, and $R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Examples of "optionally substituted $C_{1-6}$ aliphatic group" include $C_{1-6}$ alkyl (e.g. methyl, ethyl, propyl, isopropyl, butyl, isobutyl, sec-butyl, tert-butyl, pentyl, isopentyl), $C_{2-6}$ alkenyl group (e.g. ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl) or $C_{2-6}$ alkynyl group (e.g. ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl) each of which is optionally substituted by a group selected from the aforementioned substituent group X.

Examples of "optionally substituted 3-10-membered cycloaliphatic group" includes $C_{3-10}$ cycloalkyl group (e.g. cyclopropyl, cyclobutyl, cyclopentyl, cyclohexyl, cycloheptyl, cyclooctyl) optionally substituted by a group selected from the aforementioned substituent group X.

Examples of "optionally substituted $C_{1-3}$ alkylene chain" include methylene, ethylene or propylene each of which is optionally substituted by a group selected from the aforementioned substituent group X.

Examples of "optionally substituted $C_{1-4}$ aliphatic group" include $C_{1-4}$ alkyl (e.g. methyl, ethyl, propyl, isopropyl, butyl, isobutyl, sec-butyl, tert-butyl), $C_{2-4}$ alkenyl group (e.g. ethenyl, 1-propenyl, 2-propenyl, 2-methyl-1-propenyl, 1-butenyl, 2-butenyl, 3-butenyl, 3-methyl-2-butenyl) or $C_{2-4}$ alkynyl group (e.g. ethynyl, 1-propynyl, 2-propynyl, 1-butynyl, 2-butynyl, 3-butynyl) each of which is optionally substituted by a group selected from the aforementioned substituent group X.

Examples of "optionally substituted 4-10-membered heterocyclyl group having 1-5 heteroatoms independently selected from nitrogen, oxygen, or sulfur" include the 4- to 7-membered (preferably 5- or 6-membered) monocyclic non-aromatic heterocyclic group containing, as a ring constituting atom besides carbon atom, 1 to 4 heteroatoms selected from an oxygen atom, a sulfur atom and a nitrogen atom mentioned above or the fused non-aromatic heterocyclic group derived from a fused ring wherein a ring corresponding to such 4- to 7-membered monocyclic non-aromatic heterocyclic group, and 1 or 2 rings selected from a 5- or 6-membered heterocycle containing 1 or 2 nitrogen atoms, a 5-membered heterocycle containing one sulfur atom and a benzene ring are condensed each of which is optionally substituted by a group selected from the aforementioned substituent group X.

Examples of "optionally substituted 6-10-membered aryl group" include phenyl, naphthyl, anthryl, phenanthryl, acenaphthylenyl, biphenylyl and the like, especially phenyl, each of which is optionally substituted by a group selected from the aforementioned substituent group X.

Examples of "optionally substituted 5-10-membered heteroaryl group having 1-5 heteroatoms independently selected from nitrogen, oxygen, or sulfur" include the 4- to 7-membered (preferably 5- or 6-membered) monocyclic aromatic heterocyclic group containing, as a ring constituting atom besides carbon atom, 1 to 4 heteroatoms selected from an oxygen atom, a sulfur atom and a nitrogen atom mentioned above or the fused aromatic heterocyclic group derived from a fused ring wherein a ring corresponding to such 4- to 7-membered monocyclic aromatic heterocyclic group, and 1 or 2 rings selected from a 5- or 6-membered aromatic heterocycle containing 1 or 2 nitrogen atoms, a 5-membered aromatic heterocycle containing one sulfur atom and a benzene ring are condensed mentioned above each of which is optionally substituted by a group selected from the aforementioned substituent group X.

As $R^4$ and $R^{4\prime}$, hydrogen is preferable.

As $R^{4a}$, hydrogen or $C_{1-4}$ alkyl is preferable.

$R^6$ is hydrogen or optionally substituted $C_{1-4}$alkyl.

As the substituent of the "$C_{1-4}$ alkyl", a group selected from the aforementioned substituent group X is used.

As $R^{10d}$, hydrogen or $C_{1-6}$ alkyl such as methyl and the like are preferable.

$R^{10e}$ is H, hydroxy, $C_{1-6}$alkyl, $C_{1-6}$ alkoxy optionally substituted by a group selected from hydroxy, $C_{1-6}$ alkyl-carbonylamino and amino-$C_{1-6}$ alkyl-carbonylamino, $C_{6-18}$ aryl-$C_{1-4}$alkyl-oxy, 4- to 7-membered monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom optionally substituted by $C_{1-6}$ alkyl optionally substituted by halogen and 4- to 7-membered monocyclic non-aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom optionally substituted by a group selected from halogen, $C_{1-6}$ alkyl, $C_{1-6}$ alkylsulfonyloxy and $C_{1-6}$ alkyl-carbonyl optionally substituted by hydroxyl.

For the compound (I-A-i), (I-A-ii), (II-A-ii) or (I-B-i), any combinations of preferable groups for each symbol mentioned above are preferably used.

As the compound (I-A-i), (I-A-ii) or (I-B-i), the following compound is preferable.

(i) The compound (I-A-i), (I-A-ii) or (I-B-i), especially (I-A-i) or (I-A-ii) wherein, HY is (i) an optionally substituted group represented by

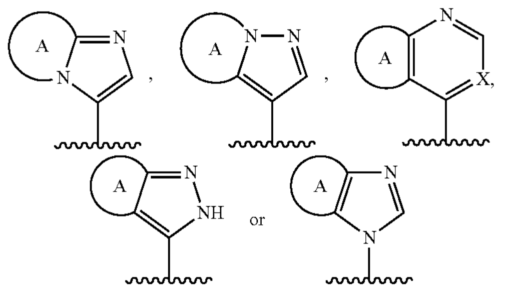

wherein A is a cyclic group and X is CH or N, or (ii) a pyridyl group, a pyrimidinyl group, a pyrazolyl group, a thiazolyl group, an oxazolyl group, an imidazolyl group, a triazolyl group, an isothiazolyl group or a pyridazinyl group, each of which is optionally substituted;

$R^2$ is an optionally substituted aryl group optionally substituted by substituents selected from substituent group X, a $C_{6-18}$ aryl-$C_{1-4}$ alkyl group optionally substituted by substituents selected from substituent group X, a 4- to 7-membered (preferably 5- or 6-membered) monocyclic aromatic heterocyclic group containing, as a ring constituting atom besides carbon atom, 1 to 4 heteroatoms selected from an oxygen atom, a sulfur atom and a nitrogen atom, or a group derived from a fused ring wherein a ring corresponding to such 4- to 7-membered monocyclic aromatic heterocyclic group, and 1 or 2 rings selected from a 5- or 6-membered aromatic heterocycle containing 1 or 2 nitrogen atoms, a 5-membered aromatic heterocycle containing one sulfur atom and a benzene ring are condensed, $R^1$ is (1) an optionally substituted 5-membered aromatic heterocyclic group containing 2 to 4 nitrogen atoms besides carbon atom, which is bonded via a carbon atom or (2) an optionally substituted 5-membered aromatic heterocyclic group containing 1 to 3 nitrogen atoms besides carbon atom and further containing one oxygen atom or sulfur atom.

(ii) The compound (I-A-i), (I-A-ii) or (I-B-i), especially (I-A-i) or (I-A-ii) wherein, HY is (i) a group represented by

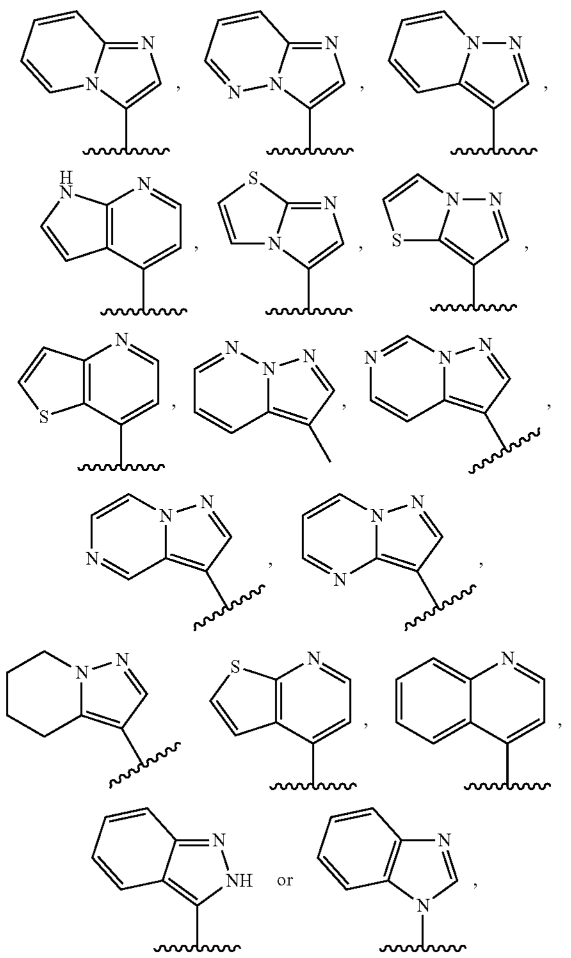

particularly, a group represented by

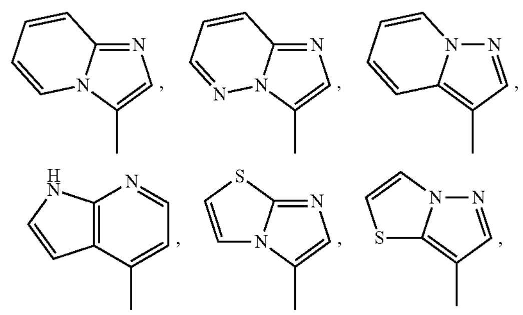

-continued

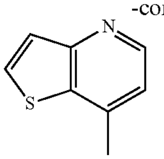 or 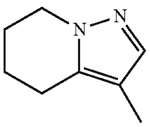, optionally substituted by the above-mentioned substituent(s), particularly, (1) hydroxy, (2) $C_{1-6}$ alkyl such as methyl and the like which is optionally substituted by 4- to 7-membered (preferably 5- or 6-membered) monocyclic aromatic heterocyclyl-carbonyl-amino or $C_{1-6}$ alkylcarbonylamino optionally substituted by amino containing, as a ring constituting atom besides carbon atom, 1 to 4 heteroatoms selected from an oxygen atom, a sulfur atom and a nitrogen atom, (3) $C_{1-6}$ alkoxy optionally substituted by hydroxy, (4) $C_{6-18}$ aryl-$C_{1-4}$ alkyl-oxy (e.g., benzyloxy), (5) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom which is optionally substituted by $C_{1-6}$ alkyl optionally substituted by halogen, (6) 4- to 7-membered (preferably 5- or 6-membered) monocyclic non-aromatic heterocyclyl-$C_{1-4}$alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom and the like (e.g., hydroxy, $C_{1-6}$ alkyl such as methyl and the like) as well as (7) halogen, (8) $C_{2-6}$ alkenyl, (9)$C_{3-8}$ cycloalkyl, (10) $C_{6-18}$ aryl optionally substituted by $C_{1-6}$ alkoxy or halogen, (11) 4- to 7-membered (preferably 5- or 6-membered) monocyclic aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, (12) 4- to 7-membered (preferably 5- or 6-membered) monocyclic non-aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, (ii) a group represented by

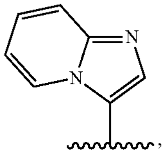, 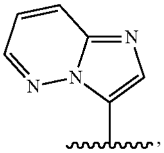, 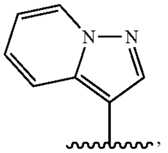,

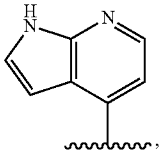, 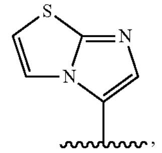, 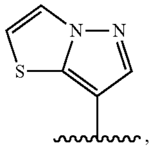,

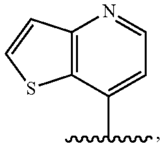, 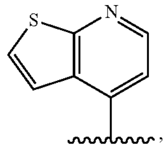, optionally substituted by the above-mentioned substituent(s), particularly, (1) hydroxy, (2) $C_{1-6}$ alkyl such as methyl and the like which is optionally substituted by 4- to 7-membered (preferably 5- or 6-membered) monocyclic aromatic heterocyclyl-carbonyl-amino or $C_{1-6}$ alkylcarbonylamino optionally substituted by amino containing, as a ring constituting atom besides carbon atom, 1 to 4 heteroatoms selected from an oxygen atom, a sulfur atom and a nitrogen atom, (3) $C_{1-6}$ alkoxy optionally substituted by hydroxy, (4) $C_{6-18}$ aryl-$C_{1-4}$ alkyl-oxy (e.g., benzyloxy), (5) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom, which is optionally substituted by $C_{1-6}$ alkyl optionally substituted by halogen (6) 4- to 7-membered (preferably 5- or 6-membered) monocyclic non-aromatic heterocyclyl-$C_{1-4}$alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom and the like (e.g., hydroxy, $C_{1-6}$ alkyl such as methyl and the like) as well as (7) halogen, (8) $C_{2-6}$ alkenyl, (9)$C_{3-8}$ cycloalkyl, (10) $C_{6-18}$ aryl optionally substituted by $C_{1-6}$ alkoxy or halogen, (11) 4- to 7-membered (preferably 5- or 6-membered) monocyclic aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, (12) 4- to 7-membered (preferably 5- or 6-membered) monocyclic non-aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, or (iii) a group represented by

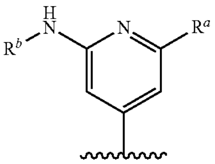 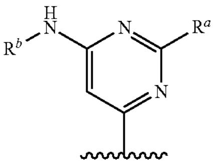

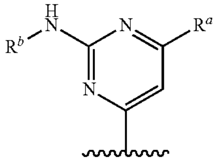 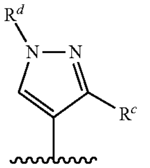 or

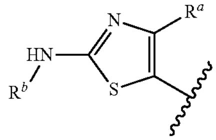

wherein $R^a$ is a hydrogen atom, a halogen atom (e.g., chlorine atom), a $C_{1-6}$ alkyl group such as methyl, ethyl, propyl and the like, $R^b$ is (1) a hydrogen atom, (2) a $C_{1-8}$ alkyl-carbonyl group (e.g., $C_{1-6}$ alkyl-carbonyl group such as acetyl, ethylcarbonyl and the like) optionally substituted by a substituent(s) selected from $C_{6-18}$ arylthio (e.g., phenylthio), 4- to 7-membered (preferably 5- or 6-membered) monocyclic aromatic heterocyclic group or monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, and the like, (3) a $C_{3-8}$ cycloalkyl-carbonyl group (e.g., cyclopropylcarbonyl) and the like, $R^c$ is a hydrogen atom, a $C_{1-6}$ alkyl group such as methyl, ethyl, propyl and the like, and $R^d$ is (i) a hydrogen atom, (ii) a $C_{1-6}$ alkyl group such as methyl, ethyl, propyl and the like, or (iii) an optionally substituted heterocyclic group represented by

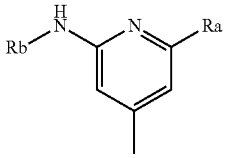
or
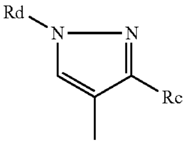
, especially, wherein $R^a$, $R^b$ and $R^c$ are as defined above, and $R^d$ is hydrogen atom, a $C_{1-6}$ alkyl group such as methyl, ethyl, propyl and the like, especially HY is (i) a group represented by

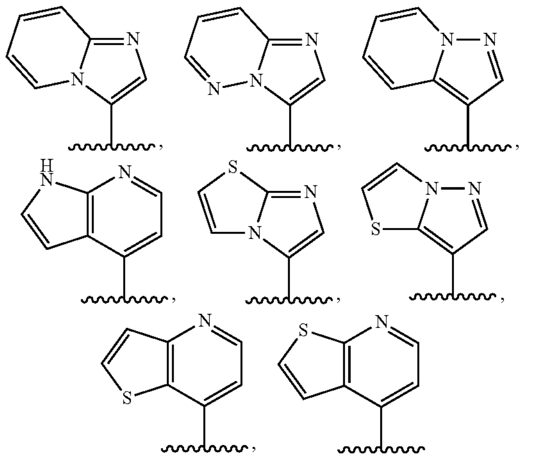

optionally substituted by the above-mentioned substituent(s), particularly, (1) hydroxy, (2) $C_{1-6}$ alkyl such as methyl and the like which is optionally substituted by 4- to 7-membered (preferably 5- or 6-membered) monocyclic aromatic heterocyclyl-carbonyl-amino or $C_{1-6}$ alkylcarbonylamino optionally substituted by amino containing, as a ring constituting atom besides carbon atom, 1 to 4 heteroatoms selected from an oxygen atom, a sulfur atom and a nitrogen atom, (3) $C_{1-6}$ alkoxy optionally substituted by hydroxy, (4) $C_{6-18}$ aryl-$C_{1-4}$alkyl-oxy (e.g., benzyloxy), (5) 4- to 7-membered (preferably 5- or 6-membered) monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom, which is optionally substituted by $C_{1-6}$ alkyl optionally substituted by halogen (6) 4- to 7-membered (preferably 5- or 6-membered) monocyclic non-aromatic heterocyclyl-$C_{1-4}$alkyl-oxy (e.g., morpholinylethyloxy, piperidinylethyloxy) containing, as a ring constituting atom besides carbon atom, 1 to 4 heteroatoms selected from an oxygen atom, a sulfur atom and a nitrogen atom and the like (e.g., hydroxy, $C_{1-6}$ alkyl such as methyl and the like) as well as (7) halogen, (8) $C_{2-6}$ alkenyl, (9) $C_{3-8}$ cycloalkyl, (10) $C_{6-18}$ aryl optionally substituted by $C_{1-6}$ alkoxy or halogen, (11) 4- to 7-membered (preferably 5- or 6-membered) monocyclic aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, (12) 4- to 7-membered (preferably 5- or 6-membered) monocyclic non-aromatic heterocyclyl containing, as a ring constituting atom besides carbon atom, 1 to 4 heteroatoms selected from an oxygen atom, a sulfur atom and a nitrogen atom which is optionally substituted by $C_{1-6}$ alkyl, or (iii) a group represented by

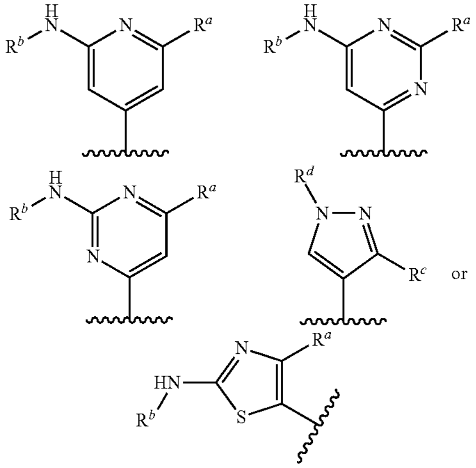

wherein $R^a$ is a hydrogen atom, a halogen atom (e.g., chlorine atom), a $C_{1-6}$ alkyl group such as methyl, ethyl, propyl and the like, $R^b$ is (1) a hydrogen atom, (2) a $C_{1-8}$ alkyl-carbonyl group (e.g., $C_{1-6}$ alkyl-carbonyl group such as acetyl, ethylcarbonyl and the like) optionally substituted by a substituent(s) selected from $C_{6-18}$ arylthio (e.g., phenylthio), 4- to 7-membered (preferably 5- or 6-membered) monocyclic aromatic heterocyclic group or monocyclic non-aromatic heterocyclic group (e.g., morpholinyl) containing, as a ring constituting atom besides carbon atom, 1 to 4 heteroatoms selected from an oxygen atom, a sulfur atom and a nitrogen atom, and the like, (3) a $C_{3-8}$ cycloalkyl-carbonyl group (e.g., cyclopropylcarbonyl) and the like, $R^c$ is a hydrogen atom, a $C_{1-6}$ alkyl group such as methyl, ethyl, propyl and the like, and $R^d$ is (i) a hydrogen atom, (ii) a $C_{1-6}$ alkyl group such as methyl, ethyl, propyl and the like, or (iii) an optionally substituted heterocyclic group represented by

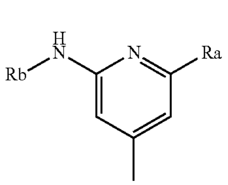
or
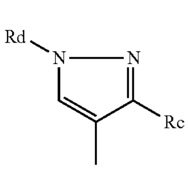
, especially, wherein $R^a$, $R^b$ and $R^c$ are as defined above, and $R^d$ is hydrogen atom, a $C_{1-6}$ alkyl group such as methyl, ethyl, propyl and the like, $R^2$ is (i) a $C_{1-8}$ alkyl group (preferably a $C_{1-6}$ alkyl group) (e.g., a tert-butyl group), (ii) a $C_{2-8}$ alkenyl group (e.g., a $C_{2-6}$ alkenyl group such as a propenyl group and the like), (iii) a $C_{3-8}$ cycloalkyl group (e.g., a cyclohexyl group), (iv) a hydroxy group (e.g., an ethyloxy group, a propyloxy group, a propenyloxy group, a benzyloxy group) optionally substituted by $C_{1-8}$ alkyl (preferably $C_{1-6}$ alkyl), $C_{2-8}$ alkenyl (preferably $C_{2-6}$ alkenyl) or $C_{6-18}$ aryl-$C_m$ alkyl (preferably phenyl-$C_m$ alkyl), (v) a $C_{6-18}$ aryl group (preferably a phenyl group) optionally substituted by a halogen atom, an optionally halogenated $C_{1-8}$ alkyl (preferably optionally halogenated $C_{1-6}$ alkyl) or $C_{1-8}$ alkoxy (preferably $C_{1-6}$ alkoxy) (e.g., a phenyl group, a trifluoromethylphenyl group, a fluorophenyl group, a difluorophenyl group, a methoxyphenyl group, a chlorophenyl group), (vi) a $C_{6-18}$ aryl-$C_{1-4}$ alkyl group (preferably a phenyl-$C_{1-4}$ alkyl group) (e.g., a benzyl group), (vii) a 4- to 7-membered (preferably 5- or 6-membered) aromatic monocyclic heterocyclic group (e.g., a thienyl group, a furyl group) containing, besides carbon atom, 1 to 3 heteroatoms selected from a nitrogen atom, an oxygen atom and a sulfur atom, or (vii) a 4- to 7-membered (preferably 5- or 6-membered) non-aromatic heterocyclic group (e.g., a tetrahydropyranyl group) containing, besides carbon atom, 1 to 3 heteroatoms selected from a nitrogen atom, an oxygen atom and a sulfur atom and the like are preferably used. Among these, a $C_{6-18}$ aryl group (e.g., phenyl group, trifluoromethylphenyl group, fluorophenyl group, difluorophenyl group, methoxyphenyl group, chlorophenyl group) optionally substituted by a halogen atom, an optionally halogenated $C_{1-8}$ alkyl or $C_{1-8}$ alkoxy, especially, (i) a $C_{6-18}$ aryl group (preferably a phenyl group) optionally substituted by a halogen atom, an optionally halogenated $C_{1-8}$ alkyl (preferably optionally halogenated $C_{1-6}$ alkyl) or $C_{1-8}$ alkoxy (preferably $C_{1-6}$ alkoxy) (e.g., a phenyl group, a trifluoromethylphenyl group, a fluorophenyl group, a difluorophenyl group, a methoxyphenyl group, a chlorophenyl group), or (ii) a 4- to 7-membered (preferably 5- or 6-membered) aromatic monocyclic heterocyclic group (e.g., a thienyl group, a furyl group) containing, besides carbon atom, 1 to 3 heteroatoms selected from a nitrogen atom, an oxygen atom and a sulfur atom, $R^1$ is triazolyl (e.g., 1,2,4-triazol-1-yl, 1,2,4-triazol-3-yl, 1,2,3-triazol-1-yl, 1,2,3-triazol-2-yl, 1,2,3-triazol-4-yl) optionally substituted by $C_{1-8}$ alkyl (preferably, $C_{1-6}$ alkyl such as methyl and the like).

For the above mentioned compounds, any combinations of preferable groups for each symbol mentioned above are preferably used.

As a salt of compound represented by the formula (IA), (IB), (I-A-i), (I-A-ii), (I-A-iv), (I-B-i), (II-A), (II-A-i), (II-A-ii), for example, metal salts, ammonium salts, salts with organic bases, salts with inorganic acids, salts with organic acids, salts with basic or acidic amino acids and the like can be mentioned. As preferable examples of the metal salt, alkali metal salts such as sodium salt, potassium salt and the like; alkaline earth metal salts such as calcium salt, magnesium salt, barium salt and the like; aluminum salt and the like can be mentioned. As preferable examples of the salts with organic bases, salts with trimethylamine, triethylamine, pyridine, picoline, 2,6-lutidine, ethanolamine, diethanolamine, triethanolamine, tromethamine[tris(hydroxymethyl)methylamine], t-butylamine, cyclohexylamine, dicyclohexylamine, N,N'-dibenzylethylenediamine and the like can be mentioned. As preferable examples of the salts with inorganic acids, salts with hydrochloric acid, hydrobromic acid, nitric acid, sulfuric acid, phosphoric acid and the like can be mentioned. As preferable examples of the salts with organic acids, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like can be mentioned. As preferable examples of the salts with basic amino acids, salts with arginine, lysine, ornithine and the like can be mentioned. As preferable examples of the salts with acidic amino acids, salts with aspartic acid, glutamic acid and the like can be mentioned.

Of those, pharmaceutically acceptable salts are preferable. For example, when a compound has an acidic functional group therein, salts with inorganic bases such as alkali metal salts (e.g., sodium salt, potassium salt and the like), alkaline earth metal salts (e.g., calcium salt, magnesium salt, barium salt and the like) and the like, ammonium salt and the like can be mentioned. When a compound has a basic functional group therein, salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like can be mentioned.

4 General Synthetic Methods and Intermediates:

The compounds of the present invention can be prepared by methods known to one of ordinary skill in the art and/or by reference to the schemes shown below and the synthetic examples that follow. Exemplary synthetic routes are set forth in Schemes 1-52 below, and in the Examples.

In methods defined below X represents halogen (Br, I or Cl), P is Hy itself or a substituent convertible to Hy by applying a generally known method, $W^a$ is $R^2$ itself or a substituent convertible to $R^2$ by applying a generally known method and Q is $R^1$ itself or a substituent convertible to $R^1$ by applying a generally known method.

Examples of the solvent for the below-mentioned reactions include, but are not limited to halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane, DME and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like.

One of ordinary skill in the art will recognise that numerous variations in reaction conditions including variations in solvent, reagents, catalysts, reaction temperatures and times are possible for each of the reactions described. Variation of order of synthetic steps and alternative synthetic routes are also possible.

In many cases, synthesis can be started from commercially available thiophene/thiazole analogs to prepare target compounds. In some cases, specially functionalized thiophene/thiazole analogs can be prepared by the procedures described in Schemes 1-4.

Scheme 1: General method for the synthesis of 2-aminothiophenes

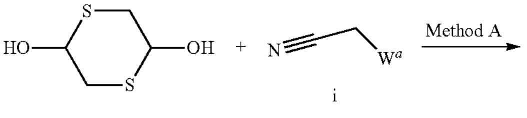

i

-continued

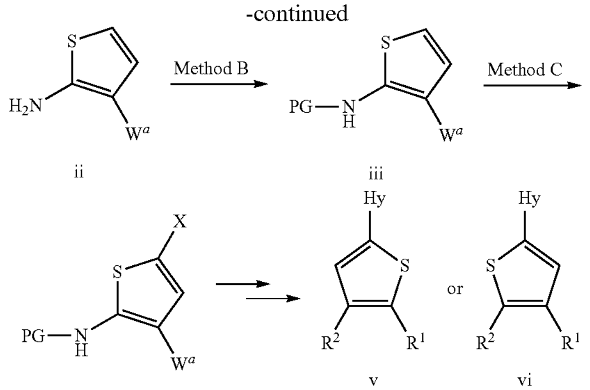

ii iii iv v vi

Scheme 1 above shows a procedure to prepare compounds of formula v. Condensation of nitriles i with 2,5-dihydroxy-1,4-dithiane can be accomplished using reported procedure (C. E. Stephens et al. Bioorg. Med. Chem., 2001, 9, 1123-1132, Method A). Aminothiophenes ii are then protected with an appropriate protecting group, for example Boc using standard conditions, such as Boc anhydride, DMAP, dioxane (Method B). Halogenation of protected thiophenes iii is achieved using a suitable reagent, for example NBS in DCM to afford halides of formula iv (Method C), that can be converted into compounds of formula v by a combination of generally known functional group conversion reactions described below.

Alternatively, reverse type of thiophene analogs vi can be also prepared using functional group transformations described below.

Scheme 2: General method for the synthesis of 4-hydroxyl thiophenes

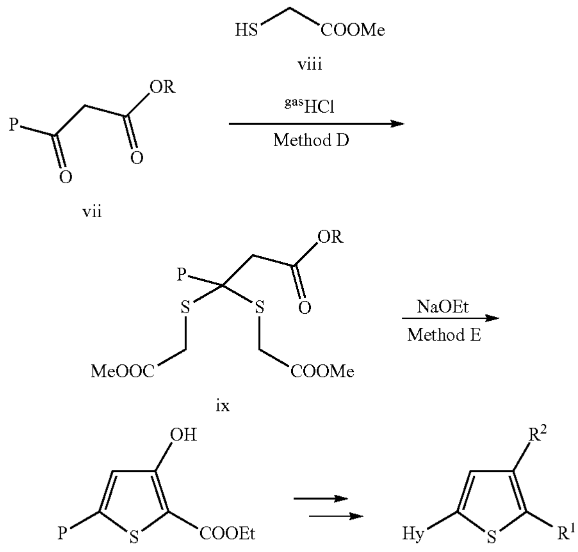

viii vii ix x v

Suitably functionalized 4-hydroxyl thiophenes can be prepared according to the published procedure such as M. D. Mullican, et al., J. Med. Chem., 1991, 34, 2186-2194. For example, scheme 2 describes a general procedure for preparing 4-hydroxythiophenes of formula x. Beta-ketoesters vii are treated with thiols, such as methyl thioglycolate, viii in the presence of suitable acid, such as HCl in ethanol (Method D), to afford dithio-ketal ix, which is then treated with an appropriate base, like sodium ethoxide in a suitable solvent, for example ethanol to give 4-hydroxythiophenes of formula x (Method E). These 4-hydroxythiophenes can be convertated to target compounds v according to the procedures described below.

Scheme 3: General method for the synthesis of substituted thiazoles

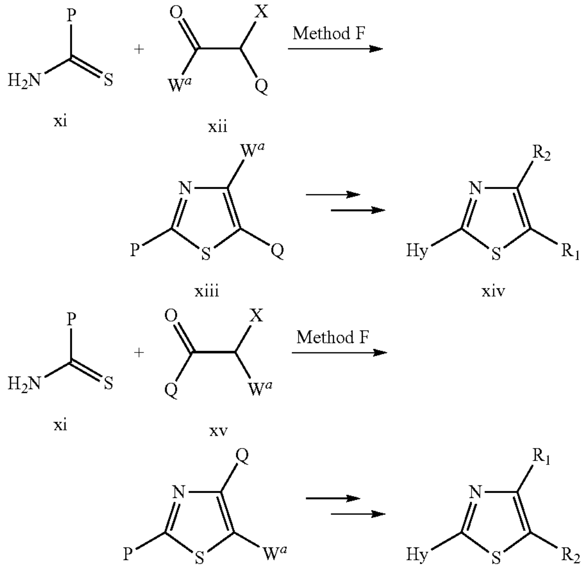

xi xii xiii xiv xi xv xvi xvii

Scheme 3 above shows a general route for the synthesis of compounds of formula xiii and xvi.

Thioamides xi or thioureas (When P=NHR) are treated with alpha-halogenated carbonyl compounds xii in a suitable solvent, such as isopropanol at elevated temperature to give thiazoles xiii. (Method F). When P=$NH_2$, 2-aminothiazoles xiii that are obtained can be then subjected to Sandmeyer reaction to afford 2-halothiazoles xxxi (P=X), which can be used for further functional transformations described below. A conversion reaction from xiii to compounds xiv can be performed, for example, by a combination of generally known functional group conversion reactions shown below. If alfa-halogenated carbonyl compound is suitably selected, i.e. xv, reverse type thiazole analogs xvi and xvii can be also prepared using well known organic functional group transformation reactions describing below.

Scheme 4: General method for the preparation of 4-hydroxythiazoles

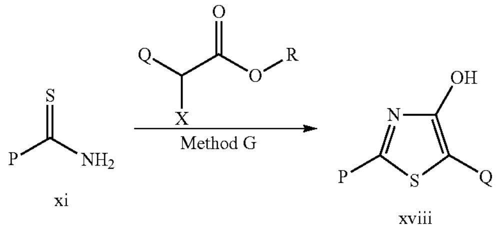

xi xviii

As shown in scheme 4 above, thioamides xi can be condensed with alfa-halogenated esters in a similar manner as reported by Rzasa, R. M. et al, Bioorg. Med. Chem. 2007, 15, 6574 to obtain 4-hydroxythiazole derivatives xviii. Reaction can be carried out in a suitable solvent, such as ethanol in the presence of an appropriate base, like pyridine under elevated temperature (Method G).

Schemes 5-19 describe procedures for basic functional group transformations on the thiophene/thiazole central core scaffolds.

In the schemes 5-8, general functional group transformation procedures for introduction of Hy group are described.

Scheme 5: Introduction of Hy to 3-cyanothiophenes

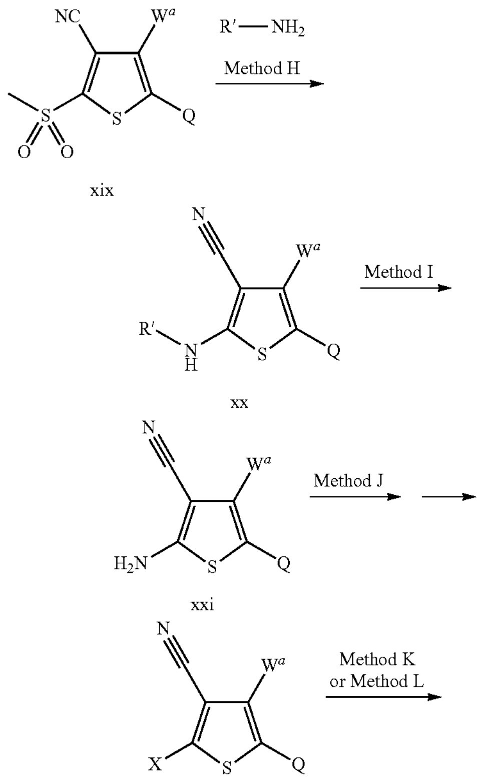

xix xx xxi xxii

-continued

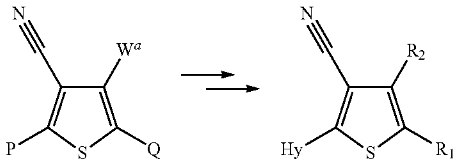

xxiii xxiv

Scheme 5 describes the procedure for the introduction of Hy to 3-cyanothiophene analogs by a known functional group transformation reaction.

As shown in Scheme 5, sulfones of formula xix (synthetic examples given in Mansanet et al, WO 2005070916) are treated with amines, preferably such as the R' group can be later deprotected, for example 2,4-dimethoxybenzylamine in a suitable solvent, such as THF at elevated temperature (Method H) to give XX.

Deprotection of R' group is carried out using a standard procedure, in the case of dimethoxybenzyl group with an acid, such as TFA in DCM to afford amines xxi (Method I).

Amines xxi are then subjected to Sandmeyer reaction using appropriate reagents, such as methylene iodide and amyl nitrite in ACN (Method J).

The resulting halogenated thiophenes xxii can be coupled with aryl stannanes under suitable conditions, for example $Pd(PPh_3)_4$, CuI, LiCl in a suitable solvent, such as dioxane at elevated temperature to give compounds of formula xxiii (Method K). Alternatively, boronic acids or esters can be used for such coupling reactions, for example $Pd(PPh_3)_4$, $Na_2CO_3$, DME/water, elevated temperature or microwave irradiation (Method L).

A conversion reaction from xxiii to compounds xxiv can be performed, for example, by a combination of generally known functional group conversion reactions shown below.

Scheme 6: General method for the introduction of Hy to 2-unsubstituted thiophenes.

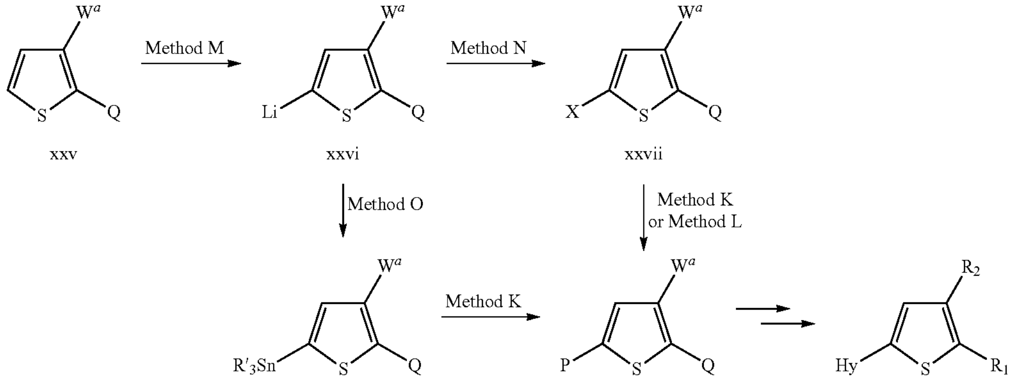

xxv xxvi xxvii xxix xxviii v

Scheme 6 above shows a general route for introducing Hy to unsubstituted 2-position of thiophene core.

2-unsubstituted thiophenes xxv can be treated with suitable base, such as n-BuLi in THF at low temperature, to produce lithiated thiophene intermediates xxvi (Method M). The intermediate organolithium species can be quenched with halogen molecule, for example iodine in a suitable solvent, such as THF to afford halogenated compounds of formula xxvii (Method N). Halides xxvii can be coupled with aryl stannanes under suitable conditions, for example $Pd(PPh_3)_4$, CuI, LiCl in a suitable solvent, such as dioxane at elevated temperature to give compounds of formula xxviii (Method K), or boronic acids or esters. with an appropriate catalyst, for example $Pd(PPh_3)_4$, in the presence of a suitable base, such as sodium carbonate in DME-water mixture at elevated temperature (Method L) to afford compounds of formula xxviii.

Alternatively, lithium intermediates xxvi can be transformed to stannanes by quenching with suitable tin halide, such as tributyltin chloride (Method O). Stannanes xxix are then coupled with aryl halides, triflates, or mesylates using appropriate conditions, such as $Pd(PPh_3)_4$, CuI, LiCl in a suitable solvent, such as dioxane at elevated temperature to give compounds of formula xxviii (Method K). A conversion reaction from xxviii to compounds v can be performed, for example, by a combination of generally known functional group conversion reactions shown below.

Scheme 7: General method for introduction of Hy to 2-position of thiazole core.

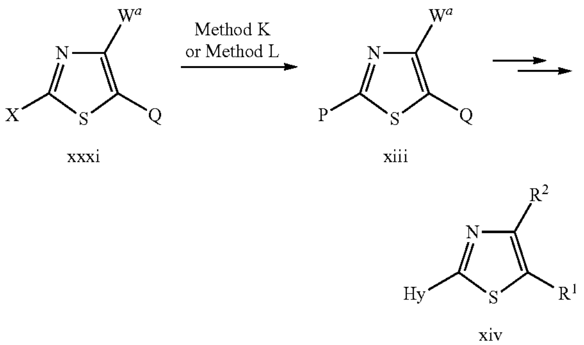

xxxi xiii xiv

Scheme 7 above shows a general route for introducing Hy to 2-position of thiazole core scaffold.

Halogenated thiazoles xxxi, which can be available by the procedure described in scheme 3, can coupled with suitable partners, such as boronic acids, stannanes, etc under standard Suzuki conditions, such as $Pd(PPh_3)_4$, $Na_2CO_3$, DME/water, elevated temperature or microwave irradiation (Method L), or standard Stille conditions, such as $Pd(PPh_3)_4$, CuI, LiCl, dioxane at elevated temperature (Method K) to afford compounds of formula xiii.

A conversion reaction from xiii to compounds xiv can be performed, for example, by a combination of generally known functional group conversion reactions shown below.

Scheme 8: Alternative method for stepwise coupling towards substituted 2,4-disubstituted thiazoles.

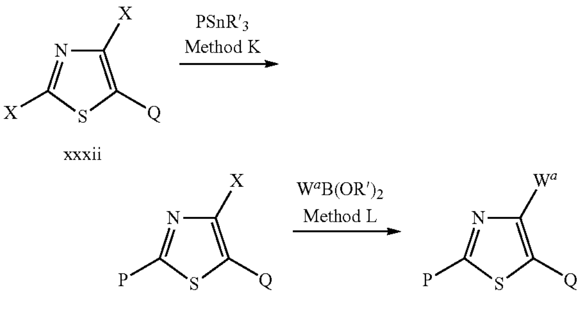

xxxii xxxiii xiii

As shown in Scheme 8, cross-coupling reaction described in scheme 7 can be regioselectively applied to the 2,4-dihalogenated thiazole derivatives xxxii. Thus, stepwise palladium mediated Stille/Suzuki cross coupling reactions afford suitably functionalized thiazole derivatives xiii. For example, 2,4-dihalothiazoles xxxii are treated with stannanes under standard Stille conditions, such as $Pd(PPh_3)_4$, CuI, LiCl, dioxane at elevated temperature (Method K) to afford intermediates xxxiii, that are then treated with organic boronic acids under standard Suzuki conditions, such as $Pd(PPh_3)_4$, $Na_2CO_3$, DME/water, elevated temperature or microwave irradiation (Method L) to afford compounds of formula xiii.

Schemes 9-21 describe methods for the introduction of $R_1$ and $R_2$ groups.

Scheme 9: General method for the synthesis of preparation of 4-alkoxythiazole derivatives.

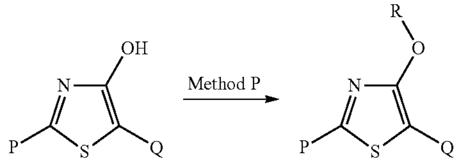

xviii xxxiv

4-Alkoxythiazoles can be obtained by the conventional alkylation method of 4-hydroxythiazole derivatives obtained in scheme 4.

As shown in scheme 9,4-hydroxythiazoles xviii can be treated with alkyl halides using a suitable base, such as potassium carbonate in a suitable solvent, for example DMF at elevated temperature to afford compounds of formula xxxiv (Method P).

Scheme 10: General method for halogenation of thiophenes/thiazoles

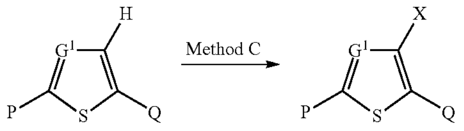

xxxv xxxvi

Scheme 10 above shows a general route for introducing halogen functionality onto 4-unsubstituted position of thiophene/thiazole core.

Halogenation of thiophene/thiazoles can be achieved in a similar manner as reported in the literature (Takami et al, Tetrahedron 2004, 60, 6155). For example, xxxv is treated with a generally known halogenating reagent such as bromine or N-bromosuccinimide, in a suitable solvent, such as DCM at elevated temperature to afford compounds of formula xxxvi (Method C).

The halogenated thiazole xxxvi can be used for further functional group transformation shown below.

Scheme 11: General method for the preparation of 4-aminothiazoles

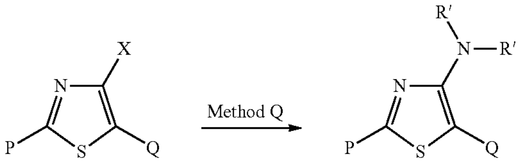

xxxiii xxxvii

Scheme 11 above shows general methods for the synthesis of 4-aminothiazole derivatives xxxvii from 4-halogenated thiazoles xxxiii which can be prepared by the procedure described in scheme 10.

Displacement of a halogen group with an amine can be achieved in a similar manner as reported in the literature (J. Med. Chem. 2006, 49, 5769). Treatment of xxxiii with an amine at elevated temperature in a suitable solvent, such as DMF can lead to amines xxxvii (Method Q). If necessary a base, such as sodium carbonate can be added.

Scheme 12: General method for introducing carbon functionality to 4-halogenated thiophenes/thiazoles.

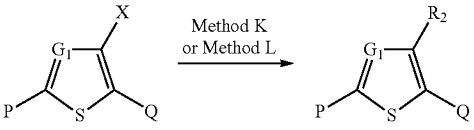

xxxvi xxxix

As shown in Scheme 12 above, carbon functionality can be introduced by the well known cross-coupling technique from the 4-halogenated thiophenes/thiazoles xxxvi which can be prepared by the procedure described in schemes 8 or 10.

For example, xxxix can be obtained from 4-halogenated thiophenes/thiazoles xxxvi by reaction with an organic boronic acid reagent, or an organic tin reagent in a presence of palladium catalyst, such as $Pd(PPh_3)_4$. Suzuki couplings can be performed using a suitable base, such as sodium carbonate in an appropriate solvent, such as DME/water at elevated temperature (Method L), while co-catalyst CuI can be used for Stille coupling reactions, together with LiCl in a suitable solvent, such as dioxane at elevated temperature (Method K).

Scheme 13: General method for introducing sulfur functionality

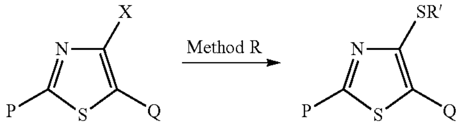

xxxiii xl

As shown in Scheme 13 above, sulfur functionality can be introduced to the 4-halogenated thiazole xxxiii by a similar manner as described by Rossignol et al, US2009036467.

Treatment of xxxiii with thiols in the presence of a copper catalyst, like CuI in a suitable solvent, such as DMF with an appropriate base, for example sodium hydroxide at elevated temperature gives thioethers of formula xl (Method R).

Scheme 14: General method for Pd-catalyzed amination/amidation of 4-halogenated thiophenes/thiazoles

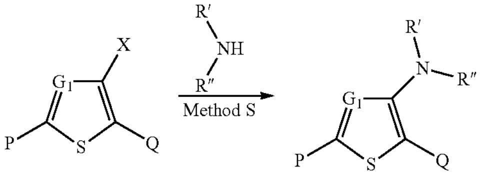

xxxvi xli

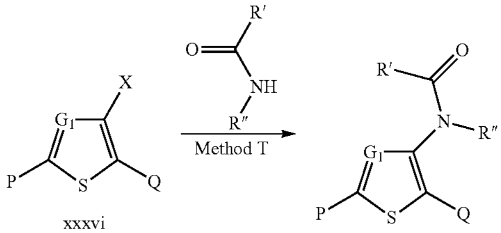

xxxvi xlii

As shown in Scheme 14, amine or amide functionality can be introduced by the well known palladium catalyzed amination/amidation reaction, so called Buchwald coupling, to the 4-halogenated thiophenes/thiazoles xxxvi.

For example, halides xxxvi can be treated with amines using an appropriate Pd catalyst, such as $Pd_2$ $dba_3$/BINAP, with a suitable solvent/base combination, for example NaOtBu in toluene at elevated temperature or using microwave irradiation to afford amines of formula xli (Method S). Coupling with amides also can be carried out using a suitable Pd catalyst, for example $Pd_2$ $dba_3$/XantPhos, with a suitable solvent/base combination, like $Cs_2CO_3$ in dioxane at elevated temperature or using microwave irradiation to give amides of formula xlii (Method T).

Scheme 15: General method for the functionalization of 4-hydroxyl group of thiophene/thiazole derivatives

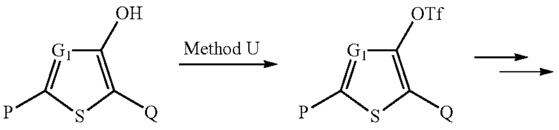

xliii xliv

-continued

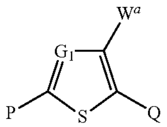

xlv

As shown in Scheme 15, 4-hydroxythiazoles or thiophenes xliii can be transformed to various functionalized thiazole/thiophene derivatives via triflate xliv.

For example, compounds xliii can be transformed into triflates xliv, for example using triflic anhydride, with pyridine as base in DCM (Method U). Triflates xliv can be then subjected to coupling reactions with amines, boronic esters, stannanes, or thiols under similar conditions as described for analogous halides in Schemes 11-14 (analogous literature examples include Rzasa, R. et al, Bioorg. Med. Chem. 2007, 15, 6574; Langille, N. F., Org. Lett. 2002, 4, 2485.) to afford compounds of formula xlv.

Scheme 16: General method for halogenation of 3-posittion onto thiophene/thiazoles.

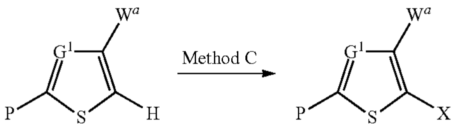

xlvi xlvii

Scheme 16 above shows a general route for introducing halogene functionality onto unsubstituted 5-position of thiophene/thiazole core scaffold.

Halogenation of 5-unsubstituted thiazoles/thiophenes can be achieved in a similar manner as reported in the literature (Haelmmerle et al, Synlett 2007, 2975). For example, xlvi is treated with a generally known halogenating reagent such as bromine or N-bromosuccinimide in a suitable solvent, such as DCM to afford compounds of formula xlvii (Method C).

The resulting halogenated thiophenes/thiazoles xlvii can be used for the further functional group transformation reaction such as described in scheme 11-14.

Scheme 17: General route for the synthesis of carboxamides

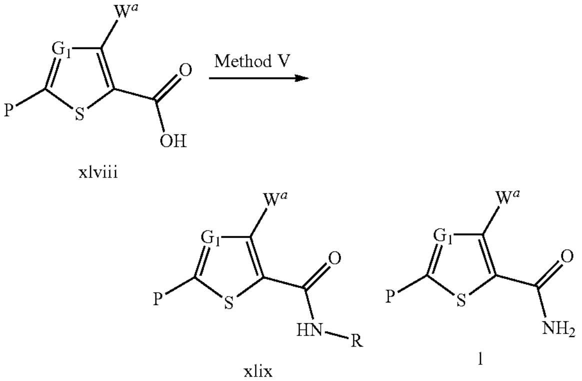

xlviii xlix l

Scheme 17 above shows a general route for preparing amide compounds of formula xlix. As shown in Scheme 17, acids xlviii are treated with amines using standard coupling conditions, such as EDCI and HOBt in DCM to afford amides xlix (Method V).

When ammonia is used as an amine source, obtained primary amide derivatives 1 can be very useful intermediates for the construction of azoles as described below.

Scheme 18: General route for the synthesis of 5-amino thiophenes/thiazoles by Curtius rearrangement

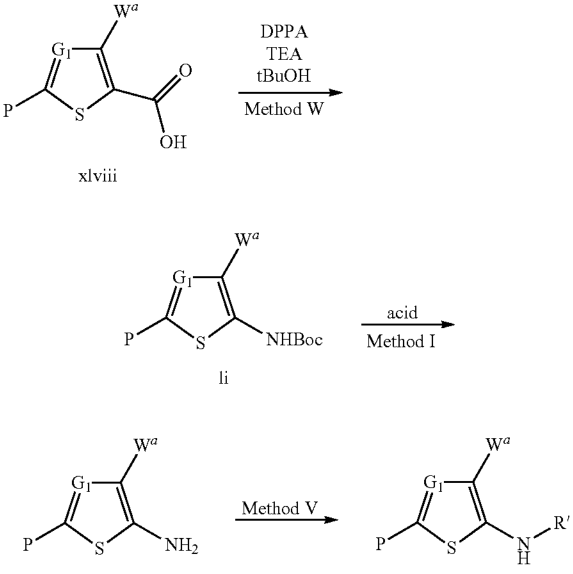

xlviii li lii liii

As shown Scheme 18, 5-amino thiophens/thiazoles Hi can be prepared by the Curtius rearrangement of the thiophene/thiazole carboxylic acid analogs xlviii.

As shown in Scheme 18, acids xlviii are treated with an azide, such as DPPA in a presence of base, like TEA in a suitable solvent, for example t-BuOH at elevated temperature to form intermediate Boc protected amines 11 (Method W), that are deprotected to amines lii using standard deprotection conditions, such as TFA in DCM (Method I).

Amines lii can be then transformed to amides, sulfonamides, ureas, carbamates HU etc using standard conditions.

Scheme 19: General route for the synthesis of 5-cyano thiophenes/thiazoles

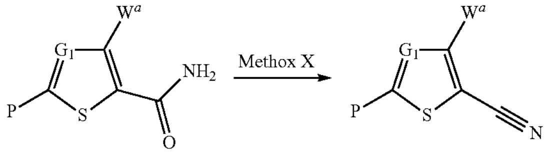

1 liv

As shown in scheme 19, amides 1, which can be prepared by the procedure described in scheme 17, are treated with phosphoryl chloride, or similar reagents to form 5-cyano thiophens/thiazoles of formula liv (Method X).

Scheme 20: General route for the synthesis of thioamides

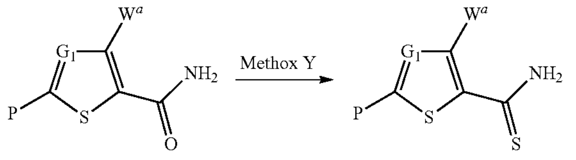

l lv

As shown in scheme 20, amides 1, which can be prepared by the procedure described in scheme 17, are treated with a suitable reagent, for example Lawesson's reagent, or $P_2S_5$ in a suitable solvent, such as toluene at elevated temperature to afford thioamides of formula Iv (Method Y).

Scheme 21: Alternative route for the synthesis of thioamides

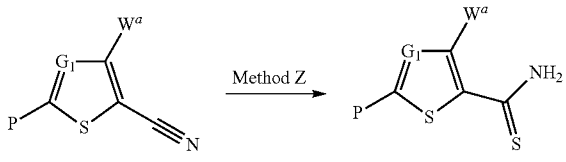

liv lv

As shown in scheme 21, 5-cyano thiazoles/thiophenes liv, which can be prepared by the procedure described in scheme 19, are treated with a suitable reagent, for example ammonium sulfide in a suitable solvent, such as methanol to afford thioamides of formula Iv (method Z).

In the schemes 22-40, general procedures for the construction of the representative azoles as $R_1$ are described.

Schemes 22-24 are explaining the formation of 1,2,4-triazolyl group as $R_1$.

Scheme 22: General route for the construction of 1,2,4-triazolyl

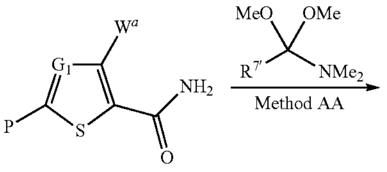

l

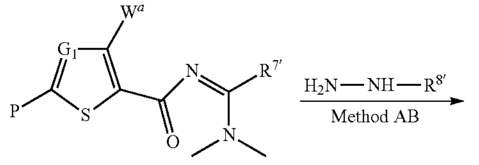

lvi

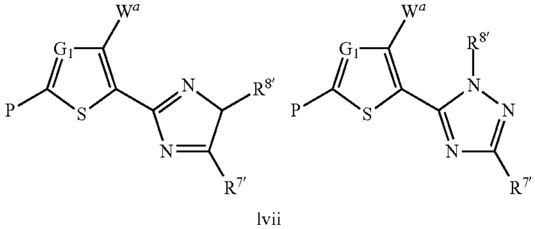

lvii

As shown in Scheme 22, amides l, which can be prepared by the procedure described in scheme 17, can be treated with dimethylformamide-dimethylacetal such as DMFDMA at elevated temperature or under microwave irradiation (Method AA) to give intermediate amidines lvi that are transformed to 1,2,4-triazoles lvii using hydrazine or substituted hydrazines in acetic acid at elevated temperature or under microwave irradiation (Method AB).

Scheme 23: General route for the construction of 5-halogenated 1,2,4-triazolyl

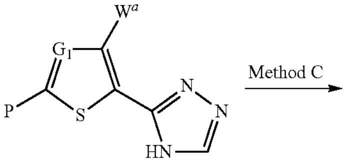

lvii

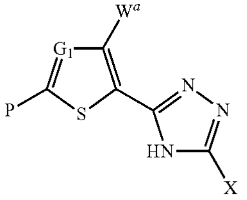

lviii

As shown in Scheme 23, 1,2,4-triazoles lvii, which can be prepared by the procedure described in scheme 22, are treated with a suitable halogenating agent, like NBS in a suitable solvent, for example tetrachloromethane to afford compounds of formula lviii (Method C).

Scheme 24: General route for the construction of 5-amino-1,2,4-triazolyl

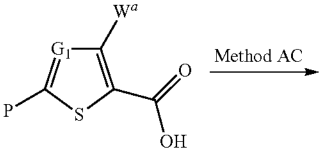

xlviii

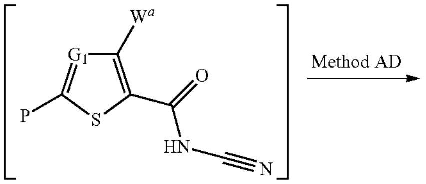

lix

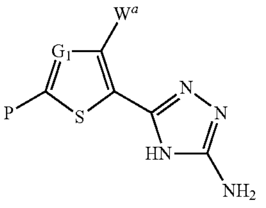

lx

As shown in Scheme 24, acids xlviii are coupled with cyanamide, for example via an intermediate acid halide in a suitable solvent, such as DCM to acylcyanamides lix (Method AC), that are in turn treated with hydrazine using appropriate conditions, for example acetic acid at elevated temperature to give compounds of formula lx (Method AD).

Scheme 25-33 is explaining the formation of 2-imidazolyl group as $R_1$

Scheme 25: General route for the construction of 2-imidazolyl

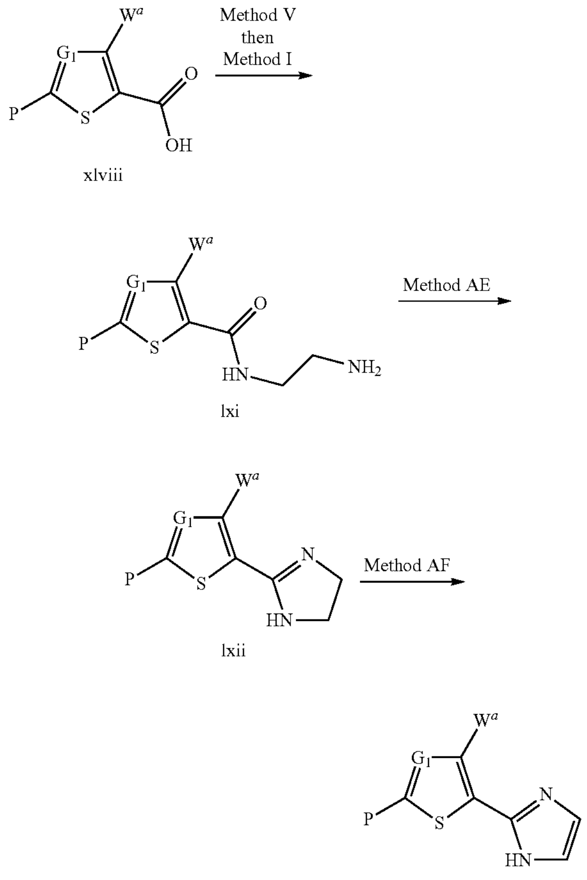

xlviii lxi lxii lxiii

As shown in Scheme 25, acids xlviii are treated with Boc protected ethylenediamine using standard coupling conditions, such as EDCI and HOBt in DCM (Method V). Protective group is removed using an appropriate acid, for example TFA in DCM to give amide lxi (Method I). Cyclization of lxi is achieved using suitable conditions, for example $POCl_3$ (Method AE) to form dihydroimidazoles lxii. Dihydroimidazoles lxii can be oxidized to imidazoles lxiii using a suitable oxidative method, for example heating with Magtrieve (Method AF).

Scheme 26: Alternative route for the construction of 2-imidazolyl

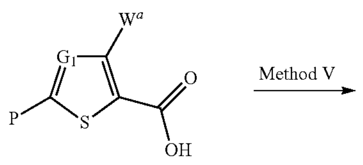

xlviii

-continued

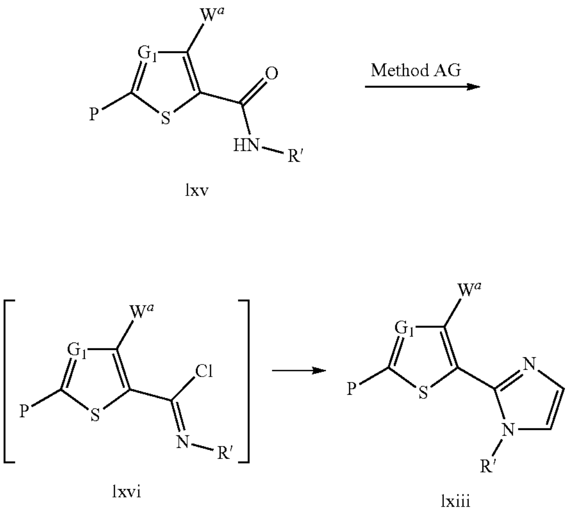

lxv lxvi lxiii

Scheme 26 above shows an alternative route for preparing imidazoles of formula lxiii. As shown in Scheme 26, acids xlviii are treated with amines using standard coupling conditions, such as EDCI and HOBt in DCM to afford amides lxv (Method V). Cyclization to imidazoles is achieved through a 3-step one pot process that involves treatment with phosphorus pentachloride and HCl in dioxane to afford carbimidoyl chloride intermediates lxvi, that are then treated with aminoacetaldehyde dimethylacetal followed by HCl in dioxane at elevated temperature to give lxiii (Method AG). When R'=allyl, benzyl or substituted benzyl, it can also serve as a protecting group.

Scheme 27: Alternative route for the synthesis of 2-imidazolyl

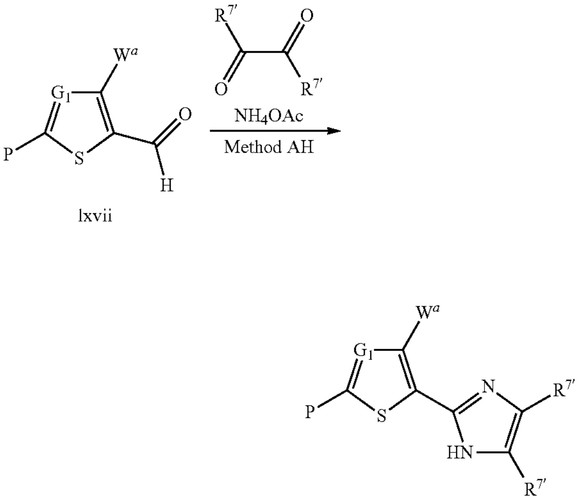

lxvii lxiii

As shown in scheme 27, aldehydes lxvii are condensed with dicarbonyl compounds, such as diketones, ketoaldehydes, or glyoxal with an appropriate ammonia source, such as ammonium acetate, with suitable acid, such as acetic acid in solvent such as methanol to form imidazoles lxiii (Method AH).

Scheme 28: Alternative method for the construction of substituted 2-imidazolyl.

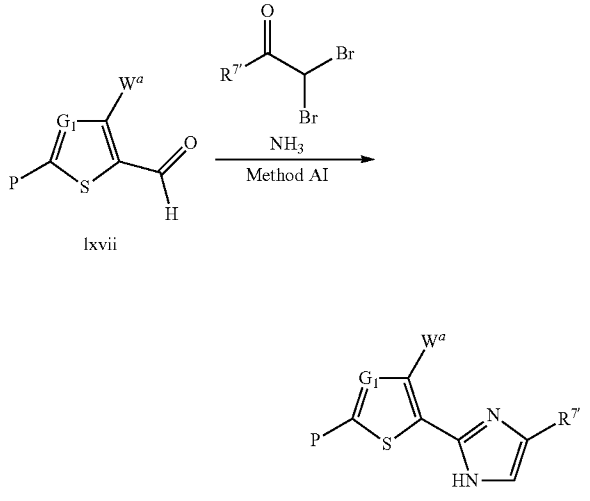

lxvii lxiii

As shown in scheme 28, aldehydes of formula lxvii can be treated with alpha, alpha-dihalo-ketones under suitable conditions, such as ammonium hydroxide, sodium acetate in an appropriate solvent, for example methanol and water to afford imidazoles of formula lxiii (Method AI).

Scheme 29: Alternative method for the construction of substituted 2-imidazolyl.

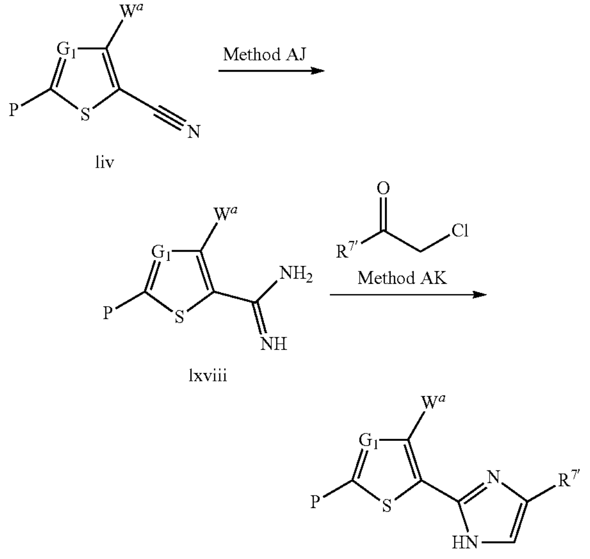

liv lxviii lxiii

As shown in scheme 29, treatment of nitriles liv, which can be prepared by the procedure described in scheme 19, with LiHMDS in a suitable solvent mixture, such as THF/ether/hexane gives amidines of formula lxviii (Method AJ) that can be treated with haloketones in the presence of a suitable base, such as potassium carbonate in an appropriate solvent, such as DCM under elevated temperature to give imidazoles of general formula lxiii (Method AK).

Scheme 30: Alternative method for the construction of substituted 2-imidazolyl.

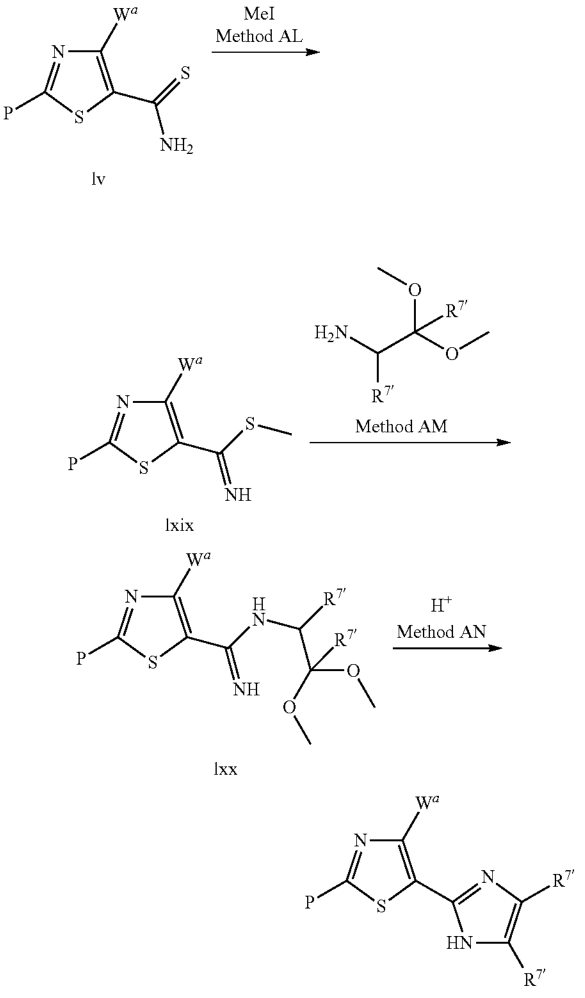

lv lxix lxx lxiii

As shown in scheme 30, treatment of thioamides lv, which can be prepared by the procedure described in scheme 20 or 21, with methyl iodide affords imidothioate intermediates lxix (Method AL), which are then treated with optionally substituted aminoacetaldehyde dimethyl acetal in a suitable solvent, like acetic acid at elevated temperature to afford intermediate amidines lxx (Method AM). Amidines lxx are then treated with an acid, such as aqueous HCl and a suitable co-solvent, like ethanol at elevated temperature to give imidazoles of formula lxiii (Method AN).

Scheme 31: Alternative method for the construction of substituted 2-imidazolyl.

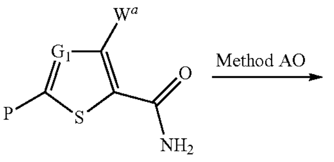

l

-continued

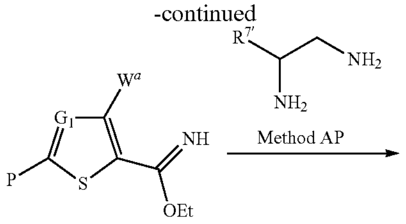

lxxi

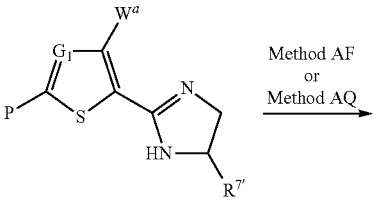

lxii

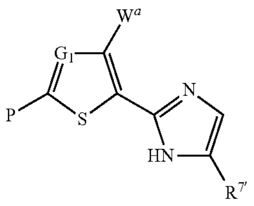

lxiii

As shown in scheme 31, treatment of amides 1, which can be prepared by the procedure described in scheme 17, with an alkylating agent, such as Meerwein's reagent in DCM (Method AO) gives iminoesters lxxi, which are then treated with diamines using appropriate conditions, for example ethanol at elevated temperature (Method AP). Formed dihydroimidazoles lxii can be then oxidized in a same manner as in Method AF described in Scheme 25, or when $R_7$ is appropriate leaving group, elimination can be carried out using a base, such as DBU in DCM (Method AQ).

Scheme 32: General route for the construction of substituted 4 (5)-imidazolyl.

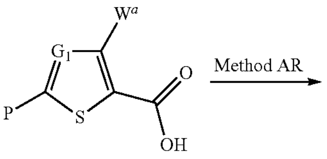

xlviii

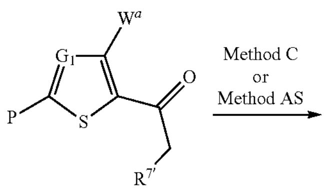

lxxii

-continued

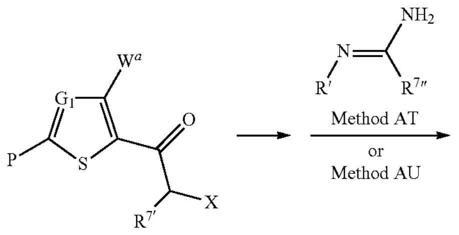

lxxiii

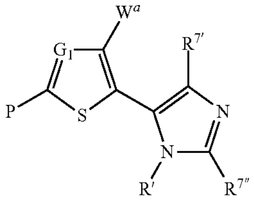

or

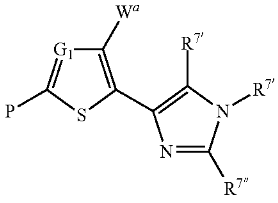

lxxiv

As shown in Scheme 32, acids xlviii are transformed to ketones lxxii using a suitable synthetic sequence, for example through a coupling with N,O-dimethylhydroxylamine and subsequent treatment of the resulting Weinreb amides with alkyllithium or Grignard reagents in a suitable solvent, like THF (Method AR).

Ketones lxxii are then halogenated with a suitable reagent, such as bromine or NBS in an appropriate solvent, like DCM (Method C) to form alpha-halogenated ketones lxxiii (X=halogen). Alternatively, treatment of ketones lxxii with a suitable oxidative sulfonylating agent, like hydroxy(tosyloxy)iodobenzene using suitable conditions, for example heating in acetonitrile (Method AS) affords sulfonyl esters of formula lxxiii ($X=OSO_2R$).

Treatment of Mill with amidine reagents in the presence of a suitable base, like potassium carbonate in a suitable solvent, such as THF-water mixture at elevated temperature or microwave irradiation affords the final imidazoles lxxiv (Method AT). Alternatively, compounds lxxiii can be treated with large excess of amides, such as formamide using microwave irradiation to afford imidazoles lxxiv (Method AU).

Scheme 33: Alternative method for the construction of substituted 4 (5)-imidazolyl.

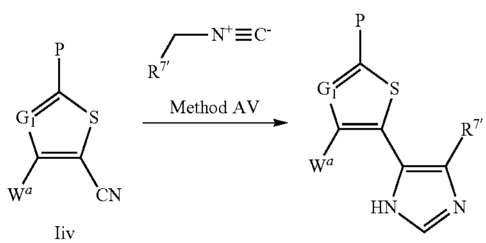

Iiv

Ixxiv

As shown in scheme 33, treatment of nitriles liv, which can be prepared by the procedure described in scheme 19, with isocyanates in the presence of a suitable base, such as tOBuK, in a suitable solvent, for example THF gives imidazoles of formula lxxiv. (Method AV).

Schemes 34 and 35 describe the procedures for introducing pyrazolyl group.

Scheme 34: General route for the construction of 3 (5)-pyrazolyl.

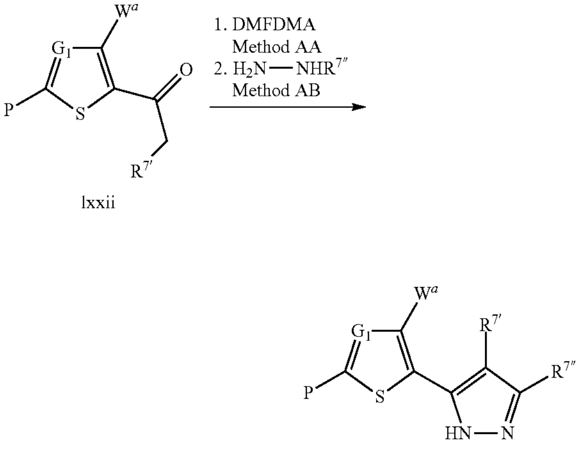

lxxii lxxv

As shown in Scheme 34, ketones lxxii, which can be prepared by the procedure describing in scheme 32, are treated with DMFDMA to afford an intermediate enamines (Method AA) followed by reaction with substituted hydrazine, or hydrazine hydrate in a suitable solvent, for example acetic acid to give pyrazoles lxxv (Method AB).

Scheme 35: General route for the introduction of 4-pyrazolyl.

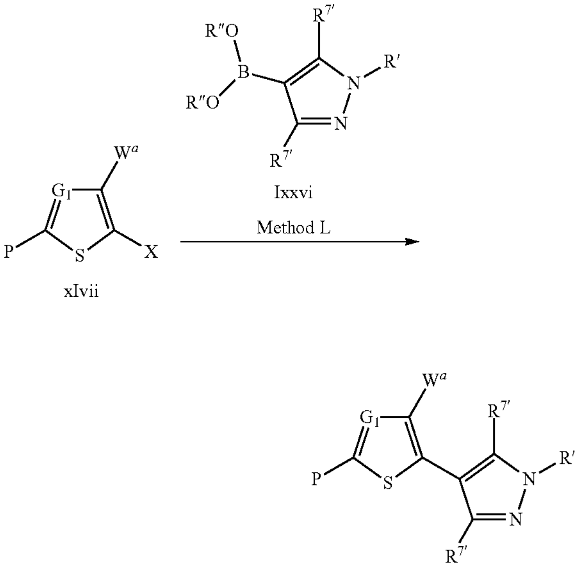

Ixxvi xlvii

Ixxvii

As shown in Scheme 35, halides xlvii which can be prepared by the procedure described in scheme 16, are treated with pyrrol boronic acid or ester lxxvi, in the presence of a suitable catalyst, for example $Pd(PPh_3)_4$, using a base, such as cesium carbonate in a suitable solvent, like dioxane-water mixture at elevated temperature to afford pyrazoles of formula lxxvii (Method L).

Scheme 36: General route for the construction of 1,2,3-triazolyl.

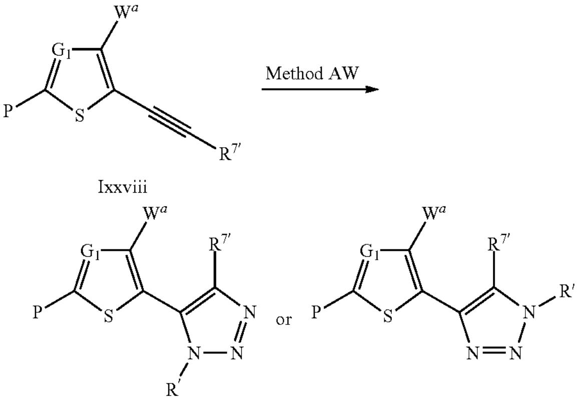

Ixxviii or

Ixxix

As shown in Scheme 36, alkynes lxxviii, which can be prepared by the known Stille- or Sonogashira-coupling reaction of halide xlvii and appropriate alkyne derivative, are treated with azides, inorganic or organic a suitable solvent, such as dioxane at elevated temperature to afford triazoles of formula lxxix (Method AW).

Scheme 37: General route for the construction of terrazolyl.

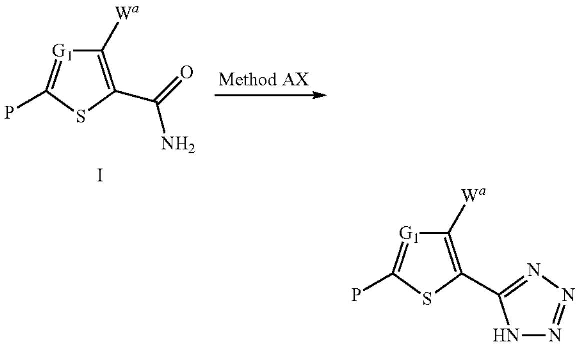

I

Ixxx

As shown in Scheme 37, amides 1, which can be prepared by the procedure described in scheme 17, are treated with an azide source, for example sodium azide using a suitable Lewis acid, for example silicon tetrachloride in an appropriate solvent, such as acetonitrile to give tetrazoles lxxx (Method AX).

Scheme 38: General route for the construction of 2-thiazolyl.

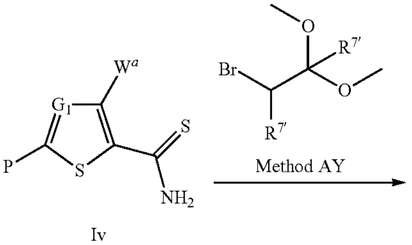

Iv

-continued

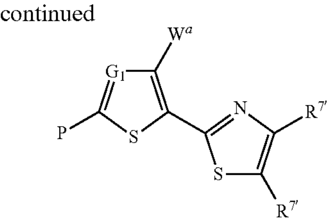

Ixxxi

As shown in scheme 38, thioamides lv, which can be prepared by the procedure described in scheme 20 or 21, are treated with substituted bromoacetaldehyde dimethyl acetals to afford thiazoles of formula lxxxi (Method AY).

Scheme 39: General route for the construction of 4-oxazolyl

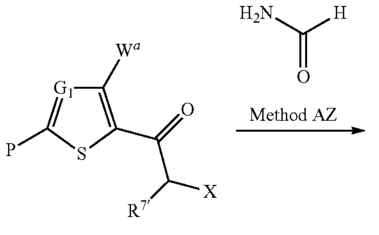

Ixxiii

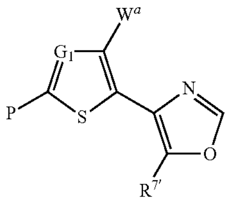

Ixxxii

As shown in scheme 39, alpha-halogenated ketones lxxiii, which can be prepared by the procedure described in scheme 32, are treated with formamide under elevated temperature or microwave irradiation to afford the final 4-oxazoles lxxxii (Method AZ).

Scheme 40: General route for the construction of 1,3,4-thiadiazolyl

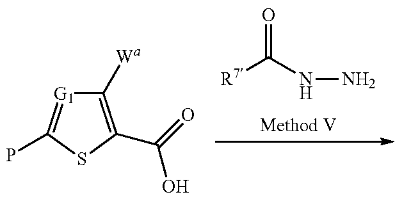

xlviii

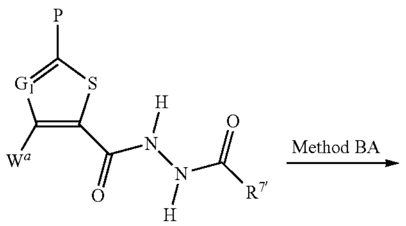

Ixxxiii

-continued

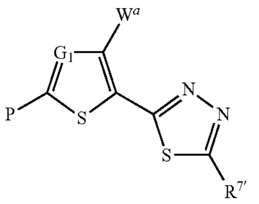

Ixxxiv

As shown in scheme 40, acids xlviii are coupled with acylhydrazines using standard coupling conditions, such as EDCI, HOBt, DMF at elevated temperature to afford intermediates lxxxiii (Method V), that are treated with Lawesson's reagent using suitable conditions, for example in toluene under reflux to afford thiadiazoles lxxxiv (Method BA).

Scheme 41-43 describe general procedure for the functional group transformation on Hy.

Scheme 41: General method for the introduction of amino group to 2-fluoropyridyl

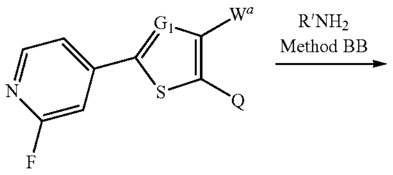

Ixxxv

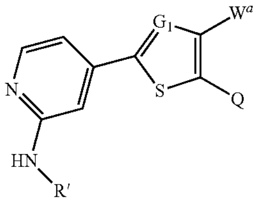

Ixxxvi

Scheme 41 above shows a general route for the transformation of 2-fluoropyridyl to 2-substituted aminopyridyl to give the compounds of formula lxxxvi.

As shown in Scheme 41, compounds lxxxv can be treated with amines at elevated temperature or under microwave irradiation to give 2-aminopyridines lxxxvi (Method BB).

Scheme 42: General method for the introduction of 2-acylaminopyridines by Buchwald reaction

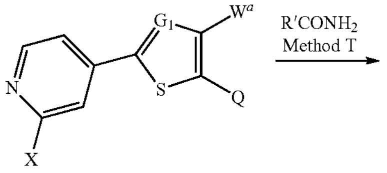

Ixxxvii

-continued

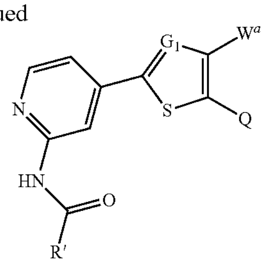

lxxxviii

Scheme 42 above shows a general route for the transformation of 2-halopyridyl to 2-acylaminopyridyl by Buchwald reaction to give the compounds formula lxxxviii.

As shown in Scheme 42, compounds lxxxvii can be treated with amides or carboxamides in the presence of a suitable catalyst, such as $Pd_2$ $dba_3$, XantPhos, base like cesium carbonate in an appropriate solvent, for example dioxane at elevated temperature or under microwave irradiation to give acylaminopyridines lxxxviii (Method T).

Scheme 43: General method for the synthesis of 2-aminopyrimidyl thiophene/thiazole

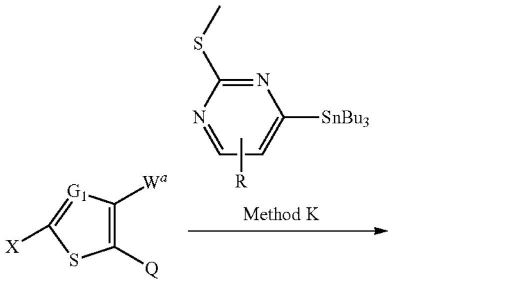

lxxxix

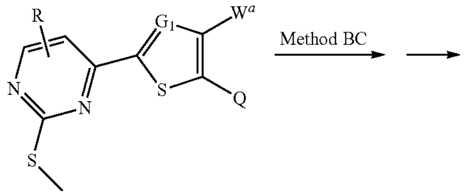

xc

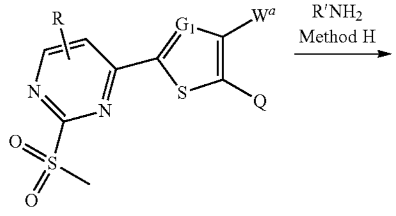

xci

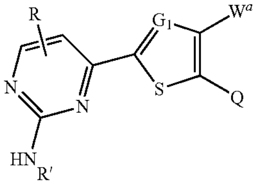

xcii

As shown in Scheme 43, compounds lxxxix can be coupled with stannanes under suitable conditions, for example $Pd(PPh_3)_4$, CuI, LiCl in dioxane at elevated temperature to give compounds xc (Method K).

Oxidation of thioethers xc to sulfones xci can be achieved using a suitable oxidant, for example mCPBA in DCM (Method BC).

Methanesulfonyl group of sulfones xci can be displaced by treatment with amines in a suitable solvent, for example THF to afford 2-aminopyrimidines xcii (method H).

Schemes 44-52 describe the procedures for the synthesis of building blocks for Hy.

Scheme 44: General method for the synthesis of imidazo[1,2-a]pyridine building blocks.

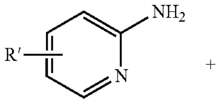

xciii

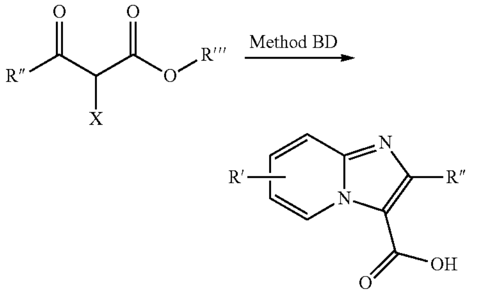

xciv

Scheme 44 above shows a general method for the synthesis of imidazo[1,2-a]pyridines xciv. As shown in Scheme 44, 2-aminopyridines xciii are condensed with alfa-halogenated beta-ketoesters in a suitable solvent, for example ethanol at elevated temperature to afford intermediate esters, that are hydrolyzed using standard conditions, such as aqueous sodium hydroxide in THF followed by acidic workup to give acids xciv (Method BD).

Scheme 45: General method for the synthesis of imidazo[1,2-b]pyridazine building blocks

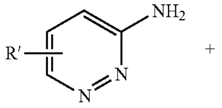

xcv

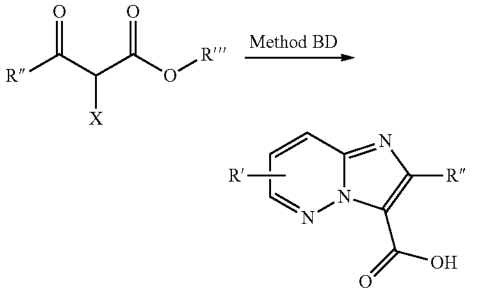

xcvi

Scheme 45 above shows a general method for the synthesis of imidazo[1,2-b]pyridazines xcvi.

As shown in Scheme 45, 2-aminopyridazines xcv are condensed with alfa-halogenated beta-ketoesters in a suitable solvent, for example ethanol at elevated temperature to afford intermediate esters, that are hydrolyzed using standard conditions, such as aqueous sodium hydroxide in THF followed by acidic workup to give acids xcvi (Method BD).

Scheme 46: General method for the synthesis of imidazo[2,1-b][1,3]thiazole building blocks

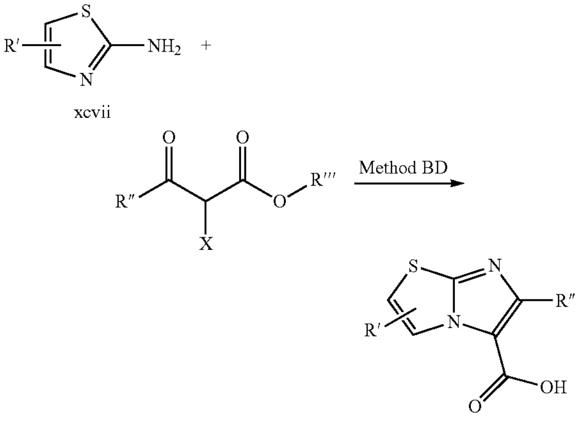

xcvii xcviii

Scheme 46 above shows a general method for the synthesis of imidazo[2,1-b][1,3]thiazoles xcviii.

As shown in Scheme 46, 2-aminothiazoles xcvii are condensed with alfa-halogenated beta-ketoesters in a suitable solvent, for example ethanol at elevated temperature to afford intermediate esters, that are hydrolyzed using standard conditions, such as aqueous sodium hydroxide in THF followed by acidic workup to give acids xcviii (Method BD).

Scheme 47: General method for the synthesis of pyrazolo[1,5-a]pyridine building blocks

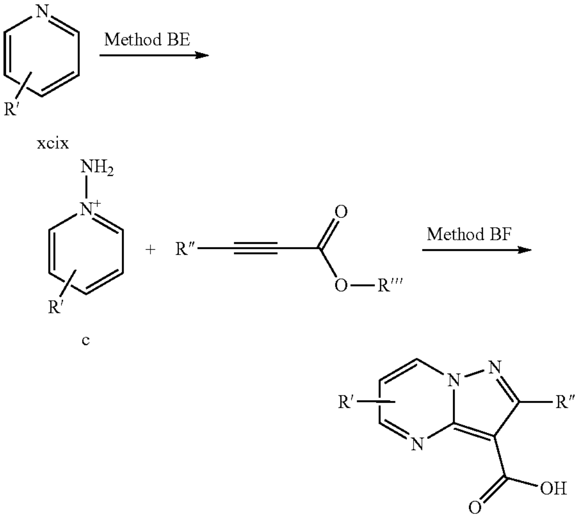

xcix c ci

Scheme 47 above shows a general method for the synthesis of pyrazolo[1,5-a]pyridines ci. As shown in Scheme 47, pyridines xcix are N-aminated with a suitable agent, such as 0-(mesitylsulfonyl)hydroxylamine using appropriate conditions, for example toluene or ethyl acetate as solvent (Method BE).

Resulting N-aminopyridinium salts c are then condensed with alkynylcarboxylic acid esters with a suitable base, such as potassium carbonate in a suitable solvent, for example DMF to afford intermediate esters, that are hydrolyzed using standard conditions, such as aqueous sodium hydroxide in THF followed by acidic workup to give acids ci (Method BF).

Scheme 48: General method for the syntheis of pyrazolo[5,1-b][1,3]thiazole building blocks

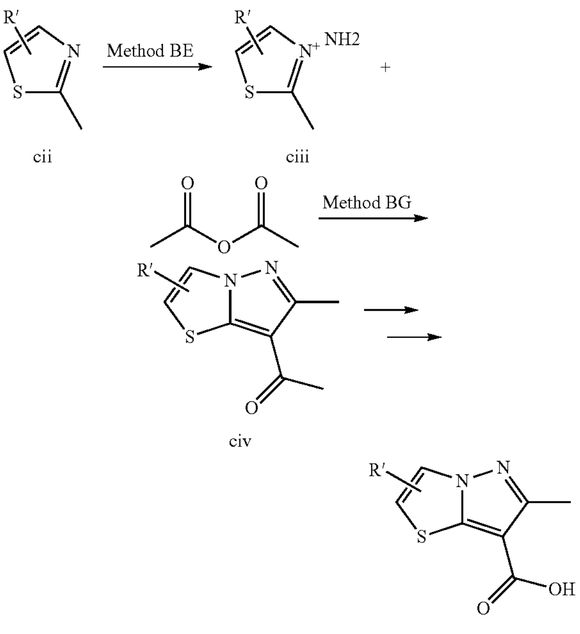

cii ciii civ cv

Scheme 48 above shows a general method for the synthesis of pyrazolo[5,1-b][1,3]thiazoles cv.

As shown in Scheme 48, 2-methylthiazoles cii are N-aminated with a suitable agent, such as O-(mesitylsulfonyl)hydroxylamine using appropriate conditions, for example toluene or ethyl acetate as solvent (Method BE).

Resulting N-aminothiazolium salts ciii are then condensed with acetic anhydride and potassium acetate at elevated temperature to afford methyl ketone intermediate civ (Method BG), which can be converted to carboxylic acid cv moiety by well known functional transformation of methyl keton to carboxylic acid.

Scheme 49: Alternative method for the syntheis of pyrazolo[5,1-b][1,3]thiazole derivatives

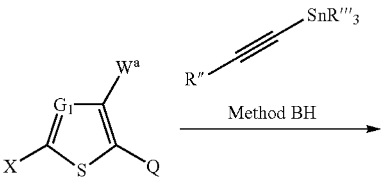

Ixxxix

-continued

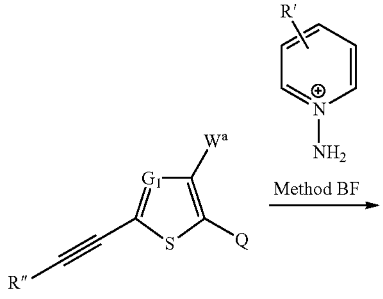

cvi

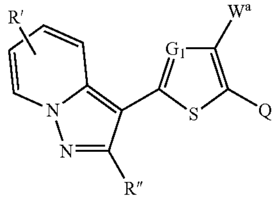

cvii

Scheme 49 above shows an alternative method for the synthesis of pyrazolopyridines cvii. As shown in Scheme 49, halides lxxxix, which can be prepared by the procedure described in schemes 3, 5, 6 are treated with alkynyl stannanes in the presence of a suitable catalysts, such as $Pd(PPh_3)_4$, CuI, with LiCl in an appropriate solvent, like dioxane at elevated temperature to give alkynes of formula cvi (Method BH). Alkynes cvi are then coupled with N-aminopyridinium salts with a base, like potassium carbonate in a suitable solvent, for example DMF to afford compounds of formula cvii (Method BF).

Scheme 50: Alternative method for the synthesis of imidazo[1,2-a]pyridine building blocks.

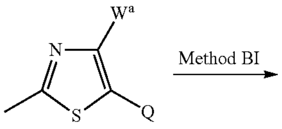

cviii

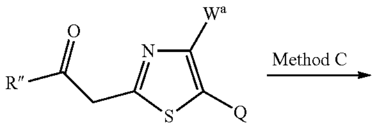

cix

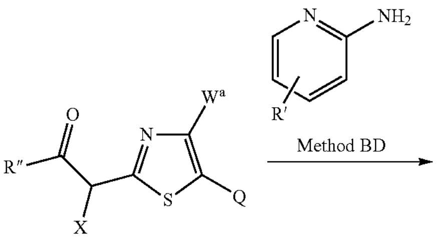

cx

-continued

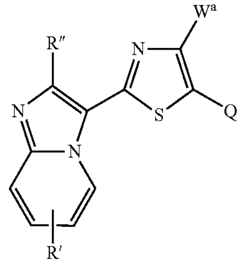

cxi

Scheme 50 above shows an alternative method for the synthesis of imidazolopyridines cxi. As shown in Scheme 50, 2-methylthiazoles cviii are deprotonated with a suitable reagent, such as n-BuLi and subsequently treated with Weinreb amides in a suitable solvent, such as THF to give ketones cix (Method BI). Halogenation of ketones is achieved using standard conditions, for example NBS in DCM (Method C) and the resulting haloketones cx are then treated with aminopyridines in a suitable solvent, for example ethanol at elevated temperature to give compounds of formula cxi (Method BD).

Scheme 51: General method for the synthesis of bicyclic lactam building blocks

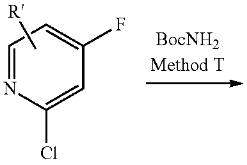

cxii

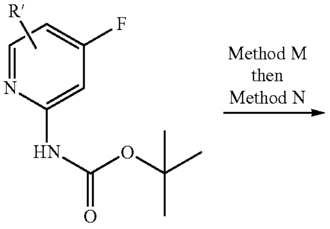

cxiii

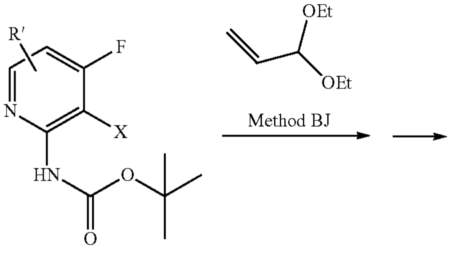

cxiv

-continued

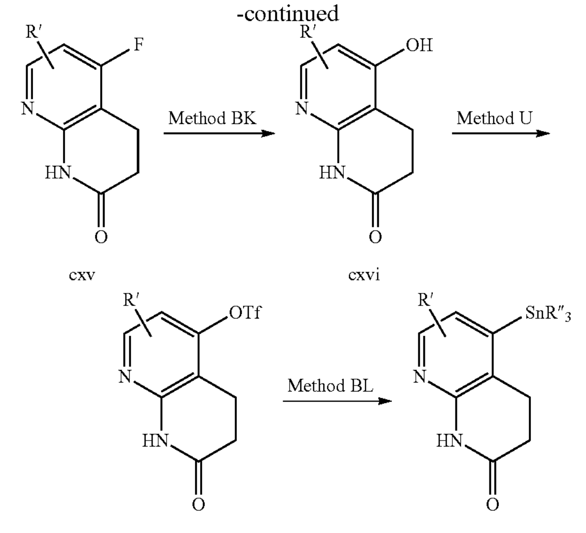

cxv cxvi cxvii cxviii

Scheme 51 above shows a general method for the synthesis of bicyclic lactam building blocks cxvii and cxviii. As shown in Scheme 51, substituted 2-chloro-4-fluoropyridines can be amidated, for example with $BocNH_2$, $Pd_2$ $dba_3$ and a suitable ligand, such as X-Phos in the presence of a base, for example cesium carbonate in an appropriate solvent, like dioxane to afford Boc-protected 2-aminopyridines cxiii (Method T). Compounds cxiii can be deprotonated, for example using n-BuLi/TMEDA in THF at low temperature (Method M) and then quenched with a molecule of halogen, such as iodine in THF (Method N) to give halogenated compounds cxiv. Compounds cxiv can be coupled with diethoxypropene using a suitable Pd catalyst, such as Di-mu-chlorobis[5-hydroxy-2-[1-(hydroxyimino-kappaN)ethyl]phenyl-kappaC]palladium (II) dimer with an appropriate base, like N,N-diisopropylethylamine in a suitable solvent, for example DMF-water mixture (Method BJ) to afford lactams of formula cxv. Transformation of fluoro cxv into hydroxyl analogs cxvi can be carried out using a standard procedure, for example treatment with benzyl alcohol in the presence of a base, such as sodium hydride at elevated temperature and subsequent debenzylation, such as using hydrogenation with Pd/C catalyst in a suitable solvent, such as ethanol (Method BK). Triflates cxvii can be formed by treatment of cxvi with a suitable reagent, for example triflic anhydride using appropriate conditions, such as pyridine as a base in DCM (Method U). Triflates cxvii can be coupled with stannanes xxix, obtained in Scheme 6 using standard Stille conditions (Method K). Alternatively, triflates cxvii can be transformed into stannanes cxviii using a suitable method, such as heating with hexamethyldistannane, $Pd(PPh_3)_4$ in a suitable solvent, like THF (Method BL). Stannanes cxviii can be then coupled with thiophene/thiazole halides lxxxix, which can be prepared by the procedures described in schemes 3, 5, 6 using standard Stille conditions (Method K).

Scheme 52: Alternative method for the synthesis of bicyclic lactam building blocks

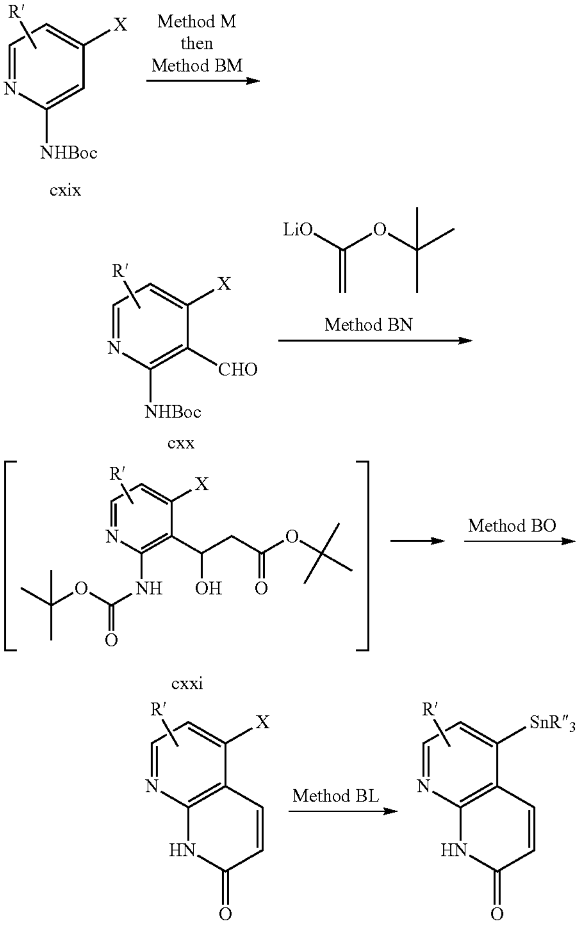

cxix cxx cxxi cxxii cxxiii

Scheme 52 above shows an alternative method for the synthesis of bicyclic lactam building blocks cxxiii. As shown in Scheme 52, compounds cxix can be deprotonated with a suitable reagent, such as n-BuLi in THF at low temperature (Method M) and then treated with DMF to produce carbaldehydes cxx (Method BM). Aldehyde group in cxx can be then treated with enolate generated from t-Butylacetate and LDA in a suitable solvent, such as THF at low temperature (Method BN) to form intermediate β-hydroxyesters cxxi, that can be cyclized to lactams cxxii using an acid, such as HCl in water at elevated temperature (Method BO). Halides cxxii can be coupled with stannanes xxix, obtained in Scheme 6 using standard Stille conditions (Method K). Alternatively, transformation of aryl halides cxxii to stannanes cxxiii can be carried out using hexamethyldistannane, $Pd(PPh_3)_4$ in a suitable solvent, like THF (Method BL). Stannanes cxviii can be then coupled with thiophene/thiazole halides lxxxix, which can be prepared by the procedures described in schemes 3, 5, 6 using standard Stille conditions (Method K).

5. Uses, Formulation and Administration

As discussed above, the present invention provides compounds that are useful as inhibitors of PI3K enzymes, and thus the present compounds are useful for treating proliferative, inflammatory, or cardiovascular disorders such as tumor and/or cancerous cell growth mediated by PI3K. In particular, the compounds are useful in the treatment of cancers in a subject, including, but not limited to, lung and bronchus, prostate, breast, pancreas, colon and rectum, thyroid, liver and intrahepatic bile duct, hepatocellular, gastric, glioma/glioblastoma, endometrial, melanoma, kidney, and renal pelvis, urinary bladder, utering corpus, uterine cervix, ovary, multiple myeloma, esophagus, acute myelogenous leukemia, chronic myelogenous leukemia, lymphocytic leukemia, myeloid leukemia, brain, oral cavity, and pharynx, small intestine, non-Hodgkin lymphoma, and villous colon adenoma.

In some embodiments, compounds of the invention are suitable for the treatment of breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

In other embodiments, compounds of the invention are suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of PI3K.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, or cardiovascular disorder, or is that amount effective for treating cancer. In other embodiments, an "effective amount" of a compound is an amount which inhibits binding of PI3K and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the inventive compounds may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents, such as other inhibitors of PI3K. In some embodiments, a compound of the invention is administered in conjunction with a therapeutic agent selected from the group consisting of cytotoxic agents, radiotherapy, and immunotherapy. It is understood that other combinations may be undertaken while remaining within the scope of the invention.

Another aspect of the invention relates to inhibiting PI3K, activity in a biological sample or a patient, which method comprises administering to the patient, or contacting said biological sample with a compound of formula I or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where PI3K kinase plays a role.

TABLE 1

Table 1 below depicts certain compounds represented by compounds of general formula I-A and I-B.

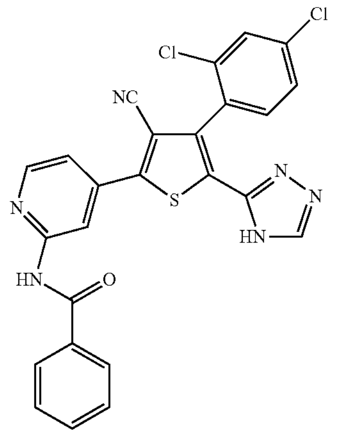

1-A

TABLE 1-continued
Table 1 below depicts certain compounds represented by compounds of general formula I-A and I-B.
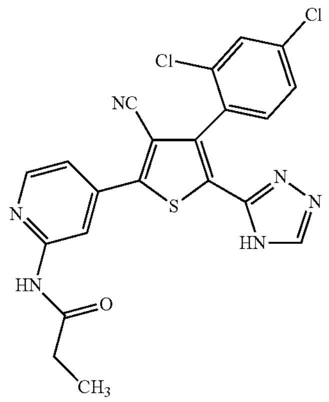
2-A
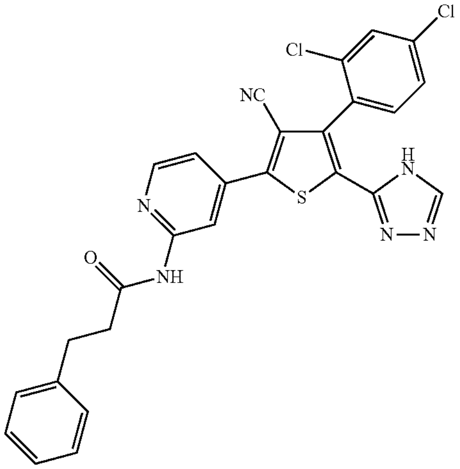
3-A
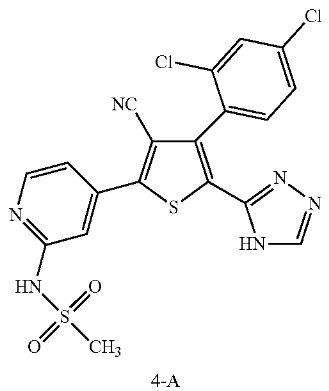 [SMILES: CS(=O)(=O)Nc1cc(-c2sc(-c3nnc[nH]3)c(-c3ccc(Cl)cc3Cl)c2C#N)ccn1]
4-A
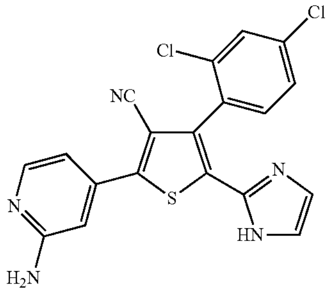
5-A
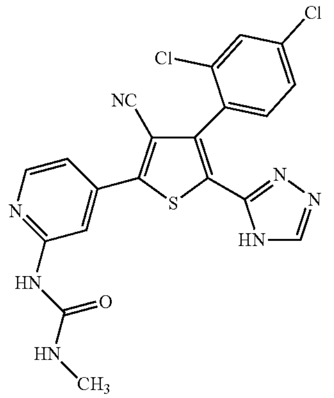
6-A
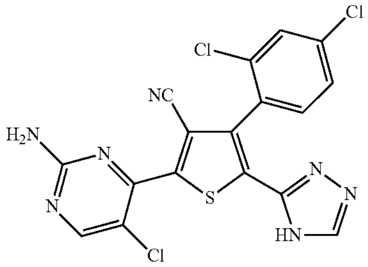
7-A
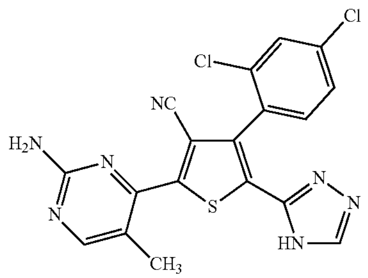
8-A TABLE 1-continued
Table 1 below depicts certain compounds represented by compounds of general formula I-A and I-B.
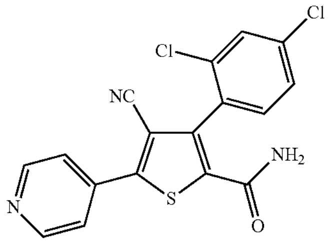
9-A
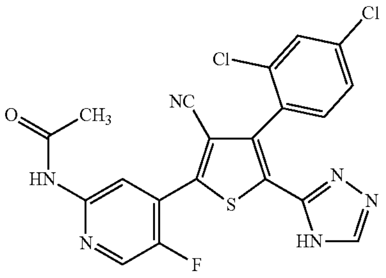
10-A
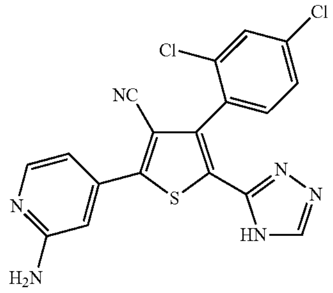
11-A
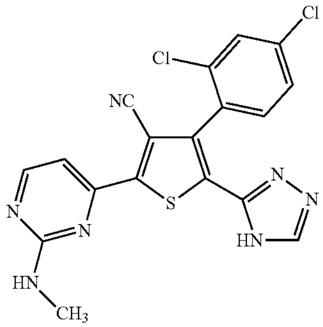
12-A
TABLE 1-continued
Table 1 below depicts certain compounds represented by compounds of general formula I-A and I-B.
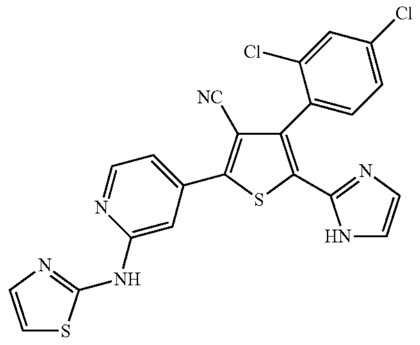
13-A
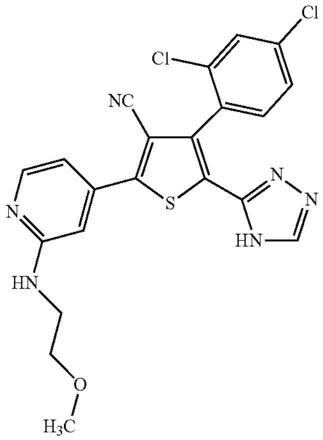
14-A
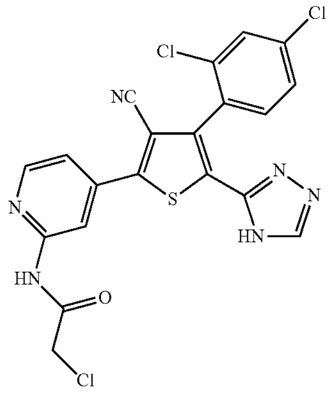
15-A TABLE 1-continued
Table 1 below depicts certain compounds represented by compounds of general formula I-A and I-B.
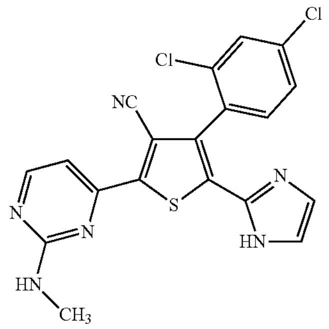
16-A
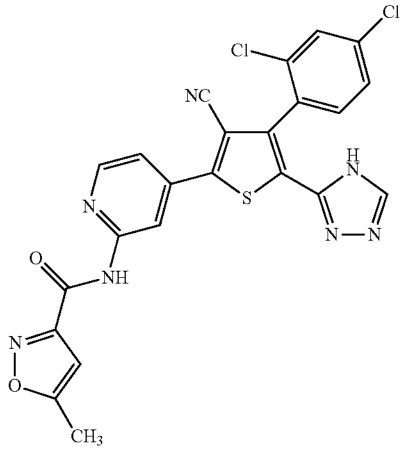
17-A
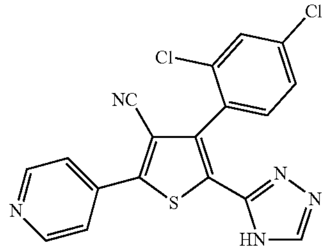
18-A
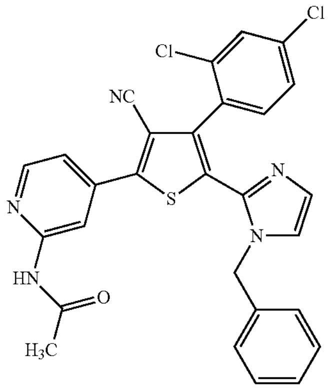
19-A
TABLE 1-continued
Table 1 below depicts certain compounds represented by compounds of general formula I-A and I-B.
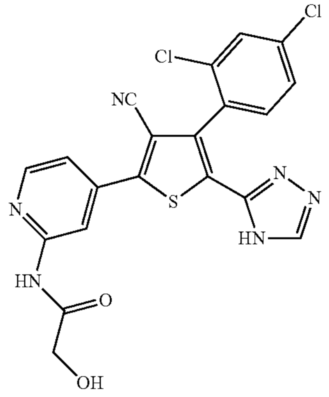
20-A
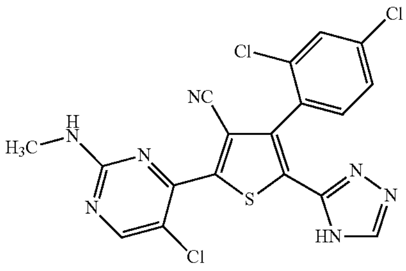
21-A
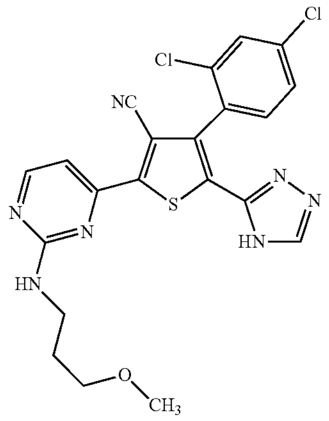
22-A TABLE 1-continued
Table 1 below depicts certain compounds represented by compounds of general formula I-A and I-B.
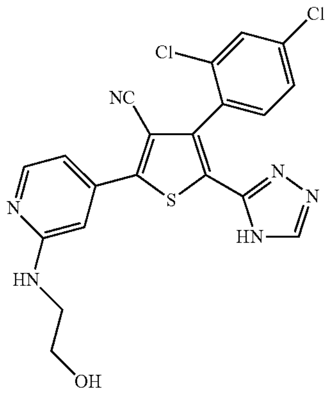
23-A
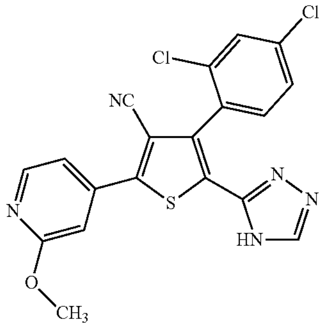
24-A
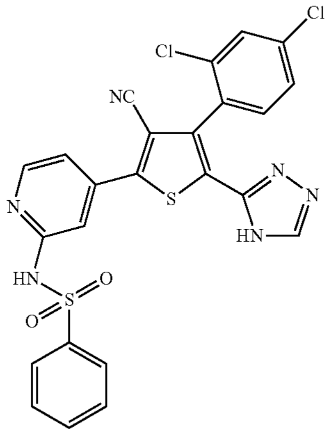
25-A
TABLE 1-continued
Table 1 below depicts certain compounds represented by compounds of general formula I-A and I-B.
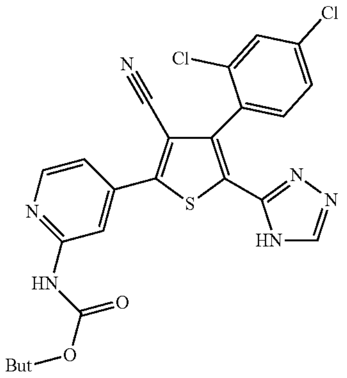
26-A
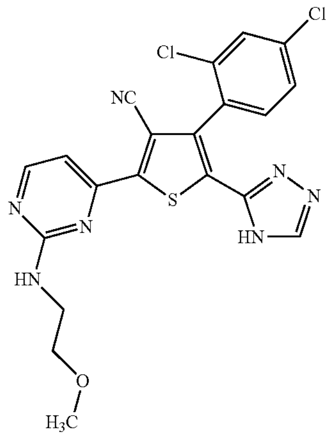
27-A
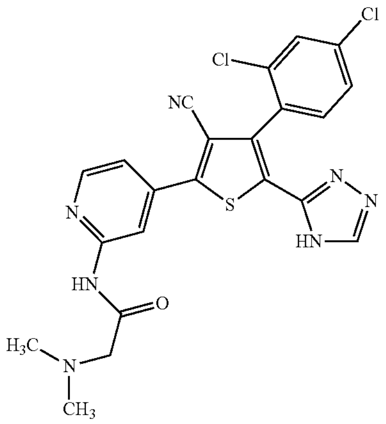
28-A Table 1 below depicts certain compounds represented by compounds of general formula I-A and I-B.
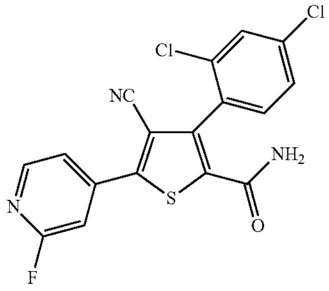
29-A
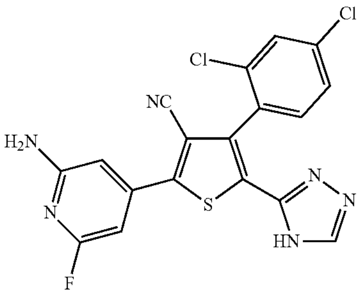
30-A
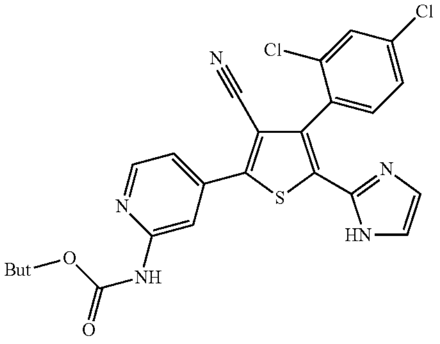
31-A
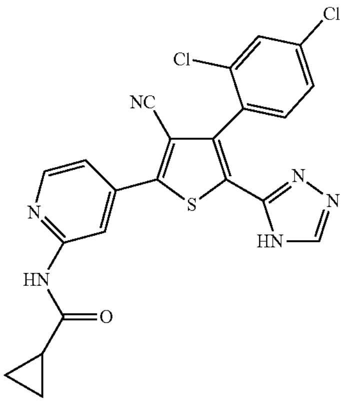
32-A
Table 1 below depicts certain compounds represented by compounds of general formula I-A and I-B.
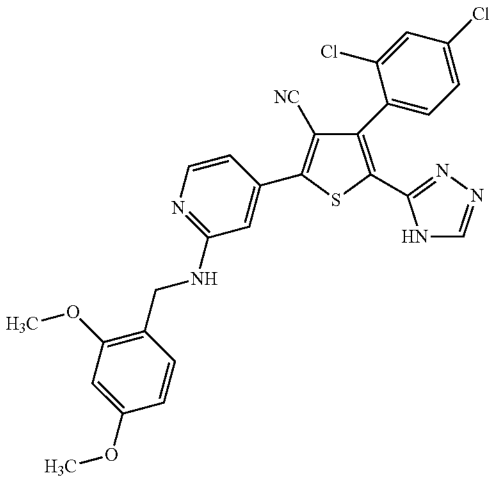
33-A
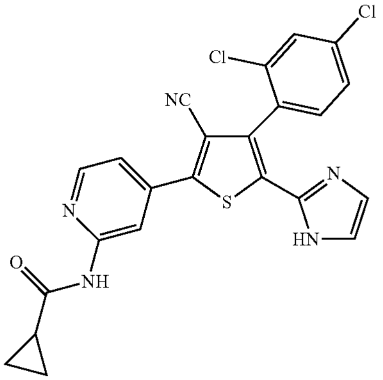
34-A
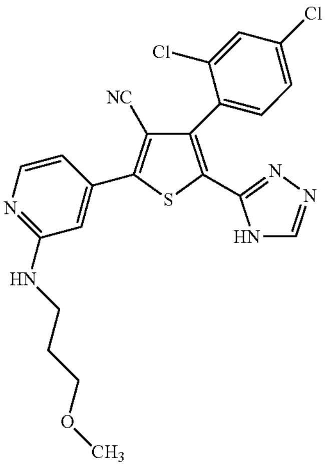
35-A TABLE 1-continued
| Table 1 below depicts certain compounds represented by compounds of general formula I-A and I-B. |
| --- |
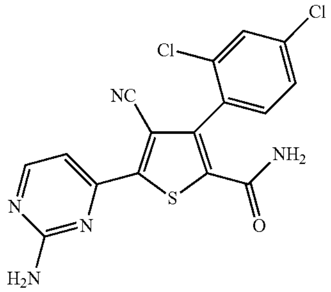
36-A
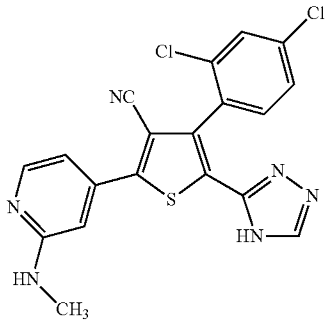 [SMILES: N#Cc1c(-c2ccnc(N)c2)sc(-c2ncc[nH]2)c1-c1ccc(Cl)cc1Cl]
37-A
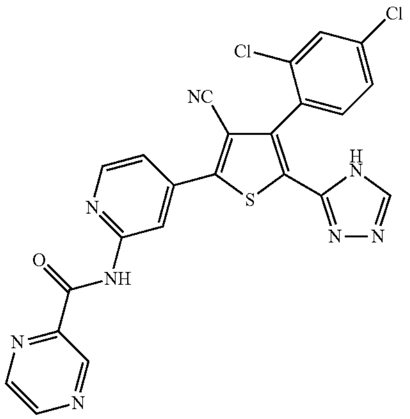
38-A
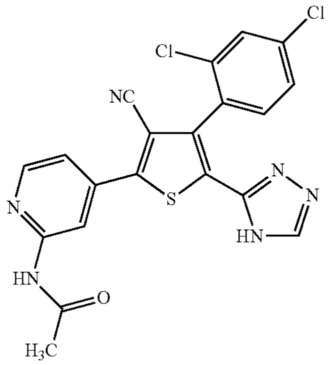
39-A
TABLE 1-continued
| Table 1 below depicts certain compounds represented by compounds of general formula I-A and I-B. |
| --- |
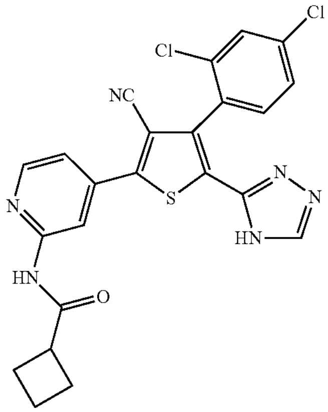
40-A
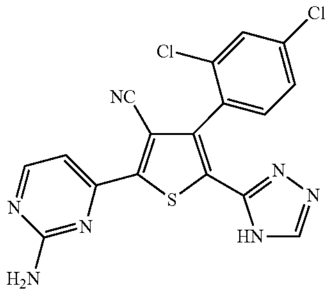
41-A
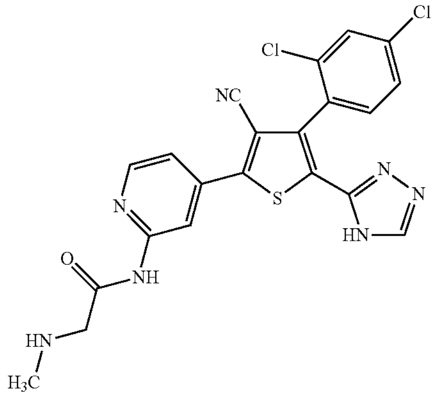
42-A
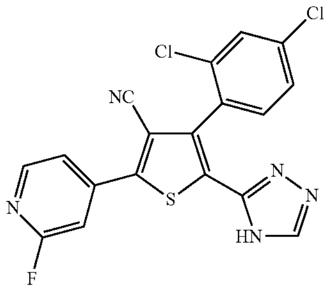
43-A TABLE 1-continued
Table 1 below depicts certain compounds represented by compounds of general formula I-A and I-B.
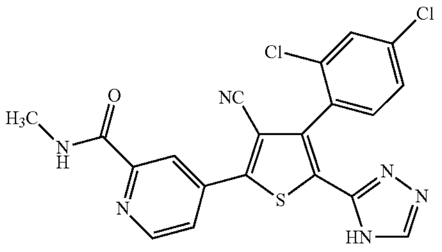
44-A
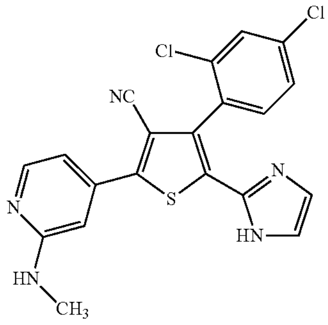
45-A
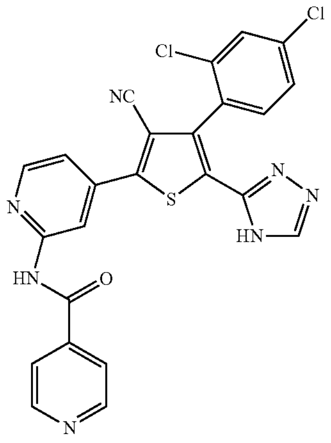
46-A
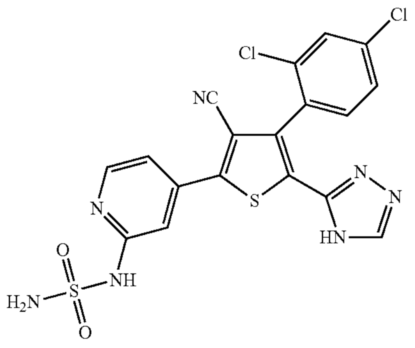
47-A
TABLE 1-continued
Table 1 below depicts certain compounds represented by compounds of general formula I-A and I-B.
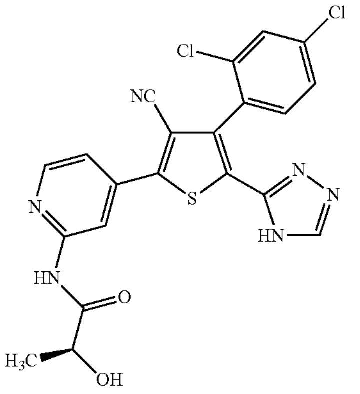
48-A
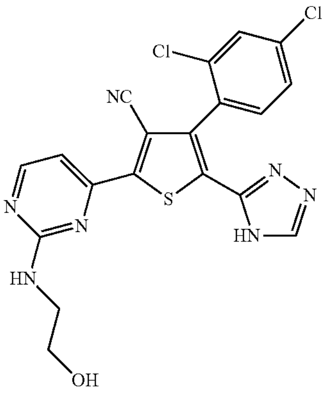
49-A
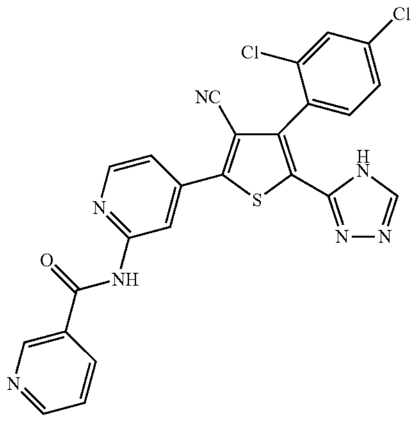
50-A TABLE 1-continued
Table 1 below depicts certain compounds represented by compounds of general formula I-A and I-B.
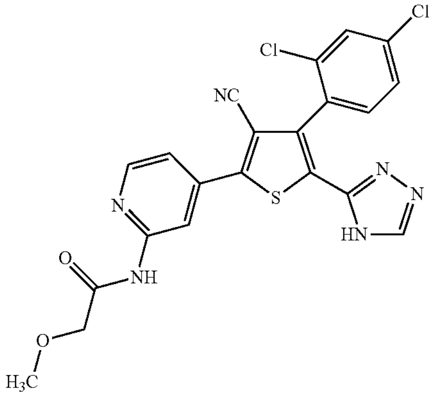
51-A
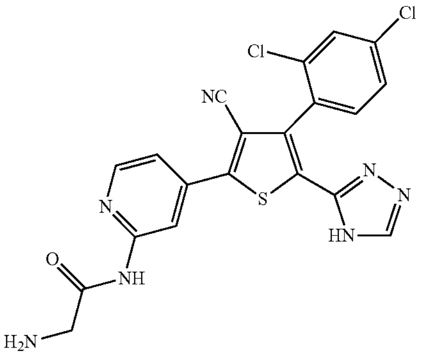
52-A
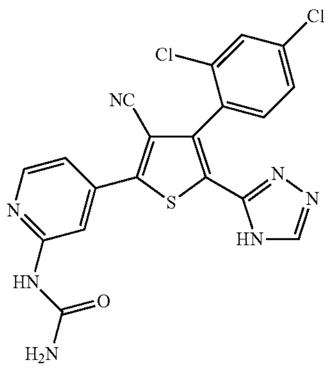
53-A
TABLE 1-continued
Table 1 below depicts certain compounds represented by compounds of general formula I-A and I-B.
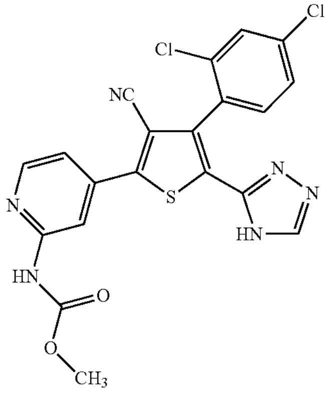
54-A
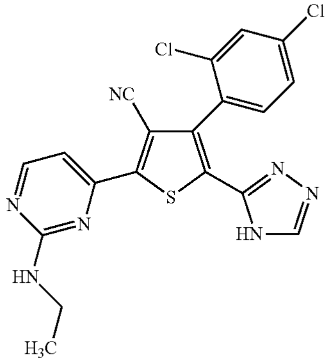
55-A
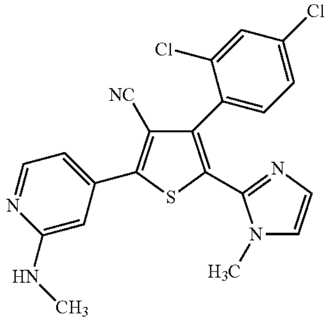
56-A
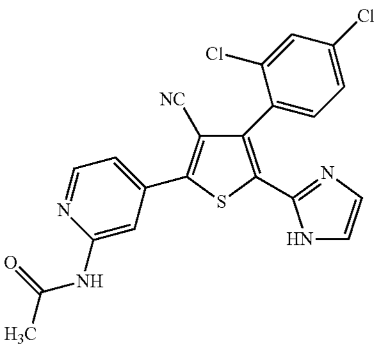
57-A TABLE 1-continued
Table 1 below depicts certain compounds represented by compounds of general formula I-A and I-B.
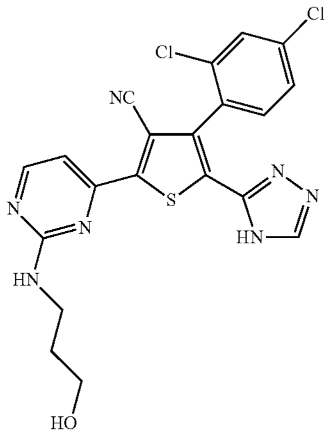
58-A
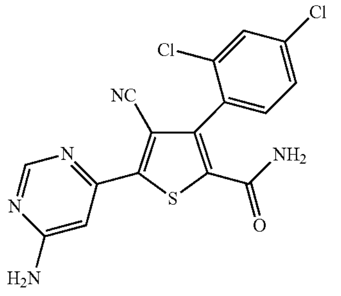
59-A
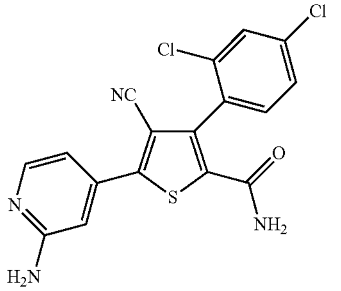
60-A
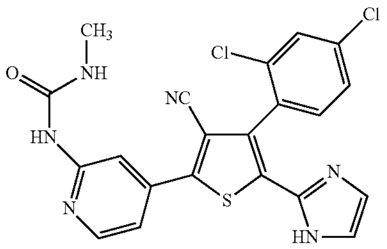
61-A
TABLE 1-continued
Table 1 below depicts certain compounds represented by compounds of general formula I-A and I-B.
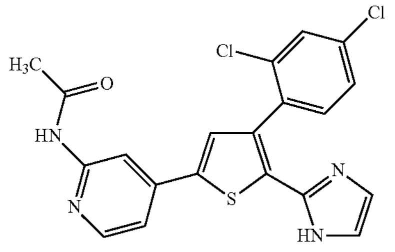
62-A
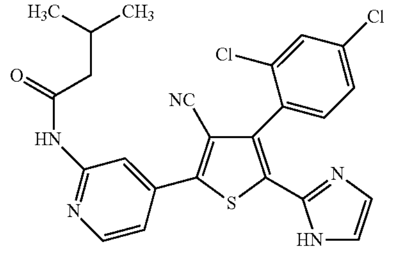
63-A
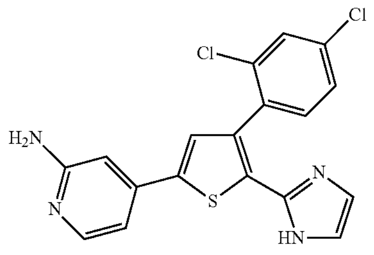
64-A
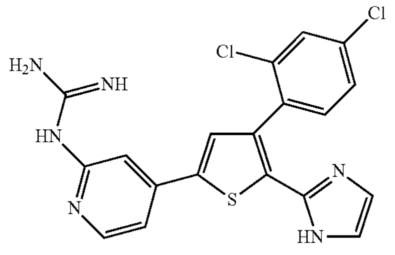
65-A
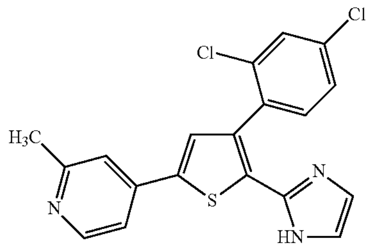
66-A TABLE 1-continued
Table 1 below depicts certain compounds represented by compounds of general formula I-A and I-B.
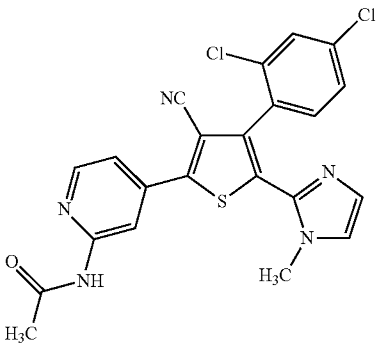
67-A
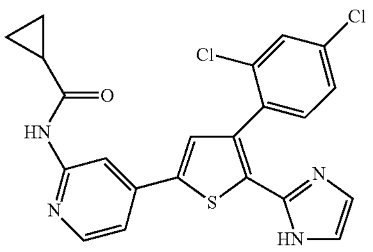
68-A
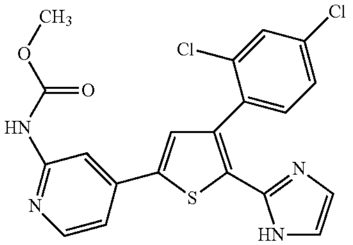
69-A
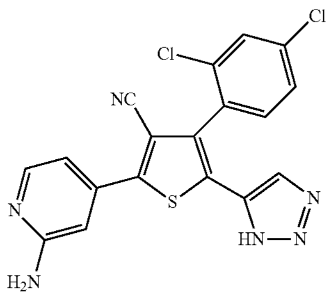
70-A
TABLE 1-continued
Table 1 below depicts certain compounds represented by compounds of general formula I-A and I-B.
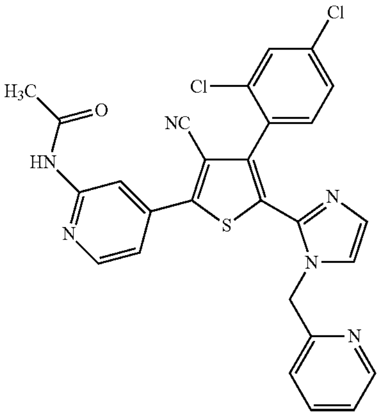
71-A
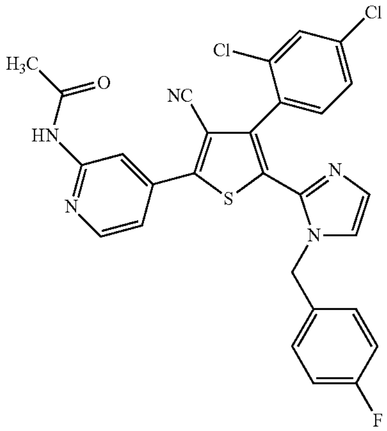
72-A
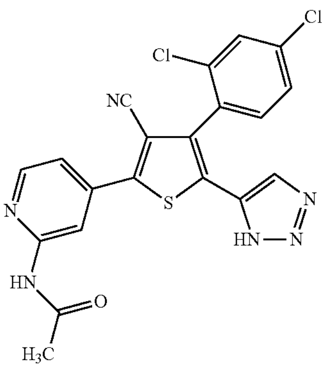
73-A Table 1 below depicts certain compounds represented by compounds of general formula I-A and I-B.
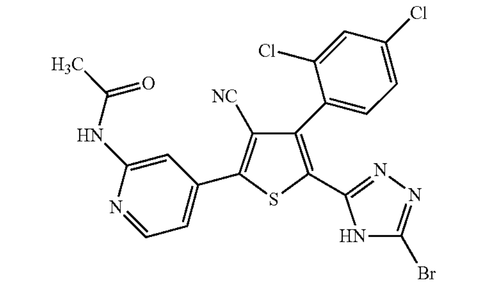
74-A
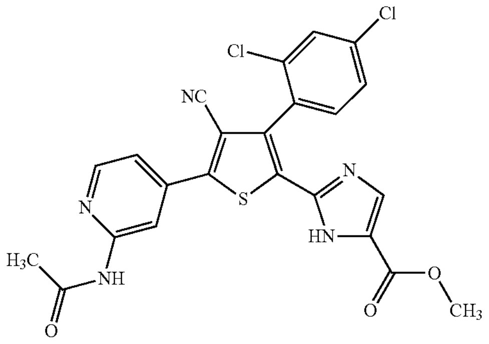
75-A
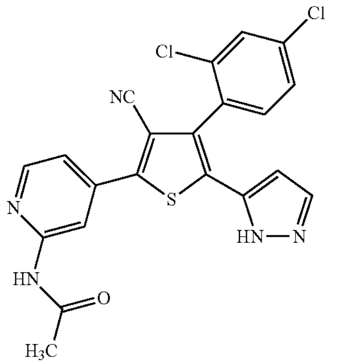
76-A
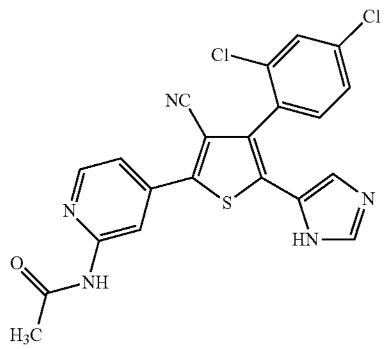
77-A
Table 1 below depicts certain compounds represented by compounds of general formula I-A and I-B.
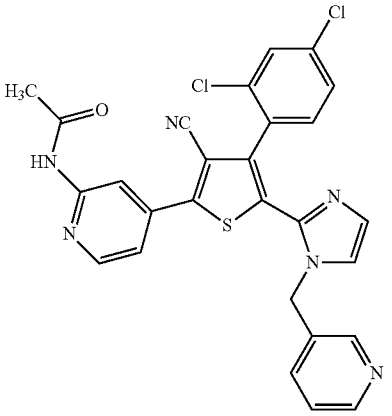
78-A
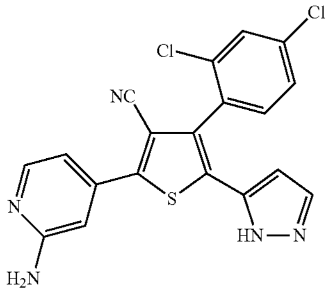
79-A
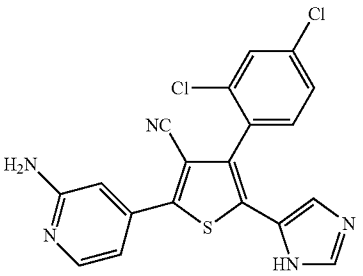
80-A
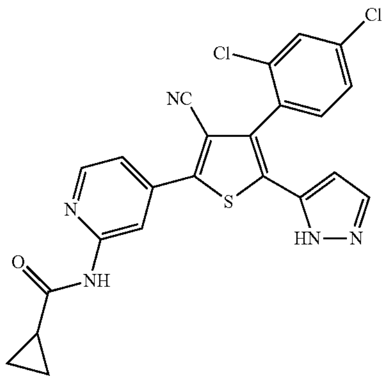
81-A TABLE 1-continued
| Table 1 below depicts certain compounds represented by compounds of general formula I-A and I-B. |
|---|
| 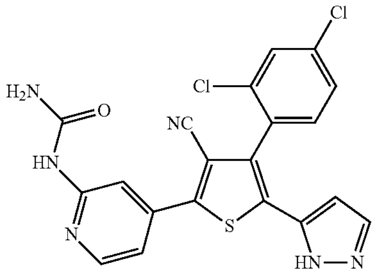 |
| 82-A |
| 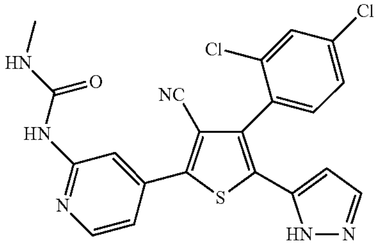 |
| 83-A |
| 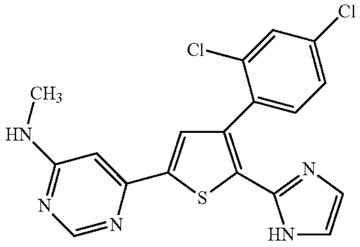 |
| 84-A |
| 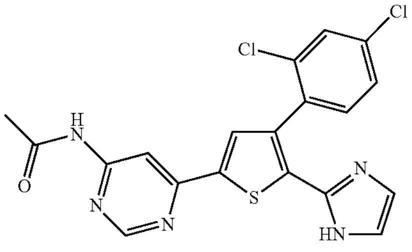 |
| 85-A |
| 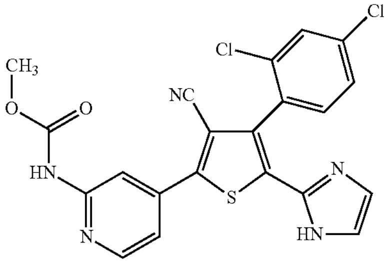 |
| 86-A |
TABLE 1-continued
| Table 1 below depicts certain compounds represented by compounds of general formula I-A and I-B. |
|---|
| 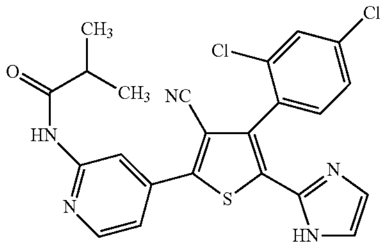 |
| 87-A |
| 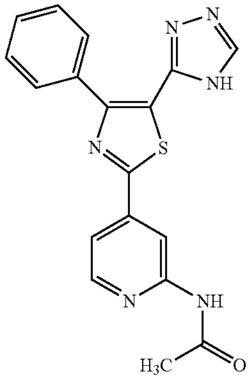 |
| 1-B |
| 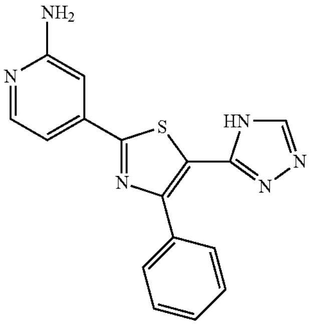 |
| 2-B |
| 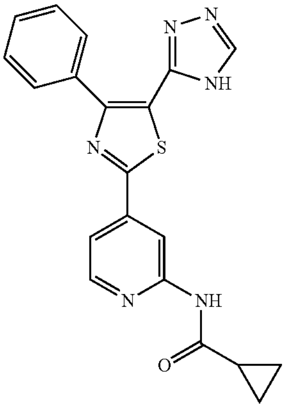 |
| 3-B |

TABLE 1-continued
| Table 1 below depicts certain compounds represented by compounds of general formula I-A and I-B. |
|---|
| 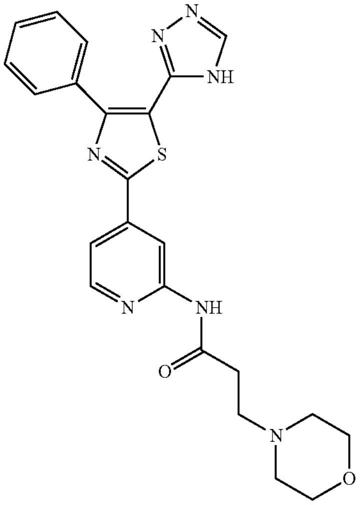 4-B |
| 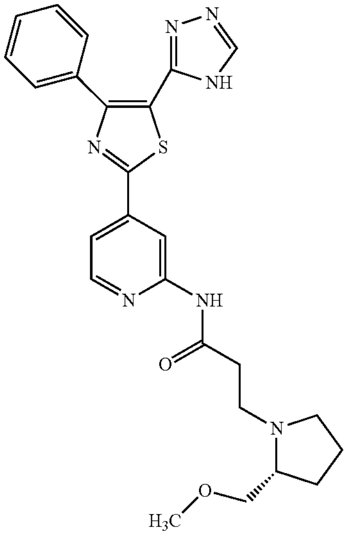 5-B |
TABLE 1-continued
| Table 1 below depicts certain compounds represented by compounds of general formula I-A and I-B. |
|---|
| 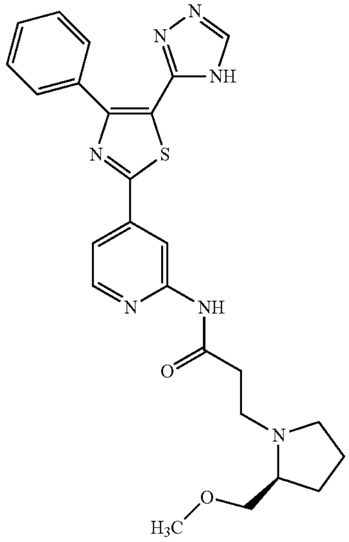 6-B |
| 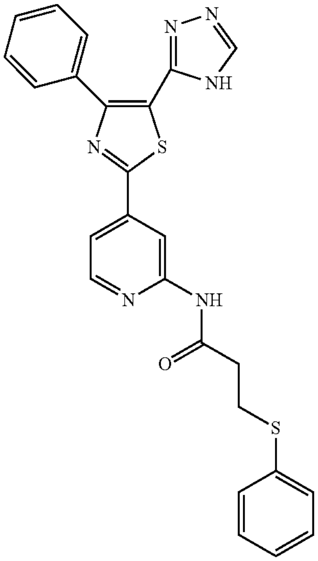 7-B |
| 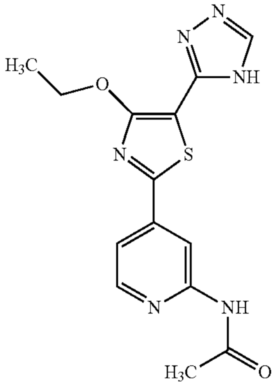 8-B |

TABLE 1-continued
Table 1 below depicts certain compounds represented by compounds of general formula I-A and I-B.
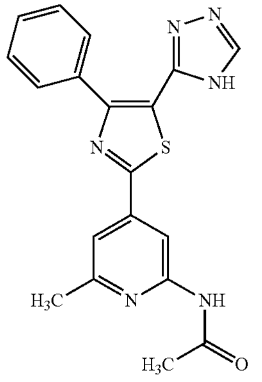
9-B
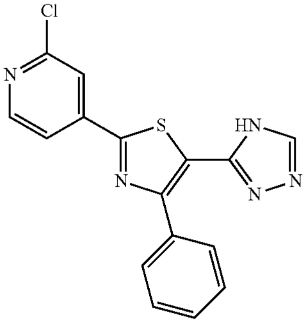
10-B
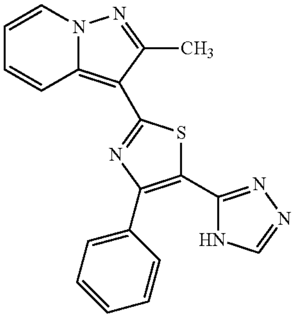
11-B
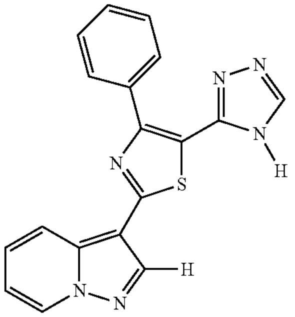
12-B
TABLE 1-continued
Table 1 below depicts certain compounds represented by compounds of general formula I-A and I-B.
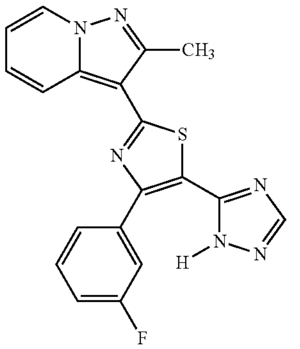
13-B
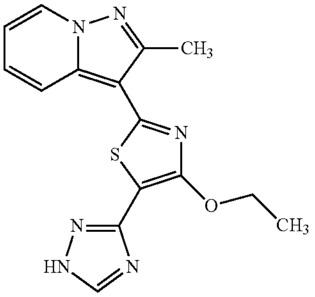
14-B
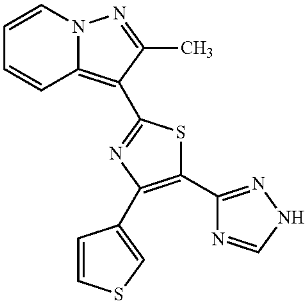
15-B
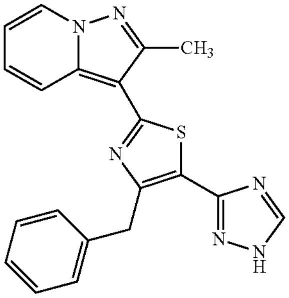
16-B TABLE 1-continued
Table 1 below depicts certain compounds represented by compounds of general formula I-A and I-B.
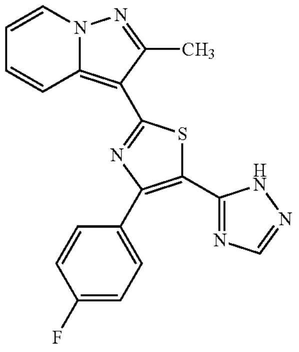
17-B
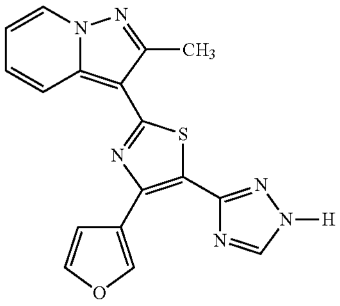
18-B
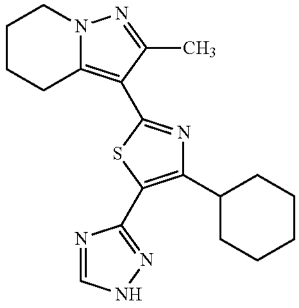
19-B
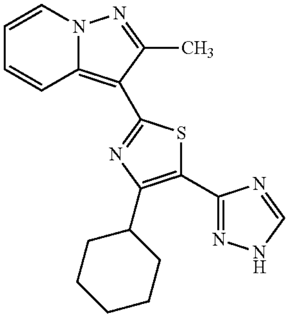
20-B
TABLE 1-continued
Table 1 below depicts certain compounds represented by compounds of general formula I-A and I-B.
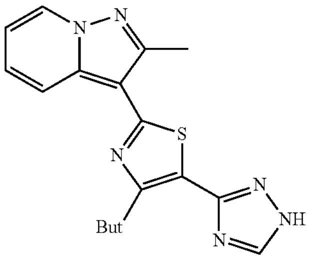
21-B
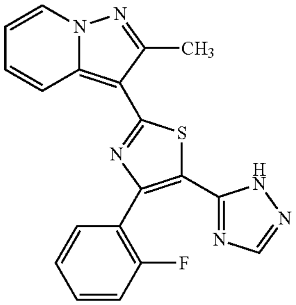
22-B
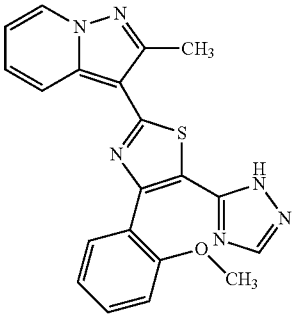
23-B
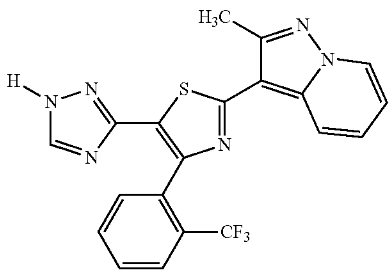
24-B TABLE 1-continued
Table 1 below depicts certain compounds represented by compounds of general formula I-A and I-B.
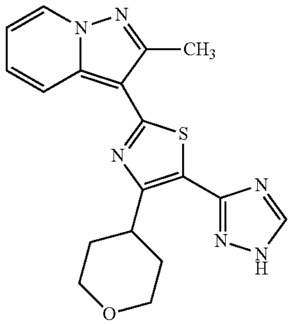
25-B
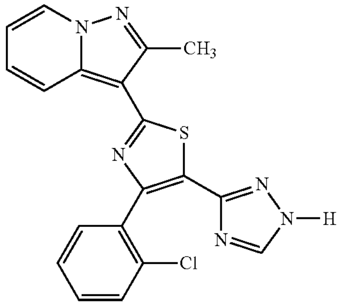
26-B
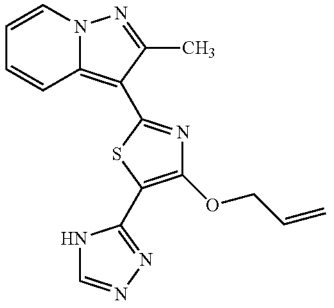
27-B
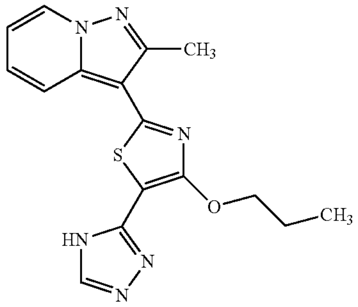
28-B
TABLE 1-continued
Table 1 below depicts certain compounds represented by compounds of general formula I-A and I-B.
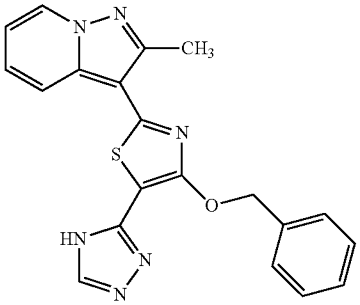
29-B
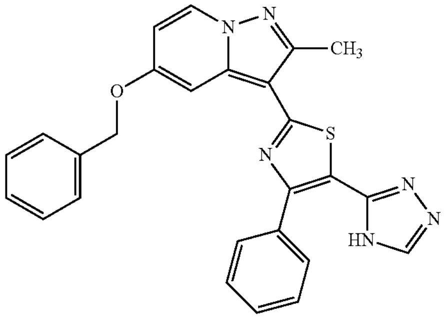
30-B
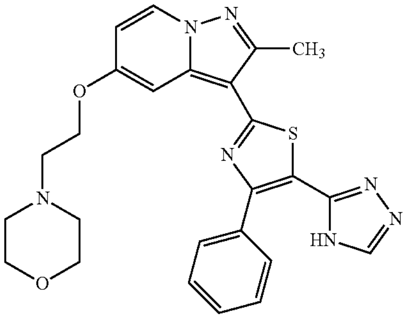
31-B
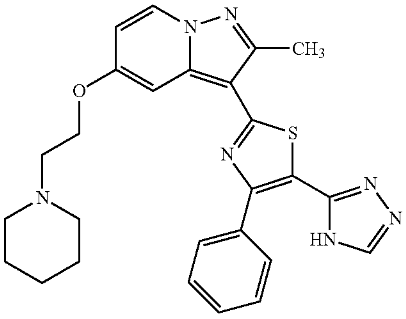
32-B TABLE 1-continued
Table 1 below depicts certain compounds represented by compounds of general formula I-A and I-B.
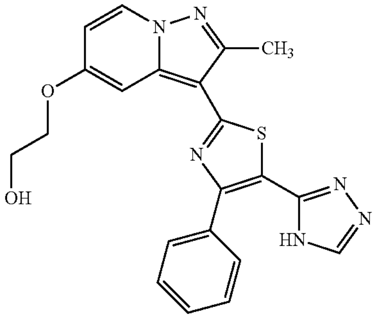
33-B
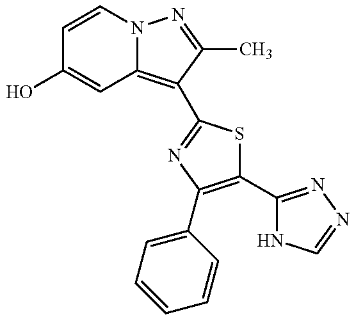
34-B
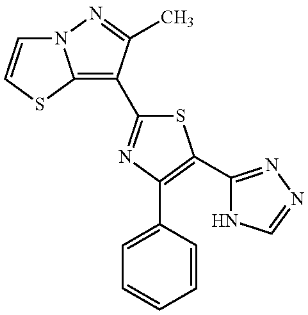
35-B
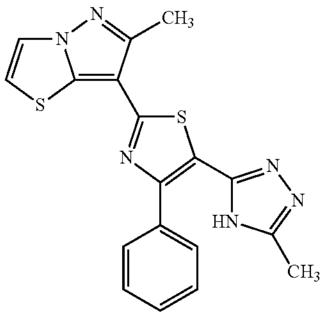
36-B
TABLE 1-continued
Table 1 below depicts certain compounds represented by compounds of general formula I-A and I-B.
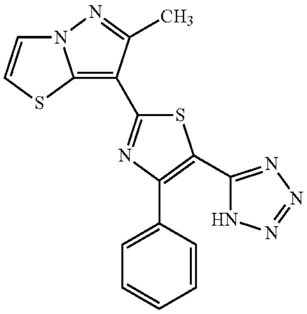
37-B
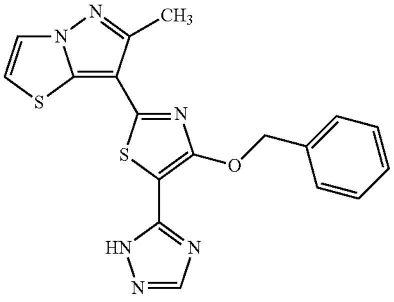
38-B
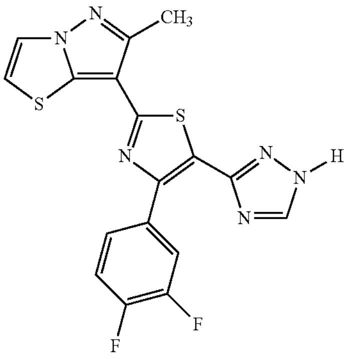
39-B
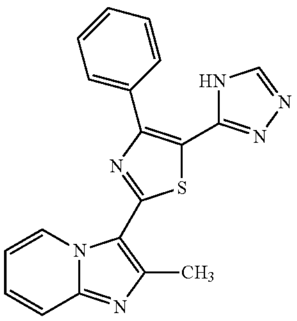
40-B TABLE 1-continued
Table 1 below depicts certain compounds represented by compounds of general formula I-A and I-B.
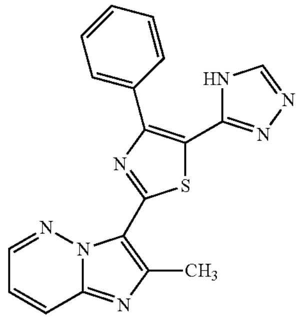
41-B
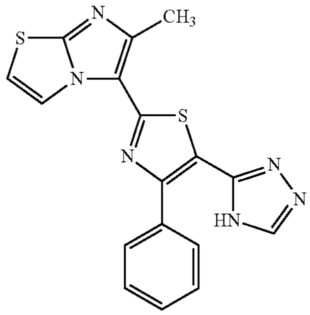
42-B
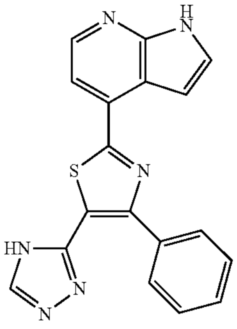
43-B
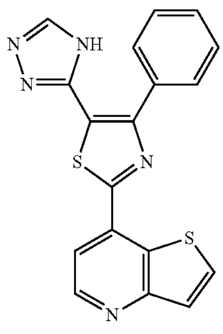
44-B
TABLE 1-continued
Table 1 below depicts certain compounds represented by compounds of general formula I-A and I-B.
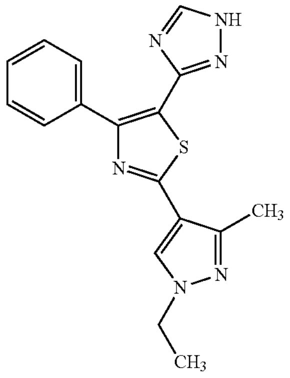
45-B
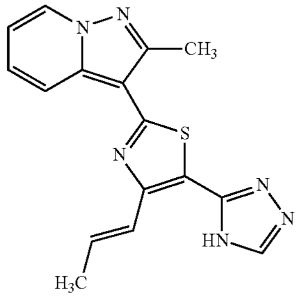
46-B
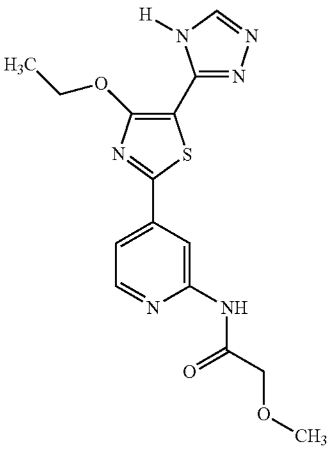
47-B TABLE 1-continued
Table 1 below depicts certain compounds represented by compounds of general formula I-A and I-B.
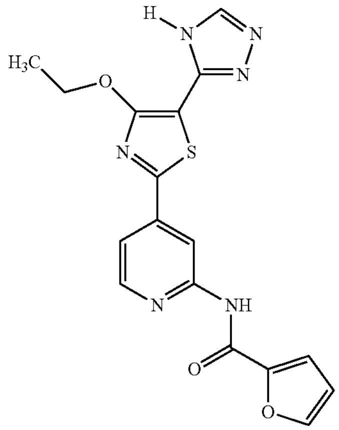
48-B
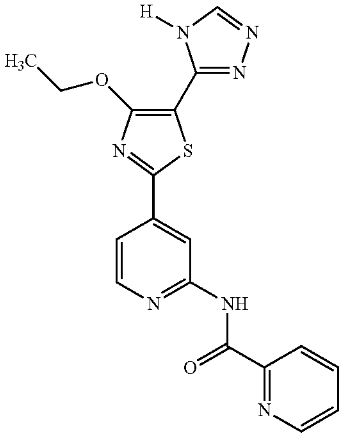
49-B
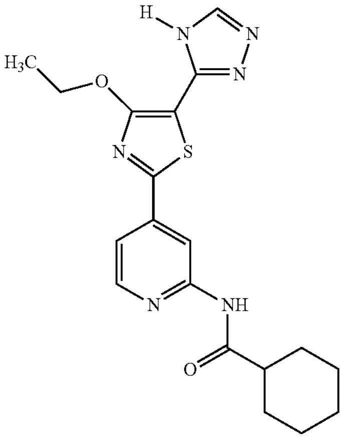
50-B
TABLE 1-continued
Table 1 below depicts certain compounds represented by compounds of general formula I-A and I-B.
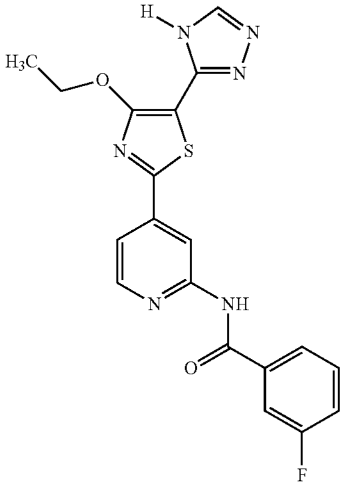
51-B
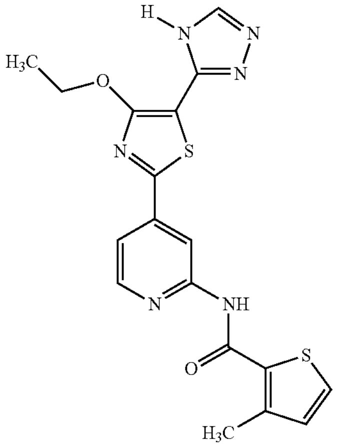
52-B
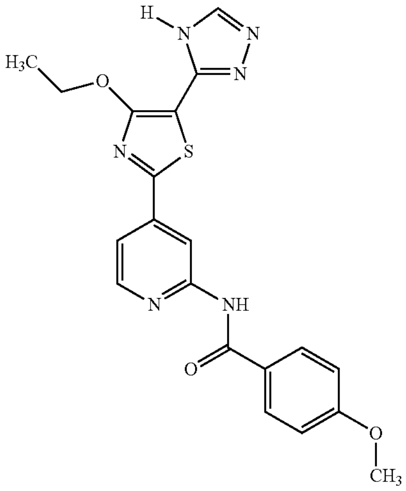
53-B TABLE 1-continued
Table 1 below depicts certain compounds represented by compounds of general formula I-A and I-B.
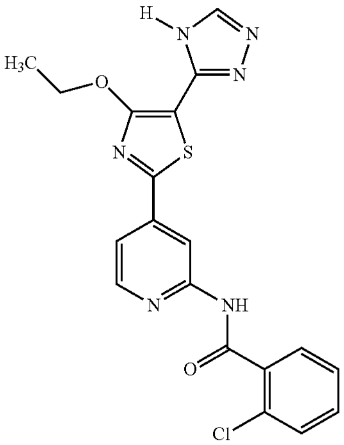
54-B
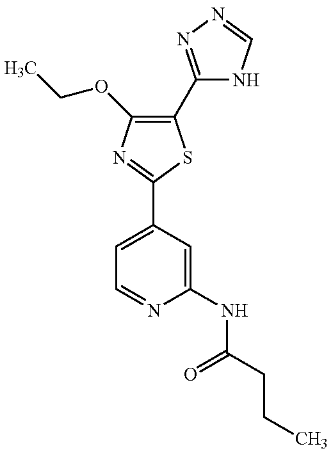
55-B
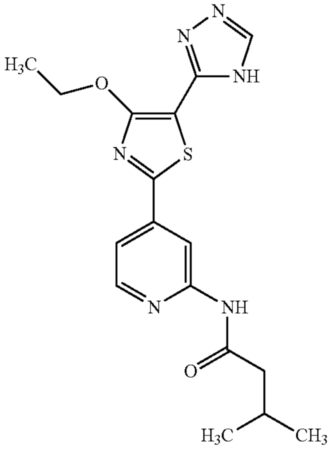
56-B
TABLE 1-continued
Table 1 below depicts certain compounds represented by compounds of general formula I-A and I-B.
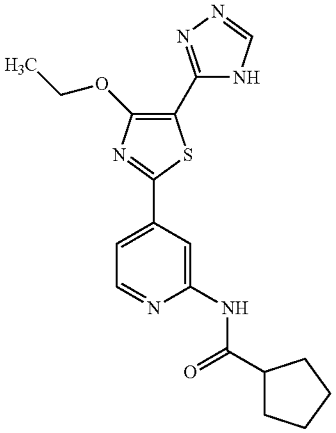
57-B
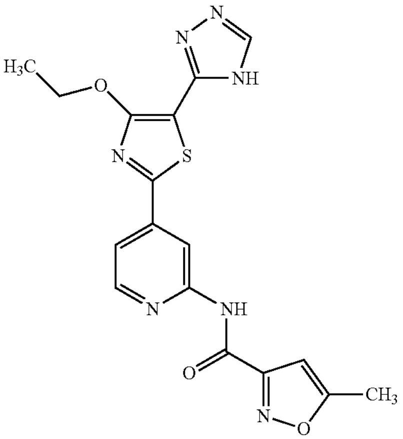
58-B
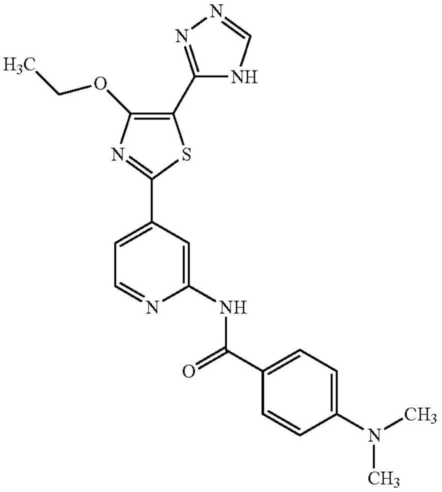
59-B TABLE 1-continued
Table 1 below depicts certain compounds represented by compounds of general formula I-A and I-B.
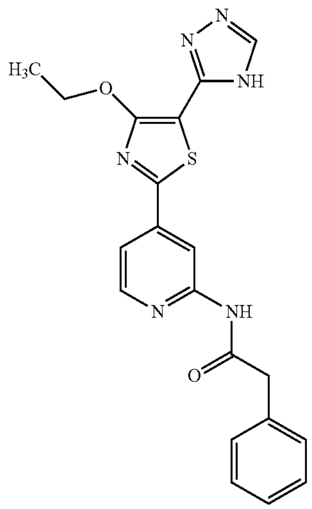
60-B
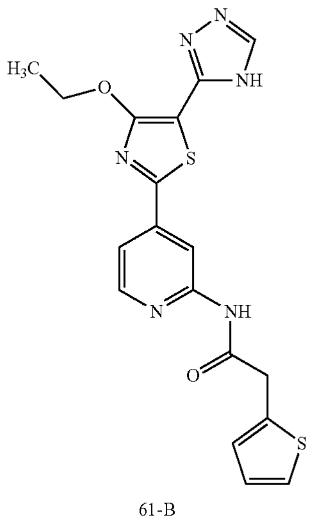 [SMILES: CCOc1nc(-c2ccnc(NC(=O)Cc3cccs3)c2)sc1-c1nnc[nH]1]
61-B
TABLE 1-continued
Table 1 below depicts certain compounds represented by compounds of general formula I-A and I-B.
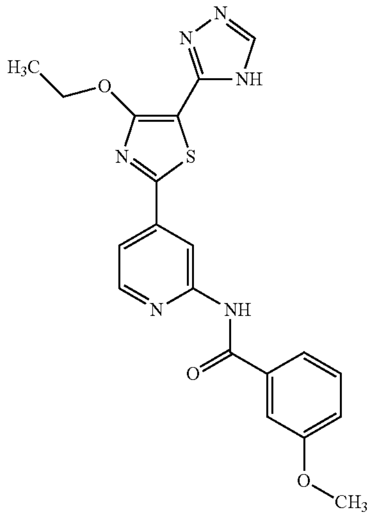
62-B
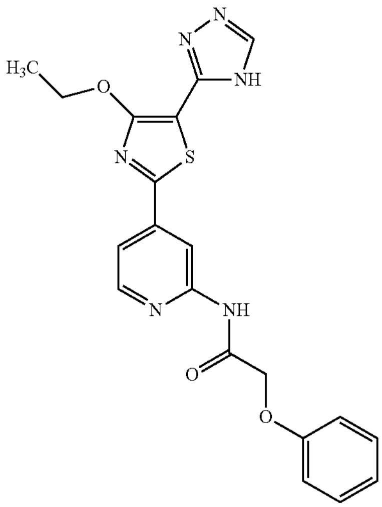
63-B
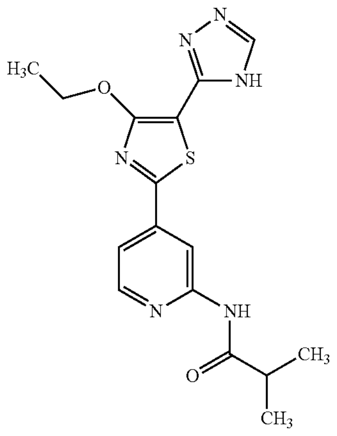
64-B TABLE 1-continued
Table 1 below depicts certain compounds represented by compounds of general formula I-A and I-B.
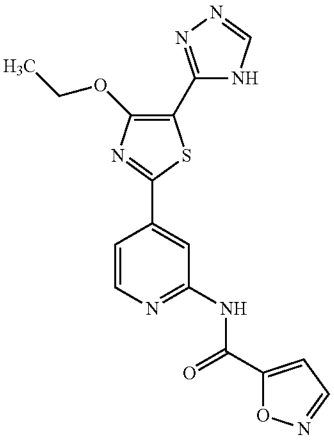
65-B
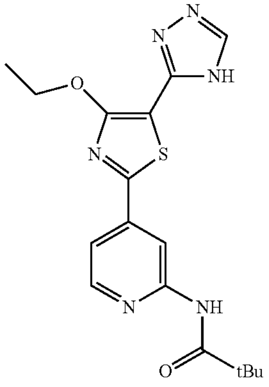
66-B
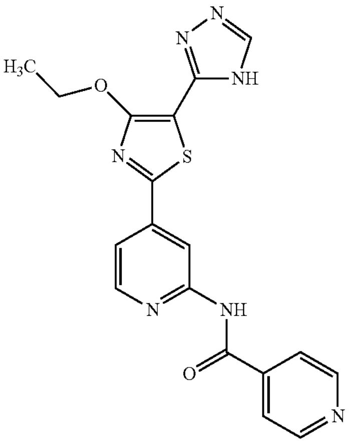
67-B
TABLE 1-continued
Table 1 below depicts certain compounds represented by compounds of general formula I-A and I-B.
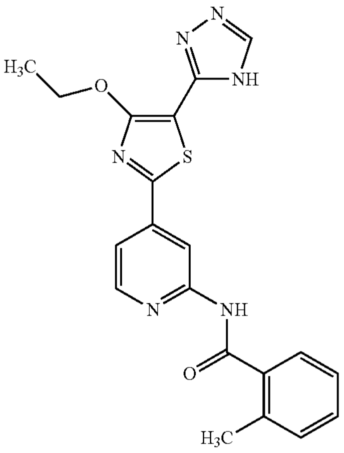
68-B
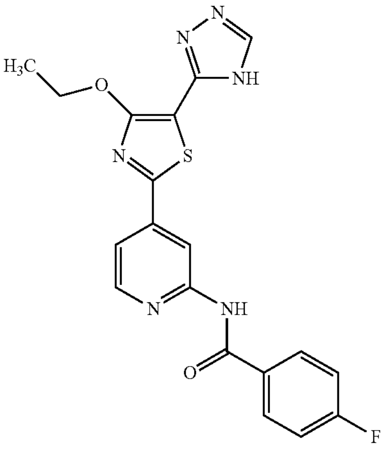
69-B
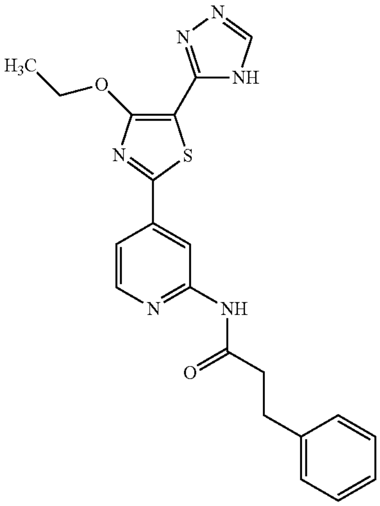
70-B TABLE 1-continued
Table 1 below depicts certain compounds represented by compounds of general formula I-A and I-B.
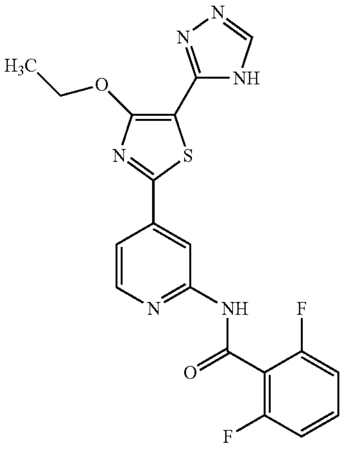
71-B
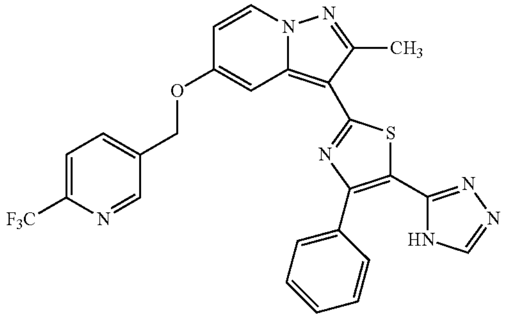
72-B
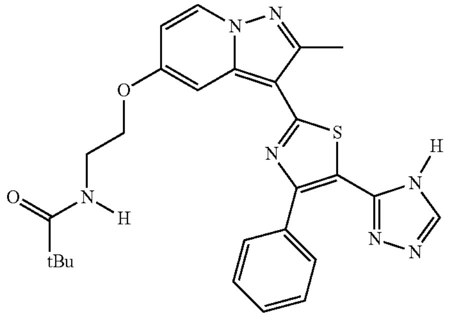
73-B
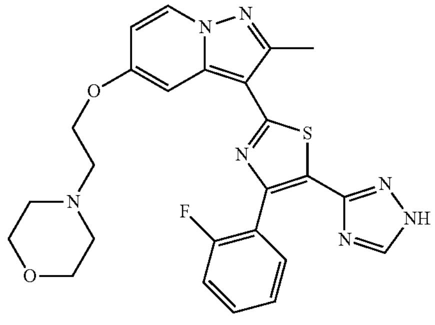
74-B
TABLE 1-continued
Table 1 below depicts certain compounds represented by compounds of general formula I-A and I-B.
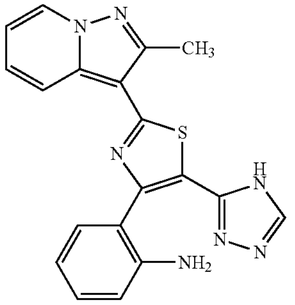
75-B
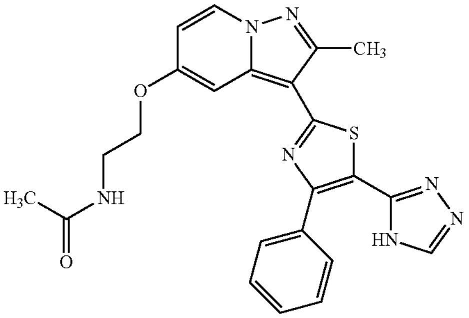
76-B
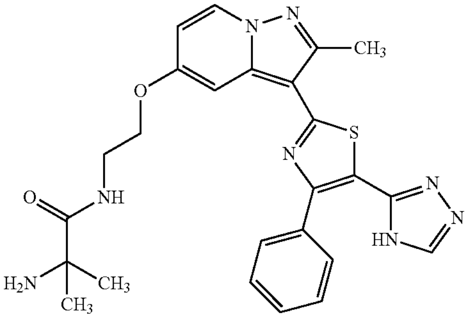
77-B
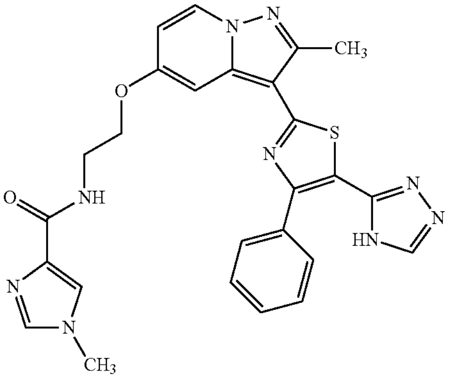
78-B TABLE 1-continued
| Table 1 below depicts certain compounds represented by compounds of general formula I-A and I-B. |
|---|
| 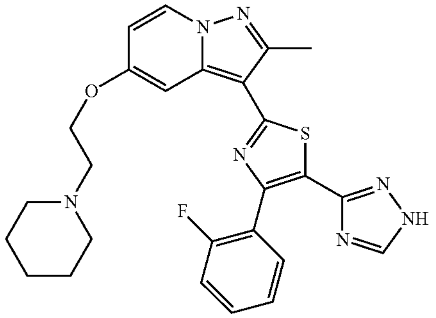 |
| 79-B |
| 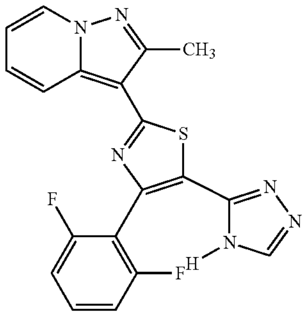 |
| 81-B |
| 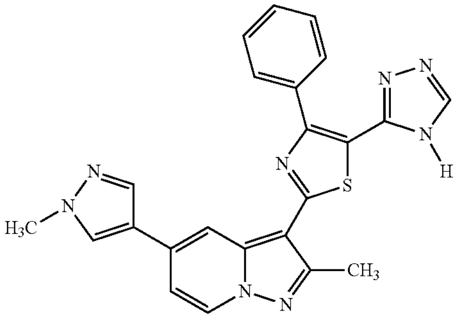 |
| 82-B |
| 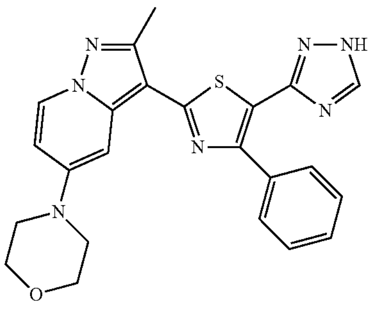 |
| 83-B |
TABLE 1-continued
| Table 1 below depicts certain compounds represented by compounds of general formula I-A and I-B. |
|---|
| 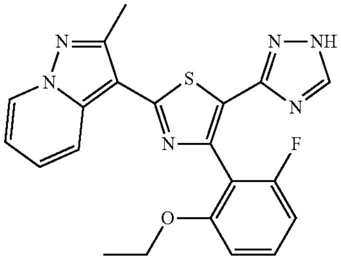 |
| 84-B |
| 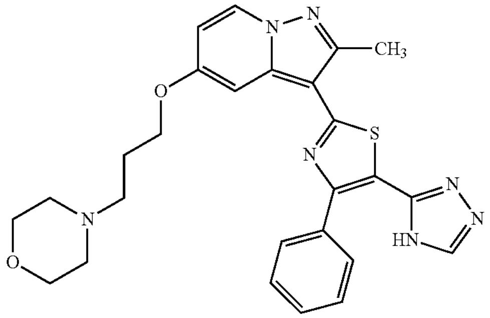 |
| 85-B |
| 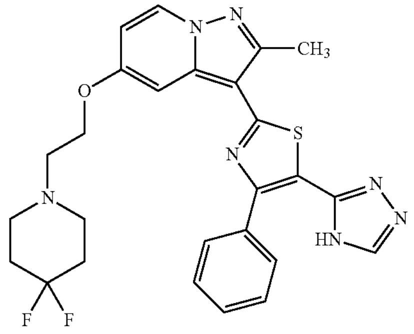 |
| 86-B |
| 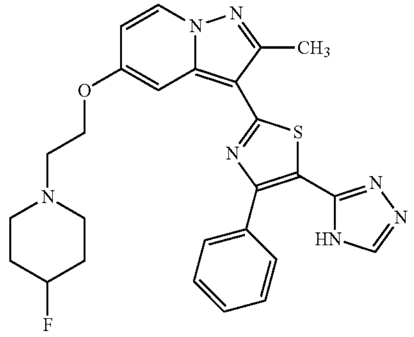 |
| 87-B |

TABLE 1-continued
| Table 1 below depicts certain compounds represented by compounds of general formula I-A and I-B. |
| --- |
| 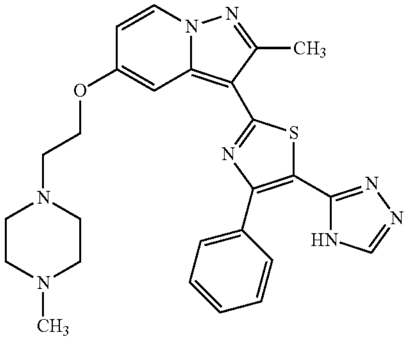 |
| 88-B |
| 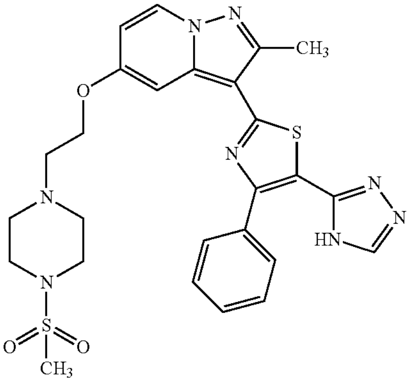 |
| 89-B |
| 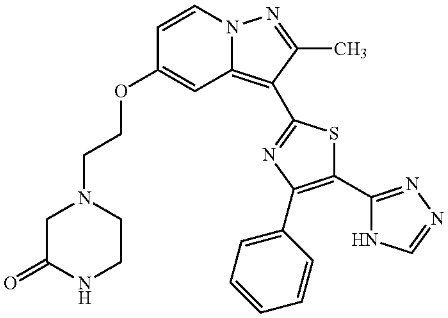 |
| 90-B |
| 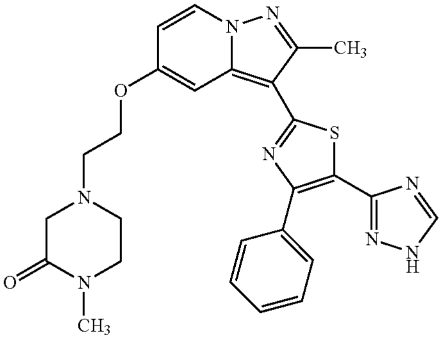 |
| 91-B |
TABLE 1-continued
| Table 1 below depicts certain compounds represented by compounds of general formula I-A and I-B. |
| --- |
| 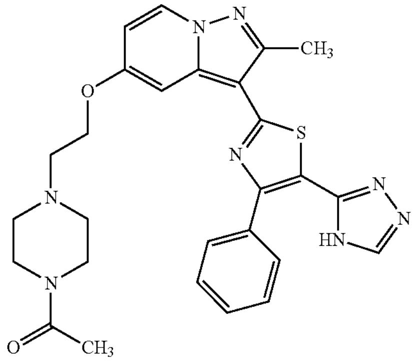 |
| 92-B |
| 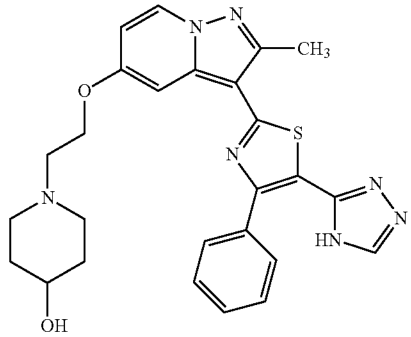 |
| 93-B |
| 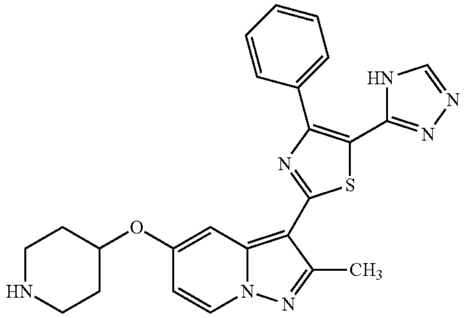 |
| 94-B |
| 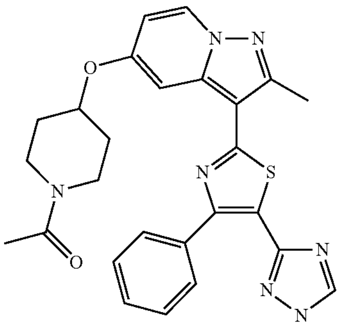 |
| 95-B |

TABLE 1-continued
| Table 1 below depicts certain compounds represented by compounds of general formula I-A and I-B. |
|---|
| 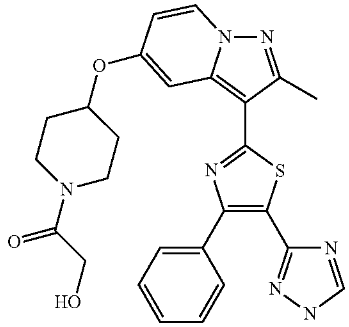 96-B |
| 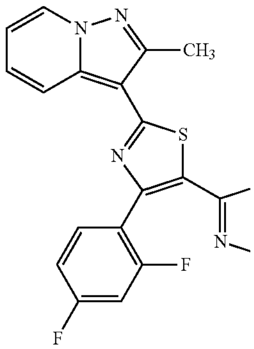 97-B |
| 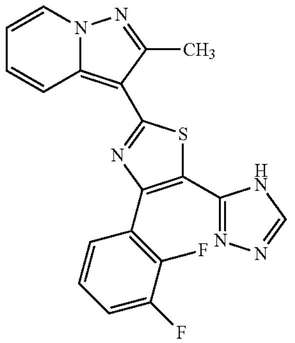 98-B |
| 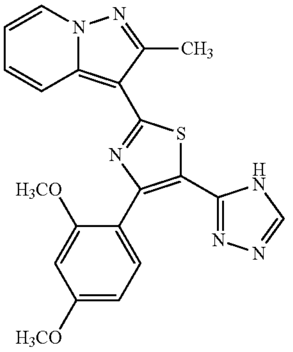 99-B |
TABLE 1-continued
| Table 1 below depicts certain compounds represented by compounds of general formula I-A and I-B. |
|---|
| 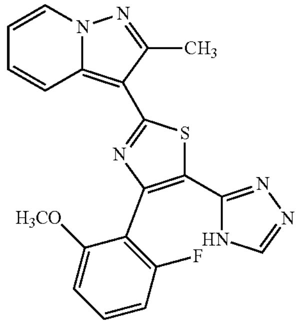 100-B |
| 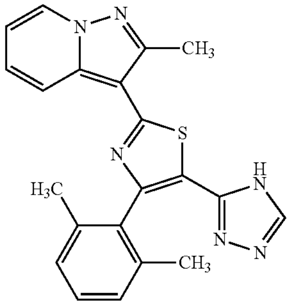 101-B |
| 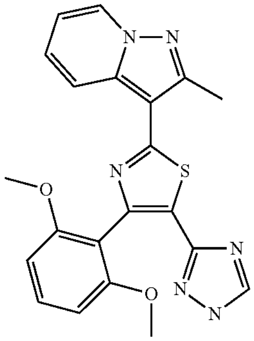 102-B |
| 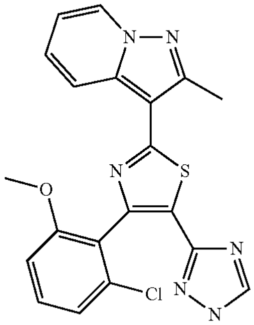 103-B |

TABLE 1-continued
Table 1 below depicts certain compounds represented by compounds of general formula I-A and I-B.
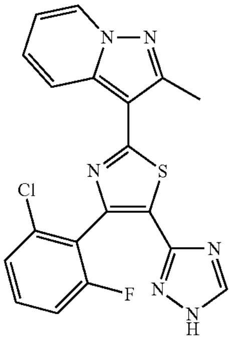
104-B
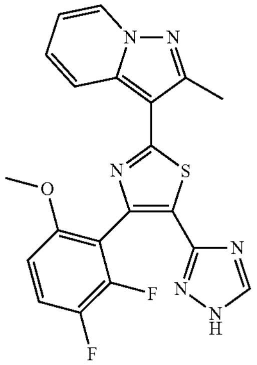
105-B
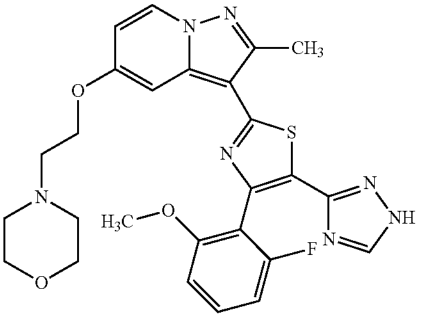
106-B
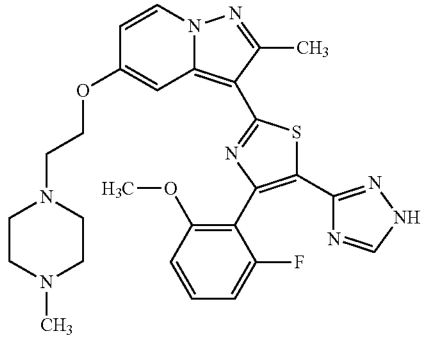
107-B
TABLE 1-continued
Table 1 below depicts certain compounds represented by compounds of general formula I-A and I-B.
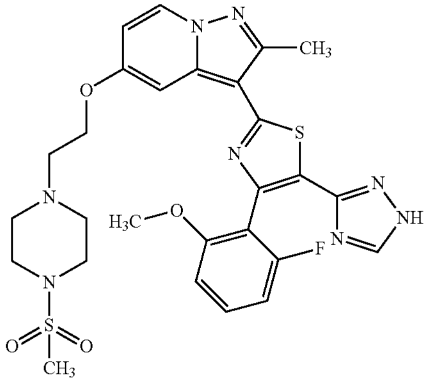
108-B
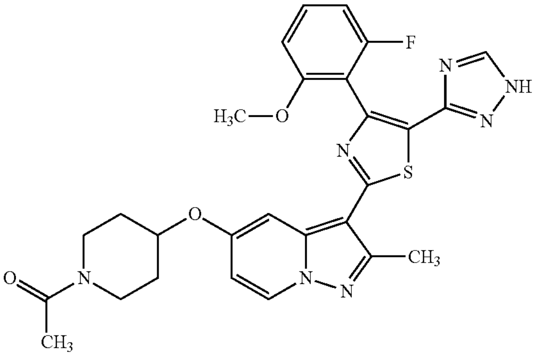
109-B
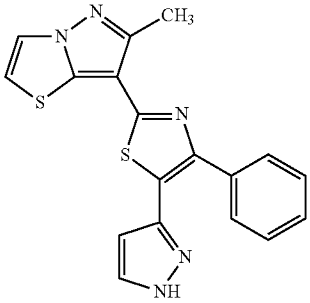
110-B
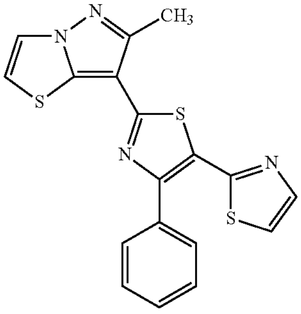
111-B TABLE 1-continued
| Table 1 below depicts certain compounds represented by compounds of general formula I-A and I-B. |
| --- |
| 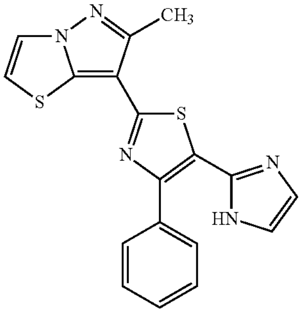 |
| 112-B |
| 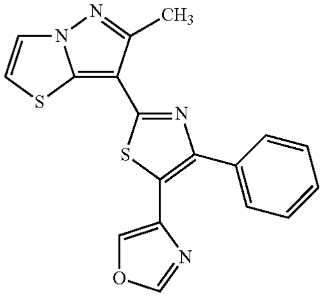 |
| 113-B |
| 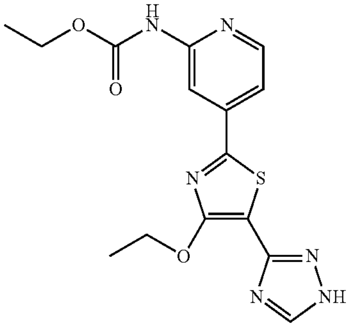 |
| 114-B |
| 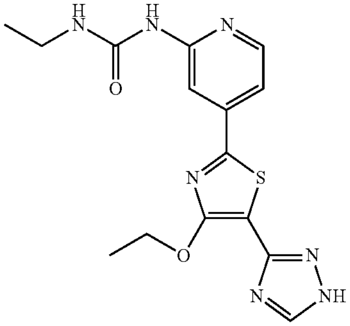 |
| 115-B |
TABLE 1-continued
| Table 1 below depicts certain compounds represented by compounds of general formula I-A and I-B. |
| --- |
| 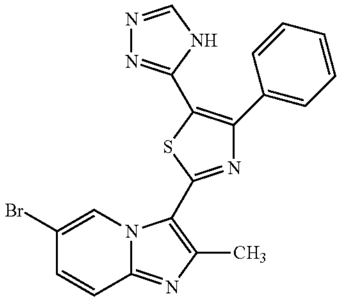 |
| 116-B |
| 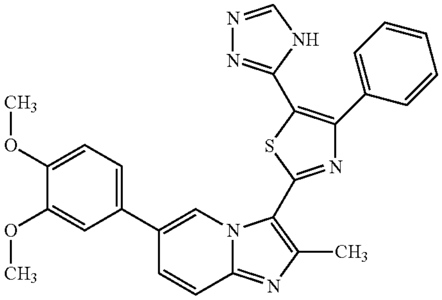 |
| 117-B |
| 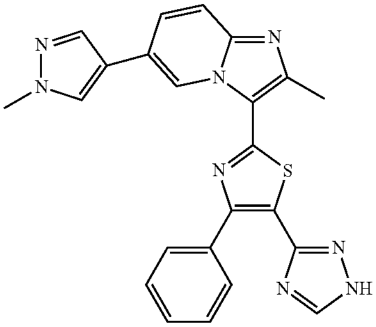 |
| 118-B |
| 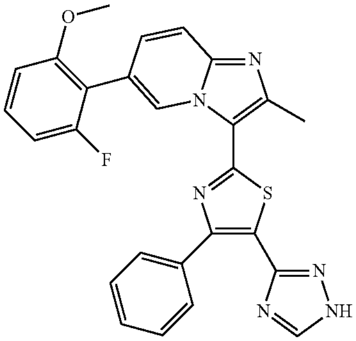 |
| 119-B |

TABLE 1-continued
Table 1 below depicts certain compounds represented by compounds of general formula I-A and I-B.
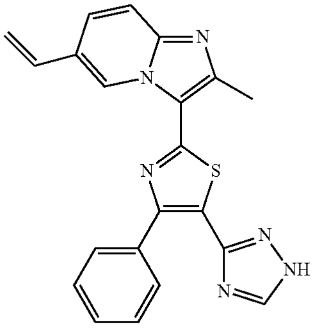
120-B
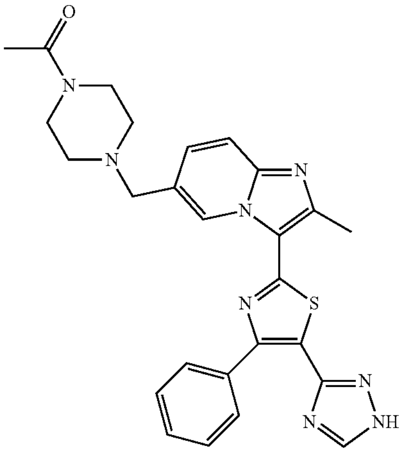
121-B
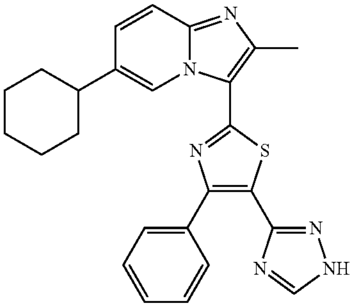
122-B
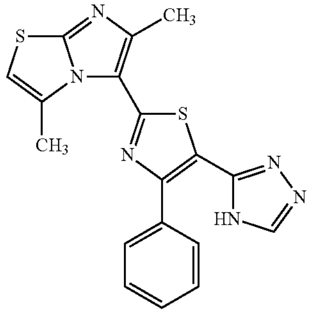
123-B
TABLE 1-continued
Table 1 below depicts certain compounds represented by compounds of general formula I-A and I-B.
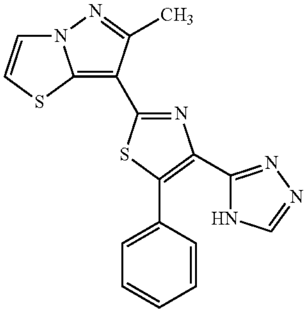
124-B
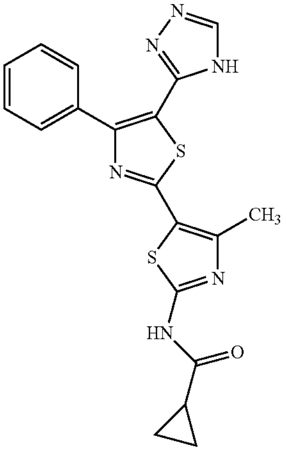
125-B
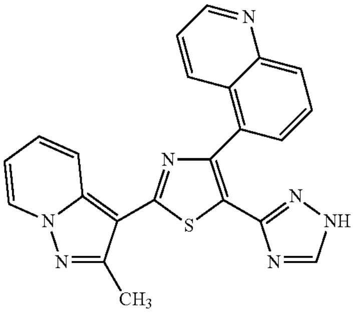
126-B
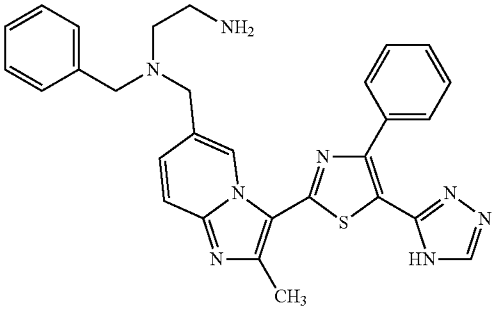
127-B TABLE 1-continued
Table 1 below depicts certain compounds represented by compounds of general formula I-A and I-B.
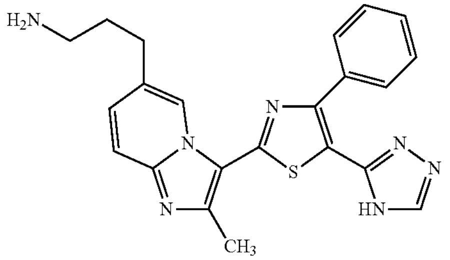
128-B
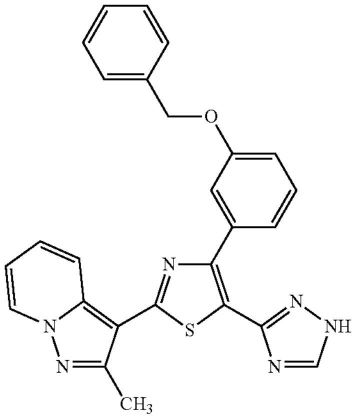
129-B
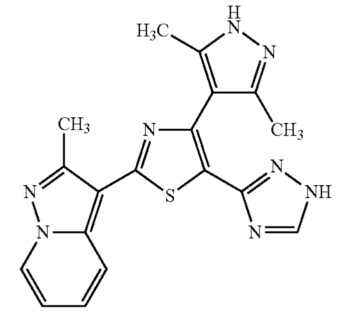
130-B
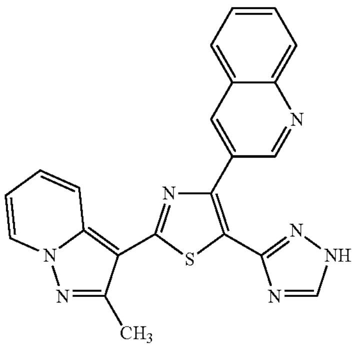
131-B
TABLE 1-continued
Table 1 below depicts certain compounds represented by compounds of general formula I-A and I-B.
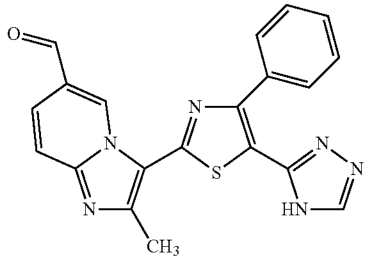
132-B
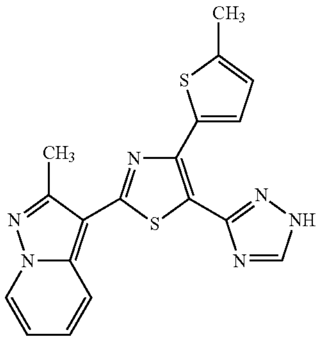
133-B
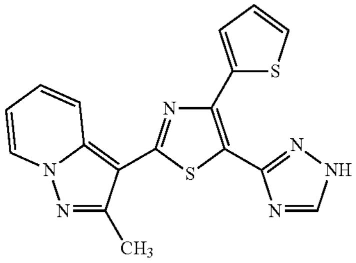
134-B
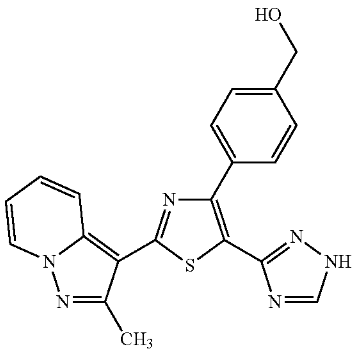
135-B TABLE 1-continued
Table 1 below depicts certain compounds represented by compounds of general formula I-A and I-B.
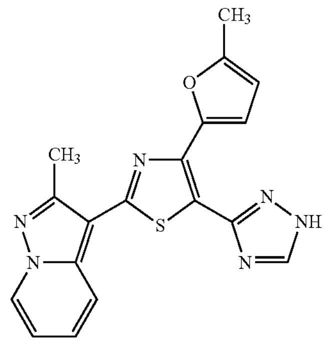
136-B
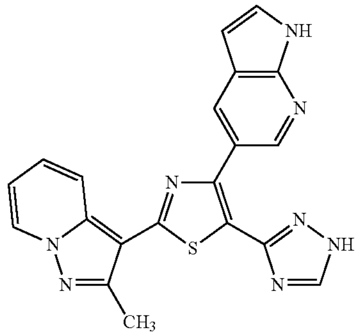
137-B
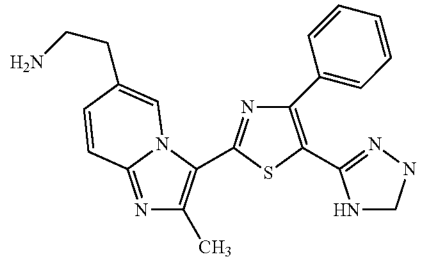
138-B
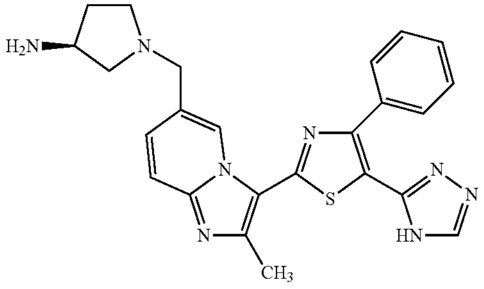
139-B
TABLE 1-continued
Table 1 below depicts certain compounds represented by compounds of general formula I-A and I-B.
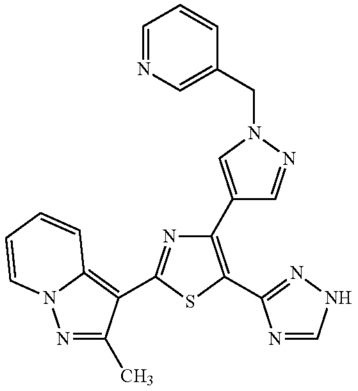
140-B
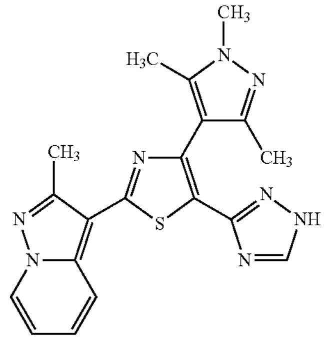
141-B
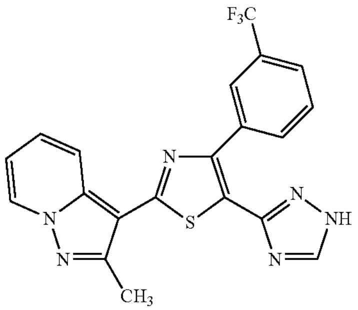
142-B
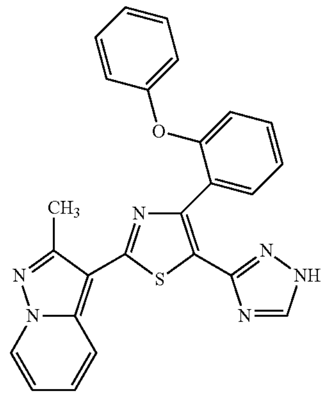
143-B TABLE 1-continued
Table 1 below depicts certain compounds represented by compounds of general formula I-A and I-B.
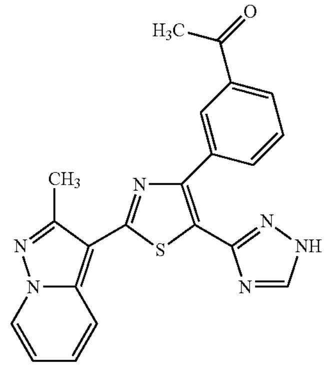
144-B
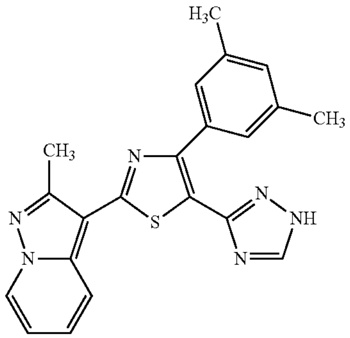
145-B
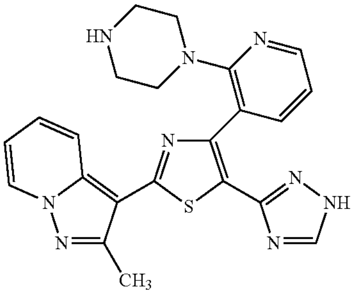
146-B
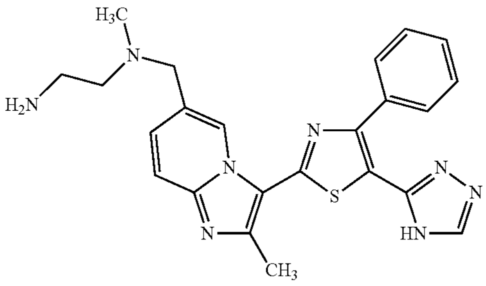
147-B
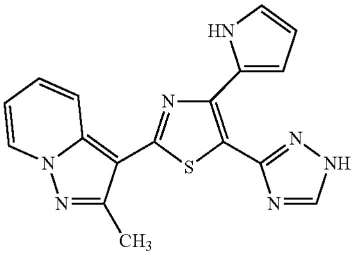
148-B
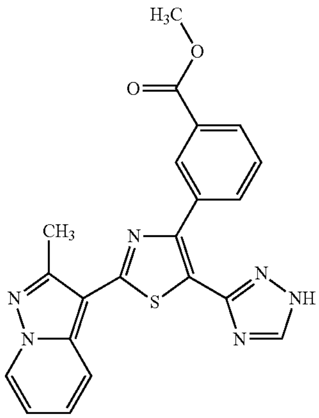
149-B
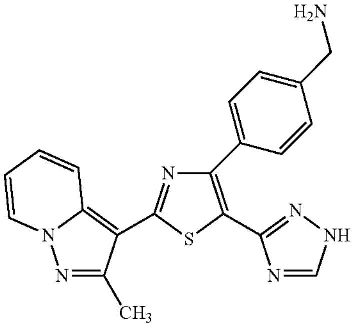
150-B
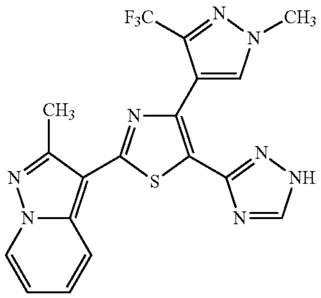
151-B TABLE 1-continued
| Table 1 below depicts certain compounds represented by compounds of general formula I-A and I-B. |
| --- |
| 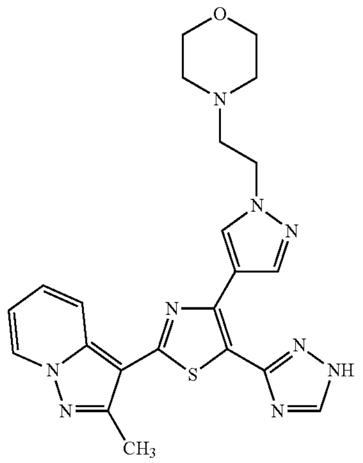 |
| 152-B |
| 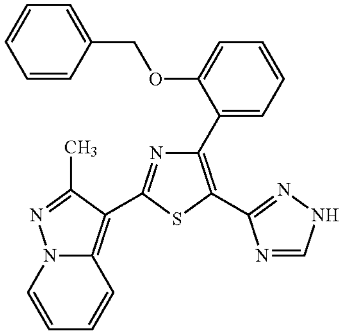 |
| 153-B |
| 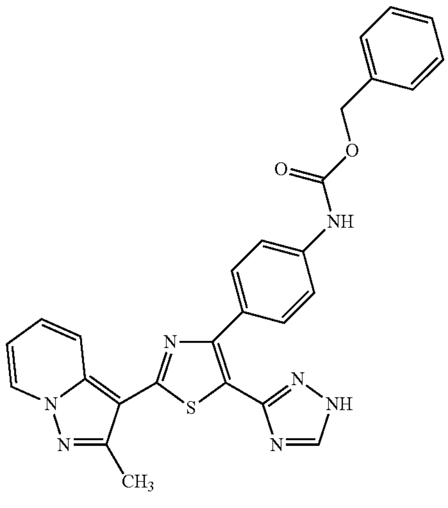 |
| 154-B |
TABLE 1-continued
| Table 1 below depicts certain compounds represented by compounds of general formula I-A and I-B. |
| --- |
| 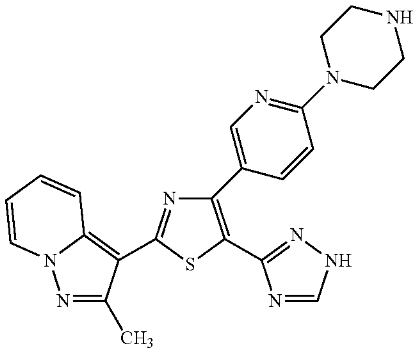 |
| 155-B |
| 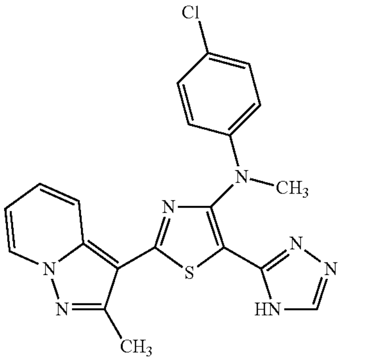 |
| 156-B |
| 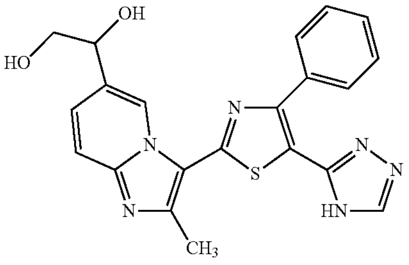 |
| 157-B |
| 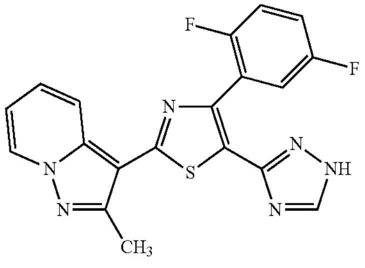 |
| 158-B |

TABLE 1-continued
Table 1 below depicts certain compounds represented by compounds of general formula I-A and I-B.
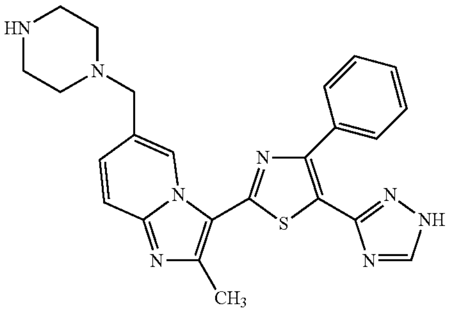
159-B
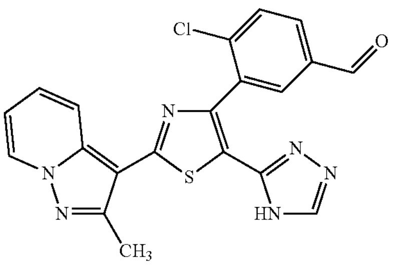
160-B
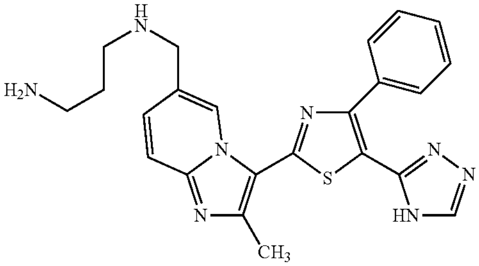
161-B
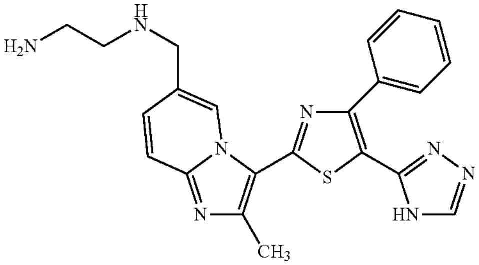
162-B
TABLE 1-continued
Table 1 below depicts certain compounds represented by compounds of general formula I-A and I-B.
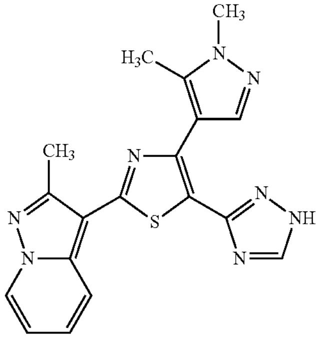
163-B
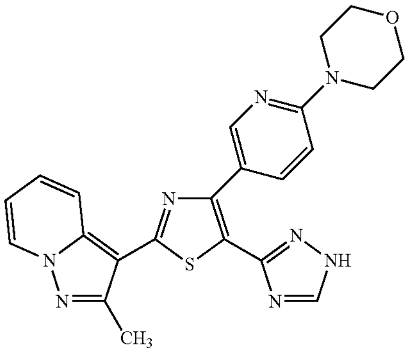
164-B
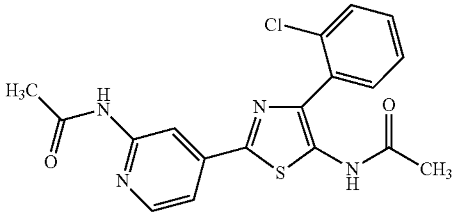
1-C
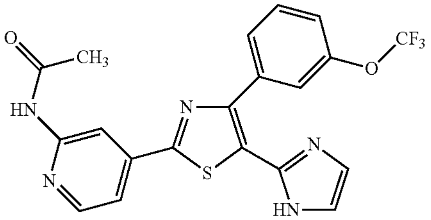
2-C
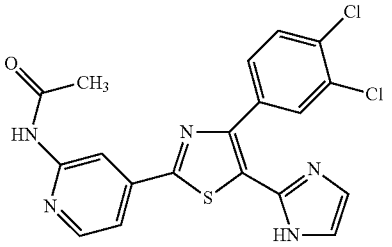
3-C TABLE 1-continued
| Table 1 below depicts certain compounds represented by compounds of general formula I-A and I-B. |
| --- |
| 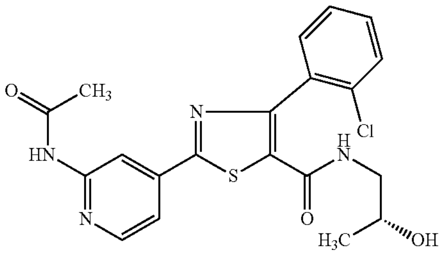 |
| 4-C |
| 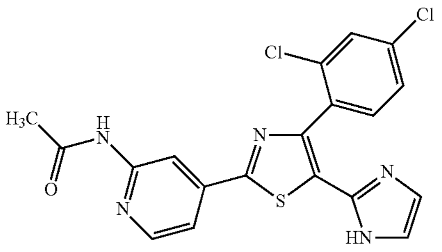 |
| 5-C |
| 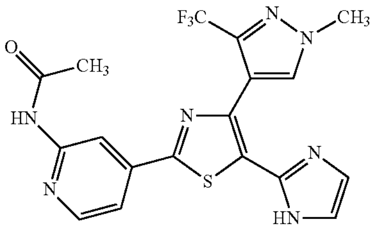 |
| 6-C |
| 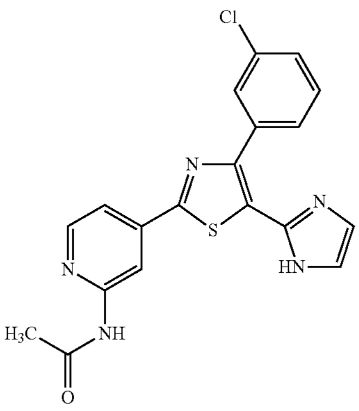 |
| 7-C |
TABLE 1-continued
| Table 1 below depicts certain compounds represented by compounds of general formula I-A and I-B. |
| --- |
| 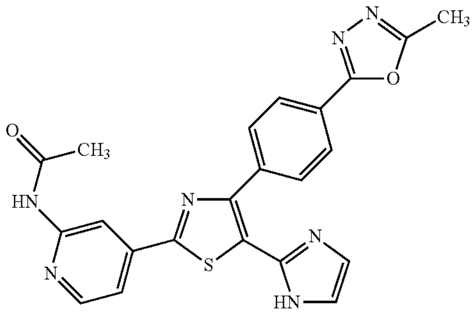 |
| 8-C |
| 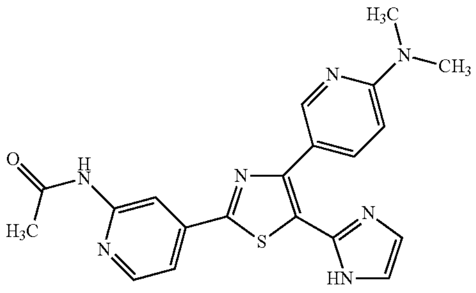 |
| 9-C |
| 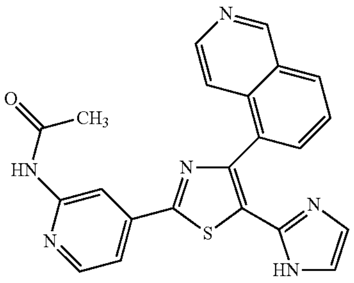 |
| 10-C |
| 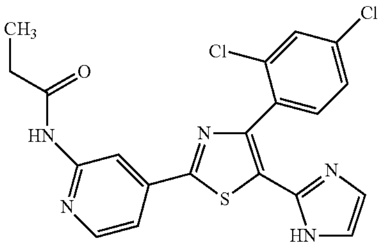 |
| 11-C |
| 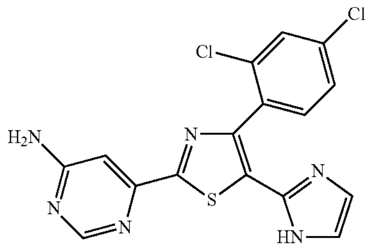 |
| 12-C |

TABLE 1-continued
| Table 1 below depicts certain compounds represented by compounds of general formula I-A and I-B. |
|---|
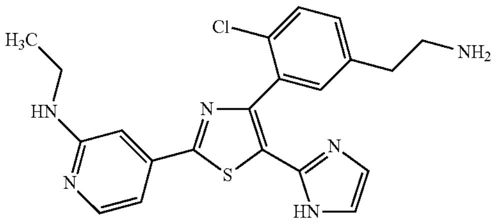
13-C
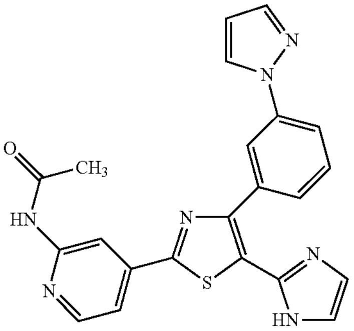
14-C
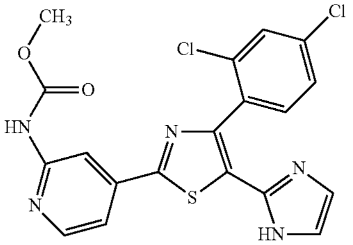
15-C
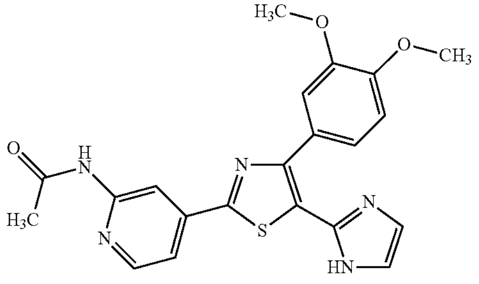
16-C
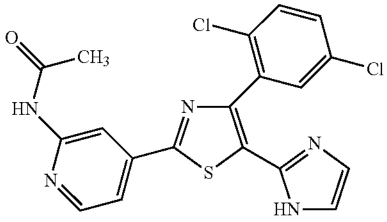
17-C
TABLE 1-continued
| Table 1 below depicts certain compounds represented by compounds of general formula I-A and I-B. |
|---|
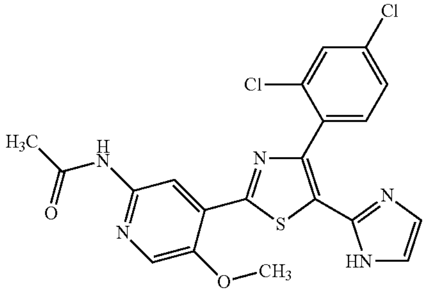
18-C
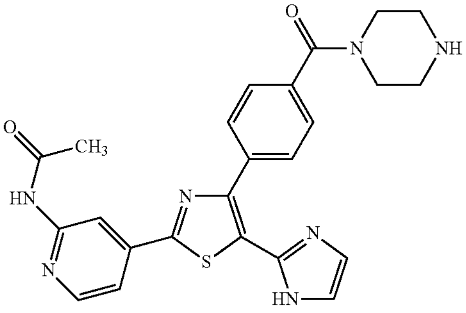
19-C
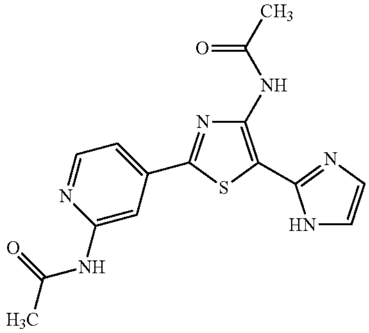
20-C
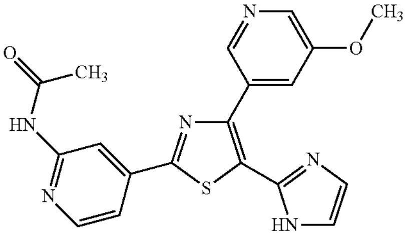
21-C
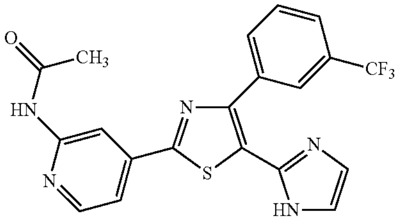
22-C TABLE 1-continued
| Table 1 below depicts certain compounds represented by compounds of general formula I-A and I-B. |
| --- |
| 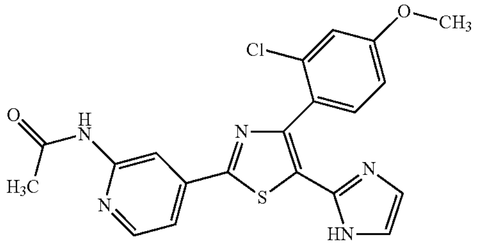 |
| 23-C |
| 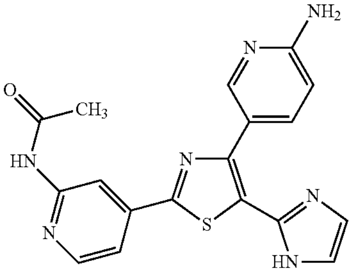 |
| 24-C |
| 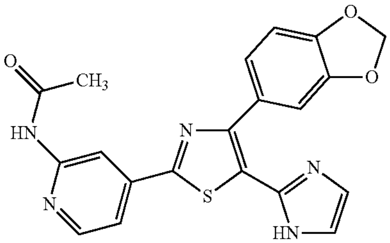 |
| 25-C |
| 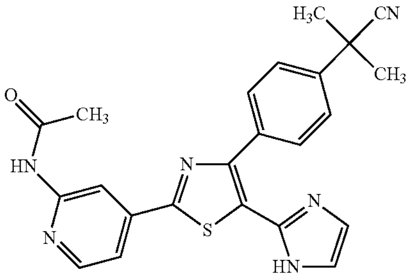 |
| 26-C |
| 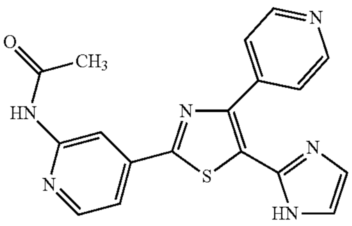 |
| 27-C |
TABLE 1-continued
| Table 1 below depicts certain compounds represented by compounds of general formula I-A and I-B. |
| --- |
| 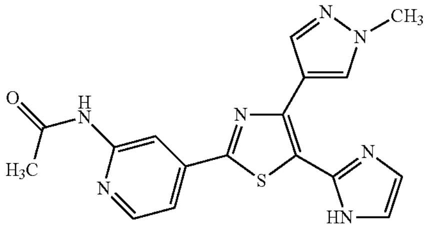 |
| 28-C |
| 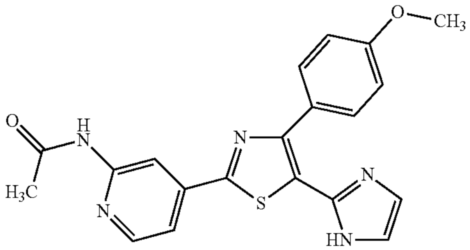 |
| 29-C |
| 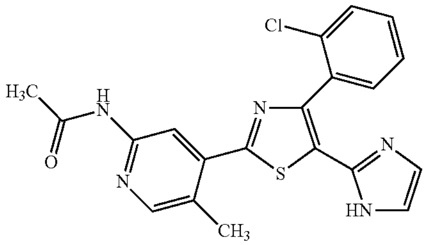 |
| 30-C |
| 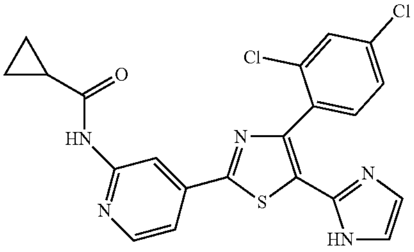 |
| 31-C |
| 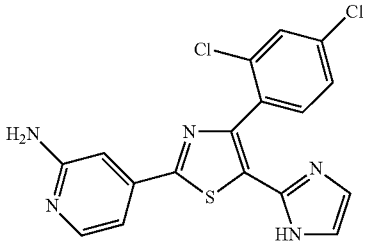 |
| 32-C |

TABLE 1-continued
| Table 1 below depicts certain compounds represented by compounds of general formula I-A and I-B. |
| --- |
| 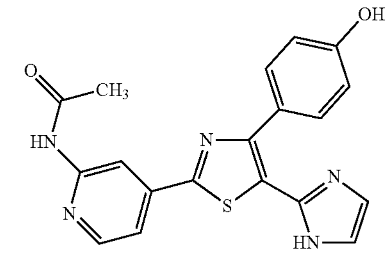 |
| 33-C |
| 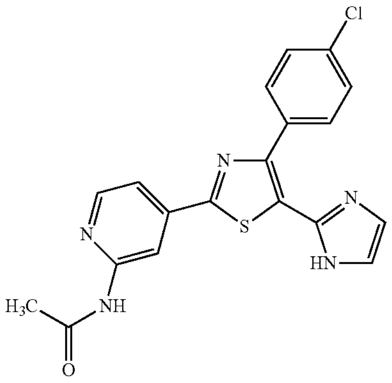 |
| 34-C |
| 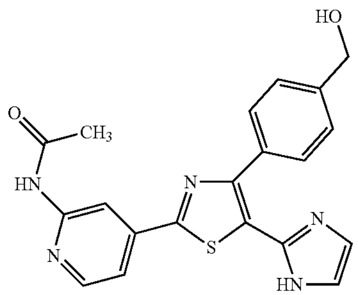 |
| 35-C |
| 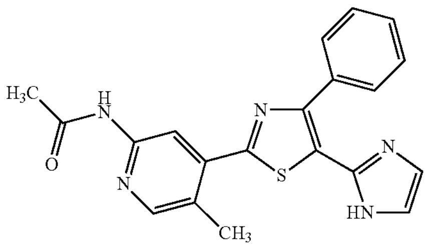 |
| 36-C |
| 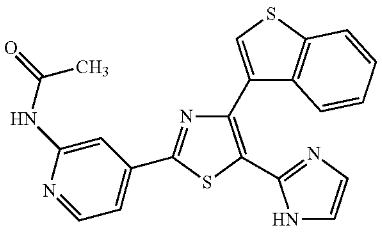 |
| 37-C |
TABLE 1-continued
| Table 1 below depicts certain compounds represented by compounds of general formula I-A and I-B. |
| --- |
| 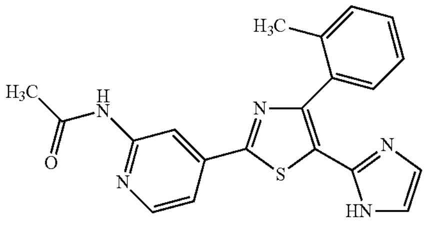 |
| 38-C |
| 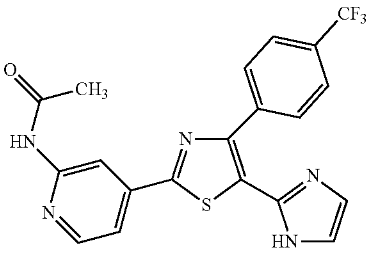 |
| 39-C |
| 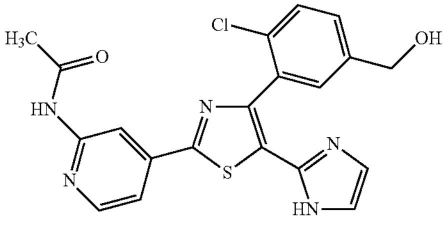 |
| 40-C |
| 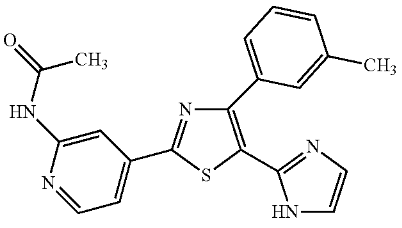 |
| 41-C |
| 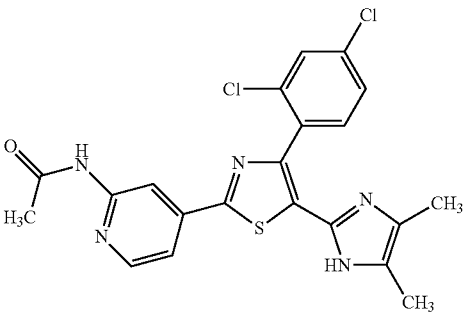 |
| 42-C |

TABLE 1-continued
Table 1 below depicts certain compounds represented by compounds of general formula I-A and I-B.
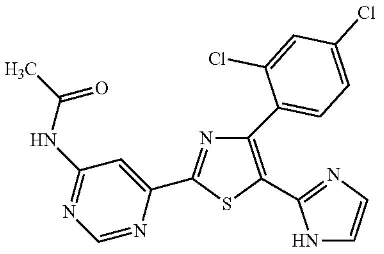
43-C
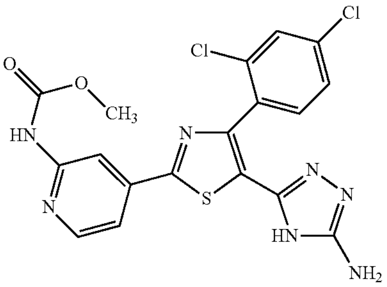
44-C
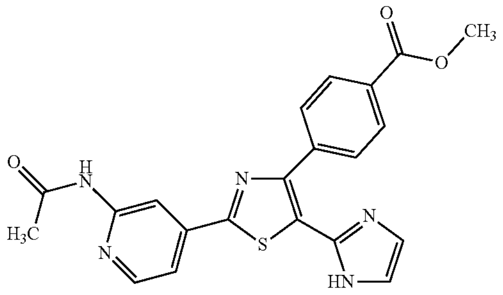
45-C
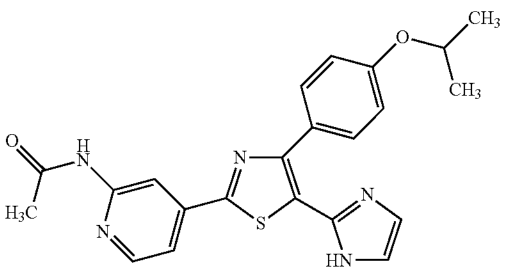
46-C
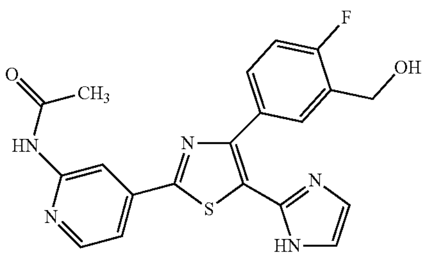
47-C
TABLE 1-continued
Table 1 below depicts certain compounds represented by compounds of general formula I-A and I-B.
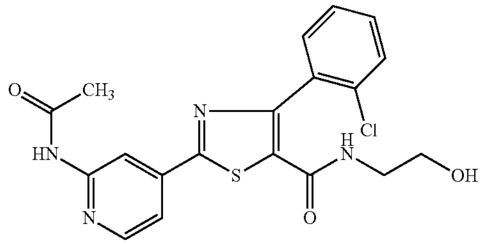
48-C
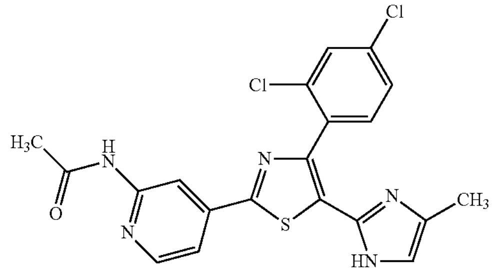
49-C
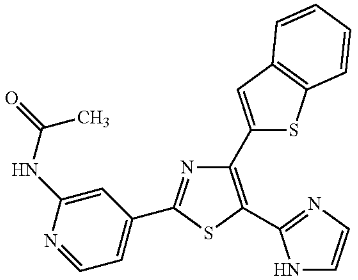
50-C
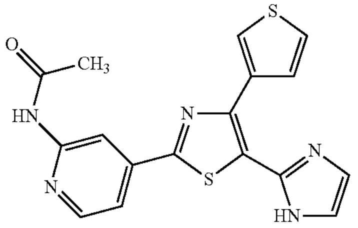
51-C
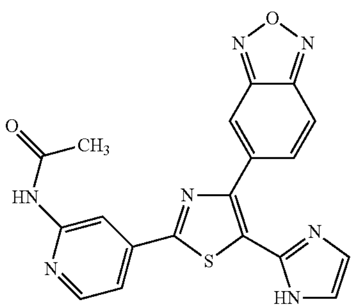
52-C TABLE 1-continued
Table 1 below depicts certain compounds represented by compounds of general formula I-A and I-B.
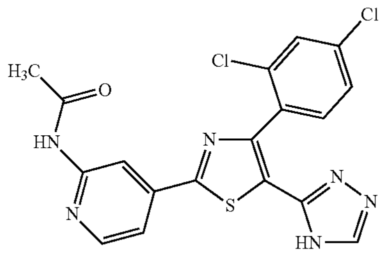
53-C
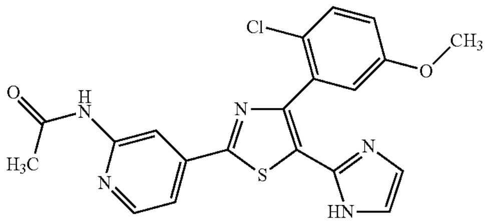
54-C
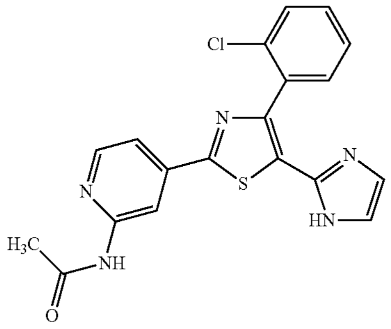
55-C
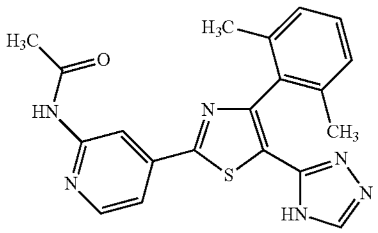
56-C
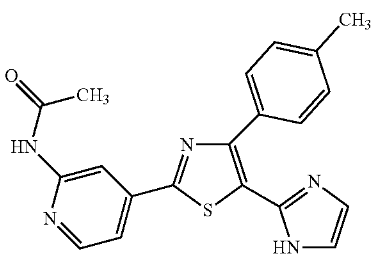
57-C
TABLE 1-continued
Table 1 below depicts certain compounds represented by compounds of general formula I-A and I-B.
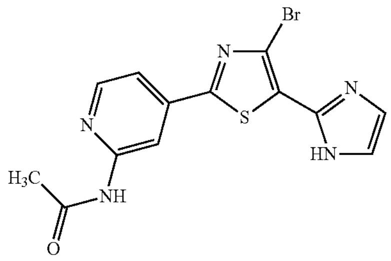
58-C
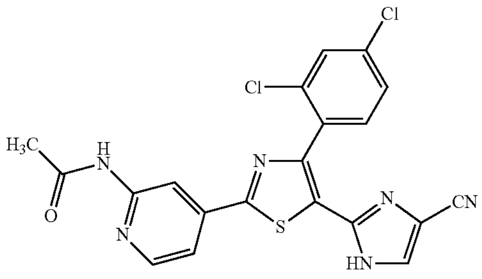
59-C
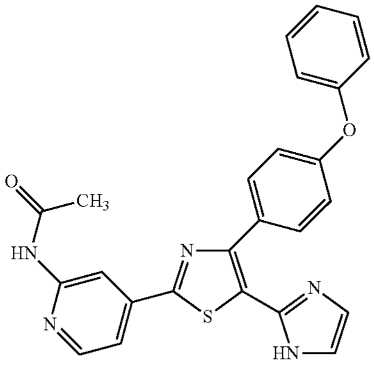
60-C
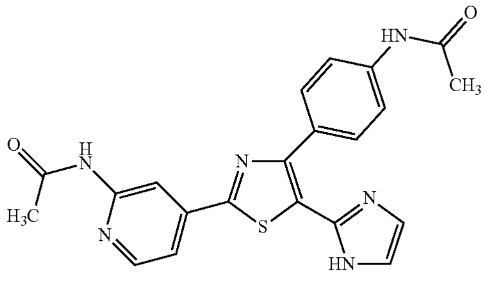
61-C TABLE 1-continued
Table 1 below depicts certain compounds represented by compounds of general formula I-A and I-B.
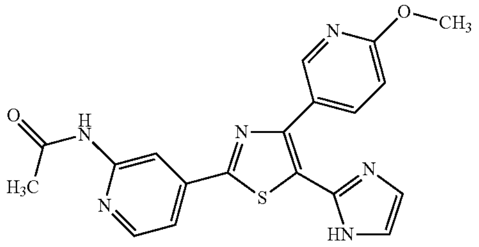
62-C
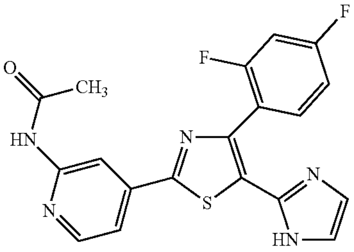
63-C
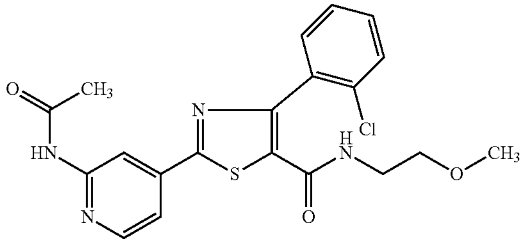
64-C
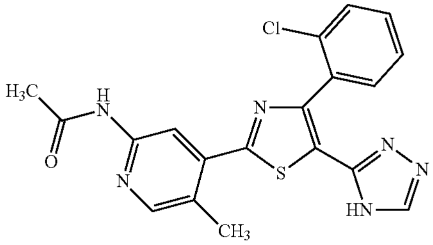
65-C
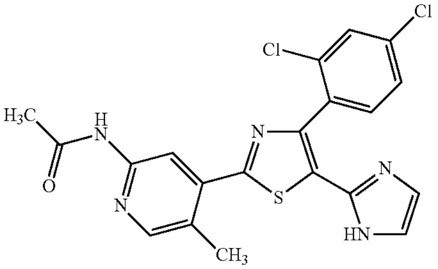
66-C
TABLE 1-continued
Table 1 below depicts certain compounds represented by compounds of general formula I-A and I-B.
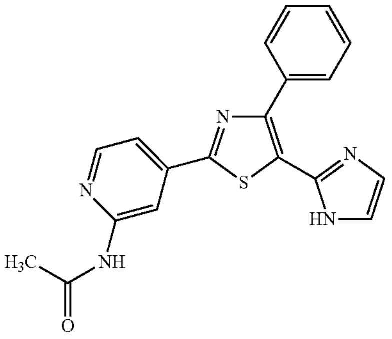
67-C
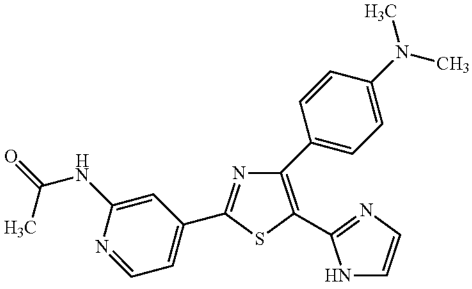
68-C
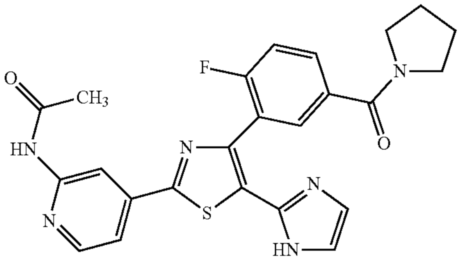
69-C
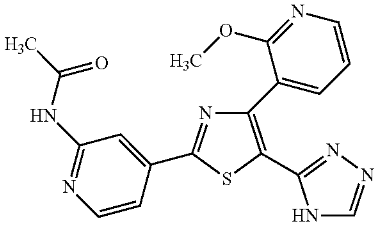
70-C
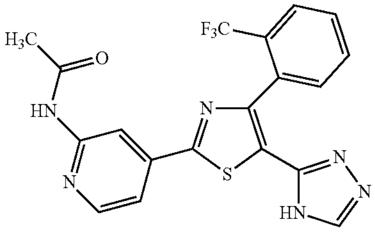
71-C TABLE 1-continued
Table 1 below depicts certain compounds represented by compounds of general formula I-A and I-B.
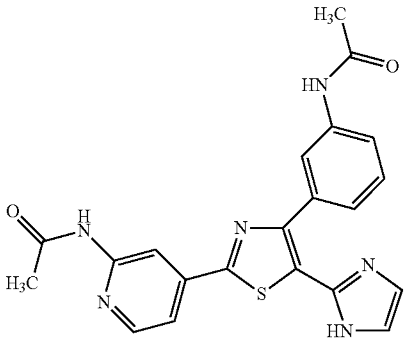
72-C
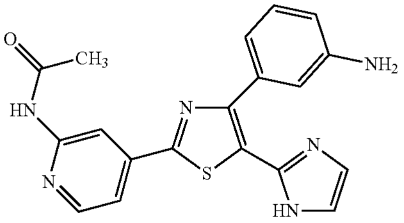
73-C
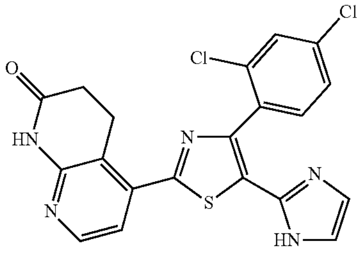
1-D
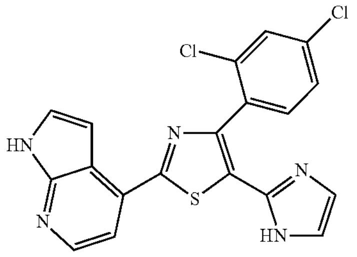
2-D
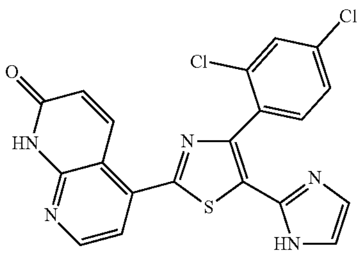
3-D
TABLE 1-continued
Table 1 below depicts certain compounds represented by compounds of general formula I-A and I-B.
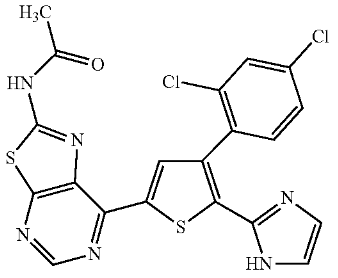
1-E
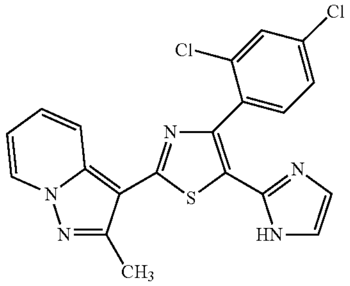
2-E
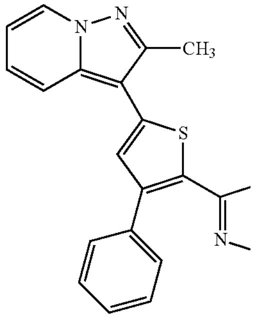
3-E
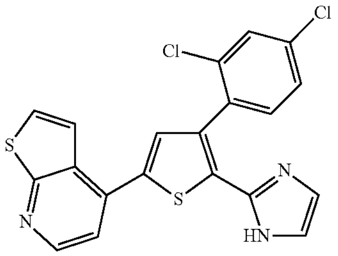
4-E
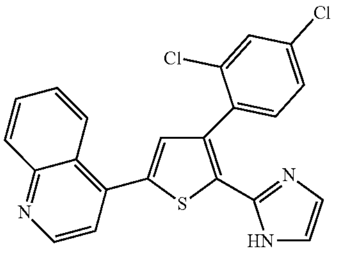
5-E TABLE 1-continued Table 1 below depicts certain compounds represented by compounds of general formula I-A and I-B.

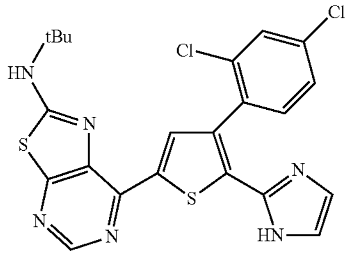

6-E

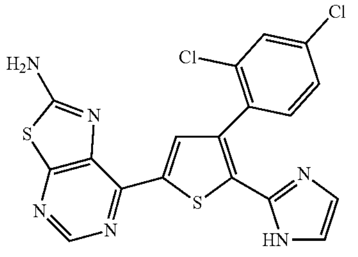

7-E

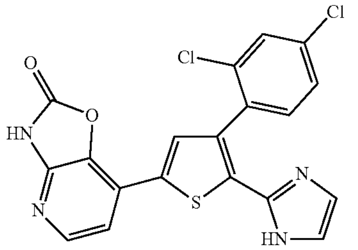

1-F

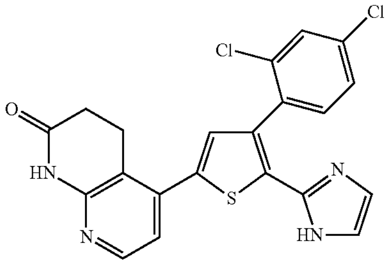

2-F

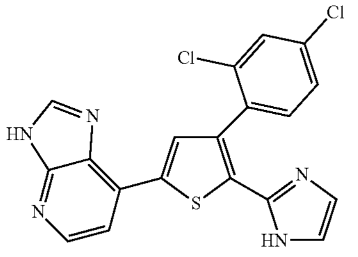

3-F

TABLE 1-continued

Table 1 below depicts certain compounds represented by compounds of general formula I-A and I-B.

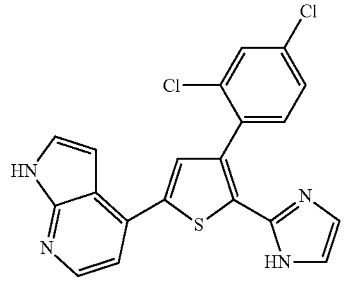

4-F

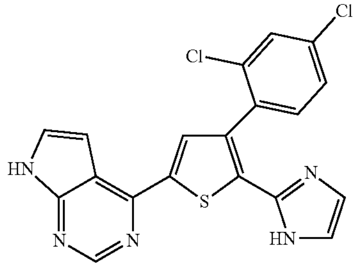

5-F

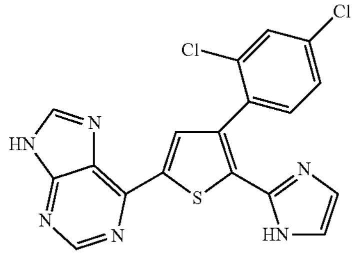

6-F

EXPERIMENTAL PROCEDURES

Definitions

AcOH acetic acid
ACN acetonitrile
ATP adenosine triphosphate
br broad
BCA bicinchoninic acid
BSA bovine serum albumin
BOC tert-butoxycarbonyl
BuLi butyllithium
m-CPBA m-chloroperbenzoic acid
d doublet
dd doublet of doublets
DCE dichloroethane
DCM dichloromethane
DDQ 2,3-dichloro-5,6-dicyano-1,4-benzoquinone
DIPEA diisopropylethyl amine
DMAP N,N-dimethylaminopyridine
DME 1,2-Dimethoxyethane
DMEM Dulbecco's Modified Eagle's Medium
DMF N,N-dimethylformamide
DMFDMA N,N-dimethylformamide dimethyl acetal
DMSO dimethylsulfoxide DPPA diphenylphosphoryl azide
DTT dithiothreitol
dppf diphenylphosphinoferrocene
EDCl N-(3-dimethylaminopropyl)-N'-ethylcarbodiimide hydrochloride
EDTA ethylenediaminetetraacetic acid
EtOAc ethyl acetate
EtOH ethanol
FA formic acid
FBS fetal bovine serum
J coupling constant
h hours
Hz: hertz
HATU N,N,N',N'-tetramethyl-o-(7-azabenzotriazole-1-yl) uronium hexafluorophosphate
HBTU o-benzotriazol-1-yl-N,N,N',N'-tetramethyluronium hexafluorophosphate
HEPES N-(2-Hydroxyethyl)piperazine-N'-(2-ethanesulfonic acid)
HOBT 1-hydroxybenztriazole hydrate
HRMS high resolution mass spectrum
LAH lithium aluminum hydride
LCMS liquid chromatography mass spectrum
LDA lithium diisopropylamide
LiHMDS Lithium bis(trimethylsilyl)amide
m multiplet
m/z mass to charge
Me methyl
MeOH methanol
min minutes
MS mass spectrum
MTT methylthiazoletetrazolium
MWI microwave irradiation
NBS N-bromosuccinimide
PBS phosphate buffered saline
PICA cAMP-dependent protein kinase
rt room temperature
s singlet
t triplet
TEA triethylamine
TFA: trifluoroacetic acid
TFFA trifluoroacetic anhydride
THF tetrahydrofuran
TMB 3,3',5,5'-Tetramethylbenzidine
TMEDA Tetramethylethylenediamine
q quartet
WST (4-[3-(4-iodophenyl)-2-(4-nitrophenyl)-2H-5-tetrazolio]-1,3-benzene disulfonate sodium salt)

In examples 1A to 87-A, 126-B to 164-B, 1-C to 73-C, 1-D to 3-D, 1-E, 2-E, 4-E to 7-E, and 1-F to 6-F the following analytical methods were used:

LCMS sectra were run on a Phenominex Luna 5 μm C18 50×4.6 mm column on a Hewlett-Packard HP1100 using the following gradients:

Method Formic Acid (FA): Acetonitrile containing 0 to 100 percent 0.1% formic acid in water (2.5 ml/min for a 3 minute run).

Method Ammonium Acetate (AA): Acetonitrile containing 0 to 100 percent 10 mM ammonium acetate in water (2.5 ml/min for a 3 minute run).

NMR spectrum is shown by proton NMR, with tetramethylsilane as the internal standard and using 300 MHz Bruker Avance spectrometer equipped with a 5 mm QNP probe and 400 MHz Bruker Avance II spectrometer equipped with a 5 mm QNP probe for the measurement; 5 values are expressed in ppm.

In Examples 1-B to 125-B, and 3-E the following analytical methods were used:

LC/MS analysis was performed using Waters LC-MS system

Column: CAPCELL PAK C18 UG120, S-3 1.5×35 mm (Shiseido Co., Ltd.)

Solvent: Solution A; 0.05% trifluoroacetic acid-containing water, Solution B: 0.04% trifluoroacetic acid-containing acetonitrile Gradient cycle: 0.00 min (Solution A/Solution B=90/10), 2.00 min (Solution A/Solution B=5/95), 2.75 min (Solution A/Solution B=5/95), 2.76 min (Solution A/Solution B=90/10), 3.60 min (Solution A/Solution B=90/10)

Flow rate: 0.5 mL/min, detection method: UV 220 nm

MS conditions: ionization method: ESI

Purification by large-scale preparative HPLC was performed under the following conditions.

Instrument: Gilson Inc. reversed-phase large-scale preparative purification system GX-281

Column: CombiPrep C18 RS S-5 μm, 50×30 mm (YMC)

Solvent: Solution A; 10% aqueous ammonium bicarbonate solution, Solution B; acetonitrile Gradient cycle: 0.00 min (Solution A/Solution B=95/5), 0.30 min (Solution A/Solution B=95/5), 3.50 min (Solution A/Solution B=0/100), 5.50 min (Solution A/Solution B=0/100), 5.60 min (Solution A/Solution B=95/5), 6.60 min (Solution A/Solution B=95/5)

Flow rate: 50 mL/min, detection method: UV 220 nm

The elution by column chromatography was performed under observation by TLC (thin layer chromatography). For TLC observation, Kieselgel 60 $F_{254}$ plate manufactured by Merck, or NH TLC plate manufactured by Fuji Silysia Chemical Ltd., or an equivalent product thereof was used as a TLC plate, and the solvent used as an elution solvent in column chromatography was used as the eluent. For detection, a UV detector was employed. As silica gel for the column, Kieselgel 60 $F_{254}$ (70-230 mesh) manufactured by Merck, or CHROMATOREX NH DM1020 (basic silica gel, 100-200 mesh) manufactured by Fuji Silysia Chemical Ltd., or an equivalent product thereof was used. The ratio of solvents in silica gel chromatography shows the volume ratio of mixed solvents. Unless otherwise specified, % means weight percent.

NMR spectrum is shown by proton NMR, with tetramethylsilane as the internal standard and using VARIAN Gemini-200 (200 MHz spectrometer) or Gemini-300 (300 MHz spectrometer) or BRUKER AVANCE300 (300 MHz spectrometer) for the measurement; 6 values are expressed in ppm.

Genetic manipulation methods described in Experimental Example below are based on the methods described in Maniatis et al., Molecular Cloning, Cold Spring Harbor Laboratory, 1989, and the appended reagent protocol.

Example 1-A

Synthesis of N-(4-(3-cyano-4-(2,4-dichlorophenyl)-5-(4H-1,2,4-triazol-3-yl)thiophen-2-yl)pyridin-2-yl) cyclopropanecarboxamide (32-A)

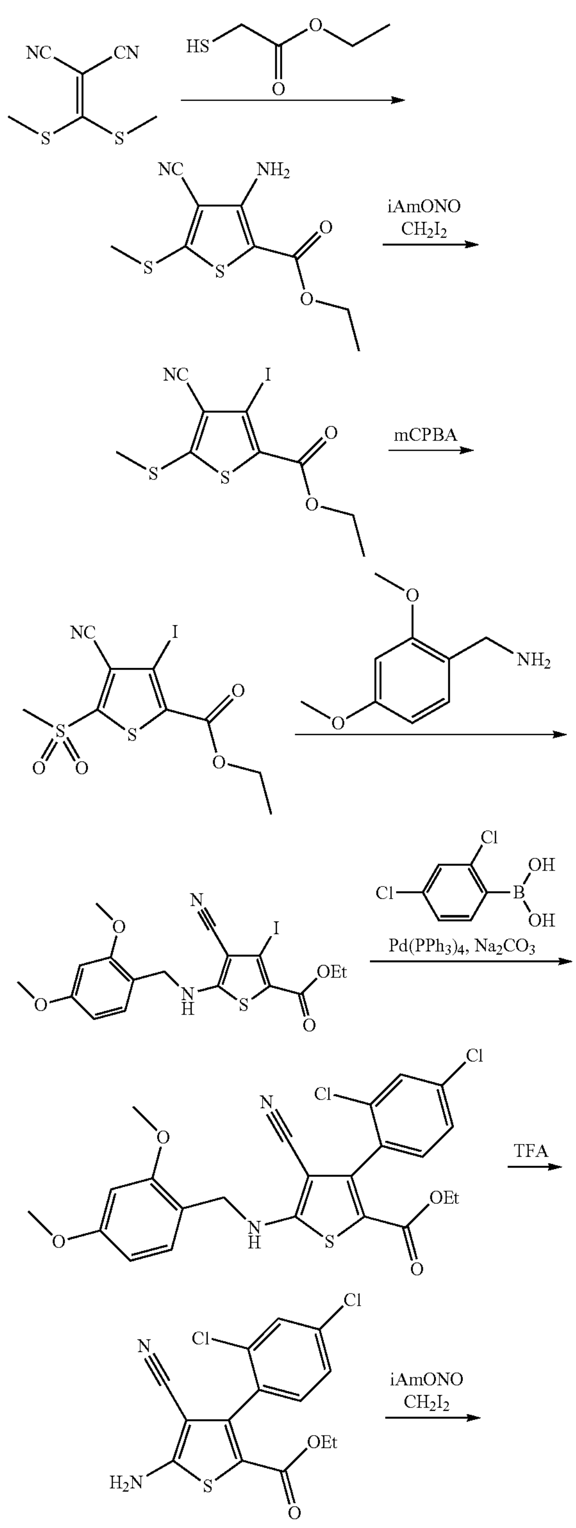

-continued

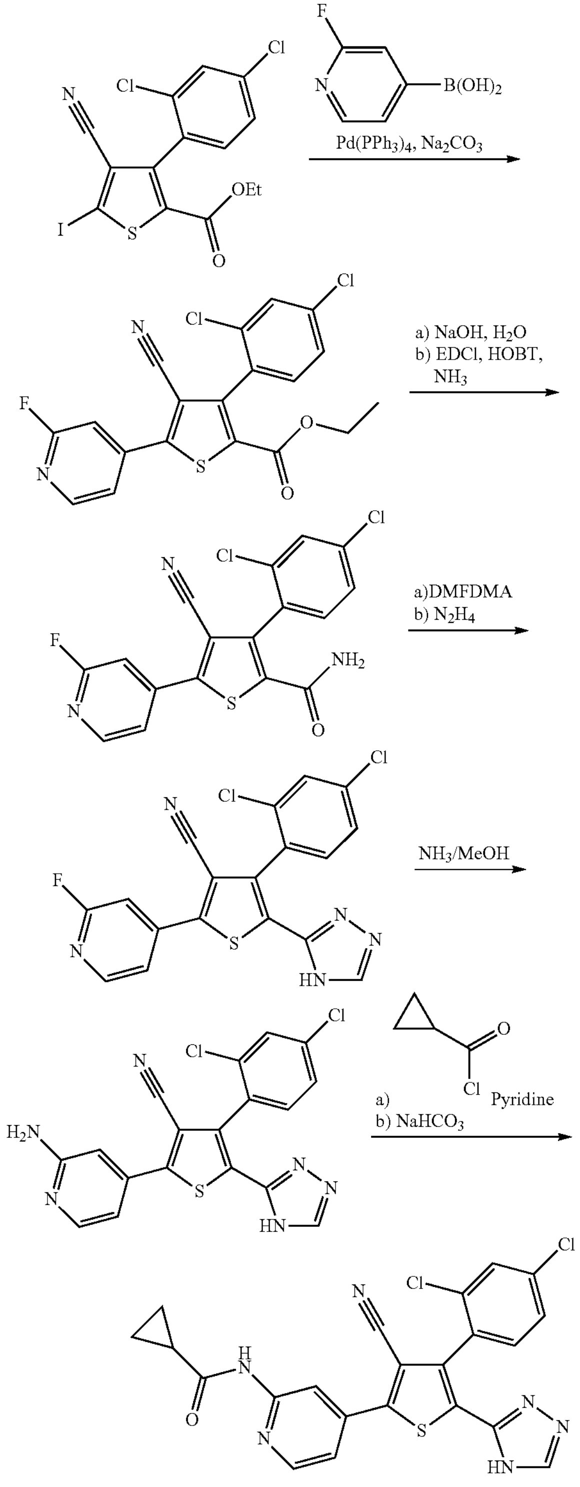

Step 1: Ethyl 3-amino-4-cyano-5-(methylsulfanyl) thiophene-2-carboxylate

A mixture of [bis(methylsulfanyl)methylene]malononitrile (40 g, 230 mmol), ethylthioglycolate (29 g, 230 mmol) and TEA (24 mL, 173 mmol) in MeOH (600 mL) was allowed to stir at reflux for 2 h. The reaction mixture was allowed to cool overnight and the precipitate was filtered off, washed with cold MeOH (3×50 mL) to give ethyl 3-amino-4-cyano-5-(methylsulfanyl)thiophene-2-carboxylate (52.4 g, 99%). LCMS: (FA) ES+ 275.

Step 2: Ethyl 4-cyano-3-iodo-5-(methylsulfanyl) thiophene-2-carboxylate

Ethyl 3-amino-4-cyano-5-(methylsulfanyl)thiophene-2-carboxylate (10 g, 41.3 mmol) was dissolved in acetonitrile (50 mL) under an atmosphere of argon. Diiodomethane (11.6 mL, 0.144 mol) was added and the mixture was heated at 40° C. Isoamyl nitrite (12.1 g, 0.103 mol) was added and the reaction was allowed to cool to room temperature and stirred for 2 hours. Mixture was cooled down at 0° C., diluted with hexane (50 mL) and the precipitate was filtered off, washed with 10:1 hexane-acetonitrile mixture (10 mL), 3:1 hexane-ether (10 mL) and hexane (10 mL). The precipitate was dried to afford ethyl 4-cyano-3-iodo-5-(methylsulfanyl)thiophene-2-carboxylate (6.90 g, 45%). LCMS: (FA) ES+ 354. $^1$H NMR (400 MHz, $d_1$-chloroform) δ: 4.38 (q, 2H), 2.70 (s, 3H), 1.40 (t, 3H).

Step 3: Ethyl 4-cyano-3-iodo-5-(methylsulfonyl) thiophene-2-carboxylate

Ethyl 4-cyano-3-iodo-5-(methylsulfanyl)thiophene-2-carboxylate (7.2 g, 20.4 mmol) was dissolved in DCM (200 mL) and THF (100 mL) and m-CPBA (9.14 g, 40.8 mmol) was added. The reaction mixture was stirred at rt overnight. Sodium sulfite (5.14 g, 40.8 mmol) was added, stirred for 10 minutes followed by addition of potassium carbonate (8.45, 61.2 mmol). The suspension was stirred at rt for 1 hour and filtered through celite, washed with DCM and the solvent was evaporated to afford ethyl 3-iodo-4-cyano-5-(methylsulfonyl)thiophene-2-carboxylate (6.80 g, 78%). LCMS: (FA) ES+ 386. $^1$H NMR (400 MHz, $d_1$-chloroform) δ: 4.45 (q, 2H), 3.38 (s, 3H), 1.43 (t, 3H).

Step 4: Ethyl 4-cyano-5-[(2,4-dimethoxybenzyl) amino]-3-iodothiophene-2-carboxylate Ethyl 4-cyano-3-iodo-5-(methylsulfonyl)thiophene-2-carboxylate (5.60 g, 0.0145 mol) and 2,4-dimethoxybenzylamine (3.51 mL, 0.0234 mol) were combined in tetrahydrofuran (100 mL) and stirred at 60° C. for 3 days. The reaction was concentrated in vacuo, diluted with dichloromethane and hexanes and the resultant precipitate was filtered to yield the title compound (5.56, 81%) as a yellow solid. LCMS: (FA) ES$^+$, 473. $^1$H NMR (400 MHz, $d_6$-DMSO) δ: 9.05 (s, 1H) 7.10 (d, 1H, J=8.57 Hz), 6.60-6.50 (m, 2H), 4.30 (s, 2H), 4.22-4.14 (m, 2H), 3.80 (s, 3H), 3.75 (s, 3H), 1.26-1.21 (m, 3H).

Step 5: Ethyl 4-cyano-3-(2,4-dichlorophenyl)-5-[(2, 4-dimethoxybenzyl)amino]thiophene-2-carboxylate Ethyl 4-cyano-5-[(2,4-dimethoxybenzyl)amino]-3-iodothiophene-2-carboxylate (3.18 g, 0.00673 mol) 2,4-dichlorophenylboronic acid (2.72 g, 0.0143 mol), $Pd(dba)_2$ (0.33 g, 0.00036 mol), $PtBu_3.BF_4$ (0.21 g, 0.00072 mmol) and sodium carbonate (2.42 g, 0.0228 mol) were suspended in 1,2-dimethoxyethane (250 mL) and water (80 mL). The suspension was flushed with argon and the reaction mixture was heated at reflux for 7 hours. The reaction mixture was diluted with a saturated solution of sodium bicarbonate in water and extracted with ethyl acetate. The organic extracts were washed with brine, dried over anhydrous sodium sulfate, filtered and concentrated in vacuo. Column chromatography was performed to yield the title compound (2.92 g, 88%). LCMS: (FA) ES$^+$, 491. $^1$H NMR (400 MHz, $d_6$-DMSO) δ: 9.05 (bs, 1H) 7.75 (d, 1H, J=2.00 Hz), 7.52-7.48 (m, 1H), 7.40 (d, 1H, J=8.28 Hz), 7.19 (d, 1H, J=8.53 Hz), 6.62-6.53 (m, 2H), 4.35 (bs, 2H), 4.04-3.92 (m, 2H), 3.83 (s, 3H), 3.76 (s, 3H), 1.01-0.96 (m, 3H).

Step 6: Ethyl 5-amino-4-cyano-3-(2,4-dichlorophenyl)thiophene-2-carboxylate

Ethyl 4-cyano-3-(2,4-dichlorophenyl)-5-[(2,4-dimethoxybenzyl)amino]thiophene-2-carboxylate (4.70 g, 0.00956 mol) was dissolved in dichloromethane (100 mL). Trifluoroacetic acid (25 mL) was added and the solution was stirred at room temperature for 10 minutes. The reaction was concentrated in vacuo, diluted with ethyl acetate and filtered. The filtrate was washed with saturated sodium bicarbonate and brine, dried over anhydrous sodium sulfate, filtered and concentrated in vacuo. Column chromatography was performed to yield the title compound (2.92 g, 90%) as a yellow solid. LCMS: (FA) ES$^+$, 341. $^1$H NMR (400 MHz, $d_6$-DMSO) δ: 8.17 (s, 2H) 7.75 (d, 1H, J=2.00 Hz), 7.52-7.48 (m, 1H), 7.39 (d, 1H, J=8.28 Hz), 4.05-3.92 (m, 2H), 1.02-0.96 (m, 3H).

Step 7: Ethyl 4-cyano-3-(2,4-dichlorophenyl)-5-iodothiophene-2-carboxylate

To a suspension of ethyl 5-amino-4-cyano-3-(2,4-dichlorophenyl)thiophene-2-carboxylate (2.92 g, 0.00856 mol) in acetonitrile (10 mL) was added diiodomethane (2.41 mL, 0.0300 mol) under an atmosphere of argon and was heated at 38° C. Isoamyl nitrite (2.61 g, 0.0214 mol) was added dropwise and the reaction mixture was cooled to room temperature and stirred for one hour. The reaction was concentrated in vacuo and column chromatography was performed to yield the title compound (1.44 g, 37%) as an orange solid. $^1$H NMR (400 MHz, $d_1$-chloroform) δ: 7.53 (d, 1H, J=2.00 Hz), 7.38-7.34 (m, 1H), 7.21 (d, 1H, J=8.28 Hz), 4.25-4.15 (m, 2H), 1.21-1.16 (m, 3H).

Step 8: Ethyl 4-cyano-3-(2,4-dichlorophenyl)-5-(2-fluoropyridin-4-yl)thiophene-2-carboxylate A mixture of ethyl 4-cyano-3-(2,4-dichlorophenyl)-5-iodothiophene-2-carboxylate (1.81 g, 0.00400 mol), 2-Fluoro-4-pyridinylboronic acid (1.13 g, 0.00801 mol), Tetrakis (triphenylphosphine)palladium(0) (0.231 g, 0.0002 mol) and sodium carbonate (1.27 g, 0.0120 mol) in 1,2-Dimethoxyethane (20 mL) and Water (10 mL) was heated under microwave irradiation at 140° C. for 15 min. The reaction mixture was diluted with EtOAc and sat. $NaHCO_3$. The layers were separated and the aqueous layer was extracted 2× with EtOAc. The combined organic extracts were washed with brine, dried over $Na_2SO_4$, filtered and concentrated to in vacuo to brown oil. The residue was loaded onto a 24 g Analogix silica gel column and eluted with hexane (3 min) to 50% EtOAc in hexanes (25 min gradient). The appropriate fractions were concentrated to a white solid (1.25 g, 74%). LCMS: (FA) ES$^+$, 421, 423. $^1$H NMR (400 MHz, $d_6$-DMSO) δ 8.42 (d, J=5.28 Hz, 1H), 7.65 (td, J=5.27, 1.51, 1.51 Hz, 1H), 7.57 (d, J=2.00 Hz, 1H), 7.45-7.34 (m, 1H), 7.29 (d, J=8.26 Hz, 1H), 4.34-4.17 (m, 1H), 1.21 (t, J=7.14, 7.14 Hz, 1H).

Step 9: 4-cyano-3-(2,4-dichlorophenyl)-5-(2-fluoropyridin-4-yl)thiophene-2-carboxamide Ethyl 4-cyano-3-(2,4-dichlorophenyl)-5-(2-fluoropyridin-4-yl)thiophene-2-carboxylate (2.33 g, 0.00553 mol) was dissolved in acetonitrile (100 mL) and 1M sodium hydroxide in water (42 mL, 0.0420 mol) was added. The mixture was stirred overnight at room temperature. The mixture was concentrated and the residue was acidified with 1N HCl. The solid was collected, dried, and used in the next step without purification. The above solid was dissolved in methylene chloride (248 mL) and N-(3-dimethylaminopropyl)-N'-ethylcarbodiimide hydrochloride (2.29 g, 0.0120 mol) and 1-hydroxybenzotriazole hydrate (1.694 g, 0.01106 mol) were added. The mixture was stirred at room temperature for 15 minutes and 33% ammonium hydroxide (20.0 mL, 0.231 mol) was added. The stirring was continued for 2 hours. The mixture was diluted with DCM and washed with water and brine. The organic layer was dried and purified by column chromatography on silica gel (80 g), elution hexane to 60% EtOAc in hexane over 30 minutes. The product was obtained as white solid (1.18 g, 55%). LCMS: (FA) $ES^+$, 392, 394. $^1H$ NMR (400 MHz, $d_6$-DMSO) δ 8.50 (d, J=5.27 Hz, 1H), 7.85 (d, J=1.79 Hz, 1H), 7.79 (td, J=5.21, 1.52, 1.52 Hz, 1H), 7.65 (s, 1H), 7.63-7.55 (m, 2H), 7.42 (bs, 1H), Step 10: 4-(2,4-dichlorophenyl)-2-(2-fluoropyridin-4-yl)-5-(4H-1,2,4-triazol-3-yl)thiophene-3-carbonitrile A mixture of 4-cyano-3-(2,4-dichlorophenyl)-5-(2-fluoropyridin-4-yl)thiophene-2-carboxamide (0.90 g, 0.0022 mol) in 1,1-dimethoxy-N,N-dimethylmethanamine (5.50 g, 0.045 mol) was stirred at 85° C. overnight. The mixture was evaporated to dryness and the residue was dissolved in acetic acid (14 mL, 0.2 mol) and hydrazine hydrate (1.4 mL, 0.02 mol) was added. The mixture was stirred at 85° C. for 5 hours. The solvent was removed and the residue was suspended in water. The precipitate was collected and dried in an oven to afford the product (0.86 g, 90%). LCMS: (FA) $ES^+$, 416, 418. $^1H$ NMR (400 MHz, $d_4$-Methanol) δ 8.42 (s, 1H), 8.41 (a, J=5.21 Hz, 1H), 7.81 (td, J=5.33, 1.58, 1.58 Hz, 1H), 7.63 (t, J=1.18, 1.18 Hz, 1H), 7.60 (s, 1H), 7.48-7.46 (m, 2H).

Step 11: 2-(2-aminopyridin-4-yl)-4-(2,4-dichlorophenyl)-5-(4H-1,2,4-triazol-3-yl)thiophene-3-carbonitrile A mixture of 4-(2,4-dichlorophenyl)-2-(2-fluoropyridin-4-yl)-5-(4H-1,2,4-triazol-3-yl)thiophene-3-carbonitrile (0.600 g, 0.00144 mol) and 7 M ammonia in methanol (40 mL, 0.280 mol) was irradiated in a microwave at 150° C. for 8 hours. Solvent was evaporated and the residue was purified by column chromatography on silica gel (40 g), gradient DCM to 6% MeOH in DCM over 30 minutes to afford the title compound as yellow solid (0.26 g, 44%). LCMS: (FA) $ES^+$, 413, 415. $^1H$ NMR (400 MHz, $d_4$-Methanol) δ 8.40 (s, 1H), 8.05 (dd, J=5.16, 1.10 Hz, 1H), 7.61 (dd, J=1.54, 0.76 Hz, 1H), 7.46-7.42 (m, 2H), 7.03-7.00 (m, 2H)

Step 12: N-(4-(3-cyano-4-(2,4-dichlorophenyl)-5-(4H-1,2,4-triazol-3-yl)thiophen-2-yl)pyridin-2-yl)cyclopropanecarboxamide (32-A)

To a mixture of 2-(2-aminopyridin-4-yl)-4-(2,4-dichlorophenyl)-5-(4H-1,2,4-triazol-3-yl)thiophene-3-carbonitrile (0.100 g, 0.24 mmol) in pyridine (0.39 mL, 4.8 mmol) and methylene chloride (10 mL) was added cyclopropanecarbonyl chloride 0.050 mL, 0.54 mmol) at 0° C. The mixture was stirred at 0° C. for 2 hours. Saturated sodium bicarbonate solution (5 mL) was added and the mixture was vigorously stirred for 15 min. The mixture was extracted with DCM, dried, filtered and evaporated and the residue was purified by column chromatography on silica gel (40 g) using DCM to 3% MeOH in DCM over 30 minutes to afford the product (0.041 g, 36%). LCMS: (FA) $ES^+$, 481, 483. $^1H$ NMR (400 MHz, $d_4$-Methanol) δ 8.49-8.42 (m, 2H), 8.40 (s, 1H), 7.66 (dd, J=5.58, 1.76 Hz, 1H), 7.62 (t, J=1.16, 1.16 Hz, 1H), 7.46-7.44 (m, 2H), 1.99-1.87 (m, 1H), 1.11-1.03 (m, 2H), 1.00-0.94 (m, 2H)

Compounds in the following table were prepared from the appropriate starting materials in a method analogous to that of Example 1-A:

| | |
|---|---|
| 1-A | LCMS: (FA) ES+ 517, 519. |
| 2-A | LCMS: (FA) ES+ 469, 471. |
| 3-A | LCMS: (FA) ES+ 545, 547. |
| 4-A | LCMS: (FA) ES+ 491, 493. |
| 6-A | LCMS: (FA) ES+ 470, 472. |
| 9-A | LCMS: (FA) ES+ 374, 376. |
| 11-A | LCMS: (FA) ES+ 413, 415. |
| 13-A | LCMS: (AA) ES+ 495, 497. |
| 15-A | LCMS: (FA) ES+ 490, 492. |
| 17-A | LCMS: (FA) ES+ 522, 524. |
| 18-A | LCMS: (FA) ES+ 398, 400. |
| 20-A | LCMS: (FA) ES+ 471, 473. |
| 24-A | LCMS: (FA) ES+ 428, 430. |
| 25-A | LCMS: (FA) ES+ 553, 555. |
| 28-A | LCMS: (FA) ES+ 498, 500. |
| 29-A | LCMS: (FA) ES+ 392, 394. |
| 30-A | LCMS: (FA) ES+ 431, 433. |
| 38-A | LCMS: (FA) ES+ 519, 521. |
| 39-A | LCMS: (FA) ES+ 455, 457. |
| 40-A | LCMS: (FA) ES+ 495, 497. |
| 42-A | LCMS: (FA) ES+ 484, 486. |
| 43-A | LCMS: (FA) ES+ 416, 418. |
| 46-A | LCMS: (FA) ES+ 518, 520. |
| 47-A | LCMS: (FA) ES+ 492, 494. |
| 48-A | LCMS: (FA) ES+ 485, 487. |
| 50-A | LCMS: (FA) ES+ 518, 520. |
| 51-A | LCMS: (FA) ES+ 485, 487. |
| 52-A | LCMS: (FA) ES+ 470, 472. |
| 53-A | LCMS: (FA) ES+ 456, 458. |
| 54-A | LCMS: (FA) ES+ 471, 473. |
| 60-A | LCMS: (FA) ES+ 389, 391. |

Example 2-A

Synthesis of 4-(2,4-dichlorophenyl)-2-(2-(methylamino)pyridin-4-yl)-5-(4H-1,2,4-triazol-3-yl) thiophene-3-carbonitrile (Compound 37-A)

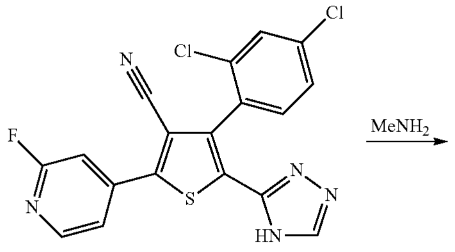

-continued

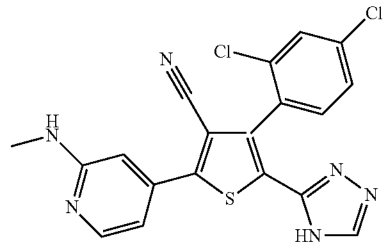

A solution of 4-(2,4-dichlorophenyl)-2-(2-fluoropyridin-4-yl)-5-(4H-1,2,4-triazol-3-yl)thiophene-3-carbonitrile (0.100 g, 0.000240 mol) and 1M Methylamine in methanol (4 mL, 0.004 mol) 0.000163 mol) was heated at 80° C. for 5 hours. The solvent was removed and the residue was purified using a silica gel chromatography (12 g), elution DCM to 5% MeOH in DCM over 20 minutes to afford the title compound (0.045 g, 44%). LCMS: (FA) $ES^+$, 427, 429. $^1$H NMR (400 MHz, $d_4$-Methanol) δ 8.38 (s, 1H), 8.12-8.07 (m, 1H), 7.60 (dd, J=1.56, 0.77 Hz, 1H), 7.44-7.42 (m, 2H), 6.94 (dd, J=4.67, 1.66 Hz, 1H), 6.93 (s, 1H), 2.92 (s, 3H).

Compounds in the following table were prepared from the appropriate starting materials in a method analogous to that of Example 2-A:

| | |
|---|---|
| 14-A | LCMS: (FA) ES+ 471, 473. |
| 23-A | LCMS: (FA) ES+ 457, 459. |
| 33-A | LCMS: (FA) ES+ 563, 565. |
| 35-A | LCMS: (FA) ES+ 485, 487. |

Example 3-A

Synthesis of tert-butyl 4-(3-cyano-4-(2,4-dichlorophenyl)-5-(4H-1,2,4-triazol-3-yl)thiophen-2-yl)pyridin-2-ylcarbamate (Compound 26-A)

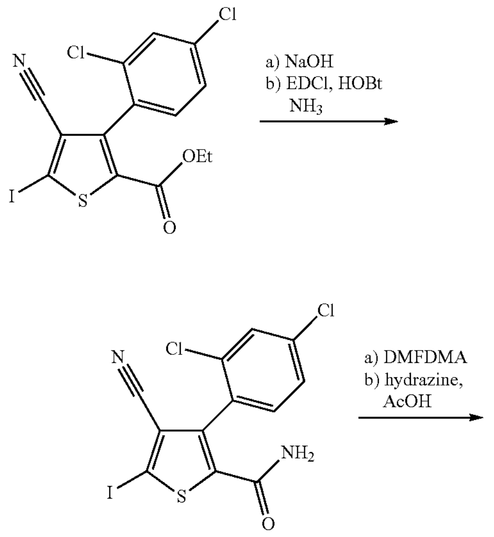

-continued

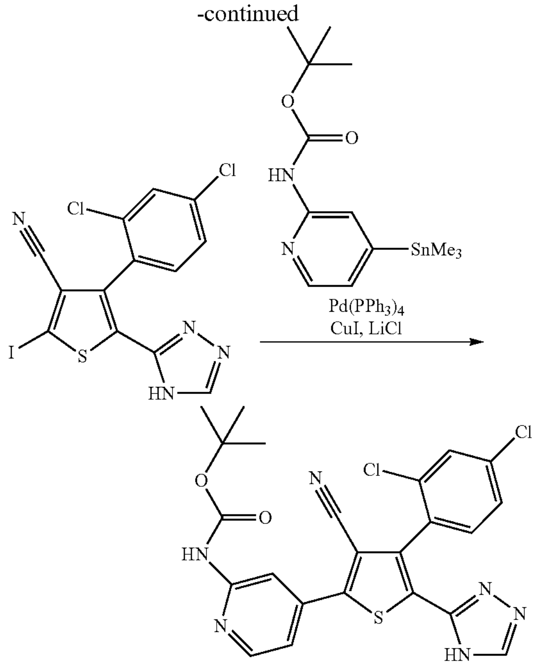

Step 1: 4-cyano-3-(2,4-dichlorophenyl)-5-iodothiophene-2-carboxylic acid

To a solution of ethyl 4-cyano-3-(2,4-dichlorophenyl)-5-iodothiophene-2-carboxylate (1.44 g, 0.00318 mol) in tetrahydrofuran (20 mL) and water (10 mL) was added a solution of 1.00M sodium hydroxide in water (16 mL). The solution was allowed to stir overnight. The reaction was quenched with a solution of 1N HCl (18 mL) and extracted with ethyl acetate. The organic extracts were washed with brine, dried over anhydrous sodium sulfate, filtered and concentrated in vacuo to afford the crude title compound (1.50 g, 100%) used directly in the next reaction. LCMS: (FA) $ES^-$, 422. $^1$H NMR (400 MHz, $d_6$-DMSO) δ: 7.68 (d, 1H, J=2.0 Hz), 7.46-7.34 (m, 2H).

Step 2: 4-cyano-3-(2,4-dichlorophenyl)-5-iodothiophene-2-carboxylamide 4-cyano-3-(2,4-dichlorophenyl)-5-iodothiophene-2-carboxylic acid (1.30 g, 0.00306 mol) was dissolved in dichloromethane (30 mL). N-(3-dimethylaminopropyl)-N'-ethylcarbodiimide hydrochloride (1.27 g, 0.00661 mol) and 1-hydroxybenzotriazole (0.880 g, 0.00651 mol) were added to the solution and the reaction was stirred for 30 minutes. Ammonium hydroxide (5.97 mL, 30% aqueous solution, 0.153 mol) was added to the solution and the biphasic mixture was stirred for 2 hours. The reaction mixture was concentrated, diluted with water and extracted with ethyl acetate. The organic extract was dried over anhydrous magnesium sulfate, filtered and column chromatography was performed to yield the title compound (1.21 g, 89%). LCMS: (FA) $ES^+$, 423. $^1$H NMR (400 MHz, $d_6$-DMSO) δ: 7.79 (d, 1H, J=2.0 Hz), 7.68 (bs, 1H), 7.57-7.45 (m, 2H), 7.30 (bs, 1H).

Step 3: 4-(2,4-dichlorophenyl)-2-iodo-5-(4H-1,2,4-triazol-3-yl)thiophene-3-carbonitrile A mixture of 4-cyano-3-(2,4-dichlorophenyl)-5-iodothiophene-2-carboxylamide (1.33 g, 0.00314 mol) and 1,1- dimethoxy-N,N-dimethylmethanamine (10.0 mL, 0.0753 mol) was irradiated in the microwave at 120° C. (300 watts) for 30 minutes. The reaction was concentrated in vacuo. The residue dissolved in acetic acid (1.0 mL, 0.18 mol) and hydrazine hydrate (0.69 mL, 0.014 mol) and subjected to microwave irradiation at 120° C. (300 watts) for 15 minutes. The solvent was removed in vacuo and the residue was azeotroped with toluene. Column chromatography was performed to yield the title compound (1.25 g, 85%). LCMS: (FA) $ES^+$, 447. $^1$H NMR (400 MHz, $d_4$-methanol) δ: 8.35 (s, 1H) 7.60 (d, 1H, J=2.0 Hz), 7.45-7.35 (m, 2H).

Step 4: tert-butyl 4-(3-cyano-4-(2,4-dichlorophenyl)-5-(4H-1,2,4-triazol-3-yl)thiophen-2-yl)pyridin-2-ylcarbamate A mixture of 4-(2,4-dichlorophenyl)-2-iodo-5-(4H-1,2,4-triazol-3-yl)thiophene-3-carbonitrile (0.180 g, 0.0004 mol), tert-butyl [4-(trimethylstannyl)pyridin-2-yl]carbamate (0.285 g, 0.0008 mol), lithium chloride (0.051 g, 0.0012 mol), copper(I) iodide (0.023 g, 0.00012 mol), tetrakis(triphenylphosphine)palladium (0.046 g, 0.00004 mol) was dissolved in dioxane (20 mL) and heated to reflux for 3 hours under an atmosphere of argon. The solvent was removed and the residue was purified using ISCO chromatography on silica gel, elution 20% ethyl acetate in hexanes to ethyl acetate to afford the title compound (0.270 g, 40%). LCMS: (FA) $ES^+$, 513, 515. $^1$H NMR (400 MHz, $d_4$-methanol) δ: 8.39 (s, 1H), 8.38 (d, J=6.31 Hz, 1H), 8.23 (s, 1H), 7.55-7.50 (m, 1H), 7.47 (dd, J=5.28, 1.56 Hz, 1H), 7.39-7.35 (m, 2H), 1.54 (s, 9H).

Compounds in the following table were prepared from the appropriate starting materials in a method analogous to that of Example 3-A:

| | |
|---|---|
| 10-A | LCMS: (FA) ES+ 473, 475. |
| 44-A | LCMS: (FA) ES+ 455, 457. |
| 59-A | LCMS: (FA) ES+ 390, 392. |

Example 4-A

Synthesis 4-(2,4-dichlorophenyl)-2-[2-(methylamino)pyrimidin-4-yl]-5-(4H-1,2,4-triazol-3-yl)thiophene-3-carbonitrile (Compound 12-A)

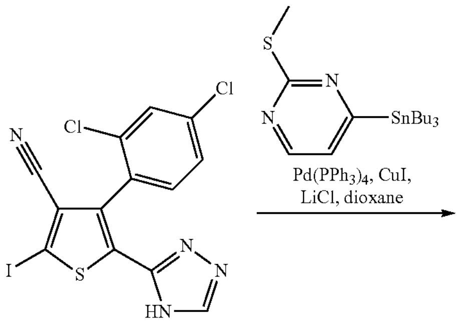

-continued

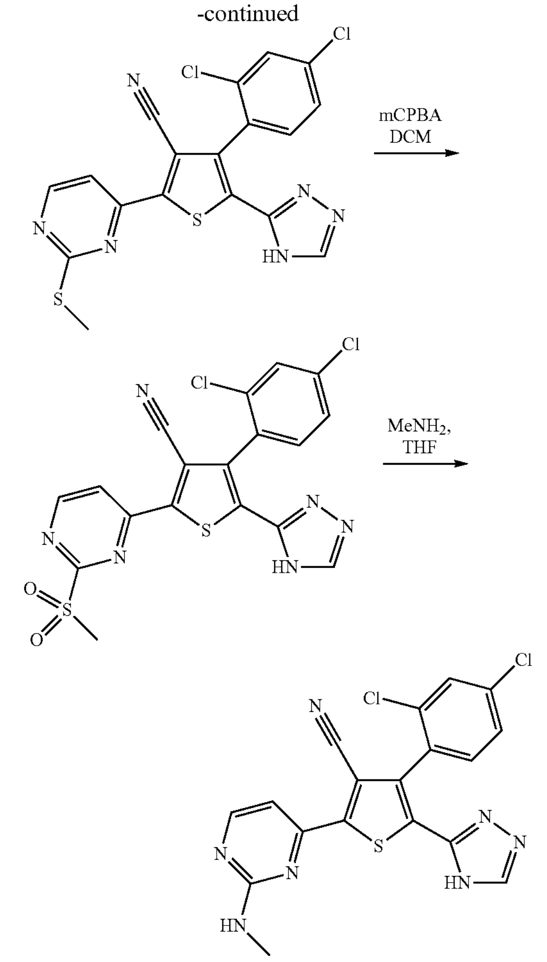

Step 1: 4-(2,4-dichlorophenyl)-2-[2-(methylsulfanyl)pyrimidin-4-yl]-5-(4H-1,2,4-triazol-3-yl)thiophene-3-carbonitrile 4-(2,4-dichlorophenyl)-2-iodo-5-(4H-1,2,4-triazol-3-yl)thiophene-3-carbonitrile (0.140 g, 0.313 mmol), Lithium chloride (0.0398 g, 0.939 mmol), Copper(I) iodide (0.0179 g, 0.0939 mmol), and Tetrakis(triphenylphosphine)palladium (0) (0.0362 g, 0.0313 mmol) were combined in a 100 mL round-bottom flask under an atmosphere of Argon. 1,4-Dioxane (8.75 mL, 0.112 mol) was added followed by 4-tributylstannyl-2-thiomethylpyrimidine (0.194 g, 0.470 mmol). The solution was heated to reflux for 2 hours. The solvent was concentrated in vacuo and the residue was purified using ISCO chromatography on silica gel, elution 20% ethyl acetate in hexanes to ethyl acetate to afford the title compound (0.066 g, 47%). LCMS: (FA) $ES^+$, 445, 447. $^1$H NMR (400 MHz, $d_1$-chloroform) δ: 8.67 (d, J=5.21 Hz, 1H), 8.21 (s, 1H), 7.86 (d, J=5.20 Hz, 1H), 7.60-7.55 (m, 1H), 7.44-7.34 (m, 2H), 2.66 (s, 3H).

Step 2: 4-(2,4-dichlorophenyl)-2-[2-(methylsulfonyl)pyrimidin-4-yl]-5-(4H-1,2,4-triazol-3-yl)thiophene-3-carbonitrile 4-(2,4-dichlorophenyl)-2-[2-(methylsulfanyl)pyrimidin-4-yl]-5-(4H-1,2,4-triazol-3-yl)thiophene-3-carbonitrile (0.0660 g, 0.148 mmol) was dissolved in Methylene chloride (5.5 mL, 0.086 mol) and Tetrahydrofuran (3.3 mL, 0.041 mol) and m-Chloroperbenzoic acid (0.0996 g, 0.444 mmol) was added. The mixture was stirred at room temperature for 4 hours. The solvent was concentrated in vacuo and the residue was purified using ISCO chromatography on silica gel, elution 40% ethyl acetate in hexanes to ethyl acetate to afford the title compound (0.047 g, 66%). LCMS: (FA) $ES^+$, 477, 479. $^1H$ NMR (400 MHz, $d_1$-chloroform) δ: 10.75 (bs, 1H), 9.08 (d, J=5.32 Hz, 1H), 8.35 (d, J=5.32 Hz, 1H), 8.25 (s, 1H), 7.59 (d, J=1.94 Hz, 1H), 7.42 (dd, J=8.22, 2.00 Hz, 1H), 7.36 (d, J=8.22 Hz, 1H), 3.48 (s, 3H).

Step 3: 4-(2,4-dichlorophenyl)-2-[2-(methylamino)pyrimidin-4-yl]-5-(4H-1,2,4-triazol-3-yl)thiophene-3-carbonitrile 4-(2,4-dichlorophenyl)-2-[2-(methylsulfonyl)pyrimidin-4-yl]-5-(4H-1,2,4-triazol-3-yl)thiophene-3-carbonitrile (0.047 g, 0.10 mmol) was dissolved in 2.0 M of Methylamine in Tetrahydrofuran (1.74 mL, 0.00349 mol) and the mixture was stirred at room temperature for 1 hour. The solvent was concentrated in vacuo and the residue was purified using ISCO chromatography on silica gel, elution 30% ethyl acetate in hexanes to ethyl acetate to afford the title compound (0.037 g, 81%). LCMS: (FA) $ES^+$, 428, 430. $^1H$ NMR (400 MHz, $d_4$-methanol) δ: 8.07-8.01 (m, 1H), 7.99 (s, 1H), 7.24-7.21 (m, 1H), 7.09-7.02 (m, 2H), 6.97 (d, J=5.04 Hz, 1H), 2.62 (s, 3H).

Compounds in the following table were prepared from the appropriate starting materials in a method analogous to that of Example 4-A:

| | |
|---|---|
| 7-A | LCMS: (FA) ES+ 448, 450. |
| 8-A | LCMS: (FA) ES+ 428, 430. |
| 21-A | LCMS: (FA) ES+ 462, 464. |
| 22-A | LCMS: (FA) ES+ 486, 488. |
| 27-A | LCMS: (FA) ES+ 472, 474. |
| 36-A | LCMS: (FA) ES+ 390, 392. |
| 41-A | LCMS: (FA) ES+ 414, 416. |
| 49-A | LCMS: (FA) ES+ 458, 460. |
| 55-A | LCMS: (FA) ES+ 442, 444. |
| 58-A | LCMS: (FA) ES+ 472, 474. |

Example 5-A

N-{4-[3-cyano-4-(2,4-dichlorophenyl)-5-(1H-imidazol-2-yl)-2-thienyl]pyridin-2-yl}cyclopropanecarboxamide (Compound 34-A)

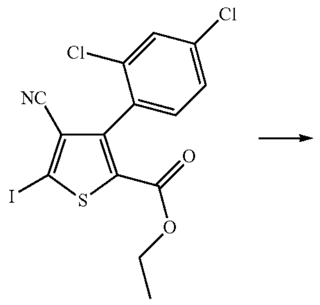

-continued

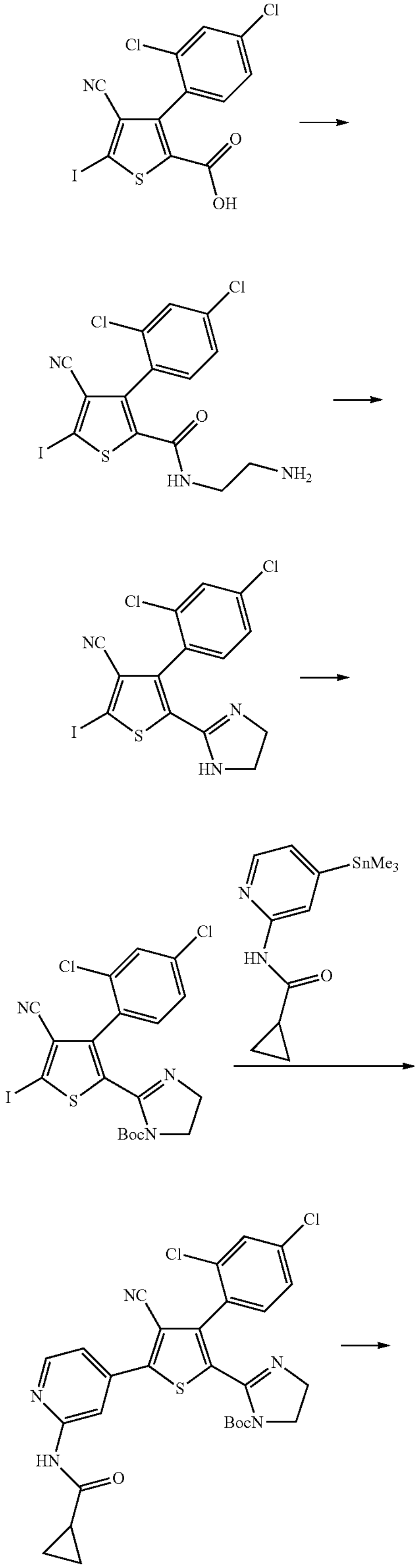

-continued

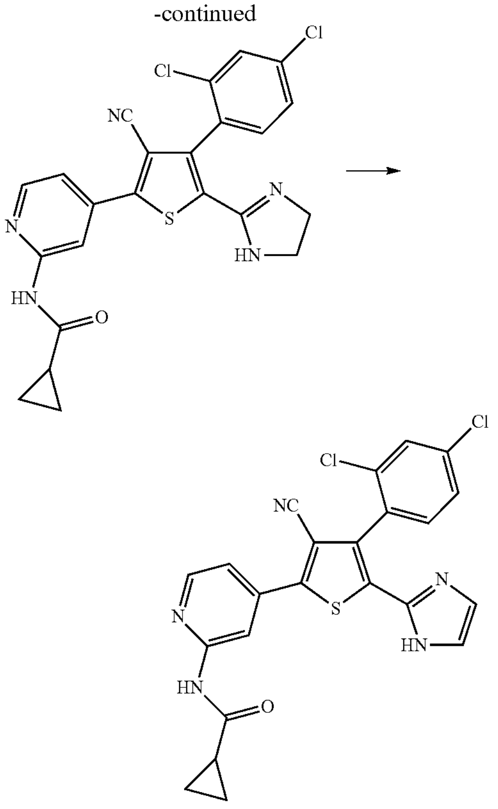

Step 1: 4-cyano-3-(2,4-dichlorophenyl)-5-iodothiophene-2-carboxylic acid

To a solution of ethyl 4-cyano-3-(2,4-dichlorophenyl)-5-iodothiophene-2-carboxylate (1.26 g, 0.00279 mol) in Tetrahydrofuran (20 mL, 0.3 mol) was added water (9.2 mL, 0.51 mol) and 1M NaOH (19.5 mL, 0.0195 mol) and the solution was stirred at room temperature for 2 days. The mixture was acidified by 1M HCl (20 mL), extracted with EtOAc (3×100 mL). The organic extracts were combined, dried over Na2SO4, filtered and evaporated to afford the product (1.17 g, 99%). LCMS: (FA) $ES^+$, 424, 426. $^1H$ NMR (400 MHz, $d_1$-chloroform) δ: 7.62-7.60 (m, 1H) 7.45-7.41 (m, 1H), 7.36-7.33 (m, 1H).

Step 2: N-(2-aminoethyl)-4-cyano-3-(2,4-dichlorophenyl)-5-iodothiophene-2-carboxamide A mixture of 4-cyano-3-(2,4-dichlorophenyl)-5-iodothiophene-2-carboxylic acid (1.17 g, 0.00276 mol), N-(2-aminoethyl)(tert-butoxy)carboxamide (0.690 mL, 0.00414 mol), N-(3-Dimethylaminopropyl)-N'-ethylcarbodiimide hydrochloride (1.06 g, 0.00552 mol) and 1-Hydroxybenzotriazole (0.746 g, 0.00552 mol) in Methylene chloride (40 mL, 0.6 mol) was stirred at room temperature overnight. The mixture was washed with water (2×20 mL), dried with MgSO4, filtered and evaporated. The residue was purified using ISCO chromatography on silica gel, elution 30% ethyl acetate in hexanes to ethyl acetate to afford the intermediate (1.40 g, 90%). LCMS: (FA) $ES^+$, 566, 568. The Boc-protected material was dissolved in 1,4-Dioxane (40 mL, 0.5 mol), 4.00 M HCl in dioxane (8.00 mL, 0.032 mol) and the mixture was stirred at room temperature for 30 minutes. The solvent was evaporated to dryness and the residue was dissolved in DCM (100 mL). Sodium hydroxide (7.2 g, 0.18 mol) in 10 ml of water was added and the mixture was stirred vigorously for 10 minutes. Organic layer was separated and the aqueous phase was extracted twice with DCM. The combined DCM layers were dried with MgSO4, filtered and evaporated to afford the free base (1.16 g, 90%). LCMS: (FA) $ES^+$, 466, 468. $^1H$ NMR (400 MHz, $d_6$-DMSO) δ: 7.80-7.78 (m, 1H) 7.57-7.53 (m, 1H), 7.51-7.48 (m, 1H), 3.72-3.63 (m, 1H), 3.51-3.43 (m, 1H), 3.07-3.02 (m, 2H).

Step 3: 4-(2,4-dichlorophenyl)-5-(4,5-dihydro-1H-imidazol-2-yl)-2-iodothiophene-3-carbonitrile To a mixture of N-(2-aminoethyl)-4-cyano-3-(2,4-dichlorophenyl)-5-iodothiophene-2-carboxamide (1.16 g, 0.00249 mol) in Toluene (20 mL, 0.19 mol) in a pressure vessel was added Phosphoryl chloride (2.0 mL, 0.022 mol) and the mixture was heated at 120° C. for 3 hours. Solvent was evaporated and the residue was diluted with water, treated with 1N NaOH (10 mL) and extracted with DCM (5×50 mL). The combined DCM layers were washed with brine, dried with MgSO4, filtered and concentrated to afford the product (1.00 g, 89%). LCMS: (FA) $ES^+$, 448, 450. $^1H$ NMR (400 MHz, $d_6$-DMSO) δ: 7.81-7.78 (m, 1H) 7.56-7.52 (m, 1H), 7.50-7.47 (m, 1H), 3.67-3.59 (m, 2H), 3.25-3.17 (m, 2H).

Step 4: tert-butyl 2-[4-cyano-3-(2,4-dichlorophenyl)-5-iodo-2-thienyl]-4,5-dihydro-1H-imidazole-1-carboxylate To a solution of 4-(2,4-dichlorophenyl)-5-(4,5-dihydro-1H-imidazol-2-yl)-2-iodothiophene-3-carbonitrile (0.859 g, 1.92 mmol) in DCM (18.6 mL, 290 mmol) at 0° C. was added triethylamine (0.313 mL, 2.24 mmol) followed by di-tert-Butyldicarbonate (0.489 g, 2.24 mmol). The mixture was stirred at room temperature for 3 days. Water (10 mL) and DCM (100 mL) were added, organic layer was separated and the aqueous layer was extracted with DCM (2×50 mL). Combined organic layers were washed with saturated NaHCO3 (10 mL) and brine (20 mL), dried with MgSO4, filtered and evaporated. The residue was purified using ISCO chromatography on silica gel, elution 5 to 55% ethyl acetate in hexanes to afford the product (0.615 g, 58%). LCMS: (FA) $ES^+$, 548, 550. $^1H$ NMR (400 MHz, $d_6$-DMSO) δ: 7.78-7.76 (m, 1H) 7.55-7.51 (m, 1H), 7.35-7.31 (m, 1H), 3.77-3.63 (m, 4H), 1.24 (s, 9H).

Step 5: tert-butyl 2-[4-cyano-5-{2-[(cyclopropylcarbonyl)amino]pyridin-4-yl}-3-(2,4-dichlorophenyl)-2-thienyl]-4,5-dihydro-1H-imidazole-1-carboxylate tert-butyl 2-[4-cyano-3-(2,4-dichlorophenyl)-5-iodo-2-thienyl]-4,5-dihydro-1H-imidazole-1-carboxylate (0.500 g, 0.912 mmol), N-[4-(trimethylstannyl)pyridin-2-yl]cyclopropanecarboxamide (0.445 g, 1.37 mmol), Lithium chloride (0.116 g, 2.74 mmol), Copper(I) iodide (0.0521 g, 0.274 mmol) and Tetrakis(triphenylphosphine)palladium(0) (0.105 g, 0.0912 mmol) were combined in a 100 mL round-bottom flask under an atmosphere of argon and 1,4-Dioxane (45.3 mL, 0.580 mol) was added. The solution was heated to reflux for 2 hours. The reaction was concentrated in vacuo and the residue was purified using ISCO chromatography on silica gel, elution 10 to 70% ethyl acetate in hexanes to afford the product (0.315 g, 59%). LCMS: (FA) $ES^+$, 582, 584. $^1H$ NMR (400 MHz, $d_1$-chloroform) δ: 8.62-8.58 (m, 1H) 8.41-8.38 (m, 1H), 8.26 (s, 1H), 7.54-7.50 (m, 1H), 7.50-7.48 (m, 1H), 7.40-7.37 (m, 1H), 7.33-7.29 (m, 1H), 3.96-3.73 (m, 4H), 1.56-1.54 (m, 1H), 1.32 (s, 9H), 1.17-1.11 (m, 2H), 0.95-0.88 (m, 2H).

Step 6: N-{4-[3-cyano-4-(2,4-dichlorophenyl)-5-(4,5-dihydro-1H-imidazol-2-yl)-2-thienyl]pyridin-2-yl}cyclopropanecarboxamide To a solution of tert-butyl 2-[4-cyano-5-{2-[(cyclopropylcarbonyl)amino]pyridin-4-yl}-3-(2,4-dichlorophenyl)-2-thienyl]-4,5-dihydro-1H-imidazole-1-carboxylate (0.315 g, 0.541 mmol) in 1,4-Dioxane (4.00 mL, 51.2 mmol) was added 4.00 M of Hydrochloric acid in 1,4-Dioxane (1.35 mL, 5.41 mmol), stirred at room temperature overnight. Solvent was evaporated, residue was diluted with DCM (50 mL) and washed with 1M NaOH (5 mL). Layers were separated and the aqueous phase was extracted with DCM (3×50 mL). Combined organic extracts were dried with MgSO4, filtered and evaporated. The residue was purified using ISCO chromatography on silica gel, elution 5 to 80% ethyl acetate in hexanes to afford the product (0.197 g, 76%). LCMS: (FA) $ES^+$, 482, 484. $^1H$ NMR (400 MHz, $d_1$-chloroform) δ: 8.66-8.64 (m, 1H) 8.41-8.38 (m, 1H), 8.25 (s, 1H), 7.61-7.59 (m, 1H), 7.48-7.45 (m, 1H), 7.44-7.41 (m, 1H), 7.37-7.34 (m, 1H), 3.97-3.68 (m, 2H), 3.60-3.25 (m, 2H), 1.57-1.52 (m, 1H), 1.17-1.11 (m, 2H), 0.95-0.88 (m, 2H).

Step 7: N-{-4-[3-cyano-4-(2,4-dichlorophenyl)-5-(1H-imidazol-2-yl)-2-thienyl]pyridin-2-yl}cyclopropanecarboxamide A mixture of N-{4-[3-cyano-4-(2,4-dichlorophenyl)-5-(4,5-dihydro-1H-imidazol-2-yl)-2-thienyl]pyridin-2-yl}cyclopropanecarboxamide (0.0650 g, 0.135 mmol) and Magtrieve (0.143 g, 1.70 mmol) was taken up in toluene (5 mL) and heated at 120° C. for 4 hours. The mixture was cooled to room temperature, diluted with DCM (10 mL) and filtered through a pad of celite. The solid residue was washed with 1% ammonia, 9% methanol in DCM mixture (10 mL) and solvent from the filtrate was evaporated. The residue was purified using ISCO chromatography on silica gel, elution 10 to 70% ethyl acetate in hexanes to afford the product (0.027 g, 47%). LCMS: (FA) $ES^+$, 480, 482. $^1H$ NMR (400 MHz, $d_6$-DMSO) δ: 11.88 (s, 1H) 11.11 (m, 1H), 8.57-8.55 (m, 1H), 8.53-8.50 (m, 1H), 7.85-7.84 (m, 1H), 7.58-7.56 (m, 2H), 7.54-7.52 (m, 1H), 7.17-7.16 (m, 1H), 7.00-6.98 (m, 1H), 2.08-2.00 (m, 1H), 0.87-0.81 (m, 4H).

Compounds in the following table were prepared from the appropriate starting materials in a method analogous to that of Example 5-A:

| | |
|---|---|
| 5-A | LCMS: (FA) ES+ 412, 414. |
| 16-A | LCMS: (FA) ES+ 427, 429. |
| 31-A | LCMS: (FA) ES+ 512, 514. |
| 45-A | LCMS: (FA) ES+ 426, 428. |
| 56-A | LCMS: (FA) ES+ 440, 442. |
| 57-A | LCMS: (FA) ES+ 454, 456. |
| 61-A | LCMS: (FA) ES+ 469, 471. |
| 63-A | LCMS: (FA) ES+ 496, 498. |
| 86-A | LCMS: (FA) ES+ 470, 472. |
| 87-A | LCMS: (FA) ES+ 482, 484. |

Example 6-A

Synthesis N-{4-[5-(1-benzyl-1H-imidazol-2-yl)-3-cyano-4-(2,4-dichlorophenyl)-2-thienyl]pyridin-2-yl}acetamide (Compound 19-A)

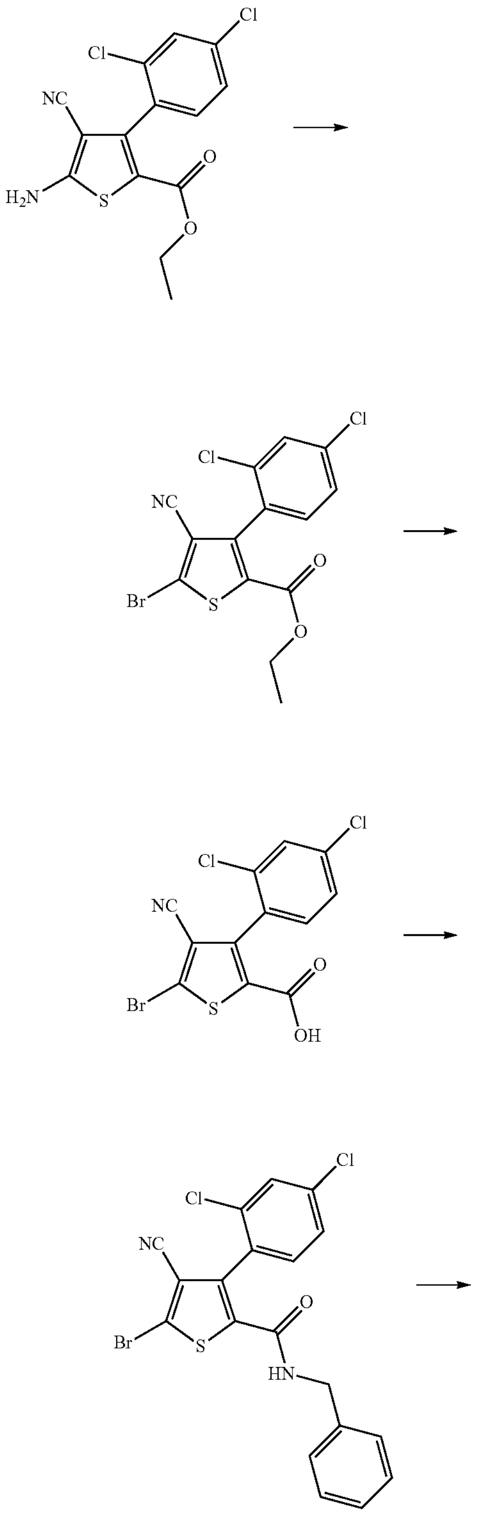

-continued

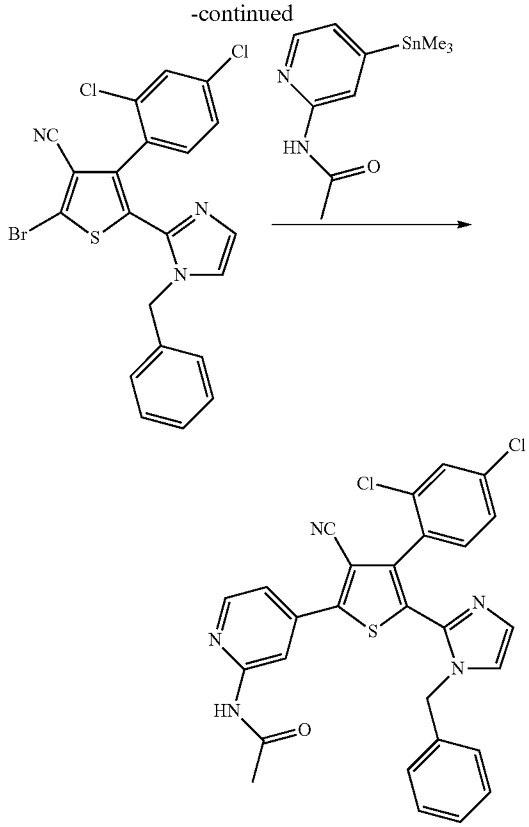

Step 1: Ethyl 5-bromo-4-cyano-3-(2,4-dichlorophenyl)thiophene-2-carboxylate

Copper(II) Bromide (9.75 g, 0.0437 mol) was dissolved in acetonitrile (194 mL, 3.72 mol). To this solution was added tert-Butyl nitrite (6.97 mL, 0.0586 mol) slowly while warming to 50° C. Heating at 50° C. was continued for 30 minutes and a solution of ethyl 5-amino-4-cyano-3-(2,4-dichlorophenyl)thiophene-2-carboxylate (10.0 g, 0.0293 mol) in acetonitrile (260 mL, 5.1 mol) was added. The reaction mixture was heated at 80° C. for 30 minutes. Solvent was concentrated in vacuo and the residue was purified using ISCO chromatography on silica gel, solid load, elution with hexanes to 25% EA in hexanes over 30 minutes to give the product (8.8 g, 74%). LCMS: (FA) $ES^+$, 404, 406, 408. $^1H$ NMR (400 MHz, $d_1$-chloroform) δ: 7.53 (d, J=2.01 Hz, 1H), 7.37 (dd, J=8.27, 2.03 Hz, 1H), 7.22 (d, J=8.27 Hz, 1H), 4.21 (dq, J=7.14, 7.10, 7.10, 3.46 Hz, 2H), 1.19 (t, J=7.13, 7.13 Hz, 3H).

Step 2: 5-bromo-4-cyano-3-(2,4-dichlorophenyl)thiophene-2-carboxylic acid

Ethyl 5-bromo-4-cyano-3-(2,4-dichlorophenyl)thiophene-2-carboxylate (4.60 g, 0.0114 mol) was dissolved in Tetrahydrofuran (100 mL) and Water (20 mL) and 1.00 M of Sodium hydroxide in Water (34.1 mL, 0.0341 mol) was added The mixture was stirred at room temperature overnight. Reaction was quenched by addition of 1N HCl (36 mL), extracted with EA (3×), dried $MgSO_4$, filtered and evaporated to give the product that was used without further purification (4.28 g, 100%). LCMS: (FA) $ES^-$, 374, 376, 378. $^1H$ NMR (400 MHz, $d_1$-chloroform) δ: 7.52 (d, J=1.99 Hz, 1H), 7.35 (dd, J=8.28, 2.02 Hz, 1H), 7.21 (d, J=8.27 Hz, 1H).

Step 3: N-benzyl-5-bromo-4-cyano-3-(2,4-dichlorophenyl)thiophene-2-carboxamide 5-bromo-4-cyano-3-(2,4-dichlorophenyl)thiophene-2-carboxylic acid (0.623 g, 1.65 mmol), 1-Hydroxybenzotriazole hydrate (0.253 g, 1.65 mmol) and N-(3-Dimethylaminopropyl)-N'-ethylcarbodiimide hydrochloride (0.570 g, 2.97 mmol) were taken up in DCM (30 mL) and the mixture was stirred for 5 minutes at room temperature. N,N-Diisopropylethylamine (0.460 mL, 2.64 mmol) was added followed by benzylamine (0.216 mL, 1.98 mmol) and the solution was stirred at room temperature overnight. The mixture was quenched with water, extracted with DCM (3×50 mL), washed with water, brine, dried over $Na_2SO_4$, filtered and evaporated. The residue was purified using ISCO chromatography on silica gel, elution with 10-25% EA in hexanes to give the product (0.574 g, 74%). LCMS: (FA) $ES^+$, 465, 467, 469. $^1H$ NMR (400 MHz, $d_1$-chloroform) δ: 7.46 (d, J=2.00 Hz, 1H), 7.32-7.27 (m, 4H), 7.26-7.23 (d, J=7.78 Hz, 1H), 6.99-6.96 (m, 2H), 5.38 (bs, 1H), 4.36 (d, J=5.52 Hz, 2H).

Step 4: 5-(1-benzyl-1H-imidazol-2-yl)-2-bromo-4-(2,4-dichlorophenyl)thiophene-3-carbonitrile N-benzyl-5-bromo-4-cyano-3-(2,4-dichlorophenyl)thiophene-2-carboxamide (0.180 g, 0.386 mmol) was dissolved in DCM (2 mL) and phosphorus pentachloride (0.0884 g, 0.425 mmol) and 4.00 M of Hydrochloric acid in 1,4-dioxane (0.050 mL, 0.20 mmol) were added. The mixture was heated in a sealed vial at 60° C. for 2 hours. After cooling down to room temperature, aminoacetaldehyde dimethyl acetal (0.252 mL, 2.32 mmol) was slowly added. The mixture was heated at 60° C. for additional 1 hour. After cooling to room temperature, 4.00 M of Hydrochloric acid in 1,4-dioxane (1.0 mL, 4.0 mmol) was added and the mixture was heated at 60° C. for 2 hours and at room temperature overnight. Solvent was concentrated and the residue was diluted with EA, washed with saturated $NaHCO_3$, brine, dried with $Na_2SO_4$, filtered and evaporated. The residue was purified using ISCO chromatography on silica gel, elution with 10-25% EA in hexanes to give the product (0.110 g, 58%). LCMS: (FA) $ES^+$, 488, 490, 492. $^1H$ NMR (300 MHz, $d_1$-chloroform) δ: 7.28 (d, J=2.07 Hz, 1H), 7.26-7.15 (m, 5H), 7.11-7.08 (d, J=8.29 Hz, 1H), 6.85 (s, 1H), 6.73-6.70 (dd, J=6.97 Hz, 1.66 Hz, 2H), 4.85-4.70 (m, 2H).

Step 5: N-{4-[5-(1-benzyl-1H-imidazol-2-yl)-3-cyano-4-(2,4-dichlorophenyl)-2-thienyl]pyridin-2-yl}acetamide 5-(1-benzyl-1H-imidazol-2-yl)-2-bromo-4-(2,4-dichlorophenyl)thiophene-3-carbonitrile (107 mg, 0.219 mmol), N-[4-(trimethylstannyl)pyridin-2-yl]acetamide (85.0 mg, 0.284 mmol), Lithium chloride (30.0 mg, 0.708 mmol), Copper(I) iodide (4.70 mg, 0.0247 mmol) and Tetrakis(triphenylphosphine)palladium(0) (24.7 mg, 0.0214 mmol) were taken up in 1,4-Dioxane (3.0 mL) under an atmosphere of argon. The mixture was heated at 90° C. for 4 hours. The solvent was evaporated and the residue was purified using ISCO chromatography on silica gel, elution with 1-2% MeOH in DCM to give the product (0.071 g, 60%). LCMS: (FA) $ES^+$ 544, 546. $^1H$ NMR (400 MHz, $d_1$-chloroform) δ: 8.59 (s, 1H), 8.40 (d, J=5.27 Hz, 1H), 8.03 (s, 1H), 7.52 (dd, J=5.27 Hz, 1.76 Hz, 1H), 7.30 (d, J=2.00 Hz, 1H), 7.27-7.16 (m, 6H), 6.87 (d, 1H), 6.77-6.75 (d, J=6.27 Hz, 2H), 4.90-4.78 (m, 2H), 2.25 (s, 3H).

Example 7-A

Synthesis of N-{4-[4-(2,4-dichlorophenyl)-5-(1H-imidazol-2-yl)-2-thienyl]pyridin-2-yl}acetamide (62-A)

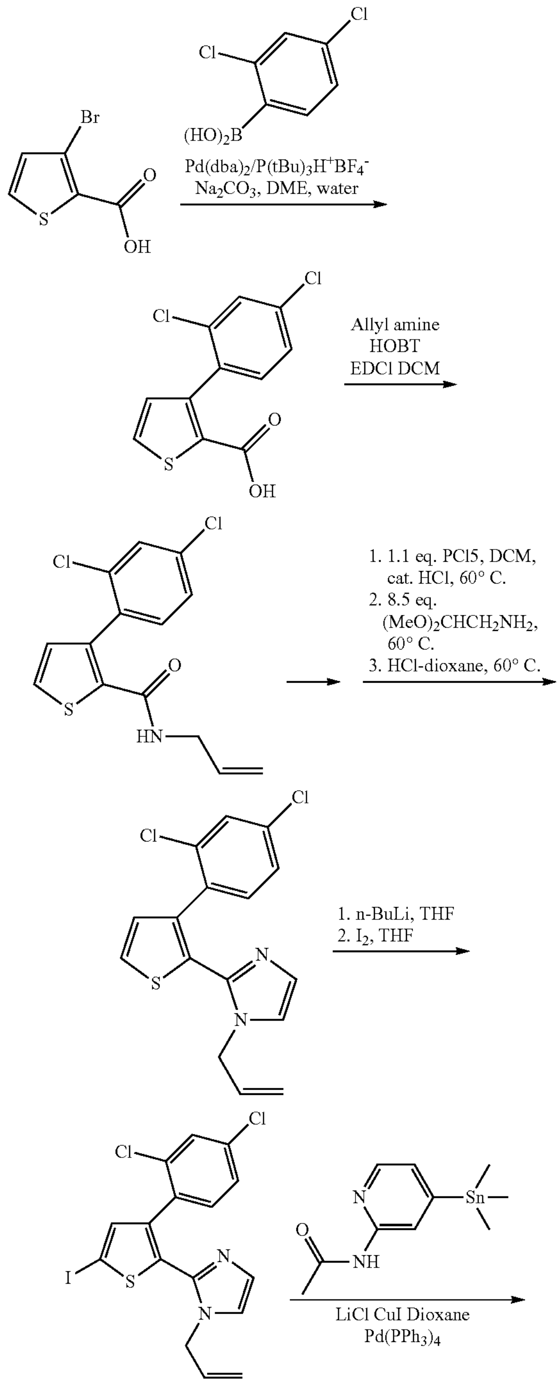

-continued

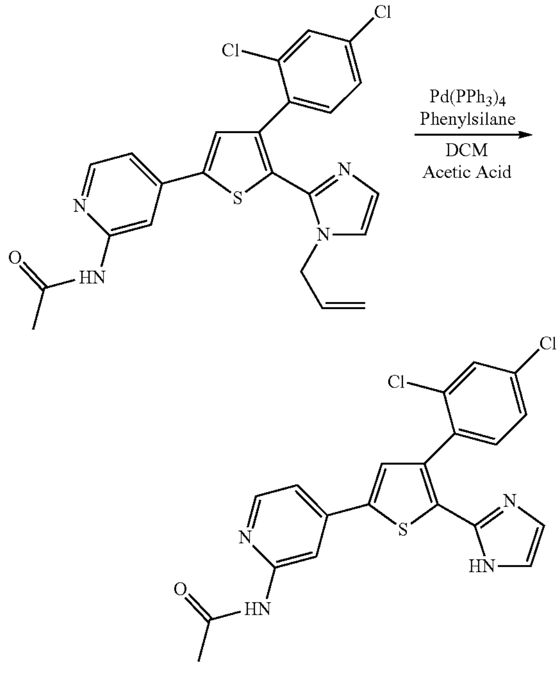

Step 1, Preparation of 3-(2,4-dichlorophenyl)thiophene-2-carboxylic acid

To a solution of tris(dibenzylideneacetone)dipalladium (1.33 g, 1.45 mmol) and tri-tert-butylphosphonium tetrafluoroborate (0.84 g, 2.90 mmol) in 1,2-dimethoxyethane (247 mL) was added water (83.5 mL) then the mixture was sonicated for 10 min under an atmosphere of Argon. To the mixture was added sodium carbonate (18.4 g, 174 mmol), 2,4-dichlorophenylboronic acid (22.1 g, 116 mmol) and 3-bromothiophene-2-carboxylic acid (12.0 g, 58.0 mmol) at room temperature. The resulting mixture was stirred for 30 min at 80° C. After cooling to room temperature, the reaction mixture was filtered through a Celite pad and the solid residue was washed with EtOAc (200 mL) and water (200 mL). The filtrate was evaporated to remove organic solvents and the remaining aqueous solution was basified with 1 N NaOH solution (300 mL) and diluted with water (300 mL). This layer was washed with DCM (3×300 mL). The combined DCM layers were extracted with 0.5 N NaOH (400 mL). All aqueous layers were combined, acidified by addition of conc HCl until pH 1~2 and the resulting suspension was extracted with EtOAc (4×800 mL). The combined organic layers were washed with brine, dried over $Na_2SO_4$, filtered, and concentrated in vacuo. The resulting colored solid was washed with EtOAc and DCM to give 10.2 g of product as an off white solid. The washings were concentrated in vacuo and were subjected to column chromatography ($SiO_2$, elution with 0-15% EtOAc in DCM) to provide additional 3.5 g of product. Solids were combined to give 13.7 g of title compound. (82% yield). LC/MS (FA) ES+ 225. $^1H$ NMR (400 MHz, $d_6$-DMSO) δ: 12.97 (br s, 1H), 7.91 (d, J=5.3 Hz, 1H), 7.68 (d, J=2.2 Hz, 1H), 7.44 (dd, J=2.2, 8.3 Hz, 1H), 7.37 (d, J=8.3 Hz, 1H), 7.10 (d, J=5.3 Hz, 1H).

Step 2, Preparation of N-allyl-3-(2,4-dichlorophenyl)thiophene-2-carboxamide To a stirred solution of 3-(2,4-dichlorophenyl)thiophene-2-carboxylic acid (9.65 g, 35.3 mmol) in DCM (290 mL) was added HOBT (4.77 g, 35.3 mmol) and EDCI (10.8 g, 56.5 mmol) at room temperature and the mixture was stirred for 30 min. To the solution was added 2-propen-1-amine (10.6 mL, 141 mmol) then the resulting mixture was stirred for 5 hrs. The reaction mixture was evaporated and saturated $NH_4Cl$ (200 mL) was added to the residue. The mixture was extracted with EtOAc (200 mL×3). The combined organic layers were washed with brine, dried over $Na_2SO_4$, filtered, and concentrated in vacuo. The residue was purified by column chromatography ($SiO_2$, elution with 20% EtOAc in hexanes) to give 11.3 g of product (2) (91% yield). LC/MS (FA) ES+ 314. $^1H$ NMR (400 MHz, $d_6$-DMSO) δ: 7.96-8.07 (br t, J=5.5 Hz, 1H), 7.75 (d, J=5.0 Hz, 1H), 7.66 (d, J=2.3 Hz, 1H), 7.45 (dd, J=2.3, 8.3 Hz, 1H), 7.36 (d, J=8.3 Hz, 1H), 7.08 (d, J=5.0 Hz, 1H), 5.69-5.80 (m, 1H), 4.98-5.06 (m, 2H), 3.68-3.74 (m, 2H).

Step 3, Preparation of 1-allyl-2-[3-(2,4-dichlorophenyl)-2-thienyl]-1H-imidazole To a solution of N-allyl-3-(2,4-dichlorophenyl)thiophene-2-carboxamide (8.60 g, 27.5 mmol) in DCM (309 mL, 4820 mmol) was added phosphorus pentachloride (6.54 g, 31.4 mmol) and 4 M hydrochloric acid in 1,4-dioxane (0.51 mL, 2.00 mmol) and the mixture was heated to 60° C. for 2 hrs. The reaction was cooled to room temperature and aminoacetaldehyde dimethyl acetal (33.9 mL, 311 mmol) was slowly added. The resulting mixture was heated at 60° C. for 2.5 hrs. To the reaction mixture was added 4 M hydrochloric acid in 1,4-dioxane (200 mL, 783 mmol) and the mixture was stirred at 60° C. overnight. After cooling to room temperature, the suspension was filtered through a Celite pad and the solid residue was washed with 1,4-dioxane. The filtrate was evaporated down and the resulting residue was dissolved in water (300 mL) and extracted with EtOAc (2×150 mL). The water layer was basified by addition of solid $NaHCO_3$ until pH 9, and the aqueous was extracted with EtOAc (3×300 mL). All organics were combined and dried over $Na_2SO_4$, filtered, and concentrated in vacuo. The residue was purified by column chromatography ($SiO_2$, elution with 8-25% EtOAc in DCM) to give crude product which was further purified by column chromatography ($SiO_2$, elution with 45% MeCN: 50% DCM: 5% EtOAc) to provide 7.12 g of product (76%). LC/MS (FA), ES+ 337. NMR (400 MHz, $d_6$ DMSO) δ: 7.80 (d, J=5.3 Hz, 1H), 7.68 (d, J=2.0 Hz, 1H), 7.35 (dd, J=2.0, 8.3 Hz, 1H), 7.26 (d, J=5.3 Hz, 1H), 7.13 (d, J=1.3 Hz, 1H), 7.08 (d, J=8.3 Hz, 1H), 6.98 (d, J=1.3 Hz, 1H), 5.47-5.58 (m, 1H), 4.98-5.02 (m, 1H), 4.75-4.82 (m, 1H), 4.19-4.23 (m, 2H).

Step 4, Preparation of 1-allyl-2-[3-(2,4-dichlorophenyl)-5-iodo-2-thienyl]-1H-imidazole To a solution of 1-allyl-2-[3-(2,4-dichlorophenyl)-2-thienyl]-1H-imidazole (2.50 g, 7.46 mmol) in THF (80.0 mL) cooled to −78° C. was added dropwise 2.50 M of n-butyllithium in hexane (3.28 mL, 8.20 mmol) and the mixture was stirred for 30 min. To the solution was added dropwise a solution of iodine (2.84 g, 11.2 mmol) in THF (10.0 mL) and the resulting solution was stirred for 15 min at −78° C. The reaction mixture was quenched by addition of saturated sodium bisulfite solution (200 mL) and the resulting mixture was warmed to room temperature while stirring for 30 min. The mixture was extracted with EtOAc (3×250 mL) and the combined organic layers were washed with brine (200 mL). The organic layer was dried over $Na_2SO_4$, filtered, and concentrated in vacuo. The residue was purified by column chromatography ($SiO_2$, elution with 1-6% EtOAc in hexane) to give crude product which was further purified by column chromatography ($SiO_2$, elution with 2% MeOH in DCM) to provide 2.57 g of product (71%). LC/MS (FA), ES+ 462. $^1H$ NMR (400 MHz, $d_6$-DMSO) δ: 7.30 (d, J=2.2 Hz, 1H), 7.09 (s, 1H), 6.97 (dd, J=2.2, 8.2 Hz, 1H), 6.75 (d, J=1.3 Hz, 1H), 6.71 (d, J=8.2 Hz, 1H), 6.60 (d, J=1.3 Hz, 1H), 5.10-5.21 (m, 1H), 4.60-4.65 (m, 1H), 4.35-4.41 (m, 1H), 3.80-3.85 (m, 2H).

Step 5, Preparation of N-{4-[5-(1-allyl-1H-imidazol-2-yl)-4-(2,4-dichlorophenyl)-2-thienyl]pyridin-2-yl}acetamide 1-allyl-2-[3-(2,4-dichlorophenyl)-5-iodo-2-thienyl]-1H-imidazole (4) (2.00 g, 4.34 mmol), N-[4-(trimethylstannyl)pyridin-2-yl]acetamide (2.59 g, 8.67 mmol), tetrakis(triphenylphosphine)palladium (0.25 g, 0.22 mmol), CuI (0.25 g, 1.30 mmol), and LiCl (0.55 g, 13.0 mmol) were weighed into a round bottom flask, equipped with reflux condenser, and the flask was purged with Argon. To this mixture was added 1,4-dioxane (100 mL) and the resulting suspension was stirred for 5 hrs at 90° C. The reaction was cooled to room temperature and concentrated in vacuo. To the solid residue was added EtOAc and DCM then the suspension was filtered through a Celite pad. The filtrate was concentrated in vacuo and the residue was purified by column chromatography ($SiO_2$, elution with 45% $CH_3CN$: 50% DCM: 5% MeOH) to give crude product which was further purified by column chromatography ($SiO_2$, elution with 4-7% MeOH in DCM) to provide 1.03 g of product (51%). LC/MS (FA) ES+ 471. $^1H$ NMR (400 MHz, $d_6$-DMSO) δ: 10.6 (s, 1H), 8.39 (s, 1H), 8.36 (d, J=5.3 Hz, 1H), 7.86 (s, 1H), 7.73 (d, J=2.3 Hz, 1H), 7.49 (dd, J=1.8, 5.3 Hz, 1H), 7.42 (dd, J=2.2, 8.3 Hz, 1H), 7.19-7.23 (m, 2H), 7.03 (d, J=1.1 Hz, 1H), 5.54-5.65 (m, 1H), 5.02-5.07 (m, 1H), 4.79-4.86 (m, 1H), 4.28-4.32 (m, 2H), 2.12 (s, 3H).

Step 6, Preparation of N-{4-[4-(2,4-dichlorophenyl)-5-(1H-imidazol-2-yl)-2-thienyl]pyridin-2-yl}acetamide (62-A)

To a solution of N-{4-[5-(1-allyl-1H-imidazol-2-yl)-4-(2,4-dichlorophenyl)-2-thienyl]pyridin-2-yl}acetamide (750 mg, 1.60 mmol) and tetrakis(triphenylphosphine)palladium (92.0 mg, 0.08 mmol) in DCM (12.0 mL) was added acetic acid (3.95 mL, 69.5 mmol) and phenylsilane (1.00 mL, 8.15 mmol) and the mixture was stirred for 24 hrs at 40° C. The reaction mixture was evaporated to remove volatiles and DCM added. To this solution was added saturated $NaHCO_3$ and the resulting mixture was stirred for 30 min. The mixture was extracted with DCM (3×100 mL) and the combined DCM layers were washed with brine. The organics were dried over $Na_2SO_4$, filtered, and concentrated in vacuo. The residue was partially purified by column chromatography ($SiO_2$, elution with 3-6% MeOH in DCM) to give crude product which was further purified by column chromatography ($SiO_2$, elution with 100% EtOAc) to provide 589 mg of the product (84%). LC/MS (FA) ES+ 431. $^1H$ NMR (400 MHz, $d_6$ DMSO) δ: 11.8-11.9 (br s, 1H), 10.6 (s, 1H), 8.39 (s, 1H), 8.32 (d, J=5.2 Hz, 1H), 7.71 (d, J=1.7 Hz, 1H), 7.69 (s, 1H), 7.45-7.49 (m, 2H), 7.42 (d, J=8.5 Hz, 1H), 6.90-7.15 (br s, 2H), 2.12 (s, 3H).

Compounds in the following table were prepared from the appropriate starting materials in a method analogous to that of Example 7-A:

| | |
|---|---|
| 64-A | LCMS: (FA) ES+ 387, 389. |
| 65-A | LCMS: (FA) ES+ 429, 431. |
| 68-A | LCMS: (FA) ES+ 455, 457. |
| 69-A | LCMS: (FA) ES+ 445, 447. |

Example 8-A

Synthesis of 4-[4-(2,4-dichlorophenyl)-5-(1H-imidazol-2-yl)-2-thienyl]-2-methylpyridine (66-A)

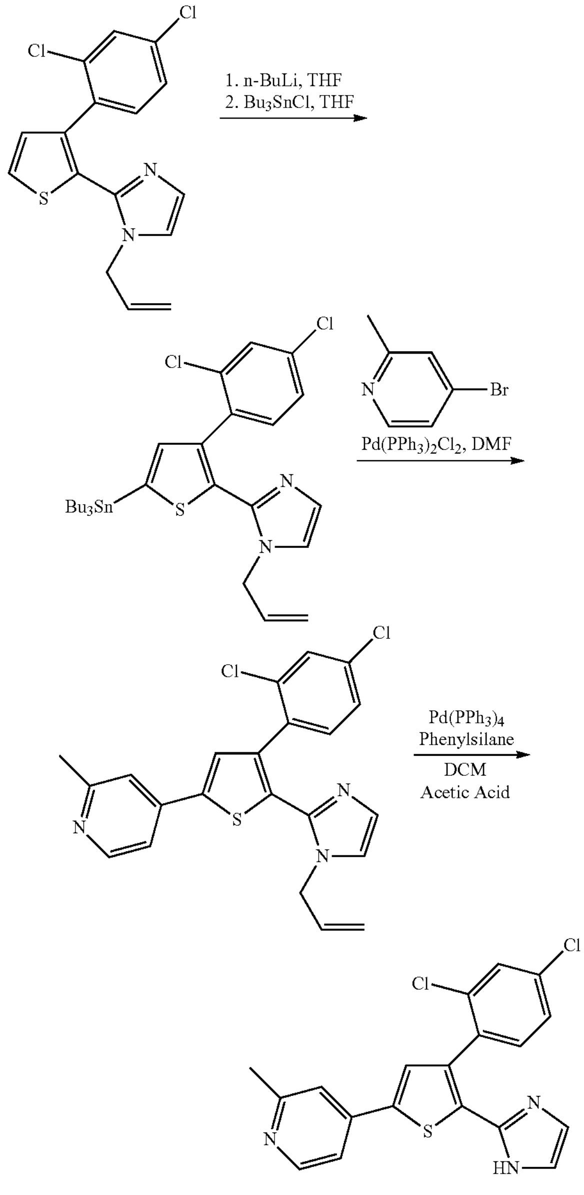

Step 1, Preparation of 1-allyl-2-[3-(2,4-dichlorophenyl)-5-(tributylstannyl)-2-thienyl]-1H-imidazole To a stirred solution of 1-allyl-2-[3-(2,4-dichlorophenyl)-2-thienyl]-1H-imidazole (3.40 g, 10.1 mmol) in THF (80 mL) was added dropwise 2.50 M of n-butyllithium in Hexane (4.46 mL, 11.2 mmol) at −78° C. and the resulting solution was stirred for 30 min. A solution of tributyltin chloride (3.44 mL, 12.7 mmol) in THF (40.0 mL) was added dropwise into the cold solution and then the resulting mixture was stirred for 1 hr at −78° C. The reaction mixture was quenched by addition of water (150 ml) and the resulting mixture was extracted with EtOAc (200 ml×3). The combined organic layers were washed with brine, dried using $Na_2SO_4$, filtered and concentrated in vacuo. The residue was purified by column chromatography ($SiO_2$, elution with 0-20% EtOAc in hexanes) to provide 3.5 g of product as a yellowish oil (71%). LC/MS (FA) ES+ 625. $^1H$ NMR (400 MHz, $d_6$ DMSO) δ: 7.67 (d, J=2.0 Hz, 1H), 7.34 (dd, J=2.0, 8.3 Hz, 1H), 7.24 (t, J=10.5 Hz, 1H), 7.12 (d, J=1.2 Hz, 1H), 7.07 (d, J=8.3 Hz, 1H), 6.97 (d, J=1.2 Hz, 1H), 5.46-5.57 (m, 1H), 4.98 (dd, J=1.5, 10.2 Hz, 1H), 4.79 (dd, J=1.5, 17.1 Hz, 1H), 4.18-4.22 (m, 2H), 1.44-1.68 (m, 6H), 1.25-1.36 (m, 6H), 1.04-1.23 (m, 6H), 0.82-0.89 (m, 9H).

Step 2, Preparation of 4-[5-(1-allyl-1H-imidazol-2-yl)-4-(2,4-dichlorophenyl)-2-thienyl]-2-methylpyridine To a solution of 1-allyl-2-[3-(2,4-dichlorophenyl)-5-(tributylstannyl)-2-thienyl]-1H-imidazole (300 mg, 0.48 mmol) and 4-bromo-2-picoline (68.9 mg, 0.40 mmol) in DMF (10.0 mL) was added bis(triphenylphosphine)palladium dichloride (14.1 mg, 0.02 mmol) under atmosphere of Argon then the mixture was heated at 90° C. for 1 h. After cooling to room temperature, the solvent was evaporated and the residue was purified by column chromatography ($SiO_2$, elution with 3-5% MeOH in, DCM) to give 121 mg of product (67%). LC/MS (AA) ES+ 428. $^1H$ NMR (400 MHz, $d_6$ DMSO) δ: 8.48 (d, J=4.8 Hz, 1H), 7.93 (s, 1H), 7.72 (d, J=2.1 Hz, 1H), 7.60 (br s, 1H), 7.50-7.53 (m, 1H), 7.41 (dd, J=2.1, 8.4 Hz, 1H), 7.18-7.21 (m, 2H), 7.03 (d, J=1.1 Hz, 1H), 5.53-5.64 (m, 1H), 5.04 (dd, J=1.3, 10.3 Hz, 1H), 4.82 (dd, J=1.3, 17.1 Hz, 1H), 4.26-4.31 (m, 2H), 2.51 (s, 3H).

Step 3, Preparation of 4-[4-(2,4-dichlorophenyl)-5-(1H-imidazol-2-yl)-2-thienyl]-2-methylpyridine (66-A)

To a solution of 4-[5-(1-allyl-1H-imidazol-2-yl)-4-(2,4-dichlorophenyl)-2-thienyl]-2-methylpyridine (115 mg, 0.26 mmol) in DCM (10.0 mL) was added phenylsilane (0.16 mL, 1.28 mmol), acetic acid (0.66 mL, 11.5 mmol), and tetrakis (triphenylphosphine)palladium (14.8 mg, 0.01 mmol) at room temperature then the mixture was stirred for 2 h at 40° C. After cooling to room temperature, the solvent was evaporated under reduced pressure and the residual acetic acid was quenched by addition of saturated $NaHCO_3$ (50 mL). The mixture was extracted with DCM (3×70 mL), and the combined DCM layers were dried over $Na_2SO_4$, filtered, and concentrated in vacuo. The residue was purified by column chromatography ($SiO_2$, elution with 3-5% MeOH in DCM) to give crude product which was further purified by column chromatography ($SiO_2$, elution with 100% EtOAc) to provide 51 mg of product (49% yield). LC/MS (FA) ES+ 388. $^1H$ NMR (400 MHz, $d_6$ DMSO) δ: 11.7 (br s, 1H), 8.46 (d, J=5.3 Hz, 1H), 7.76 (s, 1H), 7.72 (d, J=2.1 Hz, 1H), 7.57 (br s, 1H), 7.46-7.50 (m, 2H), 7.41 (d, J=8.3 Hz, 1H), 7.10 (br s, 1H), 6.95 (br s, 1H), 2.49 (s, 3H).

Compounds in the following table were prepared from the appropriate starting materials in a method analogous to that of Example 8-A:

| | |
|---|---|
| 84-A | LCMS: (AA) ES+ 402, 404. |
| 85-A | LCMS: (FA) ES+ 430, 432. |

Example 9-A

Synthesis of N-{4-[3-cyano-4-(2,4-dichlorophenyl)-5-(1H-1,2,3-triazol-5-yl)-2-thienyl]pyridin-2-yl}acetamide (70-A and 73-A)

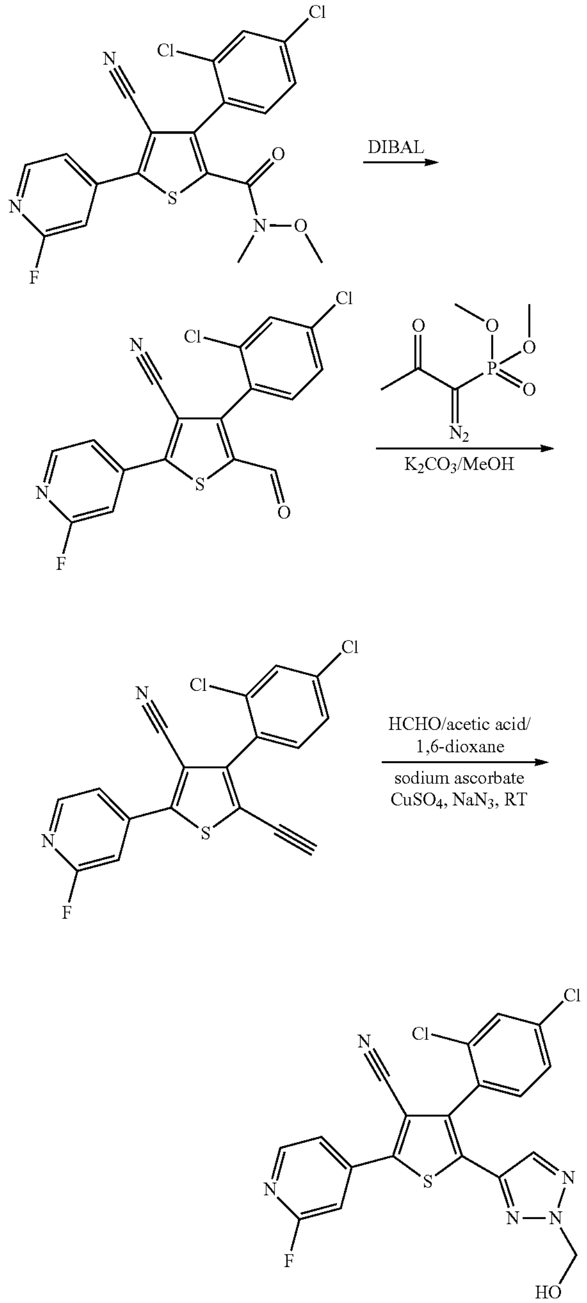

-continued

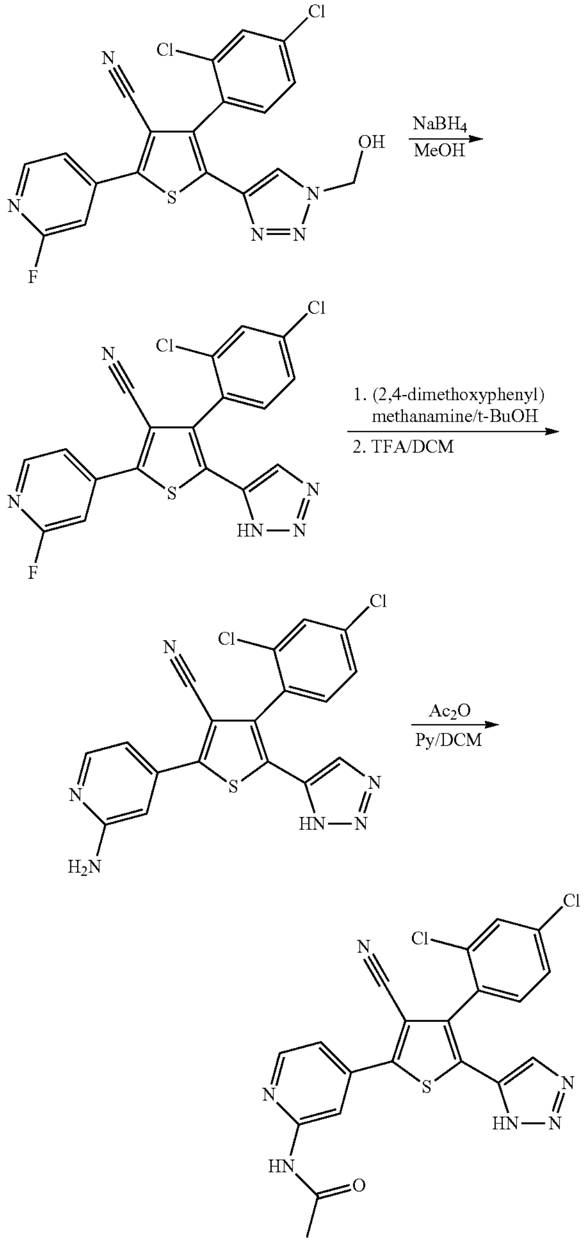

Step 1: Preparation of 4-(2,4-dichlorophenyl)-2-(2-fluoropyridin-4-yl)-5-formylthiophene-3-carbonitrile To a dried flask were added 4-cyano-3-(2,4-dichlorophenyl)-5-(2-fluoropyridin-4-yl)-N-methoxy-N-methylthiophene-2-carboxamide (1.511 g, 3.463 mmol) and Tetrahydrofuran (91 mmol, 91 mmol). The mixture was cooled to −78° C. and Diisobutylaluminum hydride (17.3 mmol, 17.3 mmol) in hexanes was added. The mixture was stirred at the same temperature for 1 h and then raised to at 0° C. for 15 min. The reaction was quenched by ammonium chloride solution and the mixture was extracted with EtOAc. The organic layer was collected and dried. After evaporation, the residue was purified by column chromatography to afford the title compound (0.97 g, 67%). LC/MS (FA) ES+ 377, 379.

Step 2: Preparation of 4-(2,4-dichlorophenyl)-5-ethynyl-2-(2-fluoropyridin-4-yl)thiophene-3-carbonitrile To a stirred solution of 4-(2,4-dichlorophenyl)-2-(2-fluoropyridin-4-yl)-5-formylthiophene-3-carbonitrile (200.0 mg, 0.5302 mmol) in dry MeOH (12 mL, 3.0E2 mmol) was added Potassium carbonate (161 mg, 1.17 mmol) and dimethyl 1-diazo-2-oxopropylphosphonate (132 mg, 0.689 mmol). The mixture was stirred at rt for 2 h. The mixture was quenched by sodium bicarbonate solution and extracted with EtOAc. The organic layer was dried and evaporated. The residue was purified by column chromatography to afford the title compound. LC/MS (A) ES+ 373, 375. $^1$H NMR (400 MHz, $d_1$-chloroform) δ: 8.39 (1H, d, J=5.29 Hz), 7.61 (2H, ddd, J=6.19, 3.83, 1.68 Hz), 7.45-7.31 (3H, m), 3.49 (1H, s)

Step 3 and 4: Preparation of 4-(2,4-dichlorophenyl)-2-(2-fluoropyridin-4-yl)-5-(1H-1,2,3-triazol-5-yl) thiophene-3-carbonitrile A solution of formaldehyde 37% in water (37:63, Formaldehyde:Water, 0.0604 mL, 0.811 mmol), AcOH (0.0069 mL, 0.12 mmol) and 1,4-Dioxane (0.0604 mL, 0.774 mmol) was stirred 15 min before Sodium azide (0.0079 g, 0.12 mmol) was added, followed by 4-(2,4-dichlorophenyl)-5-ethynyl-2-(2-fluoropyridin-4-yl)thiophene-3-carbonitrile (0.030 g, 0.080 mmol). The mixture was stirred for another 10 min. Sodium ascorbate (0.0032 g, 0.016 mmol) was added and then followed by Copper(II) sulfate (0.00064 g, 0.0040 mmol). The mixture was stirred overnight. The mixture was diluted with water and extracted with EtOAc. The organic layer was dried and evaporated to afford a crude intermediate which was purified by column chromatography to afford a mixture of 2 isomers.

To the above intermediate in MeOH (1.0 mL, 25 mmol) was added Sodium tetrahydroborate (3.04 mg, 0.0804 mmol) and the mixture was stirred at rt for 4 h. The solvent was removed and the residue was dissolved in water (0.5 ml) and 1NHCl (0.5 ml). The precipitate was collected and dried in air to afford the title compound (33 mg, 89%). LC/MS (FA) ES+ 416, 418. $^1$H NMR (400 MHz, $d_4$-methanol) δ: 8.40 (1H, d, J=5.33 Hz), 7.79 (2H, m), 7.57 (2H, m), 7.50 (1H, d, J=8.26 Hz), 7.11 (1H, s)

Step 5: Preparation of 2-(2-aminopyridin-4-yl)-4-(2,4-dichlorophenyl)-5-(1H-1,2,3-triazol-5-yl) thiophene-3-carbonitrile (70-A)

A solution of 4-(2,4-dichlorophenyl)-2-(2-fluoropyridin-4-yl)-5-(1H-1,2,3-triazol-5-yl)thiophene-3-carbonitrile (0.103 g, 0.247 mmol), 2,4-dimethoxybenzylamine (0.247 g, 1.48 mmol) and DIPEA (0.0959 g, 0.742 mmol) in 1-Butanol (15 g, 2.0E2 mmol) was irradiated in microwave at 170° C. for 2 hrs. The mixture was concentrated and the residue was purified by column chromatography to afford desired intermediate. LC/MS (FA) ES+ 563, 565. To the intermediate in DCM (5.9 mL, 93 mmol) was added TFA (2 mL, 20 mmol) and the mixture was stirred for 10 min. The reaction mixture was concentrated and the residue in MeOH was treated with sodium bicarbonate and water. The mixture was concentrated and the mixture was purified by column chromatography to afford the title compound (48 mg, 47.0%). LC/MS (FA) ES+ 413, 415. $^1$H NMR (400 MHz, $d_4$-methanol) δ: 8.03 (1H, d, J=6.26 Hz), 7.74 (1H, d, J=1.93 Hz), 7.54 (1H, dd, J=8.27, 1.97 Hz), 7.46 (1H, d, J=8.26 Hz), 7.05 (1H, s), 7.01 (2H, m)

Step 6: Preparation of N-{4-[3-cyano-4-(2,4-dichlorophenyl)-5-(1H-1,2,3-triazol-5-yl)-2-thienyl]pyridin-2-yl}acetamide (73-A)

To a solution of 2-(2-aminopyridin-4-yl)-4-(2,4-dichlorophenyl)-5-(1H-1,2,3-triazol-5-yl)thiophene-3-carbonitrile (0.048 g, 0.12 mmol) in DCM (4 mL, 60 mmol) was added Pyridine (0.470 mL, 5.81 mmol) and Acetic anhydride (329 uL, 3.48 mmol) and the mixture was stirred at rt overnight. The mixture was concentrated and the residue was dissolved in MeOH (2.0 mL, 49 mmol) and Water (0.3 mL, 20 mmol). Sodium bicarbonate (0.5 g, 6 mmol) was added to the above mixture. The mixture was stirred at rt for 30 min. The reaction mixture was concentrated and the residue was dissolved in EtOAc and MeOH. The solid was filtered out. The organic solution was evaporated to dryness, purified by column chromatography and then further by HPLC to afford pure title compound (27 mg, 52%). LC/MS (FA) ES+ 455, 457; ES− 453, 455. $^1$H-NMR (400 MHz, DMSO-$d_6$) δ: 8.59 (1H, d, J=0.75 Hz), 8.51 (1H, d, J=5.29 Hz), 7.93 (1H, d, J=1.09 Hz), 7.54 (1H, dd, J=5.25, 1.76 Hz), 7.23 (1H, s), 7.64 (2H, d, J=1.92 Hz), 10.80 (1H, s), 2.13 (3H, s), 2.07 (1H, s)

Example 10-A

Synthesis of N-(4-{3-cyano-4-(2,4-dichlorophenyl)-5-[1-(4-fluorobenzyl)-1H-imidazol-2-yl]-2-thienyl}pyridin-2-yl)acetamide (72-A)

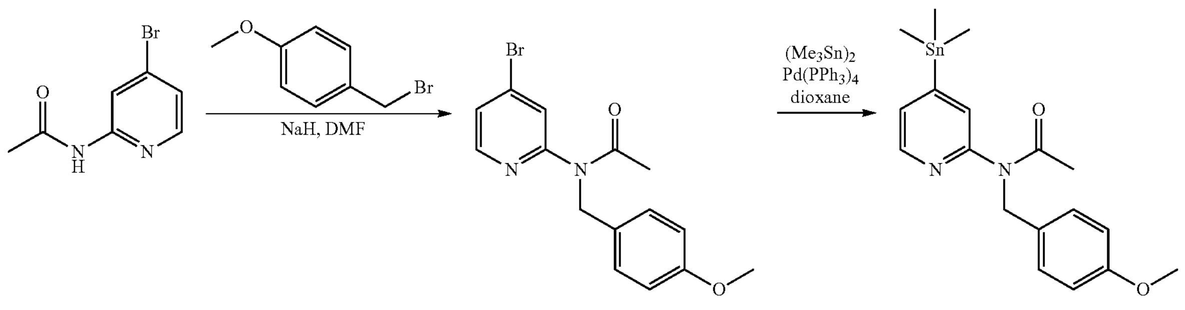

-continued

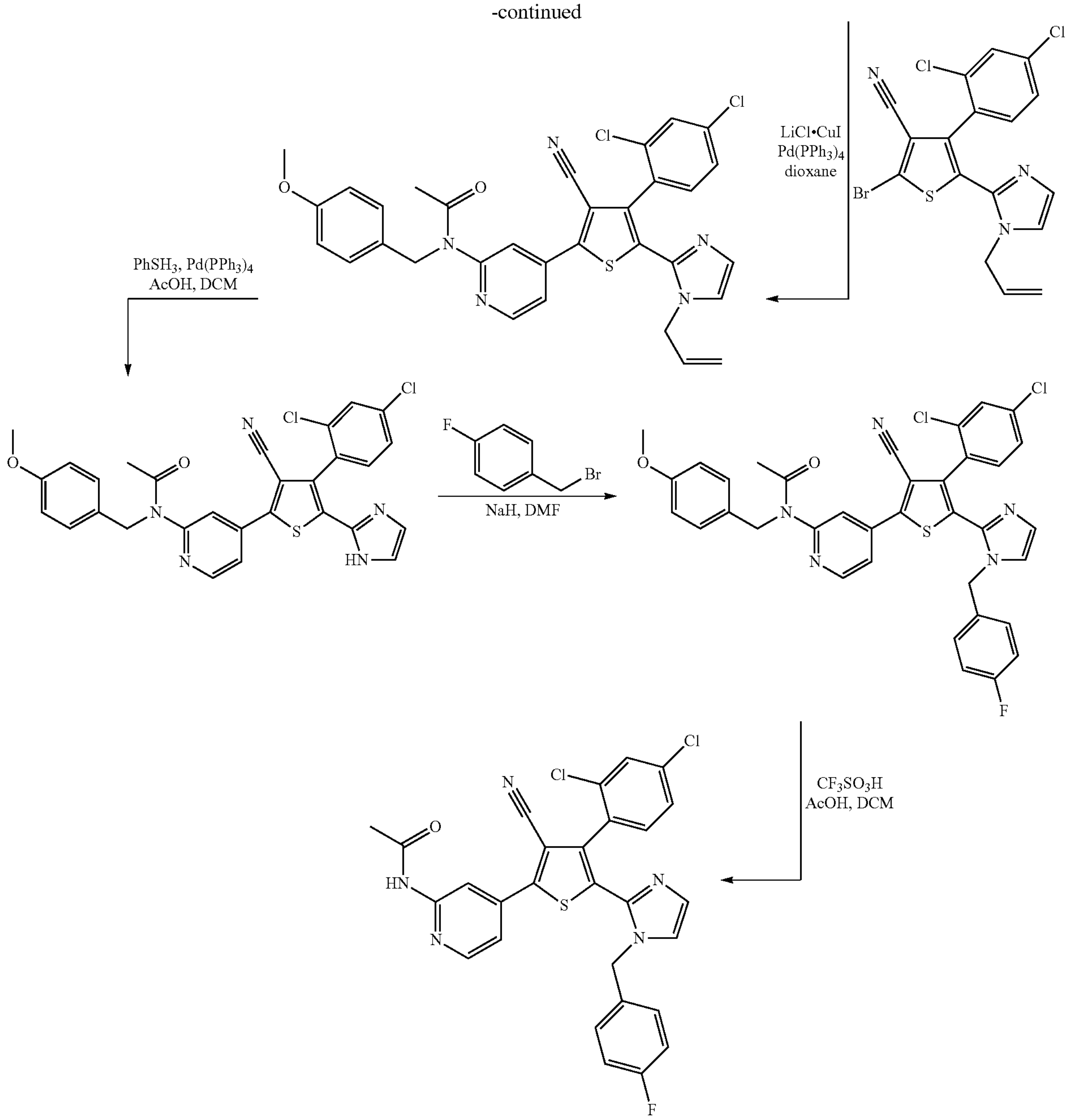

Step 1: N-(4-bromopyridin-2-yl)-N-(4-methoxybenzyl)acetamide

To a 20 mL vial charged with Sodium hydride (0.196 g, 7.76 mmol) was added dry N,N-Dimethylformamide (5.0 mL, 64 mmol), cooled with ice bath. N-(4-bromopyridin-2-yl)acetamide (1.50 g, 7.00 mmol) was added portionwise in ~3 min. The suspension was stirred at the same temperature for 15 min and turned into a clear solution. 4-methoxybenzyl bromide (1.55 g, 7.70 mmol) was added dropwise with a syringe and rinsed down with dry N,N-Dimethylformamide (2.0 mL, 26 mmol). The mixture was stirred at r.t. for 17 hours. The mixture was poured into ice chilled saturated $NaHCO_3$ (80 mL), extracted with EtOAc (2×100 mL), washed with water, brine, dried over anhydrous $Na_2SO_4$, filtered, evaporated in rotavpor to give a crude. Chromatograph using EtOAc/hexane (1/9 to 7/3) gave an oily product (1.80 g, yield 76.7%). LCMS: (AA) $ES^+$, 335, 337. $^1H$ NMR (400 MHz, $d_1$-chloroform) δ: 8.28-8.30 (d, J=5.27 Hz, 1H), 7.43 (s, 1H), 7.31-7.33 (dd, J=5.52, 1.51 Hz, 1H), 7.13-7.15 (d, J=8.78 Hz, 2H), 6.80-6.82 (d, J=8.78 Hz, 2H), 5.05 (s, 2H), 3.77 (s, 3H), 2.12 (s, 3H).

Step 2: N-(4-methoxybenzyl)-N-[4-(trimethylstannyl)pyridin-2-yl]acetamide

The mixture of N-(4-bromopyridin-2-yl)-N-(4-methoxybenzyl)acetamide (1.79 g, 5.34 mmol), Hexamethylditin (2.10 g, 6.41 mmol) and Tetrakis(triphenylphosphine)palladium(0) (0.308 g, 0.267 mmol) in dry 1,4-Dioxane (45 mL, 580 mmol) was heated to 95° C. (heating block) under $N_2$ for 3 hours. The mixture was evaporated in rotavapor and the residue was purified in a silica column using EtOAc/hexane (1/9 to 5/5) to give an oily product (1.82 g, 81.3%). LCMS:

(AA) $ES^+$, 417, 419, 421. $^1H$ NMR (400 MHz, $d_1$-chloroform) δ: 8.40-8.41 (d, J=5.52 Hz, 1H), 7.21-7.32 (m, 1H), 7.13-7.15 (d, J=8.78 Hz, 2H), 6.99-7.02 (m, 1H), 6.77-6.80 (d, J=8.78 Hz, 2H), 4.98 (s, 2H), 3.76 (s, 3H), 2.01 (s, 3H), 0.21-0.36 (m, 9H).

Step 3: N-{4-[5-(1-allyl-1H-imidazol-2-yl)-3-cyano-4-(2,4-dichlorophenyl)-2-thienyl]pyridin-2-yl}-N-(4-methoxybenzyl)acetamide The mixture of 5-(1-allyl-1H-imidazol-2-yl)-2-bromo-4-(2,4-dichlorophenyl)thiophene-3-carbonitrile (0.840 g, 1.91 mmol), N-(4-methoxybenzyl)-N-[4-(trimethylstannyl)pyridin-2-yl]acetamide (0.992 g, 2.37 mmol) Lithium chloride (0.232 g, 5.46 mmol), Copper(I) iodide (0.104 g, 0.546 mmol) and Tetrakis(triphenylphosphine)palladium(0) (0.210 g, 0.182 mmol) in dry 1,4-Dioxane (50 mL, 600 mmol) was heated under $N_2$ to reflux for 1 hour. The mixture was cooled to r.t., evaporated in rotavapor. The residue was quenched with aqueous saturated $NaHCO_3$, extracted with DCM (2×150 mL), washed with water, brine, dried over $Na_2SO_4$, filtered, evaporated in rotavapor to give a brown solid. The solid was heated in EtOAc/DCM (50 mL/15 mL) to reflux for 15 min, cooled to r.t., filtered and washed with small amount of EtOAc. The filtrate was purified on a silica column using hexane as solvent A and hexane:concentrated aqueous $NH_4OH$:MeOH:DCM (67%:0.5%:10.5%:22%) as solvent B (A/B from 100/0 to 0/100 in 5 min then 100% B for 10 min) to give a solid product (1.32 g, 75% pure by LCMS, yield 84.2%). LCMS: (AA) $ES^+$, 614, 616. The product was used for next step without further purification.

Step 4: N-{4-[3-cyano-4-(2,4-dichlorophenyl)-5-(1H-imidazol-2-yl)-2-thienyl]pyridin-2-yl}-N-(4-methoxybenzyl)acetamide To the solution of N-{4-[5-(1-allyl-1H-imidazol-2-yl)-3-cyano-4-(2,4-dichlorophenyl)-2-thienyl]pyridin-2-yl}-N-(4-methoxybenzyl)acetamide (1.32 g, 1.61 mmol) and Tetrakis (triphenylphosphine)palladium(0) (93.1 mg, 0.0805 mmol) in Acetic acid (15 mL, 260 mmol) and Methylene chloride (30 mL, 500 mmol) under $N_2$ atmosphere was added dropwise PHENYLSILANE (1.10 mL, 8.92 mmol). The mixture was stirred at 40° C. for 2 hours. The solvent was removed in rotavapor then the residue was dried in high vacuum to give a residue. The residue was chromatographed in silica column using 7N $NH_3$-MeOH/DCM (1/99, ~1 L), then EtOAc/DCM (30/70 to 60/40) to give an impure product. The second chromatograph using EtOAc/DCM (30/70 to 80/20) gave a pure product (0.469 g, yield 50.7%). LCMS: (AA) $ES^+$, 574, 576; $ES^-$, 572, 574. $^1H$ NMR (400 MHz, $d_1$-chloroform) δ: 8.60-8.62 (d, J=5.27 Hz, 1H), 7.71 (d, J=2.00 Hz, 1H), 7.63 (s, br, 1H), 7.55-7.57 (dd, J=5.27, 1.76 Hz, 1H), 7.50-7.52 (dd, J=8.28, 2.01 Hz, 1H), 7.40-7.42 (d, J=8.28 Hz, 1H), 7.18-7.20 (d, J=8.78 Hz, 2H), 7.07 (m, 2H), 6.80-6.82 (d, J=8.78 Hz, 2H), 5.14 (s, 2H), 3.76 (s, 3H), 2.19 (s, 3H).

Step 5: N-(4-{3-cyano-4-(2,4-dichlorophenyl)-5-[1-(4-fluorobenzyl)-1H-imidazol-2-yl]-2-thienyl}pyridin-2-yl)-N-(4-methoxybenzyl)acetamide To the solution of N-{4-[3-cyano-4-(2,4-dichlorophenyl)-5-(1H-imidazol-2-yl)-2-thienyl]pyridin-2-yl}-N-(4-methoxybenzyl)acetamide (60.0 mg, 0.104 mmol) in dry N,N-Dimethylformamide (5.0 mL, 64 mmol) was added Sodium hydride (3.96 mg, 0.157 mmol). The resulted red-brown solution was stirred at r.t. for 10 min. 4-Fluorobenzylbromide (32.6 mg, 0.172 mmol) was added and the mixture was stirred at r.t. for 2 hours. The mixture was quenched with aqueous saturated $NaHCO_3$ (10 mL), diluted with water, extracted with DCM (4×25 mL), washed with water, brine, dried over $Na_2SO_4$, filtered, rotovaped to give a crude residue. Chromatograph in silica column using DCM/EtOAc (30/70 to 0/100) afforded a solid product (0.055 g, yield 77.1%). LCMS: (AA) $ES^+$, 682, 684. $^1H$ NMR (400 MHz, $d_1$-chloroform) δ: 8.60-8.62 (d, J=5.02 Hz, 1H), 7.63 (s, br, 1H), 7.51-7.53 (m, 1H), 7.34 (m, 1H), 7.14-7.26 (m, 5H), 6.92-6.97 (m, 2H), 6.80-6.86 (m, 3H), 6.70-6.73 (m, 2H), 5.14 (m, 2H), 4.71-4.84 (m, 2H), 3.76 (s, 3H), 2.19 (s, 3H).

Step 6: N-(4-{3-cyano-4-(2,4-dichlorophenyl)-5-[1-(4-fluorobenzyl)-1H-imidazol-2-yl]-2-thienyl}pyridin-2-yl)acetamide (72-A)

To the solution of [A] N-(4-{3-cyano-4-(2,4-dichlorophenyl)-5-[1-(4-fluorobenzyl)-1H-imidazol-2-yl]-2-thienyl}pyridin-2-yl)-N-(4-methoxybenzyl)acetamide (55.0 mg, 0.0806 mmol) in Acetic acid (1.0 mL, 18 mmol) was added Trifluoromethanesulfonic acid (0.10 mL, 1.1 mmol) and the mixture was stirred at r.t. for 20 hours. Methylene chloride (2.0 mL, 31 mmol) and Trifluoromethanesulfonic acid (0.10 mL, 1.1 mmol) were added and the mixture was stirred at r.t. for 20 hours. The mixture was rotovaped and azeotropped with toluene twice, dried in high vacuum. The residue was neutralized with aqueous saturated $NaHCO_3$ to pH~8, extracted with EtOAc. The EtOAc solution was dried over $Na_2SO_4$, filtered, evaporated in rotavapor to give a crude residue. Chromatograph in a silica column using MeOH/DCM (0/100 to 2/98) afforded a solid product. The product was dissolved in small amount of acetonitrile and ~5 mL water, frozen in dry ice and lyophilized to give a powder product (20 mg, yield 44.1%). LCMS: (AA) $ES^+$, 562, 564; $FS^-$, 560, 562. $^1H$ NMR (400 MHz, $d_1$-methanol) δ: 8.62 (s, 1H), 8.47-8.48 (d, J=5.27 Hz, 1H), 7.53-7.55 (dd, J=5.27, 1.76 Hz, 1H), 7.47 (d, J=2.01 Hz, 1H), 7.33-7.36 (dd, J=8.28, 2.01 Hz, 1H), 7.26-7.27 (d, J=8.28 Hz, 1H), 7.16-7.19 (dd, J=7.28, 1.51 Hz, 2H), 6.98-7.02 (m, 2H), 6.83-6.86 (m, 2H), 4.98 (s, 2H), 2.21 (s, 3H).

Compounds in the following table were prepared from the appropriate starting materials in a method analogous to that of Example 10-A:

| | |
|---|---|
| 67-A | LCMS: (AA) ES+ 468, 470. |
| 71-A | LCMS: (AA) ES+ 545, 547. |
| 78-A | LCMS: (AA) ES+ 545, 547. |

Example 11-A

Synthesis of N-{4-[5-(5-bromo-4H-1,2,4-triazol-3-yl)-3-cyano-4-(2,4-dichlorophenyl)-2-thienyl]pyridin-2-yl}acetamide (74-A)

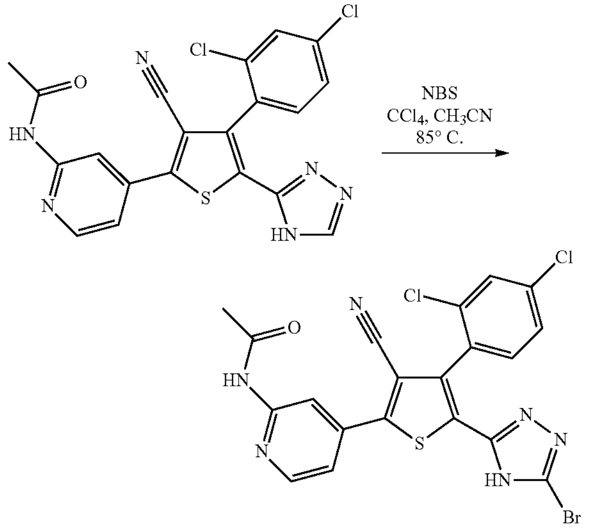

A suspension of N-(4-(3-cyano-4-(2,4-dichlorophenyl)-5-(4H-1,2,4-triazol-3-yl)thiophen-2-yl)pyridin-2-yl)acetamide (0.0700 g, 0.154 mmol) and N-Bromosuccinimide (33.1 mg, 0.186 mmol) in Carbon tetrachloride (2.5 mL, 26 mmol) was heated to 85° C. in a capped vial for 2.5 hours. To the suspension was added dry Acetonitrile (6.0 mL, 110 mmol) and the mixture was heated at 85° C. (turned into a clear solution) for additional 2 hours. The mixture was cooled to r.t., evaporated in rotavapor. The residue was dry loaded in a silica column and eluted with MeOH/DCM (0/100 to 5/95) to give a solid product (66.0 mg, yield 80.4%). LCMS: (FA) $ES^+$, 533, 535, 537 and $ES^-$ 531, 533, 535. $^1H$ NMR (400 MHz, $d_1$-chloroform) δ: 8.65 (s, 1H), 8.42 (d, J=5.02 Hz, 1H), 8.26 (s, 1H), 7.61 (d, J=2.01 Hz, 1H), 7.56 (dd, J=5.27, 1.76 Hz, 1H), 7.43-7.45 (dd, J=8.28, 2.01 Hz, 1H), 7.37-7.39 (d, J=8.28 Hz, 1H), 2.26 (s, 3H).

Example 12-A

Synthesis of N-(4-(3-cyano-4-(2,4-dichlorophenyl)-5-(1H-pyrazol-5-yl)thiophen-2-yl)pyridin-2-yl)acetamide (76-A)

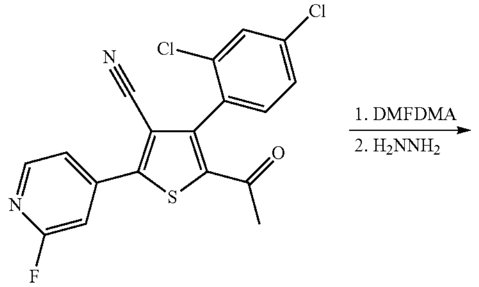

-continued

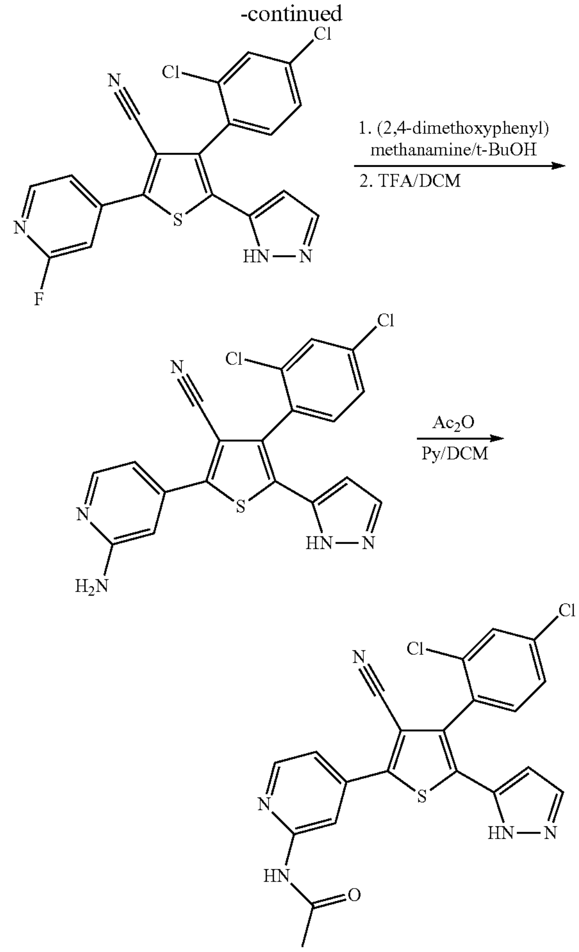

Step 1: Preparation of 4-(2,4-dichlorophenyl)-2-(2-fluoropyridin-4-yl)-5-(1H-pyrazol-5-yl)thiophene-3-carbonitrile A solution of [A] 5-acetyl-4-(2,4-dichlorophenyl)-2-(2-fluoropyridin-4-yl)thiophene-3-carbonitrile (0.407 g, 1.04 mmol) in 1,1-Dimethoxy-N,N-dimethylmethanamine (5.53 mL, 41.6 mmol) was irradiated in microwave at 120° C. for 20 min. The solvent was removed and the residue was taken up by AcOH (21 mL, 370 mmol). Hydrazine hydrate (3 mL, 60 mmol) was added the above mixture and then heated at 90° C. for 10 min. The mixture was concentrated and the residue was suspended in water. The precipitated was collected and dried in air to afford the title compound as a yellow powder (0.34 g, 79%). LC/MS (FA) ES+ 415, 417. $^1H$ NMR (400 MHz, $d_4$-methanol) δ: 8.45 (1H, d, J=5.33 Hz), 7.85 (1H, td, J=5.32, 1.57, 1.57 Hz), 7.80 (1H, d, J=1.99 Hz), 7.54 (1H, d, J=8.24 Hz), 7.60 (1H, dd, J=8.27, 2.04 Hz), 7.63 (2H, d, J=2.47 Hz), 5.69 (1H, d, J=2.44 Hz)

Step 2: Preparation of 2-(2-aminopyridin-4-yl)-4-(2,4-dichlorophenyl)-5-(1H-pyrazol-5-yl)thiophene-3-carbonitrile (79-A)

4-(2,4-dichlorophenyl)-2-(2-fluoropyridin-4-yl)-5-(1H-pyrazol-5-yl)thiophene-3-carbonitrile (0.372 g, 0.903 mmol), 2,4-dimethoxybenzylamine (821 mg, 4.91 mmol) and DIPEA (317 mg, 2.46 mmol) in 1-Butanol (3.74 mL, 40.9 mmol) was irradiated in microwave at 160° C. for 2 hr under nitrogen. The solvent was evaporated and the residue was purified by column chromatography to afford an intermediate which was in the next step. LC/MS (FA) ES+ 562, 564. The above intermediate was dissolved in DCM (26 mL, 4.0E2 mmol) and TFA (8.5 mL, 110 mmol). The mixture was stirred at rt for 30 min. The mixture was concentrated and the residue was basified by ammonium hydroxide. The solvent was evaporated and the mixture was purified by column chromatography to afford the title compound (0.375 g, 100%). LC/MS (FA) ES+ 412, 414. $^1$H NMR (400 MHz, $d_4$-methanol) δ: 8.00 (1H, d, J=6.62 Hz), 7.77 (1H, d, J=2.01 Hz), 7.59 (1H, d, J=2.45 Hz), 7.56 (1H, dd, J=8.26, 2.02 Hz), 7.49 (1H, d, J=8.27 Hz), 7.38 (1H, d, J=1.59 Hz), 7.24 (1H, dd, J=6.64, 1.77 Hz), 5.58 (1H, d, J=2.38 Hz)

Step 3: Preparation of N-(4-(3-cyano-4-(2,4-dichlorophenyl)-5-(1H-pyrazol-5-yl)thiophen-2-yl)pyridin-2-yl)acetamide (76-A)

To a mixture of 2-(2-aminopyridin-4-yl)-4-(2,4-dichlorophenyl)-5-(1H-pyrazol-5-yl)thiophene-3-carbonitrile (0.10 g, 0.12 mmol) and Pyridine (0.3923 mL, 4.851 mmol) in DCM (0.2 mL, 3 mmol) was added Acetic anhydride (0.114 mL, 1.21 mmol) at 0° C. The ice bath was removed after 2 h and stirring was continued at rt overnight. The solvent was evaporated and the residue was stirred in MeOH (5 mL, 100 mmol) and Water (1 g, 60 mmol) containing Sodium bicarbonate (0.6112 g, 7.276 mmol). The mixture was concentrated and the residue was collected with EtOAc. The mixture was washed with brine and dried. The solvent was evaporated and the residue was purified by column chromatography to afford the title compound (0.024 g, 41%). LC/MS (FA) ES+ 454, 456. $^1$H NMR (400 MHz, DMSO-$d_6$) δ: 13.28 (1H, s), 10.78 (1H, s), 8.58 (1H, s), 8.50 (1H, dd, J=5.27, 0.63 Hz), 7.93 (1H, d, J=1.71 Hz), 7.71 (1H, d, J=2.37 Hz), 7.63 (2H, dd, J=5.25, 1.77 Hz), 7.53 (1H, dd, J=5.25, 1.77 Hz), 5.49 (1H, d, J=2.38 Hz), 2.13 (3H, s)

Compounds in the following table were prepared from the appropriate starting materials in a method analogous to that of Example 12-A:

| | |
|---|---|
| 81-A | LCMS: (FA) ES+ 480, 482. |
| 82-A | LCMS: (FA) ES+ 455, 457. |
| 83-A | LCMS: (FA) ES+ 469, 471. |

Example 13-A

Synthesis of N-(4-(3-cyano-4-(2,4-dichlorophenyl)-5-(1H-imidazol-5-yl)thiophen-2-yl)pyridin-2-yl)acetamide (77-A)

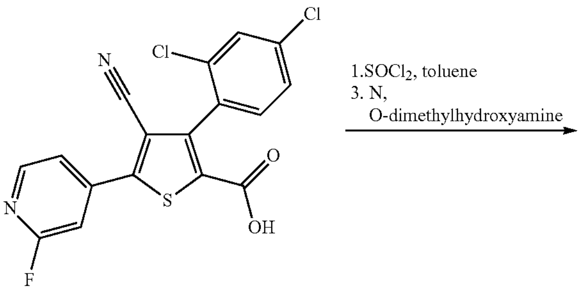

-continued

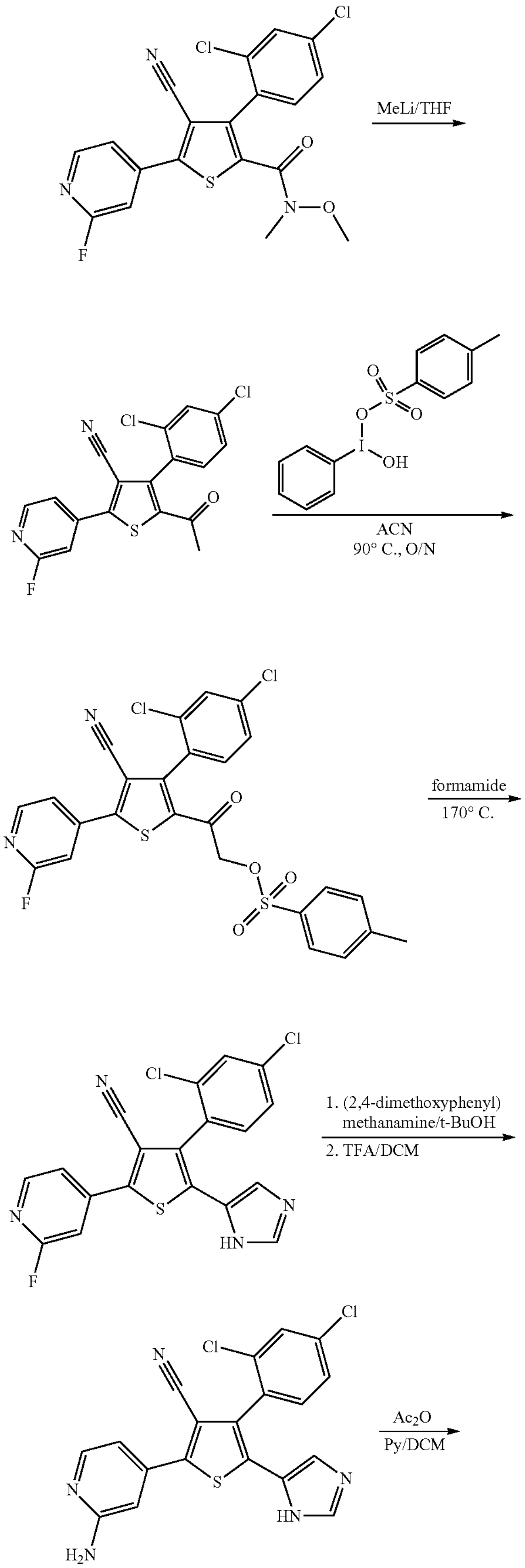

-continued

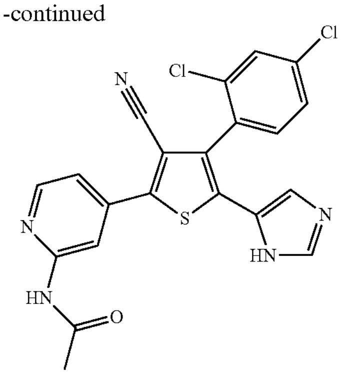

Step 1: Preparation of 4-cyano-3-(2,4-dichlorophenyl)-5-(2-fluoropyridin-4-yl)-N-methoxy-N-methylthiophene-2-carboxamide Thionyl chloride (6.2 mL, 85 mmol) was added to a mixture of 4-cyano-3-(2,4-dichlorophenyl)-5-(2-fluoropyridin-4-yl)thiophene-2-carboxylic acid (2.94 g, 7.48 mmol) in Toluene (22 mL, 210 mmol) and the mixture was heated at 90° C. for 1 h. The reaction mixture was evaporated and the residue was coevaporated with toluene twice to thick oil. This oil in DCM (20 g, 200 mmol) was added to a mixture of N,O-Dimethylhydroxylamine Hydrochloride (2.92 g, 29.9 mmol) and TEA (7.0 mL, 5.0E1 mmol) in DCM (100 mL, 2000 mmol) in a ice bath. After 2 h, the mixture was washed by water and brine. The DCM layer was collected and dried and evaporated in vacuum to afford crude intermediate, which was purified by column chromatography to afford the title compound (2.41 g, 73.9%). LCMS: (FA) $ES^+$, 436, 438. $^1H$ NMR (400 MHz, $d_1$-chloroform) δ: 8.41 (1H, d, J=5.26 Hz), 7.72-7.63 (1H, m), 7.54 (1H, d, J=1.96 Hz), 7.39 (2H, dd, J=7.70, 1.99 Hz), 7.29 (1H, d, J=8.26 Hz), 3.76 (3H, s), 3.27 (3H, s)

Step 2: Preparation of 5-acetyl-4-(2,4-dichlorophenyl)-2-(2-fluoropyridin-4-yl)thiophene-3-carbonitrile To a flame dried flask were placed 4-cyano-3-(2,4-dichlorophenyl)-5-(2-fluoropyridin-4-yl)-N-methoxy-N-methylthiophene-2-carboxamide (1.45 g, 3.32 mmol) and tetrahydrofuran (90 mL, 1000 mmol) under argon. The solution was cooled to −78° C. and Methyllithium (4.653 mmol, 4.653 mmol) in diethylether (1.6M) solution was added. After addition, the mixture was kept at this temperature for 30 min. The mixture was quenched by ammonium chloride solution. The mixture was extracted with EtOAc and the organic layer was collected and dried over $Na_2SO_4$. The solvent was evaporated and the residue was purified using column chromatography. The title compound was collected as a white solid (0.93 g, 71.5%). LCMS: (FA) $ES^+$ 391, 393. $^1H$ NMR (400 MHz, $d_1$-chloroform) δ: 8.43 (1H, d, J=5.28 Hz), 7.67-7.62 (2H, m), 7.48 (1H, dd, J=8.24, 2.01 Hz), 7.38 (1H, s), 7.35 (1H, d, J=8.24 Hz), 2.13 (3H, s)

Step 3: Preparation of 2-(4-cyano-3-(2,4-dichlorophenyl)-5-(2-fluoropyridin-4-yl)thiophen-2-yl)-2-oxoethyl 4-methylbenzenesulfonate A mixture of 5-acetyl-4-(2,4-dichlorophenyl)-2-(2-fluoropyridin-4-yl)thiophene-3-carbonitrile (0.48 g, 1.2 mmol) and [hydroxy(tosyloxy)iodo]benzene (0.819 g, 2.09 mmol) in ACN (20 mL, 400 mmol) was heated at 90° C. overnight. The mixture was cooled down to rt. The solvent was evaporated and the residue was purified by column chromatography to afford the title compound (0.31 g, 45%). NMR (300 MHz, $d_1$-chloroform) δ: 8.44 (1H, d, J=5.27 Hz), 7.69 (2H, d, J=8.34 Hz), 7.62 (2H, ddd, J=6.91, 3.43, 1.72 Hz), 7.47 (1H, dd, J=8.25, 2.02 Hz), 7.39-7.33 (3H, m), 7.30 (1H, d J=5.79), 4.47 (2H, s), 2.47 (3H, s)

Step 4: Preparation of 4-(2,4-dichlorophenyl)-2-(2-fluoropyridin-4-yl)-5-(1H-imidazol-5-yl)thiophene-3-carbonitrile 2-(4-cyano-3-(2,4-dichlorophenyl)-5-(2-fluoropyridin-4-yl)thiophen-2-yl)-2-oxoethyl 4-methylbenzenesulfonate (0.42 g, 0.75 mmol) in Formamide (140 mL, 3510 mmol) was heated to a true solution and then irradiated at 170° C. for 1 h. The reaction mixture was concentrated to remove part of solvent and the residue was partitioned between water and EtOAc. The organic layer was separated and washed with brine and then dried. After the solvent was evaporated, the residue was purified by column chromatography to give the title compound slightly impure (95 mg, 30.5%). LCMS: (FA) $ES^+$ 415, 417

Step 5: Preparation of 2-(2-aminopyridin-4-yl)-4-(2,4-dichlorophenyl)-5-(1H-imidazol-5-yl)thiophene-3-carbonitrile (80-A)

A mixture of 4-(2,4-dichlorophenyl)-2-(2-fluoropyridin-4-yl)-5-(1H-imidazol-5-yl)thiophene-3-carbonitrile (45.0 mg, 0.108 mmol), 2,4-dimethoxybenzylamine (145 mg, 0.867 mmol) and DIPEA (42.0 mg, 0.325 mmol) in 1-Butanol (4.2 mL, 46 mmol) was irradiated in microwave at 160° C. for 3 hrs. The solvent was removed by evaporation, the residue was purified by column chromatography to the desired intermediate with minor impurities. LC/MS (FA) ES+ 562, 564; ES− 560-562.

To the above intermediate in DCM (1.3 mL, 21 mmol) was added TFA (0.48 mL, 6.2 mmol) at rt. The mixture was stirred for 1 h. The solvent was evaporated and the residue was purified by HPLC to afford title compound as white powder (16.7 mg, 27.4% in 2 steps). LC/MS (FA) ES+ 412, 414; ES− 410, 412. $^1H$ NMR (400 MHz, $d_4$-methanol) δ: 8.08 (1H, d, J=5.6 Hz), 7.78 (2H, dd, J=16, 2 Hz), 7.61 (1H, dd, J=8.4, 2 Hz), 7.52 (1H, d, J=8 Hz), 7.11-7.04 (2H, m), 6.42 (1H, s)

Step 6: Preparation of N-(4-(3-cyano-4-(2,4-dichlorophenyl)-5-(1H-imidazol-5-yl)thiophen-2-yl)pyridin-2-yl)acetamide (77-A)

To a solution of 2-(2-aminopyridin-4-yl)-4-(2,4-dichlorophenyl)-5-(1H-imidazol-5-yl)thiophene-3-carbonitrile (16.3 mg, 0.0395 mmol) in Pyridine (130.5 mg, 1.650 mmol) and DCM (1.0 mL, 16 mmol) was added acetic anhydride (108.2 mg, 1.060 mmol). The mixture was stirred at rt overnight. The solvent was evaporated and the residue was dissolved in MeOH (4 mL, 90 mmol). Sodium bicarbonate (0.5 g, 6 mmol) was added and followed by water. The mixture was stirred for 30 min. The mixture was concentrated and the residue was dissolved in EtOAc. The organic phase was washed with water and the organic layer was separated and dried over sodium sulfate. The crude product was obtained by evaporation and the purified by column chromatography to afford pure title compound as a yellow solid (12.4 mg, 69.4%). LC/MS (AA) ES+ 454, 456; ES− 452, 454. $^1H$-NMR ($DMSO-d_6$, 300 MHz) δ: 12.63-12.07 (1H, br), 10.79-10.74

(1H, s), 8.57 (1H, s), 8.48 (1H, d, J=5.2 Hz), 7.94 (1H, d, J=1.89 Hz), 7.74 (1H, d, J=0.92 Hz), 7.62 (1H, s), 7.64 (1H, d, J=1.98 Hz), 7.51 (1H, dd, J=5.3, 1.7 Hz), 6.30 (1H, d, J=0.94 Hz), 2.13 (3H, s)

Example 14-A

Synthesis of Methyl 2-[5-[2-(acetylamino)pyridin-4-yl]-4-cyano-3-(2,4-dichlorophenyl)-2-thienyl]-1H-imidazole-5-carboxylate (75-A)

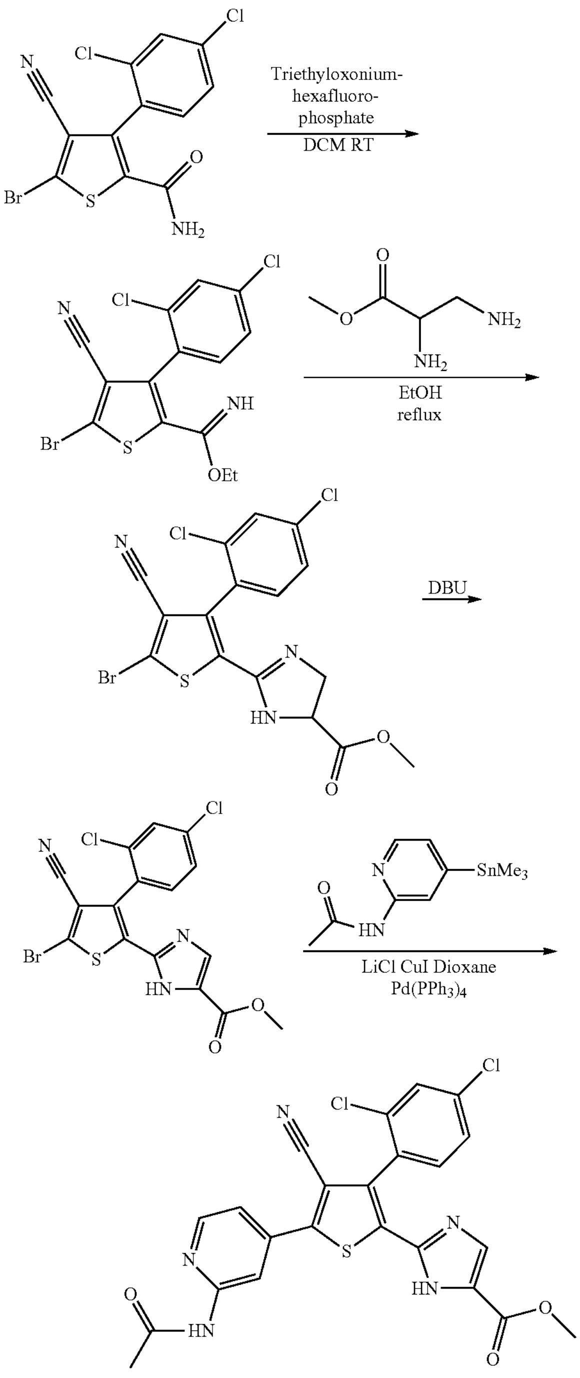

Step 1: Synthesis of Ethyl 5-bromo-4-cyano-3-(2,4-dichlorophenyl)thiophene-2-carboximidoate To a solution of 5-bromo-4-cyano-3-(2,4-dichlorophenyl) thiophene-2-carboxamide (prepared in an analogous way to the iodide intermediate shown in Example 3-A; 0.500 g, 1.33 mmol) in dichloromethane (28 mL) at 0° C. was added triethyloxonium hexafluorophosphate (2.31 g, 9.31 mmol). The mixture was allowed to slowly warm to room temperature, and stirred for 16 hours. The solution was poured into 1M sodium carbonate solution at 0° C., then the layers were separated, and the aqueous layer was extracted 3 times with dichloromethane. The organic extracts were washed with brine, dried over anhydrous sodium sulfate, filtered and concentrated in vacuo. Column chromatography was performed to yield the title compound (0.558 g, 104%). LCMS: (FA) $ES^+$, 405. $^1$H NMR (400 MHz, $d_1$-chloroform) δ: 7.60-7.57 (m, 1H), 7.43-7.38 (m, 1H), 7.29-7.25 (m, 1H), 4.30-4.22 (m, 2H), 1.40-1.37 (m, 3H).

Step 2: Synthesis of Methyl 2-[5-bromo-4-cyano-3-(2,4-dichlorophenyl)-2-thienyl]-4,5-dihydro-1H-imidazole-5-carboxylate To a solution of ethyl 5-bromo-4-cyano-3-(2,4-dichlorophenyl)thiophene-2-carboximidoate (0.548 g, 1.36 mmol) in ethanol (26 mL) was added methyl 2,3-diaminopropanoate dihydrochloride (0.313 g, 1.64 mmol). The solution was stirred at 80° C. for 4 hours. The solvent was evaporated, and column chromatography was performed to yield the title compound (0.222 g, 36%). LCMS: (FA) ES+ 460. $^1$H NMR (400 MHz, $d_4$-methanol) δ 7.70 (s, 1H), 7.55-7.43 (m, 2H), 3.76-3.66 (m, 4H), 1.36-1.26 (m, 3H).

Step 3: Synthesis of Methyl 2-[5-bromo-4-cyano-3-(2,4-dichlorophenyl)-2-thienyl]-1H-imidazole-5-carboxylate To a mixture of methyl 2-[5-bromo-4-cyano-3-(2,4-dichlorophenyl)-2-thienyl]-4,5-dihydro-1H-imidazole-5-carboxylate (0.341 g, 0.743 mmol), carbon tetrachloride (12.1 mL, 126 mmol), acetonitrile (18.3 mL, 351 mmol) and pyridine (12 mL, 150 mmol) was added 1,8-Diazabicyclo[5.4.0]undec-7-ene (0.442 mL, 2.96 mmol) slowly. The solution was stirred at room temperature for 16 hours. The mixture was evaporated, then the residue was diluted with dichloromethane and 0.5N aqueous HCl solution. The layers were separated, then the organic extracts were washed with brine, dried over anhydrous sodium sulfate, filtered and concentrated in vacuo. Column chromatography was performed to yield the title compound (0.226 g, 67%). LCMS: (FA) $ES^+$, 458. $^1$H NMR (400 MHz, $d_4$-Methanol) δ: 7.70-7.67 (m, 2H), 7.53-7.43 (m, 2H), 3.85 (s, 3H).

Step 4: Synthesis of Methyl 2-[5-[2-(acetylamino) pyridin-4-yl]-4-cyano-3-(2,4-dichlorophenyl)-2-thienyl]-1H-imidazole-5-carboxylate (75-A)

Methyl 2-[5-bromo-4-cyano-3-(2,4-dichlorophenyl)-2-thienyl]-1H-imidazole-5-carboxylate (0.216 g, 0.472 mmol), N-[4-(trimethylstannyl)pyridin-2-yl]acetamide (0.170 g, 0.567 mmol), lithium chloride (0.0601 g, 1.42 mmol), copper (I) iodide (0.0270 g, 0.142 mmol) and tetrakis(triphenylphosphine)palladium(0) (0.0273 g, 0.0236 mmol) were combined in dioxane (10 mL) under an atmosphere of Argon. The solution was heated at 110° C. for 3 hours. The solvent was evaporated, and column chromatography was performed to yield the title compound (0.0250 g, 10%). LCMS: (FA) ES+ 513. $^1$H NMR (300 MHz, $d_6$-DMSO) δ 8.59-8.57 (m, 1H), 8.54-8.50 (m, 1H), 7.88-7.82 (m, 2H), 7.61-7.58 (m, 2H), 7.56-7.52 (m, 1H), 3.75 (s, 3H), 2.13 (s, 3H).

Example 1-B

Production of N-{4-[4-phenyl-5-(4H-1,2,4-triazol-3-yl)-1,3-thiazol-2-yl]pyridin-2-yl}acetamide

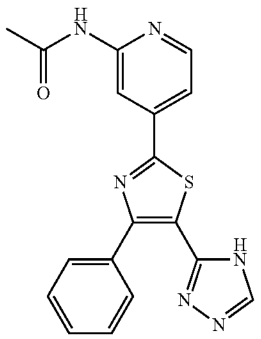 [SMILES: CC(=O)Nc1cc(-c2nc(-c3ccccc3)c(-c3nnc[nH]3)s2)ccn1]

(i) Production of 2-aminopyridine-4-carbothioamide

A mixture of 2-aminopyridine-4-carbonitrile (6.0 g, 50 mmol), O,O'-diethyl dithiophosphate (11 mL, 60 mmol), tetrahydrofuran (25 mL) and water (25 mL) was stirred at 60° C. for 4 hr. To the reaction mixture was added O,O'-diethyl dithiophosphate (2.8 mL, 15 mmol) and the mixture was stirred at 60° C. for 1 day. To the reaction mixture was added aqueous sodium bicarbonate solution, and the mixture was extracted with ethyl acetate. The combined organic layer was washed with saturated brine and dried over anhydrous magnesium sulfate, and the insoluble material was filtered off. The filtrate was concentrated under reduced pressure, and the obtained residue was washed with diisopropyl ether to give the title compound (6.2 g, 81%) as a yellow solid.

$^1$H-NMR (DMSO-$d_6$, 300 MHz) δ 6.12 (2H, s), 6.73 (1H, dd, J=1.7, 5.3 Hz), 6.77-6.81 (1H, m), 7.92 (1H, dd, J=0.6, 5.3 Hz), 9.53 (1H, br s), 9.95 (1H, br s).

(ii) Production of N-(4-carbamothioylpyridin-2-yl)acetamide

A mixture of 2-aminopyridine-4-carbothioamide (2.1 g, 18 mmol) obtained above, acetic anhydride (1.5 mL, 16 mmol) and pyridine (20 mL) was stirred at room temperature for 1 day. The reaction mixture was concentrated under reduced pressure, aqueous sodium bicarbonate solution was added to the obtained residue, and the mixture was extracted with ethyl acetate. The combined organic layer was washed with saturated brine and dried over anhydrous magnesium sulfate, and the insoluble material was filtered off. The filtrate was concentrated under reduced pressure, and the obtained residue was washed with ethyl acetate/diisopropyl ether to give the title compound (2.1 g, 76%) as a yellow solid.

$^1$H-NMR (DMSO-$d_6$, 300 MHz) δ 2.11 (3H, s), 7.29 (1H, dd, J=1.6, 5.2 Hz), 8.33 (1H, d, J=5.2 Hz), 8.36-8.42 (1H, m), 9.72 (1H, br s), 10.13 (1H, br s), 10.60 (1H, s).

(iii) Production of ethyl 2-[2-(acetylamino)pyridin-4-yl]-4-phenyl-1,3-thiazole-5-carboxylate A mixture of N-(4-carbamothioylpyridin-2-yl)acetamide (980 mg, 5.0 mmol) obtained above, ethyl 2-bromo-3-oxo-3-phenylpropanoate (1.4 g, 5.3 mmol) produced by the method described in K. Tanemura, et al.; Chemical Communications; 4; 2004; 470-471 and acetonitrile (20 mL) was stirred at 80° C. for 4 hr. To the reaction mixture was added aqueous sodium bicarbonate solution, and successively ethyl acetate and tetrahydrofuran, and the insoluble material was filtered off. The filtrate was extracted with a mixed solvent of ethyl acetate/tetrahydrofuran. The combined organic layer was washed with saturated brine and dried over anhydrous magnesium sulfate, and the insoluble material was filtered off. The filtrate was concentrated under reduced pressure, the obtained residue was purified by silica gel column chromatography (ethyl acetate/hexane=50/50→100/0) and the obtained crude product was washed with ethyl acetate/diisopropyl ether to give the title compound (910 mg, 49%) as a colorless solid.

$^1$H-NMR (DMSO-$d_6$, 300 MHz) δ 1.24 (3H, t, J=7.1 Hz), 2.14 (3H, s), 4.27 (2H, q, J=7.2 Hz), 7.46-7.53 (3H, m), 7.69 (1H, dd, J=1.7, 5.1 Hz), 7.75-7.84 (2H, m), 8.48 (1H, d, J=5.1 Hz), 8.71-8.75 (1H, m), 10.77 (1H, s).

(iv) Production of 2-[2-(acetylamino)pyridin-4-yl]-4-phenyl-1,3-thiazole-5-carboxylic acid A mixture of ethyl 2-[2-(acetylamino)pyridin-4-yl]-4-phenyl-1,3-thiazole-5-carboxylate (740 mg, 2.0 mmol) obtained above, 1N aqueous sodium hydroxide solution (2.4 mL), methanol (10 mL) and tetrahydrofuran (10 mL) was stirred at room temperature for 1 day. To the reaction mixture was added 1N hydrochloric acid (2.4 mL) and water, and the resulting precipitate was collected by filtration, washed with water and dried to give the title compound (670 mg, 99%) as a colorless solid.

$^1$H-NMR (DMSO-$d_6$, 300 MHz) δ 2.14 (3H, s), 7.44-7.53 (3H, m), 7.67 (1H, dd, J=1.7, 5.2 Hz), 7.76-7.85 (2H, m), 8.47 (1H, dd, J=0.8, 5.2 Hz), 8.69-8.73 (1H, m), 10.75 (1H, s).

(v) Production of 2-[2-(acetylamino)pyridin-4-yl]-4-phenyl-1,3-thiazole-5-carboxamide A mixture of 2-[2-(acetylamino)pyridin-4-yl]-4-phenyl-1,3-thiazole-5-carboxylic acid (670 mg, 2.0 mmol) obtained above, ammonium chloride (320 mg, 6.0 mmol), triethylamine (0.84 mL, 6.0 mmol), N-[3-(dimethylamino)propyl]-N'-ethylcarbodiimide hydrochloride (580 mg, 3.0 mmol), 1-hydroxybenzotriazole (410 mg, 3.0 mmol) and N,N-dimethylformamide (20 mL) was stirred at room temperature for 1 day. To the reaction mixture was added water, and the resulting precipitate was collected by filtration, washed with water and diethyl ether and dried. The obtained crude product was suspended in N,N-dimethylformamide (5 mL) in a hot-water bath at 90° C. Water (20 mL) was added, and the mixture was stirred at room temperature. The precipitate was collected by filtration, washed with water and dried to give the title compound (540 mg, 80%) as a colorless solid.

$^1$H-NMR (DMSO-$d_6$, 300 MHz) δ 2.14 (3H, s), 7.41-7.55 (3H, m), 7.65 (1H, dd, J=1.6, 5.2 Hz), 7.78-7.85 (2H, m), 7.87 (1H, br s), 7.96 (1H, br s), 8.47 (1H, dd, J=0.8, 5.2 Hz), 8.68-8.73 (1H, m), 10.75 (1H, s).

(vi) Production of N-{4-[4-phenyl-5-(4H-1,2,4-triazol-3-yl)-1,3-thiazol-2-yl]pyridin-2-yl}acetamide 2-[2-(Acetylamino)pyridin-4-yl]-4-phenyl-1,3-thiazole-5-carboxamide (630 mg, 1.9 mmol) obtained above was suspended in N,N-dimethylformamide dimethyl acetal (10 mL), and the mixture was stirred at 100° C. for 4 hr. The reaction mixture was concentrated under reduced pressure, hydrazine monohydrate (0.45 mL, 9.3 mmol) and acetic acid (10 mL) were added to the obtained residue, and the mixture was stirred at 100° C. for 1 hr. The reaction mixture was concentrated under reduced pressure, aqueous sodium bicarbonate solution was added to the obtained residue, and the precipitate was collected by filtration. The obtained solid was washed with water and diethyl ether and dried. The obtained crude product was purified by silica gel column chromatography (methanol/ethyl acetate=0/100→50/50), washed with water and dried to give the title compound (360 mg, 53%) as a colorless solid.

$^1$H-NMR (DMSO-$d_6$, 300 MHz) δ 2.14 (3H, s), 7.38-7.50 (3H, m), 7.67 (1H, dd, J=1.6, 5.2 Hz), 7.80-7.90 (2H, m), 8.47 (1H, dd, J=0.7, 5.2 Hz), 8.70 (1H, s), 8.71-8.74 (1H, m), 10.73 (1H, s), 14.37 (1H, s).

Example 2-B

Production of 4-[4-phenyl-5-(4H-1,2,4-triazol-3-yl)-1,3-thiazol-2-yl]pyridin-2-amine

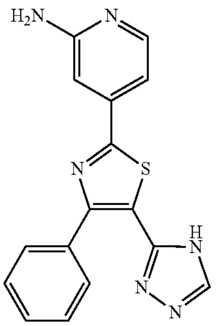 [SMILES: Nc1cc(-c2nc(-c3ccccc3)c(-c3nnc[nH]3)s2)ccn1]

A mixture of N-{4-[4-phenyl-5-(4H-1,2,4-triazol-3-yl)-1,3-thiazol-2-yl]pyridin-2-yl}acetamide (250 mg, 0.70 mmol) produced in Example 1-B (vi), 1N aqueous sodium hydroxide solution (3.5 mL), methanol (5 mL) and tetrahydrofuran (5 mL) was stirred at 60° C. for 3 hr. To the reaction mixture was added 1N aqueous sodium hydroxide solution (3.5 mL), and the mixture was stirred at 60° C. for 1 hr. The reaction mixture was neutralized with 1N hydrochloric acid, and concentrated under reduced pressure. The resulting precipitate was collected by filtration, washed with water and diethyl ether and dried to give the title compound (130 mg, 58%) as a yellow solid.

$^1$H-NMR (DMSO-$d_6$, 300 MHz) δ 7.38 (1H, dd, J=1.7, 6.6 Hz), 7.41-7.50 (3H, m), 7.60 (1H, s), 7.78-7.91 (2H, m), 8.15 (2H, br s), 8.09 (1H, d, J=6.6 Hz), 8.71 (1H, br s), 14.51 (1H, br s).

Example 3-B

Production of N-{4-[4-phenyl-5-(4H-1,2,4-triazol-3-yl)-1,3-thiazol-2-yl]pyridin-2-yl}cyclopropanecarboxamide

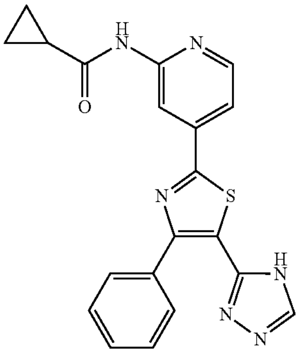 [SMILES: O=C(Nc1cc(-c2nc(-c3ccccc3)c(-c3nnc[nH]3)s2)ccn1)C1CC1]

A mixture of 4-[4-phenyl-5-(4H-1,2,4-triazol-3-yl)-1,3-thiazol-2-yl]pyridin-2-amine (150 mg, 0.47 mmol) produced in Example 2-B, cyclopropanecarbonyl chloride (0.13 mL, 1.40 mmol) and pyridine (5 mL) was stirred at room temperature for 6 hr. To the reaction mixture was added cyclopropanecarbonyl chloride (0.085 mL, 0.94 mmol) and the mixture was stirred at room temperature for 1 day. To the reaction mixture was added aqueous sodium bicarbonate solution, and the mixture was extracted with ethyl acetate. The combined organic layer was washed with saturated brine and dried over anhydrous magnesium sulfate, and the insoluble material was filtered off. The obtained residue was purified by silica gel column chromatography (ethyl acetate/hexane=20/80→100/0), and 1N aqueous sodium hydroxide solution (0.5 mL), methanol (5 mL) and tetrahydrofuran (10 mL) were added to the crude product. The mixture was stirred at room temperature for 1 hr. The reaction mixture was concentrated under reduced pressure, and water was added to the obtained residue. After neutralization with 1N hydrochloric acid, the resulting precipitate was collected by filtration, washed with water and diethyl ether and dried to give the title compound (145 mg, 80%) as a pale-yellow solid.

$^1$H-NMR (DMSO-$d_6$, 300 MHz) δ 0.79-0.93 (4H, m), 2.00-2.12 (1H, m), 7.38-7.49 (3H, m), 7.67 (1H, dd, J=1.6, 5.2 Hz), 7.80-7.90 (2H, m), 8.47 (1H, dd, J=0.8, 5.2 Hz), 8.63 (1H, s), 8.73-8.76 (1H, m), 11.05 (1H, s), 14.36 (1H, br s).

Example 4-B

Production of 3-morpholin-4-yl-N-{4-[4-phenyl-5-(4H-1,2,4-triazol-3-yl)-1,3-thiazol-2-yl]pyridin-2-yl}propanamide

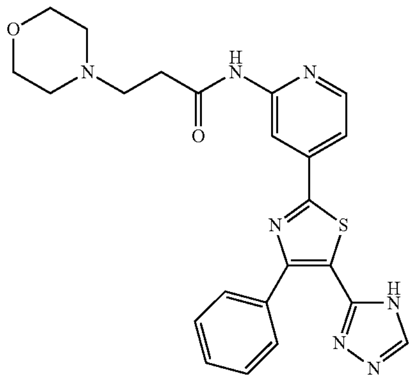 [SMILES: O=C(CCN1CCOCC1)Nc1cc(-c2nc(-c3ccccc3)c(-c3nnc[nH]3)s2)ccn1]

(i) Production of N-(4-{4-phenyl-5-[1-(tetrahydro-2H-pyran-2-yl)-1H-1,2,4-triazol-3-yl]-1,3-thiazol-2-yl}pyridin-2-yl)acetamide To a solution of N-{4-[4-phenyl-5-(4H-1,2,4-triazol-3-yl)-1,3-thiazol-2-yl]pyridin-2-yl}acetamide (65 mg, 0.18 mmol) produced in Example 1-B (vi) in tetrahydrofuran (3.0 mL) were added p-toluenesulfonic acid monohydrate (41 mg, 0.22 mmol) and 3,4-dihydro-2H-pyran (140 mg, 1.7 mmol), and the mixture was heated under reflux for 3 hr. The reaction mixture was cooled to room temperature, diluted with ethyl acetate (40 mL), and washed with saturated aqueous sodium bicarbonate solution (30 mL). The aqueous layer was extracted with ethyl acetate (40 mL), the combined organic layer was dried over anhydrous magnesium sulfate, and the insoluble material was filtered off. The filtrate was concentrated under reduced pressure, and the obtained residue was purified by silica gel column chromatography (ethyl acetate/hexane=20/80→100/0) to give the title compound (71.0 mg, 88%) as a white solid.

$^1$H-NMR ($CDCl_3$, 300 MHz) δ 1.54-1.84 (3H, m), 1.89-2.18 (3H, m), 2.24 (3H, s), 3.60-3.85 (1H, m), 3.98-4.11 (1H, m), 5.48 (1H, dd, J=3.4, 8.1 Hz), 7.32-7.47 (3H, m), 7.72 (1H, dd, J=1.6 Hz, 5.2 Hz), 7.82-7.99 (2H, m), 8.28 (1H, s), 8.35 (1H, d, J=5.2 Hz), 8.79 (2H, br s).

(ii) Production of 4-{4-phenyl-5-[1-(tetrahydro-2H-pyran-2-yl)-1H-1,2,4-triazol-3-yl]-1,3-thiazol-2-yl}pyridin-2-amine To N-(4-{4-phenyl-5-[1-(tetrahydro-2H-pyran-2-yl)-1H-1,2,4-triazol-3-yl]-1,3-thiazol-2-yl}pyridin-2-yl)acetamide (2.0 g, 4.4 mmol) prepared in the same manner as above in a mixed solvent (88 mL) of tetrahydrofuran/methanol (1:1) was added 1N aqueous sodium hydroxide solution (44 mL, 44.0 mmol), and the mixture was stirred at 60° C. for 3 hr. The reaction solution was cooled to room temperature, and diluted with ethyl acetate (300 mL) and water (150 mL). The aqueous layer was separated and extracted with ethyl acetate (200 mL), and the combined organic layer was dried over anhydrous magnesium sulfate. The insoluble material was filtered off, and the filtrate was concentrated under reduced pressure. The obtained solid was washed with diethyl ether (25 mL) and hexane (25 mL) to give the title compound (1.6 g, 87%) as a pale-yellow solid.

$^1$H-NMR (DMSO-$d_6$, 300 MHz) δ 1.47-1.70 (3H, m), 1.88-2.10 (3H, m), 3.59-3.72 (1H, m), 3.84-4.01 (1H, m), 5.61 (1H, dd, J=3.3 Hz, 8.4 Hz), 6.26 (2H, s), 7.03 (1H, dd, J=1.5 Hz, 5.1 Hz), 7.08 (1H, d, J=0.9 Hz), 7.38-7.49 (3H, m), 7.77-7.87 (2H, m), 8.06 (1H, d, J=5.1 Hz), 8.82 (1H, s).

(iii) Production of N-(4-(4-phenyl-5-[1-(tetrahydro-2H-pyran-2-yl)-1H-1,2,4-triazol-3-yl)-1,3-thiazol-2-yl]pyridin-2-yl)prop-2-enamide To a solution of 4-{4-phenyl-5-[1-(tetrahydro-2H-pyran-2-yl)-1H-1,2,4-triazol-3-yl]-1,3-thiazol-2-yl}pyridin-2-amine (680 mg, 1.7 mmol) produced above step in tetrahydrofuran (17 mL) were added triethylamine (190 mg, 1.9 mmol) and prop-2-enoyl chloride (770 mg, 8.5 mmol) at −78° C., and the mixture was stirred at the same temperature for 2 hr. The reaction mixture was warmed to 0° C., saturated aqueous sodium bicarbonate solution (50 mL) was added, and the mixture was stirred at room temperature for 12 hr. To the reaction mixture was further added saturated aqueous sodium bicarbonate solution (50 mL), and the mixture was stirred at room temperature for 3 hr. The aqueous layer was extracted with ethyl acetate (100 mL×2), the combined organic layer was dried over anhydrous magnesium sulfate, and the insoluble material was filtered off. The filtrate was concentrated under reduced pressure, and the residue was purified by silica gel column chromatography (ethyl acetate/hexane=20/80→100/0) to give the title compound (400 mg, 51%) as a yellow solid.

$^1$H-NMR (DMSO-$d_6$, 300 MHz) δ 1.45-1.74 (3H, m), 1.84-2.15 (3H, m), 3.62-3.72 (1H, m), 3.85-3.96 (1H, m), 5.62 (1H, dd, J=3.3 Hz, 8.4 Hz), 5.76-5.92 (1H, m), 6.36 (1H, dd, J=1.9, 17.0 Hz), 6.55-6.74 (1H, m), 7.38-7.53 (3H, m), 7.67-7.77 (1H, m), 7.82-7.93 (2H, m), 8.47-8.55 (1H, m), 8.82-8.93 (2H, m), 11.0 (1H, s).

(iv) Production of 3-morpholin-4-yl-N-{4-[4-phenyl-5-(4H-1,2,4-triazol-3-yl)-1,3-thiazol-2-yl]pyridin-2-yl}propanamide To a solution of N-(4-{4-phenyl-5-[1-(tetrahydro-2H-pyran-2-yl)-1H-1,2,4-triazol-3-yl]-1,3-thiazol-2-yl}pyridin-2-yl)prop-2-enamide (70 mg, 0.15 mmol) produced above in tetrahydrofuran (1.5 mL) was added morpholine (140 mg, 1.50 mmol), and the mixture was heated under reflux for 2 hr. The reaction mixture was cooled to room temperature and the solvent was evaporated under reduced pressure. The obtained residue was dissolved in trifluoroacetic acid (1.5 mL), and the mixture was stirred at room temperature for 3 hr. The reaction mixture was diluted with tetrahydrofuran (5.0 mL) and water (10 mL), and 25% aqueous ammonia (5.0 mL) was added. The aqueous layer was extracted with ethyl acetate (30 mL×2), and the combined organic layer was dried over anhydrous magnesium sulfate. The insoluble material was filtered off, the filtrate was concentrated under reduced pressure, and the obtained residue was purified by basic silica gel column chromatography (methanol/ethyl acetate=0/100→10/90) to give the title compound (50 mg, 72%) as a white solid.

$^1$H-NMR (DMSO-$d_6$, 300 MHz) δ 2.37-2.46 (4H, m), 2.57-2.70 (4H, m), 3.51-3.67 (4H, m), 7.35-7.53 (3H, m), 7.68 (1H, dd, J=1.6, 5.2 Hz), 7.78-7.92 (2H, m), 8.41-8.53 (1H, m), 8.66 (1H, s), 8.76 (1H, d, J=0.9 Hz), 10.92 (1H, s), 14.34 (1H, br s).

Example 5-B

Production of 3-[(2S)-2-(methoxymethyl)pyrrolidin-1-yl]-N-{4-[4-phenyl-5-(4H-1,2,4-triazol-3-yl)-1,3-thiazol-2-yl]pyridin-2-yl}propanamide

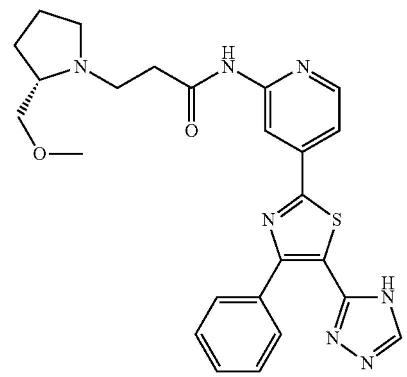 [SMILES: COC[C@@H]1CCCN1CCC(=O)Nc1cc(-c2nc(-c3ccccc3)c(-c3nnc[nH]3)s2)ccn1]

To a solution of N-(4-(4-phenyl-5-(1-(tetrahydro-2H-pyran-2-yl)-1H-1,2,4-triazol-3-yl)-1,3-thiazol-2-yl)pyridin-2-yl)prop-2-enamide (92 mg, 0.2 mmol) prepared in Example 4-B (iii) in tetrahydrofuran (2.0 mL) was added (2S)-2-(methoxymethyl)pyrrolidine (120 mg, 1.0 mmol), and the mixture was heated under reflux for 14 hr. The reaction solution was cooled to room temperature, and diluted with ethyl acetate (30 mL) and saturated aqueous sodium bicarbonate solution (30 mL). The aqueous layer was separated, extracted with ethyl acetate (40 mL), and the combined organic layer was dried over anhydrous magnesium sulfate. The insoluble material was filtered off, and the filtrate was concentrated. The obtained residue was dissolved in trifluoroacetic acid (4.0 mL), and the mixture was stirred at room temperature for 3 hr. Trifluoroacetic acid was evaporated under reduced pressure, and the residue was diluted with ethyl acetate (30 mL), and washed with saturated aqueous sodium bicarbonate solution (30 mL). The aqueous layer was separated and extracted with ethyl acetate (30 mL), and the combined organic layer was dried over anhydrous magnesium sulfate. The insoluble material was filtered off, the filtrate was concentrated under reduced pressure, and the obtained residue was purified by basic silica gel column chromatography (methanol/ethyl acetate=0/100→50/50) to give the title compound (60 mg, 62%) as a pale-yellow solid.

$^1$H-NMR (DMSO-$d_6$, 300 MHz) δ 1.43-1.55 (1H, m), 1.61-1.72 (2H, m), 1.79-1.90 (1H, m), 2.14-2.30 (1H, m), 2.53-2.76 (4H, m), 3.13-3.25 (6H, m), 3.40-3.44 (1H, m), 7.32-7.56 (3H, m), 7.67 (1H, dd, J=1.5, 5.1 Hz), 7.77-8.02 (2H, m), 8.31-8.55 (1H, m), 8.60-8.70 (1H, m), 8.74 (1H, d, J=0.8 Hz), 10.95 (1H, s), 14.36 (1H, br s).

Example 6-B

Production of 3-[(2R)-2-(methoxymethyl)pyrrolidin-1-yl]-N-{4-[4-phenyl-5-(4H-1,2,4-triazol-3-yl)-1,3-thiazol-2-yl]pyridin-2-yl}propanamide

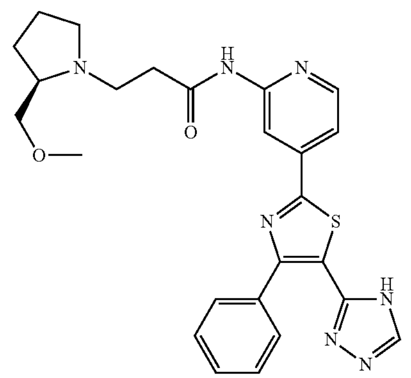 [SMILES: COC[C@H]1CCCN1CCC(=O)Nc1cc(-c2nc(-c3ccccc3)c(-c3nnc[nH]3)s2)ccn1]

In the same manner as in Example 5-B except that (2R)-2-(methoxymethyl)pyrrolidine (120 mg, 1.0 mmol) was used, the title compound (73 mg, 74%) was obtained as a pale-yellow solid from N-(4-{4-phenyl-5-[1-(tetrahydro-2H-pyran-2-yl)-1H-1,2,4-triazol-3-yl]-1,3-thiazol-2-yl}pyridin-2-yl)prop-2-enamide (91.6 mg, 0.2 mmol) prepared in Example 4-B (iii).

$^1$H-NMR (DMSO-$d_6$, 300 MHz) δ 1.39-1.57 (1H, m), 1.57-1.74 (2H, m), 1.76-1.96 (1H, m), 2.11-2.30 (1H, m), 2.53-2.68 (4H, m), 3.04-3.27 (6H, m), 3.35-3.46 (1H, m), 7.33-7.57 (3H, m), 7.67 (1H, dd, J=1.7, 5.1 Hz), 7.76-8.01 (2H, m), 8.47 (1H, dd, J=0.8, 5.1 Hz), 8.66-8.69 (1H, m), 8.75 (1H, d, J=0.8 Hz), 10.95 (1H, s), 14.37 (1H, br s).

Example 7-B

Production of 3-(phenylsulfanyl)-N-{4-[4-phenyl-5-(4H-1,2,4-triazol-3-yl)-1,3-thiazol-2-yl]pyridin-2-yl}propanamide

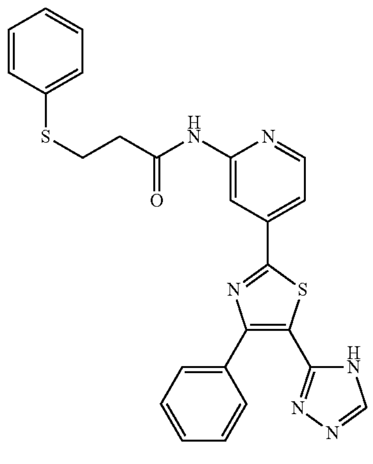 [SMILES: O=C(CCSc1ccccc1)Nc1cc(-c2nc(-c3ccccc3)c(-c3nnc[nH]3)s2)ccn1]

To a solution of N-(4-{4-phenyl-5-[1-(tetrahydro-2H-pyran-2-yl)-1H-1,2,4-triazol-3-yl]-1,3-thiazol-2-yl}pyridin-2-yl)prop-2-enamide (92 mg, 0.2 mmol) prepared in Example 4-B (iii) in tetrahydrofuran (2.0 mL) were added triethylamine (30 mg, 0.3 mmol) and thiophenol (29 mg, 0.26 mmol), and the mixture was stirred at room temperature for 15 hr. The reaction mixture was diluted with ethyl acetate (25 mL), and washed with saturated aqueous sodium bicarbonate solution (25 mL). The aqueous layer was extracted with ethyl acetate (25 mL), and the combined organic layer was dried over anhydrous magnesium sulfate. The insoluble material was filtered off, and the filtrate was concentrated under reduced pressure. The obtained residue was dissolved in trifluoroacetic acid (8.0 mL), and the mixture was stirred at room temperature for 6 hr. Trifluoroacetic acid was evaporated under reduced pressure, and the residue was diluted with ethyl acetate (40 mL) and washed with saturated aqueous sodium bicarbonate solution (30 mL). The aqueous layer was separated and extracted with ethyl acetate (40 mL), and the combined organic layer was dried over anhydrous magnesium sulfate. The insoluble material was filtered off, the filtrate was concentrated under reduced pressure, and the obtained residue was purified by silica gel column chromatography (ethyl acetate/hexane=50/50→100/0) to give the title compound (69 mg, 71%) as a white solid.

$^1$H-NMR (DMSO-$d_6$, 300 MHz) δ 2.81 (2H, t, 7.1 Hz), 3.26 (2H, t, J=7.1 Hz), 7.15-7.25 (1H, m), 7.27-7.39 (4H, m), 7.40-7.50 (3H, m), 7.68 (1H, dd, J=1.6, 5.2 Hz), 7.81-7.96 (2H, m), 8.39-8.56 (1H, m), 8.60-8.68 (1H, m), 8.71-8.82 (1H, m), 10.81 (1H, s), 14.33 (1H, s).

Example 8-B

Production of N-{4-[4-ethoxy-5-(4H-1,2,4-triazol-3-yl)-1,3-thiazol-2-yl]pyridin-2-yl}acetamide

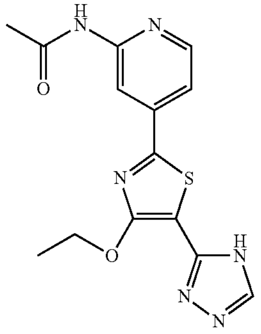 [SMILES: CCOc1nc(-c2ccnc(NC(C)=O)c2)sc1-c1nnc[nH]1]

(i) Production of ethyl 2-[2-(acetylamino)pyridin-4-yl]-4-hydroxy-1,3-thiazole-5-carboxylate To a suspension of N-(4-carbamothioylpyridin-2-yl)acetamide (15 g, 77 mmol) produced in the same manner as in Example 1-B (ii) in 2-propanol (136 mL) was added ethyl 2-chloro-3-oxo-3-phenylpropanoate, and the mixture was stirred with heating at 90° C. for 12 hr. Tetrabutylammonium bromide (1.2 g, 3.9 mmol) was added to the reaction solution, and the mixture was further stirred with heating at the same temperature for 10 hr. The reaction mixture was cooled to room temperature and diluted with ethyl acetate (200 mL), and saturated aqueous sodium bicarbonate solution (200 mL) was added. The resulting solid was collected by filtration, and washed with water (200 mL), ethanol (100 mL) and diethyl ether (100 mL×2). The obtained crude product was suspended in acetic anhydride (150 mL), concentrated sulfuric acid (0.05 mL) was added, and the mixture was heated under reflux at 120° C. for 2 hr. The reaction mixture was cooled to room temperature, and acetic anhydride was evaporated under reduced pressure. The residue was suspended in methanol (50 mL), and after stirring, methanol was evaporated under reduced pressure. The obtained residue was suspended in tetrahydrofuran (300 mL), 25% aqueous ammonia solution (150 mL) was added, and the mixture was stirred at room temperature for 1 hr. To the reaction mixture was added methanol (100 mL), and the mixture was further stirred at room temperature for 30 min. The resulting solid was collected by filtration, and washed with water (100 mL) and diethyl ether (100 mL) to give the title compound (7.4 g, 31%) as a yellow solid. The combined filtrate and washing solution was concentrated under reduced pressure, the resulting yellow solid was collected by filtration, and washed with water (500 mL), ethanol (100 mL) and diethyl ether (200 mL) to give a second crop (2.9 g, 12%) of the title compound as a yellow solid.

$^1$H-NMR (DMSO-$d_6$, 300 MHz) δ 1.22 (3H, t, J=7.2 Hz), 2.12 (3H, s), 4.11 (2H, q, J=7.2 Hz), 7.45 (1H, br s), 7.48 (1H, dd, J=1.6 Hz, 5.2 Hz), 8.30-8.44 (1H, m), 8.53-8.62 (1H, m), 10.64 (1H, s).

(ii) Production of ethyl 2-[2-(acetylamino)pyridin-4-yl]-4-ethoxy-1,3-thiazole-5-carboxylate To a solution of ethyl 2-[2-(acetylamino)pyridin-4-yl]-4-hydroxy-1,3-thiazole-5-carboxylate (11 g, 34 mmol) produced above in N,N-dimethylformamide (350 mL) were added potassium carbonate (24 g, 170 mmol) and iodoethane (15.8 g, 103 mmol), and the mixture was stirred at 50° C. for 3 hr. The reaction mixture was cooled to room temperature, water (400 mL) was added, and the mixture was cooled to 0° C. The resulting solid was collected by filtration, and washed with water (1.0 L) and diethyl ether (100 mL) to give the title compound (8.8 g, 77%) as a yellow solid.

$^1$H-NMR (DMSO-$d_6$, 300 MHz) δ 1.28 (3H, t, J=7.2 Hz), 1.39 (3H, t, J=7.1 Hz), 2.13 (3H, s), 4.25 (2H, q, J=7.2 Hz), 4.56 (2H, q, J=7.1 Hz), 7.66 (1H, dd, J=1.7 Hz, 5.2 Hz), 8.46 (1H, dd, J=0.8 Hz, 5.2 Hz), 8.60-8.69 (1H, m), 10.76 (1H, s).

(iii) Production of 2-[2-(acetylamino)pyridin-4-yl]-4-ethoxy-1,3-thiazole-5-carboxylic acid To ethyl 2-[2-(acetylamino)pyridin-4-yl]-4-ethoxy-1,3-thiazole-5-carboxylate (8.8 g, 26 mmol) produced above in a mixed solvent (240 mL) of tetrahydrofuran/methanol (1:1) was added 1N aqueous sodium hydroxide solution (29 mL, 29 mmol), and the mixture was stirred at 40° C. for 3 hr. 1N Aqueous sodium hydroxide solution (2.7 mL, 2.7 mmol) was further added, and the mixture was stirred at 40° C. for 7 hr. The reaction solution was cooled to room temperature, tetrahydrofuran and methanol were evaporated, and the residue was concentrated to about 120 mL. The residue was diluted with water (300 mL), and 1N hydrochloric acid (30 mL) was added. The resulting white solid was collected by filtration, and washed with water (100 mL) and diethyl ether (100 mL×2). After drying, the obtained white solid was suspended in acetic anhydride (100 mL), concentrated sulfuric acid (0.05 mL) was added, and the mixture was stirred at 100° C. for 5 hr. Acetic anhydride (25 mL) and concentrated sulfuric acid (1.0 mL) were further added, and the mixture was stirred for 30 min. The reaction mixture was cooled to room temperature, and acetic anhydride was evaporated under reduced pressure. The residue was suspended in methanol, and after stirring, methanol was evaporated under reduced pressure. The obtained residue was dissolved in a mixed solvent (500 mL) of tetrahydrofuran/methanol (3:7), 25% aqueous ammonia solution (150 mL) was added, and the mixture was stirred at room temperature for 1 hr. Under reduced pressure, tetrahydrofuran and methanol were evaporated, water (300 mL) was added, and the mixture was neutralized to pH 5 with 1N hydrochloric acid (30 mL). The resulting solid was collected by filtration, and washed with water (100 mL) and diethyl ether (50 mL×2) to give the title compound (7.5 g, 93%) as a yellow solid.

$^1$H-NMR (DMSO-$d_6$, 300 MHz) δ 1.39 (3H, t, J=7.0 Hz), 2.13 (3H, s), 4.54 (2H, q, J=7.0 Hz), 7.59 (1H, dd, J=1.6, 5.2 Hz), 8.45 (1H, dd, J=0.8, 5.2 Hz), 8.59-8.68 (1H, m), 10.75 (1H, s), 13.04 (1H, br s).

(iv) Production of 2-[2-(acetylamino)pyridin-4-yl]-4-ethoxy-1,3-thiazole-5-carboxamide To a solution of 2-[2-(acetylamino)pyridin-4-yl]-4-ethoxy-1,3-thiazole-5-carboxylic acid (7.5 g, 24 mmol) produced above in N,N-dimethylformamide (240 mL) were added triethylamine (10 mL, 73 mmol), ammonium chloride (3.9 g, 73 mmol), 1-hydroxybenzotriazole (5.0 g, 36 mmol) and N-[3-(dimethylamino)propyl]-N'-ethylcarbodiimide hydrochloride (7.0 g, 37 mmol), and the mixture was stirred at room temperature for 2.5 days. Under reduced pressure, the solvent was evaporated, and the residue was diluted with water (200 mL). The resulting solid was collected by filtration, and washed with water (100 mL) and diethyl ether (100 mL) to give a pale-yellow solid. The obtained solid was washed with water (300 mL) and diethyl ether (100 mL) to give the title compound (7.0 g, 94%) as a pale-yellow solid.

$^1$H-NMR (DMSO-$d_6$, 300 MHz) δ 1.43 (3H, t, J=7.0 Hz), 2.13 (3H, s), 4.59 (2H, q, J=7.0 Hz), 7.04 (1H, br s), 7.57 (1H, dd, J=1.7, 5.1 Hz), 7.82 (1H, br s), 8.39-8.50 (1H, m), 8.63 (1H, d, J=5.1 Hz), 10.73 (1H, s).

(v) Production of N-{4-[4-ethoxy-5-(4H-1,2,4-triazol-3-yl)-1,3-thiazol-2-yl]pyridin-2-yl}acetamide 2-[2-(Acetylamino)pyridin-4-yl]-4-ethoxy-1,3-thiazole-5-carboxamide (7.0 g, 23 mmol) produced above was suspended in N,N-dimethylformamide dimethyl acetal (250 mL), and the mixture was stirred at 100° C. for 2 hr. The reaction mixture was cooled to room temperature, and the solvent was evaporated under reduced pressure. The residue was suspended in acetic acid (260 mL), hydrazine monohydrate (5.7 g, 110 mmol) was added under ice-cooling, and the mixture was stirred at 90° C. for 1 hr. The reaction mixture was cooled to room temperature, and acetic acid was evaporated under reduced pressure. The obtained residue was suspended in diethyl ether (100 mL) and saturated aqueous sodium bicarbonate solution (1.2 L). The resulting solid was collected by filtration, and washed with water (500 mL) and diethyl ether (200 mL) to give the title compound (7.2 g, 96%) as a yellow solid.

$^1$H-NMR (DMSO-$d_6$, 300 MHz) δ 1.42 (3H, t, J=7.0 Hz), 2.13 (3H, s), 4.56 (2H, q, J=7.0 Hz), 7.59 (1H, dd, J=1.6 Hz, 5.2 Hz), 8.21-8.53 (2H, m), 8.57-8.72 (1H, m), 10.72 (1H, s), 14.04 (1H, br s).

Example 9-B

Production of N-{6-methyl-4-[4-phenyl-5-(4H-1,2,4-triazol-3-yl)-1,3-thiazol-2-yl]pyridin-2-yl}acetamide

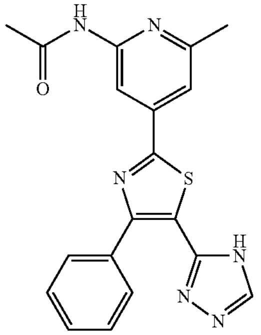 [SMILES: CC(=O)Nc1cc(-c2nc(-c3ccccc3)c(-c3nnc[nH]3)s2)cc(C)n1]

(i) Production of 2-chloro-6-methylpyridine-4-carboxamide

A mixture of 2-chloro-6-methylpyridine-4-carboxylic acid (9.6 g, 56 mmol), ammonium chloride (8.9 g, 170 mmol), triethylamine (23 mL, 170 mmol), N-[3-(dimethylamino)propyl]-N'-ethylcarbodiimide hydrochloride (13 g, 67 mmol), 1-hydroxybenzotriazole (9.1 g, 67 mmol) and N,N-dimethylformamide (100 mL) was stirred at room temperature for 1 day. The reaction mixture was concentrated under reduced pressure, aqueous sodium bicarbonate solution was added to the obtained residue, and the mixture was extracted with ethyl acetate. The combined organic layer was washed with saturated brine and dried over anhydrous magnesium sulfate, and the insoluble material was filtered off. The obtained residue was washed with diisopropyl ether to give the title compound (5.6 g, 59%) as a pale-brown solid.

$^1$H-NMR (DMSO-$d_6$, 300 MHz) δ 2.51 (3H, s), 7.64-7.67 (2H, m), 7.81 (1H, br s), 8.25 (1H, br s).

(ii) Production of 2-chloro-6-methylpyridine-4-carbonitrile

To a mixture of 2-chloro-6-methylpyridine-4-carboxamide (5.1 g, 30 mmol) obtained above, pyridine (7.3 mL, 90 mmol) and tetrahydrofuran (50 mL) was added dropwise a solution of trifluoroacetic anhydride (6.4 mL, 45 mmol) in tetrahydrofuran (10 mL) under ice-cooling, and the mixture was stirred under ice-cooling for 0.5 hr and at room temperature for 1 hr. The reaction mixture was concentrated under reduced pressure, aqueous sodium bicarbonate solution was added to the obtained residue, and the mixture was extracted with ethyl acetate. The combined organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=5/95→10/90). The obtained solution was concentrated under reduced pressure to give the title compound (4.3 g, 95%) as a colorless solid.

$^1$H-NMR (DMSO-$d_6$, 300 MHz) δ 2.52 (3H, s), 7.81 (1H, s), 7.94 (1H, s).

(iii) Production of 2-[(4-methoxybenzyl)amino]-6-methylpyridine-4-carbonitrile

A mixture of 2-chloro-6-methylpyridine-4-carbonitrile (1.5 g, 10 mmol) obtained above, 4-methoxybenzylamine (2.7 g, 20 mmol), potassium carbonate (2.1 g, 15 mmol), potassium iodide (830 mg, 5.0 mmol) and 1-methyl-2-pyrrolidone (20 mL) was stirred at 100° C. for 1 day. To the reaction mixture was added water, and the mixture was extracted with ethyl acetate. The combined organic layer was washed with saturated brine and dried over anhydrous magnesium sulfate, and the insoluble material was filtered off. The obtained residue was purified by silica gel column chromatography (ethyl acetate/hexane=10/90→20/80), and the obtained solution was concentrated under reduced pressure to give the title compound (1.4 g, 56%) as a colorless solid.

$^1$H-NMR (DMSO-$d_6$, 300 MHz) δ 2.30 (3H, s), 3.72 (3H, s), 4.39 (2H, d, J=5.9 Hz), 6.62 (1H, s), 6.67 (1H, s), 6.88 (2H, d, J=8.8 Hz), 7.26 (2H, d, J=8.8 Hz), 7.43 (1H, t, J=5.9 Hz).

(iv) Production of 2-amino-6-methylpyridine-4-carbothioamide

A mixture of 2-[(4-methoxybenzyl)amino]-6-methylpyridine-4-carbonitrile (1.3 g, 5.2 mmol) obtained above, and trifluoroacetic acid (5 mL) was stirred at 80° C. for 1.5 hr. The reaction mixture was concentrated under reduced pressure, water, tetrahydrofuran and ethyl acetate were added to the obtained residue, and the mixture was stirred. 8N Aqueous sodium hydroxide solution was added, and the mixture was extracted with a mixed solvent of ethyl acetate and tetrahydrofuran. The organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate) to give a crude product (762 mg) of 2-amino-6-methylpyridine-4-carbonitrile.

A mixture of 2-amino-6-methylpyridine-4-carbonitrile (740 mg) obtained above, O,O'-diethyl dithiophosphate (1.5 mL, 7.8 mmol), tetrahydrofuran (5 mL) and water (5 mL) was stirred at 60° C. for 8 hr. To the reaction mixture was added aqueous sodium bicarbonate solution, and the mixture was extracted with ethyl acetate. The combined organic layer was washed with saturated brine and dried over anhydrous magnesium sulfate, and the insoluble material was filtered off. The filtrate was concentrated under reduced pressure, and the obtained residue was washed with diisopropyl ether to give the title compound (770 mg, 89%) as a pale-yellow solid.

$^1$H-NMR (DMSO-$d_6$, 300 MHz) δ 2.25 (3H, s), 6.04 (2H, s), 6.58 (1H, s), 6.60 (1H, s), 9.48 (1H, br s), 9.90 (1H, br s).

(v) Production of N-(4-carbamothioyl-6-methylpyridin-2-yl)acetamide

A mixture of 2-amino-6-methylpyridine-4-carbothioamide (740 mg, 4.4 mmol) obtained above, acetic anhydride (0.62 mL, 6.6 mmol) and pyridine (10 mL) was stirred at room temperature for 1 day. The reaction mixture was concentrated under reduced pressure, aqueous sodium bicarbonate solution was added to the obtained residue, and the mixture was extracted with ethyl acetate. The combined organic layer was washed with saturated brine and dried over anhydrous magnesium sulfate, and the insoluble material was filtered off. The filtrate was concentrated under reduced pressure, and the obtained residue was washed with diisopropyl ether to give the title compound (860 mg, 93%) as a pale-yellow orange solid.

$^1$H-NMR (DMSO-$d_6$, 300 MHz) δ 2.08 (3H, s), 2.43 (3H, s), 7.16 (1H, d, J=0.9 Hz), 8.19 (1H, s), 9.67 (1H, br s), 10.09 (1H, br s), 10.56 (1H, s).

(vi) Production of ethyl 2-[2-(acetylamino)-6-methylpyridin-4-yl]-4-phenyl-1,3-thiazole-5-carboxylate A mixture of N-(4-carbamothioyl-6-methylpyridin-2-yl)acetamide (840 mg, 4.0 mmol) obtained above, ethyl 2-bromo-3-oxo-3-phenylpropanoate (1.3 g, 4.8 mmol) and acetonitrile (30 mL) was stirred at 80° C. for 1 day. To the reaction mixture were added aqueous sodium bicarbonate solution, ethyl acetate and tetrahydrofuran, and the insoluble material was filtered off. The filtrate was extracted with a mixed solvent of ethyl acetate and tetrahydrofuran. The combined organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=50/50→100/0). The obtained solution was concentrated under reduced pressure. The obtained residue was washed with ethyl acetate/diisopropyl ether to give the title compound (890 mg, 58%) as a colorless solid.

$^1$H-NMR (DMSO-$d_6$, 300 MHz) δ 1.24 (3H, t, J=7.2 Hz), 2.11 (3H, s), 2.50 (3H, s), 4.26 (2H, q, J=7.2 Hz), 7.46-7.53 (3H, m), 7.59 (1H, d, J=0.9 Hz), 7.74-7.83 (2H, m), 8.53-8.56 (1H, m), 10.72 (1H, s).

(vii) Production of 2-[2-(acetylamino)-6-methylpyridin-4-yl]-4-phenyl-1,3-thiazole-5-carboxylic acid A mixture of ethyl 2-[2-(acetylamino)-6-methylpyridin-4-yl]-4-phenyl-1,3-thiazole-5-carboxylate (760 mg, 2.0 mmol) obtained above, 1N aqueous sodium hydroxide solution (2.2 mL), methanol (10 mL) and tetrahydrofuran (10 mL) was stirred at 40° C. for 3 hr. To the reaction mixture were added 1N hydrochloric acid (2.2 mL) and water, and the resulting precipitate was collected by filtration, washed successively with water and diethyl ether and dried to give the title compound (650 mg, 93%) as a colorless solid.

$^1$H-NMR (DMSO-$d_6$, 300 MHz) δ 2.11 (3H, s), 2.50 (3H, s), 7.43-7.50 (3H, m), 7.56 (1H, d, J=0.9 Hz), 7.76-7.84 (2H, m), 8.53 (1H, s), 10.71 (1H, s), 13.65 (1H, br s).

(viii) Production of 2-[2-(acetylamino)-6-methylpyridin-4-yl]-4-phenyl-1,3-thiazole-5-carboxamide A mixture of 2-[2-(acetylamino)-6-methylpyridin-4-yl]-4-phenyl-1,3-thiazole-5-carboxylic acid (650 mg, 1.9 mmol) obtained above, ammonium chloride (320 mg, 6.0 mmol), triethylamine (0.84 mL, 6.0 mmol), N-[3-(dimethylamino)propyl]-N'-ethylcarbodiimide hydrochloride (580 mg, 3.0 mmol), 1-hydroxybenzotriazole (410 mg, 3.0 mmol) and N,N-dimethylformamide (20 mL) was stirred at room temperature for 1 day. The reaction mixture was concentrated under reduced pressure, and water was added to the obtained residue. The resulting precipitate was collected by filtration, washed successively with water and diethyl ether and dried to give the title compound (610 mg, 93%) as a colorless solid.

$^1$H-NMR (DMSO-$d_6$, 300 MHz) δ 2.12 (3H, s), 2.51 (3H, s), 7.41-7.54 (3H, m), 7.55 (1H, d, J=0.9 Hz), 7.78-7.85 (2H, m), 7.87 (1H, br s), 7.95 (1H, br s), 8.52 (1H, s), 10.70 (1H, s).

(ix) Production of N-[6-methyl-4-[4-phenyl-5-(4H-1,2,4-triazol-3-yl)-1,3-thiazol-2-yl]pyridin-2-yl]acetamide A mixture of 2-[2-(acetylamino)-6-methylpyridin-4-yl]-4-phenyl-1,3-thiazole-5-carboxamide (560 mg, 1.6 mmol) obtained above and N,N-dimethylformamide dimethyl acetal (10 mL) was stirred at 100° C. for 2 hr. The reaction mixture was concentrated under reduced pressure, hydrazine monohydrate (0.39 mL, 8.0 mmol) and acetic acid (10 mL) were added to the obtained residue, and the mixture was stirred at 100° C. for 1 hr. The reaction mixture was concentrated under reduced pressure, and aqueous sodium bicarbonate solution was added to the obtained residue. The resulting precipitate was collected by filtration, washed with water and diethyl ether and dried. The obtained crude product was purified by silica gel column chromatography (methanol/ethyl acetate=0/100→50/50), and the crude product was treated with ethanol and water. The obtained solid was collected by filtration, washed successively with water and diethyl ether and dried to give the title compound (220 mg, 36%) as a colorless solid.

$^1$H-NMR (DMSO-$d_6$, 300 MHz) δ 2.12 (3H, s), 2.51 (3H, s), 7.38-7.49 (3H, m), 7.55-7.59 (1H, m), 7.79-7.88 (2H, m), 8.54 (1H, s), 8.66 (1H, s), 10.68 (1H, s), 14.37 (1H, br s).

Example 10-B

Production of 2-chloro-4-[4-phenyl-5-(4H-1,2,4-triazol-3-yl)-1,3-thiazol-2-yl]pyridine

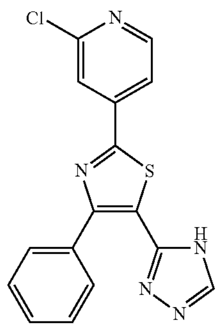 [SMILES: Clc1cc(-c2nc(-c3ccccc3)c(-c3nnc[nH]3)s2)ccn1]

(i) Production of ethyl 4-phenyl-2-pyridin-4-yl-1,3-thiazole-5-carboxylate

To a suspension of pyridine-4-carbothioamide (2.9 g, 21 mmol) in ethanol (150 mL) was added ethyl 2-bromo-3-oxo-3-phenylpropanoate (5.9 g, 22 mmol), and the mixture was heated under reflux for 8 hr. The reaction solution was allowed to cool to room temperature, and the solid was collected by filtration, washed with diethyl ether, dried, suspended in ethyl acetate (250 mL), and washed with saturated aqueous sodium bicarbonate solution (150 mL×2). The combined aqueous layer was extracted with ethyl acetate (100 mL×2). The combined organic layer was dried over anhydrous magnesium sulfate, the insoluble material was filtered off, and the filtrate was concentrated under reduced pressure. The residue was washed with diethyl ether, and collected by filtration to give the title compound (3.7 g, 57%) as a colorless solid.

$^1$H-NMR (DMSO-$d_6$, 300 MHz) δ 1.24 (3H, t, J=7.2 Hz), 4.27 (2H, q, J=7.2 Hz), 7.47-7.52 (3H, m), 7.79-7.82 (2H, m), 8.00-8.02 (2H, m), 8.77-8.79 (2H, m).

(ii) Production of ethyl 2-(1-oxidopyridin-4-yl)-4-phenyl-1,3-thiazole-5-carboxylate To a suspension of ethyl 4-phenyl-2-pyridin-4-yl-1,3-thiazole-5-carboxylate (2.6 g, 8.5 mmol) produced above in acetonitrile (300 mL) was added m-chloroperbenzoic acid (containing water, about 70%, 3.9 g, about 16.0 mmol), and the mixture was stirred at room temperature for 2 days. The reaction solution was concentrated under reduced pressure to about 100 mL, and the obtained suspension was diluted with ethyl acetate (300 mL), and washed successively with saturated aqueous sodium bisulfite solution (150 mL×2) and saturated aqueous sodium carbonate solution (150 mL×2). The combined aqueous layer was extracted with ethyl acetate (200 mL×2). The combined organic layer was dried over anhydrous magnesium sulfate, the insoluble material was filtered off, and the filtrate was concentrated under reduced pressure. The obtained solid was washed with ethyl acetate, and collected by filtration to give the title compound (2.0 g, 72%) as a yellow solid.

$^1$H-NMR (DMSO-$d_6$, 300 MHz) δ 1.23 (3H, t, J=6.9 Hz), 4.26 (2H, q, J=6.9 Hz), 7.46-7.51 (3H, m), 7.76-7.82 (2H, m), 8.03-8.07 (2H, m), 8.31-8.35 (2H, m).

(iii) Production of ethyl 2-(2-chloropyridin-4-yl)-4-phenyl-1,3-thiazole-5-carboxylate Ethyl 2-(1-oxidopyridin-4-yl)-4-phenyl-1,3-thiazole-5-carboxylate (1.8 g, 5.6 mmol) produced above was suspended in phosphorus oxychloride (31 g), and the mixture was heated under reflux for 4 hr. The obtained solution was allowed to cool to room temperature, and concentrated under reduced pressure. The obtained residue was dissolved in tetrahydrofuran (100 mL), saturated aqueous sodium bicarbonate solution (100 mL) was added to the obtained solution, and the mixture was vigorously stirred at room temperature for 1 hr. Ethyl acetate (150 mL) was added, and the aqueous layer was separated. The organic layer was washed with saturated aqueous ammonium chloride solution (100 mL). The combined aqueous layer was extracted with ethyl acetate (100 mL×2). The combined organic layer was dried over anhydrous magnesium sulfate, the insoluble material was filtered off, and the filtrate was concentrated under reduced pressure to give the title compound (1.9 g, 100%) as a yellow solid.

$^1$H-NMR ($CDCl_3$, 300 MHz) δ 1.24 (3H, t, J=7.2 Hz), 4.28 (2H, q, J=7.2 Hz), 7.48-7.52 (3H, m), 7.80-7.83 (2H, m), 8.05 (1H, dd, J=1.5, 5.3 Hz), 8.09-8.16 (1H, m), 8.61 (1H, dd, J=0.7, 5.3 Hz).

(iv) Production of 2-(2-chloropyridin-4-yl)-4-phenyl-1,3-thiazole-5-carboxylic acid To a solution of ethyl 2-(2-chloropyridin-4-yl)-4-phenyl-1,3-thiazole-5-carboxylate (540 mg, 1.6 mmol) produced above in tetrahydrofuran (20 mL) and methanol (20 mL) were added water (20 mL) and 8N aqueous sodium hydroxide solution (1 mL), and the mixture was heated under reflux for 90 min. The reaction solution was cooled to 0° C., and 6N hydrochloric acid (1.5 mL) was added to adjust the solution to about pH 5.0. The resulting solid was collected by filtration, washed with water, ethanol and diethyl ether and dried to give the title compound (260 mg, 52%) as a pale-yellow solid. The filtrate was extracted with ethyl acetate (100 mL×2), and the organic layer was washed with saturated ammonium chloride (50 mL) and dried over anhydrous magnesium sulfate. The insoluble material was filtered off, and the filtrate was concentrated under reduced pressure to give a second crop (260 mg) of the title compound.

$^1$H-NMR (DMSO-$d_6$, 300 MHz) δ 7.43-7.53 (3H, m), 7.77-7.88 (2H, m), 8.02 (1H, dd, J=1.5, 5.3 Hz), 8.09 (1H, dd, J=0.6, 1.5 Hz), 8.60 (1H, dd, J=0.6, 5.3 Hz), 13.76 (1H, br s).

(v) Production of 2-(2-chloropyridin-4-yl)-4-phenyl-1,3-thiazole-5-carboxamide

To a suspension of 2-(2-chloropyridin-4-yl)-4-phenyl-1,3-thiazole-5-carboxylic acid (480 mg, 1.5 mmol) produced above in toluene (50 mL) was added thionyl chloride (5.0 mL, 68 mmol), and the mixture was heated under reflux for 8 hr. The obtained solution was allowed to cool to room temperature, and concentrated under reduced pressure, and the obtained residue was dissolved in tetrahydrofuran (50 mL). 25% Aqueous ammonia (50 mL) was added, and the mixture was vigorously stirred for 90 min. The aqueous layer was separated, and the organic layer was diluted with ethyl acetate (150 mL), and washed with saturated aqueous ammonium chloride solution (100 mL). The combined aqueous layer was extracted with ethyl acetate (100 mL). The combined organic layer was dried over anhydrous magnesium sulfate, and decolorized with activated carbon, and the insoluble material was filtered off. The filtrate was concentrated under reduced pressure, and the obtained solid was recrystallized from ethyl acetate to give the title compound (250 mg, 53%) as a pale-yellow solid. The mother liquor was concentrated to give a second crop (220 mg, 46%) of the title compound (total yield 99%).

$^1$H-NMR (DMSO-$d_6$, 300 MHz) δ 7.40-7.57 (3H, m), 7.78-7.88 (2H, m), 7.88-8.05 (3H, m), 8.08 (1H, d, J=0.6 Hz), 8.59 (1H, dd, J=0.6, 5.1 Hz).

(vi) Production of 2-chloro-4-[4-phenyl-5-(4H-1,2,4-triazol-3-yl)-1,3-thiazol-2-yl]pyridine 2-(2-Chloropyridin-4-yl)-4-phenyl-1,3-thiazole-5-carboxamide (370 mg, 1.2 mmol) produced above was suspended in N,N-dimethylformamide dimethyl acetal (10 mL), and the mixture was stirred at 120° C. for 3 hr. The obtained solution was allowed to cool to room temperature, and concentrated under reduced pressure. The obtained solid was suspended in acetic acid (50 mL), hydrazine monohydrate (2 mL, 41 mmol) was added, and the mixture was stirred at 100° C. for 8 hr. The reaction solution was allowed to cool to room temperature, and concentrated under reduced pressure. The residue was diluted with saturated aqueous sodium bicarbonate solution (100 mL), and extracted with a mixed solvent of ethyl acetate-methanol (9:1, 50 mL×2). The combined organic layer was washed with saturated aqueous ammonium chloride solution (50 mL) and dried over anhydrous magnesium sulfate, and the insoluble material was filtered off. The filtrate was concentrated under reduced pressure. The obtained residue was purified by silica gel column chromatography (ethyl acetate/hexane=80/20→100/0) to give the title compound (130 mg, 33%) as a yellow solid.

$^1$H-NMR (DMSO-$d_6$, 300 MHz) δ 7.38-7.50 (3H, m), 7.82-7.91 (2H, m), 8.01 (1H, dd, J=1.5, 5.3 Hz), 8.06-8.11 (1H, m), 8.58 (1H, dd, J=0.6, 5.3 Hz), 8.67 (1H, s), 14.39 (1H, br s).

Example 11-B

Production of 2-methyl-3-[4-phenyl-5-(4H-1,2,4-triazol-3-yl)-1,3-thiazol-2-yl]pyrazolo[1,5-a]pyridine p-toluenesulfonate

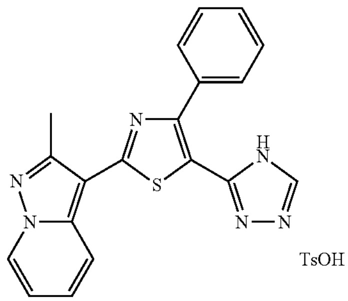

TsOH (i) Production of ethyl 2-methylpyrazolo[1,5-a]pyridine-3-carboxylate

To a suspension of 1-aminopyridinium iodide (125 g, 0.56 mmol) in N,N-dimethylformamide (1.2 L) were added ethyl 2-butynoate (54.0 g, 0.48 mmol) and potassium carbonate (79 g, 0.36 mmol) and the mixture was stirred at room temperature for 3 days. The reaction mixture was diluted with water (500 mL), ethyl acetate (500 mL) and hexane (500 mL), and the precipitated solid was collected by filtration, and washed with water (500 mL). The filtrate was extracted with a mixed solvent (1.5 L×2) of ethyl acetate/hexane (1:1) and dried over anhydrous magnesium sulfate, and the insoluble material was filtered off. The residue obtained by concentration of the filtrate and the solid collected by filtration in the above were combined, washed with diethyl ether (25 mL) and hexane (25 mL) and dried to give the title compound (36.0 g, 37%) as a white solid. The washing solution was concentrated, and the obtained residue was washed with diethyl ether (10 mL) and hexane (10 mL) and dried to give a second crop (11.0 g, 11%) of the title compound as a white solid. The washing solution of the second crop was concentrated, and the obtained residue was purified using a pad (elution solvent: ethyl acetate/hexane=1/1) with silica gel and activated carbon in 2 layers, washed with diethyl ether (5.0 mL) and hexane (5.0 mL) and dried to give a third crop (6.5 g, 7%) of the title compound as a white solid (total yield 55%).

$^1$H-NMR (DMSO-$d_6$, 300 MHz) δ 1.35 (3H, t, J=7.2 Hz), 2.57 (3H, s), 4.30 (2H, q, J=7.2 Hz), 7.09 (1H, dt, J=1.5, 6.9 Hz), 7.49-7.61 (1H, m), 8.00 (1H, td, J=1.3 Hz), 8.75 (1H, td, J=1.0, 6.9 Hz).

(ii) Production of 2-methylpyrazolo[1,5-a]pyridine-3-carboxylic acid

To a solution of ethyl 2-methylpyrazolo[1,5-a]pyridine-3-carboxylate (52 g, 260 mmol) produced above in tetrahydrofuran (300 mL) and methanol (200 mL) was added 8N aqueous sodium hydroxide solution (100 mL, 800 mmol), and the mixture was stirred at 70° C. for 3.5 hr. The reaction solution was cooled to room temperature, tetrahydrofuran and methanol were evaporated under reduced pressure, and the mixture was concentrated to about 150 mL. 6N Hydrochloric acid (130 mL, 780 mmol) and 1N hydrochloric acid (20.0 mL, 20.0 mmol) were added to the residue, and the mixture was diluted with water (500 mL). The resulting white precipitate was collected by filtration, washed with water (600 mL), ethanol (300 mL) and diethyl ether (300 mL) and dried to give the title compound (43 g, 96%) as a white solid.

$^1$H-NMR (DMSO-$d_6$, 300 MHz) δ 2.57 (3H, s), 6.94-7.16 (1H, m), 7.50 (1H, ddd, J=1.1, 6.9, 8.8 Hz), 8.01 (1H, td, J=1.3, 8.8 Hz), 8.72 (1H, td, J=1.1, 6.9 Hz), 12.31 (1H, br s).

(iii) Production of 2-methylpyrazolo[1,5-a]pyridine-3-carboxamide

To a suspension of 2-methylpyrazolo[1,5-a]pyridine-3-carboxylic acid (41 g, 230 mmol) produced above in toluene (500 mL) was added dropwise thionyl chloride (150 g, 1.2 mol), and the mixture was heated under reflux for 2 hr. The reaction mixture was cooled to room temperature, and toluene and thionyl chloride were evaporated under reduced pressure. The obtained solid was dissolved in tetrahydrofuran (400 mL), 25% aqueous ammonia solution (180 mL) was gradually added under ice-cooling, and the mixture was stirred at room temperature for 12 hr. The resulting yellow solid was collected by filtration, washed with water (100 mL) and dried to give the title compound (38 g, 89%) as a yellow solid. The filtrate and washing solution were extracted with ethyl acetate (300 mL×2), and a mixed solvent of ethyl acetate (200 mL) and tetrahydrofuran (100 mL), and the extract was dried over anhydrous magnesium sulfate. The insoluble material was filtered off, and the filtrate was concentrated to give a second crop (2.7 g, 6.0%) of the title compound as a yellow solid (total yield 95%).

$^1$H-NMR (DMSO-$d_6$, 300 MHz) δ 2.56 (3H, s), 6.96 (1H, dt, J=1.2, 6.9 Hz), 7.09 (2H, br s), 7.38 (1H, ddd, J=1.2, 6.9, 9.0 Hz), 7.96 (1H, td, J=1.2, 9.0 Hz), 8.64 (1H, td, J=1.2, 6.9 Hz)

(iv) Production of 2-methylpyrazolo[1,5-a]pyridine-3-carbonitrile

2-Methylpyrazolo[1,5-a]pyridine-3-carboxamide (41 g, 233 mmol) produced above was suspended in phosphorus oxychloride (270 g, 1.8 mol), and the mixture was heated under reflux at 80° C. for 2 hr. The reaction mixture was cooled to room temperature, and phosphorus oxychloride was evaporated under reduced pressure. The obtained residue was diluted with toluene (100 mL) and ice-cooled saturated aqueous sodium bicarbonate solution (200 mL). Then, ethyl acetate (200 mL) and 1N aqueous sodium hydroxide solution (1.00 L) were added, and the mixture was stirred. The aqueous layer was separated, and extracted 3 times with a mixed solvent of ethyl acetate (300 mL) and tetrahydrofuran (100 mL). The collected organic layer was dried over anhydrous magnesium sulfate, and decolorized with activated carbon. The insoluble material was filtered off, and the filtrate was concentrated to give the title compound (35 g, 95%) as a white solid.

$^1$H-NMR (DMSO-$d_6$, 300 MHz) δ 2.50 (3H, s), 7.15 (1H, dt, J=1.2, 6.9 Hz), 7.59 (1H, ddd, J=1.2, 6.9, 8.8 Hz), 7.81 (1H, td, J=1.2, 8.8 Hz), 8.83 (1H, td, J=1.2, 6.9 Hz, 1H).

(v) Production of 2-methylpyrazolo[1,5-a]pyridine-3-carbothioamide hydrochloride To a solution of 2-methylpyrazolo[1,5-a]pyridine-3-carbonitrile (34.9 g, 220 mmol) produced above in methanol (300 mL) were added 4N hydrogen chloride ethyl acetate solution (150 mL, 600 mmol) and O,O'-diethyl dithiophosphate (250 g, 1.3 mol), and the mixture was stirred at 60° C. for 75 min. The reaction solution was diluted with ethyl acetate (50 mL), and cooled to room temperature. Diisopropyl ether (350 mL) was added, and the mixture was stirred at 0° C. for 1 hr. The resulting yellow solid was collected by filtration, washed with diethyl ether (150 mL) and dried to give the title compound (39 g, 77%) as a yellow solid.

$^1$H-NMR (DMSO-$d_6$, 300 MHz) δ 2.57 (3H, s), 6.99 (1H, dt, J=1.4, 6.9 Hz), 7.42 (1H, ddd, J=1.1, 6.9, 9.0 Hz), 8.24 (1H, td, J=1.2, 8.9 Hz), 8.65 (1H, td, J=1.1, 6.9 Hz), 8.74 (1H, br s).

(vi) Production of ethyl 2-(2-methylpyrazolo[1,5-a]pyridin-3-yl)-4-phenyl-1,3-thiazole-5-carboxylate A mixture of 2-methylpyrazolo[1,5-a]pyridine-3-carbothioamide (400 mg, 2.1 mmol) produced in the same manner as above, ethyl 2-bromo-3-oxo-3-phenylpropanoate (569 mg, 2.1 mmol) and ethanol (10 mL) was stirred at 80° C. for 4 hr. To the reaction mixture were added aqueous sodium bicarbonate solution, ethyl acetate and tetrahydrofuran, and the insoluble material was filtered off. The filtrate was extracted with a mixed solvent of ethyl acetate and tetrahydrofuran. The collected organic layer was washed with saturated brine and dried over anhydrous magnesium sulfate, and the insoluble material was filtered off. The filtrate was concentrated under reduced pressure, the obtained residue was purified by silica gel column chromatography (ethyl acetate/hexane=20/80→100/0), and the crude purified product was washed with diisopropyl ether to give the title compound (273 mg, 36%) as a pale-yellow solid.

$^1$H-NMR (DMSO-$d_6$, 300 MHz) δ 1.24 (3H, t, J=7.2 Hz), 2.71 (3H, s), 4.25 (2H, q, J=7.2 Hz), 7.12 (1H, dt, J=1.2, 6.8 Hz), 7.45-7.55 (3H, m), 7.59 (1H, ddd, J=1.2, 6.8, 8.9 Hz), 7.80-7.89 (2H, m), 8.36 (1H, td, J=1.2, 8.9 Hz), 8.80 (1H, td, J=1.2, 6.8 Hz).

(vii) Production of 2-(2-methylpyrazolo[1,5-a]pyridin-3-yl)-4-phenyl-1,3-thiazole-5-carboxylic acid A mixture of ethyl 2-(2-methylpyrazolo[1,5-a]pyridin-3-yl)-4-phenyl-1,3-thiazole-5-carboxylate (250 mg, 0.7 mmol) produced above, 1N aqueous sodium hydroxide solution (2 mL), methanol (5 mL) and tetrahydrofuran (5 mL) was stirred at 60° C. for 1 hr. The reaction mixture was concentrated under reduced pressure to about ½ volume, and 1N hydrochloric acid (2 mL) and water were added. The resulting precipitate was collected by filtration, washed with water and diethyl ether and dried to give the title compound (230 mg, 98%) as a pale-yellow solid.

$^1$H-NMR (DMSO-$d_6$, 300 MHz) δ 2.70 (3H, s), 7.11 (1H, dt, J=1.2, 6.8 Hz), 7.42-7.53 (3H, m), 7.57 (1H, ddd, J=1.2, 6.8, 8.9 Hz), 7.83-7.92 (2H, m), 8.35 (1H, td, J=1.2, 8.9 Hz), 8.79 (1H, td, J=1.2, 6.8 Hz), 13.24 (1H, br s).

(viii) Production of 2-(2-methylpyrazolo[1,5-a]pyridin-3-yl)-4-phenyl-1,3-thiazole-5-carboxamide A mixture of 2-(2-methylpyrazolo[1,5-a]pyridin-3-yl)-4-phenyl-1,3-thiazole-5-carboxylic acid (230 mg, 0.69 mmol) produced above, ammonium chloride (110 mg, 2.1 mmol), triethylamine (0.29 mL, 2.1 mmol), N-[3-(dimethylamino)propyl]-N'-ethylcarbodiimide hydrochloride (200 mg, 1.1 mmol), 1-hydroxybenzotriazole (140 mg, 1.1 mmol) and N,N-dimethylformamide (10 mL) was stirred at room temperature for 1 day. The reaction mixture was concentrated under reduced pressure, and water was added to the obtained residue. The resulting precipitate was collected by filtration, washed with water and diethyl ether and dried to give the title compound (210 mg, 93%) as a colorless solid.

$^1$H-NMR (DMSO-$d_6$, 300 MHz) δ 2.70 (3H, s), 7.09 (1H, dt, J=1.2, 6.8 Hz), 7.40-7.60 (4H, m), 7.68 (2H, br s), 7.83-7.90 (2H, m), 8.35 (1H, td, J=1.2, 8.8 Hz), 8.78 (1H, td, J=1.2, 6.8 Hz).

(ix) Production of 2-methyl-3-[4-phenyl-5-(4H-1,2,4-triazol-3-yl)-1,3-thiazol-2-yl]pyrazolo[1,5-a]pyridine p-toluenesulfonate A mixture of 2-(2-methylpyrazolo[1,5-a]pyridin-3-yl)-4-phenyl-1,3-thiazole-5-carboxamide (200 mg, 0.6 mmol) produced above and N,N-dimethylformamide dimethyl acetal (5 mL) was stirred at 100° C. for 2 hr. The reaction mixture was concentrated under reduced pressure, hydrazine monohydrate (0.29 mL, 6.0 mmol) and acetic acid (10 mL) were added to the obtained residue, and the mixture was stirred at 100° C. for 2 hr. The reaction mixture was concentrated under reduced pressure, and aqueous sodium bicarbonate solution and diethyl ether were added to the obtained residue. The resulting precipitate was collected by filtration, washed with water and diethyl ether and dried to give 2-methyl-3-[4-phenyl-5-(4H-1,2,4-triazol-3-yl)-1,3-thiazol-2-yl]pyrazolo[1,5-a]pyridine (210 mg, 98%) as a pale-yellow solid. The obtained 2-methyl-3-[4-phenyl-5-(4H-1,2,4-triazol-3-yl)-1,3-thiazol-2-yl]pyrazolo[1,5-a]pyridine (90 mg, 0.25 mmol) and p-toluenesulfonic acid monohydrate (57 mg, 0.3 mmol) were dissolved in ethanol (6 mL) by heating, and the mixture was concentrated under reduced pressure. The obtained residue was crystallized from ethanol and ethyl acetate to give the title compound (93 mg, 70%) as a pale-orange solid.

$^1$H-NMR (DMSO-$d_6$, 300 MHz) δ 2.29 (3H, s), 2.73 (3H, s), 7.05-7.15 (3H, m), 7.36-7.51 (5H, m), 7.55 (1H, ddd, J=1.0, 6.8, 8.8 Hz), 7.87-7.94 (2H, m), 8.38 (1H, td, J=1.0, 8.8 Hz), 8.62 (1H, s), 8.78 (1H, d, J=6.8 Hz).

Example 12-B

Production of 3-[4-phenyl-5-(4H-1,2,4-triazol-3-yl)-1,3-thiazol-2-yl]pyrazolo[1,5-a]pyridine

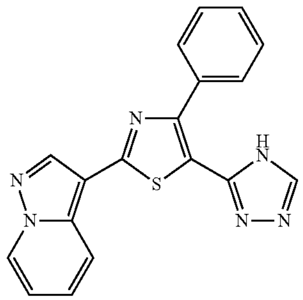 [SMILES: c1ccc(-c2nc(-c3cnn4ccccc34)sc2-c2nnc[nH]2)cc1]

(i) Production of ethyl 2-(pyrazolo[1,5-a]pyridin-3-yl)-4-phenyl-1,3-thiazole-5-carboxylate To a suspension of commercially available pyrazolo[1,5-a]pyridine-3-carbothioamide (580 mg, 3.3 mmol) in ethanol (20 mL) was added ethyl 2-bromo-3-oxo-3-phenylpropanoate (1.0 g, 3.7 mmol), and the mixture was heated under reflux for 11 hr. The reaction solution was allowed to cool to room temperature, and the resulting solid was collected by filtration and washed with methanol. The collected filtrate and washing solution was concentrated under reduced pressure, and the obtained residue was suspended in ethyl acetate (100 mL). The obtained suspension was washed with saturated aqueous sodium bicarbonate solution (50 mL×2), and the collected aqueous layer was extracted with ethyl acetate (50 mL). The collected organic layer was dried over anhydrous magnesium sulfate, the insoluble material was filtered off, and the filtrate was concentrated under reduced pressure. The obtained residue was purified by silica gel column chromatography (ethyl acetate/hexane=5/95→100/0) to give the title compound (360 mg, 31%) as a yellow solid.

$^1$H-NMR (DMSO-$d_6$, 300 MHz) δ 1.23 (3H, t, J=7.1 Hz), 4.24 (2H, q, J=7.1 Hz), 7.17 (1H, dt, J=1.2, 6.9 Hz), 7.44-7.53 (3H, m), 7.62 (1H, ddd, 1.2, 6.9, 8.9 Hz), 7.78-7.88 (2H, m), 8.33 (1H, d, J=8.9 Hz), 8.77 (1H, s), 8.90 (1H, d, J=6.9 Hz).

(ii) Production of 2-(pyrazolo[1,5-a]pyridin-3-yl)-4-phenyl-1,3-thiazole-5-carboxylic acid To a solution of ethyl 2-(pyrazolo[1,5-a]pyridin-3-yl)-4-phenyl-1,3-thiazole-5-carboxylate produced above in hot methanol (20 mL) was added 1N aqueous sodium hydroxide solution (5 mL), and the mixture was heated under reflux for 30 min. The reaction solution was cooled to 0° C., and 6N hydrochloric acid (1 mL) was added to adjust the solution to about pH 5.0. The resulting solid was collected by filtration, and washed with methanol and diethyl ether to give the title compound (192 mg, 58%). The combined filtrate and washing solution was concentrated under reduced pressure to give a second crop (110 mg, including slight amount of sodium chloride) of the title compound.

$^1$H-NMR (DMSO-$d_6$, 300 MHz) δ 7.16 (1H, dt, J=1.2, 6.9 Hz), 7.42-7.52 (3H, m), 7.60 (1H, ddd, 1.2, 6.9, 8.9 Hz), 7.80-7.90 (2H, m), 8.33 (1H, d, J=8.9 Hz), 8.73 (1H, s), 8.89 (1H, d, J=6.9 Hz), 13.25 (1H, br s).

(iii) Production of 2-(pyrazolo[1,5-a]pyridin-3-yl)-4-phenyl-1,3-thiazole-5-carboxamide To a suspension of 2-(pyrazolo[1,5-a]pyridin-3-yl)-4-phenyl-1,3-thiazole-5-carboxylic acid (263 mg, 0.82 mmol) produced above in toluene (50 mL) was added thionyl chloride (3 mL, 41 mol), and the mixture was heated under reflux for 2 hr. The obtained solution was allowed to cool to room temperature, and concentrated under reduced pressure, and the obtained residue was used as an acid chloride for the next reaction.

The acid chloride produced above was dissolved in tetrahydrofuran (50 mL), 25% aqueous ammonia (30 mL) was added, and the mixture was vigorously stirred for 1 hr. The aqueous layer was separated, and extracted with ethyl acetate (50 mL×2). The collected organic layer was dried over anhydrous magnesium sulfate, and the insoluble material was filtered off. The filtrate was concentrated under reduced pressure to give the title compound (260 mg, 99%) as a yellow solid.

$^1$H-NMR (DMSO-$d_6$, 300 MHz) δ 7.15 (1H, dt, J=1.3, 6.9 Hz), 7.38-7.54 (3H, m), 7.59 (1H, ddd, 0.9, 6.9, 8.8 Hz), 7.69 (2H, br s), 7.82-7.91 (2H, m), 8.35 (1H, ddd, J=0.9, 1.3, 8.8 Hz), 8.67 (1H, s), 8.88 (1H, d, J=6.9 Hz).

(iv) Production of 3-[4-phenyl-5-(4H-1,2,4-triazol-3-yl)-1,3-thiazol-2-yl]pyrazolo[1,5-a]pyridine 2-(Pyrazolo[1,5-a]pyridin-3-yl)-4-phenyl-1,3-thiazole-5-carboxamide (200 mg, 0.62 mmol) produced above was suspended in N,N-dimethylformamide dimethyl acetal (20 mL), and the mixture was heated under reflux for 1 hr. The obtained solution was allowed to cool to room temperature, and concentrated under reduced pressure. The obtained residue was suspended in acetic acid (10 mL), hydrazine monohydrate (0.5 mL) was added, and the mixture was stirred at 100° C. for 30 min. The reaction solution was allowed to cool to room temperature, and acetic acid was evaporated under reduced pressure. Saturated aqueous sodium bicarbonate solution (50 mL), tetrahydrofuran (20 mL) and ethyl acetate (50 mL) were added to the obtained residue, and the mixture was vigorously stirred for 15 min. The organic layer was separated, and the aqueous layer was extracted with ethyl acetate (50 mL). The collected organic layer was dried over anhydrous magnesium sulfate, the insoluble material was filtered off, and the filtrate was concentrated under reduced pressure. The residue was crystallized from tetrahydrofuran, ethyl acetate and diethyl ether to give the title compound (160 mg, 74%) as a colorless solid.

$^1$H-NMR (DMSO-$d_6$, 300 MHz) δ 7.14 (1H, dt, J=1.2, 6.8 Hz), 7.36-7.50 (3H, m), 7.59 (1H, ddd, J=1.2, 6.8, 8.8 Hz), 7.84-7.97 (2H, m), 8.37 (1H, td, J=1.2, 8.8 Hz), 8.61 (1H, s), 8.69 (1H, s), 8.88 (1H, d, J=6.8 Hz), 14.25 (1H, br s).

Example 13-B

Production of 3-[4-(3-fluorophenyl)-5-(4H-1,2,4-triazol-3-yl)-1,3-thiazol-2-yl]-2-methylpyrazolo[1,5-a]pyridine

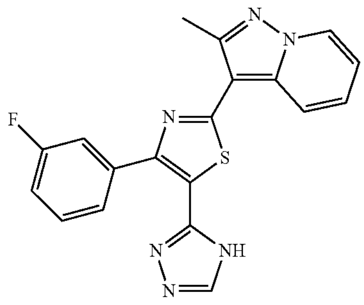 [SMILES: Cc1nn2ccccc2c1-c1nc(-c2cccc(F)c2)c(-c2nnc[nH]2)s1]

(i) Production of methyl 4-hydroxy-2-(2-methylpyrazolo[1,5-a]pyridin-3-yl)-1,3-thiazole-5-carboxylate A suspension of 2-methylpyrazolo[1,5-a]pyridine-3-carbothioamide hydrochloride (3.0 g, 13 mmol) produced in Example 11-B (v) and dimethyl chloromalonate (6.6 g, 40 mmol) in 2-propanol (40 mL) was stirred at 90° C. for 7 hr. The reaction mixture was cooled to room temperature, and the precipitated solid was collected by filtration, washed with ethyl acetate and diisopropyl ether and dried to give the title compound (3.1 g, 82%) as a yellow solid.

$^1$H-NMR (DMSO-$d_6$, 300 MHz) δ 2.64 (3H, s), 3.73 (3H, s), 7.11 (1H, dt, J=1.3, 6.8 Hz), 7.58 (1H, ddd, J=1.3, 6.8, 8.8 Hz), 8.36 (1H, td, J=1.3, 8.8 Hz), 8.76 (1H, td, J=1.3, 6.8 Hz), 11.78 (1H, s).

(ii) Production of methyl 2-(2-methylpyrazolo[1,5-a]pyridin-3-yl)-4-{[(trifluoromethyl)sulfonyl]oxy}-1,3-thiazole-5-carboxylate To a solution of methyl 4-hydroxy-2-(2-methylpyrazolo[1,5-a]pyridin-3-yl)-1,3-thiazole-5-carboxylate (2.0 g, 6.9 mmol) produced above in pyridine (150 mL) was added trifluoromethanesulfonic anhydride (9.4 g, 33 mmol) at 0° C., and the mixture was stirred at room temperature for 4 hr. The reaction solution was cooled to 0° C., saturated aqueous ammonium chloride solution (500 mL) and ethyl acetate (500 mL) were added, and the mixture was stirred for 30 min. The organic layer was washed with saturated brine and dried over anhydrous magnesium sulfate, and the insoluble material was filtered off. The filtrate was concentrated under reduced pressure. The obtained residue was purified by silica gel column chromatography (ethyl acetate) to give the title compound (2.8 g, 94%) as a yellow solid.

$^1$H-NMR (DMSO-$d_6$, 300 MHz) δ 2.67 (3H, s) 3.89 (3H, s) 7.21 (1H, dt, J=1.2, 6.8 Hz) 7.71 (1H, ddd, J=1.2, 6.8, 8.8 Hz), 8.18 (1H, td, J=1.2, 8.8 Hz), 8.87 (1H, td, J=1.2, 6.8 Hz).

(iii) Production of methyl 4-(3-fluorophenyl)-2-(2-methylpyrazolo[1,5-a]pyridin-3-yl)-1,3-thiazole-5-carboxylate Methyl 2-(2-methylpyrazolo[1,5-a]pyridin-3-yl)-4-{[(trifluoromethyl)sulfonyl]oxy}-1,3-thiazole-5-carboxylate (350 mg, 0.83 mmol) produced above, (3-fluorophenyl)boronic acid (480 mg, 3.4 mmol), [1,1-bis(diphenylphosphino)ferrocene]palladium(II) dichloride dichloromethane complex (75 mg, 0.092 mmol) and cesium carbonate (700 mg, 2.2 mmol) were suspended in 1,2-dimethoxyethane (30 mL), water (2 mL) was added, and the mixture was stirred at 80° C. for 1 hr. The reaction solution was cooled to room temperature, water (50 mL) was added, and the mixture was extracted with ethyl acetate (50 mL×2). The collected organic layer was dried over anhydrous magnesium sulfate, the insoluble material was filtered off, and the filtrate was concentrated. The obtained residue was purified by silica gel column chromatography (ethyl acetate) to give the title compound (127 mg, 42%) as a brown solid.

$^1$H-NMR (DMSO-$d_6$, 300 MHz) δ 2.65 (3H, s), 3.73 (3H, s), 7.00-7.85 (6H, m), 8.41-8.53 (1H, m), 8.88 (1H, d, J=6.8 Hz).

(iv) Production of 4-(3-fluorophenyl)-2-(2-methylpyrazolo[1,5-a]pyridin-3-yl)-1,3-thiazole-5-carboxylic acid To a solution of methyl 4-(3-fluorophenyl)-2-(2-methylpyrazolo[1,5-a]pyridin-3-yl)-1,3-thiazole-5-carboxylate (120 mg, 0.27 mmol) purified above in methanol (15 mL) and tetrahydrofuran (25 mL) was added 8N aqueous sodium hydroxide solution (6 mL), and the mixture was stirred at 70° C. for 1 hr. The reaction solution was cooled to 0° C., 6N hydrochloric acid was added to adjust the solution to about pH 3.0, and the reaction solution was extracted with ethyl acetate (100 mL×2). The collected organic layer was dried over anhydrous magnesium sulfate, the insoluble material was filtered off, and the filtrate was concentrated to give the title compound (105 mg, 91%) as a yellow solid.

$^1$H-NMR (DMSO-$d_6$, 300 MHz) δ 2.76 (3H, s), 7.02-7.78 (6H, m), 8.43-8.51 (1H, m), 8.87 (1H, d, J=6.8 Hz).

(v) Production of 4-(3-fluorophenyl)-2-(2-methylpyrazolo[1,5-a]pyridin-3-yl)-1,3-thiazole-5-carboxamide A mixture of 4-(3-fluorophenyl)-2-(2-methylpyrazolo[1,5-a]pyridin-3-yl)-1,3-thiazole-5-carboxylic acid (120 mg, 0.34 mmol) produced above, ammonium chloride (4.0 g, 75 mmol), triethylamine (3 mL), 1-hydroxybenzotriazole (100 mg, 0.74 mmol), N-[3-(dimethylamino)propyl]-N'-ethylcarbodiimide hydrochloride (450 mg, 2.3 mmol) and N,N-dimethylformamide (15 mL) was stirred at room temperature for 10 hr. Water (100 mL) and ethyl acetate (100 mL) were added to the reaction solution, and the mixture was stirred for 30 min. The organic layer was washed with saturated brine and dried over anhydrous magnesium sulfate, the insoluble material was filtered off, and the filtrate was concentrated under reduced pressure. The obtained residue was purified by basic silica gel column chromatography (ethyl acetate) to give the title compound (76 mg, 63%) as a brown solid.

$^1$H-NMR (DMSO-$d_6$, 300 MHz) δ 2.76 (3H, s), 7.02-7.38 (4H, m), 7.46-7.84 (4H, m), 8.47 (1H, d, J=8.9 Hz), 8.88 (1H, d, J=6.8 Hz).

(vi) Production of 3-[4-(3-fluorophenyl)-5-(4H-1,2,4-triazol-3-yl)-1,3-thiazol-2-yl]-2-methylpyrazolo[1,5-a]pyridine A solution of 4-(3-fluorophenyl)-2-(2-methylpyrazolo[1,5-a]pyridin-3-yl)-1,3-thiazole-5-carboxamide (75 mg, 0.21 mmol) produced above in N,N-dimethylformamide dimethyl acetal (7 mL) was stirred with heating at 90° C. for 1 hr. The reaction solution was cooled to room temperature, the solvent was evaporated, and the residue was washed with hexane (5 mL) and diethyl ether (2 mL). The solvent was removed. The obtained residue was dissolved in acetic acid (10 mL), hydrazine monohydrate (0.3 mL) was added, and the mixture was stirred with heating at 80° C. for 1 hr. The reaction solution was cooled to room temperature, saturated aqueous sodium bicarbonate solution (50 mL) and ethyl acetate (50 mL) were added, and the mixture was stirred for 30 min. The organic layer was washed with saturated brine and dried over anhydrous magnesium sulfate, and the insoluble material was filtered off. The filtrate was concentrated under reduced pressure, and the obtained residue was washed with ethyl acetate (2 mL) and diethyl ether (10 mL) to give the title compound (43 mg, 54%) as a brown solid.

$^1$H-NMR (DMSO-$d_6$, 300 MHz) δ 2.73 (3H, s), 7.09 (1H, dt, J=1.3, 6.9 Hz), 7.19-7.30 (1H, m), 7.42-7.63 (2H, m), 7.76-7.92 (2H, m), 8.37 (1H, d, J=8.9 Hz), 8.61 (1H, s), 8.78 (1H, d, J=6.9 Hz).

Example 14-B

Production of 3-[4-ethoxy-5-(4H-1,2,4-triazol-3-yl)-1,3-thiazol-2-yl]-2-methylpyrazolo[1,5-a]pyridine

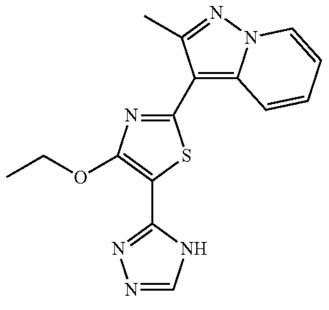 [SMILES: CCOc1nc(-c2c(C)nn3ccccc23)sc1-c1nnc[nH]1]

(i) Production of ethyl 4-hydroxy-2-(2-methylpyrazolo[1,5-a]pyridin-3-yl)-1,3-thiazole-5-carboxylate and ethyl 4-ethoxy-2-(2-methylpyrazolo[1,5-a]pyridin-3-yl)-1,3-thiazole-5-carboxylate A suspension of 2-methylpyrazolo[1,5-a]pyridine-3-carbothioamide hydrochloride (1.7 g, 7.5 mmol) produced in Example 11-B (v) and diethyl chloromalonate (2.0 g, 11 mmol) in 2-propanol (25 mL) was stirred at 90° C. for 4 hr with heating. The reaction mixture was cooled to room temperature, and the precipitated solid was collected by filtration and dried to give ethyl 4-hydroxy-2-(2-methylpyrazolo[1,5-a]pyridin-3-yl)-1,3-thiazole-5-carboxylate (1.45 g, 64%) as a yellow solid.

$^1$H-NMR (DMSO-$d_6$, 300 MHz) δ 1.27 (3H, t, J=7.1 Hz), 2.65 (3H, s), 4.23 (2H, q, J=7.1 Hz), 7.12 (1H, dt, J=1.3, 6.8 Hz), 7.51-7.65 (1H, m), 8.36 (1H, d, J=8.9 Hz), 8.79 (1H, d, J=6.8 Hz), 11.76 (1H, s).

Saturated aqueous sodium bicarbonate solution (100 mL) and ethyl acetate (100 mL) were added to the filtrate, and the mixture was stirred for 30 min. The organic layer, was dried over anhydrous magnesium sulfate, the insoluble material was filtered off, and the filtrate was concentrated. The obtained residue was purified by silica gel column chromatography (ethyl acetate) to give ethyl 4-ethoxy-2-(2-methylpyrazolo[1,5-a]pyridin-3-yl)-1,3-thiazole-5-carboxylate (200 mg, 32%) as a yellow solid.

$^1$H-NMR (DMSO-$d_6$, 300 MHz) δ 1.27 (3H, t, J=7.1 Hz), 1.42 (3H, t, J=6.9 Hz), 2.65 (3H, s), 4.23 (2H, q, J=7.1 Hz), 4.61 (2H, q, J=6.9 Hz), 7.12 (1H, dt, J=1.3, 6.9 Hz), 7.55-7.69 (1H, m), 8.32 (1H, d, J=8.9 Hz), 8.79 (1H, d, J=6.9 Hz).

(ii) Production of 4-ethoxy-2-(2-methylpyrazolo[1,5-a]pyridin-3-yl)-1,3-thiazole-5-carboxylic acid Using ethyl 4-ethoxy-2-(2-methylpyrazolo[1,5-a]pyridin-3-yl)-1,3-thiazole-5-carboxylate (500 mg, 0.27 mmol) produced above, methanol (10 mL), tetrahydrofuran (10 mL) and 8N aqueous sodium hydroxide solution (5 mL) as starting materials and in the same manner as in Example 13-B (iv), the title compound (435 mg, 95%) was obtained as a yellow solid.

$^1$H-NMR (DMSO-$d_6$, 300 MHz) δ 1.41 (3H, t, J=7.0 Hz), 2.65 (3H, s), 4.59 (2H, q, J=7.0 Hz), 7.12 (1H, dt, J=1.0, 6.8 Hz), 7.59 (1H, ddd, J=1.0, 6.8, 8.7 Hz), 8.29 (1H, d, J=8.7 Hz), 8.80 (1H, d, J=6.8 Hz), 12.54 (1H, s).

(iii) Production of 4-ethoxy-2-(2-methylpyrazolo[1,5-a]pyridin-3-yl)-1,3-thiazole-5-carboxamide Using 4-ethoxy-2-(2-methylpyrazolo[1,5-a]pyridin-3-yl)-1,3-thiazole-5-carboxylic acid (400 mg, 1.3 mmol) produced above, ammonium chloride (2.5 g, 47 mmol), triethylamine (3 mL), 1-hydroxybenzotriazole (250 mg, 1.9 mmol), N-[3-(dimethylamino)propyl]-N'-ethylcarbodiimide hydrochloride (1.2 g, 6.3 mmol) and N,N-dimethylformamide (50 mL) as starting materials and in the same manner as in Example 13-B(v), the title compound (390 mg, 98%) was obtained as a yellow solid.

$^1$H-NMR (DMSO-$d_6$, 300 MHz) δ 1.42-1.49 (3H, m), 2.65 (3H, s), 4.63 (2H, q, J=7.0 Hz), 6.87 (1H, s), 7.11 (111", dt, J=1.3, 6.8 Hz) 7.50-7.63 (2H, m), 8.25-8.35 (1H, m), 8.79 (1H, d, J=6.8 Hz).

(iv) Production of 3-[4-ethoxy-5-(4H-1,2,4-triazol-3-yl)-1,3-thiazol-2-yl]-2-methylpyrazolo[1,5-a]pyridine Using 4-ethoxy-2-(2-methylpyrazolo[1,5-a]pyridin-3-yl)-1,3-thiazole-5-carboxamide (200 mg, 0.66 mmol) produced above, N,N-dimethylformamide dimethyl acetal (45 mL), acetic acid (50 mL) and hydrazine monohydrate (0.5 mL) as starting materials and in the same manner as in Example 13-B(vi), the title compound (145 mg, 67%) was obtained as a yellow solid.

$^1$H-NMR (DMSO-$d_6$, 300 MHz) δ 1.46 (3H, t, J=7.0 Hz), 2.68 (3H, s), 4.62 (2H, q, J=7.0 Hz), 7.10 (1H, dt, J=1.2, 6.9 Hz), 7.57 (1H, ddd, J=1.2, 6.9, 8.9 Hz), 8.19 (1H, s), 8.28-8.38 (1H, m), 8.78 (1H, d, J=6.9 Hz), 13.83 (1H, s).

Example 15-B

Production of 2-methyl-3-[4-thiophen-3-yl-5-(4H-1,2,4-triazol-3-yl)-1,3-thiazol-2-yl]pyrazolo[1,5-a]pyridine

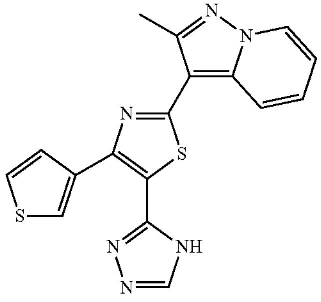 [SMILES: Cc1nn2ccccc2c1-c1nc(-c2ccsc2)c(-c2nnc[nH]2)s1]

(i) Production of ethyl 2-(2-methylpyrazolo[1,5-a]pyridin-3-yl)-4-{[(trifluoromethyl)sulfonyl]oxy}-1,3-thiazole-5-carboxylate Using ethyl 4-hydroxy-2-(2-methylpyrazolo[1,5-a]pyridin-3-yl)-1,3-thiazole-5-carboxylate (1.4 g, 4.7 mmol) produced in Example 14-B (i), pyridine (30 mL) and trifluoromethanesulfonic anhydride (3.3 g, 12 mmol) as starting materials and in the same manner as in Example 13-B (ii), the title compound (1.1 g, 53%) was obtained as a yellow solid.

$^1$H-NMR (DMSO-$d_6$, 300 MHz) δ 1.33 (3H, t, J=7.1 Hz), 2.68 (3H, s), 4.37 (2H, q, J=7.1 Hz), 7.21 (1H, dt, J=1.2, 6.9 Hz), 7.72 (1H, ddd, J=1.2, 6.9, 8.9 Hz), 8.16-8.21 (1H, m), 8.86-8.89 (1H, m).

(ii) Production of ethyl 2-(2-methylpyrazolo[1,5-a]pyridin-3-yl)-4-thiophen-3-yl-1,3-thiazole-5-carboxylate Using ethyl 2-(2-methylpyrazolo[1,5-a]pyridin-3-yl)-4-{[(trifluoromethyl)sulfonyl]oxy}-1,3-thiazole-5-carboxylate (170 mg, 0.39 mmol) produced above, thiophen-3-ylboronic acid (100 mg, 0.78 mmol), [1,1-bis(diphenylphosphino)ferrocene]palladium(II) dichloride dichloromethane complex (52 mg, 0.092 mmol), cesium carbonate (450 mg, 2.15 mmol), water (0.5 mL) and 1,2-dimethoxyethane (10 mL) as starting materials and in the same manner as in Example 13-B (iii), the title compound (121 mg, 83%) was obtained as a yellow solid.

$^1$H-NMR (DMSO-$d_6$, 300 MHz) δ 1.31 (3H, t, J=7.1 Hz), 2.71 (3H, s), 4.32 (2H, q, J=7.1 Hz), 7.14 (1H, dt, J=1.3, 6.9 Hz), 7.58-7.68 (2H, m), 7.86 (1H, dd, J=1.2, 5.1 Hz), 8.43 (1H, d, J=8.7 Hz), 8.48 (1H, dd, J=1.2, 3.0 Hz), 8.82 (1H, d, J=6.9 Hz).

(iii) Production of 2-(2-methylpyrazolo[1,5-a]pyridin-3-yl)-4-thiophen-3-yl-1,3-thiazole-5-carboxylic acid Using ethyl 2-(2-methylpyrazolo[1,5-a]pyridin-3-yl)-4-thiophen-3-yl-1,3-thiazole-5-carboxylate (150 mg, 0.27 mmol) produced above, methanol (5 mL), tetrahydrofuran (5 mL) and 8N aqueous sodium hydroxide solution (1 mL) as starting materials and in the same manner as in Example 13-B (iv), the title compound (139 mg, 99%) was obtained as a yellow solid.

$^1$H-NMR (DMSO-$d_6$, 300 MHz) δ 2.71 (3H, s), 7.11 (1H, dt, J=1.3, 6.9 Hz), 7.48-7.63 (2H, m), 7.94 (1H, d, J=5.1 Hz), 8.42 (1H, d, J=8.9 Hz), 8.56 (1H, s), 8.79 (1H, d, J=6.9 Hz).

(iv) Production of 2-(2-methylpyrazolo[1,5-a]pyridin-3-yl)-4-thiophen-3-yl-1,3-thiazole-5-carboxamide Using 2-(2-methylpyrazolo[1,5-a]pyridin-3-yl)-4-thiophen-3-yl-1,3-thiazole-5-carboxylic acid (110 mg, 0.32 mmol) produced above, ammonium chloride (1.2 g, 22 mmol), triethylamine (1.5 mL), 1-hydroxybenzotriazole (52 mg, 0.38 mmol), N-[3-(dimethylamino)propyl]-N'-ethylcarbodiimide hydrochloride (400 mg, 2.1 mmol) and N,N-dimethylformamide (25 mL) as starting materials and in the same manner as in Example 13-B (v), the title compound (95 mg, 87%) was obtained as a brown solid.

$^1$H-NMR (DMSO-$d_6$, 300 MHz) δ 2.70 (3H, s), 7.10 (1H, dt, J=1.3, 6.9 Hz), 7.53-7.97 (5H, m), 8.22 (1H, dd, J=1.3, 3.0 Hz), 8.40 (1H, dd, J=1.3, 8.9 Hz), 8.79 (1H, d, J=6.9 Hz).

v) Production of 2-methyl-3-[4-thiophen-3-yl-5-(4H-1,2,4-triazol-3-yl)-1,3-thiazol-2-yl]pyrazolo[1,5-a]pyridine Using 2-(2-methylpyrazolo[1,5-a]pyridin-3-yl)-4-thiophen-3-yl-1,3-thiazole-5-carboxamide (90 mg, 0.26 mmol) produced above, N,N-dimethylformamide dimethyl acetal (15 mL), acetic acid (15 mL) and hydrazine monohydrate (0.2 mL) as starting materials and in the same manner as in Example 13-B (vi), the title compound (71 mg, 74%) was obtained as a white solid.

$^1$H-NMR (DMSO-$d_6$, 300 MHz) δ 2.73 (3H, s), 7.09 (1H, dt, J=1.4, 6.8 Hz), 7.53-7.62 (2H, m), 7.91 (1H, d, J=5.1 Hz), 8.40-8.46 (1H, m), 8.60-8.68 (2H, m), 8.78 (1H, d, J=6.8 Hz).

Example 16-B

Production of 3-[4-benzyl-5-(4H-1,2,4-triazol-3-yl)-1,3-thiazol-2-yl]-2-methylpyrazolo[1,5-a]pyridine

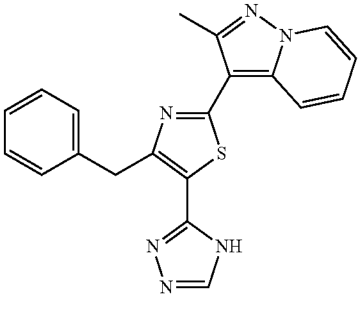 [SMILES: Cc1nn2ccccc2c1-c1nc(Cc2ccccc2)c(-c2nnc[nH]2)s1]

(i) Production of ethyl 4-benzyl-2-(2-methylpyrazolo[1,5-a]pyridin-3-yl)-1,3-thiazole-5-carboxylate Using ethyl 2-(2-methylpyrazolo[1,5-a]pyridin-3-yl)-4-{[(trifluoromethyl)sulfonyl]oxy}-1,3-thiazole-5-carboxylate (450 mg, 1.1 mmol) produced in Example 15(i), 2-benzyl-4,4,5,5-tetramethyl-1,3,2-dioxaborolane (1.0 g, 4.6 mmol), [1,1-bis(diphenylphosphino)ferrocene]palladium(II) dichloride dichloromethane complex (70 mg, 0.086 mmol), cesium carbonate (670 mg, 2.1 mmol), water (5 mL) and 1,2-dimethoxyethane (30 mL) as starting materials and in the same manner as in Example 13-B (iii), the title compound (174 mg, 43%) was obtained as a brown solid.

$^1$H-NMR (DMSO-$d_6$, 300 MHz) δ 1.32 (3H, t, J=7.1 Hz), 2.65 (3H, s), 4.34 (2H, q, J=7.1 Hz), 4.46-4.55 (2H, m), 7.05-7.42 (6H, m), 7.57 (1H, ddd, J=1.1, 6.8, 8.9 Hz), 8.24-8.33 (1H, m), 8.78 (1H, d, J=6.8 Hz).

(ii) Production of 4-benzyl-2-(2-methylpyrazolo[1,5-a]pyridin-3-yl)-1,3-thiazole-5-carboxylic acid Using ethyl 4-benzyl-2-(2-methylpyrazolo[1,5-a]pyridin-3-yl)-1,3-thiazole-5-carboxylate (150 mg, 0.41 mmol) produced above, methanol (10 mL), tetrahydrofuran (15 mL) and 8N aqueous sodium hydroxide solution (1 mL) as starting materials and in the same manner as in Example 13-B (iv), the title compound (92 mg, 64%) was obtained as a yellow solid.

$^1$H-NMR (DMSO-$d_6$, 300 MHz) δ 2.63 (3H, s), 4.52 (2H, s), 7.00-7.23 (2H, m), 7.23-7.44 (4H, m), 7.47-7.58 (1H, m), 8.23-8.31 (1H, m), 8.67-8.81 (1H, m).

(iii) Production of 4-benzyl-2-(2-methylpyrazolo[1,5-a]pyridin-3-yl)-1,3-thiazole-5-carboxamide Using 4-benzyl-2-(2-methylpyrazolo[1,5-a]pyridin-3-yl)-1,3-thiazole-5-carboxylic acid (90 mg, 0.26 mmol) produced above, ammonium chloride (300 mg, 5.6 mmol), triethylamine (2 mL), 1-hydroxybenzotriazole (70 mg, 0.5 mmol), N-[3-(dimethylamino)propyl]-N'-ethylcarbodiimide hydrochloride (250 mg, 1.3 mmol) and N,N-dimethylformamide (25 mL) as starting materials and in the same manner as in Example 13-B (v), the title compound (88 mg, 98%) was obtained as a yellow solid.

$^1$H-NMR (DMSO-$d_6$, 300 MHz) δ 2.64 (3H, s), 4.48 (2H, s), 7.04-7.42 (6H, m), 7.44-7.75 (3H, m), 8.20-8.26 (1H, m), 8.69-8.79 (1H, m).

(iv) Production of 3-[4-benzyl-5-(4H-1,2,4-triazol-3-yl)-1,3-thiazol-2-yl]-2-methylpyrazolo[1,5-a]pyridine Using 4-benzyl-2-(2-methylpyrazolo[1,5-a]pyridin-3-yl)-1,3-thiazole-5-carboxamide (85 mg, 0.73 mmol) produced above, N,N-dimethylformamide dimethyl acetal (25 mL), acetic acid (25 mL) and hydrazine monohydrate (0.4 mL) as starting materials and in the same manner as in Example 13-B(vi), the title compound (63 mg, 69%) was obtained as a yellow solid.

$^1$H-NMR (DMSO-$d_6$, 300 MHz) δ 2.67 (3H, s), 4.66 (2H, s), 7.05 (1H, dt, J=1.4, 6.9 Hz), 7.14-7.21 (1H, m), 7.24-7.32 (2H, m), 7.39-7.44 (2H, m), 7.47-7.55 (1H, m), 8.28 (1H, d, J=8.8 Hz), 8.67-8.80 (2H, m), 14.30 (1H, s).

Example 17-B

Production of 3-[4-(4-fluorophenyl)-5-(4H-1,2,4-triazol-3-yl)-1,3-thiazol-2-yl]-2-methylpyrazolo[1,5-a]pyridine

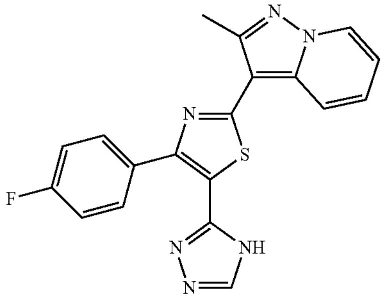 [SMILES: Cc1nn2ccccc2c1-c1nc(-c2ccc(F)cc2)c(-c2nnc[nH]2)s1]

(i) Production of ethyl 4-(4-fluorophenyl)-2-(2-methylpyrazolo[1,5-a]pyridin-3-yl)-1,3-thiazole-5-carboxylate Using ethyl 2-(2-methylpyrazolo[1,5-a]pyridin-3-yl)-4-{[(trifluoromethyl)sulfonyl]oxy}-1,3-thiazole-5-carboxylate (500 mg, 1.2 mmol) produced in Example 15-B(i), (4-fluorophenyl)boronic acid (480 mg, 3.4 mmol), [1,1-bis(diphenylphosphino)ferrocene]palladium(II) dichloride dichloromethane complex (75 mg, 0.091 mmol), cesium carbonate (700 mg, 2.2 mmol), water (2 mL) and 1,2-dimethoxyethane (30 mL) as starting materials and in the same manner as in Example 13-B(iii), the title compound (310 mg, 73%) was obtained as a brown solid.

$^1$H-NMR (DMSO-$d_6$, 300 MHz) δ 1.25 (3H, t, J=7.1 Hz), 2.69-2.72 (3H, s), 4.26 (2H, q, J=7.1 Hz), 7.09-7.39 (3H, m), 7.60 (1H, ddd, J=1.1, 7.2, 8.7 Hz), 7.79-8.00 (2H, m), 8.32-8.40 (1H, m), 8.75-8.85 (1H, m).

(ii) Production of 4-(4-fluorophenyl)-2-(2-methylpyrazolo[1,5-a]pyridin-3-yl)-1,3-thiazole-5-carboxylic acid Using ethyl 4-(4-fluorophenyl)-2-(2-methylpyrazolo[1,5-a]pyridin-3-yl)-1,3-thiazole-5-carboxylate (150 mg, 0.39 mmol) produced above, methanol (15 mL), tetrahydrofuran (15 mL) and 8N aqueous sodium hydroxide solution (1 mL) as starting materials and in the same manner as in Example 13-B (iv), the title compound (105 mg, 76%) was obtained as a white solid.

$^1$H-NMR (DMSO-$d_6$, 300 MHz) δ 2.70 (3H, s), 7.05-7.40 (3H, m), 7.52-7.64 (1H, m), 7.79-7.98 (2H, m), 8.35 (1H, d, J=8.6 Hz), 8.80 (1H, d, J=6.9 Hz), 13.29 (1H, s).

(iii) Production of 4-(4-fluorophenyl)-2-(2-methylpyrazolo[1,5-a]pyridin-3-yl)-1,3-thiazole-5-carboxamide Using 4-(4-fluorophenyl)-2-(2-methylpyrazolo[1,5-a]pyridin-3-yl)-1,3-thiazole-5-carboxylic acid (120 mg, 0.34 mmol) produced above, ammonium chloride (1.5 g, 28 mmol), N,N-dimethylformamide (30 mL), triethylamine (3 mL), 1-hydroxybenzotriazole (50 mg, 0.37 mmol) and N-[3-(dimethylamino)propyl]-N'-ethylcarbodiimide hydrochloride (1.0 g, 5.0 mmol) as starting materials and in the same manner as in Example 13-B(v), the title compound (101 mg, 84%) was obtained as a yellow solid.

$^1$H-NMR (DMSO-$d_6$, 300 MHz) δ 2.69 (3H, s), 7.10 (1H, dt, J=1.3, 6.9 Hz), 7.27-7.39 (2H, m), 7.51-7.61 (1H, m), 7.73 (2H, s), 7.88-7.95 (2H, m), 8.34 (1H, d, J=8.6 Hz), 8.79 (1H, d, J=6.9 Hz).

(iv) Production of 3-[4-(4-fluorophenyl)-5-(4H-1,2,4-triazol-3-yl)-1,3-thiazol-2-yl]-2-methylpyrazolo[1,5-a]pyridine Using 4-(4-fluorophenyl)-2-(2-methylpyrazolo[1,5-a]pyridin-3-yl)-1,3-thiazole-5-carboxamide (100 mg, 0.73 mmol) produced above, N,N-dimethylformamide dimethyl acetal (15 mL), acetic acid (25 mL) and hydrazine monohydrate (0.4 mL) as starting materials and in the same manner as in Example 13-B (vi), the title compound (73 mg, 68%) was obtained as a white solid.

$^1$H-NMR (DMSO-$d_6$, 300 MHz) δ 2.72 (3H, s), 7.09 (1H, dt, J=1.4, 6.8 Hz), 7.23-7.34 (2H, m), 7.55 (1H, ddd, J=1.1, 7.0, 8.9 Hz), 7.94-8.05 (2H, m), 8.32-8.41 (1H, m), 8.61 (1H, s), 8.75-8.81 (1H, m).

Example 18-B

Production of 3-[4-furan-3-yl-5-(4H-1,2,4-triazol-3-yl)-1,3-thiazol-2-yl]-2-methylpyrazolo[1,5-a]pyridine

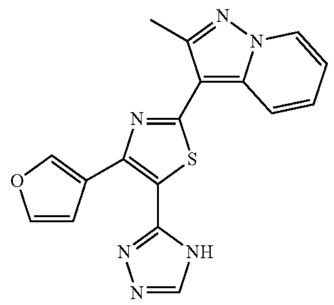 [SMILES: Cc1nn2ccccc2c1-c1nc(-c2ccoc2)c(-c2nnc[nH]2)s1]

(i) Production of methyl 4-furan-3-yl-2-(2-methylpyrazolo[1,5-a]pyridin-3-yl)-1,3-thiazole-5-carboxylate Using methyl 2-(2-methylpyrazolo[1,5-a]pyridin-3-yl)-4-{[(trifluoromethyl)sulfonyl]oxy}-1,3-thiazole-5-carboxylate (300 mg, 0.71 mmol) produced in Example 13-B (ii), furan-3-ylboronic acid (160 mg, 1.4 mmol), [1,1-bis(diphenylphosphino)ferrocene]palladium(II) dichloride dichloromethane complex (70 mg, 0.086 mmol), cesium carbonate (830 mg, 2.6 mmol), 1,2-dimethoxyethane (20 mL) and water (0.5 mL) as starting materials and in the same manner as in Example 13-B(iii), the title compound (225 mg, 93%) was obtained as a yellow solid.

$^1$H-NMR (DMSO-$d_6$, 300 MHz) δ 2.70 (3H, s), 3.87 (3H, s), 7.14 (1H, dt, J=1.3, 6.9 Hz), 7.31 (1H, dd, J=0.8, 1.9 Hz), 7.62 (1H, ddd, J=1.1, 7.0, 8.9 Hz), 7.84 (1H, t, J=1.8 Hz), 8.43-8.49 (1H, m), 8.70-8.72 (1H, m), 8.81 (1H, d, J=7.0 Hz).

(ii) Production of 4-furan-3-yl-2-(2-methylpyrazolo[1,5-a]pyridin-3-yl)-1,3-thiazole-5-carboxylic acid Using methyl 4-furan-3-yl-2-(2-methylpyrazolo[1,5-a]pyridin-3-yl)-1,3-thiazole-5-carboxylate (220 mg, 1.5 mmol) produced above, methanol (15 mL), tetrahydrofuran (15 mL) and 8N aqueous sodium hydroxide solution (1.5 mL) as starting materials and in the same manner as in Example 13-B (iv), the title compound (192 mg, 91%) was obtained as a white solid.

$^1$H-NMR (DMSO-$d_6$, 300 MHz) δ 2.70 (3H, s), 7.12 (1H, dt, J=1.3, 6.9 Hz), 7.32 (1H, d, J=1.9 Hz), 7.54-7.66 (1H, m), 7.80 (1H, t, J=1.9 Hz), 8.44 (1H, d, J=8.9 Hz), 8.70-8.72 (1H, m), 8.79 (1H, d, J=6.9 Hz).

(iii) Production of 4-furan-3-yl-2-(2-methylpyrazolo[1,5-a]pyridin-3-yl)-1,3-thiazole-5-carboxamide Using 4-furan-3-yl-2-(2-methylpyrazolo[1,5-a]pyridin-3-yl)-1,3-thiazole-5-carboxamide (200 mg, 0.61 mmol) produced above, ammonium chloride (2.1 g, 39 mmol), N,N-dimethylformamide (35 mL), triethylamine (3.0 mL), 1-hydroxybenzotriazole (50 mg, 0.37 mmol) and N-[3-(dimethylamino)propyl]-N'-ethylcarbodiimide hydrochloride (1.5 g, 7.8 mmol) as starting materials and in the same manner as in Example 13-B(v), the title compound (183 mg, 92%) was obtained as a white solid.

$^1$H-NMR (DMSO-$d_6$, 300 MHz) δ 2.70 (3H, s), 7.05-7.16 (2H, m), 7.57 (1H, ddd, J=1.0, 6.9, 8.9 Hz), 7.64-7.89 (3H, m), 8.37-8.44 (1H, m), 8.45-8.50 (1H, m), 8.78 (1H, d, J=6.9 Hz).

(iv) Production of 3-[4-furan-3-yl-5-(4H-1,2,4-triazol-3-yl)-1,3-thiazol-2-yl]-2-methylpyrazolo[1,5-a]pyridine Using 4-furan-3-yl-2-(2-methylpyrazolo[1,5-a]pyridin-3-yl)-1,3-thiazole-5-carboxamide (180 mg, 0.55 mmol) produced above, N,N-dimethylformamide dimethyl acetal (15 mL), acetic acid (25 mL) and hydrazine monohydrate (0.5 mL) as starting materials and in the same manner as in Example 13-B (vi), the title compound (143 mg, 74%) was obtained as a white solid.

$^1$H-NMR (DMSO-$d_6$, 300 MHz) δ 2.72 (3H, s), 7.07 (1H, dt, J=1.3, 6.9 Hz), 7.40 (1H, d, J=1.3 Hz), 7.55 (1H, ddd, J=1.1, 6.8, 8.9 Hz), 7.75 (1H, t, J=1.8 Hz), 8.37 (1H, d, J=1.3 Hz), 8.39-8.50 (1H, m), 8.76 (1H, d, J=6.8 Hz), 9.06 (1H, s).

Example 19-B

Production of 3-[4-cyclohexyl-5-(4H-1,2,4-triazol-3-yl)-1,3-thiazol-2-yl]-2-methyl-4,5,6,7-tetrahydropyrazolo[1,5-a]pyridine

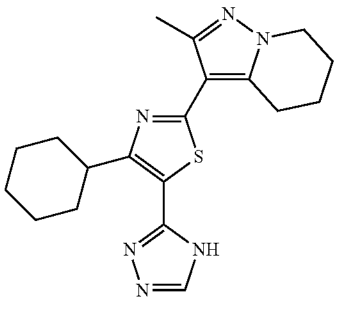 [SMILES: Cc1nn2c(c1-c1nc(C3CCCCC3)c(-c3nnc[nH]3)s1)CCCC2]

(i) Production of ethyl 4-cyclohex-1-en-1-yl-2-(2-methylpyrazolo[1,5-a]pyridin-3-yl)-1,3-thiazole-5-carboxylate Using ethyl 2-(2-methylpyrazolo[1,5-a]pyridin-3-yl)-4-{[(trifluoromethyl)sulfonyl]oxy}-1,3-thiazole-5-carboxylate (220 mg, 0.5 mmol) produced in Example 15(i), 2-cyclohex-1-en-1-yl-4,4,5,5-tetramethyl-1,3,2-dioxaborolane (620 mg, 3.0 mmol), [1,1-bis(diphenylphosphino)ferrocene]palladium (II) dichloride dichloromethane complex (72 mg, 0.088 mmol), cesium carbonate (620 mg, 1.9 mmol), water (0.5 mL) and 1,2-dimethoxyethane (15 mL) as starting materials and in the same manner as in Example 13-B (iii), the title compound (176 mg, 95%) was obtained as a yellow solid.

$^1$H-NMR (DMSO-$d_6$, 300 MHz) δ 1.25-1.34 (3H, m), 1.48-2.29 (8H, m), 2.67 (3H, s), 4.21-4.30 (2H, m), 6.21-6.48 (1H, m), 7.11 (1H, dt, J=1.4, 6.9 Hz), 7.55-7.63 (1H, m), 8.32 (1H, d, J=8.9 Hz), 8.79 (1H, d, J=6.8 Hz).

(ii) Production of ethyl 4-cyclohexyl-2-(2-methyl-4,5,6,7-tetrahydropyrazolo[1,5-a]pyridin-3-yl)-1,3-thiazole-5-carboxylate To a solution of ethyl 4-cyclohex-1-en-1-yl-2-(2-methylpyrazolo[1,5-a]pyridin-3-yl)-1,3-thiazole-5-carboxylate (150 mg, 6.5 mmol) produced above in methanol (10 mL)-tetrahydrofuran (5 mL) was added 10% palladium-carbon powder (350 mg), and the mixture was stirred at room temperature for 5 hr under a hydrogen atmosphere (1 atm). The palladium-carbon powder was filtered off, and the filtrate was concentrated under reduced pressure. The obtained residue was washed with diisopropyl ether to give the title compound (150 mg, 99%) as a gray solid.

$^1$H-NMR (DMSO-$d_6$, 300 MHz) δ 1.22-2.02 (17H, m), 2.42 (3H, s), 2.95-3.04 (2H, m), 3.49-3.64 (1H, m), 4.04 (2H, t, J=5.9 Hz), 4.27 (2H, q, J=7.2 Hz).

(iii) Production of 4-cyclohexyl-2-(2-methyl-4,5,6,7-tetrahydropyrazolo[1,5-a]pyridin-3-yl)-1,3-thiazole-5-carboxylic acid Using ethyl 4-cyclohexyl-2-(2-methyl-4,5,6,7-tetrahydropyrazolo[1,5-a]pyridin-3-yl)-1,3-thiazole-5-carboxylate (160 mg, 0.4 mmol) produced above, methanol (5 mL), tetrahydrofuran (20 mL) and 8N aqueous sodium hydroxide solution (1 mL) as starting materials and in the same manner as in Example 13(iv), the title compound was obtained (115 mg, 80%) as a yellow solid.

$^1$H-NMR (DMSO-$d_6$, 300 MHz) δ 1.19-2.04 (14H, m), 2.40 (3H, s), 2.93-3.02 (2H, m), 3.54-3.68 (1H, m), 3.97-4.08 (2H, m), 12.92 (1H, s).

(iv) Production of 4-cyclohexyl-2-(2-methyl-4,5,6,7-tetrahydropyrazolo[1,5-a]pyridin-3-yl)-1,3-thiazole-5-carboxamide Using 4-cyclohexyl-2-(2-methyl-4,5,6,7-tetrahydropyrazolo[1,5-a]pyridin-3-yl)-1,3-thiazole-5-carboxylic acid (105 mg, 0.3 mmol) produced above, ammonium chloride (500 mg, 9.3 mmol), N,N-dimethylformamide (15 mL), triethylamine (3 mL), 1-hydroxybenzotriazole (70 mg, 0.5 mmol) and N-[3-(dimethylamino)propyl]-N'-ethylcarbodiimide hydrochloride (1.0 g, 5.2 mmol) as starting materials and in the same manner as in Example 13-B (v), the title compound (65 mg, 62%) was obtained as a white solid.

$^1$H-NMR (DMSO-$d_6$, 300 MHz) δ 1.22-2.01 (14H, m), 2.40 (3H, s), 2.94-3.02 (2H, m), 3.41-3.52 (1H, m), 4.00-4.07 (2H, m), 7.36-7.49 (2H, m).

(v) Production of 3-[4-cyclohexyl-5-(4H-1,2,4-triazol-3-yl)-1,3-thiazol-2-yl]-2-methyl-4,5,6,7-tetrahydropyrazolo[1,5-a]pyridine Using 4-cyclohexyl-2-(2-methyl-4,5,6,7-tetrahydropyrazolo[1,5-a]pyridin-3-yl)-1,3-thiazole-5-carboxamide (65 mg, 0.19 mmol) produced above, N,N-dimethylformamide dimethyl acetal (20 mL), acetic acid (15 mL) and hydrazine monohydrate (0.4 mL) as starting materials and in the same manner as in Example 13-B (vi), the title compound (61 mg, 88%) was obtained as a white solid.

$^1$H-NMR (DMSO-$d_6$, 300 MHz) δ 1.21-2.04 (14H, m), 2.42 (3H, s), 3.00 (2H, t, J=6.2 Hz), 3.65-3.80 (1H, m), 4.00-4.10 (2H, m), 8.61 (1H, s).

Example 20-B

Production of 3-[4-cyclohexyl-5-(4H-1,2,4-triazol-3-yl)-1,3-thiazol-2-yl]-2-methylpyrazolo[1,5-a]pyridine

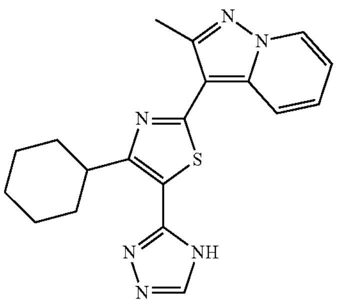 [SMILES: Cc1nn2ccccc2c1-c1nc(C2CCCCC2)c(-c2nnc[nH]2)s1]

(i) Production of ethyl 2-chloro-3-cyclohexyl-3-oxopropanoate

To a solution of ethyl 3-cyclohexyl-3-oxopropanoate (1.0 g, 5.0 mmol) in diethyl ether (15 mL) was added sulfuryl chloride (750 mg, 5.5 mmol) at 0° C., and the mixture was stirred at room temperature for 1 hr. Saturated aqueous sodium bicarbonate solution (150 mL) and ethyl acetate (150 mL) were added to the reaction solution, and the mixture was stirred for 30 min. The organic layer was washed with saturated brine (10 mL) and dried over anhydrous magnesium sulfate, and the insoluble material was filtered off. The filtrate was concentrated under reduced pressure to give the title compound (870 mg, 60%) as a colorless oil.

$^1$H-NMR (DMSO-$d_6$, 300 MHz) δ 1.08-1.34 (8H, m), 1.54-1.89 (5H, m), 2.67-2.79 (1H, m), 4.21 (2H, q, J=7.0 Hz), 5.81 (1H, s).

(ii) Production of ethyl 4-cyclohexyl-2-(2-methylpyrazolo[1,5-a]pyridin-3-yl)-1,3-thiazole-5-carboxylate Using 2-methylpyrazolo[1,5-a]pyridine-3-carbothioamide hydrochloride (300 mg, 1.3 mmol) produced in Example 11(v), ethyl 2-chloro-3-cyclohexyl-3-oxopropanoate (870 mg, 3.7 mmol) produced above and 2-propanol (50 mL) as starting materials and in the same manner as in Example 11-B (vi), the title compound (455 mg, 74%) was obtained as a yellow solid.

$^1$H-NMR (DMSO-$d_6$, 300 MHz) δ 1.13-1.92 (13H, m), 2.67 (3H, s), 3.57-3.67 (1H, m), 4.30 (2H, q, J=7.1 Hz), 7.11 (1H, dt, J=1.3, 6.9 Hz), 7.61 (1H, ddd, J=1.1, 7.2, 8.7 Hz), 8.33-8.39 (1H, m), 8.76-8.81 (1H, m).

(iii) Production of 4-cyclohexyl-2-(2-methylpyrazolo[1,5-a]pyridin-3-yl)-1,3-thiazole-5-carboxylic acid Using ethyl 4-cyclohexyl-2-(2-methylpyrazolo[1,5-a]pyridin-3-yl)-1,3-thiazole-5-carboxylate (350 mg, 0.95 mmol) produced above, methanol (10 mL), tetrahydrofuran (25 mL) and 8N aqueous sodium hydroxide solution (1 mL) as starting materials and in the same manner as in Example 13-B (iv), the title compound (275 mg, 85%) was obtained as a white solid.

$^1$H-NMR (DMSO-$d_6$, 300 MHz) δ 1.35 (10H, s), 2.65 (3H, s), 3.62-3.78 (1H, m), 7.08 (1H, dt, J=1.3, 6.9 Hz), 7.53-7.61 (1H, m), 8.31-8.38 (1H, m), 8.75 (1H, d, J=6.8 Hz).

(iv) Production of 4-cyclohexyl-2-(2-methylpyrazolo[1,5-a]pyridin-3-yl)-1,3-thiazole-5-carboxamide Using 4-cyclohexyl-2-(2-methylpyrazolo[1,5-a]pyridin-3-yl)-1,3-thiazole-5-carboxylic acid (250 mg, 0.73 mmol) produced above, ammonium chloride (1.6 g, 19 mmol), N,N-dimethylformamide (25 mL), triethylamine (5 mL), 1-hydroxybenzotriazole (100 mg, 0.73 mmol) and N-[3-(dimethylamino)propyl]-N'-ethylcarbodiimide hydrochloride (2.0 g, 10 mmol) as starting materials and in the same manner as in Example 13-B (v), the title compound (215 mg, 86%) was obtained as a white solid.

$^1$H-NMR (DMSO-$d_6$, 300 MHz) δ 1.27-1.47 (3H, m), 1.66-1.94 (7H, m), 2.65 (3H, s), 3.62-3.78 (1H, m), 7.08 (1H, dt, J=1.3, 6.9 Hz), 7.53-7.61 (3H, m), 8.31-8.38 (1H, m), 8.75 (1H, d, J=6.8 Hz).

(v) Production of 3-[4-cyclohexyl-5-(4H-1,2,4-triazol-3-yl)-1,3-thiazol-2-yl]-2-methylpyrazolo[1,5-a]pyridine Using 4-cyclohexyl-2-(2-methylpyrazolo[1,5-a]pyridin-3-yl)-1,3-thiazole-5-carboxamide (200 mg, 0.6 mmol), N,N-dimethylformamide dimethyl acetal (15 mL), acetic acid (25 mL) and hydrazine monohydrate (0.3 mL) as starting materials and in the same manner as in Example 13-B (vi), the title compound (146 mg, 68%) was obtained as a white solid.

$^1$H-NMR (DMSO-$d_6$, 300 MHz) δ 1.28-1.50 (3H, m), 1.66-1.94 (7H, m), 2.66-2.71 (3H, s), 3.71-3.86 (1H, m), 7.06 (1H, dt, J=1.4, 6.8 Hz), 7.55 (1H, ddd, J=1.0, 6.8, 8.9 Hz), 8.31-8.40 (1H, m), 8.62 (1H, s), 8.74 (1H, d, J=7.0 Hz).

Example 21-B

Production of 3-[4-tert-butyl-5-(4H-1,2,4-triazol-3-yl)-1,3-thiazol-2-yl]-2-methylpyrazolo[1,5-a]pyridine

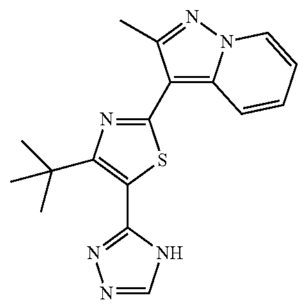 [SMILES: Cc1nn2ccccc2c1-c1nc(C(C)(C)C)c(-c2nnc[nH]2)s1]

(i) Production of methyl 2-chloro-4,4-dimethyl-3-oxopentanoate

Using 4,4-dimethyl-3-oxopentanoic acid (1.0 g, 6.3 mmol), sulfuryl chloride (940 mg, 7.0 mmol) and diethyl ether (20 mL) as starting materials and in the same manner as in Example 20-B (i), the title compound (980 mg, 80%) was obtained as a colorless oil.

$^1$H-NMR (DMSO-$d_6$, 300 MHz) δ 1.18 (9H, s), 3.71 (3H, s), 6.08 (1H, s).

(ii) Production of methyl 4-tert-butyl-2-(2-methylpyrazolo[1,5-a]pyridin-3-yl)-1,3-thiazole-5-carboxylate Using 2-methylpyrazolo[1,5-a]pyridine-3-carbothioamide hydrochloride (300 mg, 1.3 mmol) produced in Example 11-B(v), methyl 2-chloro-4,4-dimethyl-3-oxopentanoate (950 mg, 4.9 mmol) produced above and 2-propanol (25 mL) as starting materials and in the same manner as in Example 11-B (vi), the title compound (330 mg, 76%) was obtained as a yellow solid.

$^1$H-NMR (DMSO-$d_6$, 300 MHz) δ 1.54 (9H, s), 2.66 (3H, s), 3.83 (3H, s), 7.11 (1H, dt, J=1.3, 6.9 Hz), 7.55-7.66 (1H, m), 8.34 (1H, d, J=8.9 Hz), 8.79 (1H, d, J=6.9 Hz).

(iii) Production of 4-tert-butyl-2-(2-methylpyrazolo[1,5-a]pyridin-3-yl)-1,3-thiazole-5-carboxylic acid Using methyl 4-tert-butyl-2-(2-methylpyrazolo[1,5-a]pyridin-3-yl)-1,3-thiazole-5-carboxylate (320 mg, 0.41 mmol) produced above, methanol (15 mL), tetrahydrofuran (20 mL) and 8N aqueous sodium hydroxide solution (3 mL) as starting materials and in the same manner as in Example 13-B(iv), the title compound (271 mg, 88%) was obtained as a yellow solid.

$^1$H-NMR (DMSO-$d_6$, 300 MHz) δ 1.54 (9H, s), 2.66 (3H, s), 7.08 (1H, dt, J=1.3, 6.8 Hz), 7.56 (1H, ddd, J=1.1, 6.8, 8.9 Hz), 8.33 (1H, d, J=8.9 Hz), 8.77 (1H, d, J=6.8 Hz).

(iv) Production of 4-tert-butyl-2-(2-methylpyrazolo[1,5-a]pyridin-3-yl)-1,3-thiazole-5-carboxamide Using 4-tert-butyl-2-(2-methylpyrazolo[1,5-a]pyridin-3-yl)-1,3-thiazole-5-carboxylic acid (250 mg, 0.79 mmol) produced above, ammonium chloride (1.5 g, 28 mmol), N,N-dimethylformamide (30 mL), triethylamine (4 mL), 1-hydroxybenzotriazole (50 mg, 0.37 mmol) and N-[3-(dimethylamino)propyl]-N'-ethylcarbodiimide hydrochloride (1.5 g, 7.8 mmol) as starting materials and in the same manner as in Example 13(v), the title compound (240 mg, 96%) was obtained as brown solid.

$^1$H-NMR (DMSO-$d_6$, 300 MHz) δ 1.47 (9H, s), 2.64 (3H, s), 7.05 (1H, dt, J=1.4, 6.8 Hz), 7.53 (1H, ddd, J=1.0, 6.8, 8.9 Hz), 7.66 (1H, s), 7.99 (1H, s), 8.26 (1H, d, J=8.9 Hz), 8.74 (1H, d, J=6.8 Hz).

(v) Production of 3-[4-tert-butyl-5-(4H-1,2,4-triazol-3-yl)-1,3-thiazol-2-yl]-2-methylpyrazolo[1,5-a]pyridine Using 4-tert-butyl-2-(2-methylpyrazolo[1,5-a]pyridin-3-yl)-1,3-thiazole-5-carboxamide (230 mg, 0.73 mmol), N,N-dimethylformamide dimethyl acetal (25 mL), acetic acid (25 mL) and hydrazine monohydrate (0.5 mL) as starting materials and in the same manner as in Example 13(vi), the title compound (210 mg, 85%) was obtained as a brown solid.

$^1$H-NMR (DMSO-$d_6$, 300 MHz) δ 1.48 (9H, s), 2.66 (3H, s), 7.05 (1H, dt, J=1.4, 6.8 Hz), 7.53 (1H, ddd, J=1.0, 6.8, 8.9 Hz), 8.32 (1H, d, J=8.9 Hz), 8.62 (1H, s), 8.74 (1H, d, J=6.8 Hz), 14.18 (1H, s).

Example 22-B

Production of 3-[4-(2-fluorophenyl)-5-(4H-1,2,4-triazol-3-yl)-1,3-thiazol-2-yl]-2-methylpyrazolo[1,5-a]pyridine monoacetate

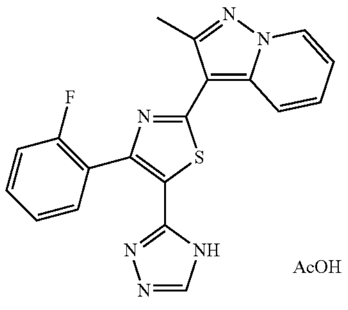 [SMILES: "AcOH" ; Cc1nn2ccccc2c1-c1nc(-c2ccccc2F)c(-c2nnc[nH]2)s1]

AcOH (i) Production of ethyl 2-chloro-3-(2-fluorophenyl)-3-oxopropanoate

Using ethyl 3-(2-fluorophenyl)-3-oxopropanoate (1.0 g, 4.75 mmol), sulfuryl chloride (771 mg, 5.7 mmol) and diethyl ether (50 mL) as starting materials and in the same manner as in Example 20-B (i), the title compound (1.13 g, 97%) was obtained as a colorless oil.

$^1$H-NMR (DMSO-$d_6$, 300 MHz) δ 1.11-1.22 (3H, m), 4.06-4.20 (2H, m), 6.28 (1H, d, J=0.8 Hz), 7.30-7.48 (2H, m), 7.64-8.03 (2H, m).

(ii) Production of ethyl 4-(2-fluorophenyl)-2-(2-methylpyrazolo[1,5-a]pyridin-3-yl)-1,3-thiazole-5-carboxylate Using 2-methylpyrazolo[1,5-a]pyridine-3-carbothioamide hydrochloride (300 mg, 1.3 mmol) produced in Example 11-B (v), ethyl 2-chloro-3-(2-fluorophenyl)-3-oxopropanoate (1.0 g, 4.09 mmol) produced above and 2-propanol (25 mL) as starting materials and in the same manner as in Example 11(vi), the title compound (341 mg, 68%) was obtained as a yellow solid.

$^1$H-NMR (DMSO-$d_6$, 300 MHz) δ 1.18 (3H, t, J=7.2 Hz), 2.70 (3H, s), 4.21 (2H, q, J=7.2 Hz), 7.12 (1H, dt, J=1.3, 6.9 Hz), 7.28-7.40 (2H, m), 7.49-7.62 (2H, m), 7.67-7.71 (1H, m), 8.27-8.37 (1H, m), 8.81 (1H, d, J=7.0 Hz).

(iii) Production of 4-(2-fluorophenyl)-2-(2-methylpyrazolo[1,5-a]pyridin-3-yl)-1,3-thiazole-5-carboxylic acid Using ethyl 4-(2-fluorophenyl)-2-(2-methylpyrazolo[1,5-a]pyridin-3-yl)-1,3-thiazole-5-carboxylate (340 mg, 0.89 mmol) produced above, methanol (15 mL), tetrahydrofuran (20 mL) and 8N aqueous sodium hydroxide solution (1 mL) as starting materials and in the same manner as in Example 13-B(iv), the title compound (312 mg, 99%) was obtained as a white solid.

$^1$H-NMR (DMSO-$d_6$, 300 MHz) δ 2.70 (3H, s), 7.11 (1H, dt, J=1.4, 6.9 Hz), 7.27-7.38 (2H, m), 7.48-7.62 (2H, m), 7.65-7.69 (1H, m), 8.31 (1H, d, J=8.9 Hz), 8.80 (1H, d, J=6.9 Hz).

(iv) Production of 4-(2-fluorophenyl)-2-(2-methylpyrazolo[1,5-a]pyridin-3-yl)-1,3-thiazole-5-carboxamide Using 4-(2-fluorophenyl)-2-(2-methylpyrazolo[1,5-a]pyridin-3-yl)-1,3-thiazole-5-carboxylic acid (300 mg, 0.85 mmol) produced above, ammonium chloride (1.5 g, 28 mmol), N,N-dimethylformamide (40 mL), triethylamine (6 mL), 1-hydroxybenzotriazole (70 mg, 0.52 mmol) and N-[3-(dimethylamino)propyl]-N'-ethylcarbodiimide hydrochloride (1.0 g, 5.2 mmol) as starting materials and in the same manner as in Example 13-B (v), the title compound (290 mg, 97%) was obtained as a white solid.

$^1$H-NMR (DMSO-$d_6$, 300 MHz) δ 2.70 (3H, s) 7.09 (1H, dt, J=1.3, 6.9 Hz), 7.24-7.42 (2H, m), 7.44-7.59 (4H, m), 7.68-7.77 (1H, m), 8.29 (1H, d, J=8.9 Hz), 8.78 (1H, d, J=6.9 Hz).

(v) Production of 3-[4-(2-fluorophenyl)-5-(4H-1,2,4-triazol-3-yl)-1,3-thiazol-2-yl]-2-methylpyrazolo[1,5-a]pyridine acetate Using 4-(2-fluorophenyl)-2-(2-methylpyrazolo[1,5-a]pyridin-3-yl)-1,3-thiazole-5-carboxamide (290 mg, 0.73 mmol) produced above, N,N-dimethylformamide dimethyl acetal (30 mL), acetic acid (40 mL) and hydrazine monohydrate (0.5 mL) as starting materials and in the same manner as in Example 13(vi), the title compound (221 mg, 62%) was obtained as a white solid.

$^1$H-NMR (DMSO-$d_6$, 300 MHz) δ 1.90 (3H, s), 2.72 (3H, s), 7.08 (1H, dt, J=1.4, 6.8 Hz), 7.21-7.35 (2H, m), 7.44-7.56 (2H, m), 7.65-7.75 (1H, m), 8.23-8.37 (1H, m), 8.54 (1H, s), 8.77 (1H, d, J=6.8 Hz).

Example 23-B

Production of 3-[4-(2-methoxyphenyl)-5-(4H-1,2,4-triazol-3-yl)-1,3-thiazol-2-yl]-2-methylpyrazolo[1,5-a]pyridine

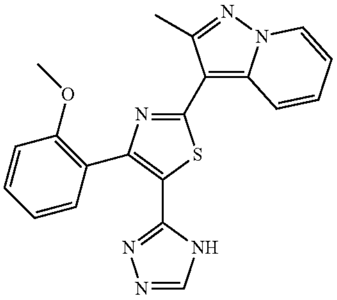 [SMILES: COc1ccccc1-c1nc(-c2c(C)nn3ccccc23)sc1-c1nnc[nH]1]

(i) Production of ethyl 2-chloro-3-(2-methoxyphenyl)-3-oxopropanoate

Using ethyl 3-(2-methoxyphenyl)-3-oxopropanoate (1.7 g, 7.4 mmol), sulfuryl chloride (1.2 g, 8.9 mmol) and diethyl ether (100 mL) as starting materials and in the same manner as in Example 20(i), the title compound (1.8 g, 97%) was obtained as colorless oil.

$^1$H-NMR (DMSO-$d_6$, 300 MHz) δ 1.11-1.23 (3H, m), 3.87 (3H, s), 4.17 (2H, q, J=7.0 Hz), 6.07 (1H, s), 7.11 (1H, t, J=7.5 Hz), 7.23 (1H, d, J=8.3 Hz), 7.59-7.72 (1H, m), 7.80 (1H, dd, J=1.8, 7.7 Hz).

(ii) Production of ethyl 4-(2-methoxyphenyl)-2-(2-methylpyrazolo[1,5-a]pyridin-3-yl)-1,3-thiazole-5-carboxylate Using 2-methylpyrazolo[1,5-a]pyridine-3-carbothioamide hydrochloride (300 mg, 1.3 mmol) produced in Example 11-B(v), ethyl 2-chloro-3-(2-methoxyphenyl)-3-oxopropanoate (600 mg, 2.3 mmol) produced above and 2-propanol (40 mL) as starting materials and in the same manner as in Example 11-B(vi), the title compound (1.8 g, 71%) was obtained as a yellow solid.

$^1$H-NMR (DMSO-$d_6$, 300 MHz) δ 1.07-1.15 (3H, m), 2.70 (3H, s), 3.74 (3H, s), 4.15 (2H, q, J=7.1 Hz), 7.02-7.17 (3H, m), 7.40-7.60 (3H, m), 8.23-8.34 (1H, m), 8.77-8.83 (1H, m).

(iii) Production of 4-(2-methoxyphenyl)-2-(2-methylpyrazolo[1,5-a]pyridin-3-yl)-1,3-thiazole-5-carboxylic acid Using ethyl 4-(2-methoxyphenyl)-2-(2-methylpyrazolo[1,5-a]pyridin-3-yl)-1,3-thiazole-5-carboxylate (320 mg, 0.81 mmol) produced above, methanol (15 mL), tetrahydrofuran (20 mL) and 8N aqueous sodium hydroxide solution (1 mL) as starting materials and in the same manner as in Example 13-B(iv), the title compound (296 mg, 99%) was obtained as a white solid.

$^1$H-NMR (DMSO-$d_6$, 300 MHz) δ 2.69 (3H, s), 3.74 (3H, s), 6.99-7.15 (3H, m), 7.37-7.47 (2H, m), 7.48-7.57 (1H, m), 8.28 (1H, d, J=8.9 Hz), 8.78 (1H, d, J=6.8 Hz).

(iv) Production of 4-(2-methoxyphenyl)-2-(2-methylpyrazolo[1,5-a]pyridin-3-yl)-1,3-thiazole-5-carboxamide Using 4-(2-methoxyphenyl)-2-(2-methylpyrazolo[1,5-a]pyridin-3-yl)-1,3-thiazole-5-carboxylic acid (300 mg, 0.82 mmol) produced above, ammonium chloride (1.5 g, 28 mmol), triethylamine (6 mL), 1-hydroxybenzotriazole (70 mg, 0.52 mmol), N-[3-(dimethylamino)propyl]-N'-ethylcarbodiimide hydrochloride (1.0 g, 5.2 mmol) and N,N-dimethylformamide (20 mL) as starting materials and in the same manner as in Example 13-B(v), the title compound (285 mg, 95%) was obtained as a white solid.

$^1$H-NMR (DMSO-$d_6$, 300 MHz) δ 2.69 (3H, s), 3.77 (3H, s), 6.86-7.23 (4H, m), 7.31-7.70 (4H, m), 8.26 (1H, d, J=8.7 Hz), 8.71-8.80 (1H, m).

(v) Production of 3-[4-(2-methoxyphenyl)-5-(4H-1,2,4-triazol-3-yl)-1,3-thiazol-2-yl]-2-methylpyrazolo[1,5-a]pyridine Using 4-(2-methoxyphenyl)-2-(2-methylpyrazolo[1,5-a]pyridin-3-yl)-1,3-thiazole-5-carboxamide (200 mg, 0.55 mmol) produced above, N,N-dimethylformamide dimethyl acetal (25 mL), acetic acid (40 mL) and hydrazine monohydrate (0.5 mL) as starting materials and in the same manner as in Example 13(vi), the title compound (145 mg, 68%) was obtained as a white solid.

$^1$H-NMR (DMSO-$d_6$, 300 MHz) δ 2.71 (3H, s), 3.52 (3H, s), 6.97-7.11 (3H, m), 7.35-7.55 (3H, m), 8.24-8.34 (1H, m), 8.45 (1H, s), 8.72-8.79 (1H, m).

Example 24-B

Production of 2-methyl-3-{5-(4H-1,2,4-triazol-3-yl)-4-[2-(trifluoromethyl)phenyl]-1,3-thiazol-2-yl}pyrazolo[1,5-a]pyridine

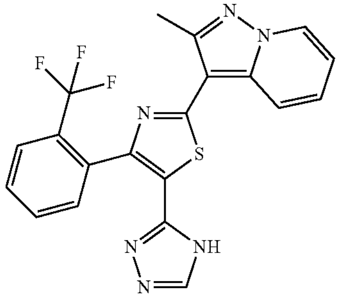 [SMILES: Cc1nn2ccccc2c1-c1nc(-c2ccccc2C(F)(F)F)c(-c2nnc[nH]2)s1]

(i) Production of ethyl 2-chloro-3-oxo-3-[2-(trifluoromethyl)phenyl]propanoate

Using ethyl 3-oxo-3-[2-(trifluoromethyl)phenyl]propanoate (1.0 g, 3.8 mmol), sulfuryl chloride (620 mg, 4.9 mmol) and diethyl ether (50 mL) as starting materials and in the same manner as in Example 20-B(i), the title compound (720 mg, 64%) was obtained as a colorless oil.

$^1$H-NMR (DMSO-$d_6$, 300 MHz) δ 1.01-1.11 (3H, m), 4.08 (2H, q, J=7.1 Hz), 6.60 (1H, s), 7.60-7.99 (4H, m).

(ii) Production of ethyl 2-(2-methylpyrazolo[1,5-a]pyridin-3-yl)-4-[2-(trifluoromethyl)phenyl]-1,3-thiazole-5-carboxylate Using 2-methylpyrazolo[1,5-a]pyridine-3-carbothioamide hydrochloride (100 mg, 0.44 mmol) produced in Example 11-B(v), ethyl 2-chloro-3-oxo-3-[2-(trifluoromethyl)phenyl]propanoate (250 mg, 0.85 mmol) produced above and 2-propanol (25 mL) as starting materials and in the same manner as in Example 11-B(vi), the title compound (158 mg, 84%) was obtained as a yellow solid.

$^1$H-NMR (DMSO-$d_6$, 300 MHz) δ 1.04 (3H, t, J=7.1 Hz), 2.70 (3H, s), 4.10 (2H, q, J=7.1 Hz), 7.08-7.15 (1H, m), 7.50-7.64 (2H, m), 7.69-7.92 (3H, m), 8.24 (1H, dt, J=1.2, 8.8 Hz), 8.81 (1H, d, J=6.8 Hz).

(iii) Production of 2-(2-methylpyrazolo[1,5-a]pyridin-3-yl)-4-[2-(trifluoromethyl)phenyl]-1,3-thiazole-5-carboxylic acid Using ethyl 2-(2-methylpyrazolo[1,5-a]pyridin-3-yl)-4-[2-(trifluoromethyl)phenyl]-1,3-thiazole-5-carboxylate (140 mg, 1.5 mmol) produced above, methanol (5 mL), tetrahydrofuran (15 mL) and 8N aqueous sodium hydroxide solution (2 mL) as starting materials and in the same manner as in Example 13-B(iv), the title compound (130 mg, 99%) was obtained as a white solid.

$^1$H-NMR (DMSO-$d_6$, 300 MHz) δ 2.68 (3H, s), 7.03-7.13 (1H, m), 7.46-7.77 (4H, m), 7.81-7.90 (1H, m), 8.19-8.28 (1H, m), 8.78 (1H, d, J=7.0 Hz).

(iv) Production of 2-(2-methylpyrazolo[1,5-a]pyridin-3-yl)-4-[2-(trifluoromethyl)phenyl]-1,3-thiazole-5-carboxamide Using 2-(2-methylpyrazolo[1,5-a]pyridin-3-yl)-4-[2-(trifluoromethyl)phenyl]-1,3-thiazole-5-carboxylic acid (130 mg, 0.32 mmol) produced above, ammonium chloride (2.0 g, 37 mmol), triethylamine (5.0 mL), 1-hydroxybenzotriazole (80 mg, 0.59 mmol), N-[3-(dimethylamino)propyl]-N'-ethylcarbodiimide hydrochloride (2.5 g, 13 mmol) and N,N-dimethylformamide (50 mL) as starting materials and in the same manner as in Example 13-B(v), the title compound (105 mg, 81%) was obtained as a white solid.

$^1$H-NMR (DMSO-$d_6$, 300 MHz) δ 2.69 (3H, s), 6.96-7.21 (2H, m), 7.37-7.62 (3H, m), 7.65-7.81 (2H, m), 7.84-7.92 (1H, m), 8.16-8.27 (1H, m), 8.77 (1H, d, J=6.8 Hz).

(v) Production of 2-methyl-3-{5-(4H-1,2,4-triazol-3-yl)-4-[2-(trifluoromethyl)phenyl]-1,3-thiazol-2-yl}pyrazolo[1,5-a]pyridine Using 2-(2-methylpyrazolo[1,5-a]pyridin-3-yl)-4-[2-(trifluoromethyl)phenyl]-1,3-thiazole-5-carboxamide (105 mg, 0.82 mmol) produced above, N,N-dimethylformamide dimethyl acetal (15 mL), acetic acid (20 mL) and hydrazine monohydrate (0.4 mL) as starting materials and in the same manner as in Example 13-B(vi), the title compound (72 mg, 65%) was obtained as a white solid.

$^1$H-NMR (DMSO-$d_6$, 300 MHz) δ 2.71 (3H, s), 7.06 (1H, dt, J=1.3, 6.8 Hz), 7.42-7.62 (2H, m), 7.63-7.77 (2H, m), 7.81-7.92 (1H, m), 8.19-8.31 (1H, m), 8.49 (1H, s), 8.76 (1H, d, J=6.8 Hz), 14.08 (1H, s).

Example 25-B

Production of 2-methyl-3-[4-(tetrahydro-2H-pyran-4-yl)-5-(4H-1,2,4-triazol-3-yl)-1,3-thiazol-2-yl]pyrazolo[1,5-a]pyridine

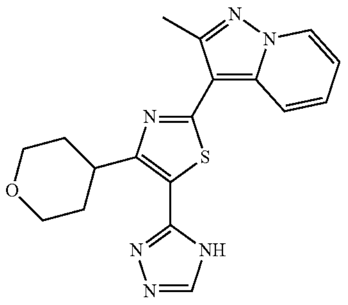 [SMILES: Cc1nn2ccccc2c1-c1nc(C2CCOCC2)c(-c2nnc[nH]2)s1]

(i) Production of ethyl 2-chloro-3-oxo-3-(tetrahydro-2H-pyran-4-yl)propanoate

Using ethyl 3-oxo-3-(tetrahydro-2H-pyran-4-yl)propanoate (1.0 g, 5.0 mmol), sulfuryl chloride (810 mg, 6.0 mmol) and diethyl ether (50 mL) as starting materials and in the same manner as in Example 20-B(i), the title compound (1.0 g, 85%) was obtained as a colorless oil.

$^1$H-NMR (DMSO-$d_6$, 300 MHz) δ 1.16-1.25 (3H, m), 1.39-1.60 (2H, m), 1.66-1.84 (2H, m), 2.95-3.10 (1H, m), 3.31-3.41 (2H, m), 3.79-3.91 (2H, m), 4.22 (2H, q, J=7.1 Hz), 5.85 (1H, s).

(ii) Production of ethyl 2-(2-methylpyrazolo[1,5-a]pyridin-3-yl)-4-(tetrahydro-2H-pyran-4-yl)-1,3-thiazole-5-carboxylate Using 2-methylpyrazolo[1,5-a]pyridine-3-carbothioamide hydrochloride (400 mg, 1.8 mmol) produced in Example 11-B(v), ethyl 2-chloro-3-oxo-3-(tetrahydro-2H-pyran-4-yl)propanoate (1.0 g, 4.3 mmol) produced above and 2-propanol (40 mL) as starting materials and in the same manner as in Example 11-B(vi), the title compound (530 mg, 81%) was obtained as a yellow solid.

$^1$H-NMR (DMSO-$d_6$, 300 MHz) δ 1.32 (3H, t, J=7.1 Hz), 1.75 (2H, d, J=14.7 Hz), 1.93-2.12 (2H, m), 2.67 (3H, s), 3.43-3.55 (2H, m), 3.81-3.96 (1H, m), 3.96-4.07 (2H, m), 4.31 (2H, q, J=7.1 Hz), 7.12 (1H, dt, J=1.3, 7.0 Hz), 7.63 (1H, ddd, J=1.3, 7.0, 8.9 Hz), 8.33-8.42 (1H, m), 8.79 (1H, d, J=7.0 Hz).

(iii) Production of 2-(2-methylpyrazolo[1,5-a]pyridin-3-yl)-4-(tetrahydro-2H-pyran-4-yl)-1,3-thiazole-5-carboxylic acid Using ethyl 2-(2-methylpyrazolo[1,5-a]pyridin-3-yl)-4-(tetrahydro-2H-pyran-4-yl)-1,3-thiazole-5-carboxylate (500 mg, 1.5 mmol) produced above, methanol (20 mL), tetrahydrofuran (20 mL) and 8N aqueous sodium hydroxide solution (2 mL) as starting materials and in the same manner as in Example 13(iv), the title compound (431 mg, 93%) was obtained as a yellow solid.

$^1$H-NMR (DMSO-$d_6$, 300 MHz) δ 1.68-1.80 (2H, m), 1.94-2.11 (2H, m), 2.67 (3H, s), 3.40-3.53 (2H, m), 3.83-4.05 (3H, m), 7.11 (1H, dt, J=1.3, 6.9 Hz), 7.55-7.66 (1H, m), 8.37 (1H, d, J=8.9 Hz), 8.78 (1H, d, J=6.9 Hz), 13.20 (1H, s).

(iv) Production of 2-(2-methylpyrazolo[1,5-a]pyridin-3-yl)-4-(tetrahydro-2H-pyran-4-yl)-1,3-thiazole-5-carboxamide Using 2-(2-methylpyrazolo[1,5-a]pyridin-3-yl)-4-(tetrahydro-2H-pyran-4-yl)-1,3-thiazole-5-carboxylic acid (400 mg, 1.2 mmol) produced above, ammonium chloride (1.0 g, 19 mmol), triethylamine (4.0 mL), 1-hydroxybenzotriazole (150 mg, 1.7 mmol), N-[3-(dimethylamino)propyl]-N'-ethylcarbodiimide hydrochloride (850 mg, 4.4 mmol) and N,N-dimethylformamide (70 mL) as starting materials and in the same manner as in Example 13(v), the title compound (347 mg, 87%) was obtained as a white solid.

$^1$H-NMR (DMSO-$d_6$, 300 MHz) δ 1.69-1.80 (2H, m), 1.95-2.05 (2H, m), 2.67 (3H, s), 3.40-3.50 (2H, m), 3.72-3.88 (1H, m), 3.92-4.01 (2H, m), 7.09 (1H, dt, J=1.3, 6.9 Hz), 7.45-7.70 (3H, m), 8.33 (1H, d, J=8.7 Hz), 8.77 (1H, d, J=6.9 Hz).

(v) Production of 2-methyl-3-[4-(tetrahydro-2H-pyran-4-yl)-5-(4H-1,2,4-triazol-3-yl)-1,3-thiazol-2-yl]pyrazolo[1,5-a]pyridine Using 2-(2-methylpyrazolo[1,5-a]pyridin-3-yl)-4-(tetrahydro-2H-pyran-4-yl)-1,3-thiazole-5-carboxamide (300 mg, 0.82 mmol) produced above, N,N-dimethylformamide dimethyl acetal (20 mL), acetic acid (30 mL) and hydrazine monohydrate (0.3 mL) as starting materials and in the same manner as in Example 13(vi), the title compound (221 mg, 69%) was obtained as a white solid.

$^1$H-NMR (DMSO-$d_6$, 300 MHz) δ 1.78 (2H, d, J=11.0 Hz), 2.00-2.16 (2H, m), 2.69 (3H, s), 3.49 (2H, t, J=11.0 Hz), 3.94-4.12 (3H, m), 7.07 (1H, dt, J=1.2, 6.8 Hz), 7.57 (1H, ddd, J=1.2, 6.8, 8.8 Hz), 8.29-8.41 (1H, m), 8.66 (1H, s), 8.76 (1H, d, J=6.8 Hz), 14.27 (1H, s).

Example 26-B

Production of 3-[4-(2-chlorophenyl)-5-(4H-1,2,4-triazol-3-yl)-1,3-thiazol-2-yl]-2-methylpyrazolo[1,5-a]pyridine

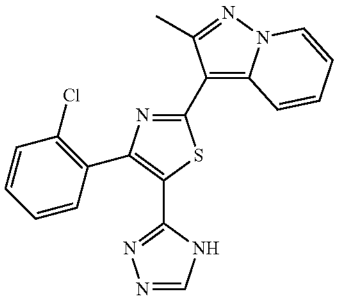 [SMILES: Cc1nn2ccccc2c1-c1nc(-c2ccccc2Cl)c(-c2nnc[nH]2)s1]

(i) Production of ethyl 2-chloro-3-(2-chlorophenyl)-3-oxopropanoate

Using ethyl 3-(2-chlorophenyl)-3-oxopropanoate (1.0 g, 5.0 mmol), sulfuryl chloride (810 mg, 6.0 mmol) and diethyl ether (50 mL) as starting materials and in the same manner as in Example 20(i), the title compound (1.0 g, 85%) was obtained as a colorless oil.

$^1$H-NMR (DMSO-$d_6$, 300 MHz) δ 1.22-1.31 (3H, m), 4.17-4.27 (2H, m), 6.47 (1H, s) 7.35-7.94 (4H, m).

(ii) Production of ethyl 4-(2-chlorophenyl)-2-(2-methylpyrazolo[1,5-a]pyridin-3-yl)-1,3-thiazole-5-carboxylate Using 2-methylpyrazolo[1,5-a]pyridine-3-carbothioamide hydrochloride (300 mg, 1.3 mmol) produced in Example 11(v), ethyl 2-chloro-3-(2-chlorophenyl)-3-oxopropanoate (1.0 g, 3.9 mmol) produced above and 2-propanol (20 mL) as starting materials and in the same manner as in Example 11-B(vi), the title compound (475 mg, 91%) was obtained as a yellow solid.

$^1$H-NMR (DMSO-$d_6$, 300 MHz) δ 1.12 (3H, t, J=7.2 Hz), 2.71 (3H, s), 4.16 (2H, q, J=7.2 Hz), 7.12 (1H, dt, J=1.3, 6.9 Hz), 7.41-7.65 (5H, m), 8.24-8.34 (1H, m), 8.81 (1H, d, J=6.9 Hz).

(iii) Production of 4-(2-chlorophenyl)-2-(2-methylpyrazolo[1,5-a]pyridin-3-yl)-1,3-thiazole-5-carboxylic acid Using ethyl 4-(2-chlorophenyl)-2-(2-methylpyrazolo[1,5-a]pyridin-3-yl)-1,3-thiazole-5-carboxylate (400 mg, 1.0 mmol) produced above, methanol (10 mL), tetrahydrofuran (20 mL) and 8N aqueous sodium hydroxide solution (2.0 mL) as starting materials and in the same manner as in Example 13-B(iv), the title compound (355 mg, 96%) was obtained as a white solid.

$^1$H-NMR (DMSO-$d_6$, 300 MHz) δ 2.70 (3H, s), 7.09 (1H, dt, J=1.3, 6.8 Hz), 7.38-7.61 (5H, m), 8.23-8.32 (1H, m), 8.78 (1H, d, J=6.8 Hz).

(iv) Production of 4-(2-chlorophenyl)-2-(2-methylpyrazolo[1,5-a]pyridin-3-yl)-1,3-thiazole-5-carboxamide Using 4-(2-chlorophenyl)-2-(2-methylpyrazolo[1,5-a]pyridin-3-yl)-1,3-thiazole-5-carboxylic acid (350 mg, 0.94 mmol) produced above, ammonium chloride (3.0 g, 56 mmol), triethylamine (4.5 mL), 1-hydroxybenzotriazole (70 mg, 0.52 mmol), N-[3-(dimethylamino)propyl]-N'-ethylcarbodiimide hydrochloride (2.0 g, 10 mmol) and N,N-dimethylformamide (50 mL) as starting materials and in the same manner as in Example 13-B(v), the title compound (341 mg, 97%) was obtained as a yellow solid.

$^1$H-NMR (DMSO-$d_6$, 300 MHz) δ 2.70 (3H, s), 7.06-7.20 (2H, m), 7.43-7.64 (6H, m), 8.26 (1H, d, J=8.7 Hz), 8.78 (1H, d, J=6.8 Hz).

(v) Production of 3-[4-(2-chlorophenyl)-5-(4H-1,2,4-triazol-3-yl)-1,3-thiazol-2-yl]-2-methylpyrazolo[1,5-a]pyridine Using 4-(2-chlorophenyl)-2-(2-methylpyrazolo[1,5-a]pyridin-3-yl)-1,3-thiazole-5-carboxamide (340 mg, 0.92 mmol) produced above, N,N-dimethylformamide dimethyl acetal (20 mL), acetic acid (25 mL) and hydrazine monohydrate (0.7 mL) as starting materials and in the same manner as in Example 13-B(vi), the title compound (322 mg, 89%) was obtained as a white solid.

$^1$H-NMR (DMSO-d$_6$, 300 MHz) δ 2.72 (3H, s), 7.05 (1H, dt, J=1.5, 6.8 Hz), 7.38-7.61 (5H, m), 8.25-8.31 (1H, m), 8.33 (1H, s), 8.76 (1H, d, J=6.8 Hz).

Example 27-B

Production of 2-methyl-3-[4-(prop-2-en-1-yloxy)-5-(4H-1,2,4-triazol-3-yl)-1,3-thiazol-2-yl]pyrazolo[1,5-a]pyridine

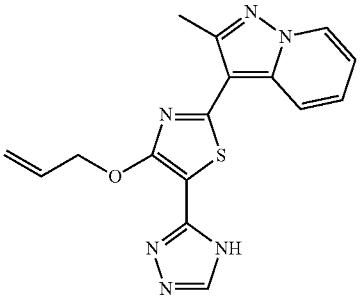 [SMILES: C=CCOc1nc(-c2c(C)nn3ccccc23)sc1-c1nnc[nH]1]

(i) Production of methyl 2-(2-methylpyrazolo[1,5-a]pyridin-3-yl)-4-(prop-2-en-1-yloxy)-1,3-thiazole-5-carboxylate Methyl 4-hydroxy-2-(2-methylpyrazolo[1,5-a]pyridin-3-yl)-1,3-thiazole-5-carboxylate (1.0 g, 3.5 mmol) produced in Example 13-B(i) was dissolved in N,N-dimethylformamide (50 mL), potassium carbonate (3.2 g, 9.7 mmol) and 3-bromoprop-1-ene (2.8 g, 23 mmol) were added, and the mixture was stirred at room temperature for 2 hr. Water (100 mL) and ethyl acetate (100 mL) were added to the reaction solution, and the mixture was stirred for 30 min. The organic layer was washed with water (100 mL×3) and saturated brine (10 mL) and dried over anhydrous sodium sulfate. The insoluble material was filtered off, and the filtrate was concentrated under reduced pressure. The obtained residue was purified by silica gel column chromatography (hexane/ethyl acetate=100/0→0/100) to give the title compound (760 mg, 67%) as a brown solid.

$^1$H-NMR (DMSO-d$_6$, 300 MHz) δ 2.66 (3H, s), 3.76 (3H, s), 5.10 (2H, td, J=1.5, 5.1 Hz), 5.30 (1H, ddd, J=1.5, 3.2, 10.5 Hz), 5.50 (1H, ddd, J=1.5, 3.2, 17.2 Hz), 6.08-6.22 (1H, m), 7.14 (1H, dt, J=1.2, 6.9 Hz), 7.62 (1H, ddd, J=1.2, 6.9, 8.8 Hz), 8.25-8.38 (1H, m), 8.81 (1H, d, J=6.9 Hz).

(ii) Production of 2-(2-methylpyrazolo[1,5-a]pyridin-3-yl)-4-(prop-2-en-1-yloxy)-1,3-thiazole-5-carboxylic acid Using methyl 2-(2-methylpyrazolo[1,5-a]pyridin-3-yl)-4-(prop-2-en-1-yloxy)-1,3-thiazole-5-carboxylate (670 mg, 2.0 mmol) produced above, methanol (10 mL), tetrahydrofuran (30 mL) and 8N aqueous sodium hydroxide solution (1.5 mL) as starting materials and in the same manner as in Example 13-B(iv), the title compound (610 mg, 95%) was obtained as a yellow solid.

$^1$H-NMR (DMSO-d$_6$, 300 MHz) δ 2.65 (3H, s), 5.08 (2H, td, J=1.5, 5.3 Hz), 5.29 (1H, ddd, J=1.5, 3.2, 10.5 Hz), 5.50 (1H, ddd, J=1.5, 3.2, 17.2 Hz), 6.11-6.17 (1H, m), 7.12 (1H, dt, J=1.3, 6.9 Hz), 7.54-7.66 (1H, m), 8.30 (1H, d, J=8.9 Hz), 8.79 (1H, d, J=6.9 Hz).

(iii) Production of 2-(2-methylpyrazolo[1,5-a]pyridin-3-yl)-4-(prop-2-en-1-yloxy)-1,3-thiazole-5-carboxamide Using 2-(2-methylpyrazolo[1,5-a]pyridin-3-yl)-4-(prop-2-en-1-yloxy)-1,3-thiazole-5-carboxylic acid (600 mg, 1.9 mmol) produced above, ammonium chloride (2.0 g, 37 mmol), triethylamine (3.5 mL), 1-hydroxybenzotriazole (40 mg, 0.3 mmol), N-[3-(dimethylamino)propyl]-N'-ethylcarbodiimide hydrochloride (2.1 g, 11 mmol) and N,N-dimethylformamide (50 mL) as starting materials and in the same manner as in Example 13(v), the title compound (415 mg, 69%) was obtained as a yellow solid.

$^1$H-NMR (DMSO-d$_6$, 300 MHz) δ 2.65 (3H, s), 5.12 (2H, td, J=1.3, 5.7 Hz), 5.28-5.39 (1H, m), 5.41-5.53 (1H, m), 6.09-6.30 (1H, m), 6.88 (1H, s), 7.11 (1H, dt, J=1.3, 6.9 Hz), 7.50-7.65 (2H, m), 8.31 (1H, d, J=8.9 Hz), 8.78 (1H, d, J=6.9 Hz).

(iv) Production of 2-methyl-3-[4-(prop-2-en-1-yloxy)-5-(4H-1,2,4-triazol-3-yl)-1,3-thiazol-2-yl]pyrazolo[1,5-a]pyridine Using 2-(2-methylpyrazolo[1,5-a]pyridin-3-yl)-4-(prop-2-en-1-yloxy)-1,3-thiazole-5-carboxamide (400 mg, 0.55 mmol) produced above, N,N-dimethylformamide dimethyl acetal (20 mL), acetic acid (30 mL) and hydrazine monohydrate (0.4 mL) as starting materials and in the same manner as in Example 13-B(vi), the title compound (277 mg, 68%) was obtained as a yellow solid.

$^1$H-NMR (DMSO-d$_6$, 300 MHz) δ 2.68 (3H, s), 5.10 (2H, td, J=1.5, 5.3 Hz), 5.28 (1H, ddd, J=1.5, 3.2, 10.6 Hz), 5.50 (1H, ddd, J=1.5, 3.2, 17.3 Hz), 6.12-6.24 (1H, m), 7.05-7.15 (1H, m), 7.57 (1H, ddd, J=1.1, 6.9, 9.0 Hz), 8.24-8.35 (2H, m), 8.78 (1H, d, J=6.9 Hz).

Example 28-B

Production of 2-methyl-3-[4-propoxy-5-(4H-1,2,4-triazol-3-yl)-1,3-thiazol-2-yl]pyrazolo[1,5-a]pyridine

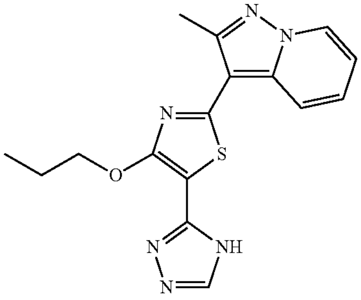 [SMILES: CCCOc1nc(-c2c(C)nn3ccccc23)sc1-c1nnc[nH]1]

To a solution of 2-methyl-3-[4-(prop-2-en-1-yloxy)-5-(4H-1,2,4-triazol-3-yl)-1,3-thiazol-2-yl]pyrazolo[1,5-a]pyridine (70 mg, 0.55 mmol) produced in Example 27 in ethanol (15 mL)-tetrahydrofuran (15 mL) was added 10% palladium/carbon (73 mg), and the mixture was stirred at room temperature for 5 hr under a hydrogen atmosphere (1 atm). Palladium/carbon was filtered off, and the filtrate was concentrated under reduced pressure. The obtained residue was washed with diisopropyl ether to give the title compound (43 mg, 61%) as a yellow solid.

$^1$H-NMR (DMSO-d$_6$, 300 MHz) δ 1.03 (3H, t, J=7.5 Hz), 1.75-1.94 (2H, m), 2.68 (3H, s), 4.51 (2H, t, J=6.6 Hz), 7.04-7.11 (1H, m), 7.50-7.63 (1H, m), 8.18 (1H, s), 8.29 (1H, d, J=8.9 Hz), 8.77 (1H, d, J=7.0 Hz).

Example 29-B

Production of 3-[4-(benzyloxy)-5-(4H-1,2,4-triazol-3-yl)-1,3-thiazol-2-yl]-2-methylpyrazolo[1,5-a]pyridine

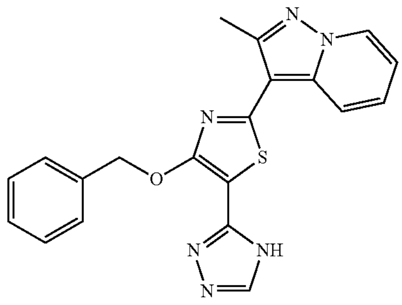 [SMILES: Cc1nn2ccccc2c1-c1nc(OCc2ccccc2)c(-c2nnc[nH]2)s1]

(i) Production of methyl 4-(benzyloxy)-2-(2-methylpyrazolo[1,5-a]pyridin-3-yl)-1,3-thiazole-5-carboxylate Using methyl 4-hydroxy-2-(2-methylpyrazolo[1,5-a]pyridin-3-yl)-1,3-thiazole-5-carboxylate (800 mg, 2.5 mmol) produced in Example 13-B(i), potassium carbonate (1.9 g, 5.9 mmol), benzyl bromide (2.8 g, 12 mmol) and N,N-dimethylformamide (50 mL) as starting materials and in the same manner as in Example 27-B(i), the title compound (560 mg, 60%) was obtained as a yellow solid.

$^1$H-NMR (DMSO-d$_6$, 300 MHz) δ 2.64 (3H, s), 3.77 (3H, s), 5.67 (2H, s), 7.14 (1H, dt, J=1.3, 6.8 Hz), 7.30-7.45 (3H, m), 7.49-7.64 (3H, m), 8.24-8.30 (1H, m), 8.80 (1H, d, J=6.8 Hz).

(ii) Production of 4-(benzyloxy)-2-(2-methylpyrazolo[1,5-a]pyridin-3-yl)-1,3-thiazole-5-carboxylic acid Using methyl 4-(benzyloxy)-2-(2-methylpyrazolo[1,5-a]pyridin-3-yl)-1,3-thiazole-5-carboxylate (560 mg, 1.5 mmol) produced above, methanol (15 mL), tetrahydrofuran (25 mL) and 8N aqueous sodium hydroxide solution (1.5 mL) as starting materials and in the same manner as in Example 13-B(iv), the title compound (515 mg, 96%) was obtained as a yellow solid.

$^1$H-NMR (DMSO-d$_6$, 300 MHz) δ 2.64 (3H, s), 5.63 (2H, s), 7.11 (1H, dt, J=1.3, 6.9 Hz), 7.28-7.45 (3H, m), 7.50-7.62 (3H, m), 8.21-8.29 (1H, m), 8.78 (1H, d, J=6.9 Hz).

(iii) Production of 4-(benzyloxy)-2-(2-methylpyrazolo[1,5-a]pyridin-3-yl)-1,3-thiazole-5-carboxamide Using 4-(benzyloxy)-2-(2-methylpyrazolo[1,5-a]pyridin-3-yl)-1,3-thiazole-5-carboxylic acid (500 mg, 1.4 mmol) produced above, ammonium chloride (2.0 g, 37 mmol), triethylamine (5.3 mL), 1-hydroxybenzotriazole (80 mg, 0.6 mmol), N-[3-(dimethylamino)propyl]-N'-ethylcarbodiimide hydrochloride (2.5 g, 13 mmol) and N,N-dimethylformamide (50 mL) as starting materials and in the same manner as in Example 13-B(v), the title compound (430 mg, 86%) was obtained as a yellow solid.

$^1$H-NMR (DMSO-d$_6$, 300 MHz) δ 2.63 (3H, s), 5.67 (2H, s), 6.93 (1H, s), 7.10 (1H, dt, J=1.4, 6.8 Hz), 7.30-7.45 (3H, m), 7.49-7.62 (4H, m), 8.21-8.29 (1H, m), 8.77 (1H, d, J=6.8 Hz).

(iv) Production of 3-[4-(benzyloxy)-5-(4H-1,2,4-triazol-3-yl)-1,3-thiazol-2-yl]-2-methylpyrazolo[1,5-a]pyridine Using 4-(benzyloxy)-2-(2-methylpyrazolo[1,5-a]pyridin-3-yl)-1,3-thiazole-5-carboxamide (300 mg, 0.82 mmol) produced above, N,N-dimethylformamide dimethyl acetal (25 mL), acetic acid (50 mL) and hydrazine monohydrate (0.5 mL) as starting materials and in the same manner as in Example 13-B(vi), the title compound (249 mg, 79%) was obtained as a yellow solid.

$^1$H-NMR (DMSO-d$_6$, 300 MHz) δ 2.65 (3H, s), 5.66 (2H, s), 7.08 (1H, dt, J=1.2, 6.8 Hz), 7.25-7.45 (3H, m), 7.49-7.63 (3H, m), 8.19-8.35 (2H, m), 8.76 (1H, d, J=6.8 Hz).

Example 30-B

Production of 5-(benzyloxy)-2-methyl-3-[4-phenyl-5-(4H-1,2,4-triazol-3-yl)-1,3-thiazol-2-yl]pyrazolo[1,5-a]pyridine p-toluenesulfonate

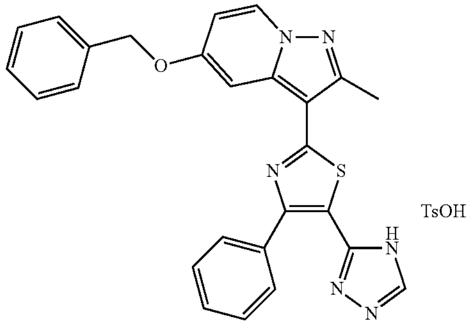

(i) Production of 4-(benzyloxy)pyridine

To 4-chloropyridine hydrochloride (15.0 g, 100 mmol) was added aqueous sodium bicarbonate solution, and the mixture was extracted with ethyl acetate. The collected organic layer was washed with saturated brine and dried over anhydrous magnesium sulfate, and the insoluble material was filtered off. The filtrate was concentrated under reduced pressure to give 4-chloropyridine. To a suspension of sodium hydride (60% in oil, 4.20 g, 105 mmol) in dimethyl sulfoxide (20 mL) was added dropwise benzyl alcohol (11.3 g, 105 mmol) under ice-cooling. The mixture was stirred at room temperature for 1 hr, 4-chloropyridine produced above was added, and the mixture was stirred at room temperature for 1 day. Water was added to the reaction mixture, and the mixture was extracted with diethyl ether. The collected organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=10/90→70/30). The obtained solution was concentrated under reduced pressure to give the title compound (10 g, 55%) as a pale-yellow solid.

$^1$H-NMR (DMSO-$d_6$, 300 MHz) δ 5.19 (2H, s), 7.00-7.07 (2H, m), 7.31-7.51 (5H, m), 8.36-8.43 (2H, m).

(ii) Production of ethyl 5-(benzyloxy)-2-methylpyrazolo[1,5-a]pyridine-3-carboxylate To a solution of ethyl (1E)-N-{[(2,4,6-trimethylphenyl)sulfonyl]oxy}ethanimidate (11 g, 37 mmol) in 1,2-dimethoxyethane (15 mL) was slowly added dropwise perchloric acid (5 mL) under ice-cooling. The mixture was stirred for 0.5 hr under ice-cooling, and water (20 mL) was added. Water (10 mL) was further added, and the mixture was stirred. The resulting precipitate was collected by filtration and washed with water. The obtained white solid was dissolved in ethyl acetate. The aqueous layer was separated and dried over anhydrous magnesium sulfate. The insoluble material was filtered off, and the obtained solution was added dropwise to a solution of 4-(benzyloxy)pyridine (5.6 g, 30 mmol) produced above in ethyl acetate (30 mL) under ice-cooling. After stirring at room temperature for 1 day, the reaction mixture was concentrated under reduced pressure. Ethyl acetate and diethyl ether were added to the obtained residue. The separated oil was washed with ethyl acetate/diethyl ether and diethyl ether, and concentrated under reduced pressure. To a solution of the obtained residue in N,N-dimethylformamide (50 mL) were added potassium carbonate (5.0 g, 36 mmol) and ethyl 2-butynoate (3.4 g, 30 mmol), and the mixture was stirred at room temperature for 1 day. The reaction mixture was concentrated under reduced pressure, water was added to the obtained residue, and the mixture was extracted with ethyl acetate. The collected organic layer was washed with saturated brine and dried over anhydrous magnesium sulfate, and the insoluble material was filtered off. The filtrate was concentrated under reduced pressure, the obtained residue was purified by silica gel column chromatography (ethyl acetate/hexane=10/90→350/50), and the obtained solution was concentrated under reduced pressure. The obtained residue was washed with diisopropyl ether to give the title compound (1.5 g, 16%) as a colorless solid.

$^1$H-NMR (DMSO-$d_6$, 300 MHz) δ 1.33 (3H, t, J=7.0 Hz), 2.50 (3H, s), 4.26 (2H, q, J=7.0 Hz), 5.26 (2H, s), 6.82 (1H, dd, J=2.8, 7.6 Hz), 7.32-7.47 (4H, m), 7.47-7.54 (2H, m), 8.61 (1H, d, J=7.6 Hz).

(iii) Production of 5-(benzyloxy)-2-methylpyrazolo[1,5-a]pyridine-3-carboxylic acid A mixture of ethyl 5-(benzyloxy)-2-methylpyrazolo[1,5-a]pyridine-3-carboxylate (1.6 g, 5.2 mmol) produced above, 1N aqueous sodium hydroxide solution (10 mL), methanol (20 mL) and tetrahydrofuran (10 mL) was stirred at 70° C. for 1 day. To the reaction mixture was added 1N aqueous sodium hydroxide solution (10 mL), and the mixture was stirred at 70° C. for 2 hr. To the reaction mixture was added 8N aqueous sodium hydroxide solution (1 mL), and the mixture was stirred at 70° C. for 2 hr. The reaction mixture was concentrated under reduced pressure, water and 6N hydrochloric acid (2.7 mL) were added to the obtained residue, and the resulting precipitate was collected by filtration, washed with water and dried to give the title compound (1.4 g, 99%) as a colorless solid.

$^1$H-NMR (DMSO-$d_6$, 300 MHz) δ 2.50 (3H, s), 5.22 (2H, s), 6.79 (1H, dd, J=2.8, 7.5 Hz), 7.32-7.47 (4H, m), 7.47-7.55 (2H, m), 8.59 (1H, d, J=7.5 Hz), 12.20 (1H, br s).

(iv) Production of 5-(benzyloxy)-2-methylpyrazolo[1,5-a]pyridine-3-carboxamide A mixture of 5-(benzyloxy)-2-methylpyrazolo[1,5-a]pyridine-3-carboxylic acid (1.4 g, 5.0 mmol) produced above, thionyl chloride (1.1 mL, 15 mmol) and toluene (10 mL) was stirred at 100° C. for 1.5 hr. The reaction mixture was concentrated under reduced pressure, toluene was added to the obtained residue, and the mixture was concentrated again under reduced pressure. The obtained residue was dissolved in tetrahydrofuran (10 mL), concentrated aqueous ammonia (5 mL) and tetrahydrofuran (20 mL) were added, and the mixture was stirred at room temperature for 1 hr. To the reaction mixture were added water and ethyl acetate, and the resulting precipitate was collected by filtration, washed with water and ethyl acetate and dried to give the title compound (917 mg, 65%) as a colorless solid. The filtrate was extracted with a mixed solvent of ethyl acetate and tetrahydrofuran, and the collected organic layer was dried over anhydrous magnesium sulfate. The insoluble material was filtered off. The filtrate was concentrated under reduced pressure, and the obtained residue was washed with diisopropyl ether to give a second crop (490 mg, 35%) of the title compound as a pale-brown solid.

$^1$H-NMR (DMSO-$d_6$, 300 MHz) δ 2.51 (3H, s), 5.21 (2H, s), 6.70 (1H, dd, J=2.7, 7.6 Hz), 6.96 (2H, br s), 7.32-7.47 (4H, m), 7.46-7.55 (2H, m), 8.51 (1H, d, J=7.6 Hz).

(v) Production of 5-(benzyloxy)-2-methylpyrazolo[1,5-a]pyridine-3-carbonitrile To a mixture of 5-(benzyloxy)-2-methylpyrazolo[1,5-a]pyridine-3-carboxamide (1.3 g, 4.8 mmol) produced above, pyridine (1.2 mL, 14 mmol) and tetrahydrofuran (20 mL) was added dropwise under ice-cooling a solution of trifluoroacetic anhydride (1.0 mL, 7.2 mmol) in tetrahydrofuran (2 mL), and the mixture was stirred under ice-cooling for 0.5 hr. Triethylamine (2.0 mL, 14 mmol) was added, and the mixture was stirred at room temperature for 0.5 hr. Trifluoroacetic anhydride (1.0 mL, 7.2 mmol) was added dropwise at room temperature, and the mixture was stirred at room temperature for 0.5 hr and concentrated under reduced pressure. Aqueous sodium bicarbonate solution was added to the obtained residue, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=20/80→100/0). The obtained solution was concentrated under reduced pressure, and the obtained residue was washed with diisopropyl ether/hexane to give the title compound (1.0 g, 79%) as a colorless solid.

$^1$H-NMR (DMSO-$d_6$, 300 MHz) δ 2.44 (3H, s), 5.28 (2H, s), 6.86 (1H, dd, J=2.5, 7.8 Hz), 7.26 (1H, d, J=2.5 Hz), 7.33-7.53 (5H, m), 8.68 (1H, d, J=7.8 Hz).

(vi) Production of 5-(benzyloxy)-2-methylpyrazolo[1,5-a]pyridine-3-carbothioamide A mixture of 5-(benzyloxy)-2-methylpyrazolo[1,5-a]pyridine-3-carbonitrile (950 mg, 3.6 mmol) produced above, O,O'-diethyl dithiophosphate (1.3 mL, 7.2 mmol), 4N hydrogen chloride/ethyl acetate (12 mL) and methanol (4 mL) was stirred at 50° C. for 3 hr. To the reaction mixture was added methanol (8 mL), and the mixture was stirred for 2 hr. To the reaction mixture were added O,O'-diethyl dithiophosphate (0.67 mL, 3.6 mmol) and methanol (6 mL), and the mixture was stirred for 4 hr. To the reaction mixture were added aqueous sodium bicarbonate solution and diethyl ether, and the resulting precipitate was collected by filtration, washed with water and diethyl ether and dried to give the title compound (1.0 g, 95%) as a pale-brown solid.

$^1$H-NMR (DMSO-$d_6$, 300 MHz) δ 2.53 (3H, s), 5.19 (2H, s), 6.76 (1H, dd, J=2.7, 7.6 Hz), 7.32-7.46 (3H, m), 7.47-7.54 (2H, m), 7.86 (1H, d, J=2.7 Hz), 8.47 (1H, br s), 8.54 (1H, d, J=7.6 Hz), 9.28 (1H, br s).

(vii) Production of ethyl 2-[5-(benzyloxy)-2-methylpyrazolo[1,5-a]pyridin-3-yl]-4-phenyl-1,3-thiazole-5-carboxylate A mixture of 5-(benzyloxy)-2-methylpyrazolo[1,5-a]pyridine-3-carbothioamide (950 mg, 3.2 mmol) produced above, ethyl 2-bromo-3-oxo-3-phenylpropanoate (1.30 g, 4.8 mmol) and ethanol (50 mL) was stirred at 80° C. for 1 day. To the reaction mixture were added aqueous sodium bicarbonate solution, ethyl acetate and tetrahydrofuran, and the insoluble material was filtered off. The filtrate was extracted with a mixed solvent of ethyl acetate and tetrahydrofuran. The collected organic layer was washed with saturated brine and dried over anhydrous magnesium sulfate; and the insoluble material was filtered off. The filtrate was concentrated under reduced pressure, and the obtained residue was purified by silica gel column chromatography (ethyl acetate/hexane=50/50→100/0). The crude product was washed with diisopropyl ether to give the title compound (800 mg, 54%) as a pale-yellow solid.

$^1$H-NMR (DMSO-$d_6$, 300 MHz) δ 1.24 (3H, t, J=7.0 Hz), 2.63 (3H, s), 4.24 (2H, q, J=7.0 Hz), 5.28 (2H, s), 6.86 (1H, dd, J=2.7, 7.5 Hz), 7.28-7.34 (3H, m), 7.41-7.56 (5H, m), 7.77 (1H, d, J=2.7 Hz), 7.82-7.90 (2H, m), 8.68 (1H, d, J=7.5 Hz).

(viii) Production of 2-[5-(benzyloxy)-2-methylpyrazolo[1,5-a]pyridin-3-yl]-4-phenyl-1,3-thiazole-5-carboxylic acid A mixture of ethyl 2-[5-(benzyloxy)-2-methylpyrazolo[1,5-a]pyridin-3-yl]-4-phenyl-1,3-thiazole-5-carboxylate (770 mg, 1.6 mmol) produced above, 1N aqueous sodium hydroxide solution (4 mL), methanol (10 mL) and tetrahydrofuran (20 mL) was stirred at 60° C. for 1 hr. To the reaction mixture were added 1N hydrochloric acid (4 mL) and water. The resulting precipitate was collected by filtration, washed with water and diethyl ether and dried to give the title compound (725 mg) as a colorless solid.

$^1$H-NMR (DMSO-$d_6$, 300 MHz) δ 2.63 (3H, s), 5.29 (2H, s), 6.85 (1H, dd, J=2.6, 7.6 Hz), 7.28-7.36 (3H, m), 7.41-7.55 (5H, m), 7.78 (1H, d, J=2.6 Hz), 7.87-7.95 (2H, m), 8.66 (1H, d, J=7.6 Hz), 13.17 (1H, br s).

(ix) Production of 2-[5-(benzyloxy)-2-methylpyrazolo[1,5-a]pyridin-3-yl]-4-phenyl-1,3-thiazole-5-carboxamide A mixture of 2-[5-(benzyloxy)-2-methylpyrazolo[1,5-a]pyridin-3-yl]-4-phenyl-1,3-thiazole-5-carboxylic acid (660 mg, 1.5 mmol) produced above, ammonium chloride (240 mg, 4.5 mmol), triethylamine (0.75 mL, 5.4 mmol), N-[3-(dimethylamino)propyl]-N'-ethylcarbodiimide hydrochloride (440 mg, 2.3 mmol), 1-hydroxybenzotriazole (311 mg, 2.3 mmol) and N,N-dimethylformamide (20 mL) was stirred at room temperature for 1 day. To the reaction mixture were added ammonium chloride (558 mg, 10.5 mmol), triethylamine (1.8 mL, 13 mmol), N-[3-(dimethylamino)propyl]-N'-ethylcarbodiimide hydrochloride (440 mg, 2.3 mmol), 1-hydroxybenzotriazole (310 mg, 2.3 mmol) and N,N-dimethylformamide (20 mL), and the mixture was stirred at room temperature for 1 day. The reaction mixture was concentrated under reduced pressure, and water was added to the obtained residue. The resulting precipitate was collected by filtration, washed with water and diethyl ether and dried to give the title compound (630 mg, 95%) as a pale-yellow solid.

$^1$H-NMR (DMSO-$d_6$, 300 MHz) δ 2.63 (3H, s), 5.31 (2H, s), 6.84 (1H, dd, J=2.6, 7.6 Hz), 7.28-7.56 (8H, m), 7.64 (2H, br s), 7.75 (1H, d, J=2.6 Hz), 7.82-7.89 (2H, m), 8.65 (1H, d, J=7.6 Hz).

(x) Production of 5-(benzyloxy)-2-methyl-3-[4-phenyl-5-(4H-1,2,4-triazol-3-yl)-1,3-thiazol-2-yl]pyrazolo[1,5-a]pyridine A mixture of 2-[5-(benzyloxy)-2-methylpyrazolo[1,5-a]pyridin-3-yl]-4-phenyl-1,3-thiazole-5-carboxamide (590 mg, 1.3 mmol) produced above and N,N-dimethylformamide dimethyl acetal (20 mL) was stirred at 100° C. for 3 hr. The reaction mixture was concentrated under reduced pressure, toluene was added to the obtained residue, and the mixture was concentrated again under reduced pressure. Hydrazine monohydrate (0.33 mL, 6.7 mmol) and acetic acid (20 mL) were added to the obtained residue, and the mixture was stirred at 100° C. for 2 hr. The reaction mixture was concentrated under reduced pressure, and aqueous sodium bicarbonate solution and diethyl ether were added to the obtained residue. The resulting precipitate was collected by filtration, washed with water and diethyl ether and dried to give the title compound (566 mg, 91%) as a pale-brown solid.

$^1$H-NMR (DMSO-$d_6$, 300 MHz) δ 2.65 (3H, s), 5.31 (2H, s), 6.83 (1H, dd, J=2.6, 7.6 Hz), 7.30-7.56 (8H, m), 7.80 (1H, d, J=2.6 Hz), 7.90-7.97 (2H, m), 8.55 (1H, s), 8.65 (1H, d, J=7.6 Hz), 14.17 (1H, br s).

(xi) Production of 5-(benzyloxy)-2-methyl-3-[4-phenyl-5-(4H-1,2,4-triazol-3-yl)-1,3-thiazol-2-yl]pyrazolo[1,5-a]pyridine p-toluenesulfonate A mixture of 5-(benzyloxy)-2-methyl-3-[4-phenyl-5-(4H-1,2,4-triazol-3-yl)-1,3-thiazol-2-yl]pyrazolo[1,5-a]pyridine (100 mg, 0.22 mmol) produced above, p-toluenesulfonic acid monohydrate (49 mg, 0.26 mmol) and ethanol (40 mL) was dissolved by heating, and concentrated under reduced pressure. The obtained residue was crystallized from ethanol and ethyl acetate to give the title compound (90 mg, 66%) as a pale-yellow solid.

$^1$H-NMR (DMSO-$d_6$, 300 MHz) δ 2.29 (3H, s), 2.65 (3H, s), 5.31 (2H, s), 6.83 (1H, dd, J=2.6, 7.6 Hz), 7.11 (2H, d,

J=7.7 Hz), 7.30-7.53 (10H, m), 7.80 (1H, d, J=2.6 Hz), 7.86-7.95 (2H, m), 8.61 (1H, s), 8.65 (1H, d, J=7.6 Hz).

Example 31-B

Production of 2-methyl-5-(2-morpholin-4-ylethoxy)-3-[4-phenyl-5-(4H-1,2,4-triazol-3-yl)-1,3-thiazol-2-yl]pyrazolo[1,5-a]pyridine di-p-toluenesulfonate

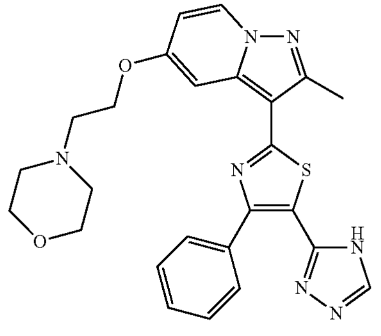

2TsOH (i) Production of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol A mixture of 5-(benzyloxy)-2-methyl-3-[4-phenyl-5-(4H-1,2,4-triazol-3-yl)-1,3-thiazol-2-yl]pyrazolo[1,5-a]pyridine (440 mg, 0.94 mmol) produced in Example 30-B(x), 3,4-dihydro-2H-pyran (0.17 mL, 1.9 mmol), p-toluenesulfonic acid monohydrate (38 mg, 0.2 mmol) and tetrahydrofuran (10 mL) was stirred at 60° C. for 1 day. The reaction mixture was concentrated under reduced pressure, aqueous sodium bicarbonate solution was added to the obtained residue, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=30/70→100/0). The obtained solution was concentrated under reduced pressure, and the obtained residue was washed with diisopropyl ether to give 5-(benzyloxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (430 mg, 84%) as a colorless solid.

To a solution of 5-(benzyloxy)-2-methyl-3-[4-phenyl-5-[1-(tetrahydro-2H-pyran-2-yl)-1H-1,2,4-triazol-3-yl]-1,3-thiazol-2-yl]pyrazolo[1,5-a]pyridine (410 mg, 0.75 mmol) produced above in tetrahydrofuran (30 mL)/ethanol (30 mL) was added 10% palladium-carbon (50% wet with water, 80 mg). The mixture was stirred at room temperature for 3 hr under a hydrogen atmosphere (1 atm), and 10% palladium-carbon was filtered off. 10% Palladium-carbon (50% wet with water, 120 mg) was added to the filtrate, and the mixture was stirred at room temperature for 14 hr under a hydrogen atmosphere (1 atm). 10% Palladium-carbon was filtered off. 10% Palladium-carbon (50% wet with water, 120 mg) was added to the filtrate, and the mixture was stirred at room temperature for 3 hr under a hydrogen atmosphere (1 atm). 10% Palladium-carbon was filtered off, and the filtrate was concentrated under reduced pressure. The obtained residue was purified by silica gel column chromatography (ethyl acetate/hexane=50/50→100/0), and the obtained solution was concentrated under reduced pressure. The obtained residue was washed with diisopropyl ether to give the title compound (273 mg, 79%) as a colorless solid.

$^1$H-NMR (DMSO-$d_6$, 300 MHz) δ 1.48-1.77 (3H, m), 1.86-2.17 (3H, m), 2.64 (3H, s), 3.55-3.73 (1H, m), 3.89-3.98 (1H, m), 5.59 (1H, dd, J=3.0, 8.9 Hz), 6.63 (1H, dd, J=2.6, 7.5 Hz), 7.36-7.51 (3H, m), 7.65 (1H, d, J=2.6 Hz), 7.88-7.96 (2H, m), 8.57 (1H, d, J=7.5 Hz), 8.77 (1H, s), 10.78 (1H, s).

(ii) Production of 2-methyl-5-(2-morpholin-4-ylethoxy)-3-[4-phenyl-5-(4H-1,2,4-triazol-3-yl)-1,3-thiazol-2-yl]pyrazolo[1,5-a]pyridine di-p-toluenesulfonate A mixture of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (60 mg, 0.13 mmol) produced above, 4-(2-chloroethyl)morpholine hydrochloride (48 g, 0.26 mmol), potassium carbonate (72 mg, 0.52 mmol) and N,N-dimethylformamide (3 mL) was stirred at room temperature for 1 hr and at 60° C. for 5 hr. To the reaction mixture was added water, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was purified by basic silica gel column chromatography (ethyl acetate/hexane=50/50→100/0), and the obtained solution was concentrated under reduced pressure. 1N Hydrochloric acid (2 mL), methanol (2 mL) and tetrahydrofuran (2 mL) were added to the obtained residue, and the mixture was stirred at room temperature for 1 hr and at 60° C. for 2 hr. To the reaction mixture was added aqueous sodium bicarbonate solution, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was washed with diisopropyl ether to give 2-methyl-5-(2-morpholin-4-ylethoxy)-3-[4-phenyl-5-(4H-1,2,4-triazol-3-yl)-1,3-thiazol-2-yl]pyrazolo[1,5-a]pyridine (55 mg, 87%) as a colorless solid.

A mixture of 2-methyl-5-(2-morpholin-4-ylethoxy)-3-[4-phenyl-5-(4H-1,2,4-triazol-3-yl)-1,3-thiazol-2-yl]pyrazolo[1,5-a]pyridine (55 mg, 0.11 mmol) produced above, p-toluenesulfonic acid monohydrate (46 mg, 0.24 mmol) and ethanol (80 mL) was dissolved by heating, and concentrated under reduced pressure. The obtained residue was crystallized from ethanol and ethyl acetate to give the title compound (73 mg, 78%) as a yellow solid.

$^1$H-NMR (DMSO-$d_6$, 300 MHz) δ 2.28 (6H, s), 2.69 (3H, s), 3.14-3.35 (2H, m), 3.51-3.62 (2H, m), 3.62-4.09 (6H, m), 4.52-4.61 (2H, m), 6.83 (1H, dd, J=2.7, 7.6 Hz), 7.11 (4H, d,

J=7.7 Hz), 7.39-7.50 (7H, m), 7.75 (1H, d, J=2.7 Hz), 7.88-7.99 (2H, m), 8.63 (1H, br s), 8.72 (1H, d, J=7.6 Hz), 9.85 (1H, br s).

Example 32-B

Production of 2-methyl-3-[4-phenyl-5-(4H-1,2,4-triazol-3-yl)-1,3-thiazol-2-yl]-5-(2-piperidin-1-ylethoxy)pyrazolo[1,5-a]pyridine di-p-toluene-sulfonate

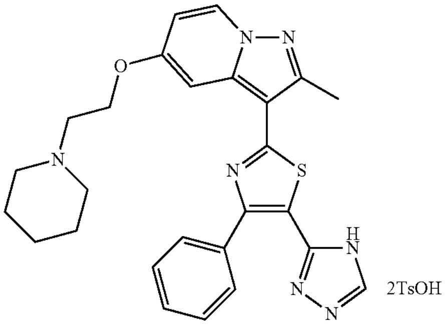

A mixture of 2-methyl-3-[4-phenyl-5-[1-(tetrahydro-2H-pyran-2-yl)-1H-1,2,4-triazol-3-yl]-1,3-thiazol-2-yl]pyrazolo[1,5-a]pyridin-5-ol (60 mg, 0.13 mmol) produced in Example 31-B(i), 1-(2-chloroethyl)piperidine hydrochloride (48 mg, 0.26 mmol), potassium carbonate (72 mg, 0.52 mmol) and N,N-dimethylformamide (3 mL) was stirred at 60° C. for 5 hr. To the reaction mixture was added water, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was purified by basic silica gel column chromatography (ethyl acetate/hexane=40/60→100/0), and the obtained solution was concentrated under reduced pressure. 1N Hydrochloric acid (2 mL), methanol (2 mL) and tetrahydrofuran (2 mL) were added to the obtained residue, and the mixture was stirred at 60° C. for 2 hr. To the reaction mixture was added aqueous sodium bicarbonate solution, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was washed with diisopropyl ether, 2-methyl-3-[4-phenyl-5-(4H-1,2,4-triazol-3-yl)-1,3-thiazol-2-yl]-5-(2-piperidin-1-ylethoxy)pyrazolo[1,5-a]pyridine (57 mg, 90%) as a colorless solid.

A mixture of 2-methyl-3-[4-phenyl-5-(4H-1,2,4-triazol-3-yl)-1,3-thiazol-2-yl]-5-(2-piperidin-1-ylethoxy)pyrazolo[1,5-a]pyridine (57 mg, 0.12 mmol) produced above, p-toluenesulfonic acid monohydrate (49 mg, 0.26 mmol) and ethanol (10 mL) was dissolved by heating, and concentrated under reduced pressure. The obtained residue was crystallized from ethanol and ethyl acetate to give the title compound (85 mg, 87%) as a yellow solid.

$^1$H-NMR (DMSO-$d_6$, 300 MHz) δ 1.29-1.50 (1H, m), 1.56-1.93 (5H, m), 2.28 (6H, s), 2.68 (3H, s), 2.96-3.14 (2H, m), 3.49-3.67 (4H, m), 4.54 (2H, t, J=4.4 Hz), 6.83 (1H, dd, J=2.6, 7.6 Hz), 7.11 (4H, d, J=7.9 Hz), 7.36-7.53 (7H, m), 7.74 (1H, d, J=2.6 Hz), 7.89-7.98 (2H, m), 8.62 (1H, s), 8.71 (1H, d, J=7.6 Hz), 9.26 (1H, br s).

Example 33-B

Production of 2-({2-methyl-3-[4-phenyl-5-(4H-1,2,4-triazol-3-yl)-1,3-thiazol-2-yl]pyrazolo[1,5-a]pyridin-5-yl}oxy)ethanol

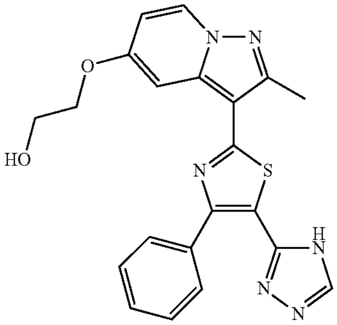 [SMILES: Cc1nn2ccc(OCCO)cc2c1-c1nc(-c2ccccc2)c(-c2nnc[nH]2)s1]

A mixture of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (73 mg, 0.16 mmol) produced in Example 31-B(i), (2-iodoethyl)benzoate (88 mg, 0.32 mmol), potassium carbonate (44 mg, 0.32 mmol) and N,N-dimethylformamide (3 mL) was stirred at 60° C. for 4 hr. To the reaction mixture was added water, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was purified by basic silica gel column chromatography (ethyl acetate/hexane=30/70→100/0). The obtained solution was concentrated under reduced pressure. 1N Hydrochloric acid (2 mL), methanol (2 mL) and tetrahydrofuran (2 mL) were added to the obtained residue, and the mixture was stirred at 60° C. for 1 hr. To the reaction mixture were added methanol (1 mL) and tetrahydrofuran (1 mL), and the mixture was stirred at 60° C. for 2 hr. To the reaction mixture was added 2N aqueous sodium hydroxide solution (2 mL), and the mixture was stirred at room temperature for 1 hr. To the reaction mixture was added water, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was washed with diisopropyl ether to give the title compound (54 mg, 81%) as a colorless solid.

$^1$H-NMR (DMSO-$d_6$, 300 MHz) δ 2.66 (3H, s), 3.81 (2H, q, J=4.8 Hz), 4.17 (2H, t, J=4.8 Hz), 4.98 (1H, t, J=4.8 Hz), 6.78 (1H, dd, J=2.7, 7.6 Hz), 7.34-7.49 (3H, m), 7.73 (1H, d, J=2.7 Hz), 7.91-7.99 (2H, m), 8.58 (1H, s), 8.64 (1H, d, J=7.6 Hz), 14.24 (1H, br s).

Example 34-B

Production of 2-methyl-3-[4-phenyl-5-(4H-1,2,4-triazol-3-yl)-1,3-thiazol-2-yl]pyrazolo[1,5-a]pyridin-5-ol

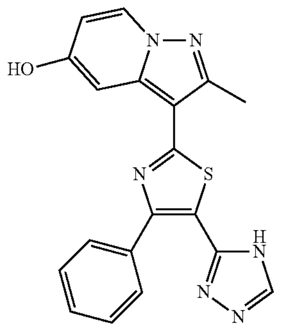 [SMILES: Cc1nn2ccc(O)cc2c1-c1nc(-c2ccccc2)c(-c2nnc[nH]2)s1]

To a solution of 5-(benzyloxy)-2-methyl-3-[4-phenyl-5-(4H-1,2,4-triazol-3-yl)-1,3-thiazol-2-yl]pyrazolo[1,5-a]pyridine (220 mg, 0.47 mmol) produced in Example 30(x) in tetrahydrofuran (20 mL) and methanol (10 mL) was added 10% palladium-carbon (50% wet with water, 110 mg). Under a hydrogen atmosphere (1 atm), the mixture was stirred at room temperature for 31 hr, and 10% palladium-carbon was filtered off. The filtrate was concentrated under reduced pressure, the obtained residue was purified by silica gel column chromatography (ethyl acetate/hexane=50/50→100/0), and the obtained solution was concentrated under reduced pressure. The obtained residue was washed with tetrahydrofuran/ethyl acetate. The obtained crude product was dissolved in ethanol, and concentrated under reduced pressure. The obtained residue was crystallized from ethanol and ethyl acetate to give the title compound (68 mg, 38%) as a pale yellow-brown solid.

$^1$H-NMR (DMSO-$d_6$, 300 MHz) δ 2.64 (3H, s), 6.63 (1H, dd, J=2.5, 7.5 Hz), 7.31-7.51 (3H, m), 7.65 (1H, d, J=2.5 Hz), 7.81-8.03 (2H, m), 8.57 (1H, d, J=7.5 Hz), 8.63 (1H, br s), 10.79 (1H, br s), 14.23 (1H, br s).

Example 35-B

Production of 6-methyl-7-[4-phenyl-5-(4H-1,2,4-triazol-3-yl)-1,3-thiazol-2-yl]pyrazolo[5,1-b][1,3]thiazole acetate

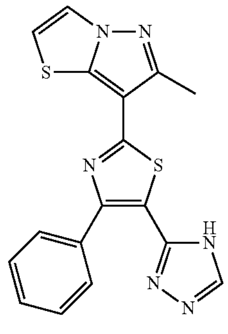 [SMILES: Cc1nn2ccsc2c1-c1nc(-c2ccccc2)c(-c2nnc[nH]2)s1]

(i) Production of 3-amino-2-methyl-1,3-thiazol-3-ium 2,4,6-trimethylbenzenesulfonate A solution of ethyl (1E)-N-{[(2,4,6-trimethylphenyl)sulfonyl]oxy}ethanimidate (19 g, 67 mmol) in 1,4-dioxane (20 mL) was ice-cooled, and perchloric acid (8 mL) was slowly added dropwise with stirring so that the inside temperature would not exceed 10° C. After stirring for 20 min, water (80 mL) was added to the reaction system, and the resulting solid was collected by filtration and washed with water. The obtained solid was added to a suspension of ethyl acetate (80 mL) and anhydrous magnesium sulfate (20 g) under ice-cooling, and the mixture was stirred for 10 min. The insoluble material was filtered off, and washed with toluene (100 mL). The obtained filtrate was used for the next reaction without purification as a solution of 2-[(aminooxy)sulfonyl]-1,3,5-trimethylbenzene in ethyl acetate-toluene.

To a solution of 2-methyl-1,3-thiazole (6.6 g, 67 mmol) in toluene (60 mL) was added a solution of 2-[(aminooxy)sulfonyl]-1,3,5-trimethylbenzene obtained in the above in ethyl acetate-toluene under ice-cooling, and the mixture was stirred for 2 hr. Diisopropyl ether (200 mL) was added to the reaction system, and the resulting solid was collected by filtration to give the title compound (13 g, 63%) as a white solid. The filtrate was concentrated under reduced pressure to about 100 mL, diisopropyl ether (100 mL) was added, and the resulting solid was collected by filtration to give the title compound (3.8 g, 18%) as a white solid (total yield 81%).

$^1$H-NMR (DMSO-$d_6$, 300 MHz) δ 2.17 (3H, s), 2.49 (6H, s), 2.83 (3H, s), 6.74 (2H, s), 7.46 (2H, br s), 8.03 (1H, d, J=3.9 Hz), 8.19 (1H, d, J=3.9 Hz).

(ii) Production of 1-(6-methylpyrazolo[5,1-b][1,3]thiazol-7-yl)ethanone

A mixture of 3-amino-2-methyl-1,3-thiazol-3-ium 2,4,6-trimethylbenzenesulfonate (17 g, 54 mmol) produced above, potassium acetate (16 g, 160 mmol) and acetic anhydride (70 mL, 740 mmol) was stirred at 140° C. for 2 hr. The reaction mixture was cooled to room temperature, 2M aqueous potassium carbonate solution (400 mL) was added, and the mixture was extracted with ethyl acetate. The organic layer was dried over anhydrous magnesium sulfate, the insoluble material was filtered off, and the filtrate was concentrated under reduced pressure. The residue was purified by silica gel column chromatography (ethyl acetate/hexane=2/98→100/0) to give the title compound (4.8 g, 50%) as an orange solid.

$^1$H-NMR (DMSO-$d_6$, 300 MHz) δ 2.51 (3H, s), 2.65 (3H, s), 7.00 (1H, d, J=3.9 Hz), 7.76 (1H, d, J=3.9 Hz).

(iii) Production of 6-methylpyrazolo[5,1-b][1,3]thiazole 1-(6-Methylpyrazolo[5,1-b][1,3]thiazol-7-yl)ethanone (2.8 g, 16 mmol) produced above was added to concentrated hydrochloric acid (28 mL), and the mixture was stirred at 100° C. for 4 days. The reaction mixture was cooled to room temperature, neutralized with an excess amount of aqueous potassium carbonate solution and extracted with ethyl acetate. The organic layer was washed with saturated brine and dried over anhydrous magnesium sulfate, and the insoluble material was filtered off. The filtrate was concentrated under reduced pressure, and the residue was purified by silica gel column chromatography (ethyl acetate/hexane=2/98→50/50) to give the title compound (1.3 g, 61%) as a yellow liquid.

$^1$H-NMR (DMSO-$d_6$, 300 MHz) δ 2.41 (3H, s), 6.51 (1H, s), 6.72 (1H, d, J=4.2 Hz), 7.66 (1H, d, J=4.2 Hz).

(iv) Production of 6-methylpyrazolo[5,1-b][1,3]thiazole-7-carbaldehyde

To a solution of 6-methylpyrazolo[5,1-b][1,3]thiazole (1.3 g, 9.5 mmol) produced above in N,N-dimethylformamide (10 mL) was added N-(chloromethylidene)-N-methylmethanaminium chloride (1.8 g, 14 mmol) with stirring, and the mixture was stirred for 30 min. The reaction solution was added to an excess amount of an aqueous sodium bicarbonate solution, and the mixture was extracted with ethyl acetate. The organic layer was washed with saturated brine and dried over anhydrous magnesium sulfate, and the insoluble material was filtered off. The filtrate was concentrated under reduced pressure, hexane was added to the residue, and the resulting solid was collected by filtration to give the title compound (1.2 g, 79%) as a white solid.

$^1$H-NMR (DMSO-$d_6$, 300 MHz) δ 2.64 (3H, s), 7.06 (1H, d, J=4.2 Hz), 7.78 (1H, d, J=3.9 Hz), 9.92 (1H, s).

(v) Production of 6-methylpyrazolo[5,1-b][1,3]thiazole-7-carbonitrile

A suspension of 6-methylpyrazolo[5,1-b][1,3]thiazole-7-carbaldehyde (170 mg, 1.0 mmol) produced above and hydroxylamine hydrochloride (83 mg, 1.2 mmol) in N,N-dimethylformamide (5 mL) was stirred at 80° C. for 30 min. Triethylamine (0.7 mL, 5 mmol) and 2-chloro-1,3-dimethyl-4,5-dihydro-1H-imidazol-3-ium chloride (250 mg, 1.5 mmol) were added to the reaction solution, and the mixture was further stirred for 30 min. The reaction mixture was cooled to room temperature, an excess amount of an aqueous sodium bicarbonate solution was added, and the mixture was extracted with ethyl acetate. The organic layer was washed with saturated brine and dried over anhydrous magnesium sulfate, and the insoluble material was filtered off. The filtrate was concentrated under reduced pressure, and the residue was purified by silica gel column chromatography (ethyl acetate/hexane=2/98→100/0) to give the title compound (80 mg, 49%) as a white solid.

$^1$H-NMR (DMSO-$d_6$, 300 MHz) δ 2.53 (3H, s), 6.99 (1H, d, J=4.2 Hz), 7.77 (1H, d, J=4.2 Hz).

(vi) Production of 6-methylpyrazolo[5,1-b][1,3]thiazole-7-carbothioamide

A mixture of 6-methylpyrazolo[5,1-b][1,3]thiazole-7-carbonitrile (470 mg, 2.9 mmol) produced above, O,O'-diethyl dithiophosphate (640 mg, 3.4 mmol) and 4N hydrogen chloride/ethyl acetate solution (5 mL) was stirred at room temperature for 30 min. Methanol (5 mL) was added to the reaction solution, and the mixture was heated to 50° C. and stirred for 30 min. The reaction mixture was cooled to room temperature, an excess amount of aqueous sodium bicarbonate solution was added, and the mixture was extracted with ethyl acetate. The organic layer was washed with saturated brine and dried over anhydrous magnesium sulfate, and the insoluble material was filtered off. The filtrate was concentrated under reduced pressure, hexane was added to the residue, and the resulting solid was collected by filtration to give the title compound (530 mg, 94%) as a gray solid.

$^1$H-NMR (DMSO-$d_6$, 300 MHz) δ 2.56 (3H, s), 7.39 (1H, d, J=4.2 Hz), 8.04 (1H, br s), 8.19 (1H, d, J=4.2 Hz), 9.34 (1H, br s).

(vii) Production of ethyl 2-(6-methylpyrazolo[5,1-b][1,3]thiazol-7-yl)-4-phenyl-1,3-thiazole-5-carboxylate 6-Methylpyrazolo[5,1-b][1,3]thiazole-7-carbothioamide (570 mg, 2.9 mmol) produced above and separately produced ethyl 2-bromo-3-oxo-3-phenylpropanoate (860 mg, 3.2 mmol) were added to ethanol (10 mL), and the mixture was stirred at 80° C. for 1 hr. The reaction mixture was cooled to room temperature, an aqueous sodium bicarbonate solution was added, and the mixture was extracted with ethyl acetate. The organic layer was washed with saturated brine and dried over anhydrous magnesium sulfate, and the insoluble material was filtered off. The filtrate was concentrated under reduced pressure, hexane was added to the residue, and the resulting solid was collected by filtration to give the title compound (670 mg, 63%) as a yellow solid.

$^1$H-NMR (DMSO-$d_6$, 300 MHz) δ 1.24 (3H, t, J=7.2 Hz), 2.63 (3H, s), 4.25 (2H, q, J=7.2 Hz), 7.45-7.54 (4H, m), 7.83-7.87 (2H, m), 8.33 (1H, d, J=4.2 Hz).

(viii) Production of 2-(6-methylpyrazolo[5,1-b][1,3]thiazol-7-yl)-4-phenyl-1,3-thiazole-5-carboxylic acid To a solution of ethyl 2-(6-methylpyrazolo[5,1-b][1,3]thiazol-7-yl)-4-phenyl-1,3-thiazole-5-carboxylate (780 mg, 2.1 mmol) produced above in tetrahydrofuran (5 mL) were added methanol (5 mL) and 1N aqueous sodium hydroxide solution (2.4 mL), and the mixture was stirred at 60° C. for 2 hr. The reaction solution was concentrated under reduced pressure, distilled water (10 mL) and 1N hydrochloric acid (2.5 mL) were added to the residue, and the mixture was concentrated under reduced pressure. Ethanol was added to the residue, and the resulting solid was collected by filtration to give the title compound (520 mg) as a yellow solid. The obtained compound was used for the next reaction without further purification.

(ix) Production of 2-(6-methylpyrazolo[5,1-b][1,3]thiazol-7-yl)-4-phenyl-1,3-thiazole-5-carboxamide A suspension of 2-(6-methylpyrazolo[5,1-b][1,3]thiazol-7-yl)-4-phenyl-1,3-thiazole-5-carboxylic acid (85 mg, 0.25 mmol) produced above, ammonium chloride (27 mg, 0.5 mmol) and triethylamine (51 mg, 0.5 mmol) in N,N-dimethylformamide (5 mL) was stirred at room temperature for 10 min. 1-Hydroxybenzotriazole (51 mg, 0.38 mmol) and N-[3-(dimethylamino)propyl]-N'-ethylcarbodiimide hydrochloride (72 mg, 0.38 mmol) were added to the reaction solution, and the mixture was further stirred at room temperature for 1 day. The reaction mixture was added to a mixed solution of ethyl acetate and saturated aqueous sodium bicarbonate solution, and the resulting solid was collected by filtration to give the title compound (10 mg, 10%) as a white solid.

The organic layer was separated from the filtrate and dried over anhydrous magnesium sulfate, and the insoluble material was filtered off. The filtrate was concentrated under reduced pressure to give the title compound (79 mg) as a white solid. The obtained compound contained a small amount of impurity, but was used for the next reaction without further purification.

$^1$H-NMR (DMSO-$d_6$, 300 MHz) δ 2.61 (3H, s), 7.44-7.52 (4H, m), 7.69 (2H, br s), 7.84-7.87 (2H, m), 8.32 (1H, d, J=4.2 Hz).

(x) Production of 6-methyl-7-[4-phenyl-5-(4H-1,2,4-triazol-3-yl)-1,3-thiazol-2-yl]pyrazolo[5,1-b][1,3]thiazole acetate A suspension of 2-(6-methylpyrazolo[5,1-b][1,3]thiazol-7-yl)-4-phenyl-1,3-thiazole-5-carboxamide (79 mg, about 0.23 mmol) produced above in N,N-dimethylformamide dimethyl acetal (2 mL) was stirred at 90° C. for 2 hr. The reaction mixture was concentrated under reduced pressure, hydrazine monohydrate (0.017 mL, 0.35 mmol) and acetic acid (2 mL) were added to the residue, and the mixture was stirred at 90° C. for 1 hr. The reaction mixture was cooled to room temperature, and the resulting solid was collected by filtration and washed with ethyl acetate to give the title compound (27.8 mg, 33%) as a white solid.

$^1$H-NMR (DMSO-$d_6$, 300 MHz) δ 1.91 (3H, s), 2.64 (3H, s), 7.39-7.52 (4H, m), 7.94 (2H, br s), 8.31 (1H, d, J=4.2 Hz), 8.66 (1H, br s), 11.95 (1H, br s), 14.28 (1H, br s).

Example 36-B

Production of 6-methyl-7-[5-(5-methyl-4H-1,2,4-triazol-3-yl)-4-phenyl-1,3-thiazol-2-yl]pyrazolo[5,1-b][1,3]thiazole acetate

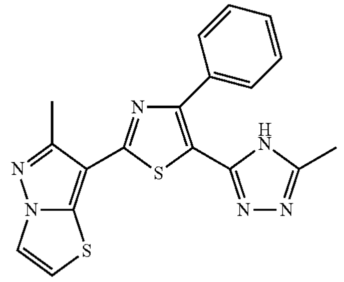 [SMILES: Cc1nnc(-c2sc(-c3c(C)nn4ccsc34)nc2-c2ccccc2)[nH]1]

2-(6-Methylpyrazolo[5,1-b][1,3]thiazol-7-yl)-4-phenyl-1,3-thiazole-5-carboxamide (79 mg, about 0.23 mmol) produced in the same manner as in Example 35-B(ix) was suspended in N,N-dimethylacetamide dimethyl acetal (2 mL), and the mixture was stirred at 90° C. for 2 hr. The reaction mixture was concentrated under reduced pressure, hydrazine monohydrate (0.017 mL, 0.35 mmol) and acetic acid (2 mL) were added to the residue, and the mixture was stirred at 90° C. for 1 hr. The reaction mixture was cooled to room temperature, and the resulting solid was collected by filtration and washed with ethyl acetate to give the title compound (72 mg, 70%) as a white solid.

$^1$H-NMR (DMSO-$d_6$, 300 MHz) δ 1.91 (3H, s), 2.39 (3H, s), 2.64 (3H, s), 7.39-7.51 (4H, m), 7.97-8.00 (2H, m), 8.31 (1H, d, J=4.2 Hz), 11.92 (1H, br s), 13.82 (1H, br s).

Example 37-B

Production of 6-methyl-7-[4-phenyl-5-(1H-tetrazol-5-yl)-1,3-thiazol-2-yl]pyrazolo[5,1-b][1,3]thiazole

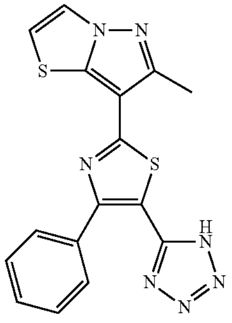 [SMILES: Cc1nn2ccsc2c1-c1nc(-c2ccccc2)c(-c2nnn[nH]2)s1]

(i) Production of 2-(6-methylpyrazolo[5,1-b][1,3]thiazol-7-yl)-4-phenyl-1,3-thiazole-5-carbonitrile To a suspension of 2-(6-methylpyrazolo[5,1-b][1,3]thiazol-7-yl)-4-phenyl-1,3-thiazole-5-carboxamide (270 mg, 0.80 mmol) produced in the same manner as in Example 35-B (ix) in tetrahydrofuran (20 mL) was added Burgess reagent (230 mg, 0.96 mmol), and the mixture was stirred for 30 min. The reaction solution was added to ethyl acetate (100 mL) and saturated aqueous sodium bicarbonate solution (100 mL). The resulting solid was collected by filtration, washed with water and dried to give the title compound (110 mg, 42%) as a colorless solid.

$^1$H-NMR (DMSO-$d_6$, 300 MHz) δ 2.64 (3H, s), 7.57-7.65 (4H, m), 8.15-8.17 (2H, m), 8.39 (1H, d, J=4.2 Hz).

(ii) Production of 6-methyl-7-[4-phenyl-5-(1H-tetrazol-5-yl)-1,3-thiazol-2-yl]pyrazolo[5,1-b][1,3]thiazole A suspension of 2-(6-methylpyrazolo[5,1-b][1,3]thiazol-7-yl)-4-phenyl-1,3-thiazole-5-carbonitrile (108 mg, 0.335 mmol) produced above, sodium azide (87 mg, 1.3 mmol) and ammonium chloride (72 mg, 1.3 mmol) in N,N-dimethylformamide (10 mL) was stirred at 120° C. for 1 day. The reaction solution was cooled to room temperature, sodium azide (100 mg, 1.5 mmol) and ammonium chloride (80 mg, 1.5 mmol) were added, and the mixture was stirred at 120° C. for 4 hr. The reaction solution was cooled to room temperature, the insoluble material was filtered off, and the filtrate was concentrated under reduced pressure. N,N-Dimethylformamide (10 mL), sodium azide (200 mg, 3.1 mmol) and ammonium chloride (160 mg, 3.0 mmol) were added to the residue, and the mixture was stirred at 140° C. for 3 hr. The reaction solution was concentrated under reduced pressure, water (about 5 mL) was added and the insoluble material was filtered off. The filtrate was concentrated under reduced pressure, and water (5 mL), ethyl acetate (5 mL) and 0.1N hydrochloric acid (3 mL) were added. The resulting solid was collected by filtration, washed with water and ethyl acetate and dried to give the title compound (67 mg, 55%).

$^1$H-NMR (DMSO-$d_6$, 300 MHz) δ 2.65 (3H, s), 7.43-7.49 (3H, m), 7.54 (1H, d, J=4.2 Hz), 7.74-7.76 (2H, m), 8.34 (1H, d, J=4.2 Hz).

Example 38-B

Production of 7-[4-(benzyloxy)-5-(4H-1,2,4-triazol-3-yl)-1,3-thiazol-2-yl]-6-methylpyrazolo[5,1-b][1,3]thiazole

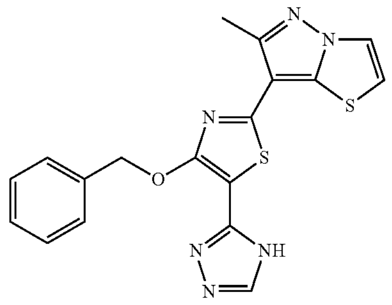 [SMILES: Cc1nn2ccsc2c1-c1nc(OCc2ccccc2)c(-c2nnc[nH]2)s1]

(i) Production of dibenzyl bromomalonate

To a solution of dibenzyl malonate (10.0 g, 35.0 mmol) in diethyl ether (20 mL) were added ammonium acetate (270 mg, 3.5 mmol) and N-bromosuccinimide (6.9 g, 39 mmol), and the mixture was stirred at room temperature for 2 hr. Saturated aqueous sodium bicarbonate solution (100 mL) and ethyl acetate (100 mL) were added to the reaction solution, and the mixture was stirred for 30 min. The organic layer was washed with saturated aqueous potassium carbonate solution (100 mL) and saturated brine (10 mL) and dried over anhydrous magnesium sulfate, and the insoluble material was filtered off. The filtrate was concentrated under reduced pressure, and the obtained residue was purified by silica gel column chromatography (ethyl acetate/hexane=0/100→50/50) to give the title compound (3.8 g, 29%) as a brown oil.

$^1$H-NMR (DMSO-$d_6$, 300 MHz) δ 5.23 (4H, s), 5.76 (1H, s), 7.27-7.42 (10H, m).

(ii) Production of benzyl 4-hydroxy-2-(6-methylpyrazolo[5,1-b][1,3]thiazol-7-yl)-1,3-thiazole-5-carboxylate hydrobromide A suspension of 6-methylpyrazolo[5,1-b][1,3]thiazole-7-carbothioamide (600 mg, 3.0 mmol) produced in Example 35-B(vi) and dibenzyl bromomalonate (980 mg, 2.7 mmol) produced above in 2-propanol (300 mL) was stirred at 80° C. for 3 hr. The reaction mixture was cooled to room temperature, and the precipitated solid was collected by filtration, washed with ethyl acetate and diisopropyl ether and dried to give the title compound (570 mg, 61%) as a yellow solid. This compound was used for the next reaction without further purification.

$^1$H-NMR (DMSO-$d_6$, 300 MHz) δ 2.60 (3H, m), 5.26 (2H, m), 7.22-7.64 (6H, m), 8.27-8.42 (1H, m), 11.95 (1H, s).

(iii) Production of benzyl 4-(benzyloxy)-2-(6-methylpyrazolo[5,1-b][1,3]thiazol-7-yl)-1,3-thiazole-5-carboxylate To a solution of benzyl 4-hydroxy-2-(6-methylpyrazolo[5,1-b][1,3]thiazol-7-yl)-1,3-thiazole-5-carboxylate hydrobromide (300 mg, 0.66 mmol) produced above and benzyl bromide (120 mg, 0.70 mmol) in N,N-dimethylformamide (30 mL) was added potassium carbonate (600 mg, 4.3 mmol), and the mixture was stirred at room temperature for 2 hr. The reaction solution was diluted with water (50 mL), and the mixture was extracted with ethyl acetate (150 mL). The organic layer was washed with saturated brine and dried over anhydrous magnesium sulfate. The insoluble material was filtered off, and the filtrate was concentrated under reduced pressure. The obtained residue was purified by silica gel column chromatography (ethyl acetate/hexane=0/100→100/0) to give the title compound (240 mg, 78%) as a yellow solid.

$^1$H-NMR (DMSO-$d_6$, 300 MHz) δ 2.57 (3H, s), 5.27 (2H, s), 5.64 (2H, s), 7.30-7.44 (8H, m), 7.47-7.55 (2H, m), 7.57 (1H, d, J=4.1 Hz), 8.35 (1H, d, J=4.1 Hz).

(iv) Production of 4-(benzyloxy)-2-(6-methylpyrazolo[5,1-b][1,3]thiazol-7-yl)-1,3-thiazole-5-carboxylic acid To a solution of benzyl 4-(benzyloxy)-2-(6-methylpyrazolo[5,1-b][1,3]thiazol-7-yl)-1,3-thiazole-5-carboxylate (300 mg, 0.65 mmol) produced above in ethanol (8 mL)-tetrahydrofuran (10 mL) were added sodium hydroxide (940 mg, 23.5 mmol) and water (4 mL), and the mixture was stirred at 80° C. for 3 hr. The reaction solution was cooled to room temperature, and the mixture was acidified with 6N hydrochloric acid to about pH 3.0 and extracted with ethyl acetate (100 mL×2). The collected organic layer was dried over anhydrous magnesium sulfate, and the insoluble material was filtered off. The filtrate was concentrated to give the title compound (220 mg, 89%) as a yellow solid.

$^1$H-NMR (DMSO-$d_6$, 300 MHz) δ 2.56 (3H, s), 5.61 (2H, s), 7.28-7.62 (6H, m), 8.33 (1H, d, J=3.9 Hz), 12.65 (1H, s).

(v) Production of 4-(benzyloxy)-2-(6-methylpyrazolo[5,1-b][1,3]thiazol-7-yl)-1,3-thiazole-5-carboxamide To a suspension of 4-(benzyloxy)-2-(6-methylpyrazolo[5,1-b][1,3]thiazol-7-yl)-1,3-thiazole-5-carboxylic acid (200 mg, 0.54 mmol) produced above in toluene (8 mL) was added thionyl chloride (0.5 mL, 6.9 mmol), and the mixture was heated under reflux for 2 hr. The solvent was evaporated under reduced pressure, and the obtained residue was dissolved in tetrahydrofuran (20 mL). 25% Aqueous ammonia (2 mL) was added, and the mixture was stirred for 30 min. The reaction solution was diluted with saturated aqueous sodium bicarbonate solution (100 mL) and extracted with ethyl acetate (100 mL). The organic layer was washed with saturated brine and dried over anhydrous magnesium sulfate, and the insoluble material was filtered off. The filtrate was concentrated under reduced pressure, and the obtained residue was washed with diisopropyl ether and dried to give the title compound (130 mg, 61%) as a yellow solid.

$^1$H-NMR (DMSO-$d_6$, 300 MHz) δ 2.55 (3H, s), 5.64 (2H, s), 7.31-7.46 (4H, m), 7.51-7.63 (4H, m), 8.32 (1H, d, J=4.1 Hz).

(vi) Production of 7-[4-(benzyloxy)-5-(4H-1,2,4-triazol-3-yl)-1,3-thiazol-2-yl]-6-methylpyrazolo[5,1-b][1,3]thiazole A solution of 4-(benzyloxy)-2-(6-methylpyrazolo[5,1-b][1,3]thiazol-7-yl)-1,3-thiazole-5-carboxamide (100 mg, 0.27 mmol) produced above in N,N-dimethylformamide dimethyl acetal (5 mL) was stirred at 85° C. for 1 hr. The reaction solution was cooled to room temperature, and the solvent was evaporated. The residue was washed with diisopropyl ether, the solvent was removed, and the residue was dried. The obtained solid was dissolved in acetic acid (5 mL), hydrazine monohydrate (0.2 mL) was added, and the mixture was stirred at 80° C. for 1 hr. The reaction solution was cooled to room temperature, saturated aqueous sodium bicarbonate solution (100 mL) and ethyl acetate (100 mL) were added, and the mixture was stirred for 30 min. The organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=100/0) to give the title compound (52 mg, 49%) as a yellow solid.

$^1$H-NMR (DMSO-$d_6$, 300 MHz) δ 2.58 (3H, s), 5.63 (2H, s), 7.26-7.42 (3H, m), 7.50-7.63 (3H, m), 8.24 (1H, s), 8.31 (1H, d, J=4.1 Hz).

Example 39-B

Production of 7-[4-(3,4-difluorophenyl)-5-(4H-1,2,4-triazol-3-yl)-1,3-thiazol-2-yl]-6-methylpyrazolo[5,1-b][1,3]thiazole

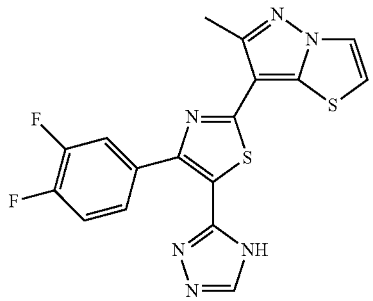 [SMILES: Cc1nn2ccsc2c1-c1nc(-c2ccc(F)c(F)c2)c(-c2nnc[nH]2)s1]

(i) Production of benzyl 2-(6-methylpyrazolo[5,1-b][1,3]thiazol-7-yl)-4-{[(trifluoromethyl)sulfonyl]oxy}-1,3-thiazole-5-carboxylate To a solution of benzyl 4-hydroxy-2-(6-methylpyrazolo[5,1-b][1,3]thiazol-7-yl)-1,3-thiazole-5-carboxylate hydrobromide (1.0 g, 2.2 mmol) produced in Example 38-B(ii) in pyridine (20 mL) was added trifluoromethanesulfonic anhydride (1.5 mL, 8.9 mmol) at 0° C., and the mixture was stirred at room temperature for 1 hr. The reaction solution was cooled to 0° C., saturated aqueous sodium bicarbonate solution (500 mL) and ethyl acetate (500 mL) were added, and the mixture was stirred for 30 min. The organic layer was washed with saturated brine and dried over anhydrous magnesium sulfate, and the insoluble material was filtered off. The filtrate was concentrated under reduced pressure, and the obtained residue was purified by basic silica gel column chromatography (ethyl acetate) to give the title compound (1.0 g, 90%) as a yellow solid.

$^1$H-NMR (DMSO-$d_6$, 300 MHz) δ 2.58 (3H, s), 5.39 (2H, s), 7.36-7.51 (5H, m), 7.60 (1H, d, J=3.9 Hz), 8.39 (1H, d, J=3.9 Hz).

(ii) Production of benzyl 4-(3,4-difluorophenyl)-2-(6-methylpyrazolo[5,1-b][1,3]thiazol-7-yl)-1,3-thiazole-5-carboxylate Benzyl 2-(6-methylpyrazolo[5,1-b][1,3]thiazol-7-yl)-4-{[(trifluoromethyl)sulfonyl]oxy}-1,3-thiazole-5-carboxylate (430 mg, 0.85 mmol) produced above, (3,4-difluorophenyl)boronic acid (220 mg, 1.4 mmol), [1,1-bis(diphenylphosphino)ferrocene]palladium(II) dichloride dichloromethane complex (45 mg, 0.055 mmol) and cesium carbonate (850 mg, 2.6 mmol) were suspended in 1,2-dimethoxyethane (15 mL), water (2 mL) was added, and the mixture was stirred at 80° C. for 1 hr. The reaction solution was cooled to room temperature, water (50 mL) was added, and the mixture was extracted with ethyl acetate (50 mL×2). The collected organic layer was dried over anhydrous magnesium sulfate, and the insoluble material was filtered off. The filtrate was concentrated under reduced pressure, and the obtained residue was subjected to silica gel column chromatography (ethyl acetate) to give the title compound (200 mg, 51%) as a brown solid.

$^1$H-NMR (DMSO-$d_6$, 300 MHz) δ 2.61 (3H, s), 5.41 (2H, s), 7.35-7.44 (5H, m), 7.45-7.62 (2H, m), 7.75-7.88 (1H, m), 7.99-8.07 (1H, m), 8.33 (1H, d, J=4.1 Hz).

(iii) Production of 4-(3,4-difluorophenyl)-2-(6-methylpyrazolo[5,1-b][1,3]thiazol-7-yl)-1,3-thiazole-5-carboxylic acid To a solution of benzyl 4-(3,4-difluorophenyl)-2-(6-methylpyrazolo[5,1-b][1,3]thiazol-7-yl)-1,3-thiazole-5-carboxylate (130 mg, 0.27 mmol) produced above in methanol (5 mL)-tetrahydrofuran (5 mL) was added 8N aqueous sodium hydroxide solution (1.5 mL), and the mixture was stirred at 70° C. for 1 hr. The reaction solution was cooled to 0° C., and 1N hydrochloric acid (10 mL) was added. The precipitated solid was collected by filtration and dried to give the title compound (102 mg, 97%) as a yellow solid.

$^1$H-NMR (DMSO-$d_6$, 300 MHz) δ 2.61 (3H, s), 7.46-7.61 (2H, m), 7.78-7.86 (1H, m), 7.98-8.07 (1H, m), 8.33 (1H, d, J=4.1 Hz).

(iv) Production of 4-(3,4-difluorophenyl)-2-(6-methylpyrazolo[5,1-b][1,3]thiazol-7-yl)-1,3-thiazole-5-carboxamide To a suspension of 4-(3,4-difluorophenyl)-2-(6-methylpyrazolo[5,1-b][1,3]thiazol-7-yl)-1,3-thiazole-5-carboxylic acid (70 mg, 0.19 mmol) produced above in toluene (5 mL) was added thionyl chloride (1.0 mL, 14 mmol), and the mixture was heated under reflux for 1 hr. The solvent was evaporated, and the obtained residue was dissolved in tetrahydrofuran (7 mL). 25% Aqueous ammonia (3 mL) was added, and the mixture was stirred for 30 min. The reaction solution was diluted with water (50 mL), and the mixture was extracted with ethyl acetate (50 mL×2). The organic layer was washed with saturated brine and dried over anhydrous magnesium sulfate, and the insoluble material was filtered off. The filtrate was concentrated under reduced pressure, and the obtained residue was washed with diisopropyl ether and dried to give the title compound (52 mg, 74%) as a yellow solid.

$^1$H-NMR (DMSO-$d_6$, 300 MHz) δ 2.62 (3H, s), 7.52 (1H, d, J=4.1 Hz), 7.53-7.65 (1H, m), 7.68-7.97 (4H, m), 8.33 (1H, d, J=4.1 Hz).

(v) Production of 7-[4-(3,4-difluorophenyl)-5-(4H-1,2,4-triazol-3-yl)-1,3-thiazol-2-yl]-6-methylpyrazolo[5,1-b][1,3]thiazole A solution of 4-(3,4-difluorophenyl)-2-(6-methylpyrazolo[5,1-b][1,3]thiazol-7-yl)-1,3-thiazole-5-carboxamide (50 mg, 0.13 mmol) produced above in N,N-dimethylformamide dimethyl acetal (5 mL) was stirred at 90° C. for 1 hr. The reaction solution was cooled to room temperature, and the solvent was evaporated. The residue was washed with hexane (5 mL) and diethyl ether (2 mL) and dried. The obtained residue was dissolved in acetic acid (10 mL), hydrazine monohydrate (0.3 mL) was added, and the mixture was stirred at 80° C. for 1 hr. The reaction solution was cooled to room temperature, saturated aqueous sodium bicarbonate solution (50 mL) and ethyl acetate (50 mL) were added, and the mixture was stirred for 30 min. The organic layer was washed with saturated brine and dried over anhydrous magnesium sulfate, and the insoluble material was filtered off. The filtrate was concentrated under reduced pressure, and the obtained residue was washed with ethyl acetate (2 mL) and diethyl ether (10 mL) to give the title compound (32 mg, 60%) as a yellow solid.

$^1$H-NMR (DMSO-$d_6$, 300 MHz) δ 2.64 (3H, s), 7.45-7.62 (2H, m), 7.88-7.97 (1H, m), 8.14-8.24 (1H, m), 8.32 (1H, d, J=4.1 Hz), 8.63 (1H, s)

Example 40-B

Production of 2-methyl-3-[4-phenyl-5-(4H-1,2,4-triazol-3-yl)-1,3-thiazol-2-yl]imidazo[1,2-a]pyridine

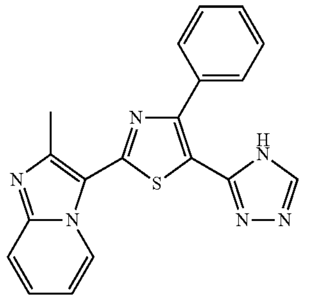 [SMILES: Cc1nc2ccccn2c1-c1nc(-c2ccccc2)c(-c2nnc[nH]2)s1]

(i) Production of 2-methylimidazo[1,2-a]pyridine-3-carboxylic acid

A mixture of pyridin-2-amine (10 g, 106 mmol), ethyl 2-chloro-3-oxobutanoate (16 g, 97 mmol) and ethanol (200 mL) was stirred at 80° C. for 2 days. The reaction mixture was concentrated under reduced pressure, saturated aqueous sodium bicarbonate solution was added to the obtained residue, and the mixture was extracted with ethyl acetate. The collected organic layer was washed with saturated brine and dried over anhydrous magnesium sulfate, and the insoluble material was filtered off. The filtrate was concentrated under reduced pressure, 8N aqueous sodium hydroxide solution (25 mL), water (75 mL) and ethanol (200 mL) were added to the obtained residue, and the mixture was stirred at 70° C. for 1 hr. 6N Hydrochloric acid (34 mL) was added dropwise to the reaction mixture under ice-cooling. The resulting precipitate was collected by filtration, washed with water, ethanol and diethyl ether and dried to give the title compound (7.6 g, 44%) as a pale-pink solid.

$^1$H-NMR (DMSO-$d_6$, 300 MHz) δ 2.60 (3H, s), 7.14 (1H, dt, J=1.3, 6.9 Hz), 7.50 (1H, ddd, J=1.3, 7.0, 8.7 Hz), 7.65 (1H, td, J=1.0, 9.0 Hz), 9.27 (1H, td, J=1.1, 7.0 Hz), 13.04 (1H, br s).

(ii) Production of 2-methylimidazo[1,2-a]pyridine-3-carboxamide

A mixture of 2-methylimidazo[1,2-a]pyridine-3-carboxylic acid (7.1 g, 40 mmol) produced above, thionyl chloride (30 mL, 410 mmol) and toluene (50 mL) was stirred at 100° C. for 1 day, and the reaction mixture was concentrated under reduced pressure. A suspension of the obtained residue in tetrahydrofuran (50 mL) was added to 25% aqueous ammonia (50 mL), and the mixture was stirred at room temperature for 3 hr. Water was added to the reaction mixture, and the mixture was extracted with a mixed solvent of ethyl acetate and tetrahydrofuran. The collected organic layer was washed with saturated brine and dried over anhydrous sodium sulfate, and the insoluble material was filtered off. The filtrate was concentrated under reduced pressure to give the title compound (6.86 g, 98%) as a colorless solid.

$^1$H-NMR (DMSO-$d_6$, 300 MHz) δ 2.58 (3H, s), 7.02 (1H, dt, J=1.3, 6.9 Hz), 7.24-7.52 (2H, m), 7.39 (1H, ddd, J=1.3, 6.8, 8.9 Hz), 7.57 (1H, td, J=1.1, 8.9 Hz), 9.16 (1H, td, J=1.1, 7.0 Hz).

(iii) Production of 2-methylimidazo[1,2-a]pyridine-3-carbonitrile

To a mixture of 2-methylimidazo[1,2-a]pyridine-3-carboxamide (3.50 g, 20 mmol) produced above, pyridine (4.85 mL, 60 mmol) and tetrahydrofuran (50 mL) was added dropwise a solution of trifluoroacetic anhydride (4.24 mL, 30 mmol) in tetrahydrofuran (10 mL) under ice-cooling. The mixture was stirred at room temperature for 1 hr, saturated aqueous sodium bicarbonate solution was added, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was washed with ethyl acetate/diisopropyl ether to give the title compound (2.5 g, 80%) as a pale-brown solid.

$^1$H-NMR (DMSO-$d_6$, 300 MHz) δ 2.49 (3H, s), 7.19 (1H, dt, J=1.1, 6.8 Hz), 7.56 (1H, ddd, J=1.2, 7.0, 9.0 Hz), 7.73 (1H, td, J=1.1, 9.0 Hz), 8.59 (1H, td, J=1.1, 6.8 Hz).

(iv) Production of 2-methylimidazo[1,2-a]pyridine-3-carbothioamide

A mixture of 2-methylimidazo[1,2-a]pyridine-3-carbonitrile (2.76 g, 18 mmol) produced above, O,O'-diethyl dithiophosphate (3.9 mL, 21 mmol), 4N hydrogen chloride ethyl acetate solution (30 mL) and methanol (30 mL) was stirred at 60° C. for 5 hr. Saturated aqueous sodium bicarbonate solution, ethyl acetate and tetrahydrofuran were added to the reaction mixture, and the resulting precipitate was collected by filtration. The obtained solid was washed with water and ethyl acetate and dried to give the title compound (805 mg, 24%) as a pale-yellow solid. The filtrate was extracted with a mixed solvent of ethyl acetate and tetrahydrofuran. The collected organic layer was washed with saturated brine and dried over anhydrous sodium sulfate, and the insoluble material was filtered off. The filtrate was concentrated under reduced pressure, and the obtained residue was washed with ethyl acetate/diisopropyl ether to give the title compound (1.9 g, 55%) as a pale-yellow solid.

$^1$H-NMR (DMSO-$d_6$, 300 MHz) δ 2.52 (3H, s), 7.03 (1H, dt, J=1.3, 6.9 Hz), 7.39 (1H, ddd, J=1.3, 6.8, 8.9 Hz), 7.56 (1H, td, J=1.1, 9.1 Hz), 9.10 (1H, br s), 9.40 (1H, td, J=1.2, 7.0 Hz), 9.78 (1H, br s).

(iv) Production of ethyl 2-(2-methylimidazo[1,2-a]pyridin-3-yl)-4-phenyl-1,3-thiazole-5-carboxylate hydrobromide A mixture of 2-methylimidazo[1,2-a]pyridine-3-carbothioamide (2.5 g, 13 mmol) produced above, ethyl 2-bromo-3-oxo-3-phenylpropanoate (3.5 g, 13 mmol) and ethanol (50 mL) was stirred at 80° C. for 5 hr. The reaction mixture was concentrated under reduced pressure, and ethyl acetate was added. The resulting precipitate was collected by filtration, washed with ethyl acetate and dried to give the title compound (3.0 g, 51%) as a colorless solid.

$^1$H-NMR (DMSO-$d_6$, 300 MHz) δ 1.25 (3H, t, J=7.1 Hz), 2.80 (3H, s), 4.29 (2H, q, J=7.1 Hz), 7.44-7.59 (4H, m), 7.79-8.02 (4H, m), 9.84 (1H, d, J=6.8 Hz).

(v) Production of 2-(2-methylimidazo[1,2-a]pyridin-3-yl)-4-phenyl-1,3-thiazole-5-carboxylic acid A mixture of ethyl 2-(2-methylimidazo[1,2-a]pyridin-3-yl)-4-phenyl-1,3-thiazole-5-carboxylate hydrobromide (2.7 g, 6.0 mmol) produced above, 8N aqueous sodium hydroxide solution (3 mL), water (9 mL), methanol (20 mL) and tetrahydrofuran (20 mL) was stirred at 60° C. for 2 hr. The reaction mixture was concentrated under reduced pressure, and 6N hydrochloric acid (4 mL) was added. The resulting precipitate was collected by filtration, washed with water and ethanol and dried to give the title compound (1.6 g, 81%) as a colorless solid.

$^1$H-NMR (DMSO-$d_6$, 300 MHz) δ 2.71 (3H, s), 7.23 (1H, dt, J=1.2, 6.9 Hz), 7.46-7.58 (4H, m), 7.73 (1H, d, J=8.9 Hz), 7.83-7.92 (2H, m), 9.77 (1H, d, J=6.8 Hz), 13.41 (1H, br s).

(vi) Production of 2-(2-methylimidazo[1,2-a]pyridin-3-yl)-4-phenyl-1,3-thiazole-5-carboxamide hydrochloride A mixture of 2-(2-methylimidazo[1,2-a]pyridin-3-yl)-4-phenyl-1,3-thiazole-5-carboxylic acid (1.6 g, 4.9 mmol) produced above, ammonium chloride (1.6 g, 30 mmol), triethylamine (4.2 mL, 30 mmol), N-[3-(dimethylamino)propyl]-N'-ethylcarbodiimide hydrochloride (1.2 g, 6.0 mmol), 1-hydroxybenzotriazole (810 mg, 6.0 mmol) and N,N-dimethylformamide (50 mL) was stirred at room temperature for 1 day. The reaction mixture was concentrated under reduced pressure, water, ethyl acetate and tetrahydrofuran were added to the obtained residue, and the resulting precipitate was collected by filtration, washed with water, tetrahydrofuran and ethyl acetate and dried to give 2-(2-methylimidazo[1,2-a]pyridin-3-yl)-4-phenyl-1,3-thiazole-5-carboxamide (665 mg, 41%) as a colorless solid. The filtrate was extracted with a mixed solvent of ethyl acetate and tetrahydrofuran. The collected organic layer was washed with saturated brine and dried over anhydrous magnesium sulfate, and the insoluble material was filtered off. The filtrate was concentrated under reduced pressure, and the obtained residue was washed with ethyl acetate/diisopropyl ether to give a crude product (1.1 g) of 2-(2-methylimidazo[1,2-a]pyridin-3-yl)-4-phenyl-1,3-thiazole-5-carboxamide as a yellow solid. 2-(2-Methylimidazo[1,2-a]pyridin-3-yl)-4-phenyl-1,3-thiazole-5-carboxamide (200 mg, 0.60 mmol) produced above was dissolved in 4N hydrogen chloride ethyl acetate solution (0.3 mL) and methanol (10 mL), and the mixture was concentrated under reduced pressure. The obtained residue was washed with methanol/ethyl acetate to give the title compound (185 mg, 83%) as a gray solid.

$^1$H-NMR (DMSO-$d_6$, 300 MHz) δ 2.81 (3H, s), 7.44-7.64 (4H, m), 7.84-8.05 (6H, m), 9.87 (1H, d, J=7.0 Hz).

(vii) Production of 2-methyl-3-[4-phenyl-5-(4H-1,2,4-triazol-3-yl)-1,3-thiazol-2-yl]imidazo[1,2-a]pyridine hydrochloride A mixture of 2-(2-methylimidazo[1,2-a]pyridin-3-yl)-4-phenyl-1,3-thiazole-5-carboxamide (670 mg, 2.0 mmol) produced above and N,N-dimethylformamide dimethyl acetal (20 mL) was stirred at 120° C. for 2 hr. The reaction mixture was concentrated under reduced pressure, and the obtained residue was washed with ethyl acetate to give a solid (628 mg). Hydrazine monohydrate (0.4 mL, 8.0 mmol) and acetic acid (20 mL) were added to the obtained solid (312 mg), and the mixture was stirred at 100° C. for 1 day. The reaction mixture was concentrated under reduced pressure, and saturated aqueous sodium bicarbonate solution and ethanol were added to the obtained residue. The resulting precipitate was collected by filtration, washed with water and ethanol and dried. A mixture of the obtained crude product (254 mg), 4N hydrogen chloride ethyl acetate solution (0.3 mL) and methanol (30 mL) was dissolved by heating, and the mixture was concentrated under reduced pressure. The obtained residue was washed with methanol/ethyl acetate to give the title compound (143 mg, 36%) as a pale-brown solid.

$^1$H-NMR (DMSO-$d_6$, 300 MHz) δ 2.83 (3H, s), 7.40-7.62 (4H, m), 7.85-8.02 (4H, m), 8.70 (1H, s), 9.91 (1H, d, J=7.0 Hz).

Example 41-B

Production of 2-methyl-3-[4-phenyl-5-(4H-1,2,4-triazol-3-yl)-1,3-thiazol-2-yl]imidazo[1,2-b]pyridazine

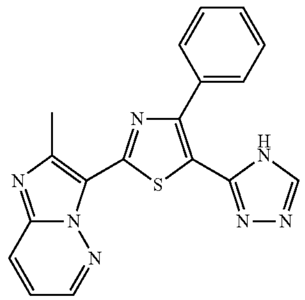 [SMILES: Cc1nc2cccnn2c1-c1nc(-c2ccccc2)c(-c2nnc[nH]2)s1]

(i) Production of ethyl 6-chloro-2-methylimidazo[1,2-b]pyridazine-3-carboxylate

A mixture of 6-chloropyridazin-3-amine (5.3 g, 41 mmol), ethyl 2-chloro-3-oxobutanoate (6.7 g, 41 mmol) and ethanol (50 mL) was heated under reflux for 2 days. The reaction mixture was concentrated under reduced pressure, saturated aqueous sodium bicarbonate solution and ethyl acetate were added to the obtained residue, and the insoluble material was filtered off. The filtrate was extracted with ethyl acetate, and the collected organic layer was washed with saturated brine and dried over anhydrous magnesium sulfate. The insoluble material was filtered off, and the filtrate was concentrated under reduced pressure. Ethyl acetate and diisopropyl ether were added to the obtained residue, and the insoluble material was filtered off. The obtained residue was purified by silica gel column chromatography (ethyl acetate/hexane=50/50→100/0) and washed with ethyl acetate/diisopropyl ether to give the title compound (3.2 g, 32%) as a colorless solid.

$^1$H-NMR (DMSO-$d_6$, 300 MHz) δ 1.35 (3H, t, J=7.1 Hz), 2.63 (3H, s), 4.37 (2H, q, J=7.1 Hz), 7.59 (1H, d, J=9.4 Hz), 8.25 (1H, d, J=9.4 Hz).

(ii) Production of 6-chloro-2-methylimidazo[1,2-b]pyridazine-3-carboxamide

A mixture of ethyl 6-chloro-2-methylimidazo[1,2-b]pyridazine-3-carboxylate (2.4 g, 10 mmol) produced above, 8N aqueous sodium hydroxide solution (2 mL) and methanol (50 mL) was stirred at 70° C. for 1.5 hr. To the reaction mixture was added 6N hydrochloric acid (2.6 mL), and the resulting precipitate was collected by filtration, washed with ethanol and dried. Thionyl chloride (3.7 mL, 50 mmol) and toluene (20 mL) were added to the obtained solid, and the mixture was stirred at 80° C. for 1.5 hr. The reaction mixture was concentrated under reduced pressure, toluene was added to the obtained residue, and the mixture was concentrated again under reduced pressure. A suspension of the obtained residue in tetrahydrofuran (20 mL) was added to 25% aqueous ammonia (20 mL), and the mixture was stirred at room temperature for 1 hr. The resulting precipitate was collected by filtration, washed with water and ethyl acetate and dried to give the title compound (1.0 g, 49%) as a colorless solid. The filtrate was extracted with a mixed solvent of ethyl acetate and tetrahydrofuran, and the collected organic layer was washed with saturated brine and dried over anhydrous sodium sulfate, and the insoluble material was filtered off. The filtrate was concentrated under reduced pressure to give the title compound (0.5 g, 23%) as a colorless solid.

$^1$H-NMR (DMSO-$d_6$, 300 MHz) δ 2.65 (3H, s), 7.55 (1H, d, J=9.4 Hz), 7.82 (1H, br s), 7.95 (1H, br s), 8.27 (1H, d, J=9.4 Hz).

(iii) Production of 6-chloro-2-methylimidazo[1,2-b]pyridazine-3-carbonitrile

To a mixture of 6-chloro-2-methylimidazo[1,2-b]pyridazine-3-carboxamide (1.5 g, 7.0 mmol) produced above, pyridine (1.7 mL, 21 mmol) and tetrahydrofuran (20 mL) was added dropwise under ice-cooling a solution of trifluoroacetic anhydride (1.5 mL, 11 mmol) in tetrahydrofuran (5 mL), and the mixture was stirred at room temperature for 2 hr. A saturated aqueous sodium bicarbonate solution was added to the reaction mixture, and the mixture was extracted with ethyl acetate. The collected organic layer was washed with saturated brine and dried over anhydrous magnesium sulfate, and the insoluble material was filtered off. The filtrate was concentrated under reduced pressure, the obtained residue was purified by silica gel column chromatography (ethyl acetate/hexane=50/50→100/0), and the obtained solution was concentrated under reduced pressure. The obtained residue was washed with diisopropyl ether to give the title compound (887 mg, 66%) as a colorless solid.

$^1$H-NMR (DMSO-$d_6$, 300 MHz) δ 2.54 (3H, s), 7.68 (1H, d, J=9.6 Hz), 8.34 (1H, d, J=9.6 Hz).

(iv) Production of 6-chloro-2-methylimidazo[1,2-b]pyridazine-3-carbothioamide

A mixture of 6-chloro-2-methylimidazo[1,2-b]pyridazine-3-carbonitrile (830 mg, 4.3 mmol) produced above, O,O'-diethyl dithiophosphate (1.0 mL, 5.2 mmol), 4N hydrogen chloride ethyl acetate solution (10 mL) and methanol (10 mL) was stirred at 60° C. for 1 day. To the reaction mixture was added saturated aqueous sodium bicarbonate solution, and the resulting precipitate was collected by filtration, washed with water and diethyl ether and dried to give the title compound (766 mg, 79%) as a yellow solid.

$^1$H-NMR (DMSO-$d_6$, 300 MHz) δ 2.70 (3H, s), 7.53 (1H, d, J=9.4 Hz), 8.25 (1H, d, J=9.4 Hz), 9.55 (1H, br s), 10.13 (1H, br s).

(v) Production of ethyl 2-(6-chloro-2-methylimidazo[1,2-b]pyridazin-3-yl)-4-phenyl-1,3-thiazole-5-carboxylate A mixture of 6-chloro-2-methylimidazo[1,2-b]pyridazine-3-carbothioamide (725 mg, 3.2 mmol) produced above, ethyl 2-bromo-3-oxo-3-phenylpropanoate (868 mg, 3.2 mmol) and ethanol (20 mL) was stirred at 80° C. for 5 hr. To the reaction mixture were added saturated aqueous sodium bicarbonate solution, ethyl acetate and tetrahydrofuran, and the insoluble material was filtered off. The filtrate was extracted with a mixed solvent of ethyl acetate and tetrahydrofuran. The collected organic layer was washed with saturated brine and dried over anhydrous sodium sulfate, and the insoluble material was filtered off. The filtrate was concentrated under reduced pressure, the obtained residue was purified by silica gel column chromatography (methanol/ethyl acetate=0/100→100/0), and the obtained solution was concentrated under reduced pressure. The obtained residue was washed with ethyl acetate/diisopropyl ether to give the title compound (564 mg, 44%) as a yellow solid.

$^1$H-NMR (DMSO-$d_6$, 300 MHz) δ 1.26 (3H, t, J=7.2 Hz), 2.86 (3H, s), 4.29 (2H, q, J=7.2 Hz), 7.45-7.55 (3H, m), 7.64 (1H, d, J=9.4 Hz), 7.80-7.90 (2H, m), 8.37 (1H, d, J=9.3 Hz).

(vi) Production of 2-(6-chloro-2-methylimidazo[1,2-b]pyridazin-3-yl)-4-phenyl-1,3-thiazole-5-carboxamide hydrochloride A mixture of ethyl 2-(6-chloro-2-methylimidazo[1,2-b]pyridazin-3-yl)-4-phenyl-1,3-thiazole-5-carboxylate (520 mg, 1.3 mmol) produced above, 1N aqueous sodium hydroxide solution (1.6 mL), ethanol (5 mL) and tetrahydrofuran (10 mL) was stirred at 50° C. for 3 hr. To the reaction mixture were added 1N hydrochloric acid (1.6 mL) and water, and the resulting precipitate was collected by filtration, washed with water and diethyl ether and dried. Ammonium chloride (346 mg, 6.5 mmol), triethylamine (0.9 mL, 6.5 mmol), N-[3-(dimethylamino)propyl]-N'-ethylcarbodiimide hydrochloride (383 mg, 2.0 mmol), 1-hydroxybenzotriazole (270 mg, 2.0 mmol) and N,N-dimethylformamide (10 mL) were added to the obtained 2-(6-chloro-2-methylimidazo[1,2-b]pyridazin-3-yl)-4-phenyl-1,3-thiazole-5-carboxylic acid (408 mg), and the mixture was stirred at room temperature for 3 days. The reaction mixture was concentrated under reduced pressure, water and ethyl acetate were added to the obtained residue, and the resulting precipitate was collected by filtration, washed with water and ethyl acetate and dried. 4N Hydrogen chloride ethyl acetate solution (0.5 mL) and methanol (10 mL) were added to the obtained crude product (379 mg), and the mixture was heated, and concentrated under reduced pressure. The obtained residue was washed with methanol to give the title compound (294 mg, 56%) as a yellow solid.

$^1$H-NMR (DMSO-$d_6$, 300 MHz) δ 2.91 (3H, s), 7.40-7.56 (3H, m), 7.61 (1H, d, J=9.4 Hz), 7.72-8.00 (4H, m), 8.36 (1H, d, J=9.4 Hz).

(vii) Production of 2-(2-methylimidazo[1,2-b]pyridazin-3-yl)-4-phenyl-1,3-thiazole-5-carboxamide To a solution of 2-(6-chloro-2-methyl imidazo[1,2-b]pyridazin-3-yl)-4-phenyl-1,3-thiazole-5-carboxamide hydrochloride (162 mg, 0.40 mmol) produced above and triethylamine (0.28 mL, 2 mmol) in N,N-dimethylformamide (30 mL) was added 10% palladium-carbon (50% wet with water, 50 mg). Under a hydrogen atmosphere (1 atm), the mixture was stirred at room temperature for 1 day, and 10% palladium-carbon was filtered off. The filtrate was concentrated under reduced pressure, and the obtained residue was washed with water and ethyl acetate to give the title compound (144 mg, quantitative) as a gray solid.

$^1$H-NMR (DMSO-$d_6$, 300 MHz) δ 2.92 (3H, s), 7.39-7.55 (4H, m), 7.69-7.94 (4H, m), 8.29 (1H, dd, J=1.5, 9.1 Hz), 8.86 (1H, dd, J=1.6, 4.6 Hz).

(viii) Production of 2-methyl-3-[4-phenyl-5-(4H-1,2,4-triazol-3-yl)-1,3-thiazol-2-yl]imidazo[1,2-b]pyridazine A mixture of 2-(2-methylimidazo[1,2-b]pyridazin-3-yl)-4-phenyl-1,3-thiazole-5-carboxamide (124 mg, 0.37 mmol) produced above and N,N-dimethylformamide dimethyl acetal (10 mL) was stirred at 120° C. for 4 hr. The reaction mixture was concentrated under reduced pressure, and the obtained residue was washed with ethyl acetate/diethyl ether. Hydrazine monohydrate (0.18 mL, 3.7 mmol) and acetic acid (10 mL) were added to the obtained solid, and the mixture was stirred at 100° C. for 2 hr. The reaction mixture was concentrated under reduced pressure, and water and saturated aqueous sodium bicarbonate solution were added to the obtained residue. The resulting precipitate was collected by filtration, washed with water and ethyl acetate and dried. The obtained crude product was purified by silica gel column chromatography (methanol/ethyl acetate=20/80→100/0), and the obtained solution was concentrated under reduced pressure. Water was added to the obtained residue, and the precipitate was collected by filtration, washed with water, ethanol and ethyl acetate and dried to give the title compound (93 mg, 71%) as a yellow solid.

$^1$H-NMR (DMSO-$d_6$, 300 MHz) δ 2.94 (3H, s), 7.36-7.51 (4H, m), 7.92-8.00 (2H, m), 8.29 (1H, dd, J=1.6, 9.2 Hz), 8.61 (1H, br s), 8.86 (1H, dd, J=1.6, 4.6 Hz), 14.31 (1H, br s).

Example 42-B

Production of 6-methyl-5-[4-phenyl-5-(4H-1,2,4-triazol-3-yl)-1,3-thiazol-2-yl]imidazo[2,1-b][1,3]thiazole p-toluenesulfonate

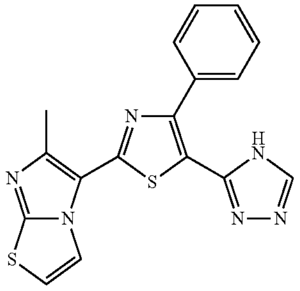

TsOH (i) Production of ethyl 6-methylimidazo[2,1-b][1,3]thiazole-5-carboxylate

A mixture of 1,3-thiazol-2-amine (10 g, 100 mmol), ethyl 2-chloro-3-oxobutanoate (16 g, 100 mmol) and ethanol (100 mL) was stirred at 80° C. for 1 day. The reaction mixture was concentrated under reduced pressure, saturated aqueous sodium bicarbonate solution was added to the obtained residue, and the mixture was extracted with ethyl acetate. The collected organic layer was washed with saturated brine and dried over anhydrous magnesium sulfate. The insoluble material was filtered off, and the filtrate was concentrated under reduced pressure. The obtained residue was purified by silica gel column chromatography (ethyl acetate/hexane=20/80→50/50) and washed with diisopropyl ether to give the title compound (5.5 g, 26%) as a colorless solid.

$^1$H-NMR (DMSO-$d_6$, 300 MHz) δ 1.34 (3H, t, J=7.2 Hz), 2.51 (3H, s), 4.33 (2H, q, J=7.2 Hz), 7.44 (1H, d, J=4.3 Hz), 8.08 (1H, d, J=4.3 Hz).

(ii) Production of 6-methylimidazo[2,1-b][1,3]thiazole-5-carboxamide

A mixture of ethyl 6-methylimidazo[2,1-b][1,3]thiazole-5-carboxylate (2.1 g, 10 mmol) produced above, 8N aqueous sodium hydroxide solution (2 mL) and methanol (10 mL) was stirred at room temperature for 1 day. To the reaction mixture was added 6N hydrochloric acid (2.6 mL), and the mixture was concentrated under reduced pressure. Toluene was added to the obtained residue, and the mixture was concentrated again under reduced pressure. Thionyl chloride (3.7 mL, 50 mmol) and toluene (30 mL) were added to the obtained solid, and the mixture was stirred at 100° C. for 1 day. The reaction mixture was concentrated under reduced pressure, toluene was added to the obtained residue, and the mixture was concentrated again under reduced pressure. To a suspension of the obtained residue in tetrahydrofuran (20 mL) was added 25% aqueous ammonia (10 mL), and the mixture was stirred at room temperature for 2 hr. The reaction mixture was concentrated under reduced pressure, tetrahydrofuran was added to the obtained residue, and the insoluble material was filtered off. The filtrate was concentrated under reduced pressure, and the obtained residue was purified by silica gel column chromatography (methanol/ethyl acetate=0/100→20/80). The obtained solution was concentrated under reduced pressure to give the title compound (588 mg, 32%) as a brown solid.

$^1$H-NMR (DMSO-$d_6$, 300 MHz) δ 2.48 (3H, s), 7.24 (2H, br s), 7.31 (1H, d, J=4.3 Hz), 8.11 (1H, d, J=4.3 Hz).

(iii) Production of 6-methyl imidazo[2,1-b][1,3]thiazole-5-carbonitrile

To a mixture of 6-methylimidazo[2,1-b][1,3]thiazole-5-carboxamide (544 mg, 3.0 mmol) produced above, pyridine (0.7 mL, 9.0 mmol) and tetrahydrofuran (10 mL) was added dropwise under ice-cooling trifluoroacetic anhydride (0.6 mL, 4.5 mmol). After stirring at room temperature for 1 day, saturated aqueous sodium bicarbonate solution was added, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was purified by silica gel column chromatography (ethyl acetate/hexane=30/70→50/50). The obtained solution was concentrated under reduced pressure to give the title compound (433 mg, 86%) as a pale-brown solid.

$^1$H-NMR (DMSO-$d_6$, 300 MHz) δ 2.40 (3H, s), 7.51 (1H, d, J=4.5 Hz), 8.17 (1H, d, J=4.5 Hz).

(iv) Production of ethyl 2-(6-methylimidazo[2,1-b][1,3]thiazol-5-yl)-4-phenyl-1,3-thiazole-5-carboxylate A mixture of 6-methylimidazo[2,1-b][1,3]thiazole-5-carbonitrile (408 mg, 2.5 mmol) produced above, O,O'-diethyl dithiophosphate (0.6 mL, 3.0 mmol), 4N hydrogen chloride ethyl acetate solution (5 mL) and methanol (5 mL) was stirred at 50° C. for 2 hr. To the reaction mixture was added saturated aqueous sodium bicarbonate solution, and the resulting precipitate was collected by filtration, washed with water and diethyl ether and dried. To the obtained crude product of 6-methylimidazo[2,1-b][1,3]thiazole-5-carbothioamide were added ethyl 2-bromo-3-oxo-3-phenylpropanoate (542 mg, 2.0 mmol) and ethanol (10 mL), and the mixture was stirred at 80° C. for 2 hr. The reaction mixture was concentrated under reduced pressure, saturated aqueous sodium bicarbonate solution was added to the obtained residue, and the mixture was extracted with ethyl acetate. The collected organic layer was washed with saturated brine and dried over anhydrous magnesium sulfate, and the insoluble material was filtered off. The filtrate was concentrated under reduced pressure, the obtained residue was washed with ethyl acetate/diisopropyl ether, and the filtrate was concentrated under reduced pressure. The obtained residue was purified by silica gel column chromatography (ethyl acetate/hexane=50/50→100/0). The obtained solution was concentrated under reduced pressure to give the title compound (115 mg, 12%) as a colorless solid.

$^1$H-NMR (DMSO-$d_6$, 300 MHz) δ 1.24 (3H, t, J=7.1 Hz), 2.59 (3H, s), 4.26 (2H, q, J=7.2 Hz), 7.46-7.53 (4H, m), 7.81-7.89 (2H, m), 8.45 (1H, d, J=4.5 Hz).

(v) Production of 2-(6-methylimidazo[2,1-b][1,3]thiazol-5-yl)-4-phenyl-1,3-thiazole-5-carboxylic acid A mixture of ethyl 2-(6-methylimidazo[2,1-b][1,3]thiazol-5-yl)-4-phenyl-1,3-thiazole-5-carboxylate (111 mg, 0.30 mmol) produced above, 1N aqueous sodium hydroxide solution (1 mL), methanol (5 mL) and tetrahydrofuran (5 mL) was stirred at room temperature for 1 day. The reaction mixture was concentrated under reduced pressure, and water and 1N hydrochloric acid (1 mL) were added. The resulting precipitate was collected by filtration, washed with water and diethyl ether and dried to give the title compound (80 mg, 78%) as a pale-brown solid.

$^1$H-NMR (DMSO-$d_6$, 300 MHz) δ 2.59 (3H, s), 7.44-7.53 (4H, m), 7.82-7.90 (2H, m), 8.45 (1H, d, J=4.5 Hz), 13.39 (1H, br s).

(vi) Production of 2-(6-methylimidazo[2,1-b][1,3]thiazol-5-yl)-4-phenyl-1,3-thiazole-5-carboxamide A mixture of 2-(6-methylimidazo[2,1-b][1,3]thiazol-5-yl)-4-phenyl-1,3-thiazole-5-carboxylic acid (60 mg, 0.18 mmol) produced above, ammonium chloride (53 mg, 1.0 mmol), triethylamine (0.14 mL, 1.0 mmol), N-[3-(dimethylamino)propyl]-N'-ethylcarbodiimide hydrochloride (77 mg, 0.4 mmol), 1-hydroxybenzotriazole (54 mg, 0.4 mmol) and N,N-dimethylformamide (5 mL) was stirred at room temperature for 3 days. The reaction mixture was concentrated under reduced pressure, and water and diethyl ether were added to the obtained residue. The resulting precipitate was collected by filtration, washed with water and diethyl ether and dried to give the title compound (56 mg, 94%) as a colorless solid.

$^1$H-NMR (DMSO-$d_6$, 300 MHz) δ 2.58 (3H, s), 7.41-7.55 (4H, m), 7.75 (2H, s), 7.82-7.90 (2H, m), 8.49 (1H, d, J=4.3 Hz).

(vii) Production of 6-methyl-5-[4-phenyl-5-(4H-1,2,4-triazol-3-yl)-1,3-thiazol-2-yl]imidazo[2,1-b][1,3]thiazole p-toluenesulfonate A mixture of 2-(6-methylimidazo[2,1-b][1,3]thiazol-5-yl)-4-phenyl-1,3-thiazole-5-carboxamide (150 mg, 0.44 mmol) produced above and N,N-dimethylformamide dimethyl acetal (10 mL) was stirred at 100° C. for 3 hr. The reaction mixture was concentrated under reduced pressure, and the obtained residue was washed with diethyl ether. Hydrazine monohydrate (0.22 mL, 4.4 mmol) and acetic acid (10 mL) were added to the obtained solid, and the mixture was stirred at 100° C. for 2 hr. The reaction mixture was concentrated under reduced pressure, saturated aqueous sodium bicarbonate solution and diethyl ether were added to the obtained residue, and the mixture was stirred. The resulting precipitate was collected by filtration, washed with water and diethyl ether and dried to give 6-methyl-5-[4-phenyl-5-(4H-1,2,4-triazol-3-yl)-1,3-thiazol-2-yl]imidazo[2,1-b][1,3]thiazole (123 mg, 77%) as a pale-yellow solid.

A mixture of 6-methyl-5-[4-phenyl-5-(4H-1,2,4-triazol-3-yl)-1,3-thiazol-2-yl]imidazo[2,1-b][1,3]thiazole (51 mg, 0.14 mmol) produced above, p-toluenesulfonic acid monohydrate (32 mg, 0.17 mmol) and ethanol (40 mL) was dissolved by heating and concentrated under reduced pressure. The obtained residue was crystallized from ethanol to give the title compound (72 mg, 96%) as a pale-pink solid.

$^1$H-NMR (DMSO-$d_6$, 300 MHz) δ 2.29 (3H, s), 2.63 (3H, s), 7.11 (2H, d, J=7.9 Hz), 7.38-7.51 (5H, m), 7.53 (1H, d, J=4.5 Hz), 7.87-7.95 (2H, m), 8.55 (1H, d, J=4.3 Hz), 8.65 (1H, s).

Example 43-B

Production of 4-[4-phenyl-5-(4H-1,2,4-triazol-3-yl)-1,3-thiazol-2-yl]-1H-pyrrolo[2,3-b]pyridine p-toluenesulfonate

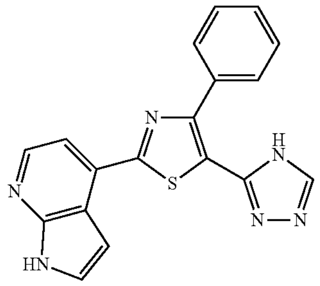

TsOH (i) Production of 1H-pyrrolo[2,3-b]pyridine-4-carbonitrile

A mixture of 4-chloro-1H-pyrrolo[2,3-b]pyridine (3.1 g, 20 mmol), zinc cyanide (1.4 g, 12 mmol), zinc (130 mg, 2.0 mmol), tris(dibenzylideneacetone)dipalladium(0) (370 mg, 0.40 mmol), 1,1'-bis(diphenylphosphino)ferrocene (440 mg, 0.80 mmol) and N,N-dimethylacetamide (20 mL) was stirred at 120° C. for 1.5 hr under an argon atmosphere. The reaction mixture was purified by silica gel column chromatography (ethyl acetate/hexane=20/80→100/0), and the obtained solution was concentrated under reduced pressure. The obtained residue was washed with diisopropyl ether to give the title compound (2.60 g, 91%) as a red-brown solid.

$^1$H-NMR (DMSO-$d_6$, 300 MHz) δ 6.65 (1H, dd, J=1.7, 3.4 Hz), 7.56 (1H, d, J=4.9 Hz), 7.81-7.87 (1H, m), 8.41 (1H, d, J=4.9 Hz), 12.38 (1H, br s).

(ii) Production of 1H-pyrrolo[2,3-b]pyridine-4-carbothioamide

A mixture of 1H-pyrrolo[2,3-b]pyridine-4-carbonitrile (1.0 g, 7.0 mmol) produced above, O,O'-diethyl dithiophosphate (1.6 mL, 8.4 mmol), 4N hydrogen chloride ethyl acetate solution (15 mL) and methanol (15 mL) was stirred at 50° C. for 3.5 hr and at 60° C. for 4.5 hr. Saturated aqueous sodium bicarbonate solution was added to the reaction mixture, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was washed with diisopropyl ether to give the title compound (751 mg, 61%) as a yellow solid.

$^1$H-NMR (DMSO-$d_6$, 300 MHz) δ 6.67 (1H, dd, J=1.7, 3.4 Hz), 7.18 (1H, d, J=5.1 Hz), 7.55 (1H, dd, J=2.5, 3.2 Hz), 8.24 (1H, d, J=4.9 Hz), 9.58 (1H, br s), 10.11 (1H, br s), 11.82 (1H, br s).

(iii) Production of 4-phenyl-2-(1H-pyrrolo[2,3-b]pyridin-4-yl)-1,3-thiazole-5-carboxylic acid A mixture of 1H-pyrrolo[2,3-b]pyridine-4-carbothioamide (710 mg, 4.0 mmol) produced above, ethyl 2-bromo-3-oxo-3-phenylpropanoate (1.2 g, 4.4 mmol) and ethanol (20 mL) was stirred at 80° C. for 1 day. Saturated aqueous sodium bicarbonate solution and water were added to the reaction mixture, and the resulting precipitate was collected by filtration, washed with water and diethyl ether and dried. 1N Aqueous sodium hydroxide solution (4.5 mL), methanol (10 mL) and tetrahydrofuran (10 mL) were added to the obtained solid, and the mixture was stirred at 60° C. for 2 hr. Water was added to the reaction mixture, the insoluble material was filtered off, and 1N hydrochloric acid (4.5 mL) was added to the filtrate. The resulting precipitate was collected by filtration, washed with water and diethyl ether and dried to give the title compound (678 mg, 53%) as a yellow solid.

$^1$H-NMR (DMSO-$d_6$, 300 MHz) δ 7.08 (1H, dd, J=1.9, 3.4 Hz), 7.44-7.56 (3H, m), 7.70-7.76 (2H, m), 7.84-7.93 (2H, m), 8.38 (1H, d, J=4.9 Hz), 12.09 (1H, br s), 13.59 (1H, br s).

(iv) Production of 4-phenyl-2-(1H-pyrrolo[2,3-b]pyridin-4-yl)-1,3-thiazole-5-carboxamide A mixture of 4-phenyl-2-(1H-pyrrolo[2,3-b]pyridin-4-yl)-1,3-thiazole-5-carboxylic acid (640 mg, 2.0 mmol) produced above, ammonium chloride (320 mg, 6.0 mmol), triethylamine (0.84 mL, 6.0 mmol), N-[3-(dimethylamino)propyl]-N'-ethylcarbodiimide hydrochloride (580 mg, 3.0 mmol), 1-hydroxybenzotriazole (410 mg, 3.0 mmol) and N,N-dimethylformamide (20 mL) was stirred at room temperature for 6 hr. The reaction mixture was concentrated under reduced pressure, and water, ethyl acetate and diethyl ether were added to the obtained residue. The resulting precipitate was collected by filtration, washed with water and diethyl ether and dried to give the title compound (507 mg, 79%) as a yellow solid.

$^1$H-NMR (DMSO-$d_6$, 300 MHz) δ 7.11 (1H, dd, J=1.9, 3.4 Hz), 7.38-7.58 (3H, m), 7.69 (1H, d, J=5.1 Hz), 7.71-7.76 (1H, m), 7.81-8.09 (4H, m), 8.38 (1H, d, J=5.1 Hz), 12.07 (1H, br s).

(v) Production of 4-[4-phenyl-5-(4H-1,2,4-triazol-3-yl)-1,3-thiazol-2-yl]-1H-pyrrolo[2,3-b]pyridine A mixture of 4-phenyl-2-(1H-pyrrolo[2,3-b]pyridin-4-yl)-1,3-thiazole-5-carboxamide (320 mg, 1.0 mmol) produced above and N,N-dimethylformamide dimethyl acetal (20 mL) was stirred at 100° C. for 1 day. The reaction mixture was concentrated under reduced pressure, hydrazine monohydrate (0.49 mL, 10 mmol) and acetic acid (10 mL) were added to the obtained residue, and the mixture was stirred at 100° C. for 2 hr. The reaction mixture was concentrated under reduced pressure, saturated aqueous sodium bicarbonate solution was added to the obtained residue, and the mixture was extracted with ethyl acetate. The collected organic layer was washed with saturated brine and dried over anhydrous magnesium sulfate, and the insoluble material was filtered off. The filtrate was concentrated under reduced pressure, the obtained residue was purified by silica gel column chromatography (methanol/ethyl acetate=0/100→100/0), and the obtained solution was concentrated under reduced pressure. The obtained residue was washed with ethyl acetate/diisopropyl ether to give the title compound (244 mg, 71%) as a yellow solid.

$^1$H-NMR (DMSO-$d_6$, 300 MHz) δ 7.13 (1H, dd, J=1.9, 3.4 Hz), 7.39-7.52 (3H, m), 7.68-7.75 (2H, m), 7.85-8.01 (2H, m), 8.38 (1H, d, J=5.1 Hz), 8.71 (1H, br s), 12.04 (1H, br s), 14.38 (1H, br s).

(vi) Production of 4-[4-phenyl-5-(4H-1,2,4-triazol-3-yl)-1,3-thiazol-2-yl]-1H-pyrrolo[2,3-b]pyridine p-toluenesulfonate A mixture of 4-[4-phenyl-5-(4H-1,2,4-triazol-3-yl)-1,3-thiazol-2-yl]-1H-pyrrolo[2,3-b]pyridine (69 mg, 0.20 mmol) produced above, p-toluenesulfonic acid monohydrate (46 mg, 0.24 mmol) and ethanol (5 mL) was dissolved by heating, and the mixture was concentrated under reduced pressure. The obtained residue was crystallized from ethanol and ethyl acetate to give the title compound (88 mg, 85%) as a yellow solid.

$^1$H-NMR (DMSO-$d_6$, 300 MHz) δ 2.29 (3H, s), 7.11 (2H, d, J=7.7 Hz), 7.15 (1H, dd, J=1.9, 3.4 Hz), 7.39-7.52 (5H, m), 7.71-7.77 (2H, m), 7.88-7.95 (2H, m), 8.39 (1H, d, J=5.3 Hz), 8.68 (1H, s), 12.11 (1H, br s).

Example 44-B

Production of 7-[4-phenyl-5-(4H-1,2,4-triazol-3-yl)-1,3-thiazol-2-yl]thieno[3,2-b]pyridine p-toluenesulfonate

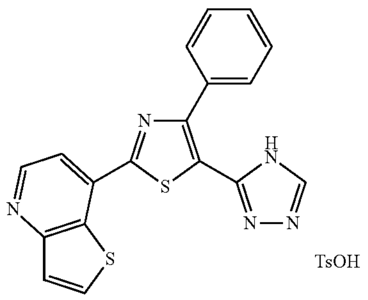

(i) Production of 7-chlorothieno[3,2-b]pyridine

A mixture of thieno[3,2-b]pyridin-7-ol (3.8 g, 25 mmol) and phosphorus oxychloride (18 g, 120 mmol) was stirred at 105° C. for 2 hr. The reaction mixture was added to ice water, and basified with 8N aqueous sodium hydroxide solution. Ethyl acetate was added, the insoluble material was filtered off, and the filtrate was extracted with ethyl acetate. The collected organic layer was washed with saturated brine and dried over anhydrous magnesium sulfate, and the insoluble material was filtered off. The filtrate was concentrated under reduced pressure, the obtained residue was purified by silica gel column chromatography (ethyl acetate/hexane=10/90→30/70), and the obtained solution was concentrated under reduced pressure to give the title compound (2.8 g, 66%) as a pale-yellow solid.

$^1$H-NMR (DMSO-$d_6$, 300 MHz) δ 7.59 (1H, d, J=5.1 Hz), 7.69 (1H, d, J=5.5 Hz), 8.28 (1H, d, J=5.5 Hz), 8.67 (1H, d, J=5.1 Hz).

(ii) Production of thieno[3,2-b]pyridine-7-carbonitrile

A mixture of 7-chlorothieno[3,2-b]pyridine (1.7 g, 10 mmol) produced above, zinc cyanide (0.71 g, 6.0 mmol), zinc (65 mg, 1.0 mmol), tris(dibenzylideneacetone)dipalladium (0) (180 mg, 0.20 mmol), 1,1'-bis(diphenylphosphino)ferrocene (220 mg, 0.40 mmol) and N,N-dimethylacetamide (10 mL) was stirred at 120° C. for 2 hr under an argon atmosphere. The reaction mixture was purified by silica gel column chromatography (ethyl acetate/hexane=5/95→50/50), and the obtained solution was concentrated under reduced pressure. The obtained residue was washed with hexane to give the title compound (1.1 g, 72%) as a colorless solid.

$^1$H-NMR (DMSO-$d_6$, 300 MHz) δ 7.77 (1H, d, J=5.5 Hz), 7.95 (1H, d, J=4.7 Hz), 8.40 (1H, d, J=5.5 Hz), 8.91 (1H, d, J=4.7 Hz).

(iii) Production of thieno[3,2-b]pyridine-7-carbothioamide

A mixture of thieno[3,2-b]pyridine-7-carbonitrile (800 mg, 5.0 mmol) produced above, O,O'-diethyl dithiophosphate (1.4 mL, 7.5 mmol), 4N hydrogen chloride ethyl acetate solution (10 mL) and methanol (2 mL) was stirred at room temperature for 15 min and at 50° C. for 2 hr. Saturated aqueous sodium bicarbonate solution was added to the reaction mixture, and the mixture was extracted with ethyl acetate. The collected organic layer was washed with saturated brine and dried over anhydrous magnesium sulfate, and the insoluble material was filtered off. The filtrate was concentrated under reduced pressure, and the obtained residue was washed with diisopropyl ether to give the title compound (715 mg, 74%) as a yellow solid.

$^1$H-NMR (DMSO-$d_6$, 300 MHz) δ 7.49 (1H, d, J=4.9 Hz), 7.59 (1H, d, J=5.7 Hz), 8.20 (1H, d, J=5.7 Hz), 8.77 (1H, d, J=4.9 Hz), 9.92 (1H, br s), 10.34 (1H, br s).

(iv) Production of ethyl 4-phenyl-2-thieno[3,2-b]pyridin-7-yl-1,3-thiazole-5-carboxylate A mixture of thieno[3,2-b]pyridine-7-carbothioamide (680 mg, 3.5 mmol) produced above, ethyl 2-bromo-3-oxo-3-phenylpropanoate (950 mg, 3.5 mmol) and ethanol (10 mL) was stirred at 80° C. for 2 hr. Saturated aqueous sodium bicarbonate solution and ethyl acetate were added to the reaction mixture, the insoluble material was filtered off, and the filtrate was extracted with ethyl acetate. The collected organic layer was washed with saturated brine and dried over anhydrous magnesium sulfate, and the insoluble material was filtered off. The filtrate was concentrated under reduced pressure, the obtained residue was purified by silica gel column chromatography (ethyl acetate/hexane=20/80→100/0), and the obtained solution was concentrated under reduced pressure. The obtained residue was washed with ethyl acetate/hexane to give the title compound (510 mg, 40%) as a colorless solid.

$^1$H-NMR (DMSO-$d_6$, 300 MHz) δ 1.28 (3H, t, J=7.1 Hz), 4.32 (2H, q, J=7.1 Hz), 7.51-7.60 (3H, m), 7.69 (1H, d, J=5.7 Hz), 7.92-8.02 (2H, m), 8.06 (1H, d, J=4.9 Hz), 8.30 (1H, dd, J=0.4, 5.7 Hz), 8.87 (1H, d, J=4.9 Hz).

(v) Production of 4-phenyl-2-thieno[3,2-b]pyridin-7-yl-1,3-thiazole-5-carboxylic acid A mixture of ethyl 4-phenyl-2-thieno[3,2-b]pyridin-7-yl-1,3-thiazole-5-carboxylate (480 mg, 1.3 mmol) produced above, 1N aqueous sodium hydroxide solution (3 mL), methanol (5 mL) and tetrahydrofuran (5 mL) was stirred at 60° C. for 1 hr. The reaction mixture was concentrated under reduced pressure to about half volume, and 1N hydrochloric acid (3 mL) was added. The resulting precipitate was collected by filtration, washed with water and diethyl ether and dried to give the title compound (433 mg, 98%) as a pale yellow-white solid.

$^1$H-NMR (DMSO-$d_6$, 300 MHz) δ 7.47-7.59 (3H, m), 7.68 (1H, d, J=5.7 Hz), 7.94-8.06 (3H, m), 8.29 (1H, d, J=5.7 Hz), 8.86 (1H, d, J=4.9 Hz), 13.81 (1H, br s).

(vi) Production of 4-phenyl-2-thieno[3,2-b]pyridin-7-yl-1,3-thiazole-5-carboxamide A mixture of 4-phenyl-2-thieno[3,2-b]pyridin-7-yl-1,3-thiazole-5-carboxylic acid (380 mg, 1.1 mmol) produced above, ammonium chloride (180 mg, 3.4 mmol), triethylamine (0.5 mL, 3.4 mmol), N-[3-(dimethylamino)propyl]-N'-ethylcarbodiimide hydrochloride (330 mg, 1.7 mmol), 1-hydroxybenzotriazole (230 mg, 1.7 mmol) and N,N-dimethylformamide (10 mL) was stirred at room temperature for 1 day. The reaction mixture was concentrated under reduced pressure, and water was added to the obtained residue. The resulting precipitate was collected by filtration, washed with water and diethyl ether and dried to give the title compound (348 mg, 91%) as a colorless solid.

$^1$H-NMR (DMSO-$d_6$, 300 MHz) δ 7.45-7.60 (3H, m), 7.69 (1H, d, J=5.7 Hz), 7.94-8.03 (4H, m), 8.17 (1H, br s), 8.31 (1H, d, J=5.7 Hz), 8.86 (1H, d, J=4.9 Hz).

(vii) Production of 7-[4-phenyl-5-(4H-1,2,4-triazol-3-yl)-1,3-thiazol-2-yl]thieno[3,2-b]pyridine p-toluenesulfonate A mixture of 4-phenyl-2-thieno[3,2-b]pyridin-7-yl-1,3-thiazole-5-carboxamide (300 mg, 0.90 mmol) produced above and N,N-dimethylformamide dimethyl acetal (10 mL) was stirred at 100° C. for 2 hr. The reaction mixture was concentrated under reduced pressure, and the obtained residue was washed with diethyl ether. Hydrazine monohydrate (0.4 mL, 9.0 mmol) and acetic acid (10 mL) were added to the obtained solid, and the mixture was stirred at 100° C. for 1 hr. The reaction mixture was concentrated under reduced pressure, and saturated aqueous sodium bicarbonate solution and diethyl ether were added to the obtained residue. The resulting precipitate was collected by filtration, washed with water and diethyl ether and dried to give 7-[4-phenyl-5-(4H-1,2,4-triazol-3-yl)-1,3-thiazol-2-yl]thieno[3,2-b]pyridine (301 mg, 93%) as a pale-yellow solid.

A mixture of 7-[4-phenyl-5-(4H-1,2,4-triazol-3-yl)-1,3-thiazol-2-yl]thieno[3,2-b]pyridine (110 mg, 0.30 mmol) produced above, p-toluenesulfonic acid monohydrate (68 mg, 0.36 mmol) and ethanol (25 mL) was dissolved by heating, and the mixture was concentrated under reduced pressure. The obtained residue was crystallized from ethanol to give the title compound (132 mg, 82%) as a yellow solid.

$^1$H-NMR (DMSO-$d_6$, 300 MHz) δ 2.29 (3H, s), 7.11 (2H, d, J=7.9 Hz), 7.42-7.55 (5H, m), 7.71 (1H, d, J=5.7 Hz), 8.00-8.10 (3H, m), 8.37 (1H, d, J=5.7 Hz), 8.74 (1H, s), 8.90 (1H, d, J=5.1 Hz).

Example 45-B

Production of 3-[2-(1-ethyl-3-methyl-1H-pyrazol-4-yl)-4-phenyl-1,3-thiazol-5-yl]-4H-1,2,4-triazole

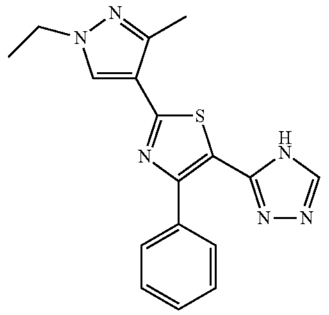 [SMILES: CCn1cc(-c2nc(-c3ccccc3)c(-c3nnc[nH]3)s2)c(C)n1]

(i) Production of 1-ethyl-3-methyl-1H-pyrazole-4-carboxamide

To a suspension of 1-ethyl-3-methyl-1H-pyrazole-4-carboxylic acid (2.0 g, 13 mmol) in toluene (50 mL) was added thionyl chloride (5 mL, 69 mmol), and the mixture was heated under reflux for 2 hr. The solvent was evaporated, and the obtained residue was dissolved in tetrahydrofuran (30 mL). 25% Aqueous ammonia (15 mL) was added, and the mixture was stirred for 30 min. Ethyl acetate (100 mL) was added to the reaction solution, and the mixture was stirred for 30 min. The organic layer was washed with saturated brine and dried over anhydrous magnesium sulfate, and the insoluble material was filtered off. The filtrate was concentrated under reduced pressure, the obtained residue was purified by silica gel column chromatography (methanol/ethyl acetate=0/100→20/80), and the obtained solution was concentrated under reduced pressure. The residue was triturated with ethyl acetate/diisopropyl ether to give the title compound (1.7 g, 86%) as a colorless solid.

$^1$H-NMR (DMSO-$d_6$, 300 MHz) δ 1.34 (3H, t, J=7.4 Hz), 2.29 (3H, s), 4.03 (2H, q, J=7.4 Hz), 6.82 (1H, s), 7.24 (1H, s), 8.09 (1H, s).

(ii) Production of 1-ethyl-3-methyl-1H-pyrazole-4-carbothioamide

To a suspension of 1-ethyl-3-methyl-1H-pyrazole-4-carboxamide (1.7 g, 11 mmol) produced above in toluene (80 mL) was added Lawesson's reagent (7.0 g, 17 mmol), and the mixture was heated under reflux for 1.5 hr. The reaction solution was cooled to room temperature and purified by basic silica gel column chromatography (ethyl acetate/hexane=0/100→20/80) to give the title compound (445 mg, 24%) as a yellow oil.

$^1$H-NMR (DMSO-$d_6$, 300 MHz) δ 1.27-1.38 (3H, m), 2.40 (3H, s), 3.97-4.08 (2H, m), 8.09 (1H, s), 8.69 (1H, s), 9.16 (1H, s).

(iii) Production of 2-(1-ethyl-3-methyl-1H-pyrazol-4-yl)-4-phenyl-1,3-thiazole-5-carboxylic acid A solution of 1-ethyl-3-methyl-1H-pyrazole-4-carbothioamide (230 mg, 1.3 mmol) produced above and ethyl 2-bromo-3-oxo-3-phenylpropanoate (1.7 g, 6.3 mmol) in 2-propanol (30 mL) was stirred at 80° C. for 2 hr. The reaction solution was cooled to room temperature, saturated aqueous sodium bicarbonate solution (100 mL) and ethyl acetate (100 mL) were added, and the mixture was stirred for 30 min. The organic layer was washed with saturated brine and dried over anhydrous magnesium sulfate, and the insoluble material was filtered off. The filtrate was concentrated under reduced pressure, and the obtained residue was dissolved in tetrahydrofuran (15 mL). Methanol (5 mL) and 1N aqueous sodium hydroxide solution (2.0 mL) were added, and the mixture was stirred at 70° C. for 1 hr. The reaction solution was cooled to 0° C., 1N hydrochloric acid (1.9 mL) was added, and the mixture was extracted with ethyl acetate (100 mL). The organic layer was washed with saturated brine and dried over anhydrous magnesium sulfate, and the insoluble material was filtered off. The filtrate was concentrated under reduced pressure, and the obtained residue was triturated with ethyl acetate and diisopropyl ether to give the title compound (190 mg, 46%) as a white solid.

$^1$H-NMR (DMSO-$d_6$, 300 MHz) δ 1.39 (3H, t, J=7.4 Hz), 2.45 (3H, s), 4.12 (2H, q, J=7.4 Hz), 7.35-7.50 (3H, m), 7.71-7.85 (2H, m), 8.42 (1H, s), 13.23 (1H, s).

(iv) Production of 2-(1-ethyl-3-methyl-1H-pyrazol-4-yl)-4-phenyl-1,3-thiazole-5-carboxamide To a suspension of 2-(1-ethyl-3-methyl-1H-pyrazol-4-yl)-4-phenyl-1,3-thiazole-5-carboxylic acid (160 mg, 13 mmol) produced above in toluene (25 mL) was added thionyl chloride (1.5 mL, 21 mmol), and the mixture was heated under reflux for 1 hr. The solvent was evaporated, and the obtained residue was dissolved in tetrahydrofuran (25 mL). 25% Aqueous ammonia (2.5 mL) was added, and the mixture was stirred for 30 min. Ethyl acetate (100 mL) was added to the reaction solution, and the mixture was stirred for 30 min. The organic layer was washed with saturated brine and dried over anhydrous magnesium sulfate, and the insoluble material was filtered off. The filtrate was concentrated under reduced pressure, and the obtained residue was washed with diisopropyl ether and dried to give the title compound (155 mg, 97%) as a white solid.

$^1$H-NMR (DMSO-$d_6$, 300 MHz) δ 1.35-1.45 (3H, m), 2.46 (3H, s), 4.12 (2H, q, J=7.4 Hz), 7.38-7.50 (3H, m), 7.61-7.73 (2H, m), 7.74-7.82 (2H, m), 8.37 (1H, s).

(v) Production of 3-[2-(1-ethyl-3-methyl-1H-pyrazol-4-yl)-4-phenyl-1,3-thiazol-5-yl]-4H-1,2,4-triazole A solution of 2-(1-ethyl-3-methyl-1H-pyrazol-4-yl)-4-phenyl-1,3-thiazole-5-carboxamide (130 mg, 0.41 mmol) produced above in N,N-dimethylformamide dimethyl acetal (20 mL) was stirred with heating at 100° C. for 1 hr. The reaction solution was cooled to room temperature, the solvent was evaporated, and the residue was washed with hexane (5 mL) and diethyl ether (2 mL). The obtained residue was dissolved in acetic acid (10 mL), hydrazine monohydrate (0.4 mL) was added, and the mixture was stirred with heating at 80° C. for 1 hr. The reaction solution was cooled to room temperature, saturated aqueous sodium bicarbonate solution (150 mL) and ethyl acetate (100 mL) were added, and the mixture was stirred for 30 min. The organic layer was washed with saturated brine and dried over anhydrous magnesium sulfate, and the insoluble material was filtered off. The filtrate was concentrated under reduced pressure, and the obtained residue was washed with ethyl acetate (2 mL) and diisopropyl ether (10 mL) to give the title compound (105 mg, 75%) as a white solid.

$^1$H-NMR (DMSO-$d_6$, 300 MHz) δ 1.40 (3H, t, J=7.3 Hz), 2.48 (3H, s), 4.13 (2H, q, J=7.3 Hz), 7.33-7.46 (3H, m), 7.78-7.86 (2H, m), 8.38 (1H, s), 8.57 (1H, s).

Example 46-B

Production of 2-methyl-3-{4-[(1E)-prop-1-en-1-yl]-5-(4H-1,2,4-triazol-3-yl)-1,3-thiazol-2-yl}pyrazolo[1,5-a]pyridine

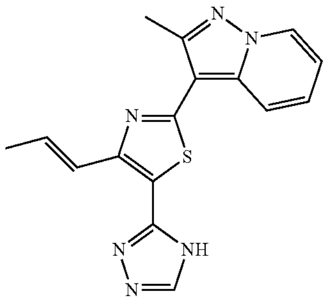 [SMILES: C/C=C/c1nc(-c2c(C)nn3ccccc23)sc1-c1nnc[nH]1]

(i) Production of methyl 2-(2-methylpyrazolo[1,5-a]pyridin-3-yl)-4-prop-2-en-1-yl-1,3-thiazole-5-carboxylate Using methyl 2-(2-methylpyrazolo[1,5-a]pyridin-3-yl)-4-{[(trifluoromethyl)sulfonyl]oxy}-1,3-thiazole-5-carboxylate (1.5 g, 3.6 mmol) produced in Example 13-B (ii), 4,4,5,5-tetramethyl-2-prop-2-en-1-yl-1,3,2-dioxaborolane (897 mg, 5.3 mmol), [1,1-bis(diphenylphosphino)ferrocene]palladium(II) dichloride dichloromethane complex (180 mg, 0.22 mmol), cesium carbonate (3.5 g, 11 mmol), 1,2-dimethoxyethane (50 mL) and water (3 mL) as starting materials and in the same manner as in Example 13-B (iii), the title compound (815 mg, 73%) was obtained as a yellow solid.

$^1$H-NMR (DMSO-$d_6$, 300 MHz) δ 2.68 (3H, s), 3.84 (3H, s) 3.93 (2H, dt, J=1.5, 6.6 Hz), 5.02-5.24 (2H, m), 5.99-6.21 (1H, m), 7.12 (1H, dt, J=1.3, 6.9 Hz), 7.59 (1H, ddd, J=1.1, 6.9, 8.9 Hz), 8.30-8.40 (1H, m), 8.71-8.84 (1H, m).

(ii) Production of 2-(2-methylpyrazolo[1,5-a]pyridin-3-yl)-4-[(1E)-prop-1-en-1-yl]-1,3-thiazole-5-carboxylic acid Using methyl 2-(2-methylpyrazolo[1,5-a]pyridin-3-yl)-4-prop-2-en-1-yl-1,3-thiazole-5-carboxylate (800 mg, 2.6 mmol) produced above, methanol (15 mL), tetrahydrofuran (15 mL) and 8N aqueous sodium hydroxide solution (1.5 mL) as starting materials and in the same manner as in Example 13-B (iv), the title compound (470 mg, 62%) was obtained as a white solid.

$^1$H-NMR (DMSO-$d_6$, 300 MHz) δ 1.98 (3H, dd, J=1.7, 6.8 Hz), 2.67 (3H, s), 6.97-7.36 (3H, m), 7.60 (1H, ddd, J=1.0, 6.8, 8.9 Hz), 8.34-8.48 (1H, m), 8.73-8.84 (1H, m).

(iii) Production of 2-(2-methylpyrazolo[1,5-a]pyridin-3-yl)-4-[(1E)-prop-1-en-1-yl]-1,3-thiazole-5-carboxamide Using 2-(2-methylpyrazolo[1,5-a]pyridin-3-yl)-4-[(1E)-prop-1-en-1-yl]-1,3-thiazole-5-carboxylic acid (400 mg, 1.3 mmol) produced above, ammonium chloride (2.0 g, 37 mmol), triethylamine (4.0 mL), 1-hydroxybenzotriazole (100 mg, 0.74 mmol) and N-[3-(dimethylamino)propyl]-N'-ethylcarbodiimide hydrochloride (750 mg, 3.9 mmol) and N,N-dimethylformamide (20 mL) as starting materials and in the same manner as in Example 13-B (v), the title compound (383 mg, 96%) was obtained as a white solid.

$^1$H-NMR (DMSO-$d_6$, 300 MHz) δ 1.95 (3H, dd, J=1.5, 6.8 Hz), 2.69 (3H, s), 6.85-7.00 (1H, m), 7.04-7.26 (2H, m), 7.42-7.73 (2H, m), 7.95 (1H, s), 8.33-8.42 (1H, m), 8.71-8.82 (1H, m).

(iv) Production of 2-methyl-3-{4-[(1E)-prop-1-en-1-yl]-5-(4H-1,2,4-triazol-3-yl)-1,3-thiazol-2-yl}pyrazolo[1,5-a]pyridine Using 2-(2-methylpyrazolo[1,5-a]pyridin-3-yl)-4-[(1E)-prop-1-en-1-yl]-1,3-thiazole-5-carboxamide (150 mg, 0.50 mmol) produced above, N,N-dimethylformamide dimethyl acetal (20 mL), acetic acid (20 mL) and hydrazine monohydrate (0.3 mL) as starting materials and in the same manner as in Example 13(vi), the title compound (78 mg, 48%) was obtained as a white solid.

$^1$H-NMR (DMSO-$d_6$, 300 MHz) δ 1.98 (3H, dd, J=1.7, 6.9 Hz), 2.71 (3H, s), 6.91 (1H, dd, J=6.9, 15.4 Hz), 7.08 (1H, dt, J=1.4, 6.8 Hz), 7.48-7.60 (2H, m), 8.41 (1H, d, J=8.9 Hz), 8.65 (1H, s), 8.77 (1H, d, J=7.0 Hz).

Example 47-B

N-{4-[4-ethoxy-5-(4H-1,2,4-triazol-3-yl)-1,3-thiazol-2-yl]pyridin-2-yl}-2-methoxyacetamide

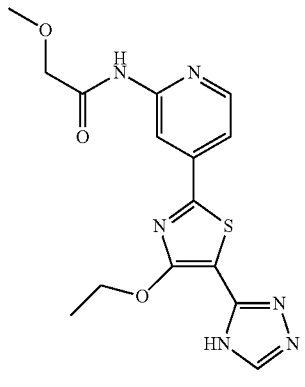 [SMILES: CCOc1nc(-c2ccnc(NC(=O)COC)c2)sc1-c1nnc[nH]1]

(i) Production of N-(4-{4-ethoxy-5-[1-(tetrahydro-2H-pyran-2-yl)-1H-1,2,4-triazol-3-yl]-1,3-thiazol-2-yl}pyridin-2-yl)acetamide Using N-{4-[4-ethoxy-5-(4H-1,2,4-triazol-3-yl)-1,3-thiazol-2-yl]pyridin-2-yl}acetamide (6.2 g, 19 mmol) produced in Example 8-B (v), p-toluenesulfonic acid monohydrate (4.3 g, 23 mmol), 3,4-dihydro-2H-pyran (7.9 g, 94 mmol) and tetrahydrofuran (188 mL) as starting materials and in the same manner as in Example 4-B(i), the title compound (4.7 g, 60%) was obtained as a yellow solid.

$^1$H-NMR (DMSO-$d_6$, 300 MHz) δ 1.40 (3H, t, J=7.1 Hz), 1.50-1.80 (3H, m), 1.89-2.15 (3H, m), 2.13 (3H, s), 3.60-3.78 (1H, m), 3.90-4.03 (1H, m), 4.54 (2H, q, J=7.1 Hz), 5.60 (1H, dd, J=2.6 Hz, 9.4 Hz), 7.58 (1H, dd, J=1.6 Hz, 5.2 Hz), 8.31-8.55 (1H, m), 8.64 (1H, d, J=0.8 Hz), 8.78 (1H, s), 10.70 (1H, s).

(ii) Production of 4-{4-ethoxy-5-[1-(tetrahydro-2H-pyran-2-yl)-1H-1,2,4-triazol-3-yl]-1,3-thiazol-2-yl}pyridin-2-amine To N-(4-{4-ethoxy-5-[1-(tetrahydro-2H-pyran-2-yl)-1H-1,2,4-triazol-3-yl]-1,3-thiazol-2-yl}pyridin-2-yl)acetamide (4.6 g, 11 mmol) produced above in a mixed solvent (224 mL) of tetrahydrofuran/methanol (1:1) was added 8N aqueous sodium hydroxide solution (19 mL, 152 mmol), and the mixture was stirred at 80° C. for 1 hr. The reaction solution was cooled to room temperature and diluted with ethyl acetate (500 mL) and water (300 mL). The aqueous layer was separated and extracted with ethyl acetate (300 mL×2), and the combined organic layer was dried over anhydrous magnesium sulfate. The insoluble material was filtered off, and the filtrate was concentrated under reduced pressure to give the title compound (4.1 g, 98%) as a yellow solid.

$^1$H-NMR (DMSO-$d_6$, 300 MHz) δ 1.39 (3H, t, J=7.0 Hz), 1.53-1.78 (3H, m), 1.90-2.19 (3H, m), 3.59-3.74 (1H, m), 3.92-4.01 (1H, m), 4.52 (2H, q, J=7.0 Hz), 5.99 (1H, dd, J=2.6 Hz, 9.4 Hz), 6.23 (2H, s), 6.88-7.06 (2H, m), 8.03 (1H, dd, J=0.8, 5.3 Hz), 8.76 (1H, s).

(iii) Production of N-{4-[4-ethoxy-5-(4H-1,2,4-triazol-3-yl)-1,3-thiazol-2-yl]pyridin-2-yl}-2-methoxyacetamide To a solution of 4-{4-ethoxy-5-[1-(tetrahydro-2H-pyran-2-yl)-1H-1,2,4-triazol-3-yl]-1,3-thiazol-2-yl}pyridin-2-amine (110 mg, 0.3 mmol) produced above in N,N-dimethylacetamide (2 mL) was added methoxyacetyl chloride (160 mg, 1.4 mmol), and the mixture was stirred at 40° C. for 60 hr. The reaction mixture was diluted with 2% aqueous sodium bicarbonate solution (5.0 mL) and ethyl acetate (10.0 mL), and the organic layer was dehydrated with Presep Tube, Wako Pure Chemical Industries, Ltd., and concentrated. The obtained residue was dissolved in 1N methanesulfonic acid acetonitrile solution (5.0 mL, 5.0 mmol), and the mixture was stirred at room temperature for 16 hr. The reaction solution was neutralized by adding 1N diisopropylamine acetonitrile solution (5.0 mL, 5.0 mmol). Water (2.0 mL) and dimethyl sulfoxide (5.0 mL) were added, and the mixture was purified by preparative HPLC to give the title compound (71.2 mg, yield 66%) as a yellow solid. LC-MS 361.15 (ESI+)

Examples 48-B to 71-B were each produced in the same manner as in Example 47-B(iii) and using 4-{4-ethoxy-5-[1-(tetrahydro-2H-pyran-2-yl)-1H-1,2,4-triazol-3-yl]-1,3-thiazol-2-yl}pyridin-2-amine produced in Example 47-B(ii), and corresponding acid chloride as starting materials.

The structural formula, name, m/z value detected by LC-MS, yield and yield (%) in Examples 48-B to 71-Bare collectively shown in Table 2-1 to Table 2-8.

TABLE 2-1

| Example | structure | name | molecular formula | molecular weight | LCMS m/z | yield (mg) | yield (%) |
|---|---|---|---|---|---|---|---|
| 48-B | 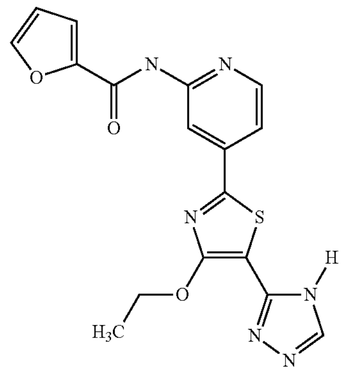 [SMILES: CCOc1nc(-c2ccnc(NC(=O)c3ccco3)c2)sc1-c1nnc[nH]1] | N-{4-[4-ethoxy-5-(4H-1,2,4-triazol-3-yl)-1,3-thiazol-2-yl]pyridin-2-yl}furan-2-carboxamide | C17H14N6O3S | 382.40 | 383.12 | 18.7 | 16 |
| 49-B | 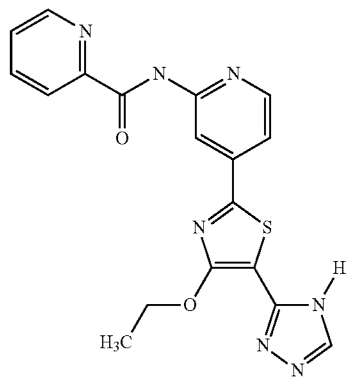 [SMILES: CCOc1nc(-c2ccnc(NC(=O)c3ccccn3)c2)sc1-c1nnc[nH]1] | N-{4-[4-ethoxy-5-(4H-1,2,4-triazol-3-yl)-1,3-thiazol-2-yl]pyridin-2-yl}pyridine-2-carboxamide | C18H15N7O2S | 393.42 | 394.15 | 54.4 | 46 |

TABLE 2-1-continued

| Example | structure | name | molecular formula | molecular weight | LCMS m/z | yield (mg) | yield (%) |
|---|---|---|---|---|---|---|---|
| 50-B | 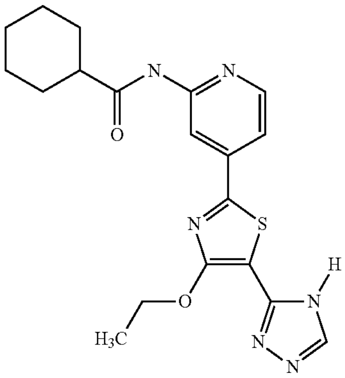 [SMILES: CCOc1nc(-c2ccnc(NC(=O)C3CCCCC3)c2)sc1-c1nnc[nH]1] | N-{4-[4-ethoxy-5-(4H-1,2,4-triazol-3-yl)-1,3-thiazol-2-yl]pyridin-2-yl}cyclohexanecarboxamide | C19H22N6O2S | 398.48 | 399.2 | 60.9 | 51 |

TABLE 2-2

| Example | structure | name | molecular formula | molecular weight | LCMS m/z | yield (mg) | yield (%) |
|---|---|---|---|---|---|---|---|
| 51-B | 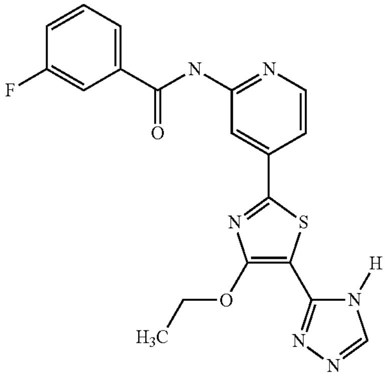 [SMILES: CCOc1nc(-c2ccnc(NC(=O)c3cccc(F)c3)c2)sc1-c1nnc[nH]1] | N-{4-[4-ethoxy-5-(4H-1,2,4-triazol-3-yl)-1,3-thiazol-2-yl]pyridin-2-yl}-3-fluorobenzamide | C19H15FN6O2S | 410.43 | 411.15 | 40.5 | 33 |
| 52-B | 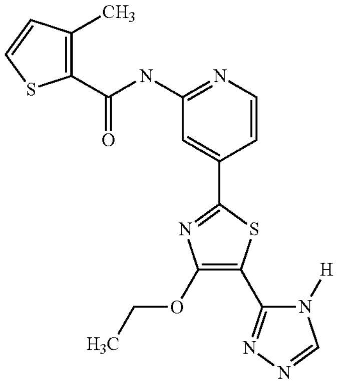 [SMILES: CCOc1nc(-c2ccnc(NC(=O)c3sccc3C)c2)sc1-c1nnc[nH]1] | N-{4-[4-ethoxy-5-(4H-1,2,4-triazol-3-yl)-1,3-thiazol-2-yl]pyridin-2-yl}-3-methylthiophene-2-carboxamide | C18H16N6O2S2 | 412.49 | 413.15 | 6.40 | 5 |

TABLE 2-2-continued

| Example | structure | name | molecular formula | molecular weight | LCMS m/z | yield (mg) | yield (%) |
|---|---|---|---|---|---|---|---|
| 53-B | 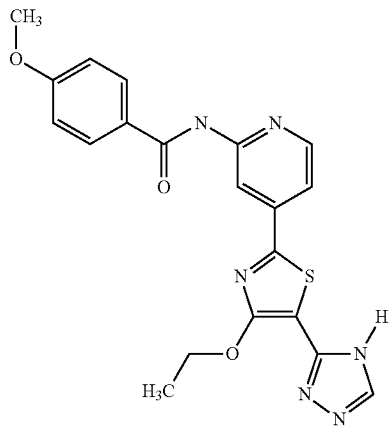 [SMILES: CCOc1nc(-c2ccnc(NC(=O)c3ccc(OC)cc3)c2)sc1-c1nnc[nH]1] | N-{4-[4-ethoxy-5-(4H-1,2,4-triazol-3-yl)-1,3-thiazol-2-yl]pyridin-2-yl}-4-methoxybenzamide | C20H18N6O3S | 422.46 | 423.16 | 46.0 | 36 |

TABLE 2-3

| Example | structure | name | molecular formula | molecular weight | LCMS m/z | yield (mg) | yield (%) |
|---|---|---|---|---|---|---|---|
| 54-B | 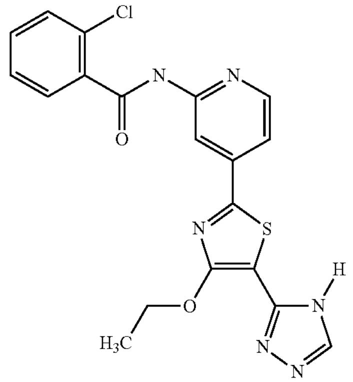 [SMILES: CCOc1nc(-c2ccnc(NC(=O)c3ccccc3Cl)c2)sc1-c1nnc[nH]1] | 2-chloro-N-{4-[4-ethoxy-5-(4H-1,2,4-triazol-3-yl)-1,3-thiazol-2-yl]pyridin-2-yl}benzamide | C19H15ClN6O2S | 426.88 | 427.11 | 19.7 | 15 |
| 55-B | 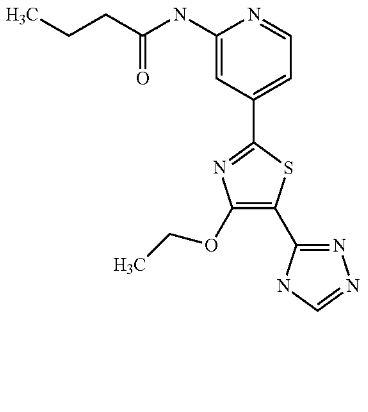 [SMILES: CCCC(=O)Nc1cc(-c2nc(OCC)c(-c3nnc[nH]3)s2)ccn1] | N-{4-[4-ethoxy-5-(4H-1,2,4-triazol-3-yl)-1,3-thiazol-2-yl]pyridin-2-yl}butanamide | C16H18N6O2S | 358.42 | 359.17 | 70.8 | 66 |

TABLE 2-3-continued

| Example | structure | name | molecular formula | molecular weight | LCMS m/z | yield (mg) | yield (%) |
|---|---|---|---|---|---|---|---|
| 56-B | 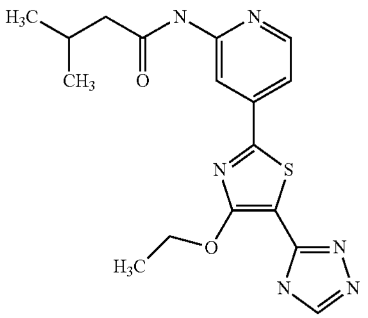 [SMILES: CCOc1nc(-c2ccnc(NC(=O)CC(C)C)c2)sc1-c1nnc[nH]1] | N-{4-[4-ethoxy-5-(4H-1,2,4-triazol-3-yl)-1,3-thiazol-2-yl]pyridin-2-yl}-3-methylbutanamide | C17H20N6O2S | 372.45 | 373.18 | 56.5 | 51 |

TABLE 2-4

| Example | structure | name | molecular formula | molecular weight | LCMS m/z | yield (mg) | yield (%) |
|---|---|---|---|---|---|---|---|
| 57-B | 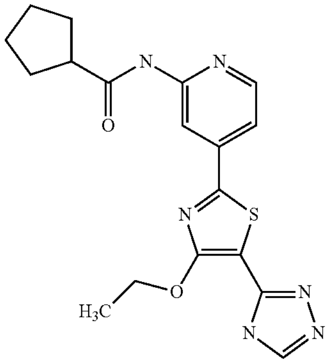 [SMILES: CCOc1nc(-c2ccnc(NC(=O)C3CCCC3)c2)sc1-c1nnc[nH]1] | N-{4-[4-ethoxy-5-(4H-1,2,4-triazol-3-yl)-1,3-thiazol-2-yl]pyridin-2-yl}cyclopentanecarboxamide | C18H20N6O2S | 384.46 | 385.19 | 70.0 | 61 |
| 58-B | 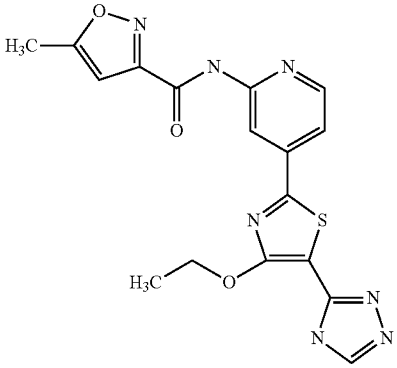 [SMILES: CCOc1nc(-c2ccnc(NC(=O)c3cc(C)on3)c2)sc1-c1nnc[nH]1] | N-{4-[4-ethoxy-5-(4H-1,2,4-triazol-3-yl)-1,3-thiazol-2-yl]pyridin-2-yl}-5-methylisoxazole-3-carboxamide | C17H15N7O3S | 397.41 | 398.15 | 57.0 | 48 |

TABLE 2-4-continued

| Example | structure | name | molecular formula | molecular weight | LCMS m/z | yield (mg) | yield (%) |
|---|---|---|---|---|---|---|---|
| 59-B | 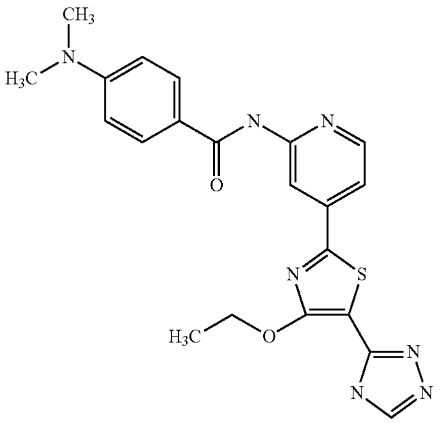 [SMILES: CCOc1nc(-c2ccnc(NC(=O)c3ccc(N(C)C)cc3)c2)sc1-c1nnc[nH]1] | 4-(dimethylamino)-N-{4-[4-ethoxy-5-(4H-1,2,4-triazol-3-yl)-1,3-thiazol-2-yl]pyridin-2-yl}benzamide | C21H21N7O2S | 435.50 | 436.19 | 11.3 | 9 |

TABLE 2-5

| Example | structure | name | molecular formula | molecular weight | LCMS m/z | yield (mg) | yield (%) |
|---|---|---|---|---|---|---|---|
| 60-B | 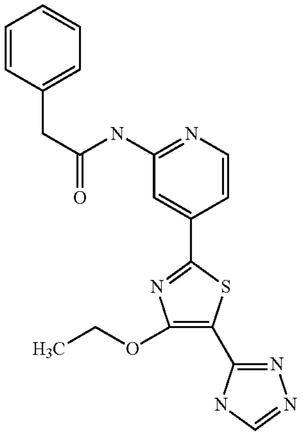 [SMILES: CCOc1nc(-c2ccnc(NC(=O)Cc3ccccc3)c2)sc1-c1nnc[nH]1] | N-{4-[4-ethoxy-5-(4H-1,2,4-triazol-3-yl)-1,3-thiazol-2-yl]pyridin-2-yl}-2-phenylacetamide | C20H18N6O2S | 406.46 | 407.16 | 91.1 | 75 |
| 61-B | 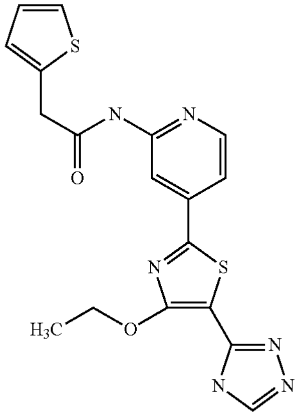 [SMILES: CCOc1nc(-c2ccnc(NC(=O)Cc3cccs3)c2)sc1-c1nnc[nH]1] | N-{4-[4-ethoxy-5-(4H-1,2,4-triazol-3-yl)-1,3-thiazol-2-yl]pyridin-2-yl}-2-thiophen-2-ylacetamide | C18H16N6O2S2 | 412.49 | 413.13 | 21.6 | 17 |

TABLE 2-5-continued

| Example structure | | name | molecular formula | molecular weight | LCMS m/z | yield (mg) | yield (%) |
|---|---|---|---|---|---|---|---|
| 62-B | 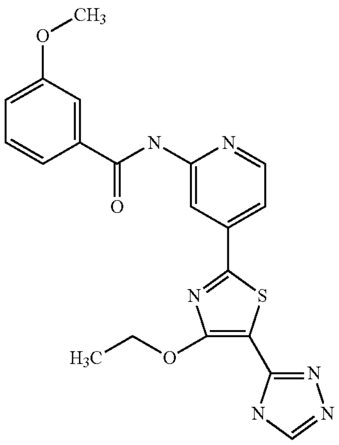 [SMILES: CCOc1nc(-c2ccnc(NC(=O)c3cccc(OC)c3)c2)sc1-c1nnc[nH]1] | N-{4-[4-ethoxy-5-(4H-1,2,4-triazol-3-yl)-1,3-thiazol-2-yl]pyridin-2-yl}-3-methoxybenzamide | C20H18N6O3S | 422.46 | 423.18 | 24.9 | 20 |

TABLE 2-6

| Example structure | | name | molecular formula | molecular weight | LCMS m/z | yield (mg) | yield (%) |
|---|---|---|---|---|---|---|---|
| 63-B | 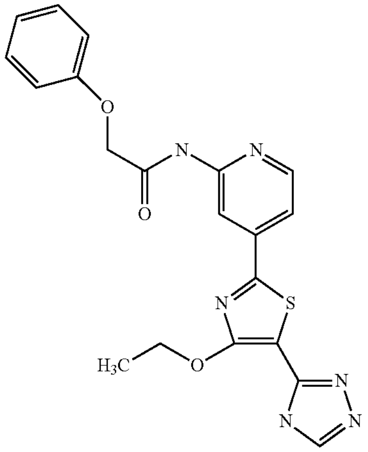 [SMILES: CCOc1nc(-c2ccnc(NC(=O)COc3ccccc3)c2)sc1-c1nnc[nH]1] | N-{4-[4-ethoxy-5-(4H-1,2,4-triazol-3-yl)-1,3-thiazol-2-yl]pyridin-2-yl}-2-phenoxyacetamide | C20H18N6O3S | 422.46 | 423.17 | 60.3 | 48 |
| 64-B | 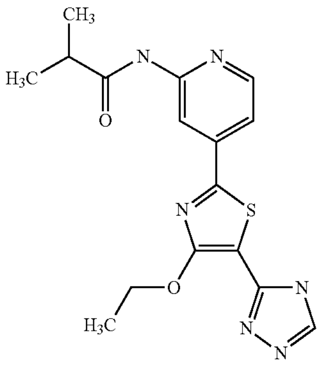 [SMILES: CCOc1nc(-c2ccnc(NC(=O)C(C)C)c2)sc1-c1nnc[nH]1] | N-{4-[4-ethoxy-5-(4H-1,2,4-triazol-3-yl)-1,3-thiazol-2-yl]pyridin-2-yl}-2-methylpropanamide | C16H18N6O2S | 358.42 | 359.19 | 27.0 | 25 |

TABLE 2-6-continued

| Example | structure | name | molecular formula | molecular weight | LCMS m/z | yield (mg) | yield (%) |
|---|---|---|---|---|---|---|---|
| 65-B | 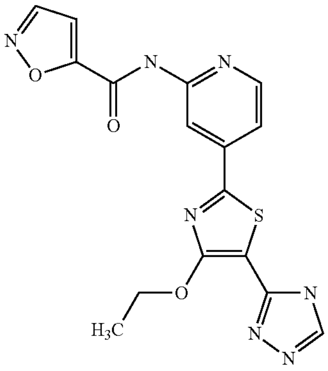 [SMILES: CCOc1nc(-c2ccnc(NC(=O)c3ccno3)c2)sc1-c1nnc[nH]1] | N-{4-[4-ethoxy-5-(4H-1,2,4-triazol-3-yl)-1,3-thiazol-2-yl]pyridin-2-yl}isoxazole-5-carboxamide | C16H13N7O3S | 383.39 | 384.08 | 30.9 | 27 |

TABLE 2-7

| Example | structure | name | molecular formula | molecular weight | LCMS m/z | yield (mg) | yield (%) |
|---|---|---|---|---|---|---|---|
| 66-B | 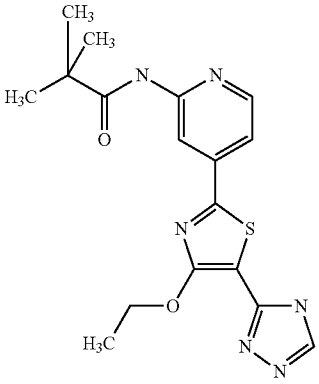 [SMILES: CCOc1nc(-c2ccnc(NC(=O)C(C)(C)C)c2)sc1-c1nnc[nH]1] | N-{4-[4-ethoxy-5-(4H-1,2,4-triazol-3-yl)-1,3-thiazol-2-yl]pyridin-2-yl}-2,2-dimethylpropanamide | C17H20N6O2S | 372.45 | 373.17 | 33.9 | 30 |
| 67-B | 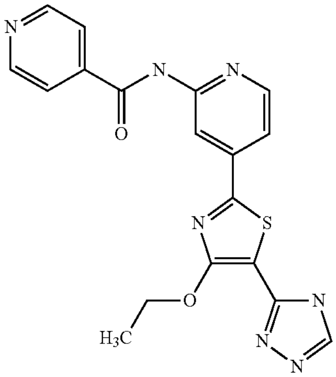 [SMILES: CCOc1nc(-c2ccnc(NC(=O)c3ccncc3)c2)sc1-c1nnc[nH]1] | N-{4-[4-ethoxy-5-(4H-1,2,4-triazol-3-yl)-1,3-thiazol-2-yl]pyridin-2-yl}pyridine-4-carboxamide | C18H15N7O2S | 393.42 | 394.16 | 56.8 | 48 |

TABLE 2-7-continued

| Example | structure | name | molecular formula | molecular weight | LCMS m/z | yield (mg) | yield (%) |
|---|---|---|---|---|---|---|---|
| 68-B | 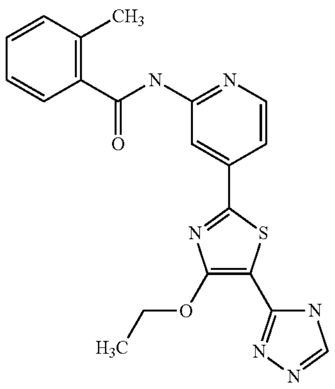 [SMILES: CCOc1nc(-c2ccnc(NC(=O)c3ccccc3C)c2)sc1-c1nnc[nH]1] | N-{4-[4-ethoxy-5-(4H-1,2,4-triazol-3-yl)-1,3-thiazol-2-yl]pyridin-2-yl}-2-methylbenzamide | C20H18N6O2S | 406.46 | 407.16 | 14.7 | 12 |

TABLE 2-8

| Example | structure | name | molecular formula | molecular weight | LCMS m/z | yield (mg) | yield (%) |
|---|---|---|---|---|---|---|---|
| 69-B | 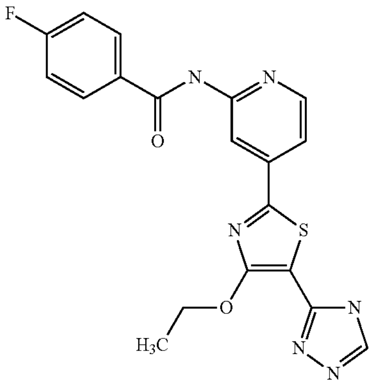 [SMILES: CCOc1nc(-c2ccnc(NC(=O)c3ccc(F)cc3)c2)sc1-c1nnc[nH]1] | N-{4-[4-ethoxy-5-(4H-1,2,4-triazol-3-yl)-1,3-thiazol-2-yl]pyridin-2-yl}-4-fluorobenzamide | C19H15FN6O2S | 410.43 | 411.15 | 39.7 | 32 |
| 70-B | 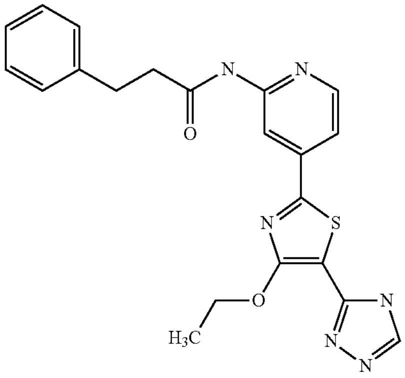 [SMILES: CCOc1nc(-c2ccnc(NC(=O)CCc3ccccc3)c2)sc1-c1nnc[nH]1] | N-{4-[4-ethoxy-5-(4H-1,2,4-triazol-3-yl)-1,3-thiazol-2-yl]pyridin-2-yl}-3-phenylpropanamide | C21H20N6O2S | 420.49 | 421.19 | 57.1 | 45 |

TABLE 2-8-continued

| Example | structure | name | molecular formula | molecular weight | LCMS m/z | yield (mg) | yield (%) |
|---|---|---|---|---|---|---|---|
| 71-B | 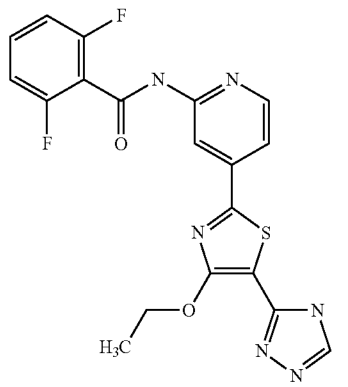 [SMILES: CCOc1nc(-c2ccnc(NC(=O)c3c(F)cccc3F)c2)sc1-c1nnc[nH]1] | N-{4-[4-ethoxy-5-(4H-1,2,4-triazol-3-yl)-1,3-thiazol-2-yl]pyridin-2-yl}-2,6-difluorobenzamide | C19H14F2N6O2S | 428.42 | 429.14 | 25.7 | 20 |

Example 72-B

Production of 2-methyl-3-[4-phenyl-5-(1H-1,2,4-triazol-3-yl)-1,3-thiazol-2-yl]-5-{[6-(trifluoromethyl)pyridin-3-yl]methoxy}pyrazolo[1,5-a]pyridine

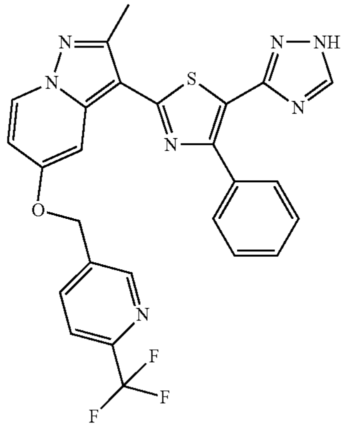 [SMILES: Cc1nn2ccc(OCc3ccc(C(F)(F)F)nc3)cc2c1-c1nc(-c2ccccc2)c(-c2nc[nH]n2)s1]

A mixture of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (100 mg, 0.22 mmol) obtained in Example 31-B(i), 5-(chloromethyl)-2-(trifluoromethyl)pyridine (64 mg, 0.33 mmol), potassium carbonate (60 mg, 0.44 mmol) and DMF (4 mL) was stirred at 60° C. for 2 h. Water (100 mL) and EtOAc (100 mL) were added to the reaction mixture, and the mixture was stirred for 30 min. The organic layer was washed with brine and dried over anhydrous magnesium sulfate. Insoluble materials were removed by filtration, and the filtrate was concentrated under reduced pressure. The residue was dissolved in MeOH (5 mL) and THF (30 mL), 6 N hydrochloric acid (3 mL) was added, and the mixture was stirred at 70° C. for 3 h. The reaction mixture was allowed to cool to rt, and the mixture was concentrated under reduced pressure. To the residue were added EtOAc (50 mL), THF (50 mL), 8 N aqueous sodium hydroxide solution (3 mL) and water (30 mL), and the mixture was stirred for 30 min. The organic layer was washed with brine and dried over anhydrous magnesium sulfate, and insoluble materials were removed by filtration. The filtrate was concentrated under reduced pressure. The residue was crystallized from EtOAc to give the title compound (107 mg, 92%) as a white solid.

$^1$H-NMR (DMSO-$d_6$, 300 MHz) δ 2.67 (3H, s), 5-0.51 (2H, s), 6.88 (1H, dd, J=2.6, 7.6, Hz), 7.31-7.53 (3H, m), 7.80 (1H, d, J=2.6 Hz), 7.84-7.98 (3H, m), 8.21 (1H, d, J=8.1 Hz), 8.52-8.64 (1H, m), 8.70 (1H, d, J=7.7 Hz), 8.92 (1H, s), 13.99 (1H, br s).

Example 73-B

Production of 2,2-dimethyl-N-[2-({2-methyl-3-[4-phenyl-5-(1H-1,2,4-triazol-3-yl)-1,3-thiazol-2-yl]pyrazolo[1,5-a]pyridin-5-yl}oxy)ethyl]propanamide

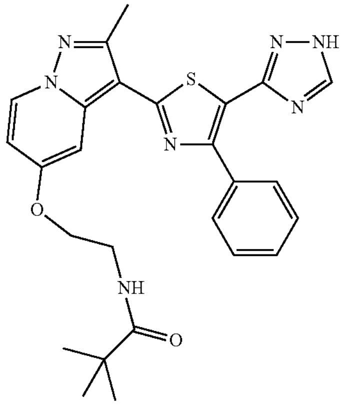 [SMILES: Cc1nn2ccc(OCCNC(=O)C(C)(C)C)cc2c1-c1nc(-c2ccccc2)c(-c2nc[nH]n2)s1]

(i) Production of 2-({2-methyl-3-[4-phenyl-5-(1H-1,2,4-triazol-3-yl)-1,3-thiazol-2-yl]pyrazolo[1,5-a]pyridin-5-yl}oxy)ethanamine di-hydrochloride A mixture of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (150 mg, 0.33 mmol) obtained in Example 31-B(i), 2-(BOC-amino)ethyl bromide (103 mg, 0.46 mmol), potassium carbonate (90 mg, 0.65 mmol) and DMF (5 mL) was stirred at 60° C. for 2 h. The reaction mixture was allowed to cool to rt, water (100 mL)

and EtOAc (50 mL) were added, and the mixture was stirred for 30 min. The organic layer was washed with brine and dried over anhydrous magnesium sulfate. Insoluble materials were removed by filtration, and the filtrate was concentrated under reduced pressure. The residue was dissolved in MeOH (15 mL) and THF (10 mL), and then 6N hydrochloric acid (1.5 mL) was added. The mixture was stirred at 70° C. for 3 h. The reaction mixture was allowed to cool to rt, and the mixture was concentrated under reduced pressure. The residue was washed with diisopropyl ether and dried to give the title compound (132 mg, 79%) as a white solid.

$^1$H-NMR (DMSO-$d_6$, 300 MHz) δ 3.27-3.39 (2H, m), 4.34-4.39 (2H, m), 6.80 (1H, dd, J=2.7, 7.5 Hz), 7.37-7.50 (3H, m), 7.73 (1H, d, J=2.7 Hz), 7.87-7.97 (2H, m), 8.14 (3H, br s), 8.62 (1H, s), 8.71 (1H, d, J=7.6 Hz).

(ii) Production of 2,2-dimethyl-N-[2-({2-methyl-3-[4-phenyl-5-(1H-1,2,4-triazol-3-yl)-1,3-thiazol-2-yl]pyrazolo[1,5-a]pyridin-5-yl}oxy)ethyl]propanamide To a solution of 2-({2-methyl-3-[4-phenyl-5-(1H-1,2,4-triazol-3-yl)-1,3-thiazol-2-yl]pyrazolo[1,5-a]pyridin-5-yl}oxy)ethanamine di-hydrochloride (130 mg, 0.27 mmol) obtained above in TEA (430 mg, 4.3 mmol) and THF (5 mL) was added 2,2-dimethylpropanoyl chloride (76 mg, 0.51 mmol) at 0° C., and the mixture was stirred at 0° C. for 1 h. To the reaction mixture, were added saturated aqueous solution of sodium bicarbonate (50 mL) and EtOAc (50 mL), and the mixture was stirred for 30 min. The organic layer was washed with brine and dried over anhydrous magnesium sulfate. Insoluble materials were removed by filtration, and the filtrate was concentrated under reduced pressure.

The residue was washed with EtOAc and diisopropyl ether, and dried to give the title compound (120 mg, 90%) as a white solid.

$^1$H-NMR (DMSO-$d_6$, 300 MHz) δ 1.09 (9H, s), 2.66 (3H, s), 3.51 (2H, q, J=5.8 Hz), 4.16 (2H, t, J=5.8 Hz), 6.75 (1H, dd, J=2.7, 7.5 Hz), 7.31-7.48 (3H, m), 7.74 (2H, d, J=2.7 Hz), 7.99-8.08 (2H, m), 8.43 (1H, s), 8.64 (1H, d, J=7.5 Hz).

Example 74-B

Production of 3-[4-(2-fluorophenyl)-5-(1H-1,2,4-triazol-3-yl)-1,3-thiazol-2-yl]-2-methyl-5-(2-morpholin-4-ylethoxy)pyrazolo[1,5-a]pyridine di-p-toluenesulfonate

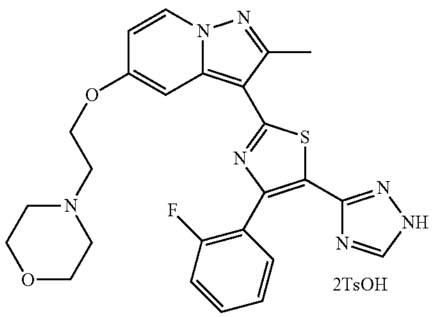

(i) Production of ethyl 2-[5-(benzyloxy)-2-methylpyrazolo[1,5-a]pyridin-3-yl]-4-(2-fluorophenyl)-1,3-thiazole-5-carboxylate A suspension of 5-(benzyloxy)-2-methylpyrazolo[1,5-a]pyridine-3-carbothioamide (820 mg, 2.8 mmol) obtained in Example 30-B(vi) and ethyl 2-chloro-3-(2-fluorophenyl)-3-oxopropanoate (3.1 g, 13 mmol) obtained in Example 22-B(i) in 2-propanol (50 mL) was stirred at 90° C. for 7 h. The reaction mixture was allowed to cool to room temperature, and the precipitated solid was collected by filtration. The solid was washed with EtOAc and diisopropyl ether, and dried to give the title compound (1.0 g, 75%) as a yellow solid.

$^1$H-NMR (DMSO-$d_6$, 300 MHz) δ 1.13-1.21 (3H, m), 2.62 (3H, s), 4.20 (2H, q, J=7.2 Hz), 5.25 (2H, s), 6.86 (1H, dd, J=2.8, 7.4 Hz), 7.22-7.61 (8H, m), 7.67-7.77 (2H, m), 8.67 (1H, d, J=7.4 Hz).

(ii) Production of 2-[5-(benzyloxy)-2-methylpyrazolo[1,5-a]pyridin-3-yl]-4-(2-fluorophenyl)-1,3-thiazole-5-carboxylic acid To a solution of ethyl 2-[5-(benzyloxy)-2-methylpyrazolo[1,5-a]pyridin-3-yl]-4-(2-fluorophenyl)-1,3-thiazole-5-carboxylate (1.0 g, 2.1 mmol) obtained above in MeOH (10 mL) and THF (25 mL), was added 8N aqueous sodium hydroxide solution (2.5 mL), and the mixture was stirred at 70° C. for 1 h. The reaction mixture was allowed to cool to 0° C., 1N hydrochloric acid was added to adjust the solution to about pH 3.0, and the reaction mixture was extracted with a 1:1 mixture of THF and EtOAc. The combined organic layers were dried over anhydrous magnesium sulfate and insoluble materials were removed by filtration, and the filtrate was concentrated to give the title compound (810 mg, 86%) as a yellow solid.

$^1$H-NMR (DMSO-$d_6$, 300 MHz) δ 2.59 (3H, s), 5.21 (2H, s), 6.77 (1H, dd, J=2.8, 7.6 Hz), 7.19-7.33 (5H, m), 7.37-7.52 (3H, m), 7.58-7.68 (1H, m), 7.72 (1H, d, J=2.6 Hz), 8.59 (1H, d, J=7.6 Hz).

(iii) Production of 2-[5-(benzyloxy)-2-methylpyrazolo[1,5-a]pyridin-3-yl]-4-(2-fluorophenyl)-1,3-thiazole-5-carboxamide A mixture of 2-[5-(benzyloxy)-2-methylpyrazolo[1,5-a]pyridin-3-yl]-4-(2-fluorophenyl)-1,3-thiazole-5-carboxylic acid (750 mg, 1.6 mmol) obtained above, TEA (3.2 mL), ammonium chloride (1.5 g, 28 mmol), HOBT (150 mg, 1.1 mmol), EDCI (2.5 g, 13 mmol) and DMF (50 mL) was stirred at rt for 16 h. To the reaction mixture were added water (200 mL) and EtOAc (200 mL), and the mixture was stirred for 30 min. The organic layer was washed with brine and dried over anhydrous magnesium sulfate. Insoluble materials were removed by filtration, and the filtrate was concentrated under reduced pressure. The residue was washed with EtOAc and diisopropyl ether, and dried to give the title compound (520 mg, 69%) as a yellow solid.

$^1$H-NMR (DMSO-$d_6$, 300 MHz) δ 2.62 (3H, s), 5.26 (2H, s), 6.83 (1H, dd, J=2.8, 7.6 Hz), 7.26-7.56 (10H, m), 7.69-7.78 (2H, m), 8.65 (1H, d, J=7.6 Hz).

(iv) Production of 5-(benzyloxy)-3-[4-(2-fluorophenyl)-5-(1H-1,2,4-triazol-3-yl)-1,3-thiazol-2-yl]-2-methylpyrazolo[1,5-a]pyridine A suspension of 2-[5-(benzyloxy)-2-methylpyrazolo[1,5-a]pyridin-3-yl]-4-(2-fluorophenyl)-1,3-thiazole-5-carboxamide (500 mg, 1.1 mmol) obtained above in N,N-dimethylformamide dimethylacetal (50 mL) was stirred at 90° C. for 2 h. The reaction mixture was allowed to cool to rt, the solvent was evaporated and the residue was washed with diisopropyl ether (5 mL). The residue was dissolved in AcOH (50 mL) and then hydrazine monohydrate (0.5 mL) was added. The mixture was stirred at 90° C. for 1 h and then the reaction mixture was allowed to cool to rt. Then the mixture was concentrated under reduced pressure. To the residue were added saturated aqueous solution of sodium bicarbonate (150 mL) and EtOAc (100 mL), and then the mixture was stirred for 30 min. The organic layer was washed with brine and dried over anhydrous magnesium sulfate. Insoluble materials were removed by filtration and the filtrate was concentrated under reduced pressure. The residue was washed with EtOAc and diisopropyl ether, and dried to give the title compound (395 mg, 75%) as a white solid.

$^1$H-NMR (DMSO-$d_6$, 300 MHz) δ 2.65 (3H, s), 5.25 (2H, s), 6.81 (1H, dd, J=2.6, 7.4 Hz), 7.23-7.59 (8H, m), 7.67-7.80 (2H, m), 8.51 (1H, s), 8.64 (1H, d, J=7.6 Hz), 14.08 (1H, s).

(v) Production of 5-(benzyloxy)-3-{4-(2-fluorophenyl)-5-[1-(tetrahydro-2H-pyran-2-yl)-1H-1,2,4-triazol-3-yl]-1,3-thiazol-2-yl}-2-methylpyrazolo[1,5-a]pyridine A mixture of 5-(benzyloxy)-3-[4-(2-fluorophenyl)-5-(1H-1,2,4-triazol-3-yl)-1,3-thiazol-2-yl]-2-methylpyrazolo[1,5-a]pyridine (395 mg, 0.82 mmol) obtained above, 3,4-dihydro-2H-pyran (344 mg, 4.1 mmol), p-toluenesulfonic acid monohydrate (78 mg, 0.41 mmol) and THF (30 mL) was stirred at 70° C. for 17 h. The reaction mixture was concentrated under reduced pressure. To the residue, saturated aqueous solution of sodium bicarbonate was added and the mixture was extracted with EtOAc. The organic layer was washed with brine and dried over anhydrous magnesium sulfate. Insoluble materials were removed by filtration and the filtrate was concentrated under reduced pressure. The residue was washed with diisopropyl ether and dried to give the title compound (412 mg, 88%) as a white solid.

$^1$H-NMR (DMSO-$d_6$, 300 MHz) δ 1.42-1.63 (3H, m), 1.84-2.06 (3H, m), 2.64 (3H, s), 3.36-3.96 (2H, m), 5.25 (2H, s), 5.56 (1H, dd, J=3.2, 8.3 Hz), 6.82 (1H, dd, J=2.7, 7.5 Hz), 7.22-7.58 (8H, m), 7.68-7.82 (2H, m), 8.64 (1H, d, J=7.6 Hz), 8.69 (1H, s).

(vi) Production of 3-{4-(2-fluorophenyl)-5-[1-(tetrahydro-2H-pyran-2-yl)-1H-1,2,4-triazol-3-yl]-1,3-thiazol-2-yl}-2-methylpyrazolo[1,5-a]pyridin-5-ol To a solution of 5-(benzyloxy)-3-{4-(2-fluorophenyl)-5-[1-(tetrahydro-2H-pyran-2-yl)-1H-1,2,4-triazol-3-yl]-1,3-thiazol-2-yl}-2-methylpyrazolo[1,5-a]pyridine (400 mg, 0.71 mmol) obtained above in THF (15 mL) and EtOH (3 mL), was added 10% palladium-carbon (50% wet with water, 120 mg). The mixture was stirred at rt for 49 h under hydrogen atmosphere (1 atm), and then 10% palladium-carbon was removed by filtration. The filtrate was concentrated under reduced pressure and the residue was purified by silica gel column chromatography (EtOAc/hexane=50/50→100/0) to give the title compound (321 mg, 96%) as a brown sirup.

$^1$H-NMR (DMSO-$d_6$, 300 MHz) δ 1.40-1.73 (3H, m), 1.80-2.04 (3H, m), 2.63 (3H, s), 3.54-3.72 (1H, m), 3.82-3.94 (1H, m), 5.55 (1H, dd, J=3.3, 8.0 Hz), 6.61 (1H, dd, J=2.7, 7.5 Hz), 7.19-7.37 (2H, m), 7.44-7.53 (1H, m), 7.56 (1H, s), 7.68 (1H, dt, J=1.8, 7.5 Hz), 8.56 (1H, d, J=7.4 Hz), 8.67 (1H, s), 10.81 (1H, br s).

(vii) Production of 3-[4-(2-fluorophenyl)-5-(1H-1,2,4-triazol-3-yl)-1,3-thiazol-2-yl]-2-methyl-5-(2-morpholin-4-ylethoxy)pyrazolo[1,5-a]pyridine A mixture of 3-(4-(2-fluorophenyl)-5-[1-(tetrahydro-2H-pyran-2-yl)-1H-1,2,4-triazol-3-yl]-1,3-thiazol-2-yl)-2-methylpyrazolo[1,5-a]pyridin-5-ol (150 mg, 0.31 mmol) obtained above, 2-(4-morpholine)ethyl bromide (122 mg, 0.63 mmol), potassium carbonate (130 mg, 0.94 mmol) and DMF (10 mL) was stirred at 50° C. for 1 h. The mixture was allowed to cool to rt. To the reaction mixture were added water (100 mL) and EtOAc (100 mL), and the mixture was stirred for 30 min. The organic layer was washed with brine and dried over anhydrous magnesium sulfate. Insoluble materials were removed by filtration and the filtrate was concentrated under reduced pressure. The residue was purified by basic silica gel column chromatography (MeOH/EtOAc=0/100→45/95) to give 3-{4-(2-fluorophenyl)-5-[1-(tetrahydro-2H-pyran-2-yl)-1H-1,2,4-triazol-3-yl]-1,3-thiazol-2-yl}-2-methyl-5-(2-morpholin-4-ylethoxy)pyrazolo[1,5-a]pyridine (181 mg, 97%) as a white solid.

To a solution of 3-(4-(2-fluorophenyl)-5-[1-(tetrahydro-2H-pyran-2-yl)-1H-1,2,4-triazol-3-yl]-1,3-thiazol-2-yl)-2-methyl-5-(2-morpholin-4-ylethoxy)pyrazolo[1,5-a]pyridine (180 mg, 0.31 mmol) obtained above in MeOH (5 mL) and THF (2 mL), was added 2N hydrochloric acid (2.5 mL), and the mixture was stirred for 1 h at 70° C. The reaction mixture was allowed to cool to rt, and the solvent was evaporated. To the residue were added EtOAc (50 mL), THF (50 mL), 8N aqueous sodium hydroxide solution (2 mL) and water (30 mL), and the mixture was stirred for 30 min. The organic layer was washed with brine and dried over anhydrous magnesium sulfate. Insoluble materials were removed by filtration and the filtrate was concentrated under reduced pressure. The residue was washed with diisopropyl ether and dried to give the title compound (141 mg, 92%) as a white solid.

$^1$H-NMR (DMSO-$d_6$, 300 MHz) δ 2.42-2.47 (4H, m), 2.65 (3H, s), 2.74 (2H, t, J=5.9 Hz), 3.51-3.60 (4H, m), 4.22 (2H, t, J=5.9 Hz), 6.77 (1H, dd, J=2.8, 7.6 Hz), 7.16-7.38 (2H, m), 7.40-7.58 (1H, m), 7.60-7.82 (2H, m), 8.37-8.78 (2H, m), 14.14 (1H, br s).

(viii) Production of 3-[4-(2-fluorophenyl)-5-(1H-1,2,4-triazol-3-yl)-1,3-thiazol-2-yl]-2-methyl-5-(2-morpholin-4-ylethoxy)pyrazolo[1,5-a]pyridine di-p-toluenesulfonate A mixture of 3-[4-(2-fluorophenyl)-5-(1H-1,2,4-triazol-3-yl)-1,3-thiazol-2-yl]-2-methyl-5-(2-morpholin-4-ylethoxy) pyrazolo[1,5-a]pyridine (138 mg, 0.27 mmol) obtained above, p-toluenesulfonic acid monohydrate (114 mg, 0.60 mmol), EtOH (1.5 mL) and THF (5 mL) was heated to obtain clear solution, and then concentrated under reduced pressure. The residue was crystallized from EtOH to give the title compound (181 mg, 78%) as a pale yellow solid.

$^1$H-NMR (DMSO-$d_6$, 300 MHz) δ 2.28 (6H, s), 2.68 (3H, s), 3.11-3.32 (2H, m), 3.47-3.78 (6H, m), 3.93-4.05 (2H, m), 4.45-4.59 (2H, m), 6.83 (1H, dd, J=2.7, 7.5 Hz), 7.11 (5H, d, J=7.9 Hz), 7.20-7.35 (2H, m), 7.43-7.55 (6H, m), 7.61-7.76 (2H, m), 8.54 (1H, s), 8.72 (1H, d, J=7.6 Hz), 9.81 (1H, br s).

Example 75-B

Production of 2-[2-(2-methylpyrazolo[1,5-a]pyridin-3-yl)-5-(1H-1,2,4-triazol-3-yl)-1,3-thiazol-4-yl]aniline

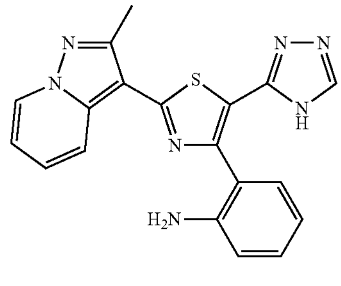 [SMILES: Cc1nn2ccccc2c1-c1nc(-c2ccccc2N)c(-c2nnc[nH]2)s1]

(i) Production of ethyl 2-chloro-3-(2-nitrophenyl)-3-oxopropanoate

To a solution of ethyl 3-(2-nitrophenyl)-3-oxopropanoate (2.0 g, 8.4 mmol) in diethyl ether (50 mL), was added sulfuryl chloride (1.37 g, 10 mmol) at 0° C., and the mixture was stirred for 3 h at rt. To the reaction mixture were added water (200 mL) and EtOAc (100 mL), and the mixture was stirred for 30 min. The organic layer was washed with brine (10 mL) and dried over anhydrous magnesium sulfate. Insoluble materials were removed by filtration and the filtrate was concentrated under reduced pressure to give the title compound (1.7 g, 75%) as colorless oil.

$^1$H-NMR (DMSO-$d_6$, 300 MHz) δ 1.13-1.27 (3H, m), 4.00-4.14 (2H, m), 4.99 (1H, s), 7.27-7.90 (4H, m).

(ii) Production of 2-(2-methylpyrazolo[1,5-a]pyridin-3-yl)-4-(2-nitrophenyl)-1,3-thiazole-5-carboxylic acid A mixture of 2-methylpyrazolo[1,5-a]pyridine-3-carbothioamide hydrochloride (1.2 g, 5.2 mmol) obtained in Example 11-B(v), ethyl 2-chloro-3-(2-nitrophenyl)-3-oxopropanoate (1.7 g, 8.4 mmol) obtained above and 2-propanol (20 mL) was stirred at 80° C. for 4 h. To the reaction mixture were added saturated aqueous solution of sodium bicarbonate, EtOAc and THF. Insoluble materials were removed by filtration and the filtrate was extracted with a 1:1 mixture of EtOAc and THF. The organic layer was washed with brine and dried over anhydrous magnesium sulfate. Insoluble materials were removed by filtration and the filtrate was concentrated under reduced pressure. To the residue were added MeOH (10 mL), THF (25 mL) and 8N aqueous sodium hydroxide solution (2.5 mL), and the mixture was stirred at 70° C. for 1 h. The reaction mixture was allowed to cool to 0° C., 6N hydrochloric acid was added to adjust the solution to about pH 3.0. The resulting precipitate was collected by filtration, washed with diisopropyl ether, and dried to give the title compound (620 mg, 31%) as a yellow solid.

$^1$H-NMR (DMSO-$d_6$, 300 MHz) δ 2.69 (3H, s), 7.11 (1H, dt, J=1.3, 6.9 Hz), 7.55 (1H, ddd, J=1.1, 7.0, 8.9 Hz), 7.69-7.89 (3H, m), 8.13 (1H, dd, J=0.9, 8.1 Hz), 8.21 (1H, dt, J=1.3, 8.8 Hz), 8.77-8.83 (1H, m), 13.36 (1H, br s).

(iii) Production of 2-(2-methylpyrazolo[1,5-a]pyridin-3-yl)-4-(2-nitrophenyl)-1,3-thiazole-5-carboxamide A mixture of 2-(2-methylpyrazolo[1,5-a]pyridin-3-yl)-4-(2-nitrophenyl)-1,3-thiazole-5-carboxylic acid (600 mg, 1.6 mmol) obtained above, TEA (4.2 mL), ammonium chloride (2.5 g, 47 mmol), HOBT (170 mg, 1.3 mmol), EDCI (1.1 g, 5.7 mmol) and DMF (200 mL) was stirred for 14 h at rt. To the reaction mixture were added water (200 mL) and EtOAc (200 mL), and the mixture was stirred for 30 min. The organic layer was washed with water and brine, and dried over anhydrous magnesium sulfate. Insoluble materials were removed by filtration and the filtrate was concentrated under reduced pressure. The residue was washed with EtOAc and diisopropyl ether, and dried to give the title compound (592 mg, 99%) as a yellow solid.

$^1$H-NMR (DMSO-$d_6$, 300 MHz) δ 2.66 (3H, s), 7.09 (1H, dt, J=1.3, 6.9 Hz), 7.47-7.85 (5H, m), 7.95 (1H, s), 8.04-8.19 (2H, m), 8.78 (1H, d, J=6.9 Hz).

(iv) Production of 2-methyl-3-[4-(2-nitrophenyl)-5-(1H-1,2,4-triazol-3-yl)-1,3-thiazol-2-yl]pyrazolo[1,5-a]pyridine A suspension of 2-(2-methylpyrazolo[1,5-a]pyridin-3-yl)-4-(2-nitrophenyl)-1,3-thiazole-5-carboxamide (500 mg, 1.3 mmol) obtained above in N,N-dimethylformamide dimethylacetal (25 mL) was stirred at 90° C. for 2 h. The reaction mixture was allowed to cool to rt, and the solvent was evaporated. The residue was washed with diisopropyl ether (5 mL) and then the solvent was removed. The residue was dissolved in AcOH (25 mL) and hydrazine monohydrate (0.5 mL) was added. The mixture was stirred at 90° C. for 1 h and then allowed to cool to rt. The mixture was concentrated under reduced pressure and the residue was suspended in saturated aqueous solution of sodium bicarbonate (150 mL) and EtOAc (100 mL). The mixture was stirred for 30 min and the organic layer was washed with brine, then dried over anhydrous magnesium sulfate. Insoluble materials were removed by filtration and the filtrate was concentrated under reduced pressure. The residue was washed with EtOAc and diisopropyl ether, and dried to give the title compound (363 mg, 68%) as a white solid.

$^1$H-NMR (DMSO-$d_6$, 300 MHz) δ 2.70 (3H, s), 7.08 (1H, dt, J=1.4, 6.9, Hz), 7.51 (1H, ddd, J=1.0, 6.9, 8.9 Hz), 7.65-7.85 (3H, m), 8.10 (1H, d, J=7.9 Hz), 8.16-8.23 (1H, m), 8.55 (1H, br s), 8.77 (1H, d, J=7.0 Hz), 14.21 (1H, br s).

(v) Production of 2-[2-(2-methylpyrazolo[1,5-a]pyridin-3-yl)-5-(1H-1,2,4-triazol-3-yl)-1,3-thiazol-4-yl]aniline To a solution of 2-methyl-3-[4-(2-nitrophenyl)-5-(1H-1,2,4-triazol-3-yl)-1,3-thiazol-2-yl]pyrazolo[1,5-a]pyridine (500 mg, 1.3 mmol) obtained above in THF (30 mL), were added EtOH (10 mL), reduced iron (2.2 g, 39 mmol) and 1N hydrochloric acid (3 mL), and the mixture was stirred at 80° C. for 3 h. The reaction mixture was allowed to cool to rt and insoluble materials were removed by filtration. To the filtrate, were added EtOAc (100 mL), 1N aqueous sodium hydroxide solution (5 mL) and water (50 mL). The mixture was stirred for 30 min. The organic layer was washed with brine, and dried over anhydrous magnesium sulfate. Insoluble materials were removed by filtration, and the filtrate was concentrated under reduced pressure. The residue was purified by basic silica gel column chromatography (EtOAc/hexane=50/50→100/0) to give the title compound (302 mg, 93%) as a yellow solid.

$^1$H-NMR (DMSO-$d_6$, 300 MHz) δ 2.72 (3H, s), 5.25 (2H, br s), 6.55 (1H, t, J=7.7 Hz), 6.78 (1H, d, J=7.4 Hz), 6.99-7.15

(2H, m), 7.21 (1H, d, J=7.4 Hz), 7.52 (1H, t, J=7.7 Hz), 8.28 (1H, d, J=9.6 Hz), 8.50 (1H, br s), 8.70-8.83 (1H, m), 14.02 (1H, br s).

Example 76-B

Production of N-[2-({2-methyl-3-[4-phenyl-5-(1H-1,2,4-triazol-3-yl)-1,3-thiazol-2-yl]pyrazolo[1,5-a]pyridin-5-yl}oxy)ethyl]acetamide

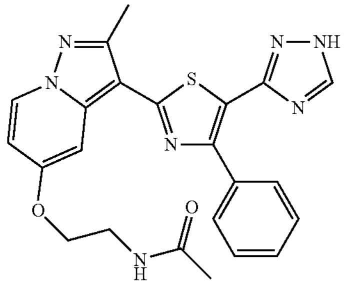 [SMILES: CC(=O)NCCOc1ccn2nc(C)c(-c3nc(-c4ccccc4)c(-c4nc[nH]n4)s3)c2c1]

To a suspension of 2-({2-methyl-3-[4-phenyl-5-(1H-1,2,4-triazol-3-yl)-1,3-thiazol-2-yl]pyrazolo[1,5-a]pyridin-5-yl}oxy)ethanamine di-hydrochloride (100 mg, 0.20 mmol) obtained in Example 73-B(i) and TEA (0.75 mL) in THF (10 mL), was added acetic anhydride (0.5 mL, 5.3 mmol) at 0° C., and the mixture was stirred at 0° C. for 1 h. To the reaction mixture were added saturated aqueous solution of sodium bicarbonate (50 mL) and EtOAc (50 mL), and the mixture was stirred for 30 min. The organic layer was washed with brine and dried over anhydrous magnesium sulfate. Insoluble materials were removed by filtration, and the filtrate was concentrated under reduced pressure. The residue was washed with EtOAc and diisopropyl ether, and dried to give the title compound (33 mg, 35%) as a white solid.

$^1$H-NMR (DMSO-$d_6$, 300 MHz) δ 1.84 (3H, s), 2.67 (3H, s), 3.44-3.55 (2H, m), 4.11-4.23 (2H, m), 6.77 (1H, dd, J=2.8, 7.7 Hz), 7.35-7.51 (3H, m), 7.72 (1H, s), 7.87-8.00 (2H, m), 8.16 (1H, s), 8.64-8.68 (2H, m).

Example 77-B

Production of 2-amino-2-methyl-N-[2-({2-methyl-3-[4-phenyl-5-(1H-1,2,4-triazol-3-yl)-1,3-thiazol-2-yl]pyrazolo[1,5-a]pyridin-5-yl}oxy)ethyl]propanamide

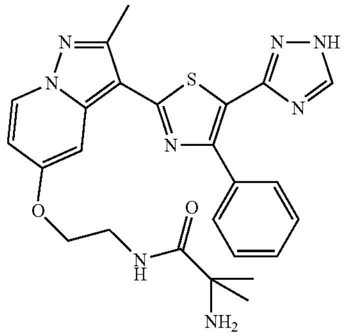 [SMILES: Cc1nn2ccc(OCCNC(=O)C(C)(C)N)cc2c1-c1nc(-c2ccccc2)c(-c2nc[nH]n2)s1]

A mixture of 2-({2-methyl-3-[4-phenyl-5-(1H-1,2,4-triazol-3-yl)-1,3-thiazol-2-yl]pyrazolo[1,5-a]pyridin-5-yl}oxy)ethanamine di-hydrochloride (100 mg, 0.20 mmol) obtained in Example 73-B(i), TEA (1.5 mL), 2-[(tert-butoxycarbonyl)amino]-2-methylpropanoic acid (75 mg, 0.37 mmol), HOBT (50 mg, 0.37 mmol), EDCI (210 mg, 1.1 mmol) and DMF (20 mL) was stirred at rt for 14 h. To the reaction mixture were added water (200 mL) and EtOAc (200 mL) and the mixture was stirred for 30 min. The organic layer was washed with water and brine, and dried over anhydrous magnesium sulfate. Insoluble materials were removed by filtration, and the filtrate was concentrated under reduced pressure. To a solution of the above residue in MeOH (10 mL) and THF (15 mL) was added 6N hydrochloric acid (3 mL), and the mixture was stirred at 70° C. for 1 h. The reaction mixture was allowed to cool to rt and then the solvent was evaporated. To the reaction mixture were added EtOAc (100 mL), 8N aqueous sodium hydroxide solution (3 mL) and water (100 mL), and the mixture was stirred for 30 min. The organic layer was washed with brine and dried over anhydrous magnesium sulfate. Insoluble materials were removed by filtration, and the filtrate was concentrated under reduced pressure. The residue was washed with diisopropyl ether and dried to give the title compound (46 mg, 45%) as a white solid.

$^1$H-NMR (DMSO-$d_6$, 300 MHz) δ 1.19 (6H, s), 2.66 (3H, s), 3.32 (2H, br s), 3.47-3.59 (2H, m), 4.12-4.23 (2H, m), 6.77 (1H, dd, J=2.8, 7.4 Hz), 7.35-7.49 (3H, m), 7.72 (1H, d, J=2.6 Hz), 7.94 (2H, dd, J=1.5, 8.1 Hz), 8.16 (1H, br s), 8.58 (1H, s), 8.65 (1H, d, J=7.6 Hz).

Example 78-B

Production of 1-methyl-N-[2-({2-methyl-3-[4-phenyl-5-(1H-1,2,4-triazol-3-yl)-1,3-thiazol-2-yl]pyrazolo[1,5-a]pyridin-5-yl}oxy)ethyl]-1H-imidazole-4-carboxamide

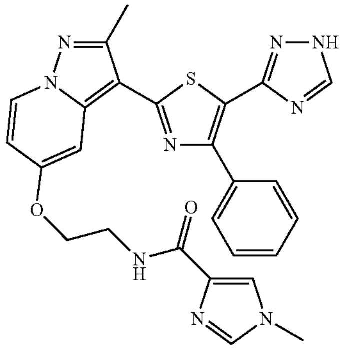 [SMILES: Cc1nn2ccc(OCCNC(=O)c3cn(C)cn3)cc2c1-c1nc(-c2ccccc2)c(-c2nc[nH]n2)s1]

A mixture of 2-({2-methyl-3-[4-phenyl-5-(1H-1,2,4-triazol-3-yl)-1,3-thiazol-2-yl]pyrazolo[1,5-a]pyridin-5-yl}oxy)ethanamine di-hydrochloride (100 mg, 0.20 mmol) obtained in Example 73-B(i), TEA (1.5 mL), 1-methyl-1H-imidazole-4-carboxylic acid (120 mg, 0.95 mmol), HOBT (220 mg, 1.6 mmol), EDCI (350 mg, 1.8 mmol) and DMF (10 mL) was stirred at rt for 14 h. To the reaction mixture were added water (200 mL) and EtOAc (200 mL) and the mixture was stirred for 30 min. The organic layer was washed with water and brine, and dried over anhydrous magnesium sulfate. Insoluble materials were removed by filtration, and the filtrate was concentrated under reduced pressure. The residue was washed with EtOAc and diisopropyl ether, and dried to give the title compound (31 mg, 29%) as a yellow solid.

$^1$H-NMR (DMSO-$d_6$, 300 MHz) δ 2.66 (3H, s), 3.52-3.75 (5H, m), 4.19-4.32 (2H, m), 6.78 (1H, dd, J=2.8, 7.7 Hz), 7.27-7.44 (3H, m), 7.61-7.71 (2H, m), 7.74-7.81 (1H, m), 7.89-8.00 (2H, m), 8.09-8.18 (1H, m), 8.53-8.62 (1H, m), 8.64 (1H, d, J=7.7 Hz).

Example 79-B

Production of 3-[4-(2-fluorophenyl)-5-(1H-1,2,4-triazol-3-yl)-1,3-thiazol-2-yl]-2-methyl-5-(2-piperidin-1-ylethoxy)pyrazolo[1,5-a]pyridine p-toluenesulfonate

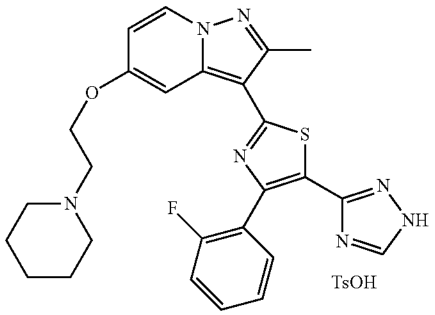

(i) Production of 3-{4-(2-fluorophenyl)-5-[1-(tetrahydro-2H-pyran-2-yl)-1H-1,2,4-triazol-3-yl]-1,3-thiazol-2-yl}-2-methyl-5-(2-piperidin-1-ylethoxy)pyrazolo[1,5-a]pyridine A mixture of 3-{4-(2-fluorophenyl)-5-[1-(tetrahydro-2H-pyran-2-yl)-1H-1,2,4-triazol-3-yl]-1,3-thiazol-2-yl}-2-methylpyrazolo[1,5-a]pyridin-5-ol (100 mg, 0.20 mmol) obtained in Example 74-B(vi), 1-(2-chloroethyl)piperidine hydrochloride (112 mg, 0.61 mmol), potassium carbonate (260 mg, 1.9 mmol) and DMF (10 mL) was stirred at 50° C. for 1 h. The mixture was allowed to cool to rt. To the reaction mixture were added water (100 mL) and EtOAc (100 mL), and the mixture was stirred for 30 min. The organic layer was washed with brine and dried over anhydrous magnesium sulfate. Insoluble materials were removed by filtration, and the filtrate was concentrated under reduced pressure. The residue was purified by basic silica gel column chromatography (MeOH/EtOAc=0/100→45/95) to give the title compound (112 mg, 95%) as a yellow solid.

$^1$H-NMR (DMSO-$d_6$, 300 MHz) δ 1.31-1.69 (9H, m), 1.69-2.11 (3H, m), 2.32-2.47 (4H, m), 2.66 (3H, s), 2.68-2.76 (2H, m), 3.55-3.70 (1H, m), 3.81-3.95 (1H, m), 4.20 (2H, t, J=6.2 Hz), 5.51-5.61 (1H, m), 6.76 (1H, dd, J=2.7, 7.5 Hz), 7.18-7.35 (2H, m), 7.41-7.56 (1H, m), 7.66-7.80 (2H, m), 8.63 (1H, d, J=7.5 Hz), 8.69 (1H, s).

(ii) Production of 3-[4-(2-fluorophenyl)-5-(1H-1,2,4-triazol-3-yl)-1,3-thiazol-2-yl]-2-methyl-5-(2-piperidin-1-ylethoxy)pyrazolo[1,5-a]pyridine p-toluenesulfonate To a solution of 3-[4-(2-fluorophenyl)-5-[1-(tetrahydro-2H-pyran-2-yl)-1H-1,2,4-triazol-3-yl]-1,3-thiazol-2-yl]-2-methyl-5-(2-piperidin-1-ylethoxy)pyrazolo[1,5-a]pyridine (110 mg, 0.19 mmol) obtained above in EtOH (5 mL) and THF (15 mL), was added 6N hydrochloric acid (1.5 mL), and the mixture was stirred at 70° C. for 1 h. The reaction mixture was allowed to cool to rt, and the solvent was evaporated. To the residue were added EtOAc (50 mL), THF (30 mL), 8N aqueous sodium hydroxide solution (1 mL) and saturated aqueous solution of sodium bicarbonate (300 mL), and the mixture was stirred for 30 min. The organic layer was washed with brine and dried over anhydrous magnesium sulfate. Insoluble materials were removed by filtration, and the filtrate was concentrated under reduced pressure. The residue was washed with EtOAc and diisopropyl ether, and dried to give 3-[4-(2-fluorophenyl)-5-(1H-1,2,4-triazol-3-yl)-1,3-thiazol-2-yl]-2-methyl-5-(2-piperidin-1-ylethoxy)pyrazolo[1,5-a]pyridine (81 mg, 86%) as a white solid, which was used in the next step without further purification.

A mixture of 3-[4-(2-fluorophenyl)-5-(1H-1,2,4-triazol-3-yl)-1,3-thiazol-2-yl]-2-methyl-5-(2-piperidin-1-ylethoxy)pyrazolo[1,5-a]pyridine (40 mg, 0.079 mmol) obtained above, p-toluenesulfonic acid monohydrate (33 mg, 0.17 mmol) and EtOH (1.5 mL) was heated to obtain clear solution. The solution was allowed to cool to rt and the resulting precipite was collected by filtration to give the title compound (41 mg, 76%) as a pale yellow solid.

$^1$H-NMR (DMSO-$d_6$, 300 MHz) δ 1.24-1.94 (6H, m), 2.28 (3H, s), 2.68 (3H, s), 2.91-3.11 (2H, m), 3.47-3.65 (4H, m) 4.49 (2H, br s), 6.83 (1H, dd; J=2.6, 7.6, Hz), 7.04-7.17 (2H, m), 7.20-7.35 (2H, m), 7.44-7.58 (3H, m), 7.62-7.81 (2H, m), 8.57 (1H, s), 8.72 (1H, d, J=7.6 Hz), 9.22 (1H, br s), 14.15 (1H, br s).

Example 81-B

Production of 3-[4-(2,6-difluorophenyl)-5-(1H-1,2,4-triazol-3-yl)-1,3-thiazol-2-yl]-2-methylpyrazolo[1,5-a]pyridine

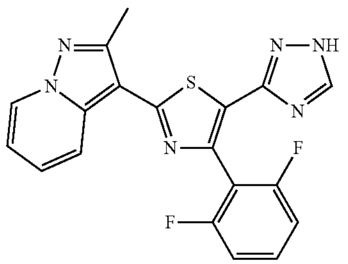 [SMILES: Cc1nn2ccccc2c1-c1nc(-c2c(F)cccc2F)c(-c2nc[nH]n2)s1]

(i) Production of methyl 4-(2,6-difluorophenyl)-2-(2-methylpyrazolo[1,5-a]pyridin-3-yl)-1,3-thiazole-5-carboxylate To a mixture of Methyl 2-(2-methylpyrazolo[1,5-a]pyridin-3-yl)-4-{[(trifluoromethyl)sulfonyl]oxy}-1,3-thiazole-5-carboxylate (500 mg, 1.2 mmol) obtained in Example 13-B (ii), 2,6-difluorophenylboronic acid (375 mg, 2.4 mmol), [1,1-bis(diphenylphosphino)ferrocene]palladium(II) dichloride dichloromethane complex (97 mg, 0.12 mmol) and cesium carbonate (1.2 g, 3.6 mmol) in DME (20 mL), was added water (1 mL) and the mixture was stirred at 80° C. for 3 h. The reaction mixture was allowed to cool to room temperature, and then water (100 mL) was added. The aqueous mixture was extracted with EtOAc (100 mL×2) and the combined organic layer was dried over anhydrous magnesium sulfate. Insoluble materials were removed by filtration and the filtrate was concentrated. The residue was purified by silica gel column chromatography (EtOAc) to give the title compound (147 mg, 32%) as a yellow solid.

$^1$H-NMR (DMSO-$d_6$, 300 MHz) δ 2.72 (3H, s), 3.76 (3H, s), 7.03-7.19 (1H, m), 7.20-7.36 (2H, m), 7.52-7.69 (2H, m), 8.23-8.33 (1H, m), 8.76-8.87 (1H, m).

(ii) Production of 4-(2,6-difluorophenyl)-2-(2-methylpyrazolo[1,5-a]pyridin-3-yl)-1,3-thiazole-5-carboxylic acid Using methyl 4-(2,6-difluorophenyl)-2-(2-methylpyrazolo[1,5-a]pyridin-3-yl)-1,3-thiazole-5-carboxylate (140 mg, 0.36 mmol) obtained above, MeOH (5 mL), THF (20 mL) and 8N aqueous sodium hydroxide solution (1.5 mL) as starting materials and in the similar manner described in Example 13-B(iv), the title compound (125 mg, 93%) was obtained as a white solid.

$^1$H-NMR (DMSO-$d_6$, 300 MHz) δ 2.70 (3H, s), 6.99-7.35 (3H, m), 7.45-7.72 (2H, m), 8.26 (1H, d, J=8.9 Hz), 8.80 (1H, d, J=6.8 Hz), 13.34 (1H, s).

(iii) Production of 4-(2,6-difluorophenyl)-2-(2-methylpyrazolo[1,5-a]pyridin-3-yl)-1,3-thiazole-5-carboxamide Using 4-(2,6-difluorophenyl)-2-(2-methylpyrazolo[1,5-a]pyridin-3-yl)-1,3-thiazole-5-carboxylic acid (120 mg, 11 mmol) obtained above, ammonium chloride (560 mg, 21 mmol), TEA (3 mL), HOBT (130 mg, 0.96 mmol), EDCI (350 mg, 1.8 mmol) and DMF (20 mL) as starting materials and in the similar manner described in Example 13-B(v), the title compound (105 mg, 88%) was obtained as a white solid.

$^1$H-NMR (DMSO-$d_6$, 300 MHz) δ 2.70 (3H, s), 7.09 (1H, dt, J=1.3, 6.9 Hz), 7.16-7.33 (2H, m), 7.41-7.83 (4H, m), 8.20-8.29 (1H, m), 8.79 (1H, d, J=6.9 Hz).

(iv) Production of 3-[4-(2,6-difluorophenyl)-5-(1H-1,2,4-triazol-3-yl)-1,3-thiazol-2-yl]-2-methylpyrazolo[1,5-a]pyridine Using 4-(2,6-difluorophenyl)-2-(2-methylpyrazolo[1,5-a]pyridin-3-yl)-1,3-thiazole-5-carboxamide (100 mg, 0.27 mmol) obtained above, N,N-dimethylformamide dimethylacetal (20 mL), AcOH (25 mL) and hydrazine monohydrate (0.4 mL) as starting materials and in the similar manner described in Example 13-B(vi), the title compound (70 mg, 66%) was obtained as a brown solid.

$^1$H-NMR (DMSO-$d_6$, 300 MHz) δ 2.70 (3H, s), 7.05 (1H, dt, J=1.3, 6.8 Hz), 7.13-7.26 (2H, m), 7.44-7.58 (2H, m), 8.17 (1H, s), 8.25 (1H, d, J=8.9 Hz), 8.75 (1H, d, J=6.8 Hz).

Example 82-B

Production of 2-methyl-5-(1-methyl-1H-pyrazol-4-yl)-3-[4-phenyl-5-(1H-1,2,4-triazol-3-yl)-1,3-thiazol-2-yl]pyrazolo[1,5-a]pyridine

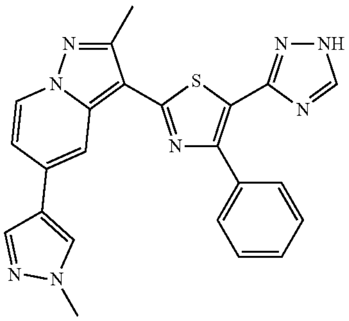 [SMILES: Cc1nn2ccc(-c3cnn(C)c3)cc2c1-c1nc(-c2ccccc2)c(-c2nc[nH]n2)s1]

(i) Production of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl trifluoromethanesulfonate To a solution of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (300 mg, 0.65 mmol) obtained in Example 31-B(i) in pyridine (15 mL), was added trifluoromethanesulfonic anhydride (280 mg, 1.0 mmol) at 0° C., and the mixture was stirred at 50° C. for 4 h. The reaction mixture was allowed to cool to 0° C., and then were added water (200 mL) and EtOAc (200 mL). The mixture was stirred for 30 min and then the organic layer was washed with brine and dried over anhydrous magnesium sulfate. Insoluble materials were removed by filtration and the filtrate was concentrated under reduced pressure. The residue was purified by silica gel column chromatography (EtOAc) to give the title compound (303 mg, 78%) as a yellow solid.

$^1$H-NMR (DMSO-$d_6$, 300 MHz) δ 1.50-1.81 (3H, m), 1.87-2.14 (3H, m), 2.74 (3H, s), 3.60-3.75 (1H, m), 3.88-3.99 (1H, m), 5.61 (1H, dd, J=2.9, 8.8 Hz), 7.27-7.49 (3H, m), 7.90-7.99 (2H, m), 8.50 (1H, d, J=2.6 Hz), 8.58 (1H, dd, J=1.8, 5.8 Hz), 8.82 (1H, s), 9.03 (1H, d, J=7.6 Hz).

(ii) Production of 2-methyl-5-(1-methyl-1H-pyrazol-4-yl)-3-[4-phenyl-5-(1H-1,2,4-triazol-3-yl)-1,3-thiazol-2-yl]pyrazolo[1,5-a]pyridine To a mixture of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl trifluoromethanesulfonate (150 mg, 0.25 mmol) obtained above, 1-methyl-4-(4,4,5,5-tetramethyl-1,3,2-dioxaborolan-2-yl)-1H-pyrazole (106 mg, 0.51 mmol), [1,1-bis(diphenylphosphino)ferrocene]palladium(II) dichloride dichloromethane complex (41 mg, 0.052 mmol) and cesium carbonate (248 mg, 0.76 mmol) in DME (15 mL) was added water (3 mL) and the mixture was stirred at 80° C. for 2 h. The reaction mixture was allowed to cool to room temperature, water (100 mL) was added, and the mixture was extracted with EtOAc (100 mL×2). The combined organic layer was dried over anhydrous magnesium sulfate and insoluble materials were removed by filtration. The filtrate was concentrated. The residue was dissolved in THF (25 mL), and then were added EtOH (5 mL) and 2N hydrochloric acid (3 mL). The mixture was stirred at 70° C. for 1 h. The reaction mixture was allowed to cool to rt. To the reaction mixture were added EtOAc (200 mL), 1N aqueous sodium hydroxide solution (10 mL) and water (100 mL), and the mixture was stirred for 1 h. The organic layer was washed with brine and dried over anhydrous magnesium sulfate. Insoluble materials were removed by filtration and the filtrate was concentrated under reduced pressure. The residue was crystallized from EtOAc to give the title compound (77 mg, 69%) as a yellow solid.

$^1$H-NMR (DMSO-$d_6$, 300 MHz) δ 2.71 (3H, s), 3.92 (3H, s), 7.30 (1H, dd, J=1.9, 7.2, Hz), 7.32-7.59 (3H, m), 7.83-8.07 (3H, m), 8.24-8.47 (2H, m), 8.62 (1H, br s), 8.75 (1H, d, J=7.2 Hz), 14.27 (1H, br s).

Example 83-B

Production of 2-methyl-5-morpholin-4-yl-3-[4-phenyl-5-(1H-1,2,4-triazol-3-yl)-1,3-thiazol-2-yl]pyrazolo[1,5-a]pyridine

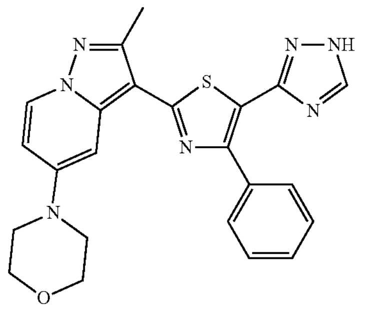 [SMILES: Cc1nn2ccc(N3CCOCC3)cc2c1-c1nc(-c2ccccc2)c(-c2nc[nH]n2)s1]

(i) Production of 2-methyl-5-morpholin-4-yl-3-{4-phenyl-5-[1-(tetrahydro-2H-pyran-2-yl)-1H-1,2,4-triazol-3-yl]-1,3-thiazol-2-yl}pyrazolo[1,5-a]pyridine A suspension 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl trifluoromethanesulfonate (150 mg, 0.25 mmol) obtained in Example 82-B(i), morpholine (501 mg, 5.73 mmol), tris(dibenzylideneacetone)dipalladium (0) (45 mg, 0.049 mmol), (R)-BINAP (50 mg, 0.080 mmol) and cesium carbonate (720 mg, 2.21 mmol) in toluene (30 mL) was stirred at 110° C. for 1 h. The reaction mixture was allowed to cool to room temperature, and then water (150 mL) was added. The mixture was extracted with EtOAc (150 mL×2). The combined organic layers were dried over anhydrous magnesium sulfate and insoluble materials were removed by filtration. The filtrate was concentrated and the residue was purified by silica gel column chromatography (EtOAc/hexane=10/90→100/0) to give the title compound (75 mg, 56%) as a yellow solid.

$^1$H-NMR (DMSO-$d_6$, 300 MHz) δ 1.47-1.78 (3H, m), 1.86-2.17 (3H, m), 2.64 (3H, s), 3.21-3.36 (4H, m), 3.59-3.72 (1H, m), 3.75-3.85 (4H, m), 3.88-4.00 (1H, m), 5.60 (1H, dd, J=3.0, 8.8 Hz), 6.96 (1H, dd, J=2.5, 7.7 Hz), 7.32-7.50 (3H, m), 7.54 (1H, d, J=2.5 Hz), 7.88-8.03 (2H, m), 8.54 (1H, d, J=7.7 Hz), 8.79 (1H, s).

(ii) Production of 2-methyl-5-morpholin-4-yl-3-[4-phenyl-5-(1H-1,2,4-triazol-3-yl)-1,3-thiazol-2-yl]pyrazolo[1,5-a]pyridine To a solution of 2-methyl-5-morpholin-4-yl-3-{4-phenyl-5-[1-(tetrahydro-2H-pyran-2-yl)-1H-1,2,4-triazol-3-yl]-1,3-thiazol-2-yl}pyrazolo[1,5-a]pyridine (75 mg, 0.14 mmol) obtained above in THF (25 mL), were added EtOH (5 mL) and 4N solution of hydrogen chloride in EtOAc (3 mL), and the mixture was stirred at 70° C. for 2 h. The reaction mixture was allowed to cool to rt. To the reaction mixture were added EtOAc (200 mL), saturated aqueous solution of sodium bicarbonate (200 mL) and 1N aqueous sodium hydroxide solution (10 mL), and the mixture was stirred for 30 min. The organic layer was washed with brine and dried over anhydrous magnesium sulfate. Insoluble materials were removed by filtration, and the filtrate was concentrated under reduced pressure.

The residue was crystallized from 2-propanol to give the title compound (48 mg, 76%) as a white solid.

$^1$H-NMR (DMSO-$d_6$, 300 MHz) δ 2.64 (3H, s), 3.40-3.48 (4H, m), 3.73-3.87 (4H, m), 6.96 (1H, dd, J=2.6, 2.6 Hz), 7.31-7.62 (4H, m), 7.88-8.04 (2H, m), 8.54 (1H, d, J=7.7 Hz), 8.66 (1H, s), 14.25 (1H, s).

Example 84-B

Production of 3-[4-(2-ethoxy-6-fluorophenyl)-5-(1H-1,2,4-triazol-3-yl)-1,3-thiazol-2-yl]-2-methylpyrazolo[1,5-a]pyridine

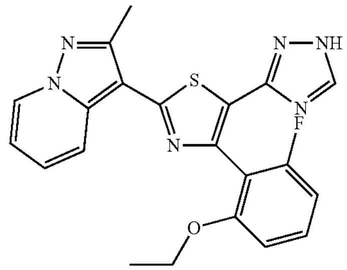 [SMILES: CCOc1cccc(F)c1-c1nc(-c2c(C)nn3ccccc23)sc1-c1nc[nH]n1]

(i) Production of methyl 4-(2-ethoxy-6-fluorophenyl)-2-(2-methylpyrazolo[1,5-a]pyridin-3-yl)-1,3-thiazole-5-carboxylate A suspension of Methyl 2-(2-methylpyrazolo[1,5-a]pyridin-3-yl)-4-{[(trifluoromethyl)sulfonyl]oxy}-1,3-thiazole-5-carboxylate (306 mg, 0.72 mmol) obtained in Example 13-B(ii), (2-ethoxy-6-fluorophenyl)boronic acid (262 mg, 1.4 mmol), [1,1-bis(diphenylphosphino)ferrocene]palladium (II) dichloride dichloromethane complex (80 mg, 0.098 mmol) and cesium carbonate (850 mg, 2.6 mmol) in DME (20 mL), was added water (2 mL), and the mixture was stirred at 90° C. for 5 h. The reaction mixture was allowed to cool to rt, water (200 mL) was added, and the mixture was extracted with EtOAc (100 mL×2). The combined organic layers were dried over anhydrous magnesium sulfate, insoluble materials were removed by filtration, and the filtrate was concentrated. The residue was purified by silica gel column chromatography (EtOAc/hexane=50/50→100/0) to give the title compound (295 mg, 100%) as a yellow solid. $^1$H-NMR (DMSO-$d_6$, 300 MHz) δ 1.07-1.23 (3H, m), 2.70 (3H, s), 3.72 (3H, s), 3.97-4.13 (2H, m), 6.85-7.61 (5H, m), 8.29 (1H, d, J=8.9 Hz), 8.80 (1H, d, J=6.8 Hz).

(ii) Production of 4-(2-ethoxy-6-fluorophenyl)-2-(2-methylpyrazolo[1,5-a]pyridin-3-yl)-1,3-thiazole-5-carboxylic acid Using methyl 4-(2-ethoxy-6-fluorophenyl)-2-(2-methylpyrazolo[1,5-a]pyridin-3-yl)-1,3-thiazole-5-carboxylate (295 mg, 0.72 mmol) obtained above, MeOH (5 mL), THF (25 mL) and 8N aqueous sodium hydroxide solution (2 mL) as starting materials and in the similar manner described in Example 13-B(iv), the title compound (281 mg, 98%) was obtained as a yellow solid.

$^1$H-NMR (DMSO-$d_6$, 300 MHz) δ 1.11-1.26 (3H, m), 2.69 (3H, s), 3.94-4.16 (2H, m), 6.81-7.01 (2H, m), 7.04-7.18 (1H, m), 7.35-7.67 (2H, m), 8.13-8.36 (1H, m), 8.78 (1H, d, J=7.0 Hz), 13.04 (1H, br s).

(iii) Production of 4-(2-ethoxy-6-fluorophenyl)-2-(2-methylpyrazolo[1,5-a]pyridin-3-yl)-1,3-thiazole-5-carboxamide Using 4-(2-ethoxy-6-fluorophenyl)-2-(2-methylpyrazolo[1,5-a]pyridin-3-yl)-1,3-thiazole-5-carboxylic acid (280 mg, 0.70 mmol) obtained above, ammonium chloride (1.4 g, 26 mmol), TEA (2 mL), HOBT (150 mg, 1.1 mmol), EDCI (720 mg, 3.6 mmol) and DMF (5 mL) as starting materials and in the similar manner described in Example 13-B(v), the title compound (277 mg, 99%) was obtained as a white solid.

$^1$H-NMR (DMSO-$d_6$, 300 MHz) δ 1.16-1.28 (3H, m), 2.69 (3H, s), 3.91-4.14 (2H, m), 6.80-7.13 (4H, m), 7.33-7.59 (3H, m), 8.13-8.34 (1H, m), 8.77 (1H, d, J=6.8 Hz).

(iv) Production of 3-[4-(2-ethoxy-6-fluorophenyl)-5-(1H-1,2,4-triazol-3-yl)-1,3-thiazol-2-yl]-2-methylpyrazolo[1,5-a]pyridine Using 4-(2-ethoxy-6-fluorophenyl)-2-(2-methylpyrazolo[1,5-a]pyridin-3-yl)-1,3-thiazole-5-carboxamide (270 mg, 0.68 mmol) obtained above, N,N-dimethylformamide dimethylacetal (15 mL), AcOH (25 mL) and hydrazine monohydrate (0.4 mL) as starting materials and in the similar manner described in Example 13-B(vi), the title compound (147 mg, 51%) was obtained as a pale yellow solid.

$^1$H-NMR (DMSO-$d_6$, 300 MHz) δ 0.86-1.05 (3H, m), 2.72 (3H, s), 3.80-4.09 (2H, m), 6.83-6.97 (2H, m), 7.01-7.11 (1H, m), 7.33-7.55 (2H, m), 8.20-8.34 (1H, m), 8.52 (1H, br s), 8.76 (1H, d, J=7.0 Hz), 14.07 (1H, s).

Example 85-B

Production of 2-methyl-5-(3-morpholin-4-ylpropoxy)-3-[4-phenyl-5-(1H-1,2,4-triazol-3-yl)-1,3-thiazol-2-yl]pyrazolo[1,5-a]pyridine p-toluenesulfonate

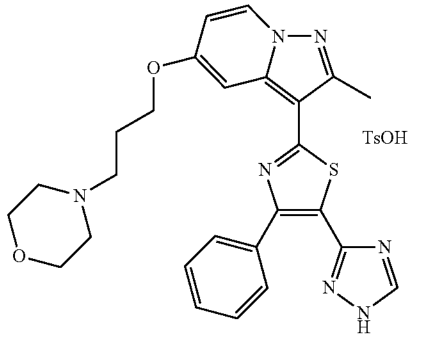

(i) Production of 4-(3-chloropropyl)morpholine

To a solution of morpholine (2.00 g, 23.0 mmol) in toluene (200 mL), was added 1-bromo-3-chloropropane (4.55 mL, 45.9 mmol) and the mixture was stirred for 4 h at 70° C. Insoluble materials were removed by filtration and the filtrate has been concentrated under reduced pressure. The residue was purified by silica gel column chromatography (EtOAc/hexane=70/30→100/0) to give the title compound (1.27 g, 68%) as a colorless oil.

$^1$H-NMR (DMSO-$d_6$, 300 MHz) δ 1.95 (2H, quin, J=6.6 Hz), 2.34-2.55 (6H, m), 3.61 (2H, t, J=6.6 Hz), 3.66-3.77 (4H, m).

(ii) Production of 2-methyl-5-(3-morpholin-4-ylpropoxy)-3-{4-phenyl-5-[1-(tetrahydro-2H-pyran-2-yl)-1H-1,2,4-triazol-3-yl]-1,3-thiazol-2-yl}pyrazolo[1,5-a]pyridine To a suspension of 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (100 mg, 0.218 mmol) obtained in Example 31-B-(i) and potassium carbonate (60.3 mg, 0.436 mmol) in DMF (4 mL), was added 4-(3-chloropropyl)morpholine (71.3 mg, 0.436 mmol) obtained above and the mixture was stirred for 5 h at 60° C. To the reaction mixture, were added EtOAc (20 mL) and saturated aqueous solution of sodium bicarbonate (15 mL). The organic layer was separated and then aqueous layer was extracted with EtOAc (5 mL). The combined organic layers were washed with brine (5 mL) and then dried over anhydrous sodium sulfate. Insoluble materials were removed by filtration and the filtrate was concentrated under reduced pressure. The residue was purified by silica gel column chromatography (EtOAc/hexane=30/70→60/40) to give the title compound (128 mg, quant) as a colorless solid $^1$H-NMR (DMSO-$d_6$, 300 MHz) δ 1.51-1.62 (2H, m), 1.79-2.12 (6H, m), 2.28-2.41 (2H, m), 2.30-2.40 (1H, m), 2.45 (2H, t, J=7.0 Hz), 2.66 (3H, s), 3.48-3.61 (6H, m), 3.84-4.01 (1H, m), 4.19 (2H, t, J=6.5 Hz), 5.60 (1H, dd, J=3.0, 8.9 Hz), 6.75 (1H, dd, J=2.7, 7.7 Hz), 7.30-7.53 (3H, m), 7.74 (1H, d, J=2.7 Hz), 7.85-8.03 (2H, m), 8.63 (1H, d, J=7.7 Hz), 8.79 (1H, s).

(iii) Production of 2-methyl-5-(3-morpholin-4-ylpropoxy)-3-[4-phenyl-5-(1H-1,2,4-triazol-3-yl)-1,3-thiazol-2-yl]pyrazolo[1,5-a]pyridine To a solution of 2-methyl-5-(3-morpholin-4-ylpropoxy)-3-{4-phenyl-5-[1-(tetrahydro-2H-pyran-2-yl)-1H-1,2,4-triazol-3-yl]-1,3-thiazol-2-yl}pyrazolo[1,5-a]pyridine (128 mg, 0.218 mmol) obtained above in THF (3 mL) and MeOH (1 mL), was added 3N hydrochloric acid (1 mL) and the mixture was stirred for 1 h at 60° C. To the reaction mixture was added a 3:1 mixture of EtOAc and THF (20 mL) and saturated aqueous solution of sodium bicarbonate (15 mL) and then organic layer was separated. The organic layer was concentrated under reduced pressure and the residue was washed with EtOAc (5 mL) to give title compound (86 mg, 79%) as a pale yellow solid.

$^1$H-NMR (DMSO-$d_6$, 300 MHz) δ 1.91-2.03 (2H, m), 2.33-2.40 (4H, m), 2.45 (2H, t, J=7.2 Hz), 2.66 (3H, s), 3.49-3.58 (4H, m), 4.19 (2H, t, J=6.5 Hz), 6.76 (1H, dd, J=2.7, 7.6 Hz), 7.36-7.48 (3H, m), 7.74 (1H, d, J=2.7 Hz), 7.89-8.00 (2H, m), 8.61 (1H, br s), 8.63 (1H, d, J=7.6 Hz), 14.25 (1H, br s).

(iv) Production of 2-methyl-5-(3-morpholin-4-ylpropoxy)-3-[4-phenyl-5-(1H-1,2,4-triazol-3-yl)-1,3-thiazol-2-yl]pyrazolo[1,5-a]pyridine p-toluenesulfonate To a suspension of 2-methyl-5-(3-morpholin-4-ylpropoxy)-3-[4-phenyl-5-(1H-1,2,4-triazol-3-yl)-1,3-thiazol-2-yl]pyrazolo[1,5-a]pyridine (85.8 mg, 0.171 mmol) obtained above in EtOH (10 mL), was added a solution of p-toluene sulfonic acid monohydrate (71.6 mg, 0.376 mmol) in EtOH (2 mL) and then resulting mixture was concentrated under reduced pressure. The residue was crystallized from EtOH (2 mL) and EtOAc (6 mL) to obtain title compound (106 mg, 92%) as a pale yellow solid.

$^1$H-NMR (DMSO-$d_6$, 300 MHz) δ 2.17-2.26 (2H, m), 2.27 (3H, s), 2.67 (3H, s), 2.95-3.21 (2H, m), 3.35-3.41 (2H, m), 3.42-3.56 (2H, m), 3.56-3.75 (2H, m), 3.93-4.08 (2H, m), 4.19-4.36 (2H, m), 6.76 (1H, dd, J=2.7, 7.6 Hz), 7.11 (2H, d, J=7.9 Hz), 7.30-7.54 (5H, m), 7.71 (1H, d, J=2.7 Hz), 7.90-8.02 (2H, m), 8.58-8.74 (2H, m), 9.51 (1H, br s), 14.27 (1H, br s). Acidic proton from p-toluenesulfonic acid has been observed with intensity of 1H.

Example 86-B

Production of 5-[2-(4,4-difluoropiperidin-1-yl)ethoxy]-2-methyl-3-[4-phenyl-5-(1H-1,2,4-triazol-3-yl)-1,3-thiazol-2-yl]pyrazolo[1,5-a]pyridine di-p-toluenesulfonate

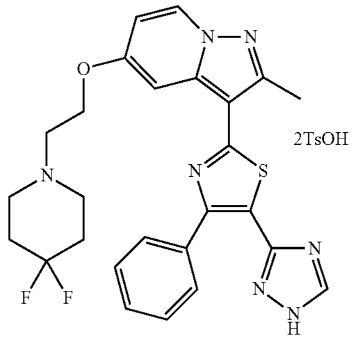

2TsOH (i) Production of 1-(2-chloroethyl)-4,4-difluoropiperidine

To a solution of 4,4-difluoropiperidine (1.00 g, 6.35 mmol) in acetone (15 mL), were added potassium carbonate (2.19 g, 15.9 mmol) and 1-bromo-2-chloroethane (635 μL, 7.62 mmol) and the mixture was stirred for 8 h at 50° C. Insoluble materials were removed by filtration and the filtrate was concentrated under reduced pressure. The residue was purified by silica gel column chromatography (EtOAc/hexane=0/100→30/70) to obtain title compound (188 mg, 16%) as a pale yellow oil.

$^1$H-NMR (DMSO-$d_6$, 300 MHz) δ 1.92-2.09 (4H, m), 2.58-2.68 (4H, m), 2.78 (2H, t, J=6.9 Hz), 3.57 (2H, t, J=6.9 Hz).

(ii) Production of 5-[2-(4,4-difluoropiperidin-1-yl)ethoxy]-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine The title compound has been prepared according to the similar manner described in 85-B (ii) using 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (100 mg, 0.218 mmol) obtained in Example 31-B-(i), potassium carbonate (75.3 mg, 0.545 mmol) and 1-(2-chloroethyl)-4,4-difluoropiperidine (80.0 mg, 0.436 mmol) obtained above. The crude product was purified by basic silica gel column chromatography (EtOAc/hexane=20/80→50/50) to give pure title compound (120 mg, 91%) as a colorless solid.

$^1$H-NMR (DMSO-$d_6$, 300 MHz) δ 1.50-1.62 (2H, m), 1.62-1.76 (1H, m), 1.82-2.14 (7H, m), 2.58-2.69 (4H, m), 2.66 (3H, s), 2.87 (2H, t, J=5.9 Hz), 3.61-3.73 (1H, m), 3.84-4.04 (1H, m), 4.27 (2H, t, J=5.9 Hz), 5.60 (1H, dd, J=3.0, 8.9 Hz), 6.77 (1H, dd, J=2.7, 7.6 Hz), 7.26-7.54 (3H, m), 7.76 (1H, d, J=2.7 Hz), 7.90-8.04 (2H, m), 8.64 (1H, d, J=7.6 Hz), 8.80 (1H, s).

(iii) Production of 5-[2-(4,4-difluoropiperidin-1-yl)ethoxy]-2-methyl-3-[4-phenyl-5-(1H-1,2,4-triazol-3-yl)-1,3-thiazol-2-yl]pyrazolo[1,5-a]pyridine The title compound has been prepared according to the similar manner described in 85-B (iii) using 5-[2-(4,4-difluoropiperidin-1-yl)ethoxy]-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (120 mg, 0.198 mmol) obtained above. The crude product was purified by washing with EtOAc (3 mL) to give pure title compound (89 mg, 86%) as a colorless solid.

$^1$H-NMR (DMSO-$d_6$, 300 MHz) δ 1.83-2.05 (4H, m), 2.60-2.66 (4H, m), 2.66 (3H, s), 2.87 (2H, t, J=5.9 Hz), 4.28 (2H, t, J=5.9 Hz), 6.77 (1H, dd, J=2.7, 7.5 Hz), 7.35-7.52 (3H, m), 7.75 (1H, d, J=2.7 Hz), 7.91-8.06 (2H, m), 8.52 (1H, br s), 8.63 (1H, d, J=7.6 Hz). No acidic proton of triazole.

(iv) Production of 5-[2-(4,4-difluoropiperidin-1-yl)ethoxy]-2-methyl-3-[4-phenyl-5-(1H-1,2,4-triazol-3-yl)-1,3-thiazol-2-yl]pyrazolo[1,5-a]pyridine di-p-toluenesulfonate The title compound has been prepared according to the similar manner described in 85-B (iv) from 5-[2-(4,4-difluoropiperidin-1-yl)ethoxy]-2-methyl-3-[4-phenyl-5-(1H-1,2,4-triazol-3-yl)-1,3-thiazol-2-yl]pyrazolo[1,5-a]pyridine (87.8 mg, 0.168 mmol) and p-toluenesulfonic acid monohydrate (70.3 mg, 0.370 mmol). The crude product was washed with EtOH (4 mL) to give pure title compound (100 mg, 69%) as a yellow solid.

$^1$H-NMR (DMSO-$d_6$, 300 MHz) δ 2.20-2.50 (4H, m), 2.29 (6H, s), 2.69 (3H, s), 3.18-3.39 (2H, m), 3.74 (4H, br s), 4.47-4.66 (2H, m), 6.84 (1H, dd, J=2.6, 7.5 Hz), 7.11 (4H, d, J=7.9 Hz), 7.33-7.55 (7H, m), 7.75 (1H, d, J=2.6 Hz), 7.87-8.01 (2H, m), 8.63 (1H, br s), 8.73 (1H, d, J=7.5 Hz), 9.75 (1H, br s), 14.28 (1H, br s). acidic proton of p-toluenesulfonic acid has been observed with intensity of 1H.

Example 87-B

Production of 5-[2-(4-fluoropiperidin-1-yl)ethoxy]-2-methyl-3-[4-phenyl-5-(1H-1,2,4-triazol-3-yl)-1,3-thiazol-2-yl]pyrazolo[1,5-a]pyridine di-p-toluenesulfonate

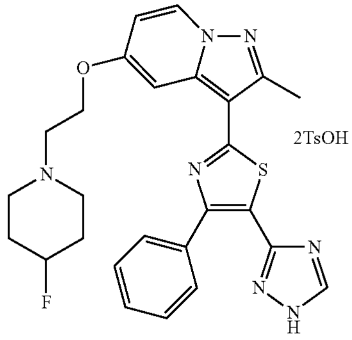

2TsOH (i) Production of 1-(2-chloroethyl)-4-fluoropiperidine

The title compound has been prepared according to the similar manner described in 86-B (i) using 4-fluoropiperidine hydrochloride (1.00 g, 7.16 mmol) and 1-bromo-2-chloroethane (717 μL, 8.60 mmol). The crude product has been purified by silica gel column chromatography (EtOAc/hexane=10/90→40/60) to obtain pure title compound (250 mg, 21%) as a pale yellow oil.

$^1$H-NMR (DMSO-$d_6$, 300 MHz) δ 1.80-2.02 (4H, m), 2.41-2.54 (2H, m), 2.57-2.69 (2H, m), 2.73 (2H, t, J=7.1 Hz), 3.58 (2H, t, J=7.1 Hz), 4.56-4.81 (1H, m).

(ii) Production of 5-[2-(4-fluoropiperidin-1-yl) ethoxy]-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine The title compound has been prepared according to the similar manner described in 85-B (ii) from 1-(2-chloroethyl)-4-fluoropiperidine (72.2 mg, 0.436 mmol) obtained above, 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (100 mg, 0.218 mmol) obtained in Example 31-B-(i) and potassium carbonate (75.3 mg, 0.545 mmol). The crude product has been roughly purified by simple filtration through basic silica gel pad and was used without further purification (pale yellow oil).

$^1$H-NMR (DMSO-$d_6$, 300 MHz) δ 1.48-2.15 (10H, m), 2.30-2.58 (4H, m), 2.66 (3H, s), 2.78 (2H, t, J=6.0 Hz), 3.54-3.75 (1H, m), 3.87-4.00 (1H, m), 4.26 (2H, t, J=6.0 Hz), 4.48-4.86 (1H, m), 5.60 (1H, dd, J=2.8, 8.9 Hz), 6.77 (1H, dd, J=2.7, 7.6 Hz), 7.35-7.51 (3H, m), 7.77 (1H, d, J=2.7 Hz), 7.90-8.03 (2H, m), 8.63 (1H, d, J=7.6 Hz), 8.80 (1H, s).

(iii) Production of 5-[2-(4-fluoropiperidin-1-yl) ethoxy]-2-methyl-3-[4-phenyl-5-(1H-1,2,4-triazol-3-yl)-1,3-thiazol-2-yl]pyrazolo[1,5-a]pyridine The title compound has been prepared according to the similar manner described in 85-B (iii) from 5-[2-(4-fluoropiperidin-1-yl)ethoxy]-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine obtained above. The crude product was purified by washing with EtOAc (5 mL) to give pure title compound (89 mg, 81%) as a colorless solid.

$^1$H-NMR (DMSO-$d_6$, 300 MHz) δ 1.60-1.95 (4H, m), 2.37-2.46 (2H, m), 2.60-2.70 (2H, m), 2.66 (3H, s), 2.79 (2H, t, J=5.9 Hz), 4.26 (2H, t, J=5.9 Hz), 4.50-4.84 (1H, m), 6.76 (1H, dd, J=2.7, 7.6 Hz), 7.32-7.48 (3H, m), 7.76 (1H, d, J=2.7 Hz), 7.94-8.10 (2H, m), 8.50 (1H, br s), 8.63 (1H, d, J=7.6 Hz). Acidic proton of triazole was not observed.

(iv) Production of 5-[2-(4-fluoropiperidin-1-yl) ethoxy]-2-methyl-3-[4-phenyl-5-(1H-1,2,4-triazol-3-yl)-1,3-thiazol-2-yl]pyrazolo[1,5-a]pyridine di-p-toluenesulfonate The title compound has been prepared according to the similar manner described in 85-B (iv) from 5-[2-(4-fluoropiperidin-1-yl)ethoxy]-2-methyl-3-[4-phenyl-5-(1H-1,2,4-triazol-3-yl)-1,3-thiazol-2-yl]pyrazolo[1,5-a]pyridine (89.3 mg, 0.177 mmol) and p-toluenesulfonic acid monohydrate (74.1 mg, 0.389 mmol). The crude product was crystallized from EtOH (1 mL) and EtOAc (4 mL) to give pure title compound (137 mg, 91%) as a yellow solid.

$^1$H-NMR (DMSO-$d_6$, 300 MHz) δ 2.05-2.17 (2H, m), 2.21-2.36 (2H, m), 2.29 (6H, s), 2.69 (3H, s), 3.50-3.74 (6H, m), 4.49-4.61 (2H, m), 4.87-5.12 (1H, m), 6.80-6.89 (1H, m), 7.11 (4H, d, J=7.7 Hz), 7.36-7.53 (7H, m), 7.72-7.77 (1H, m), 7.88-8.01 (2H, m), 8.64 (1H, br s), 8.73 (1H, d, J=7.4 Hz), 9.45 (1H, br s), 14.24 (1H, br s). Acidic proton of p-toluenesulfonic acid has been observed with intensity of 1H.

Example 88-B

Production of 2-methyl-5-[2-(4-methylpiperazin-1-yl)ethoxy]-3-[4-phenyl-5-(1H-1,2,4-triazol-3-yl)-1,3-thiazol-2-yl]pyrazolo[1,5-a]pyridinedi-p-toluenesulfonate

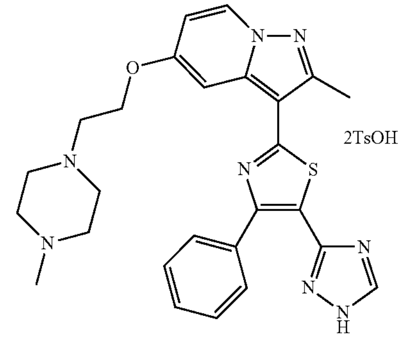

(i) Production of 5-(2-chloroethoxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine The title compound has been prepared according to the similar manner described in 85-B (ii) from 1-bromo-2-chloroethane (163 μL, 1.96 mmol), 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (300 mg, 0.654 mmol) obtained in Example 31-B-(i) and cesium carbonate (639 mg, 1.96 mmol). The crude product has been roughly purified by simple filtration through silica gel pad (5 g) and then washed with diethyl ether (20 mL) to give title compound (319 mg, 93%) as a colorless solid.

$^1$H-NMR (DMSO-$d_6$, 300 MHz) δ 1.49-1.74 (3H, m), 1.89-2.12 (3H, m), 2.67 (3H, s), 3.60-3.72 (1H, m), 3.89-3.99 (1H, m), 4.05 (2H, t, J=5.2 Hz), 4.44 (2H, t, J=5.2 Hz), 5.60 (1H, dd, J=2.9, 8.8 Hz), 6.82 (1H, dd, J=2.7, 7.6 Hz), 7.39-7.50 (3H, m), 7.73 (1H, d, J=2.7 Hz), 7.91-7.99 (2H, m), 8.67 (1H, d, J=7.6 Hz), 8.80 (1H, s).

(ii) Production of 2-methyl-5-[2-(4-methylpiperazin-1-yl)ethoxy]-3-{4-phenyl-5-[1-(tetrahydro-2H-pyran-2-yl)-1H-1,2,4-triazol-3-yl]-1,3-thiazol-2-yl}pyrazolo[1,5-a]pyridine To a solution of 5-(2-chloroethoxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (77.0 mg, 0.148 mmol) obtained above in DMF (2 mL), were added TEA (183 μL, 1.33 mmol) and 1-methylpiperazine (148 μL, 1.33 mmol) and the mixture was stirred for 18 h at 90° C. To the mixture were added EtOAc (20 mL) and saturated aqueous solution of sodium bicarbonate (15 mL) and then organic layer was separated. The organic layer was washed with brine (5 mL) and then dried over anhydrous sodium sulfate. Insoluble materials were removed by filtration and the filtrate was concentrated under reduced pressure. The residue was purified by basic silica gel column chromatography (EtOAc/hexane=80/20→100/0) to obtain crude title compound as a pale yellow syrup. This crude product has been used in the next step without further purification.

(iii) Production of 2-methyl-5-[2-(4-methylpiperazin-1-yl)ethoxy]-3-[4-phenyl-5-(1H-1,2,4-triazol-3-yl)-1,3-thiazol-2-yl]pyrazolo[1,5-a]pyridine The title compound has been prepared according to the similar manner described in 85-B (iii) from 2-methyl-5-[2-(4-methylpiperazin-1-yl)ethoxy]-3-{4-phenyl-5-[1-(tetrahydro-2H-pyran-2-yl)-1H-1,2,4-triazol-3-yl]-1,3-thiazol-2-yl}pyrazolo[1,5-a]pyridine obtained above. The crude product was purified by washing with EtOAc (4 mL) to give pure title compound (33 mg, 64%) as a colorless solid.

$^1$H-NMR (DMSO-$d_6$, 300 MHz) δ 2.14 (3H, s), 2.25-2.38 (4H, m), 2.41-2.50 (4H, m), 2.66 (3H, s), 2.77 (2H, t, J=5.9 Hz), 4.25 (2H, t, J=5.9 Hz), 6.76 (1H, dd, J=2.7, 7.4 Hz), 7.35-7.47 (3H, m), 7.76 (1H, d, J=2.7 Hz), 7.92-8.04 (2H, m), 8.56 (1H, s), 8.63 (1H, d, J=7.4 Hz), 14.24 (1H, br s).

(iv) Production of 2-methyl-5-[2-(4-methylpiperazin-1-yl)ethoxy]-3-[4-phenyl-5-(1H-1,2,4-triazol-3-yl)-1,3-thiazol-2-yl]pyrazolo[1,5-a]pyridine di-p-toluenesulfonate The title compound has been prepared according to the similar manner described in 85-B (iv) from 2-methyl-5-[2-(4-methylpiperazin-1-yl)ethoxy]-3-[4-phenyl-5-(1H-1,2,4-triazol-3-yl)-1,3-thiazol-2-yl]pyrazolo[1,5-a]pyridine (32.5 mg, 0.0649 mmol) and p-toluenesulfonic acid monohydrate (27.2 mg, 0.143 mmol). Title compound (48 mg, 87%) has been obtained as a yellow solid by the addition of EtOAc to the reaction mixture followed by collection of the resulting precipitate by filtration.

$^1$H-NMR (DMSO-$d_6$, 300 MHz) δ 2.29 (6H, s), 2.67 (3H, s), 2.80 (3H, br s), 2.92-3.54 (10H, m), 4.34 (2H, br s), 6.78 (1H, dd, J=2.7, 7.5 Hz), 7.11 (4H, d, J=7.7 Hz), 7.35-7.54 (7H, m), 7.72 (1H, d, J=2.7 Hz), 7.85-8.01 (2H, m), 8.63 (1H, br s), 8.67 (1H, d, J=7.5 Hz), 9.37 (1H, br s), 14.24 (1H, br s). Acidic proton of p-toluenesulfonic acid has been observed with intensity of 1H.

Example 89-B

Production of 2-methyl-5-{2-[4-(methylsulfonyl)piperazin-1-yl]ethoxy}-3-[4-phenyl-5-(1H-1,2,4-triazol-3-yl)-1,3-thiazol-2-yl]pyrazolo[1,5-a]pyridine di-p-toluenesulfonate

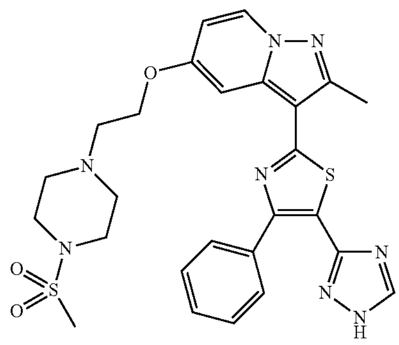 [SMILES: Cc1nn2ccc(OCCN3CCN(S(C)(=O)=O)CC3)cc2c1-c1nc(-c2ccccc2)c(-c2nc[nH]n2)s1]

(i) Production of 2-methyl-5-{2-[4-(methylsulfonyl)piperazin-1-yl]ethoxy}-3-{4-phenyl-5-[1-(tetrahydro-2H-pyran-2-yl)-1H-1,2,4-triazol-3-yl]-1,3-thiazol-2-yl}pyrazolo[1,5-a]pyridine Title compound has been prepared according to the similar manner described in 88-B (ii) from 5-(2-chloroethoxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (120.0 mg, 0.230 mmol) obtained 88-B (i), 1-(methylsulfonyl)piperazine (75.7 mg, 0.461 mmol), potassium carbonate (63.7 mg, 0.461 mmol) as a base instead of TEA and sodium iodide (69.1 mg, 0.461 mmol) as an additive. Crude title compound has been obtained as yellow oil after extraction and was used in the next step without further purification.

(ii) Production of 2-methyl-5-{2-[4-(methylsulfonyl)piperazin-1-yl]ethoxy}-3-[4-phenyl-5-(1H-1,2,4-triazol-3-yl)-1,3-thiazol-2-yl]pyrazolo[1,5-a]pyridine The title compound has been prepared according to the similar manner described in 85-B (iii) from 2-methyl-5-{2-[4-(methylsulfonyl)piperazin-1-yl]ethoxy}-3-{4-phenyl-5-[1-(tetrahydro-2H-pyran-2-yl)-1H-1,2,4-triazol-3-yl]-1,3-thiazol-2-yl}pyrazolo[1,5-a]pyridine obtained above. The crude product was purified by washing with EtOAc (5 mL) to give pure title compound (111 mg, 85%) as a colorless solid.

$^1$H-NMR (DMSO-$d_6$, 300 MHz) δ 2.57-2.65 (4H, m), 2.67 (3H, s), 2.81-2.90 (2H, m), 2.87 (3H, s), 3.05-3.16 (4H, m), 4.28 (2H, t, J=5.7 Hz), 6.77 (1H, dd, J=2.6, 7.6 Hz), 7.37-7.48 (3H, m), 7.74 (1H, d, J=2.6 Hz), 7.88-8.04 (2H, m), 8.56 (1H, s), 8.63 (1H, d, J=7.6 Hz), 14.25 (1H, br s).

(iii) Production of 2-methyl-5-{2-[4-(methylsulfonyl)piperazin-1-yl]ethoxy}-3-[4-phenyl-5-(1H-1,2,4-triazol-3-yl)-1,3-thiazol-2-yl]pyrazolo[1,5-a]pyridine di-p-toluenesulfonate The title compound has been prepared according to the similar manner described in 85-B (iv) from 2-methyl-5-{2-[4-(methylsulfonyl)piperazin-1-yl]ethoxy}-3-[4-phenyl-5-(1H-1,2,4-triazol-3-yl)-1,3-thiazol-2-yl]pyrazolo[1,5-a]pyridine (45.3 mg, 0.0802 mmol) and p-toluenesulfonic acid monohydrate (33.6 mg, 0.176 mmol). The pure title compound (62 mg, 85%) has been obtained as a yellow solid by crystallization from EtOH (1 mL) and EtOAc (3 mL).

$^1$H-NMR (DMSO-$d_6$, 300 MHz) δ 2.29 (6H, s), 2.41-2.46 (2H, m), 2.69 (3H, s), 3.03 (3H, s), 3.08-3.23 (4H, m), 3.72 (4H, br s), 4.57 (2H, br s), 6.83 (1H, dd, J=2.7, 7.6 Hz), 7.11 (4H, d, J=7.7 Hz), 7.38-7.51 (7H, m), 7.74 (1H, d, J=2.7 Hz), 7.89-7.99 (2H, m), 8.56-8.69 (1H, m), 8.73 (1H, d, J=7.6 Hz), 14.24 (1H, br s).

Example 90-B

Production of 4-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperazin-2-one p-toluenesulfonate

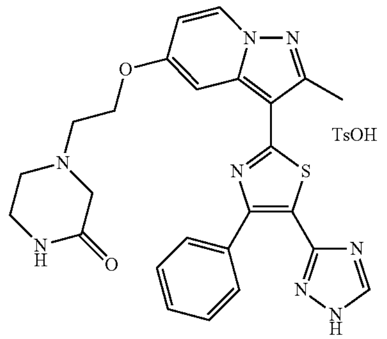

(i) Production of 4-{2-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]ethyl}piperazin-2-one Title compound has been prepared according to the similar manner described in 88-B (ii) from 5-(2-chloroethoxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (78.0 mg, 0.150 mmol), piperazine-2-one (29.9 mg, 0.299 mmol) obtained 88-B (i), potassium carbonate (41.3 mg, 0.299 mmol) as a base instead of TEA and sodium iodide (44.8 mg, 0.299 mmol) as a additive. After extraction, the crude product has been washed with EtOAc (5 mL) to give title compound (66 mg, 75%) as a colorless solid.

$^1$H-NMR (DMSO-$d_6$, 300 MHz) δ 1.47-1.75 (3H, m), 1.91-2.15 (3H, m), 2.67 (3H, s), 2.70-2.75 (2H, m), 2.86 (2H, t, J=5.6 Hz), 3.08 (2H, s), 3.11-3.19 (2H, m), 3.61-3.73 (1H, m), 3.88-3.99 (1H, m), 4.29 (2H, t, J=5.6 Hz), 5.60 (1H, dd, J=2.8, 8.7 Hz), 6.78 (1H, dd, J=2.8, 7.6 Hz), 7.37-7.48 (3H, m), 7.73-7.78 (2H, m), 7.93-7.98 (2H, m), 8.65 (1H, d, J=7.6 Hz), 8.80 (1H, s).

(ii) Production of 4-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperazin-2-one The title compound has been prepared according to the similar manner with the procedure described in 85-B (iii) from 4-{2-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]ethyl}piperazin-2-one (65.0 mg, 0.111 mmol) obtained above. The crude product was purified by washing with EtOAc (5 mL) to give pure title compound (38 mg, 68%) as a colorless solid.

$^1$H-NMR (DMSO-$d_6$, 300 MHz) δ 2.64-2.75 (2H, m), 2.67 (3H, s), 2.86 (2H, t, J=5.6 Hz), 3.08 (2H, s), 3.11-3.21 (2H, m), 4.30 (2H, t, J=5.6 Hz), 6.78 (1H, dd, J=2.7, 7.6 Hz), 7.29-7.54 (3H, m), 7.75 (1H, d, J=2.7 Hz), 7.75 (1H, br s), 7.85-8.05 (2H, m), 8.64 (1H, d, J=7.6 Hz), 8.64 (1H, br s), 14.24 (1H, br s).

(iii) Production of 4-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperazin-2-one p-toluenesulfonate The title compound has been prepared according to the similar manner described in 85-B (iv) from 4-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperazin-2-one (38.0 mg, 0.0759 mmol) and p-toluenesulfonic acid (31.8 mg, 0.167 mmol). The pure title compound (35 mg, 68%) has been obtained as a pale yellow solid by crystallization from EtOH (8 mL) and EtOAc (2 mL).

$^1$H-NMR (DMSO-$d_6$, 300 MHz) δ 2.25-2.30 (2H, m), 2.29 (3H, s), 2.41-2.46 (2H, m), 2.54-2.59 (2H, m), 2.68 (3H, s), 2.70-2.75 (2H, m), 4.18-4.64 (2H, m), 6.78-6.84 (1H, m), 7.11 (2H, d, J=7.7 Hz), 7.37-7.51 (5H, m), 7.75 (1H, d, J=2.8 Hz), 7.88-8.04 (2H, m), 8.53-8.76 (2H, m), 14.26 (1H, br s). Lactam proton has not been observed.

Example 91-B

Production of 1-methyl-4-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperazin-2-one hydrochloride

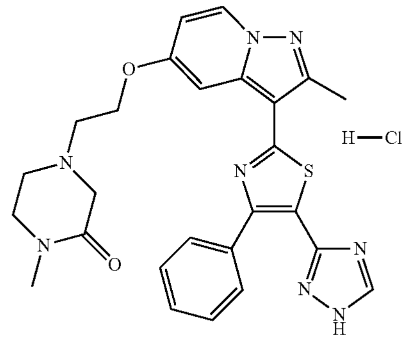

(i) Production of 4-benzyloxycarbonylpiperazine-2-one

To a suspension of piperazine-2-one (2.00 g, 20.0 mmol) in EtOAc (50 mL) and water (50 mL), were added sodium carbonate (6.36 g, 60.0 mmol) and 95% benzyl chloroformate (3.59 mL, 24.0 mmol) and the mixture was stirred for 3 days at rt. To the mixture were added EtOAc (50 mL) and water (20 mL) and then organic layer was separated. The aqueous layer was extracted with EtOAc (30 mL×2). The combined organic layer was washed with brine (20 mL) and then dried over anhydrous sodium sulfate. Insoluble materials were removed by filtration and the filtrate was concentrated under reduced pressure. The residue was washed with diethyl ether (50 mL) to give title compound (3.98 g, 85%) as a colorless solid.

$^1$H-NMR ($CDCl_3$, 300 MHz) δ 3.41 (2H, br s), 3.71 (2H, t, J=5.4 Hz), 4.18 (2H, s), 5.16 (2H, s), 6.02 (1H, br s), 7.30-7.42 (5H, m).

(ii) Production of benzyl 4-methyl-3-oxopiperazine-1-carboxylate

To a solution of 4-benzyloxycarbonylpiperazine-2-one (3.98 g, 17.0 mmol) obtained above in DMF (50 mL), was added 60% sodium hydride (815 mg, 20.4 mmol) and the mixture was stirred for 10 min at 0° C. To the mixture was added iodomethane (3.17 mL, 51.0 mmol) and the mixture was stirred for 4.5 h at rt. To the mixture were added EtOAc (100 mL) and water (50 mL) and then organic layer was separated. The aqueous layer was extracted with EtOAc (20 mL×4). The combined organic layer was washed with brine (15 mL) and then dried over anhydrous sodium sulfate. Insoluble materials were removed by filtration and the filtrate was concentrated under reduced pressure. The residue was purified by basic silica gel column chromatography (EtOAc/hexane=20/80→60/40) to give title compound (3.59 g, 85%) as a pale yellow oil.

$^1$H-NMR ($CDCl_3$, 300 MHz) δ 3.00 (3H, s), 3.29-3.45 (2H, m), 3.73 (2H, t, J=5.4 Hz), 4.15 (2H, s), 5.15 (2H, s), 7.29-7.43 (5H, m).

(iii) Production of 1-methylpiperazine-2-one

To a solution of benzyl 4-methyl-3-oxopiperazine-1-carboxylate (3.59 g, 14.5 mmol) in THF (30 mL) and EtOH (10 mL), was added 10% palladium-carbon (1.54 g, 1.45 mmol) and the mixture was stirred for 4 h at rt under hydrogen atmosphere (1 atm). The mixture was filtered through Celite pad and the filtrate was concentrated under reduced pressure to give title compound (1.61 g, 97%) as pale yellow oil.

$^1$H-NMR ($CDCl_3$, 300 MHz) δ 1.88 (1H, br s), 2.97 (3H, s), 3.08 (2H, t, J=5.4 Hz), 3.32 (2H, t, J=5.4 Hz), 3.51 (2H, s).

(iv) Production of 1-methyl-4-{2-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]ethyl}piperazin-2-one Title compound has been prepared according to the similar manner described in 88-B (ii) from 5-(2-chloroethoxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (236 mg, 0.453 mmol) obtained example 88-B (i), 1-methylpiperazine-2-one (129 mg, 1.13 mmol) obtained above, potassium carbonate (156 mg, 1.13 mmol) as a base instead of TEA and sodium iodide (169 mg, 1.13 mmol) as a additive. After extraction, the crude product has been purified by silica gel column chromatography (MeOH/EtOAc=0/100→10/90) to give title compound as a yellow syrup. This crude product was used in the next step without further purification.

(v) Production of 1-methyl-4-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperazin-2-one hydrochloride To a suspension of 1-methyl-4-{2-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]ethyl}piperazin-2-one obtained above in THF (6 mL) and MeOH (2 mL), was added 2M hydrochloric acid (2 mL) and the mixture was stirred for 1 h at 60° C. To the mixture was added EtOAc (5 mL) and the resulting precipitate has been collected by filtration to obtain title compound (217 mg, 87%) as a yellow solid.

$^1$H-NMR (DMSO-$d_6$, 300 MHz) δ 2.68 (3H, s), 2.90 (3H, s), 3.39-3.79 (4H, m), 3.70 (2H, br s), 3.98 (2H, br s), 4.55-4.66 (2H, m), 6.84 (1H, dd, J=2.7, 7.5 Hz), 7.35-7.51 (3H, m), 7.74 (1H, d, J=2.7 Hz), 7.88-7.99 (2H, m), 8.62 (1H, br s), 8.72 (1H, d, J=7.5 Hz), 14.34 (1H, br s).

Example 92-B

Production of 5-[2-(4-acetylpiperazin-1-yl)ethoxy]-2-methyl-3-[4-phenyl-5-(1H-1,2,4-triazol-3-yl)-1,3-thiazol-2-yl]pyrazolo[1,5-a]pyridine di-p-toluenesulfonate

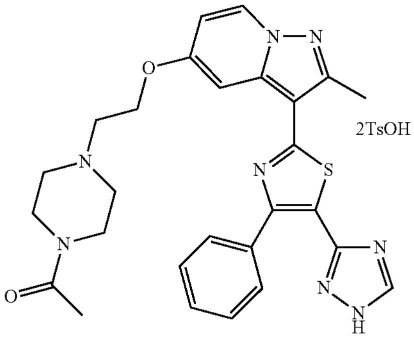 [SMILES: CC(=O)N1CCN(CCOc2ccn3nc(C)c(-c4nc(-c5ccccc5)c(-c5nc[nH]n5)s4)c3c2)CC1]

2TsOH (i) Production of 5-[2-(4-acetylpiperazin-1-yl)ethoxy]-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine Title compound has been prepared according to the similar manner described in 88-B (ii) from 5-(2-chloroethoxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (100.0 mg, 0.192 mmol) obtained in Example 88-B (i), 1-acetylpiperazine (49.2 mg, 0.384 mmol) obtained above, potassium carbonate (53.1 mg, 0.384 mmol) as a base instead of TEA and sodium iodide (57.6 mg, 0.384 mmol) as a additive. After extraction, the crude product has been used in the next step without further purification.

(ii) Production of 5-[2-(4-acetylpiperazin-1-yl)ethoxy]-2-methyl-3-[4-phenyl-5-(1H-1,2,4-triazol-3-yl)-1,3-thiazol-2-yl]pyrazolo[1,5-a]pyridine The title compound has been prepared according to the similar manner described in 85-B (iii) from 5-[2-(4-acetylpiperazin-1-yl)ethoxy]-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine obtained above. The crude product was purified by silica gel column chromatography (MeOH/EtOAc=0/100→20/80) to give pure title compound (63 mg, 62%) as a colorless solid.

$^1$H-NMR (DMSO-$d_6$, 300 MHz) δ 1.98 (3H, s), 2.41-2.47 (4H, m), 2.66 (3H, s), 2.82 (2H, t, J=5.9 Hz), 3.38-3.49 (4H, m), 4.29 (2H, t, J=5.9 Hz), 6.77 (1H, dd, J=2.6, 7.6 Hz), 7.34-7.49 (3H, m), 7.76 (1H, d, J=2.6 Hz), 7.95-8.04 (2H, m), 8.52 (1H, s), 8.63 (1H, d, J=7.6 Hz). Acidic proton of triazole was not observed.

(iii) Production of 5-[2-(4-acetylpiperazin-1-yl)ethoxy]-2-methyl-3-[4-phenyl-5-(1H-1,2,4-triazol-3-yl)-1,3-thiazol-2-yl]pyrazolo[1,5-a]pyridine di-p-toluenesulfonate The title compound has been prepared according to the similar manner described in 85-B (iv) from 5-[2-(4-acetylpiperazin-1-yl)ethoxy]-2-methyl-3-[4-phenyl-5-(1H-1,2,4-triazol-3-yl)-1,3-thiazol-2-yl]pyrazolo[1,5-a]pyridine (63.1 mg, 0.119 mmol) obtained above and p-toluenesulfonic acid monohydrate (50.0 mg, 0.263 mmol). The pure title compound (70 mg, 67%) has been obtained as a yellow solid by crystallization from EtOH (1 mL) and EtOAc (4 mL).

$^1$H-NMR (DMSO-$d_6$, 300 MHz) δ 2.05 (3H, s), 2.28 (6H, s), 2.69 (3H, s), 2.86-3.32 (4H, m), 3.33-3.54 (2H, m), 3.73-3.88 (2H, m), 3.95-4.12 (1H, m), 4.36-4.51 (1H, m), 4.52-4.64 (2H, m), 6.83 (1H, dd, J=2.7, 7.6 Hz), 7.11 (4H, d, J=7.9 Hz), 7.33-7.56 (7H, m), 7.74 (1H, d, J=2.7 Hz), 7.85-8.03 (2H, m), 8.64 (1H, br s), 8.73 (1H, d, J=7.6 Hz), 9.84 (1H, br s), 14.32 (1H, br s). Acidic proton of p-toluenesulfonic acid has been observed with intensity of 1H.

Example 93-B

Production of 1-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperidin-4-ol di-p-toluenesulfonate

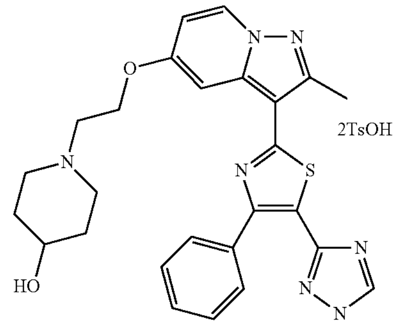 [SMILES: Cc1nn2ccc(OCCN3CCC(O)CC3)cc2c1-c1nc(-c2ccccc2)c(-c2nc[nH]n2)s1]

(i) Production of 1-{2-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]ethyl}piperidin-4-ol Title compound has been prepared according to the similar manner described in 88-B (ii) from 5-(2-chloroethoxy)-2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridine (100.0 mg, 0.192 mmol) obtained in Example 88-B (i), 4-hydroxypiperazine (38.8 mg, 0.384 mmol), potassium carbonate (53.1 mg, 0.384 mmol) as a base instead of TEA and sodium iodide (57.6 mg, 0.384 mmol) as a additive. After extraction, the crude title product has been used in the next step without further purification.

(ii) Production of 1-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperidin-4-ol The title compound has been prepared according to the similar manner described in 85-B (iii) from 1-{2-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]ethyl}piperidin-4-ol obtained above. The crude product was purified by washing with EtOAc (5 mL) to give pure title compound (80 mg, 82%) as a colorless solid.

$^1$H-NMR (DMSO-$d_6$, 300 MHz) δ 1.30-1.48 (2H, m), 1.63-1.78 (2H, m), 2.08-2.23 (2H, m), 2.66 (3H, s), 2.70-2.86 (4H, m), 3.40-3.50 (1H, m), 4.24 (2H, t, J=6.0 Hz), 4.55 (1H, br s), 6.76 (1H, dd, J=2.6, 7.5 Hz), 7.36-7.49 (3H, m), 7.77 (1H, d, J=2.6 Hz), 7.88-8.04 (2H, m), 8.58 (1H, s), 8.63 (1H, d, J=7.5 Hz), 14.24 (1H, br s).

(iii) Production of 1-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperidin-4-ol di-p-toluenesulfonate The title compound has been prepared according to the similar manner described in 85-B (iv) from 1-[2-({2-methyl-3-[4-phenyl-5-(1H-1,2,4-triazol-3-yl)-1,3-thiazol-2-yl]pyrazolo[1,5-a]pyridin-5-yl}oxy)ethyl]piperidin-4-ol (78.8 mg, 0.157 mmol) obtained above and p-toluenesulfonic acid monohydrate (65.7 mg, 0.345 mmol). The pure title compound (85 mg, 64%) has been obtained as a yellow solid by washing with EtOH (4 mL) and acetone (4 mL).

$^1$H-NMR (DMSO-$d_6$, 300 MHz) δ 1.52-2.05 (4H, m), 2.28 (6H, s), 2.68 (3H, s), 3.03-3.48 (4H, m), 3.50-3.62 (2H, m), 3.94 (1H, br s), 4.44-4.62 (2H, m), 6.83 (1H, td, J=2.4, 7.6 Hz), 7.11 (4H, d, J=7.7 Hz), 7.34-7.55 (7H, m), 7.74 (1H, t, J=2.4 Hz), 7.83-8.07 (2H, m), 8.63 (1H, br s), 8.72 (1H, d, J=7.6 Hz), 9.29 (1H, br s), 14.27 (1H, br s). Acidic proton of p-toluenesulfonic acid has been observed with intensity of 1H. Proton of OH has not been observed.

Example 94-B

Production of 2-methyl-3-[4-phenyl-5-(1H-1,2,4-triazol-3-yl)-1,3-thiazol-2-yl]-5-(piperidin-4-yloxy)pyrazolo[1,5-a]pyridine di-p-toluenesulfonate

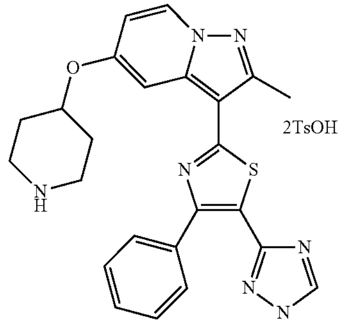 [SMILES: Cc1nn2ccc(OC3CCNCC3)cc2c1-c1nc(-c2ccccc2)c(-c2nc[nH]n2)s1]

(i) Production of 1-[(tert-butoxycarbonyl)oxy]piperidin-4-yl methanesulfonate

To a solution of 1-[(tert-butoxycarbonyl)oxy]piperidin-4-ol (10.0 g, 49.7 mmol) in THF (200 mL), were added TEA (20.7 mL, 149 mmol) and methanesulfonyl chloride (7.69 mL, 99.4 mmol) at 0° C. The mixture was stirred for 2.5 h at the same temperature. To the mixture was added EtOAc (100 mL) and water (100 mL) and then organic layer has been separated. The aqueous layer has been extracted with EtOAc (50 mL) and the combined organic layer was washed with brine (30 mL). The organic layer was dried over anhydrous magnesium sulfate and then insoluble materials were removed by filtration. The filtrate was concentrated under reduced pressure, and the residue was purified by silica gel column chromatography (EtOAc/hexane=20/80→50/50). Concentration of appropriate fractions afforded crude product, which was washed with a 1:1 mixture of diethyl ether and hexane (50 mL) to give title compound (12.9 g, 92%) as a pale yellow solid.

$^1$H-NMR (DMSO-$d_6$, 300 MHz) δ 1.46 (9H, s), 1.74-1.89 (2H, m), 1.90-2.04 (2H, m), 3.04 (3H, s), 3.30 (2H, ddd, J=3.8, 8.1, 13.7 Hz), 3.71 (2H, ddd, J=4.0, 6.9, 13.7 Hz), 4.88 (1H, tt, J=3.7, 7.7 Hz).

(ii) Production of tert-butyl 4-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]piperidine-1-carboxylate The title compound has been prepared according to the similar manner described in 85-B (ii) from 2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-ol (490 mg, 1.07 mmol) obtained in Example 31-B-(i), potassium carbonate (444 mg, 3.21 mmol) and 1-[(tert-butoxycarbonyl)oxy]piperidin-4-yl methanesulfonate (897 mg, 3.21 mmol) obtained above. The crude product was purified by basic silica gel column chromatography (EtOAc/hexane=20/80→50/50) to give pure title compound (630 mg, 92%) as a pale yellow solid.

$^1$H-NMR (DMSO-$d_6$, 300 MHz) δ 1.43 (9H, s), 1.50-1.79 (5H, m), 1.86-2.16 (5H, m), 2.65 (3H, s), 3.06-3.22 (2H, m), 3.60-3.72 (1H, m), 3.72-3.85 (2H, m), 3.88-3.99 (1H, m), 4.63-4.77 (1H, m), 5.60 (1H, dd, J=2.8, 8.9 Hz), 6.77 (1H, dd, J=2.7, 7.6 Hz), 7.36-7.49 (3H, m), 7.86 (1H, d, J=2.7 Hz), 7.91-8.00 (2H, m), 8.65 (1H, d, J=7.6 Hz), 8.80 (1H, s).

(iii) Production of 2-methyl-3-[4-phenyl-5-(1H-1,2,4-triazol-3-yl)-1,3-thiazol-2-yl]-5-(piperidin-4-yloxy)pyrazolo[1,5-a]pyridine A solution of tert-butyl 4-[(2-methyl-3-{4-phenyl-5-[1-(tetrahydro-2H-pyran-2-yl)-1H-1,2,4-triazol-3-yl]-1,3-thiazol-2-yl}pyrazolo[1,5-a]pyridin-5-yl)oxy]piperidine-1-carboxylate (630 mg, 0.982 mmol) obtained above in TFA (10 mL) was stirred for 2 h at rt and then the mixture was concentrated under reduced pressure. To the residue were added a 1:1 mixture of THF and EtOAc (30 mL) and saturated aqueous solution of sodium bicarbonate (20 mL). The organic layer has been separated and the aqueous layer was extracted with a 1:1 mixture of THF and EtOAc (10 mL). The combined organic layer has been dried over anhydrous sodium sulfate and then insoluble materials were removed by filtration. Concentration of the filtrate afforded crude product, which was washed with EtOAc (5 mL) to give title compound (383 mg, 85%) as a pale yellow solid.

$^1$H-NMR (DMSO-$d_6$, 300 MHz) δ 1.82-2.01 (2H, m), 2.11-2.34 (2H, m), 2.66 (3H, s), 3.00-3.17 (2H, m), 3.27-3.31 (2H, m), 4.74-4.90 (1H, m), 6.80 (1H, dd, J=2.8, 7.6 Hz), 7.35-7.54 (3H, m), 7.84 (1H, d, J=2.8 Hz), 7.90-8.01 (2H, m), 8.63 (1H, br s), 8.69 (1H, d, J=7.6 Hz), 14.32 (1H, br s). proton of NH was not observed.

(iv) Production of 2-methyl-3-[4-phenyl-5-(1H-1,2,4-triazol-3-yl)-1,3-thiazol-2-yl]-5-(piperidin-4-yloxy)pyrazolo[1,5-a]pyridine di-p-toluenesulfonate The title compound has been prepared according to the similar manner described in 85-B (iv) from 2-methyl-3-[4-phenyl-5-(1H-1,2,4-triazol-3-yl)-1,3-thiazol-2-yl]-5-(piperidin-4-yloxy)pyrazolo[1,5-a]pyridine (79.0 mg, 0.173 mmol) obtained above and p-toluenesulfonic acid monohydrate (72.4 mg, 0.381 mmol). The pure title compound (67 mg, 49%) has been obtained as a colorless solid by crystallization from EtOH (5 mL) and EtOAc (5 mL).

$^1$H-NMR (DMSO-$d_6$, 300 MHz) δ 1.89-2.05 (2H, m), 2.17-2.26 (2H, m), 2.29 (6H, s), 2.66 (3H, s), 3.01-3.22 (2H, m), 3.24-3.39 (2H, m), 4.79-4.98 (1H, m), 6.81 (1H, dd, J=2.7, 7.5 Hz), 7.11 (4H, d, J=7.9 Hz), 7.32-7.59 (7H, m), 7.83 (1H, d, J=2.7 Hz), 7.88-8.02 (2H, m), 8.62 (1H, br s), 8.69 (1H, d, J=7.5 Hz), 8.80 (2H, br s), 14.27 (1H, br s).

Example 95-B

Production of 5-[(1-acetylpiperidin-4-yl)oxy]-2-methyl-3-[4-phenyl-5-(1H-1,2,4-triazol-3-yl)-1,3-thiazol-2-yl]pyrazolo[1,5-a]pyridine

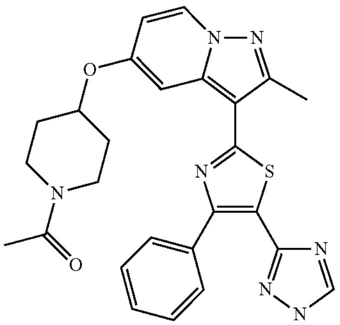 [SMILES: CC(=O)N1CCC(Oc2ccn3nc(C)c(-c4nc(-c5ccccc5)c(-c5nc[nH]n5)s4)c3c2)CC1]

To a solution of 2-methyl-3-[4-phenyl-5-(1H-1,2,4-triazol-3-yl)-1,3-thiazol-2-yl]-5-(piperidin-4-yloxy)pyrazolo[1,5-a]pyridine (100 mg, 0.219 mmol) obtained 85-B (iii) in DMF (3 mL), was added acetyl chloride (31.2 μL, 0.438 mmol) and the mixture was stirred for 2 h at rt. To the mixture, were added MeOH (1 mL) and potassium carbonate (90.8 mg, 0.657 mmol), and then the mixture was stirred for additional 1.5 h at the same temperature. To the mixture were added a 1:1 mixture of THF and EtOAc (20 mL) and saturated aqueous solution of sodium bicarbonate (15 mL), and then organic layer was separated. The aqueous layer was extracted with a 1:1 mixture of THF and EtOAc (5 mL×4) and the combined organic layer was washed with brine (5 mL). The organic layer was dried over anhydrous sodium sulfate and then insoluble materials were removed by filtration. The filtrate was concentrated under reduced pressure and the residue was purified by basic silica gel column chromatography (MeOH/EtOAc=0/100→15/85). Concentration of the appropriate fractions afforded crude product, which was crystallized from THF (1 mL) and EtOAc (5 mL) to obtain title compound (47 mg, 43%) as a colorless solid.

$^1$H-NMR (DMSO-$d_6$, 300 MHz) δ 1.51-1.81 (2H, m), 2.00-2.19 (2H, m), 2.05 (3H, s), 2.65 (3H, s), 3.11-3.22 (1H, m), 3.30-3.40 (1H, m), 3.72-3.83 (1H, m), 3.95-4.07 (1H, m), 4.71-4.84 (1H, m), 6.78 (1H, dd, J=2.7, 7.6 Hz), 7.35-7.49 (3H, m), 7.87 (1H, d, J=2.7 Hz), 7.93-8.03 (2H, m), 8.54 (1H, br s), 8.65 (1H, d, J=7.6 Hz), 14.25 (1H, br s).

Example 96-B

Production of 2-[4-({2-methyl-3-[4-phenyl-5-(4H-1,2,4-triazol-3-yl)-1,3-thiazol-2-yl]pyrazolo[1,5-a]pyridin-5-yl}oxy)piperidin-1-yl]-2-oxoethanol

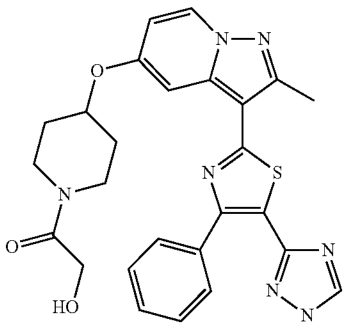 [SMILES: Cc1nn2ccc(OC3CCN(C(=O)CO)CC3)cc2c1-c1nc(-c2ccccc2)c(-c2nc[nH]n2)s1]

The title compound has been prepared according to the similar manner described in 85-B1 from 2-methyl-3-[4-phenyl-5-(1H-1,2,4-triazol-3-yl)-1,3-thiazol-2-yl]-5-(piperidin-4-yloxy)pyrazolo[1,5-a]pyridine (120 mg, 0.262 mmol) obtained 85-BO (iii) and acetoxyacetyl chloride (56.4 μL, 0.524 mmol). The pure title compound (62 mg, 46%) has been obtained as a colorless solid after silica gel column chromatographic purification (MeOH/EtOAc=0/100→15/85) followed by crystallization from EtOAc (5 mL) and THF (1 mL).

$^1$H-NMR (DMSO-$d_6$, 300 MHz) δ 1.57-1.82 (2H, m), 2.02-2.18 (2H, m), 2.66 (3H, s), 3.18-3.29 (2H, m), 3.60-3.75 (1H, m), 3.93-4.06 (1H, m), 4.14 (2H, d, J=5.4 Hz), 4.57 (1H, t, J=5.4 Hz), 4.73-4.84 (1H, m), 6.78 (1H, dd, J=7.6, 2.7 Hz), 7.35-7.48 (3H, m), 7.87 (1H, d, J=2.7 Hz), 7.91-8.01 (2H, m), 8.56 (1H, br s), 8.65 (1H, d, J=7.6 Hz), 14.25 (1H, br s).

Example 97-B

Production of 3-[4-(2,4-difluorophenyl)-5-(1H-1,2,4-triazol-3-yl)-1,3-thiazol-2-yl]-2-methylpyrazolo[1,5-a]pyridine

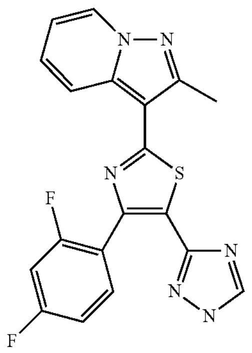 [SMILES: Cc1nn2ccccc2c1-c1nc(-c2ccc(F)cc2F)c(-c2nc[nH]n2)s1]

(i) Production of methyl 4-(2,4-difluorophenyl)-2-(2-methylpyrazolo[1,5-a]pyridin-3-yl)-1,3-thiazole-5-carboxylate To a suspension of methyl 2-(2-methylpyrazolo[1,5-a]pyridin-3-yl)-4-{[(trifluoromethyl)sulfonyl]oxy}-1,3-thiazole-5-carboxylate (100 mg, 0.237 mmol) obtained in Example 13-B (ii), 2,4-difluorophenylboronic acid (56.2 mg, 0.356 mmol), and cesium carbonate (154 mg, 0.474 mmol) in DME (5 mL) and water (1 mL) under argon atmosphere was added [1,1'-Bis(diphenylphosphino)ferrocene] palladium(II) dichloride complex with dichloromethane (1:1) (19.4 mg, 0.0237 mmol) and the mixture was stirred for 80° C. To the mixture were added EtOAc (20 mL) and saturated aqueous solution of sodium bicarbonate (15 mL) and then organic layer was separated. The aqueous layer was extracted with EtOAc (5 mL) and the combined organic layer was washed with brine (5 mL). The organic layer was separated and then filtered through silica gel pad (3 g). After the concentration of the filtrate, the residue was washed with EtOAc (2 mL) to obtain title compound (79 mg, 87%) as a colorless solid.

$^1$H-NMR (DMSO-$d_6$, 300 MHz) δ 2.71 (3H, s), 3.77 (3H, s), 7.13 (1H, dt, J=1.2, 6.9 Hz), 7.25 (1H, ddt, J=0.8, 2.5, 8.5 Hz), 7.40 (1H, ddd, J=2.5, 9.5, 10.5 Hz), 7.59 (1H, ddd, J=1.2, 6.9, 8.8 Hz), 7.77 (1H, td, J=6.7, 8.5 Hz), 8.32 (1H, td, J=1.2, 8.8 Hz), 8.82 (1H, td, J=1.2, 6.9 Hz).

(ii) Production of 4-(2,4-difluorophenyl)-2-(2-methylpyrazolo[1,5-a]pyridin-3-yl)-1,3-thiazole-5-carboxylic acid To a suspension of methyl 4-(2,4-difluorophenyl)-2-(2-methylpyrazolo[1,5-a]pyridin-3-yl)-1,3-thiazole-5-carboxylate (250 mg, 0.649 mmol) obtained above in THF (5 mL) and MeOH (5 mL), was added 2N aqueous solution of sodium hydroxide (1 mL) and the mixture was stirred for 2 h at 60° C. To the mixture, was added a 2:1 mixture of EtOAc and THF (60 mL) and 1N hydrochloric acid. The organic layer was separated and the aqueous layer was extracted with a 2:1 mixture of EtOAc and THF (10 mL). The combined organic layers were washed with brine (5 mL) and then dried over anhydrous sodium sulfate. Insoluble materials were removed by filtration and the filtrate was concentrated under reduced pressure to obtain title compound (225 mg, 93%) as a pale yellow solid.

$^1$H-NMR (DMSO-$d_6$, 300 MHz) δ 2.70 (3H, s), 7.11 (1H, dt, J=1.2, 6.9 Hz), 7.17-7.27 (1H, m), 7.37 (1H, dt, J=2.5, 10.0 Hz), 7.56 (1H, ddd, J=1.0, 6.9, 8.8 Hz), 7.68-7.78 (1H, m), 8.30 (1H, td, J=1.2, 8.8 Hz), 8.80 (1H, ddd, J=1.0, 1.2, 6.9 Hz), 13.28 (1H, br s).

(iii) Production of 4-(2,4-difluorophenyl)-2-(2-methylpyrazolo[1,5-a]pyridin-3-yl)-1,3-thiazole-5-carboxamide To a stirred suspension of 4-(2,4-difluorophenyl)-2-(2-methylpyrazolo[1,5-a]pyridin-3-yl)-1,3-thiazole-5-carboxylic acid (220 mg, 0.592 mmol) obtained above, ammonium chloride (126 mg, 2.37 mmol), EDCI (226 mg, 1.18 mmol) and HOBT (160 mg, 1.18 mmol) in DMF, (3 mL) was added TEA (329 μL, 2.37 mL) and the mixture was stirred for 3 h at rt. To the mixture were added a 1:1 mixture of THF and EtOAc (20 mL) and saturated aqueous solution of sodium bicarbonate (15 mL). The organic layer was separated and then washed with brine (5 mL). The organic layer was dried over anhydrous sodium sulfate and insoluble materials were removed by filtration. Concentration of the filtrate afforded pale yellow solid of title compound (182 mg, 76%) as adduct of 0.5 equivalent of DMF.

$^1$H-NMR (DMSO-$d_6$, 300 MHz) δ 2.70 (3H, s), 7.09 (1H, dt, J=1.4, 6.9 Hz), 7.18-7.27 (1H, m), 7.35 (1H, ddd, J=2.7, 9.6, 10.5 Hz), 7.55 (2H, br s), 7.55 (1H, ddd, J=1.0, 6.9, 8.9 Hz), 7.77 (1H, dt, J=6.7, 8.5 Hz), 8.29 (1H, ddd, J=1.0, 1.4, 8.9 Hz), 8.78 (1H, td, J=1.0, 6.9 Hz).

(iv) Production of 3-[4-(2,4-difluorophenyl)-5-(1H-1,2,4-triazol-3-yl)-1,3-thiazol-2-yl]-2-methylpyrazolo[1,5-a]pyridine A suspension of 4-(2,4-difluorophenyl)-2-(2-methylpyrazolo[1,5-a]pyridin-3-yl)-1,3-thiazole-5-carboxamide (180 mg, 0.442 mmol, 0.5 equiv DMF adduct) obtained above in 1,1-Dimethoxy-N,N-dimethylmethanamine (3 mL) was stirred for 1 h at 100° C. and then the mixture was concentrated under reduced pressure. The residue was dissolved in AcOH (3 mL) and then was added hydrazine monohydrate (108 μL, 2.21 mmol). The resulting mixture was stirred for 1 h at 100° C. and then concentrated under reduced pressure. To the residue, were added a 1:1 mixture of EtOAc and THF (20 mL) and saturated aqueous solution of sodium bicarbonate (15 mL) and then the organic layer was separated, which was washed with brine (5 mL) and dried over anhydrous sodium sulfate. Insoluble materials were removed by filtration and the filtrate was concentrated under reduced pressure. The residue was crystallized from THF (3 mL) and hexane (6 mL) to obtain title compound (147 mg, 84%) as a yellow solid.

$^1$H-NMR (DMSO-$d_6$, 300 MHz) δ 2.72 (3H, s), 7.08 (1H, dt, J=1.4, 6.9 Hz), 7.15-7.25 (1H, m), 7.31 (1H, ddd, J=2.4, 9.7, 10.3 Hz), 7.52 (1H, ddd, J=1.0, 6.9, 8.8 Hz), 7.75 (1H, dt, J=6.7, 8.5 Hz), 8.30 (1H, ddd, J=1.0, 1.4, 8.8 Hz), 8.52 (1H, br s), 8.77 (1H, td, J=1.0, 6.9 Hz), 14.15 (1H, br s).

Example 98-B

Production of 3-[4-(2,3-difluorophenyl)-5-(1H-1,2,4-triazol-3-yl)-1,3-thiazol-2-yl]-2-methylpyrazolo[1,5-a]pyridine

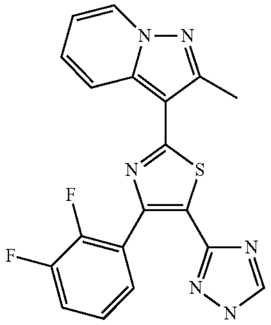 [SMILES: Cc1nn2ccccc2c1-c1nc(-c2cccc(F)c2F)c(-c2nc[nH]n2)s1]

(i) Production of 4-(2,3-difluorophenyl)-2-(2-methylpyrazolo[1,5-a]pyridin-3-yl)-1,3-thiazole-5-carboxylic acid According to the similar manner described in Example 97-B (i) and (ii), the title compound (193 mg, 93%) has been obtained as a colorless solid by the Suzuki coupling reaction using methyl 2-(2-methylpyrazolo[1,5-a]pyridin-3-yl)-4-[(trifluoromethyl)sulfonyl]oxy-1,3-thiazole-5-carboxylate (236 mg, 0.561 mmol) obtained in Example 13-B (ii) and 2,3-Difluorobenzeneboronic acid (133 mg, 0.842 mmol) followed by standard ester hydrolysis procedure.

$^1$H-NMR (DMSO-$d_6$, 300 MHz) δ 2.70 (3H, s), 7.11 (1H, dt, J=1.2, 6.9 Hz), 7.33 (1H, m), 7.45-7.62 (3H, m), 8.30 (1H, td, J=1.2, 8.8 Hz), 8.80 (1H, td, J=1.2, 6.9 Hz), 13.40 (1H, br s).

(ii) Production of 4-(2,3-difluorophenyl)-2-(2-methylpyrazolo[1,5-a]pyridin-3-yl)-1,3-thiazole-5-carboxamide According to the similar manner described in Example 97-B (iii), the title compound (134 mg, 70%) has been obtained as a pale yellow solid using 4-(2,3-difluorophenyl)-2-(2-methylpyrazolo[1,5-a]pyridin-3-yl)-1,3-thiazole-5-carboxylic acid (191 mg, 0.514 mmol) obtained above.

$^1$H-NMR (DMSO-$d_6$, 300 MHz) δ 2.70 (3H, s), 7.10 (1H, dt, J=1.2, 6.9 Hz), 7.28-7.39 (1H, m), 7.46-7.75 (5H, m), 8.29 (1H, td, J=1.2, 8.8 Hz), 8.79 (1H, td, J=1.2, 6.9 Hz).

(iii) Production of 3-[4-(2,3-difluorophenyl)-5-(1H-1,2,4-triazol-3-yl)-1,3-thiazol-2-yl]-2-methylpyrazolo[1,5-a]pyridine According to the similar manner described in Example 97-B (iv), the title compound (96 mg, 69%) has been obtained as a pale yellow solid using 4-(2,3-difluorophenyl)-2-(2-methylpyrazolo[1,5-a]pyridin-3-yl)-1,3-thiazole-5-carboxamide (130 mg, 0.351 mmol) obtained above.

$^1$H-NMR (DMSO-$d_6$, 300 MHz) δ 2.73 (3H, s), 7.08 (1H, dt, J=1.2, 6.8 Hz), 7.27-7.39 (1H, m), 7.45-7.59 (3H, m), 8.31 (1H, td, J=1.2, 8.9 Hz), 8.56 (1H, s), 8.78 (1H, td, J=1.2, 6.8 Hz), 14.21 (1H, br s).

Example 99-B

Production of 3-[4-(2,4-dimethoxyphenyl)-5-(1H-1,2,4-triazol-3-yl)-1,3-thiazol-2-yl]-2-methylpyrazolo[1,5-a]pyridine

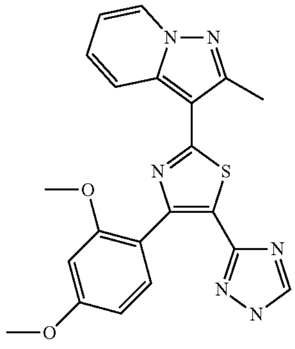 [SMILES: COc1ccc(-c2nc(-c3c(C)nn4ccccc34)sc2-c2nc[nH]n2)c(OC)c1]

(i) Production of 4-(2,4-dimethoxyphenyl)-2-(2-methylpyrazolo[1,5-a]pyridin-3-yl)-1,3-thiazole-5-carboxylic acid According to the similar manner described in Example 97-B (i) and (ii), the title compound (205 mg, 92%) has been obtained as a colorless solid by the Suzuki coupling reaction using methyl 2-(2-methylpyrazolo[1,5-a]pyridin-3-yl)-4-{

[(trifluoromethyl)sulfonyl]oxy}-1,3-thiazole-5-carboxylate (236 mg, 0.561 mmol) obtained in Example 13-B (ii) and 2,4-Dimethoxybenzeneboronic acid (153 mg, 0.842 mmol) followed by standard ester hydrolysis procedure.

$^1$H-NMR (DMSO-$d_6$, 300 MHz) δ 2.68 (3H, s), 3.73 (3H, s), 3.84 (3H, s), 6.58-6.68 (2H, m), 7.08 (1H, dt, J=1.2, 7.0 Hz), 7.39 (1H, d, J=8.3 Hz), 7.53 (1H, ddd, J=1.2, 7.0, 8.7 Hz), 8.29 (1H, td, J=1.2, 8.7 Hz), 8.77 (1H, d, J=7.0 Hz), 12.77 (1H, br s).

(ii) Production of 3-[4-(2,4-dimethoxyphenyl)-5-(1H-1,2,4-triazol-3-yl)-1,3-thiazol-2-yl]-2-methylpyrazolo[1,5-a]pyridine According to the similar manner described in Example 97-B (iii) and (iv), the title compound (131 mg, 61%) has been obtained as a pale yellow solid using 4-(2,4-dimethoxyphenyl)-2-(2-methylpyrazolo[1,5-a]pyridin-3-yl)-1,3-thiazole-5-carboxylic acid obtained above.

The pure title compound has been obtained by the crystallization of crude compound from THF (8 mL) and hexane (4 mL).

$^1$H-NMR (DMSO-$d_6$, 300 MHz) δ 2.71 (3H, s), 3.50 (3H, s), 3.83 (3H, s), 6.58-6.66 (2H, m), 7.05 (1H, dt, J=1.2, 6.8 Hz), 7.43 (1H, d, J=8.1 Hz), 7.49 (1H, ddd, J=1.2, 6.8, 8.9 Hz), 8.29 (1H, td, J=1.2, 8.9 Hz), 8.43 (1H, br s), 8.75 (1H, td, J=1.2, 6.8 Hz), 13.98 (1H, br s).

Example 100-B

Production of 3-[4-(2-fluoro-6-methoxyphenyl)-5-(1H-1,2,4-triazol-3-yl)-1,3-thiazol-2-yl]-2-methylpyrazolo[1,5-a]pyridine

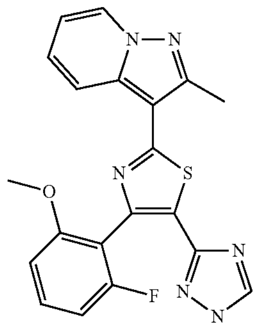 [SMILES: COc1cccc(F)c1-c1nc(-c2c(C)nn3ccccc23)sc1-c1nc[nH]n1]

(i) Production of methyl 4-(2-fluoro-6-methoxyphenyl)-2-(2-methylpyrazolo[1,5-a]pyridin-3-yl)-1,3-thiazole-5-carboxylate According to the similar manner described in Example 97-B (i), the title compound (86 mg, 93%) has been obtained as a yellow solid by the Suzuki coupling reaction using methyl 2-(2-methylpyrazolo[1,5-a]pyridin-3-yl)-4-{[(trifluoromethyl)sulfonyl]oxy}-1,3-thiazole-5-carboxylate (97.3 mg, 0.231 mmol) obtained in Example 13-B (ii) and (2-fluoro-6-methoxyphenyl)boronic acid (78.5 mg, 0.462 mmol. The pure title compound has been obtained by the basic silica gel column chromatographic purification (EtOAc/hexane=0/100→30/70).

$^1$H-NMR (DMSO-$d_6$, 300 MHz) δ 2.70 (3H, s), 3.72 (3H, s), 3.76 (3H, s), 6.85-7.04 (2H, m), 7.11 (1H, dt, J=1.2, 6.9 Hz), 7.43-7.60 (2H, m), 8.25 (1H, td, J=1.2, 8.9 Hz), 8.80 (1H, td, J=1.2, 6.9 Hz).

(ii) Production of 4-(2-fluoro-6-methoxyphenyl)-2-(2-methylpyrazolo[1,5-a]pyridin-3-yl)-1,3-thiazole-5-carboxylic acid According to the similar manner described in Example 97-B (ii), the title compound (129 mg, 83%) has been obtained as a pale blue solid by standard ester hydrolysis reaction using methyl 4-(2-fluoro-6-methoxyphenyl)-2-(2-methylpyrazolo[1,5-a]pyridin-3-yl)-1,3-thiazole-5-carboxylate (161 mg, 0.405 mmol) obtained above. The pure title compound has been obtained by washing of crude compound with EtOAc (5 mL).

$^1$H-NMR (DMSO-$d_6$, 300 MHz) δ 2.69 (3H, s), 3.76 (3H, s), 6.87-7.01 (2H, m), 7.09 (1H, dt, J=1.1, 6.9 Hz), 7.46 (1H, dt, J=7.0, 8.4 Hz), 7.53 (1H, ddd, J=1.1, 6.9, 8.9 Hz), 8.24 (1H, td, J=1.1, 8.9 Hz), 8.78 (1H, td, J=1.1, 6.8 Hz), 13.05 (1H, br s).

(iii) Production of 4-(2-fluoro-6-methoxyphenyl)-2-(2-methylpyrazolo[1,5-a]pyridin-3-yl)-1,3-thiazole-5-carboxamide According to the similar manner described in Example 97-B (iii), the title compound (93 mg, 73%) has been obtained as a pale orange solid by the standard amidation reaction using 4-(2-fluoro-6-methoxyphenyl)-2-(2-methylpyrazolo[1,5-a]pyridin-3-yl)-1,3-thiazole-5-carboxylic acid (128 mg, 0.334 mmol) obtained above. The pure title compound has been obtained by washing of crude compound with diethyl ether (5 mL).

$^1$H-NMR (DMSO-$d_6$, 300 MHz) δ 2.69 (3H, s), 3.77 (3H, s), 6.88-7.03 (3H, m), 7.07 (1H, dt, J=1.2, 6.9 Hz), 7.42-7.57 (3H, m), 8.21 (1H, td, J=1.2, 8.9 Hz), 8.77 (1H, td, J=1.2, 6.9 Hz).

(iv) Production of 3-[4-(2-fluoro-6-methoxyphenyl)-5-(1H-1,2,4-triazol-3-yl)-1,3-thiazol-2-yl]-2-methylpyrazolo[1,5-a]pyridine According to the similar manner described in Example 97-B (iv), the title compound (65 mg, 67%) has been obtained as a yellow solid using 4-(2-fluoro-6-methoxyphenyl)-2-(2-methylpyrazolo[1,5-a]pyridin-3-yl)-1,3-thiazole-5-carboxamide (91 mg, 0.238 mmol) obtained above. The pure title compound has been obtained by crystallization of the crude compound from THF (9 mL) and hexane (6 mL).

$^1$H-NMR (DMSO-$d_6$, 300 MHz) δ 2.71 (3H, s), 3.66 (3H, s), 6.83-6.99 (2H, m), 7.06 (1H, dt, J=1.2, 6.8 Hz), 7.38-7.55 (2H, m), 8.24 (1H, td, J=1.2, 8.8 Hz), 8.48 (1H, br s), 8.76 (1H, td, J=1.2, 6.8 Hz), 14.08 (1H, br s).

Example 101-B

Production of 3-[4-(2,6-dimethylphenyl)-5-(1H-1,2,4-triazol-3-yl)-1,3-thiazol-2-yl]-2-methylpyrazolo[1,5-a]pyridine

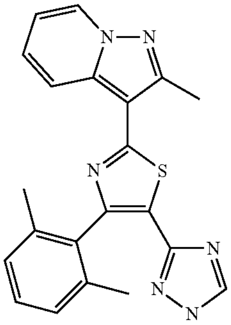 [SMILES: Cc1cccc(C)c1-c1nc(-c2c(C)nn3ccccc23)sc1-c1nc[nH]n1]

(i) Production of methyl 4-(2,6-dimethylphenyl)-2-(2-methylpyrazolo[1,5-a]pyridin-3-yl)-1,3-thiazole-5-carboxylate According to the similar manner described in Example 97-B (i), the title compound has been obtained as a yellow solid by the Suzuki coupling reaction using methyl 2-(2-methylpyrazolo[1,5-a]pyridin-3-yl)-4-{[(trifluoromethyl)sulfonyl]oxy}-1,3-thiazole-5-carboxylate (189 mg, 0.449 mmol) obtained in Example 13-B (ii) and 2,6-dimethylphenylboronic acid (135 mg, 0.898 mmol. The crude compound has been used in the next step without further purification.

$^1$H-NMR (DMSO-$d_6$, 300 MHz) δ 2.03 (6H, s), 2.70 (3H, s), 3.69 (3H, s), 7.10 (1H, td, J=1.3, 6.9 Hz), 7.12-7.16 (2H, m), 7.24 (1H, dd, J=6.6, 8.4 Hz), 7.54 (1H, ddd, J=1.3, 6.9, 8.8 Hz), 8.24 (1H, td, J=1.3, 8.8 Hz), 8.80 (1H, td, J=1.3, 6.9 Hz).

(ii) Production of 4-(2,6-dimethylphenyl)-2-(2-methylpyrazolo[1,5-a]pyridin-3-yl)-1,3-thiazole-5-carboxamide According to the similar manner described in Example 97-B (ii) and (iii), the title compound (64 mg, 71%) has been obtained as a brown solid by the standard ester hydrolysis reaction followed by amidation reaction using methyl 4-(2,6-dimethylphenyl)-2-(2-methylpyrazolo[1,5-a]pyridin-3-yl)-1,3-thiazole-5-carboxylate obtained above.

$^1$H-NMR (DMSO-$d_6$, 300 MHz) δ 2.09 (6H, s), 2.69 (3H, s), 5.88 (1H, br s), 7.08 (1H, dt, J=1.2, 6.9 Hz), 7.19-7.27 (2H, m), 7.32 (1H, dd, J=6.3, 8.4 Hz), 7.51 (1H, br s), 7.51 (1H, ddd, J=1.2, 6.9, 8.9 Hz), 8.22 (1H, td, J=1.2, 8.9 Hz), 8.78 (1H, td, J=1.2, 6.9 Hz).

(iii) Production of 3-[4-(2,6-dimethylphenyl)-5-(1H-1,2,4-triazol-3-yl)-1,3-thiazol-2-yl]-2-methylpyrazolo[1,5-a]pyridine According to the similar manner described in Example 97-B (iv), the title compound (58 mg, 88%) has been obtained as a yellow solid using 4-(2,6-dimethylphenyl)-2-(2-methylpyrazolo[1,5-a]pyridin-3-yl)-1,3-thiazole-5-carboxamide (62.0 mg, 0.171 mmol) obtained above. The pure compound has been obtained by crystallization from acetone and hexane.

$^1$H-NMR (DMSO-$d_6$, 300 MHz) δ 2.02 (6H, s), 2.72 (3H, s), 7.06 (1H, dt, J=1.2, 6.8 Hz), 7.08-7.15 (2H, m), 7.21 (1H, dd, J=6.1, 8.3 Hz), 7.44-7.54 (1H, m), 8.24 (1H, td, J=1.2, 8.8 Hz), 8.51 (1H, br s), 8.76 (1H, td, J=1.2, 6.8 Hz), 14.05 (1H, br s).

Example 102-B

Production of 3-[4-(2,6-dimethoxyphenyl)-5-(1H-1,2,4-triazol-3-yl)-1,3-thiazol-2-yl]-2-methylpyrazolo[1,5-a]pyridine

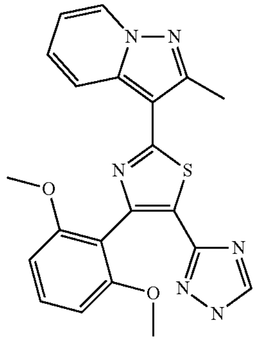 [SMILES: COc1cccc(OC)c1-c1nc(-c2c(C)nn3ccccc23)sc1-c1nc[nH]n1]

(i) Production of methyl 4-(2,6-dimethoxyphenyl)-2-(2-methylpyrazolo[1,5-a]pyridin-3-yl)-1,3-thiazole-5-carboxylate According to the similar manner described in Example 97-B (i), the title compound (174 mg, 89%) has been obtained as a gray solid by the Suzuki coupling reaction using methyl 2-(2-methylpyrazolo[1,5-a]pyridin-3-yl)-4-{[(trifluoromethyl)sulfonyl]oxy}-1,3-thiazole-5-carboxylate (200 mg, 0.475 mmol) obtained in Example 13-B (ii) and 2,6-dimethoxyphenylboronic acid (173 mg, 0.949 mmol. The pure compound has been obtained by washing of crude product with EtOAc (5 mL).

$^1$H-NMR (DMSO-$d_6$, 300 MHz) δ 2.69 (3H, s), 3.67 (3H, s), 3.68 (6H, s), 6.76 (2H, d, J=8.5 Hz), 7.09 (1H, dt, J=1.2, 6.9 Hz), 7.39 (1H, t, J=8.5 Hz), 7.53 (1H, ddd, J=1.2, 6.9, 8.9 Hz), 8.24 (1H, td, J=1.2, 8.9 Hz), 8.78 (1H, td, J=1.2, 6.9 Hz)

(ii) Production of 4-(2,6-dimethoxyphenyl)-2-(2-methylpyrazolo[1,5-a]pyridin-3-yl)-1,3-thiazole-5-carboxylic acid According to the similar manner described in Example 97-B (ii), the title compound (144 mg, 87%) has been obtained as a pale yellow solid by standard ester hydrolysis reaction using methyl 4-(2,6-dimethoxyphenyl)-2-(2-methylpyrazolo[1,5-a]pyridin-3-yl)-1,3-thiazole-5-carboxylate (172 mg, 0.420 mmol) obtained above. The pure compound has been obtained by washing of crude product with EtOAc (5 mL).

$^1$H-NMR (DMSO-$d_6$, 300 MHz) δ 2.68 (3H, s), 3.68 (6H, s), 6.74 (2H, d, J=8.5 Hz), 7.07 (1H, dt, J=1.2, 6.9 Hz), 7.36 (1H, t, J=8.5 Hz), 7.50 (1H, ddd, J=1.2, 6.9, 8.9 Hz), 8.22 (1H, td, J=1.2, 8.9 Hz), 8.76 (1H, td, J=1.2, 6.9 Hz), 12.76 (1H, br s).

(iii) Production of 4-(2,6-dimethoxyphenyl)-2-(2-methylpyrazolo[1,5-a]pyridin-3-yl)-1,3-thiazole-5-carboxamide According to the similar manner described in Example 97-B (iii), the title compound (113 mg, 80%) has been obtained as a pale yellow solid by standard amidation reaction using 4-(2,6-dimethoxyphenyl)-2-(2-methylpyrazolo[1,5-a]pyridin-3-yl)-1,3-thiazole-5-carboxylic acid (142 mg, 0.359 mmol) obtained above. The pure compound has been obtained by washing of crude product with EtOAc (5 mL).

$^1$H-NMR (DMSO-d$_6$, 300 MHz) δ 2.67 (3H, s), 3.73 (6H, s), 5.99 (1H, br s), 6.83 (2H, d, J=8.5 Hz), 7.06 (1H, dt, J=1.2, 6.9 Hz), 7.31-7.58 (3H, m), 8.20 (1H, dt, J=1.2, 8.8 Hz), 8.76 (1H, td, J=1.2, 6.9 Hz).

(iv) Production of 3-[4-(2,6-dimethoxyphenyl)-5-(1H-1,2,4-triazol-3-yl)-1,3-thiazol-2-yl]-2-methylpyrazolo[1,5-a]pyridine According to the similar manner described in Example 97-B (iv), the title compound (87 mg, 74%) has been obtained as a yellow solid using 4-(2,6-dimethoxyphenyl)-2-(2-methylpyrazolo[1,5-a]pyridin-3-yl)-1,3-thiazole-5-carboxamide (111 mg, 0.281 mmol) obtained above. The pure compound has been obtained by washing of crude product with EtOAc (5 mL).

$^1$H-NMR (DMSO-d$_6$, 300 MHz) δ 2.71 (3H, s), 3.60 (6H, s), 6.73 (2H, d, J=8.4 Hz), 7.04 (1H, dt, J=1.1, 6.8 Hz), 7.35 (1H, t, J=8.4 Hz), 7.47 (1H, ddd, J=1.1, 6.8, 8.9 Hz), 8.23 (1H, td, J=1.1, 8.9 Hz), 8.42 (1H, br s), 8.74 (1H, td, J=1.1, 6.8 Hz), 13.94 (1H, br s).

Example 103-B

Production of 3-[4-(2-chloro-6-methoxyphenyl)-5-(1H-1,2,4-triazol-3-yl)-1,3-thiazol-2-yl]-2-methylpyrazolo[1,5-a]pyridine

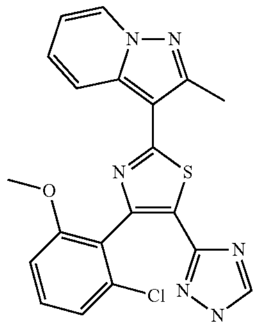 [SMILES: COc1cccc(Cl)c1-c1nc(-c2c(C)nn3ccccc23)sc1-c1nc[nH]n1]

(i) production of methyl 4-(2-chloro-6-methoxyphenyl)-2-(2-methylpyrazolo[1,5-a]pyridin-3-yl)-1,3-thiazole-5-carboxylate According to the similar manner described in Example 97-B (i), the title compound (226 mg, 76%) has been obtained as a pale yellow solid by the Suzuki coupling reaction using methyl 2-(2-methylpyrazolo[1,5-a]pyridin-3-yl)-4-{[(trifluoromethyl)sulfonyl]oxy}-1,3-thiazole-5-carboxylate (300 mg, 0.712 mmol) obtained in Example 13-B (ii) and 2-Chloro-6-methoxyphenylboronic acid (265 mg, 1.42 mmol. The pure compound has been obtained by basic silicagel column chromatographic purification (EtOAc/hexane=10/90→40/60).

$^1$H-NMR (DMSO-d$_6$, 300 MHz) δ 2.70 (3H, s), 3.70 (3H, s), 3.72 (3H, s), 7.06-7.22 (3H, m), 7.47 (1H, t, J=8.1 Hz), 7.55 (1H, ddd, J=1.2, 6.9, 8.9 Hz), 8.25 (1H, td, J=1.2, 8.9 Hz), 8.80 (1H, td, J=1.2, 6.9 Hz).

(ii) Production of 4-(2-chloro-6-methoxyphenyl)-2-(2-methylpyrazolo[1,5-a]pyridin-3-yl)-1,3-thiazole-5-carboxylic acid According to the similar manner described in Example 97-B (ii), the title compound has been obtained as a pale yellow solid by standard ester hydrolysis reaction using methyl 4-(2-chloro-6-methoxyphenyl)-2-(2-methylpyrazolo[1,5-a]pyridin-3-yl)-1,3-thiazole-5-carboxylate (172 mg, 0.420 mmol) obtained above. The crude product has been used in the next step.

$^1$H-NMR (DMSO-d$_6$, 300 MHz) δ 2.69 (3H, s), 3.73 (3H, s), 7.05-7.20 (3H, m), 7.44 (1H, t, J=8.2 Hz), 7.53 (1H, ddd, J=1.1, 6.9, 8.9 Hz), 8.24 (1H, td, J=1.1, 8.9 Hz), 8.79 (1H, td, J=1.1, 6.9 Hz), 12.97 (1H, br s).

(iii) Production of 4-(2-chloro-6-methoxyphenyl)-2-(2-methylpyrazolo[1,5-a]pyridin-3-yl)-1,3-thiazole-5-carboxamide According to the similar manner described in Example 97-B (iii), the title compound (147 mg, 69%) has been obtained as a colorless solid by standard amidation reaction using 4-(2-chloro-6-methoxyphenyl)-2-(2-methylpyrazolo[1,5-a]pyridin-3-yl)-1,3-thiazole-5-carboxylic acid obtained above. The pure compound has been obtained by washing of crude product with a 1:1 mixture of EtOAc and diethyl ether (10 mL).

$^1$H-NMR (DMSO-d$_6$, 300 MHz) δ 2.69 (3H, s), 3.75 (3H, s), 6.66 (1H, br s), 7.07 (1H, td, J=1.2, 6.9 Hz), 7.12-7.25 (2H, m), 7.30-7.61 (3H, m), 8.21 (1H, td, J=1.2, 8.9 Hz), 8.77 (1H, td, J=1.2, 6.8 Hz).

(iv) Production of 3-[4-(2-chloro-6-methoxyphenyl)-5-(1H-1,2,4-triazol-3-yl)-1,3-thiazol-2-yl]-2-methylpyrazolo[1,5-a]pyridine According to the similar manner described in Example 97-B (iv), the title compound (94 mg, 61%) has been obtained as a yellow solid using 4-(2-chloro-6-methoxyphenyl)-2-(2-methylpyrazolo[1,5-a]pyridin-3-yl)-1,3-thiazole-5-carboxamide (145 mg, 0.364 mmol) obtained above. The pure compound has been obtained by crystallization from EtOAc (5 mL) and THF (1 mL).

$^1$H-NMR (DMSO-d$_6$, 300 MHz) δ 2.72 (3H, s), 3.64 (3H, s), 7.01-7.18 (3H, m), 7.43 (1H, t, J=8.2 Hz), 7.49 (1H, ddd, J=1.1, 6.9, 8.9 Hz), 8.24 (1H, td, J=1.1, 8.9 Hz), 8.48 (1H, br s), 8.76 (1H, td, J=1.1, 6.9 Hz), 14.05 (1H, br s).

Example 104-B

Production of 3-[4-(2-chloro-6-fluorophenyl)-5-(1H-1,2,4-triazol-3-yl)-1,3-thiazol-2-yl]-2-methylpyrazolo[1,5-a]pyridine

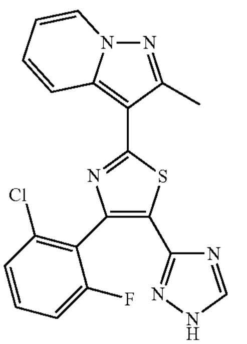 [SMILES: Cc1nn2ccccc2c1-c1nc(-c2c(F)cccc2Cl)c(-c2nc[nH]n2)s1]

(i) production of methyl 4-(2-chloro-6-fluorophenyl)-2-(2-methylpyrazolo[1,5-a]pyridin-3-yl)-1,3-thiazole-5-carboxylate According to the similar manner described in Example 97-B (i), the title compound (315 mg, 33%) has been obtained as a yellow solid by the Suzuki coupling reaction using methyl 2-(2-methylpyrazolo[1,5-a]pyridin-3-yl)-4-{[(trifluoromethyl)sulfonyl]oxy}-1,3-thiazole-5-carboxylate (1.00 g, 2.37 mmol) obtained in Example 13-B (ii) and 2-Chloro-6-fluorophenylboronic acid (828 mg, 4.75 mmol. The pure compound has been obtained by washing of crude product with EtOAc (5 mL).

$^1$H-NMR (DMSO-$d_6$, 300 MHz) δ 2.71 (3H, s), 3.75 (3H, s), 7.13 (1H, dt, J=1.2, 6.9 Hz), 7.39 (1H, dt, J=1.2, 8.9 Hz), 7.47-7.65 (3H, m), 8.27 (1H, td, J=1.2, 8.9 Hz), 8.82 (1H, td, J=1.2, 6.9 Hz).

(ii) Production of 4-(2-chloro-6-fluorophenyl)-2-(2-methylpyrazolo[1,5-a]pyridin-3-yl)-1,3-thiazole-5-carboxylic acid According to the similar manner described in Example 97-B (ii), the title compound (237 mg, 78%) has been obtained as a pale yellow solid by standard ester hydrolysis reaction using methyl 4-(2-chloro-6-fluorophenyl)-2-(2-methylpyrazolo[1,5-a]pyridin-3-yl)-1,3-thiazole-5-carboxylate (313 mg, 0.779 mmol) obtained above. The pure title compound has been obtained by washing of crude product with EtOAc (10 mL).

$^1$H-NMR (DMSO-$d_6$, 300 MHz) δ 2.70 (3H, s), 7.11 (1H, dt, J=1.2, 6.9 Hz), 7.32-7.42 (1H, m), 7.44-7.51 (1H, m), 7.51-7.62 (2H, m), 8.26 (1H, td, J=1.2, 8.9 Hz), 8.80 (1H, td, J=1.2, 6.9 Hz), 13.35 (1H, br s).

(iii) Production of 4-(2-chloro-6-fluorophenyl)-2-(2-methylpyrazolo[1,5-a]pyridin-3-yl)-1,3-thiazole-5-carboxamide According to the similar manner described in Example 97-B (iii), the title compound (124 mg, 53%) has been obtained as a brown solid by standard amidation reaction using 4-(2-chloro-6-fluorophenyl)-2-(2-methylpyrazolo[1,5-a]pyridin-3-yl)-1,3-thiazole-5-carboxylic acid (235 mg, 0.606 mmol) obtained above. The pure compound has been obtained by washing of crude product with EtOAc (3 mL).

$^1$H-NMR (DMSO-$d_6$, 300 MHz) δ 2.70 (3H, s), 7.09 (1H, dt, J=1.2, 6.9 Hz), 7.33 (1H, dt, J=1.2, 8.8 Hz); 7.40-7.62 (5H, m), 8.23 (1H, td, J=1.2, 8.8 Hz), 8.79 (1H, td, J=1.2, 6.9 Hz).

(iv) Production of 3-[4-(2-chloro-6-fluorophenyl)-5-(1H-1,2,4-triazol-3-yl)-1,3-thiazol-2-yl]-2-methylpyrazolo[1,5-a]pyridine According to the similar manner described in Example 97-B (iv), the title compound (92 mg, 71%) has been obtained as a pale yellow solid using 4-(2-chloro-6-fluorophenyl)-2-(2-methylpyrazolo[1,5-a]pyridin-3-yl)-1,3-thiazole-5-carboxamide (122 mg, 0.315 mmol) obtained above. The pure compound has been obtained by washing of crude compound with EtOAc (5 mL).

$^1$H-NMR (DMSO-$d_6$, 300 MHz) δ 2.73 (3H, s), 7.07 (1H, dt, J=1.2, 6.8 Hz), 7.34 (1H, dt, J=1.2, 8.8 Hz), 7.42-7.59 (3H, m), 8.26 (1H, td, J=1.2, 8.8 Hz), 8.53 (1H, br s), 8.77 (1H, td, J=1.2, 6.8 Hz), 14.17 (1H, br s).

Example 105-B

Production of 3-[4-(2,3-difluoro-6-methoxyphenyl)-5-(1H-1,2,4-triazol-3-yl)-1,3-thiazol-2-yl]-2-methylpyrazolo[1,5-a]pyridine

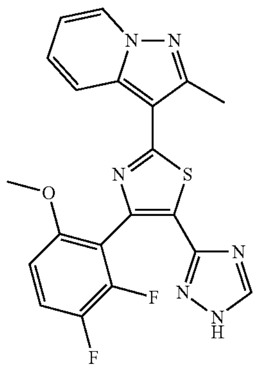 [SMILES: COc1ccc(F)c(F)c1-c1nc(-c2c(C)nn3ccccc23)sc1-c1nc[nH]n1]

(i) Production of 4-(2,3-difluoro-6-methoxyphenyl)-2-(2-methylpyrazolo[1,5-a]pyridin-3-yl)-1,3-thiazole-5-carboxylic acid According to the similar manner described in Example 97-B (i) and (ii), the title compound (237 mg, 78%) has been obtained as a brown solid by the Suzuki coupling reaction followed by standard ester hydrolysis reaction using methyl 2-(2-methylpyrazolo[1,5-a]pyridin-3-yl)-4-{[(trifluoromethyl)sulfonyl]oxy}-1,3-thiazole-5-carboxylate (339 mg, 0.805 mmol) obtained in Example 13-B (ii) and 2,3-difluoro-6-methoxyphenylboronic acid (303 mg, 1.61 mmol). The pure title compound has been obtained by washing with EtOAc (10 mL).

$^1$H-NMR (DMSO-$d_6$, 300 MHz) δ 2.69 (3H, s), 3.75 (3H, s), 6.96 (1H, ddd, J=2.1, 3.7, 9.3 Hz), 7.10 (1H, dt, J=1.2, 6.9

Hz), 7.43-7.63 (2H, m), 8.24 (1H, td, J=1.2, 8.9 Hz), 8.79 (1H, td, J=1.2, 6.9 Hz), 13.21 (1H, br s).

(ii) Production of 4-(2,3-difluoro-6-methoxyphenyl)-2-(2-methylpyrazolo[1,5-a]pyridin-3-yl)-1,3-thiazole-5-carboxamide According to the similar manner described in Example 97-B (iii), the title compound (102 mg, 59%) has been obtained as a brown solid by standard amidation reaction using 4-(2,3-difluoro-6-methoxyphenyl)-2-(2-methylpyrazolo[1,5-a]pyridin-3-yl)-1,3-thiazole-5-carboxylic acid (173 mg, 0.431 mmol) obtained above. The pure compound has been obtained by washing of crude product with EtOAc (5 mL)

$^1$H-NMR (DMSO-$d_6$, 300 MHz) δ 2.69 (3H, s), 3.74 (3H, s), 6.95 (1H, ddd, J=2.0, 3.8, 9.3 Hz), 7.08 (1H, dt, J=1.2, 6.9 Hz), 7.37 (2H, br s), 7.44-7.58 (2H, m), 8.22 (1H, td, J=1.2, 8.8 Hz), 8.78 (1H, td, J=1.2, 6.9 Hz).

(iii) Production of 3-[4-(2,3-difluoro-6-methoxyphenyl)-5-(1H-1,2,4-triazol-3-yl)-1,3-thiazol-2-yl]-2-methylpyrazolo[1,5-a]pyridine According to the similar manner described in Example 97-B (iv), the title compound (58 mg, 55%) has been obtained as a yellow solid using 4-(2,3-difluoro-6-methoxyphenyl)-2-(2-methylpyrazolo[1,5-a]pyridin-3-yl)-1,3-thiazole-5-carboxamide (100 mg, 0.250 mmol) obtained above. The pure compound has been obtained by crystallization from EtOAc (1 mL) and diethyl ether (1 mL).

$^1$H-NMR (DMSO-$d_6$, 300 MHz) δ 2.72 (3H, s), 3.65 (3H, s), 6.94 (1H, ddd, J=1.8, 3.7, 9.4 Hz), 7.07 (1H, dt, J=1.2, 6.9 Hz), 7.42-7.56 (2H, m), 8.25 (1H, d, J=8.9 Hz), 8.55 (1H, s), 8.77 (1H, d, J=6.9 Hz), 14.14 (1H, s).

Example 106-B

Production of 3-[4-(2-fluoro-6-methoxyphenyl)-5-(1H-1,2,4-triazol-3-yl)-1,3-thiazol-2-yl]-2-methyl-5-(2-morpholin-4-ylethoxy)pyrazolo[1,5-a]pyridine

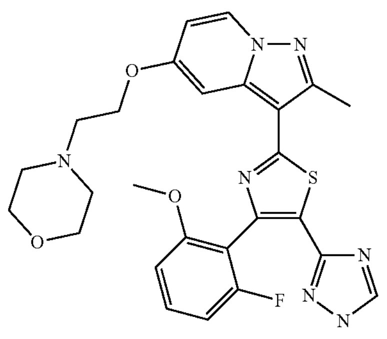 [SMILES: COc1cccc(F)c1-c1nc(-c2c(C)nn3ccc(OCCN4CCOCC4)cc23)sc1-c1nc[nH]n1]

(i) Production of methyl 2-[5-(benzyloxy)-2-methylpyrazolo[1,5-a]pyridin-3-yl]-4-{[(trifluoromethyl)sulfonyl]oxy}-1,3-thiazole-5-carboxylate To a suspension of 5-(benzyloxy)-2-methylpyrazolo[1,5-a]pyridine-3-carbothioamide hydrochloride (3.45 g, 10.3 mmol) in DMF (100 mL), was added 94% dimethyl chloromalonate (2.79 mL, 20.6 mmol) and the mixture was stirred for 7.5 h at 100° C. The reaction mixture was allowed to cool to 50° C. and then was dropwise added water (100 mL). The resulting precipitate was collected by filtration and then washed with EtOH (20 mL) and diethyl ether (20 mL) to obtain methyl 2-[5-(benzyloxy)-2-methylpyrazolo[1,5-a]pyridin-3-yl]-4-hydroxy-1,3-thiazole-5-carboxylate as a orange solid, which was used in the next step without further purification. $^1$H-NMR (DMSO-$d_6$, 300 MHz) 2.59 (3H, s), 3.75 (3H, s), 5.27 (2H, s), 6.87 (1H, dd, J=2.6, 7.6 Hz), 7.32-7.51 (3H, m), 7.52-7.64 (2H, m), 7.88 (1H, d, J=2.6 Hz), 8.67 (1H, d, J=7.6 Hz), 11.79 (1H, br s).

To a suspension of methyl 2-[5-(benzyloxy)-2-methylpyrazolo[1,5-a]pyridin-3-yl]-4-hydroxy-1,3-thiazole-5-carboxylate obtained above in pyridine (100 mL), was added Trifluoromethanesulfonic anhydride (3.46 mL, 20.6 mmol) and the mixture was stirred for 3 h at 50° C. The mixture was concentrated under reduced pressure until half volume and then were added a 2:1 mixture of EtOAc and THF (150 mL) and saturated aqueous solution of ammonium chloride (100 mL). The organic layer was separated and the aqueous layer was extracted with a 2:1 mixture of EtOAc and THF (30 mL). The combined organic layer was washed with brine (20 mL) and then filtered through silica gel pad (100 g). The filtrate was concentrated under reduced pressure and the residue was washed with EtOAc (20 mL) to obtain title compound (2.51 g, 46%) as a red solid.

$^1$H-NMR (DMSO-$d_6$, 300 MHz) δ 2.62 (3H, s), 3.89 (3H, s), 5.26 (2H, s), 6.96 (1H, dd, J=2.6, 7.6 Hz), 7.35-7.48 (3H, m), 7.48-7.55 (2H, m), 7.63 (1H, d, J=2.6 Hz), 8.76 (1H, d, J=7.6 Hz).

(ii) Production of 2-[5-(benzyloxy)-2-methylpyrazolo[1,5-a]pyridin-3-yl]-4-(2-fluoro-6-methoxyphenyl)-1,3-thiazole-5-carboxylic acid According to the similar manner described in Example 97-B (i) and (ii), the title compound (2.19 g, 73%) has been obtained as a pale purple solid by the Suzuki coupling reaction followed by standard ester hydrolysis reaction using methyl 2-[5-(benzyloxy)-2-methylpyrazolo[1,5-a]pyridin-3-yl]-4-{[(trifluoromethyl)sulfonyl]oxy}-1,3-thiazole-5-carboxylate (3.21 g, 6.09 mmol) obtained above and (2-fluoro-6-methoxyphenyl)boronic acid (2.07 g, 12.2 mmol). The pure title compound has been obtained by washing of the crude product, which was precipitated from reaction mixture after acidic work-up, with water (30 mL), MeOH (30 mL) and EtOAc (30 mL).

$^1$H-NMR (DMSO-$d_6$, 300 MHz) δ 2.61 (3H, s), 3.78 (3H, s), 5.19 (2H, s), 6.83 (1H, dd, J=2.6, 7.6 Hz), 6.95 (1H, t, J=8.7 Hz), 7.02 (1H, d, J=8.7 Hz), 7.19-7.34 (3H, m), 7.35-7.42 (2H, m), 7.48 (1H, dt, J=6.9, 8.7 Hz), 7.67 (1H, d, J=2.6 Hz), 8.65 (1H, d, J=7.6 Hz), 13.03 (1H, br s).

(iii) Production of 2-[5-(benzyloxy)-2-methylpyrazolo[1,5-a]pyridin-3-yl]-4-(2-fluoro-6-methoxyphenyl)-1,3-thiazole-5-carboxamide According to the similar manner described in Example 97-B (iii), the title compound (2.09 g, 89%) has been obtained as a yellow solid by standard amidation reaction using 2-[5-(benzyloxy)-2-methylpyrazolo[1,5-a]pyridin-3-yl]-4-(2-fluoro-6-methoxyphenyl)-1,3-thiazole-5-carboxylic acid (2.33 g, 4.76 mmol) obtained above. The pure title compound has been obtained by washing of the crude product, which was precipitated from reaction mixture after aqueous work-up, with water (50 mL) and EtOAc (20 mL).

$^1$H-NMR (DMSO-$d_6$, 300 MHz) δ 2.61 (3H, s), 3.79 (3H, s), 5.18 (2H, s), 6.81 (1H, dd, J=7.6, 2.7 Hz), 6.90-7.10 (1H, m), 6.97 (1H, t, J=8.6 Hz), 7.03 (1H, d, J=8.6 Hz), 7.21-7.35 (3H, m), 7.35-7.56 (3H, m), 7.49 (1H, dt, J=6.9, 8.6 Hz), 7.66 (1H, d, J=2.7 Hz), 8.64 (1H, d, J=7.6 Hz).

(iv) Production of 5-(benzyloxy)-3-[4-(2-fluoro-6-methoxyphenyl)-5-(1H-1,2,4-triazol-3-yl)-1,3-thiazol-2-yl]-2-methylpyrazolo[1,5-a]pyridine According to the similar manner described in Example 97-B (iv), the title compound has been obtained as a pale yellow solid using 2-[5-(benzyloxy)-2-methylpyrazolo[1,5-a]pyridin-3-yl]-4-(2-fluoro-6-methoxyphenyl)-1,3-thiazole-5-carboxamide (1.87 g, 3.83 mmol) obtained above. The crude compound has been used in the next step without further purification.

$^1$H-NMR (DMSO-$d_6$, 300 MHz) δ 2.64 (3H, s), 3.68 (3H, s), 5.19 (2H, s), 6.79 (1H, dd, J=2.7, 7.6 Hz), 6.92 (1H, t, J=8.4 Hz), 6.99 (1H, d, J=8.4 Hz), 7.19-7.36 (3H, m), 7.36-7.52 (3H, m), 7.68 (1H, d, J=2.7 Hz), 8.50 (1H, br s), 8.62 (1H, d, J=7.6 Hz), 14.04 (1H, br s).

(v) Production of 5-(benzyloxy)-3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridine To a solution of 5-(benzyloxy)-3-[4-(2-fluoro-6-methoxyphenyl)-5-(1H-1,2,4-triazol-3-yl)-1,3-thiazol-2-yl]-2-methylpyrazolo[1,5-a]pyridine obtained above in THF (50 mL), were added 3,4-dihydro-2H-pyran (1.05 mL, 11.5 mmol) and p-toluenesulfonic acid monohydrate (364 mg, 1.92 mmol) and the mixture was stirred for 1.5 h at 70° C. To the mixture were added EtOAc (50 mL) and saturated aqueous solution of sodium bicarbonate (50 mL). The organic layer was separated and the aqueous layer was extracted with EtOAc (30 mL). The combined organic layer was washed with brine (20 mL) and then dried over anhydrous magnesium sulfate. Insoluble materials were removed by filtration and the filtrate was concentrated under reduced pressure. The residue was purified by basic silica gel column chromatography (EtOAc/hexane=40/60→70/30) to give title compound (1.68 g, 73%) as a pale yellow solid.

$^1$H-NMR (DMSO-$d_6$, 300 MHz) δ 1.43-1.70 (3H, m), 1.80-2.00 (3H, m), 2.64 (3H, s), 3.56-3.66 (1H, m), 3.68 (3H, s), 3.80-3.92 (1H, m), 5.20 (2H, s), 5.54 (1H, dd, J=3.4, 7.9 Hz), 6.80 (1H, dd, J=2.7, 7.6 Hz), 6.92 (1H, t, J=8.6 Hz), 6.99 (1H, d, J=8.6 Hz), 7.22-7.34 (3H, m), 7.38-7.52 (3H, m), 7.68 (1H, d, J=2.7 Hz), 8.63 (1H, d, J=7.6 Hz), 8.64 (1H, s).

(vi) Production of 3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridin-5-ol To a solution of 5-(benzyloxy)-3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridine (1.65 g, 2.77 mmol) obtained above in THF (60 mL) and EtOH (20 mL), was added 10% palladium-carbon (884 mg, 0.831 mmol) and the mixture was stirred for 2.5 h at rt under hydrogen atmosphere (1 atm). The mixture was filtered through Celite pad and the filtrate was concentrated under reduced pressure. The residue was crystallized from EtOAc (10 mL) to give title compound (1.30 g, 93%) as a pale yellow solid.

$^1$H-NMR (DMSO-$d_6$, 300 MHz) δ 1.43-1.69 (3H, m), 1.78-1.97 (3H, m), 2.63 (3H, s), 3.55-3.65 (1H, m), 3.66 (3H, s), 3.79-3.89 (1H, m), 5.53 (1H, dd, J=3.5, 7.6 Hz), 6.60 (1H, dd, J=2.6, 7.5 Hz), 6.89 (1H, t, J=8.5 Hz), 6.95 (1H, d, J=8.5 Hz), 7.44 (1H, dt, J=7.0, 8.5 Hz), 7.53 (1H, d, J=2.6 Hz), 8.55 (1H, d, J=7.5 Hz), 8.61 (1H, s), 10.70 (1H, s).

(vii) Production of 3-[4-(2-fluoro-6-methoxyphenyl)-5-(1H-1,2,4-triazol-3-yl)-1,3-thiazol-2-yl]-2-methyl-5-(2-morpholin-4-ylethoxy)pyrazolo[1,5-a]pyridine According to the similar manner described in Example 85-B (ii) and (iii), the title compound (110 mg, 69%) has been obtained as a colorless solid using 3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridin-5-ol (150 mg, 0.296 mmol) obtained above and 4-(2-chloroethyl)morpholine hydrochloride (110 mg, 0.592 mmol) by standard alkylation reaction followed by deprotection of THP group using 2 N hydrochloric acid (2 mL) in THF (6 mL) and MeOH (2 mL) by standard manner. The pure title compound has been obtained by crystallization from THF (2 mL) and AcOEt (4 mL).

$^1$H-NMR (DMSO-$d_6$, 300 MHz) δ 2.41-2.48 (4H, m), 2.65 (3H, s), 2.73 (2H, t, J=5.8 Hz), 3.50-3.59 (4H, m), 3.67 (3H, s), 4.19 (2H, t, J=5.8 Hz), 6.75 (1H, dd, J=2.8, 7.6 Hz), 6.87 (1H, t, J=8.5 Hz), 6.96 (1H, d, J=8.5 Hz), 7.43 (1H, dt, J=6.9, 8.5 Hz), 7.59 (1H, d, J=2.8 Hz), 8.49 (1H, br s), 8.62 (1H, d, J=7.6 Hz), 14.06 (1H, br s).

Example 107-B

Production of 3-[4-(2-fluoro-6-methoxyphenyl)-5-(1H-1,2,4-triazol-3-yl)-1,3-thiazol-2-yl]-2-methyl-5-[2-(4-methylpiperazin-1-yl)ethoxy]pyrazolo[1,5-a]pyridine

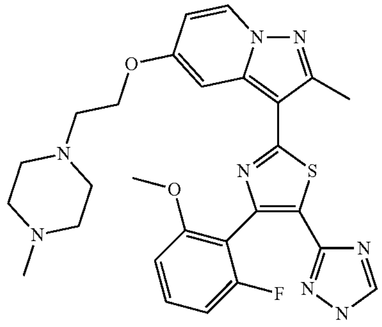 [SMILES: COc1cccc(F)c1-c1nc(-c2c(C)nn3ccc(OCCN4CCN(C)CC4)cc23)sc1-c1nc[nH]n1]

(i) Production of 5-(2-chloroethoxy)-3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridine According to the similar manner described in 85-B (ii), the title compound (429 mg, 95%) has been obtained as a pale yellow amorphous solid using 1-bromo-2-chloroethane (329 μL, 3.95 mmol) and 3-[4-(2-fluoro-6-methoxyphenyl)-5-[1-(tetrahydro-2H-pyran-2-yl)-1H-1,2,4-triazol-3-yl]-1,3-thiazol-2-yl]-2-methylpyrazolo[1,5-a]pyridin-5-ol obtained in Example 86-B (vi) and cesium carbonate (1.29 g, 3.95 mmol)

by standard alkylation reaction. The crude product has been purified by silica gel column chromatography (EtOAc/hexane=30/70→70/30).

$^1$H-NMR (DMSO-$d_6$, 300 MHz) δ 1.43-1.70 (3H, m), 1.80-2.02 (3H, m), 2.66 (3H, s), 3.55-3.66 (1H, m), 3.68 (3H, s), 3.80-3.91 (1H, m), 4.01 (2H, t, J=5.3 Hz), 4.36 (2H, t, J=5.3 Hz), 5.53 (1H, dd, J=3.5, 7.8 Hz), 6.81 (1H, dd, J=2.8, 7.6 Hz), 6.88 (1H, t, J=8.6 Hz), 6.96 (1H, d, J=8.6 Hz), 7.44 (1H, dt, J=6.9, 8.6 Hz), 7.57 (1H, d, J=2.8 Hz), 8.64 (1H, s), 8.66 (1H, d, J=7.6 Hz).

(ii) Production of 3-[4-(2-fluoro-6-methoxyphenyl)-5-(1H-1,2,4-triazol-3-yl)-1,3-thiazol-2-yl]-2-methyl-5-[2-(4-methylpiperazin-1-yl)ethoxy]pyrazolo[1,5-a]pyridine according to the similar manner described in Example 88-B (ii) and (iii), the title compound (104 mg, 50%) has been obtained as a colorless solid using 5-(2-chloroethoxy)-3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridine (213 mg, 0.374 mmol) obtained above, 1-methylpiperazine (83.4 μL, 0.749 mmol), potassium carbonate (104 mg, 0.749 mmol) and sodium iodide (112 mg, 0.749 mmol) by standard alkylation reaction followed by deprotection of THP group using 2 N hydrochloric acid (2 mL) in THF (6 mL) and MeOH (2 mL) by standard manner. The pure title compound has been obtained by crystallization from EtOH (6 mL) and hexane (2 mL).

$^1$H-NMR (DMSO-$d_6$, 300 MHz) δ 2.14 (3H, s), 2.28 (4H, br s), 2.46 (4H, br s), 2.65 (3H, s), 2.72 (2H, t, J=5.9 Hz), 3.67 (3H, s), 4.16 (2H, t, J=5.9 Hz), 6.75 (1H, dd, J=2.7, 7.6 Hz), 6.87 (1H, t, J=8.5 Hz), 6.95 (1H, d, J=8.5 Hz), 7.43 (1H, dt, J=6.9, 8.5 Hz), 7.58 (1H, d, J=2.7 Hz), 8.48 (1H, s), 8.61 (1H, d, J=7.6 Hz), 14.05 (1H, br s).

Example 108-B

Production of 3-[4-(2-fluoro-6-methoxyphenyl)-5-(1H-1,2,4-triazol-3-yl)-1,3-thiazol-2-yl]-2-methyl-5-{2-[4-(methylsulfonyl)piperazin-1-yl]ethoxy}pyrazolo[1,5-a]pyridine

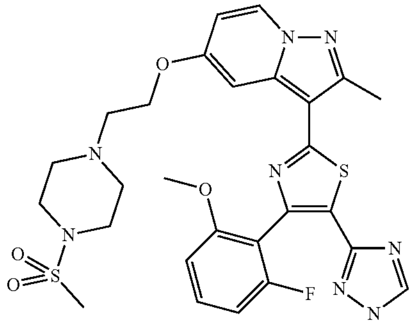 [SMILES: COc1cccc(F)c1-c1nc(-c2c(C)nn3ccc(OCCN4CCN(S(C)(=O)=O)CC4)cc23)sc1-c1nc[nH]n1]

According to the similar manner described in Example 88-B (ii) and (iii), the title compound (162 mg, 70%) has been obtained as a colorless solid using 5-(2-chloroethoxy)-3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridine (215 mg, 0.378 mmol) obtained in Example 86-B (i), 1-methanesulfonylpiperazine (124 mg, 0.756 mmol), potassium carbonate (104 mg, 0.756 mmol) and sodium iodide (113 mg, 0.756 mmol) by standard alkylation reaction followed by deprotection of THP group using 2 N hydrochloric acid (2 mL) in THF (6 mL) and MeOH (2 mL) by standard manner. The pure title compound has been obtained by crystallization from THF (2 mL) and EtOAc (4 mL).

$^1$H-NMR (DMSO-$d_6$, 300 MHz) δ 2.54-2.61 (4H, m), 2.65 (3H, s), 2.80 (2H, t, J=5.8 Hz), 2.86 (3H, s), 3.04-3.12 (4H, m), 3.67 (3H, s), 4.20 (2H, t, J=5.8 Hz), 6.76 (1H, dd, J=2.6, 7.6 Hz), 6.88 (1H, t, J=8.5 Hz), 6.96 (1H, d, J=8.5 Hz), 7.43 (1H, dt, J=6.9, 8.5 Hz), 7.58 (1H, d, J=2.6 Hz), 8.48 (1H, br s), 8.62 (1H, d, J=7.6 Hz), 14.05 (1H, br s).

Example 109-B

Production of 5-[(1-acetylpiperidin-4-yl)oxy]-3-[4-(2-fluoro-6-methoxyphenyl)-5-(1H-1,2,4-triazol-3-yl)-1,3-thiazol-2-yl]-2-methylpyrazolo[1,5-a]pyridine

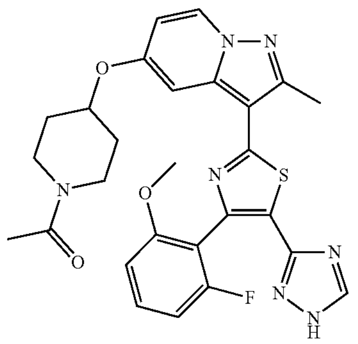 [SMILES: COc1cccc(F)c1-c1nc(-c2c(C)nn3ccc(OC4CCN(C(C)=O)CC4)cc23)sc1-c1nc[nH]n1]

To a stirred solution of 3-{4-(2-fluoro-6-methoxyphenyl)-5-[1-(tetrahydro-2H-pyran-2-yl)-1H-1,2,4-triazol-3-yl]-1,3-thiazol-2-yl}-2-methylpyrazolo[1,5-a]pyridin-5-ol (250 mg, 0.494 mmol) obtained in Example 86-B (vi) in DMF (4 mL) were added potassium carbonate (272 mg, 1.97 mmol) and 1-[(tert-butoxycarbonyl)oxy]piperidin-4-yl methanesulfonate (550 mg, 1.97 mmol) obtained in Example 85-B (i) and the mixture was stirred for 4.5 h at 80° C. To the mixture were added a 1:1 mixture of THF and EtOAc (20 mL) and saturated aqueous solution of sodium bicarbonate (15 mL). The organic layer was separated and the aqueous layer was extracted with a 1:1 mixture of THF and EtOAc (5 mL). The combined organic layer was washed with brine (5 mL) and then filtered through basic silica gel pad (3 g). The filtrate was concentrated under reduced pressure.

The residue was dissolved in TFA (10 mL) and the mixture was stirred for 2 h at rt. The mixture was concentrated under reduced pressure. To the residue were added a 1:1 mixture of THF and EtOAc (20 mL) and saturated aqueous solution of sodium carbonate (15 mL). The organic layer was separated and the aqueous layer was extracted with a 1:1 mixture of THF and EtOAc (5 mL×4). The combined organic layers were dried over anhydrous sodium sulfate. Insoluble materials were removed by filtration and the filtrate was concentrated under reduced pressure.

To the solution of above residue in DMF (3 mL), was added acetyl chloride (318 μL, 4.44 mmol) and the mixture was stirred for 2 h at rt. To the mixture, were added MeOH (3 mL) and potassium carbonate (820 mg, 5.72 mmol) and the mixture was stirred for 13 h at rt. To the mixture were added a 1:1 mixture of THF and EtOAc (20 mL) and saturated aqueous solution of sodium carbonate (15 mL). The organic layer was separated and the aqueous layer was extracted with a 1:1 mixture of THF and EtOAc (5 mL×2). The combined organic layer was washed with brine (5 mL) and then dried over anhydrous sodium sulfate. Insoluble materials were removed by filtration and the filtrate was concentrated under reduced pressure. The residue was purified by silica gel column chromatography (MeOH/AcOEt=0/100→10/90). Concentration of appropriate fractions afforded crude compound, which was crystallized from THF (2 mL) and EtOAc (4 mL) to obtain pure title compound (104 mg, 38%) as a colorless solid.

$^1$H-NMR (DMSO-$d_6$, 300 MHz) δ 1.49-1.76 (2H, m), 1.90-2.10 (2H, m), 2.03 (3H, s), 2.65 (3H, s), 3.06-3.18 (1H, m), 3.21-3.29 (1H, m), 3.59-3.75 (1H, m), 3.64 (3H, s), 3.83-3.95 (1H, m), 4.60-4.72 (1H, m), 6.80 (1H, dd, J=2.7, 7.6 Hz), 6.89 (1H, t, J=8.5 Hz), 6.95 (1H, d, J=8.5 Hz), 7.43 (1H, dt, J=7.0, 8.5 Hz), 7.69 (1H, d, J=2.7 Hz), 8.49 (1H, br s), 8.65 (1H, d, J=7.6 Hz), 14.05 (1H, br s).

Example 110-B

Production of 6-methyl-7-[4-phenyl-5-(1H-pyrazol-5-yl)-1,3-thiazol-2-yl]pyrazolo[5,1-b][1,3]thiazole

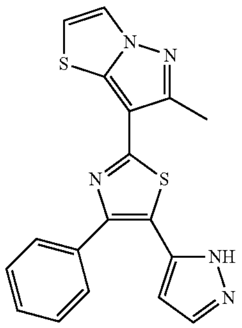 [SMILES: Cc1nn2ccsc2c1-c1nc(-c2ccccc2)c(-c2ccn[nH]2)s1]

(i) Production of N-methoxy-N-methyl-2-(6-methylpyrazolo[5,1-b][1,3]thiazol-7-yl)-4-phenyl-1,3-thiazole-5-carboxamide A mixture of 2-(6-methylpyrazolo[5,1-b][1,3]thiazol-7-yl)-4-phenyl-1,3-thiazole-5-carboxylic acid (1.53 g, 4.5 mmol) obtained in Example 35-B (viii), TEA (1.9 mL), N,O-dimethylamine hydrochloride (1.32 g, 13.5 mmol), HOBT (912 mg, 6.75 mmol), EDCI (1.30 g, 6.75 mmol) and DMF (45 mL) was stirred at rt for 16 h. The reaction mixture was concentrated under reduced pressure, and water (50 mL) was added to the reaction mixture. The aqueous layer was extracted with EtOAc (50 mL×2), and the combined organic layer was washed with saturated aqueous solution of sodium bicarbonate (50 mL) and dried over anhydrous magnesium sulfate. Insoluble materials were removed by filtration and the filtrate was concentrated under reduced pressure. The residue was purified by silica gel column chromatography (EtOAc/hexane=20/80→100/0) to give the title compound (1.43 g, 83%) as a yellow solid.

$^1$H-NMR (DMSO-$d_6$, 300 MHz) δ 2.63 (3H, s), 3.23 (3H, s), 3.61 (3H, s), 7.35-7.58 (4H, m), 7.67-7.87 (2H, m), 8.33 (1H, d, J=4.2 Hz)

(ii) Production of 1-[2-(6-methylpyrazolo[5,1-b][1,3]thiazol-7-yl)-4-phenyl-1,3-thiazol-5-yl]ethanone To a solution of N-methoxy-N-methyl-2-(6-methylpyrazolo[5,1-b][1,3]thiazol-7-yl)-4-phenyl-1,3-thiazole-5-carboxamide (1.15 g, 3.0 mmol) obtained above in THF (20 mL) was added 2M methylmagnesium bromide in THF (7.2 mL, 7.2 mmol) at 0° C., the reaction mixture was stirred for 2 h at the same temperature, and then stirred for 1 h at rt. To the reaction mixture were added saturated aqueous solution of sodium bicarbonate (50 mL) and EtOAc (50 mL), the aqueous layer was extracted with EtOAc (50 mL), and the combined organic layers were dried over anhydrous magnesium sulfate. Insoluble materials were removed by filtration, and the filtrate was concentrated under reduced pressure to give the title compound (1.02 g, 99%) as a yellow solid.

$^1$H-NMR (DMSO-$d_6$, 300 MHz) δ2.19 (3H, s), 2.62 (3H, s), 7.47-7.61 (4H, m), 7.63-7.82 (2H, m), 8.32 (1H, d, J=4.2 Hz).

(iii) Production of 6-methyl-7-[4-phenyl-5-(1H-pyrazol-5-yl)-1,3-thiazol-2-yl]pyrazolo[5,1-b][1,3]thiazole A solution of 1-[2-(6-methylpyrazolo[5,1-b][1,3]thiazol-7-yl)-4-phenyl-1,3-thiazol-5-yl]ethanone (170 mg, 0.5 mmol) obtained by similar manner with Example 110-8 (ii) in N,N-dimethylformamide dimethylacetal (10 mL) was refluxed at 90° C. for 4 h. The reaction mixture was allowed to cool to rt, and the solvent was evaporated. The residue was suspended in EtOH (5 mL), and then was added hydrazine monohydrate (50 mg, 1.0 mmol). The mixture was stirred at 80° C. for 5 h. The mixture was allowed to cool to rt, and then concentrated. The residue was purified by silica gel column chromatography (EtOAc/hexane=30/70→100/0) to give the title compound (143 mg, 79%) as a yellow solid.

$^1$H-NMR (DMSO-$d_6$, 300 MHz) δ2.63 (3H, s), 6.05 (1H, d, J=2.3 Hz), 7.38-7.53 (4H, m), 7.66-7.79 (3H, m), 8.29 (1H, d, J=4.2 Hz), 13.08 (1H, br s).

Example 111-B

Production of 2'-(6-methylpyrazolo[5,1-b][1,3]thiazol-7-yl)-4'-phenyl-2,5'-bi-1,3-thiazole

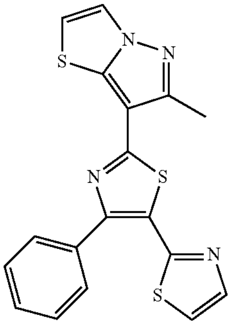 [SMILES: Cc1nn2ccsc2c1-c1nc(-c2ccccc2)c(-c2nccs2)s1]

(i) Production of 2-(6-methylpyrazolo[5,1-b][1,3]thiazol-7-yl)-4-phenyl-1,3-thiazole-5-carboxamide A mixture of 2-(6-methylpyrazolo[5,1-b][1,3]thiazol-7-yl)-4-phenyl-1,3-thiazole-5-carboxylic acid (1.70 g, 5.0 mmol) obtained in Example 35-B(viii), TEA (2.1 mL), ammonium chloride (803 mg, 15.0 mmol), HOBT (1.01 g, 7.5 mmol), EDCI (1.44 g, 7.5 mmol) and DMF (50 mL) was stirred at rt for 16 h. The reaction mixture was concentrated under reduced pressure. To the residue was added saturated aqueous solution of sodium bicarbonate (30 mL). The resulting precipitate was collected by filtration and was washed with water and diethyl ether to give the title compound (1.54 g, 90%) as a white solid.

$^1$H-NMR (DMSO-$d_6$, 300 MHz) δ2.62 (3H, s), 7.37-7.56 (4H, m), 7.68 (2H, br s), 7.81-7.90 (2H, m), 8.31 (1H, d, J=4.0 Hz).

(ii) Production of 2-(6-methylpyrazolo[5,1-b][1,3]thiazol-7-yl)-4-phenyl-1,3-thiazole-5-carbothioamide To a suspension of 2-(6-methylpyrazolo[5,1-b][1,3]thiazol-7-yl)-4-phenyl-1,3-thiazole-5-carboxamide (340 mg, 1.0 mmol) obtained above in DME (10 mL) was added 2,4-Bis(4-methoxyphenyl)-2,4-dithioxo-1,3,2,4-dithiadiphosphetane (485 mg, 1.2 mmol), and the mixture was stirred at 80° C. for 1 h. The reaction mixture was allowed to cool to rt, and then were added EtOAc (15 mL) and 1N hydrochloric acid (15 mL) and then the resulting suspension was filtered. The residue was washed with water (5 mL) and EtOAc (5 mL) to give the title compound (172 mg, 48%) as a yellow solid.

$^1$H-NMR (DMSO-$d_6$, 300 MHz) δ2.60 (3H, s), 7.33-7.58 (4H, m), 7.74-7.89 (2H, m), 8.31 (1H, d, J=4.2 Hz), 9.22 (1H, br s), 10.02 (1H, br s)

(iii) Production of 2'-(6-methylpyrazolo[5,1-b][1,3]thiazol-7-yl)-4'-phenyl-2,5'-bi-1,3-thiazole To a solution of 2-(6-methylpyrazolo[5,1-b][1,3]thiazol-7-yl)-4-phenyl-1,3-thiazole-5-carbothioamide (142 mg, 0.42 mmol) obtained above in AcOH (4 mL) were added p-toluenesulfonic acid monohydrate (3.8 mg, 0.02 mmol) and bromoacetaldehyde dimethylacetal (70 μL), and the reaction mixture was stirred at 100° C. for 2 h. The reaction mixture was allowed to cool to rt, and then solvent was evaporated. To the residue was added saturated aqueous solution of sodium bicarbonate (40 mL) and the mixture was extracted with EtOAc (40 mL×2). The combined organic layers were dried over anhydrous magnesium sulfate. Insoluble materials were removed by filtration, and the filtrate was concentrated under reduced pressure and the residue was purified by silica gel column chromatography (EtOAc/hexane=20/80→100/0) to give the title compound (83.2 mg, 54%) as a yellow solid.

$^1$H-NMR (DMSO-$d_6$, 300 MHz) δ2.64 (3H, s), 7.51 (1H, d, J=4.2 Hz), 7.53-7.60 (3H, m), 7.63 (1H, d, J=3.2 Hz), 7.65-7.71 (2H, m), 7.84 (1H, d, J=3.2 Hz), 8.32 (1H, d, J=4.0 Hz).

Example 112-B

Production of 7-[5-(1H-imidazol-2-yl)-4-phenyl-1,3-thiazol-2-yl]-6-methylpyrazolo[5,1-b][1,3]thiazole

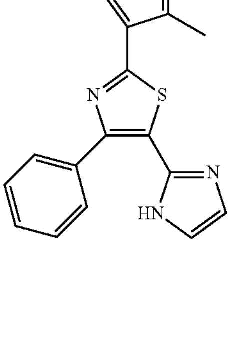

To a suspension of 2-(6-methylpyrazolo[5,1-b][1,3]thiazol-7-yl)-4-phenyl-1,3-thiazole-5-carbothioamide (223 mg, 0.6 mmol) obtained in the similar manner described in Example 111-B(ii) in acetone (12 mL), was added iodomethane (75 μL, 1.2 mmol), and the mixture was stirred at rt for 2 h. The solvent was evaporated, and the residue was suspended in AcOH (12 mL). To the residue was added aminoacetaldehyde dimethylacetal (100 μL, 0.9 mmol), and the mixture was stirred at 90° C. for 16 h. The reaction mixture was allowed to cool to rt, then concentrated, and the residue was dissolved in THF (12 mL). To the solution was added 6N hydrochloric acid (400 μL, 2.4 mmol), and the mixture was stirred at 70° C. for 2 h. The reaction mixture was allowed to cool to rt, and then were added saturated aqueous solution of sodium bicarbonate (50 mL) and EtOAc (50 mL). The aqueous layer was extracted with EtOAc (50 mL), and the organic layer was dried over anhydrous magnesium sulfate. Insoluble materials were removed by filtration, and the filtrate was concentrated under reduced pressure. The residue was purified by silica gel column chromatography (EtOAc/hexane=20/80→100/0) to give the title compound (133 mg, 61%) as a yellow solid.

$^1$H-NMR (DMSO-$d_6$, 300 MHz) δ2.63 (3H, s), 7.05-7.15 (1H, m), 7.20-7.31 (1H, m), 7.34-7.46 (3H, m), 7.52 (1H, d, J=4.0 Hz), 7.63-7.76 (2H, m), 8.32 (1H, d, J=4.2 Hz), 12.30 (1H, br s)

Example 113-B

Production of 6-methyl-7-[5-(1,3-oxazol-4-yl)-4-phenyl-1,3-thiazol-2-yl]pyrazolo[5,1-b][1,3]thiazole

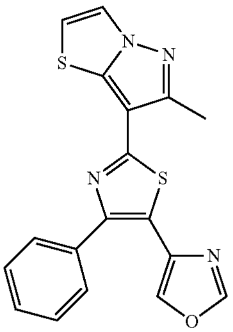 [SMILES: Cc1nn2ccsc2c1-c1nc(-c2ccccc2)c(-c2cocn2)s1]

To a solution of 1-[2-(6-methylpyrazolo[5,1-b][1,3]thiazol-7-yl)-4-phenyl-1,3-thiazol-5-yl]ethanone (136 mg, 0.4 mmol) obtained in the similar manner described in Example 110-B(ii) in AcOH (12 ml), was added 0.9N solution of bromine in AcOH (250 μL, 0.225 mmol) at 40° C., and the mixture was stirred at same temperature for 3 h. To the mixture was added 0.9N solution of bromine in AcOH (250 μL, 0.225 mmol), and the mixture was stirred for additional 1 h at the same temperature. The reaction mixture was allowed to cool to rt, and the mixture was concentrated under reduced pressure. To the residue, were added saturated aqueous solution of sodium bicarbonate (50 mL) and EtOAc (50 mL), and the aqueous layer was extracted with EtOAc (50 mL). The organic layer was dried over anhydrous magnesium sulfate. Insoluble materials were removed by filtration, and the filtrate was concentrated under reduced pressure. To the residue was added formamide (4 mL), and the mixture was stirred at 180° C. for 2 h. The reaction mixture was allowed to cool to rt, and then were added saturated aqueous solution of sodium bicarbonate (50 mL) and EtOAc (50 mL. The aqueous layer was extracted with EtOAc (50 mL), and the organic layer was dried over anhydrous magnesium sulfate. Insoluble materials were removed by filtration, and the filtrate was concentrated under reduced pressure. The residue was purified by silica gel column chromatography (EtOAc/hexane=30/70→100/0) to give the title compound (37.8 mg, 26%) as a yellow solid.

$^1$H-NMR (DMSO-$d_6$, 300 MHz) δ2.63 (3H, s), 7.37-7.58 (4H, m), 7.68-7.79 (2H, m), 8.08 (1H, d, J=1.0 Hz), 8.31 (1H, d, J=4.0 Hz), 8.54 (1H, d, J=1.0 Hz).

Example 114-B

Production of ethyl {4-[4-ethoxy-5-(1H-1,2,4-triazol-3-yl)-1,3-thiazol-2-yl]pyridin-2-yl}carbamate

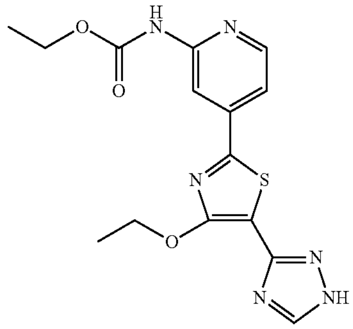 [SMILES: CCOC(=O)Nc1cc(-c2nc(OCC)c(-c3nc[nH]n3)s2)ccn1]

(i) Production of ethyl (4-{4-ethoxy-5-[1-(tetrahydro-2H-pyran-2-yl)-1H-1,2,4-triazol-3-yl]-1,3-thiazol-2-yl}pyridin-2-yl)carbamate To a solution of 4-{4-ethoxy-5-[1-(tetrahydro-2H-pyran-2-yl)-1H-1,2,4-triazol-3-yl]-1,3-thiazol-2-yl}pyridin-2-amine (100 mg, 0.268 mmol) obtained by similar manner with Example 47-B(ii) in pyridine (2.7 mL), was added ethyl chloroformate (100 μL, 1.08 mmol) at 0° C., and the mixture was stirred for 3 h. The reaction mixture was diluted with water (20 mL), and the mixture was stirred for 1 h. The resulting precipitate was collected by filtration and was washed with water and diethyl ether to give the title compound (99.1 mg, 83%) as a yellow solid.

$^1$H-NMR (DMSO-$d_6$, 300 MHz) δ1.27 (3H, t, J=7.1 Hz), 1.40 (3H, t, J=7.1 Hz), 1.49-1.79 (3H, m), 1.87-2.24 (3H, m), 3.60-3.78 (1H, m), 3.88-4.05 (1H, m), 4.19 (2H, q, J=7.0 Hz), 4.54 (2H, q, J=7.0 Hz), 5.60 (1H, dd, J=2.6, 9.4 Hz), 7.46-7.63 (1H, m), 8.24-8.51 (2H, m), 8.79 (1H, s), 10.36 (1H, s).

(ii) Production of ethyl {4-[4-ethoxy-5-(1H-1,2,4-triazol-3-yl)-1,3-thiazol-2-yl]pyridin-2-yl}carbamate A solution of ethyl (4-{4-ethoxy-5-[1-(tetrahydro-2H-pyran-2-yl)-1H-1,2,4-triazol-3-yl]-1,3-thiazol-2-yl}pyridin-2-yl)carbamate (99.0 mg, 0.222 mmol) obtained above in TFA (4 mL) was stirred at rt for 15 h. The solvent was evaporated under reduced pressure, and saturated aqueous solution of sodium bicarbonate (20 mL) and EtOAc (15 mL) were added to the residue. The resulting precipitate was collected by filtration and then washed with water, EtOH and diethyl ether sequentially, to give the title compound (99.1 mg, 83%) as a yellow solid.

$^1$H-NMR (DMSO-$d_6$, 300 MHz) δ1.27 (3H, t, J=7.1 Hz), 1.42 (3H, t, J=7.1 Hz), 4.19 (2H, q, J=7.0 Hz), 4.56 (2H, q, J=7.1 Hz), 7.54 (1H, dd, J=1.6, 5.2 Hz), 8.31-8.48 (3H, m), 10.37 (1H, s), 14.04 (1H, br s).

Example 115-B

Production of N-{4-[4-ethoxy-5-(1H-1,2,4-triazol-3-yl)-1,3-thiazol-2-yl]pyridin-2-yl}-N'-ethylurea

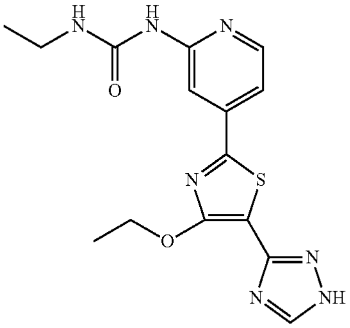 [SMILES: CCNC(=O)Nc1cc(-c2nc(OCC)c(-c3nc[nH]n3)s2)ccn1]

To a solution of 4-{4-ethoxy-5-[1-(tetrahydro-2H-pyran-2-yl)-1H-1,2,4-triazol-3-yl]-1,3-thiazol-2-yl}pyridin-2-amine (100 mg, 0.268 mmol) obtained in the similar manner described in Example 47-B(ii) in DMF (2 mL), was added ethyl isocyanate (36 μL, 0.457 mmol), and the mixture was stirred at rt for 15 h. To the reaction mixture, again was added ethyl isocyanate (100 μL, 1.27 mmol), and the mixture was stirred at 80° C. for 24 h. The reaction mixture was allowed to cool to rt, and then were added saturated aqueous solution of sodium bicarbonate (30 mL) and EtOAc (40 mL). The aqueous layer was extracted with EtOAc (40 mL), and the combined organic layer was dried over anhydrous magnesium sulfate. Insoluble materials were removed by filtration, and the filtrate was concentrated under reduced pressure. The residue was purified by silica gel column chromatography (EtOAc/hexane=20/80→100/0) to give a yellow solid.

The resulting yellow solid was dissolved in TFA (4 mL) and was stirred at it for 3 h. The solvent was evaporated under reduced pressure, and were added saturated aqueous solution of sodium bicarbonate (8 mL) and EtOAc (3 mL). The resulting precipitate was collected by filtration and washed with water, EtOH and diethyl ether sequentially to give the title compound (34.0 mg, 29%) as a yellow solid.

$^1$H-NMR (DMSO-$d_6$, 300 MHz) δ1.10 (3H, t, J=7.2 Hz), 1.29-1.57 (3H, m), 3.11-3.28 (2H, m), 4.52 (1.2H, q, J=7.0 Hz), 4.62 (0.8H, q, J=6.9 Hz), 7.29-7.50 (1H, m), 7.67-7.90 (1H, m), 8.03 (1H, br s), 8.08 (0.4H, br s), 8.19-8.44 (1H, m), 8.63 (0.6H, br s), 9.18-9.47 (1H, m), 13.95 (0.6H, br s), 14.17 (0.4H, br s).

Example 116-B

Production of 6-bromo-2-methyl-3-[4-phenyl-5-(1H-1,2,4-triazol-3-yl)-1,3-thiazol-2-yl]imidazo[1,2-a]pyridine

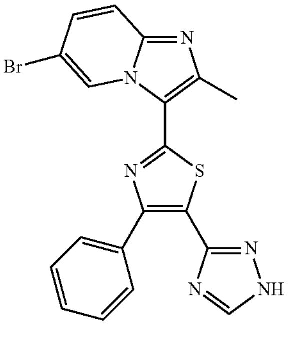 [SMILES: Cc1nc2ccc(Br)cn2c1-c1nc(-c2ccccc2)c(-c2nc[nH]n2)s1]

(i) Production of 2-methyl-4-phenyl-1,3-thiazole-5-carboxylic acid

To a solution of ethanethioamide (80.0 g, 1.06 mol) in EtOH (600 mL), was added ethyl 2-chloro-3-oxo-3-phenylpropanoate (141.5 g, 0.64 mol), which was prepared by published procedure in M. Altuna-Urquijo, et al.; Tetrahedron; 65; 2009; 975-984, and the mixture was stirred at 80° C. for 2 h. The reaction mixture was allowed to cool to 50° C., 8N aqueous sodium hydroxide solution (120 mL) was added, and the mixture was stirred 80° C. for 2 h. The reaction mixture was allowed to cool to 50° C., 8N aqueous sodium hydroxide solution (240 mL) was added, and the mixture was stirred 80° C. for 1 h. The reaction mixture was allowed to cool to 0° C., and was then neutralized by the addition of 6N hydrochloric acid (400 mL). The mixture was stirred at rt for 12 h and the resulting precipitate was collected by filtration and washed with water, EtOH and diethyl ether sequentially to give the title compound (105.6 g, 75%) as a white solid.

$^1$H-NMR (DMSO-$d_6$, 300 MHz) δ 2.70 (3H, s), 7.30-7.50 (3H, m), 7.59 (2H, m), 13.22 (1H, br s).

(ii) Production of 2-methyl-4-phenyl-1,3-thiazole-5-carboxamide

A mixture of 2-methyl-4-phenyl-1,3-thiazole-5-carboxylic acid (104.6 g, 0.48 mol) obtained above, TEA (200 mL), ammonium chloride (76.1 g, 1.43 mol), HOBT (103.5 g, 0.77 mol), EDCI (146.8 g, 0.77 mol) and DMF (1.0 L) was stirred at 40° C. for 3 h. The reaction mixture was allowed to cool to rt, and insoluble materials were removed by filtration. The filtrate was concentrated under reduced pressure, and then were added water (1.6 L) and saturated aqueous solution of sodium bicarbonate (400 mL). The resulting precipitate was collected by filtration and sequentially washed with water, EtOH and diethyl ether to give the title compound (64.7 g, 61%) as a pale brown solid.

$^1$H-NMR (DMSO-$d_6$, 300 MHz) δ 2.69 (3H, s), 7.30-7.51 (3H, m), 7.64 (2H, br s), 7.67-7.75 (2H, m).

(iii) Production of 3-(2-methyl-4-phenyl-1,3-thiazol-5-yl)-1H-1,2,4-triazole

A suspension of 2-methyl-4-phenyl-1,3-thiazole-5-carboxamide (82.0 g, 0.377 mol) obtained above in N,N-dimethylformamide dimethylacetal (97.4 mL, 1.13 mmol) and toluene (1.8 L) was stirred at 50° C. for 3 h. The reaction mixture was allowed to cool to rt, decolorized with activated carbon. Insoluble materials were removed by filtration and the filtrate was concentrated under reduced pressure.

The residue was suspended in AcOH (900 mL), then was added hydrazine monohydrate (84 mL). The mixture was stirred at 90 C for 2 h and then allowed to cool to rt. The resulting precipitate was collected by filtration, and washed with EtOAc and diethyl ether to give the title compound (62.4 g, 68%) as a white solid.

$^1$H-NMR (DMSO-$d_6$, 300 MHz) δ 2.71 (3H, s), 7.20-7.53 (3H, m), 7.54-7.92 (2H, m), 8.55 (1H, s), 14.15 (1H, br s).

(iv) Production of 3-(2-methyl-4-phenyl-1,3-thiazol-5-yl)-1-(tetrahydro-2H-pyran-2-yl)-1H-1,2,4-triazole A mixture of 3-(2-methyl-4-phenyl-1,3-thiazol-5-yl)-1H-1,2,4-triazole (85.0 g, 0.351 mol) obtained above, 3,4-dihydro-2H-pyran (63.8 g, 0.702 mol), p-toluenesulfonic acid monohydrate (80.0 g, 0.423 mol) and THF (2.1 L) was stirred at 90° C. for 2 h. The reaction mixture was allowed to cool to rt, then the solvent was evaporated. To the residue, were added EtOAc (1.0 L) and 1N aqueous sodium hydroxide solution (600 mL). The aqueous layer was extracted with EtOAc, the combined organic layer was washed with saturated aqueous ammonium chloride and dried over anhydrous magnesium sulfate. Insoluble materials were removed by filtration and the filtrate was concentrated under reduced pressure. The residue was purified by a basic silica gel pad. The obtained solution was concentrated under reduced pressure, and the residue was washed with diethyl ether to give the title compound (61.2 g, 57%) as a pale yellow solid.

$^1$H-NMR (DMSO-$d_6$, 300 MHz) δ 1.45-1.77 (3H, m), 1.83-2.14 (3H, m), 2.71 (3H, s), 3.54-3.73 (1H, m), 3.80-3.98 (1H, m), 5.57 (1H, J=3.1, 8.6 Hz, d), 7.21-7.48 (3H, m), 7.63-7.87 (2H, m), 8.76 (1H, s).

(v) Production of 1-{4-phenyl-5-[1-(tetrahydro-2H-pyran-2-yl)-1H-1,2,4-triazol-3-yl]-1,3-thiazol-2-yl}acetone To a solution of 3-(2-methyl-4-phenyl-1,3-thiazol-5-yl)-1-(tetrahydro-2H-pyran-2-yl)-1H-1,2,4-triazole (32.6 g, 100 mmol) in THF (1.8 L), was dropwise added 1.6M solution of n-butyllithium in hexane (150 mL, 240 mmol) at −78° C. over 1 h, and the mixture was stirred for 1 h at the same temperature. To the reaction mixture was dropwise added a solution of N-methoxy-N-methylacetamide (10.3 g, 100 mmol) in THF (600 mL) at −78° C. over 3 h. After addition, the mixture was stirred for 30 min at the same temperature. The reaction mixture was neutralized by the addition of AcOH (13.8 mL), and the mixture was allowed to warm to rt. The solvent was evaporated under reduced pressure and then, to the residue, were added EtOAc (400 mL) and saturated aqueous ammonium chloride (300 mL). The aqueous layer was extracted with EtOAc, the combined organic layer was washed with saturated aqueous ammonium chloride, dried over anhydrous magnesium sulfate, and then insoluble materials were removed by filtration. The filtrate was concentrated under reduced pressure, and the residue was purified by silica gel column chromatography (EtOAc/hexane=5/95→80/20) to give the title compound (28.4 g, 74%) as a pale yellow oil.

$^1$H-NMR (DMSO-$d_6$, 300 MHz) δ 1.40-1.73 (3H, m), 1.84-2.14 (3H, m), 2.28 (3H, s), 3.54-3.73 (1H, m), 3.86-3.96 (1H, m), 4.38 (2H, s), 5.58 (1H, dd, J=3.0, 8.5 Hz), 7.29-7.48 (3H, m), 7.66-7.85 (2H, m), 8.75 (1H, br s).

(vi) Production of 1-bromo-1-{4-phenyl-5-[1-(tetrahydro-2H-pyran-2-yl)-1H-1,2,4-triazol-3-yl]-1,3-thiazol-2-yl}acetone A mixture of 1-{4-phenyl-5-[1-(tetrahydro-2H-pyran-2-yl)-1H-1,2,4-triazol-3-yl]-1,3-thiazol-2-yl}acetone (5.08 g, 13.8 mmol) obtained above, N-bromosuccinimide (2.69 g, 15.1 mmol), benzoyl peroxide (16.5 mg, 0.068 mmol) and benzotrifluoride (110 mL) was stirred at 80° C. for 2 h. The reaction mixture was allowed to cool to rt, and then were added saturated aqueous solution of sodium bicarbonate (30 mL) and EtOAc (100 mL). The aqueous layer was extracted with EtOAc (100 mL×2), and the combined organic layer was dried over anhydrous magnesium sulfate. Insoluble materials were removed by filtration, and the filtrate was concentrated under reduced pressure to give the title compound (5.66 g, 92%) as a brown solid.

$^1$H-NMR (DMSO-$d_6$, 300 MHz) δ1.47-1.70 (3H, m), 1.85-2.08 (3H, m), 2.47 (1.8H, s), 2.52 (1.2H, s), 3.55-3.73 (1H, m), 3.83-3.98 (1H, m), 5.54-5.70 (1H, m), 6.55 (0.4H, s), 7.29-7.48 (3H, m), 7.70-7.84 (2H, m), 8.82 (0.6H, s), 8.88 (0.4H, s), 11.08 (0.6H, br s).

(vii) Production of 6-bromo-2-methyl-3-[4-phenyl-5-(1H-1,2,4-triazol-3-yl)-1,3-thiazol-2-yl]imidazo[1,2-a]pyridine To a solution of 1-bromo-1-{4-phenyl-5-[1-(tetrahydro-2H-pyran-2-yl)-1H-1,2,4-triazol-3-yl]-1,3-thiazol-2-yl}acetone (448 mg, 1.0 mmol) obtained above in a mixed solvent of THF (5 mL) and 2-propanol (5 mL), was added 2-amino-5-bromopyridine (173 mg, 1.0 mmol), and the mixture was stirred at 80° C. for 14 h. The reaction mixture was allowed to cool to rt, and then were added saturated aqueous solution of sodium bicarbonate (50 mL) and EtOAc (50 mL). The aqueous layer was extracted with EtOAc (50 mL) and a 1:1 mixture of EtOAc and THF (60 mL×2). The combined organic layers were dried over anhydrous magnesium sulfate. Insoluble materials were removed by filtration, and the filtrate was concentrated under reduced pressure. The residue was purified by basic silica gel column chromatography (EtOAc/hexane=30/70→100/0; then MeOH/EtOAc=30/70). Concentration of appropriate fraction afforded crude product, which was washed with THF and diethyl ether to give the pure title compound (17.0 mg, 4%) as a brown solid.

$^1$H-NMR (DMSO-$d_6$, 300 MHz) δ2.73 (3H, s), 7.40-7.54 (3H, m), 7.64 (1H, dd, J=2.1 Hz, 9.4 Hz), 7.72 (1H, dd, J=0.8 Hz, 9.4 Hz), 7.86-7.95 (2H, m), 8.67 (1H, br s), 10.04 (1H, dd, J=0.8, 1.9 Hz), 14.35 (1H, br s).

Example 117-B

Production of 6-(3,4-dimethoxyphenyl)-2-methyl-3-[4-phenyl-5-(1H-1,2,4-triazol-3-yl)-1,3-thiazol-2-yl]imidazo[1,2-a]pyridine

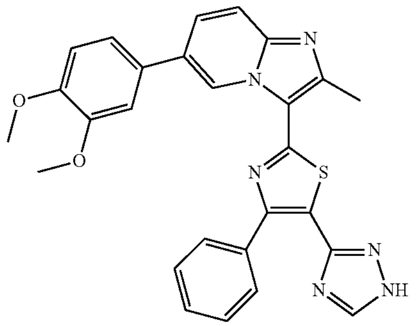 [SMILES: COc1ccc(-c2ccc3nc(C)c(-c4nc(-c5ccccc5)c(-c5nc[nH]n5)s4)n3c2)cc1OC]

(i) Production of 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine To a solution of 1-bromo-1-{4-phenyl-5-[1-(tetrahydro-2H-pyran-2-yl)-1H-1,2,4-triazol-3-yl]-1,3-thiazol-2-yl}acetone (2.96 g, 6.6 mmol) obtained in Example 116-B(vi) in THF (33 mL) and 2-propanol (33 mL), was added 2-amino-5-bromopyridine (5.71 g, 33.0 mmol), and the mixture was stirred at 80° C. for 3 h. The reaction mixture was allowed to cool to rt, and then were added saturated aqueous solution of sodium bicarbonate (60 mL) and EtOAc (150 mL). The aqueous layer was extracted with EtOAc (80 mL), and the combined organic layer was dried over anhydrous magnesium sulfate. Insoluble materials were removed by filtration, and the filtrate was concentrated under reduced pressure. The residue was purified by silica gel column chromatography (EtOAc/hexane=20/80→100/0; then MeOH/EtOAc=20/80), and then basic silica gel column chromatography (EtOAc/hexane=10/90→80/20) to give the title compound (520 mg, 15%) as a pale yellow solid.

$^1$H-NMR (DMSO-$d_6$, 300 MHz) δ 1.46-1.72 (3H, m), 1.88-2.13 (3H, m), 2.73 (3H, s), 3.58-3.73 (1H, m), 3.87-3.98 (1H, m), 5.62 (1H, dd, J=3.1, 8.8 Hz), 7.38-7.55 (3H, m), 7.64 (1H, dd, J=2.1, 9.4 Hz), 7.72 (1H, dd, J=0.8, 9.4 Hz), 7.83-7.99 (2H, m), 8.83 (1H, s), 10.04 (1H, dd, J=0.8, 1.9 Hz).

(ii) Production of 6-(3,4-dimethoxyphenyl)-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine To a suspension of 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (157 mg, 0.3 mmol) obtained above in DME (10 mL) and water (2 mL), were added (3,4-dimethoxyphenyl)boronic acid (81.9 mg, 0.45 mmol), [1,1-bis(diphenylphosphino)ferrocene]palladium(II) dichloride dichloromethane complex (24.5 mg, 0.03 mmol) and cesium carbonate (293 mg, 0.9 mmol) under a nitrogen atmosphere, and the mixture was stirred at 95° C. for 1 h. The reaction mixture was allowed to cool to rt, and then were added saturated aqueous solution of sodium bicarbonate (30 mL) and EtOAc (50 mL). The resulting precipitate was collected by filtration and washed with THF and diethyl ether to give the title compound (142 mg, 81%) as a white solid.

$^1$H-NMR (DMSO-$d_6$, 300 MHz) δ1.48-1.79 (3H, m), 1.88-2.16 (3H, m), 2.75 (3H, s), 3.55-3.73 (1H, m), 3.80 (3H, s), 3.82 (3H, s), 3.87-4.01 (1H, m), 5.62 (1H, dd, J=3.0, 8.7 Hz), 7.06-7.15 (1H, m), 7.25-7.32 (2H, m), 7.40-7.50 (3H, m), 7.77 (1H, dd, J=0.8, 9.3 Hz), 7.86 (1H, dd, J=1.9, 9.3 Hz), 7.93-8.03 (2H, m), 8.82 (1H, s), 10.10-10.33 (1H, m).

(iii) Production of 6-(3,4-dimethoxyphenyl)-2-methyl-3-[4-phenyl-5-(1H-1,2,4-triazol-3-yl)-1,3-thiazol-2-yl]imidazo[1,2-a]pyridine A solution of 6-(3,4-dimethoxyphenyl)-2-methyl-3-[4-phenyl-5-[1-(tetrahydro-2H-pyran-2-yl)-1H-1,2,4-triazol-3-yl]-1,3-thiazol-2-yl]imidazo[1,2-a]pyridine (99.0 mg, 0.222 mmol) obtained above in TFA (5 mL) was stirred at rt for 3 h. To the mixture, again, was added TFA (2.5 mL), and the mixture was stirred at rt for 12 h. TFA was evaporated under reduced pressure, and the residue was treated with saturated aqueous solution of sodium bicarbonate (5 mL), EtOAc (5 mL) and water (5 mL). The resulting precipitate was collected by filtration and sequentially washed with water, EtOH and diethyl ether to give the title compound (109 mg, 90%) as a white solid.

$^1$H-NMR (DMSO-$d_6$, 300 MHz) δ2.74 (3H, s), 3.80 (3H, s), 3.82 (3H, s), 7.06-7.14 (1H, m), 7.24-7.32 (2H, m), 7.38-

7.49 (3H, m), 7.75 (1H, dd, J=0.6, 9.3 Hz), 7.85 (1H, dd, J=1.9, 9.3 Hz), 7.93-8.03 (2H, m), 8.65 (1H, s), 10.01-10.49 (1H, m), 14.25 (1H, br s).

Example 118-B

Production of 2-methyl-6-(1-methyl-1H-pyrazol-4-yl)-3-[4-phenyl-5-(1H-1,2,4-triazol-3-yl)-1,3-thiazol-2-yl]imidazo[1,2-a]pyridine

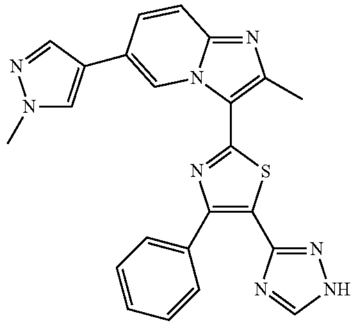 [SMILES: Cc1nc2ccc(-c3cnn(C)c3)cn2c1-c1nc(-c2ccccc2)c(-c2nc[nH]n2)s1]

(i) Production of 2-methyl-6-(1-methyl-1H-pyrazol-4-yl)-3-{4-phenyl-5-[1-(tetrahydro-2H-pyran-2-yl)-1H-1,2,4-triazol-3-yl]-1,3-thiazol-2-yl}imidazo[1,2-a]pyridine To a suspension of 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (157 mg, 0.3 mmol) obtained in Example 117-B(i) in DME (10 mL) and water (2 mL), were added 1-methyl-4-(4,4,5,5-tetramethyl-1,3,2-dioxaborolan-2-yl)-1H-pyrazole (93.6 mg, 0.45 mmol), [1,1-bis(diphenylphosphino)ferrocene]palladium(II) dichloride dichloromethane complex (24.5 mg, 0.03 mmol) and cesium carbonate (293 mg, 0.9 mmol) under a nitrogen atmosphere, and the mixture was stirred at 95° C. for 12 h. The reaction mixture was allowed to cool to rt, and then were added water (40 mL) and EtOAc (40 mL). The aqueous layer was extracted with EtOAc (40 mL) and then a 1:1 mixture of EtOAc and THF (60 mL×2), and the combined organic layers were dried over anhydrous magnesium sulfate. Insoluble materials were removed by filtration, and the filtrate was concentrated under reduced pressure. The residue was washed with THF to give the title compound (64.0 mg, 41%) as a white solid.

$^1$H-NMR (DMSO-$d_6$, 300 MHz) δ1.52-1.79 (3H, m), 1.89-2.16 (3H, m), 2.72 (3H, s), 3.63-3.75 (1H, m), 3.86-4.01 (4H, m), 5.63 (1H, dd, J=3.0, 8.9 Hz), 7.45-7.54 (3H, m), 7.72-7.75 (2H, m), 7.79-7.82 (1H, m), 7.99-8.09 (2H, m), 8.17 (1H, br s), 8.84 (1H, s), 10.15 (1H, t, J=1.3 Hz).

(ii) Production of 2-methyl-6-(1-methyl-1H-pyrazol-4-yl)-3-[4-phenyl-5-(1H-1,2,4-triazol-3-yl)-1,3-thiazol-2-yl]imidazo[1,2-a]pyridine A solution of 2-methyl-6-(1-methyl-1H-pyrazol-4-yl)-3-(4-phenyl-5-[1-(tetrahydro-2H-pyran-2-yl)-1H-1,2,4-triazol-3-yl]-1,3-thiazol-2-yl)imidazo[1,2-a]pyridine (84 mg, 0.16 mmol) obtained above in TFA (10 mL) was stirred at rt for 4 h. TFA was evaporated under reduced pressure, and then were added saturated aqueous solution of sodium bicarbonate (10 mL), water (10 mL) and EtOAc (20 mL). The resulting precipitate was collected by filtration, and then purified by silica gel column chromatography (EtOAc/hexane=80/20→100/0; then MeOH/EtOAc=30/70) to give the title compound (49.5 mg, 70%) as a yellow solid.

$^1$H-NMR (DMSO-$d_6$, 300 MHz) δ2.72 (3H, s), 3.91 (3H, s), 7.41-7.55 (3H, m), 7.68-7.78 (2H, m), 7.79-7.83 (1H, m), 7.99-8.07 (2H, m), 8.16-8.20 (1H, m), 8.64-8.70 (1H, m), 10.12-10.18 (1H, m), 14.36 (1H, br s).

Example 119-B

Production of 6-(2-fluoro-6-methoxyphenyl)-2-methyl-3-[4-phenyl-5-(1H-1,2,4-triazol-3-yl)-1,3-thiazol-2-yl]imidazo[1,2-a]pyridine

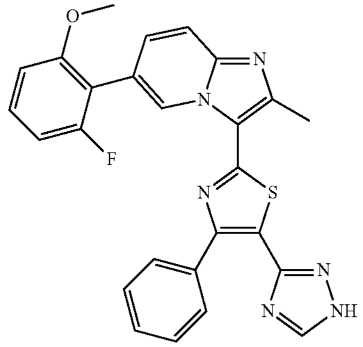 [SMILES: COc1cccc(F)c1-c1ccc2nc(C)c(-c3nc(-c4ccccc4)c(-c4nc[nH]n4)s3)n2c1]

(i) Production of 6-(2-fluoro-6-methoxyphenyl)-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine To a suspension of 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (157 mg, 0.3 mmol) obtained in Example 117-B(i) in DME (10 mL) and water (2 mL) were added (2-fluoro-6-methoxyphenyl)boronic acid (102 mg, 0.6 mmol), [1,1-bis(diphenylphosphino)ferrocene]palladium(II) dichloride dichloromethane complex (51 mg, 0.06 mmol) and cesium carbonate (293 mg, 0.9 mmol) under a nitrogen atmosphere, and the mixture was stirred at 95° C. for 2 h. The reaction mixture was allowed to cool to rt, and then were added water (40 mL) and EtOAc (40 mL). The aqueous layer was extracted with EtOAc (40 mL), and the combined organic layer was dried over anhydrous magnesium sulfate. Insoluble materials were removed by filtration, and the filtrate was concentrated under reduced pressure. The residue was purified by basic silica gel column chromatography (EtOAc/hexane=10/90→50/50) to give the title compound (156 mg, 92%) as a yellow solid.

$^1$H-NMR (DMSO-$d_6$, 300 MHz) δ1.51-1.73 (3H, m), 1.88-2.10 (3H, m), 2.76 (3H, s), 3.58-3.73 (1H, m), 3.81 (3H, s), 3.86-3.99 (1H, m), 5.62 (1H, dd, J=2.9, 8.8 Hz), 6.95-7.10 (2H, m), 7.39-7.50 (4H, m), 7.52-7.58 (1H, m), 7.78 (1H, dd, J=0.8 Hz, 9.3 Hz), 7.85-7.95 (2H, m), 8.83 (1H, m), 9.97-10.12 (1H, m).

(ii) Production of 6-(2-fluoro-6-methoxyphenyl)-2-methyl-3-[4-phenyl-5-(1H-1,2,4-triazol-3-yl)-1,3-thiazol-2-yl]imidazo[1,2-a]pyridine Using 6-(2-fluoro-6-methoxyphenyl)-2-methyl-3-{4-phenyl-5-[1-(tetrahydro-2H-pyran-2-yl)-1H-1,2,4-triazol-3-yl]-

1,3-thiazol-2-yl}imidazo[1,2-a]pyridine (156 mg, 0.275 mmol) obtained above and TFA (5.5 mL) as starting materials and in the similar manner described in Example 114-B(ii), the title compound (75 mg, 54%) was obtained as a white solid.

$^1$H-NMR (DMSO-$d_6$, 300 MHz) δ2.76 (3H, s), 3.81 (3H, s), 6.96-7.12 (2H, m), 7.36-7.51 (4H, m), 7.52-7.59 (1H, m), 7.75-7.82 (1H, m), 7.87-7.97 (2H, m), 8.57-8.78 (1H, m), 9.86-10.20 (1H, m), 14.34 (1H, br s).

Example 120-B

Production of 2-methyl-3-[4-phenyl-5-(1H-1,2,4-triazol-3-yl)-1,3-thiazol-2-yl]-6-vinylimidazo[1,2-a]pyridine

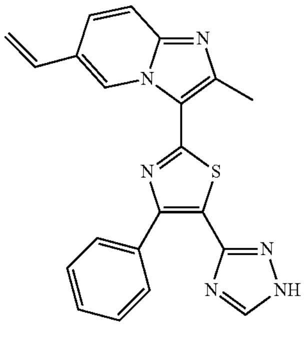 [SMILES: C=Cc1ccc2nc(C)c(-c3nc(-c4ccccc4)c(-c4nc[nH]n4)s3)n2c1]

(i) Production of 2-methyl-3-{4-phenyl-5-[1-(tetrahydro-2H-pyran-2-yl)-1H-1,2,4-triazol-3-yl]-1,3-thiazol-2-yl}-6-vinylimidazo[1,2-a]pyridine To a suspension of 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (1.04 g, 2.0 mmol) obtained by similar manner with Example 117-B(i) in DME (70 mL) and water (14 mL), were added potassiumvinyltrifluoroborate (410 mg, 3.0 mmol), [1,1-bis(diphenylphosphino)ferrocene]palladium(II) dichloride dichloromethane complex (170 mg, 0.2 mmol) and cesium carbonate (1.90 g, 6.0 mmol) under a nitrogen atmosphere, and the mixture was stirred at 95° C. for 4 h. The reaction mixture was allowed to cool to rt, and then was added EtOAc (40 mL). The resulting precipitate was collected by filtration and washed with water and diethyl ether to give the title compound (890 mg, 95%) as a gray solid.

$^1$H-NMR (DMSO-$d_6$, 300 MHz) δ 1.51-1.77 (3H, m), 1.89-2.15 (3H, m), 2.71 (3H, s), 3.62-3.74 (1H, m), 3.96-3.99 (1H, m), 5.39 (1H, d, J=11.0 Hz), 5.62 (1H, dd, J=2.8, 8.7 Hz), 5.93 (1H, d, J=17.6 Hz), 6.81 (1H, dd, J=11.1, 17.6 Hz), 7.40-7.59 (3H, m), 7.66-7.73 (1H, m), 7.75-7.82 (1H, m), 7.92-8.03 (2H, m), 8.83 (1H, s), 9.75-9.88 (1H, m).

(ii) Production of 2-methyl-3-[4-phenyl-5-(1H-1,2,4-triazol-3-yl)-1,3-thiazol-2-yl]-6-vinylimidazo[1,2-a]pyridine A solution of 2-methyl-3-{4-phenyl-5-[1-(tetrahydro-2H-pyran-2-yl)-1H-1,2,4-triazol-3-yl]-1,3-thiazol-2-yl}-6-vinylimidazo[1,2-a]pyridine (141 mg, 0.3 mmol) obtained above in TFA (6.0 mL), was stirred at rt for 2 h. TFA was evaporated under reduced pressure, and then were added saturated aqueous solution of sodium bicarbonate (5 mL), water (5 mL) and EtOAc (5 mL) were. The resulting precipitate was collected by filtration and dissolved in DMF (3 mL), which was subjected to basic silica gel column chromatography (EtOAc/hexane=20/80→100/0; then MeOH/EtOAc=30/70) to yield the title compound (70.5 mg, 61%) as a yellow solid.

$^1$H-NMR (DMSO-$d_6$, 300 MHz) δ 2.72 (3H, s), 5.40 (1H, d, J=11.0 Hz), 5.94 (1H, d, J=17.6 Hz), 6.82 (1H, dd, J=11.0, 17.4 Hz), 7.40-7.53 (3H, m), 7.68-7.74 (1H, m), 7.76-7.83 (1H, m), 7.93-7.98 (2H, m), 8.70 (1H, s), 9.84 (1H, s), 14.35 (1H, br s).

Example 121-B

Production of 6-[(4-acetylpiperazin-1-yl)methyl]-2-methyl-3-[4-phenyl-5-(1H-1,2,4-triazol-3-yl)-1,3-thiazol-2-yl]imidazo[1,2-a]pyridine

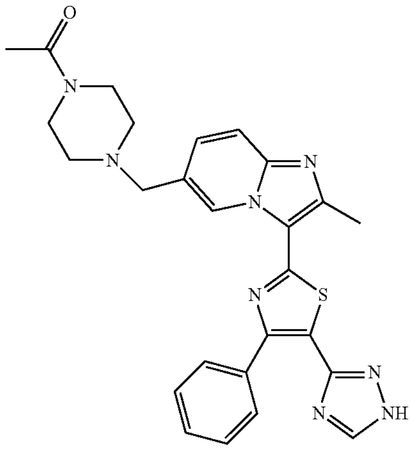 [SMILES: CC(=O)N1CCN(Cc2ccc3nc(C)c(-c4nc(-c5ccccc5)c(-c5nc[nH]n5)s4)n3c2)CC1]

(i) Production of 6-[(4-acetylpiperazin-1-yl)methyl]-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine To a suspension of 2-methyl-3-{4-phenyl-5-[1-(tetrahydro-2H-pyran-2-yl)-1H-1,2,4-triazol-3-yl]-1,3-thiazol-2-yl}-6-vinylimidazo[1,2-a]pyridine (282 mg, 0.60 mmol) obtained in Example 110-B (i) in THF (21 mL) and water (6 mL), were added 4% aqueous osmium tetraoxide solution (375 μL, 0.03 mmol) and sodium periodate (320 mg, 1.5 mmol), and the mixture was stirred at rt for 24 h. To the reaction mixture was added water (50 mL), and the resulting precipitate was collected by filtration. The residue was washed with water and diethyl ether to obtain a gray solid.

The above solid was suspended in DMF (4.3 mL), and then were added AcOH (430 μL), 1-acetylpiperazine (300 mg, 2.6 mmol) and sodium triacetoxyborohydride (540 mg, 2.6 mmol). The mixture was stirred at 50° C. for 2 h, allowed to cool to rt, and then concentrated under reduced pressure. To the residue, were added saturated aqueous solution of sodium bicarbonate (50 mL) and EtOAc (50 mL). The aqueous layer was extracted with EtOAc (50 mL), and the combined organic layers were dried over anhydrous magnesium sulfate. Insoluble materials were removed by filtration, and the filtrate was concentrated under reduced pressure. The residue was purified by basic silica gel column chromatography (EtOAc/ hexane=20/80→100/0; then MeOH/EtOAc=20/80) to give the title compound (79 mg, 23%) as a pale yellow solid.

$^1$H-NMR (DMSO-$d_6$, 300 MHz) δ1.53-1.73 (3H, m), 1.90-2.12 (6H, s), 2.37-2.47 (4H, m), 2.72 (3H, s), 3.39-3.48 (4H, m), 3.62 (2H, s), 3.65-3.73 (1H, m), 3.89-3.98 (1H, m), 5.62 (1H, dd, J=2.6, 8.4 Hz), 7.40-7.48 (4H, m), 7.65-7.71 (1H, m), 7.91-7.98 (2H, m), 8.80-8.83 (1H, m), 9.86 (1H, s).

(ii) Production of 6-[(4-acetylpiperazin-1-yl)methyl]-2-methyl-3-[4-phenyl-5-(1H-1,2,4-triazol-3-yl)-1,3-thiazol-2-yl]imidazo[1,2-a]pyridine A solution of 6-[(4-acetylpiperazin-1-yl)methyl]-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (77.0 mg, 0.13 mmol) obtained above in TFA (5.0 mL) was stirred at rt for 1 h. TFA was evaporated under reduced pressure, and the residue was again dissolved in TFA (5 mL). The mixture was stirred at rt for 1 h, and then TFA was evaporated under reduced pressure. To the residue were added saturated aqueous solution of sodium bicarbonate (5 mL), water (5 mL) and EtOAc (5 mL). The resulting precipitate was collected by filtration and washed with water and diethyl ether to give the title compound (25 mg, 38%) as a pale yellow solid.

$^1$H-NMR (DMSO-$d_6$, 300 MHz) δ 1.96 (3H, s), 2.33-2.48 (4H, s), 2.71 (3H, s), 3.34-3.48 (4H, m), 3.63 (2H, s), 7.34-7.48 (5H, m), 7.62-7.71 (1H, m), 8.05-8.16 (2H, m), 8.37 (1H, s), 9.87 (1H, s).

Example 122-B

Production of 6-cyclohexyl-2-methyl-3-[4-phenyl-5-(1H-1,2,4-triazol-3-yl)-1,3-thiazol-2-yl]imidazo[1,2-a]pyridine

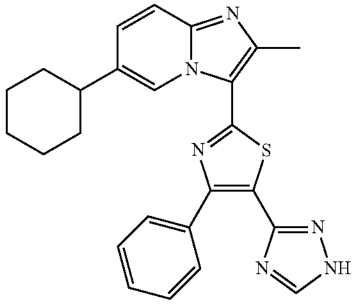 [SMILES: Cc1nc2ccc(C3CCCCC3)cn2c1-c1nc(-c2ccccc2)c(-c2nc[nH]n2)s1]

(i) Production of 6-bromo-2-methylimidazo[1,2-a]pyridine-3-carboxylic acid

To a solution of 2-amino-5-bromopyridine (25.0 g, 144.5 mmol) in EtOH (150 mL), was added methyl 2-chloro-3-acetoacetate (18.6 mL, 144.5 mmol), and the mixture was refluxed at 80° C. for 12 h. Then the reaction mixture was allowed to cool to rt, and then were added 8N aqueous sodium hydroxide solution (60 mL, 480 mmol) and water (30 mL). The mixture was stirred at 80° C. for 12 h, allowed to cool to 0° C., and then neutralized by the addition of 6N hydrochloric acid (300 mL). The resulting precipitate was collected by filtration and sequentially washed with water, EtOH and diethyl ether to give the title compound (11.1 g, 30%) as a brown solid.

$^1$H-NMR (DMSO-$d_6$, 300 MHz) δ2.59 (3H, s), 7.55-7.77 (2H, m), 9.41 (1H, dd, J=1.3, 1.3 Hz), 13.29 (1H, br s).

(ii) Production of 6-bromo-2-methylimidazo[1,2-a]pyridine-3-carboxamide

To a suspension of 6-bromo-2-methylimidazo[1,2-a]pyridine-3-carboxylic acid (11.0 g, 43.1 mmol) obtained above in toluene (200 mL), was added thionyl chloride (31.5 mL, 430 mmol), and the mixture was refluxed for 4 h. The mixture was allowed to cool to rt, and volatiles were removed under reduced pressure. The residue was dissolved in THF (200 mL), and was slowly added 25% aqueous ammonia solution (30 mL) at 0° C. The mixture was stirred at rt for 14 h. The resulting precipitate was collected by filtration and washed with water, EtOH and diethyl ether to give the title compound (5.0 g, 46%) as a brown solid.

$^1$H-NMR (DMSO-$d_6$, 300 MHz) δ2.56 (3H, s), 7.71-7.77 (1H, m), 7.82 (1H, dd, J=1.9, 9.4 Hz), 9.54 (1H, br s), 9.60 (1H, dd, J=0.9, 1.9 Hz), 10.22 (1H, br s).

(iii) Production of 6-bromo-2-methylimidazo[1,2-a]pyridine-3-carbonitrile 6-bromo-2-methylimidazo[1,2-a]pyridine-3-carboxamide (10.8 g, 42.4 mmol) obtained above was treated with phosphoryl chloride (85 mL) and DMF (50 μL) under reflux condition for 17 h. The mixture was allowed to cool to rt, and then volatiles were removed under reduced pressure. The residue was diluted with toluene (50 mL) and then was added ice-cooled saturated aqueous solution of sodium bicarbonate (200 mL). The mixture was neutralized by the addition of 1N aqueous sodium hydroxide solution (40 mL), the aqueous layer was extracted with EtOAc (250 mL×3), and the combined organic layer was dried over anhydrous magnesium sulfate and decolorized with activated carbon. Insoluble materials were removed by filtration and the filtrate was concentrated under reduced pressure to give the title compound (7.25 g, 73%) as a pale yellow solid.

$^1$H-NMR (DMSO-$d_6$, 300 MHz) δ 2.49 (3H, s), 7.63-7.77 (2H, m), 8.86 (1H, dd, J=1.3 Hz).

(iv) production of 6-bromo-2-methylimidazo[1,2-a]pyridine-3-carbothioamide

To a suspension of 6-bromo-2-methylimidazo[1,2-a]pyridine-3-carbonitrile (6.2 g, 26.4 mmol) obtained above in MeOH (88 mL), were added 4N solution of hydrogen chloride in EtOAc (22 mL, 88.0 mmol) and O,O-diethyl hydrogen dithiophosphate (25 mL, 158 mol), and the mixture was stirred at 60° C. for 3 h. The mixture was allowed to cool to rt, and diluted with diisopropyl ether (100 mL). The resulting precipitate was collected by filtration and washed with diethyl ether to give the title compound (6.2 g, 77%) as a pale yellow solid.

$^1$H-NMR (DMSO-$d_6$, 300 MHz) δ 2.56 (3H, s), 7.71-7.77 (1H, m), 7.82 (1H, dd, J=1.9, 9.4 Hz), 9.54 (1H, br s), 9.60 (1H, dd, 0.9, 1.9 Hz), 10.22 (1H, br s).

(v) production of ethyl 2-(6-bromo-2-methylimidazo[1,2-a]pyridin-3-yl)-4-phenyl-1,3-thiazole-5-carboxylate To a suspension of 6-bromo-2-methylimidazo[1,2-a]pyridine-3-carbothioamide (700 mg, 2.59 mmol) obtained as described above in DMF (60 mL), was added ethyl 2-chloro-3-oxo-3-phenylpropanoate (1.76 g, 7.77 mmol), and the mixture was stirred at 90° C. for 21 h. The mixture was allowed to cool to rt, and the solvent was removed under reduced pressure. The residue was washed with water, EtOH and diethyl ether to give the titled compound (750 mg, 66%) as a pale yellow solid.

$^1$H-NMR (DMSO-$d_6$, 300 MHz) δ 1.25 (3H, t, J=7.1 Hz), 2.72 (3H, s), 4.27 (2H, q, J=7.0 Hz), 7.47-7.57 (3H, m), 7.69 (1H, dd, J=1.9, 9.4 Hz), 7.71-7.78 (1H, m), 7.82-7.90 (2H, m), 9.89-10.09 (1H, m).

(vi) Production of ethyl 2-(6-cyclohex-1-en-1-yl-2-methylimidazo[1,2-a]pyridin-3-yl)-4-phenyl-1,3-thiazole-5-carboxylate To a mixture of ethyl 2-(6-bromo-2-methylimidazo[1,2-a] pyridin-3-yl)-4-phenyl-1,3-thiazole-5-carboxylate (267 mg, 0.6 mmol) obtained above in DME (18 mL) and water (3.6 mL), were added 2-cyclohex-1-en-1-yl-4,4,5,5-tetramethyl-1,3,2-dioxaborolane (250 mg, 1.2 mmol), cesium carbonate (586 mg, 1.8 mmol) and [1,1-bis(diphenylphosphino)ferrocene]palladium(II) dichloride dichloromethane complex (49.1 mg, 0.06 mmol) under a nitrogen atmosphere, and the mixture was stirred at 95° C. for 3 h. The reaction mixture was allowed to cool to rt. The resulting precipitate was collected by filtration and washed with water and diethyl ether to give the title compound (223 mg, 84%) as a white solid.

$^1$H-NMR (DMSO-$d_6$, 300 MHz) δ 1.27 (3H, t, J=7.1 Hz), 1.58-1.69 (2H, m), 1.71-1.81 (2H, m), 2.17-2.30 (2H, m), 2.36-2.46 (2H, m), 2.69 (3H, s), 4.29 (2H, q, J=7.2 Hz), 6.38-6.48 (1H, m), 7.47-7.55 (3H, m), 7.62-7.68 (1H, m), 7.78 (1H, dd, J=1.9, 9.4 Hz), 7.93-7.99 (2H, m), 9.99-10.05 (1H, m).

(vii) Production of ethyl 2-(6-cyclohexyl-2-methylimidazo[1,2-a]pyridin-3-yl)-4-phenyl-1,3-thiazole-5-carboxylate To a mixture of ethyl 2-(6-cyclohex-1-en-1-yl-2-methylimidazo[1,2-a]pyridin-3-yl)-4-phenyl-1,3-thiazole-5-carboxylate (200 mg, 0.45 mmol) obtained above in acetic acid (18 mL) and MeOH (18 mL), was added 10% palladium-carbon (100 mg), and the mixture was stirred at rt for 15 h under a hydrogen atmosphere (1 atm). Insoluble materials were removed by filtration, and the filtrate was concentrated under reduced pressure. To the residue was added saturated aqueous solution of sodium bicarbonate (10 mL) and water (10 mL), and the resulting precipitate was collected by filtration, which was washed with diethyl ether to give the title compound (154 mg, 69%) as a black solid.

$^1$H-NMR (DMSO-$d_6$, 300 MHz) δ1.15-1.31 (4H, m), 1.35-1.47 (3H, m), 1.68-1.86 (3H, m), 1.92-2.06 (2H, m), 2.19-2.34 (1H, m), 2.55-2.66 (1H, m), 2.69 (3H, m), 4.28 (2H, q, 7.0 Hz), 7.45-7.57 (4H, m), 7.61-7.71 (1H, m), 7.88-8.02 (2H, m), 9.77-9.85 (1H, m).

(viii) Production of 2-(6-cyclohexyl-2-methylimidazo[1,2-a]pyridin-3-yl)-4-phenyl-1,3-thiazole-5-carboxylic acid A mixture of ethyl 2-(6-cyclohexyl-2-methylimidazo[1,2-a]pyridin-3-yl)-4-phenyl-1,3-thiazole-5-carboxylate (204 mg, 0.458 mmol) obtained above in THF (5 mL) and MeOH (5 mL), was added 2N aqueous sodium hydroxide (750 μL), and the mixture was stirred at 50° C. for 12 h. The mixture was allowed to cool to rt and then neutralized by the addition of 1N aqueous hydrochloric acid (1.5 mL). The resulting precipitate was collected by filtration and then washed with water and diethyl ether to give the title compound (159 mg, 83%) as a gray solid.

$^1$H-NMR (DMSO-$d_6$, 300 MHz) δ1.15-1.30 (1H, m), 1.31-1.49 (3H, m), 1.67-1.87 (3H, m), 1.92-2.07 (2H, m), 2.36-2.45 (1H, m), 2.56-2.79 (4H, m), 7.41-7.59 (4H, m), 7.60-7.70 (1H, m), 7.90-8.06 (2H, m), 9.66-9.90 (1H, m), 13.38 (1H, br s).

(ix) Production of 2-(6-cyclohexyl-2-methylimidazo[1,2-a]pyridin-3-yl)-4-phenyl-1,3-thiazole-5-carboxamide To a suspension of 2-(6-cyclohexyl-2-methylimidazo[1,2-a]pyridin-3-yl)-4-phenyl-1,3-thiazole-5-carboxylic acid (169 mg, 0.405 mmol) obtained above in DMF (8 mL), were added TEA (170 μL, 1.22 mmol), ammonium chloride (65.0 mg, 1.22 mmol), HOBT (82 mg, 0.61 mmol) and EDCI (120 mg, 0.61 mmol), and the mixture was stirred at it for 12 h. To the mixture was added DMF (8.0 mL), and the mixture was stirred 40° C. for 2 h. The reaction mixture was allowed to cool to rt, DMF (30 mL) was added, and the mixture was warmed to 60° C. The solution was concentrated until ca 10 mL under reduced pressure. The residue was subjected to basic silica gel column chromatography (EtOAc/hexane=20/80→100/0; then MeOH/EtOAc=30/70). Concentration of the appropriate solution afforded crude product, which was suspended in saturated aqueous solution of sodium bicarbonate (10 mL) and water (10 mL). The resulting precipitate was collected by filtration and washed with water and diethyl ether to give the titled compound (104 mg, 62%) as a orange solid.

$^1$H-NMR (DMSO-$d_6$, 300 MHz) δ 1.21-1.33 (1H, m), 1.40-1.52 (3H, m), 1.69-1.91 (3H, m), 1.96-2.05 (2H, m), 2.23-2.32 (1H, m), 2.68 (3H, s), 2.71-2.76 (1H, m), 7.41-7.57 (4H, m), 7.61-7.68 (1H, m), 7.82 (2H, br s), 7.92 (2H, s), 9.76-9.83 (1H, m).

(x) Production of 6-cyclohexyl-2-methyl-3-[4-phenyl-5-(1H-1,2,4-triazol-3-yl)-1,3-thiazol-2-yl]imidazo[1,2-a]pyridine A suspension of 2-(6-cyclohexyl-2-methylimidazo[1,2-a] pyridin-3-yl)-4-phenyl-1,3-thiazole-5-carboxamide (104 mg, 0.25 mmol) obtained above in N,N-dimethylformamide dimethylacetal (20 mL) was stirred at 100° C. for 12 h. The reaction mixture was allowed to cool to rt and then concentrated under reduced pressure. The residue was suspended in AcOH (5 mL), and then was added hydrazine monohydrate (70 mL, 1.4 mmol) at 0° C., and the mixture was stirred at 90° C. for 1 h, allowed to cool to rt, and then concentrated under reduced pressure. The residue was diluted with EtOAc (20 mL), water (10 mL) and saturated aqueous solution of sodium bicarbonate (10 mL), and the aqueous layer was extracted with a 2:1 mixture of EtOAc and THF (30 mL). The combined organic layers were dried over anhydrous magnesium sulfate. Insoluble materials were removed by filtration, and the filtrate was concentrated under reduced pressure.

The residue was purified by silica gel column chromatography (EtOAc/hexane=20/80→100/0; then MeOH/EtOAc=20:80) to give the title compound (57.3 mg, 52%) as a pale yellow solid.

$^1$H-NMR (DMSO-$d_6$, 300 MHz) δ 1.20-1.32 (1H, m), 1.38-1.50 (3H, m), 1.70-1.88 (4H, m), 1.96-2.07 (2H, m), 2.59-2.78 (4H, m), 7.36-7.52 (4H, m), 7.60-7.68 (1H, m), 8.00-8.10 (2H, m), 8.60 (1H, s), 9.75-9.94 (1H, m), 14.13 (1H, br s).

Example 123-B

Production of 3,6-dimethyl-5-[4-phenyl-5-(1H-1,2,4-triazol-3-yl)-1,3-thiazol-2-yl]imidazo[2,1-b][1,3]thiazole

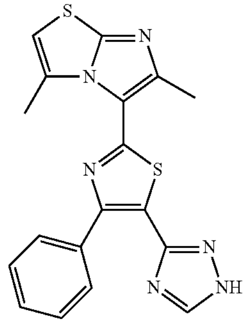 [SMILES: Cc1nc2scc(C)n2c1-c1nc(-c2ccccc2)c(-c2nc[nH]n2)s1]

To a mixture of 1-bromo-1-{4-phenyl-5-[1-(tetrahydro-2H-pyran-2-yl)-1H-1,2,4-triazol-3-yl]-1,3-thiazol-2-yl}acetone (1.15 g, 2.5 mmol) obtained by similar manner with Example 116-B(vi) in THF (12.5 mL) and 2-propanol (12.5 mL), was added 2-amino-4-methylthiazole (1.43 g, 12.5 mmol), the mixture was stirred at 80° C. for 4 h. The reaction mixture was allowed to cool to 50° C., 2N hydrochloric acid (12.5 mL) was added, and the mixture was stirred for 12 h. The reaction mixture was allowed to cool to rt, and then neutralized by the addition of 2N aqueous sodium hydroxide solution (12.5 mL). The mixture was extracted with EtOAc (50 mL×2), and the combined organic layers were dried over anhydrous magnesium sulfate. Insoluble materials were removed by filtration, and the filtrate was concentrated under reduced pressure. The residue was purified by basic silica gel column chromatography (EtOAc/hexane=50/50→100/0; then MeOH/EtOAc=30/70) followed by silica gel column chromatography (EtOAc/hexane=30/70→100/0) to give the title compound (88 mg, 9%) as a yellow solid.

$^1$H-NMR (DMSO-$d_6$, 300 MHz) δ2.45 (3H, d, J=1.1 Hz), 2.48 (3H, s), 6.98 (1H, d, J=1.3 Hz), 7.34-7.49 (3H, m), 7.76-7.86 (2H, m), 8.60-8.77 (1H, m), 14.34 (1H, br s).

Example 124-B

Production of 6-methyl-7-[5-phenyl-4-(1H-1,2,4-triazol-3-yl)-1,3-thiazol-2-yl]pyrazolo[5,1-b][1,3]thiazole

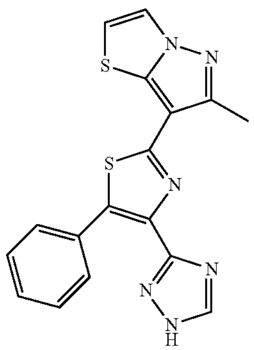 [SMILES: Cc1nn2ccsc2c1-c1nc(-c2nc[nH]n2)c(-c2ccccc2)s1]

(i) Production of 3-bromo-2-oxo-3-phenylpropanoic acid

To a stirred suspension of Phenylpyruvic acid (5.0 g, 30.5 mmol) in AcOH (20 ml), was added dropwise a solution of bromine (1.57 mL, 30.5 mmol) in AcOH (5 ml) over 1 h at rt. After complete addition, stirring was continued for additional 30 min at the same temperature and then the reaction mixture was concentrated under reduced pressure. To the residue was added diisopropyl ether (30 ml) and the mixture was concentrated under reduced pressure. To the residue was added 1,2-dichloroethane (30 ml) and then the solution was kept on standing for 3 days at room temperature. The resultant precipitate was removed by filtration. To the filtrate was added hexane (20 mL) and the resulting precipitate was collected by filtration to obtain title compound (837 mg, 11%) as a colorless solid.

From the filtrate, second crop of the title compound (1.55 g, 21%) has been obtained as a colorless solid which was used in the next step without further purification. $^1$H-NMR (300 MHz, DMSO-$d_6$) δ 6.53 (1H, s), 7.36-7.48 (6H, m).

(ii) Production of 2-(6-methylpyrazolo[5,1-b][1,3]thiazol-7-yl)-5-phenyl-1,3-thiazole-4-carboxylic acid A mixture of 3-bromo-2-oxo-3-phenylpropanoic acid (197 mg, 1.00 mmol) and 6-methylpyrazolo[5,1-b][1,3]thiazole-7-carbothioamide (267 mg, 1.10 mmol) in EtOH (10 ml) was stirred at 50° C. for 1 h. The reaction mixture was allowed to cool to rt, the resulting precipitate was collected by filtration and then washed with EtOAc to obtain title compound (328 mg, 96%) as a colorless solid. 1H-NMR (DMSO-d6) δ 2.61 (3H, s), 7.43-7.59 (6H, m) 8.31 (1H, d, J=4.2 Hz), 12.99 (1H, br s).

(iii) Production of 2-(6-methylpyrazolo[5,1-b][1,3]thiazol-7-yl)-5-phenyl-1,3-thiazole-4-carboxamide According to the similar manner described in Example 97-B (iii), the title compound (126 mg, 45%) has been obtained as a colorless solid by standard amidation reaction using 2-(6-methylpyrazolo[5,1-b][1,3]thiazol-7-yl)-5-phenyl-1,3-thiazole-4-carboxylic acid (280 mg, 0.820 mmol) obtained above. The pure title compound has been obtained by washing of the crude product, which was precipitated from reaction mixture after aqueous work-up, with water and EtOAc. Second crop of the title compound (77.7 mg, 28%) has been obtained from above filtrate after standard extraction of the aqueous mixture. 1H-NMR (DMSO-d6) δ 2.62 (3H, s), 7.40-7.48 (3H, m), 7.54 (1H, d, J=3.9 Hz), 7.60-7.65 (3H, m), 7.69 (1H, br s), 8.32 (1H, d, J=4.2 Hz).

(iv) Production of 6-methyl-7-[5-phenyl-4-(1H-1,2,4-triazol-3-yl)-1,3-thiazol-2-yl]pyrazolo[5,1-b][1,3]thiazole According to the similar manner described in Example 97-B (iv), the title compound (24.2 mg, 18%) has been obtained as a pale yellow solid using 2-(6-methylpyrazolo[5,1-b][1,3]thiazol-7-yl)-5-phenyl-1,3-thiazole-4-carboxamide (126 mg, 0.370 mmol) obtained above. The pure title compound was obtained by extraction of the reaction mixture with EtOAc and then crystallized from EtOAc. The second crop of the title compound (34.2 mg, 25%) has been obtained from aqueous layer by spontaneous crystallization. 1H-NMR (DMSO-d6) δ 2.66 (3H, s), 7.39-7.54 (7H, m), 8.32 (1H, d, J=4.2 Hz), 14.26 (1H, brs).

Example 125-B

Production of N-[4'-methyl-4-phenyl-5-(1H-1,2,4-triazol-3-yl)-2,5'-bi-1,3-thiazol-2'-yl]cyclopropanecarboxamide hydrochloride

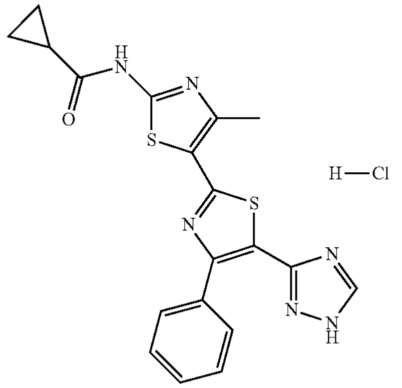 [SMILES: Cc1nc(NC(=O)C2CC2)sc1-c1nc(-c2ccccc2)c(-c2nc[nH]n2)s1 ; Cl]

To a solution of 1-bromo-1-{4-phenyl-5-[1-(tetrahydro-2H-pyran-2-yl)-1H-1,2,4-triazol-3-yl]-1,3-thiazol-2-yl}acetone (700 mg, 1.93 mmol) obtained in Example 116-B (vi) in THF (30 mL) and isopropyl alcohol (30 mL), was added thiourea (2.3 g, 30.2 mmol). The mixture was refluxed for 4 h with vigorous stirring. The mixture was allowed to cool to rt and the diluted with EtOAc (100 mL), which was washed with saturated aqueous solution of sodium bicarbonate (100 mL). The aqueous layer was extracted with EtOAc (100 mL). The combined organic layers were dried over anhydrous magnesium sulfate. Insoluble materials were removed by filtration and the filtrate was concentrated under reduced pressure. The residue (680 mg) has been used in the next step with out further purification.

To a solution of above residue (329 mg) in pyridine (10 mL) were added cyclopropanecarbonyl chloride (1.0 mL, 11.0 mmol) and DMAP (21.5 mg, 0.176 mmol) and the mixture was stirred for 1 h at rt. To the mixture, was added MeOH (30 mL) and the mixture was stirred for 10 h at rt. The mixture was concentrated under reduced pressure and the residue was suspended in water (50 mL). The aqueous mixture was extracted with EtOAc (50 mL×2) and the combined organic layers were washed with saturated aqueous solution of ammonium chloride (50 mL), dried over anhydrous magnesium sulfate. Insoluble materials were removed by filtration and the filtrate was concentrated under reduced pressure. The residue was suspended in EtOAc and insoluble materials were removed by filtration and the filtrate was purified by silica gel column chromatography (EtOAc/hexane=80/100→100/0) to obtain yellow foam (132 mg).

To a solution of above yellow foam in THF (3 mL) were added MeOH (3 mL) and 4 N solution of hydrogen chloride in EtOAc (3 mL). The mixture was refluxed for 2.5 h with vigorous stirring. The mixture was allowed to cool to rt and then concentrated under reduced pressure. The residual crystalline material was washed with hot EtOAc and the remaining precipitate was collected by filtration to obtain title compound (80 mg, 19%) as an off-white solid. $^{1}$H-NMR (DMSO-$d_6$, 300 MHz) δ 0.74-1.02 (4H, m), 1.76-2.07 (1H, m), 2.61 (3H, s), 7.20-7.52 (3H, m), 7.81 (2H, d, J=9.6 Hz), 8.63 (1H, s), 12.70 (1H, br s).

Example 126-B

Synthesis of {4-[2-(2-methylpyrazolo[1,5-a]pyridin-3-yl)-5-(1H-1,2,4-triazol-3-yl)-1,3-thiazol-4-yl]phenyl}methanol (135-B)

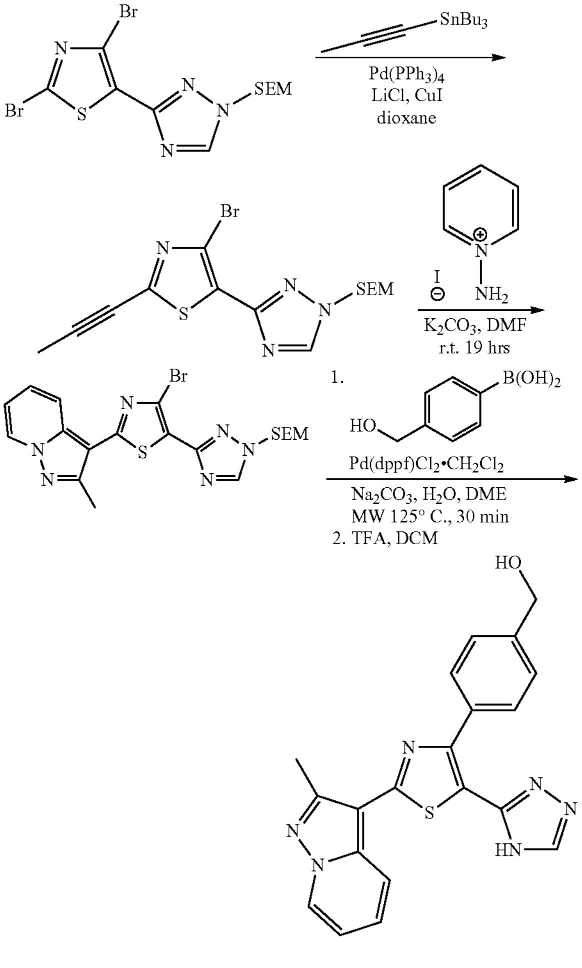

Step 1: Synthesis of 3-(4-bromo-2-prop-1-yn-1-yl-1,3-thiazol-5-yl)-1-{[2-(trimethylsilyl)ethoxy]methyl}-1H-1,2,4-triazole A mixture of 3-(2,4-dibromo-1,3-thiazol-5-yl)-1-{[2-(trimethylsilyl)ethoxy]methyl}-1H-1,2,4-triazole (6.00 g, 13.6 mmol), Lithium chloride (1.73 g, 40.9 mmol), Copper(I) iodide (0.779 g, 4.09 mmol) and Tetrakis(triphenylphosphine)platinum (0) (0.848 g, 0.681 mmol) in anhydrous 1,4-Dioxane (120 mL, 1500 mmol) was sonicated under Argon atmosphere for 2 minutes in a 250 mL RBF. Tributyl(1-propynyl)tin (4.80 mL, 15.0 mmol) was added. The mixture was heated to 100° C. for 1 hour under Argon atmosphere. The mixture was cooled to r.t., diluted with DCM (~150 mL), filtered through Celite, and washed with DCM. The filtrate was rotavaped to give a crude residue. Chromatograph in a 330 g ISCO column using EtOAc/hexane (0/100 to 50/50)

gave a pure solid product (4.14 g, 76% yield). LCMS: (FA) $ES^+$ 399, 401. $^1$H NMR (400 MHz, $d_1$-chloroform) δ 8.29 (s, 1H), 5.54 (s, 2H), 3.69-3.74 (m, 2H), 2.15 (s, 3H), 0.93-0.97 (m, 2H), 0.00 (s, 9H).

Step 2: Synthesis of 3-[4-bromo-5-(1-{[2-(trimethylsilyl)ethoxy]methyl}-1H-1,2,4-triazol-3-yl)-1,3-thiazol-2-yl]-2-methylpyrazolo[1,5-a]pyridine A mixture of 3-(4-bromo-2-prop-1-yn-1-yl-1,3-thiazol-5-yl)-1-{[2-(trimethylsilyl)ethoxy]methyl}-1H-1,2,4-triazole (0.514 g, 1.29 mmol), 1-Aminopyridinium iodide (0.343 g, 1.54 mmol) and Potassium carbonate (0.231 g, 1.67 mmol) in N,N-Dimethylformamide (8.0 mL, 1.0E2 mmol) was stirred at r.t. for 29 hours. The mixture was quenched with ice water (80 mL), extracted with EtOAc 3 times. The combined EtOAc solution was washed with water, brine, dried over $Na_2SO_4$, filtered and EtOAc/hexane (0/100 to 30/70) to afford a solid product. (0.410 g, 64.8% yield). LCMS: (FA) $ES^+$491, 493. $^1$H NMR (400 MHz, $d_1$-chloroform) δ 8.43-8.46 (m, 2H), 8.32 (s, 1H), 7.39-7.42 (m, 1H), 6.90-6.93 (m, 1H), 5.57 (s, 2H), 3.72-3.76 (m, 2H), 2.76 (s, 3H), 0.96-1.00 (m, 2H), 0.00 (s, 9H).

Step 3: Synthesis of {4-[2-(2-methylpyrazolo[1,5-a]pyridin-3-yl)-5-(1H-1,2,4-triazol-3-yl)-1,3-thiazol-4-yl]phenyl}methanol (135-B)

Into a microwave vial containing a mixture of 4-bromo-2-(2-methylpyrazolo[1,5-a]pyridin-3-yl)-5-(1-((2-(trimethylsilyl)ethoxy)methyl)-1H-1,2,4-triazol-3-yl)thiazole (0.030 g, 0.061 mmol) and 4-(hydroxymethyl)phenylboronic acid (0.026 g, 0.17 mmol) was added 1M aqueous $NaHCO_3$ (0.15 mL, 0.15 mmol), [1,1'-Bis(diphenylphosphino)ferrocene] palladium(II) dichloride (0.0021 g, 0.003 mmol) and 1,2-dimethoxyethane (0.60 mL). The vial was flushed with nitrogen gas and the reaction mixture was heated at 125° C. in a Biotage Microwave reactor for 30 minutes. Upon cooling to room temperature, the reaction was concentrated in vacuo and the residue obtained was partitioned between water (2 mL) & a mixture of $CHCl_3$/THF (4:1, 3 mL). Upon separation of the layers, the aqueous layer was extracted with additional $CHCl_3$/THF (4:1, 3 mL), the combined layers were filtered and concentrated. The material obtained was dissolved in methylene chloride (0.75 mL) and to this solution was added trifluoroacetic acid (0.5 mL, 6.4 mmol). The resulting reaction mixture was stirred overnight at room temperature. The reaction was concentrated in vacuo, the residue re-dissolved in DMSO (1 mL), filtered and purified on Agilent A2 prep instrument mass triggered reverse phase chromatography (Waters Sunfire prep C18 10 mm 19×150 mm column). Concentration of fractions containing desired product afforded product (0.0061 g, 26% yield). LCMS: (FA) $ES^+$ 390.

Compounds in the following table were prepared from the appropriate starting materials in a method analogous to that of Example 126-B:

| | |
|---|---|
| 126-B | LCMS: (FA) ES+ 411. |
| 129-B | LCMS: (FA) ES+ 466. |
| 130-B | LCMS: (FA) ES+ 378. |
| 131-B | LCMS: (FA) ES+ 411. |
| 133-B | LCMS: (FA) ES+ 380. |
| 134-B | LCMS: (FA) ES+ 365. |
| 136-B | LCMS: (FA) ES+ 361. |
| 137-B | LCMS: (FA) ES+ 400. |
| 140-B | LCMS: (FA) ES+ 441. |
| 141-B | LCMS: (FA) ES+ 392. |
| 142-B | LCMS: (FA) ES+ 428. |
| 143-B | LCMS: (FA) ES+ 452. |
| 144-B | LCMS: (FA) ES+ 402. |
| 145-B | LCMS: (FA) ES+ 388. |
| 146-B | LCMS: (FA) ES+ 445. |
| 148-B | LCMS: (FA) ES+ 348. |
| 149-B | LCMS: (FA) ES+ 418. |
| 150-B | LCMS: (FA) ES+ 389. |
| 151-B | LCMS: (FA) ES+ 432. |
| 152-B | LCMS: (FA) ES+ 463. |
| 153-B | LCMS: (FA) ES+ 466. |
| 154-B | LCMS: (FA) ES+ 494. |
| 155-B | LCMS: (FA) ES+ 445. |
| 158-B | LCMS: (FA) ES+ 396. |
| 163-B | LCMS: (FA) ES+ 378. |
| 164-B | LCMS: (FA) ES+ 446. |

Example 127-B

Synthesis of 4-chloro-3-[2-(2-methylpyrazolo[1,5-a]pyridin-3-yl)-5-(1-{[2-(trimethylsilyl)ethoxy]methyl}-1H-1,2,4-triazol-3-yl)-1,3-thiazol-4-yl]benzaldehyde (160-B)

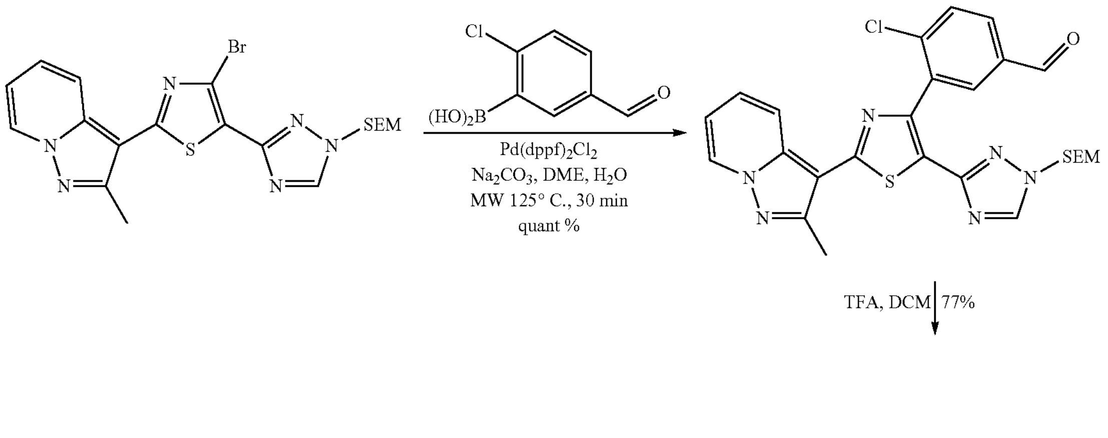

-continued

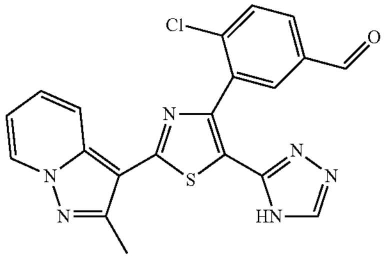

Step 1: Synthesis of 4-chloro-3-[2-(2-methylpyrazolo[1,5-a]pyridin-3-yl)-5-(1-{[2-(trimethylsilyl)ethoxy]methyl}-1H-1,2,4-triazol-3-yl)-1,3-thiazol-4-yl]benzaldehyde A mixture of 3-[4-bromo-5-(1-{[2-(trimethylsilyl)ethoxy]methyl}-1H-1,2,4-triazol-3-yl)-1,3-thiazol-2-yl]-2-methylpyrazolo[1,5-a]pyridine (0.0220 g, 0.0448 mmol), 2-Chloro-5-formylphenylboronicacid (15.0 mg, 0.0814 mmol), sodium carbonate (8.63 mg, 0.0814 mmol) and [1,1'-Bis(diphenylphosphino)ferrocene]dichloropalladium(II), complex with dichloromethane (1:1) (1.8 mg, 0.0022 mmol) in 1,2-Dimethoxyethane (0.50 mL, 4.8 mmol) with Water (0.050 mL, 2.8 mmol) in a MW vial was heated to 125° C. for 30 min. The mixture was cooled to r.t., diluted with DCM, filtered through Celite/$Na_2SO_4$. The filtrate was concentrated in rotavapor to give a crude product. Chromatograph in a 12 g ISCO column using EtOAc/hexane (0/100 to 40/60) to afford a solid product. (0.0265 g, 99.9% yield). LCMS: (FA) $ES^+$ 551, 553. $^1H$ NMR (400 MHz, $d_1$-chloroform) δ 10.05 (s, 1H), 8.44 (m, 2H), 8.13-8.15 (m, 2H), 7.90-7.93 (m, 1H), 7.64-7.66 (m, 1H), 7.33 (m, 1H), 6.88-6.90 (m, 1H), 5.40 (s, 2H), 3.58 (t, J=8.03 Hz, 2H), 2.82 (s, 3H), 0.90 (t, J=8.03 Hz, 2H), δ 0.00 (s, 9H).

Step 2: Synthesis of 4-chloro-3-[2-(2-methylpyrazolo[1,5-a]pyridin-3-yl)-5-(4H-1,2,4-triazol-3-yl)-1,3-thiazol-4-yl]benzaldehyde (160-B)

4-Chloro-3-[2-(2-methylpyrazolo[1,5-a]pyridin-3-yl)-5-(1-{[2-(trimethylsilyl)ethoxy]methyl}-1H-1,2,4-triazol-3-yl)-1,3-thiazol-4-yl]benzaldehyde (0.0230 g, 0.0388 mmol) was treated with Trifluoroacetic Acid (1.0 mL, 13 mmol) in Methylene chloride (1.0 mL, 16 mmol) at r.t. for 20 hours. The mixture was rotavaped. The residue was basified with saturated $NaHCO_3$, extracted with EtOAc. The EtOAc solution was washed with water, brine, dried over $Na_2SO_4$, filtered, rotavaped to give a crude product. Chromatograph in a 12 g ISCO column using MeOH/DCM (0/100 to 5/95) gave a solid product. (0.0125 g, 76.5% yield). LCMS: (FA) $ES^+$ 421, 423. $^1H$ NMR (400 MHz, $d_1$-chloroform & d4-methanol) δ 9.93 (s, 1H), 8.32-8.37 (m, 2H), 8.04-8.07 (m, 2H), 7.82-7.85 (m, 1H), 7.57-7.60 (m, 1H), 7.26-7.30 (m, 1H), 6.82-6.86 (m, 1H), 2.72 (s, 3H).

Example 128-B

Synthesis of N-(4-chlorophenyl)-N-methyl-2-(2-methylpyrazolo[1,5-a]pyridin-3-yl)-5-(4H-1,2,4-triazol-3-yl)-1,3-thiazol-4-amine (156-B)

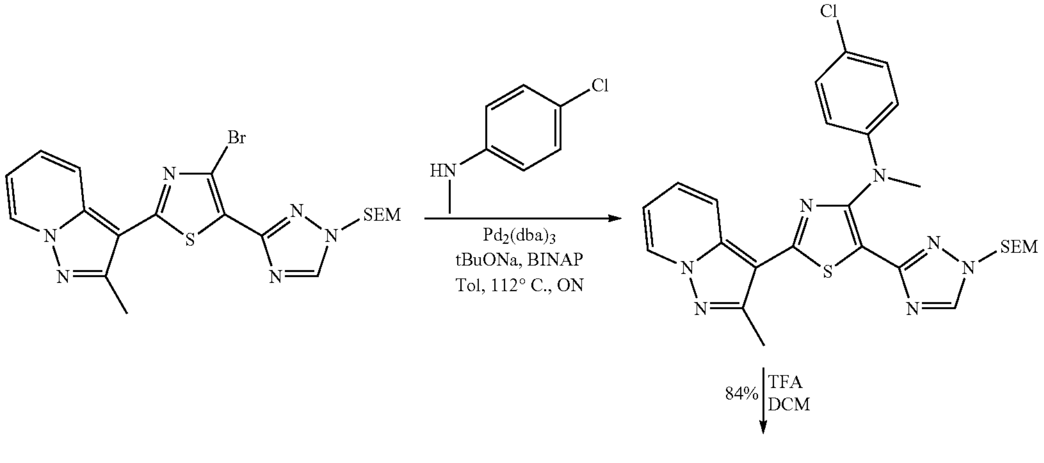

-continued

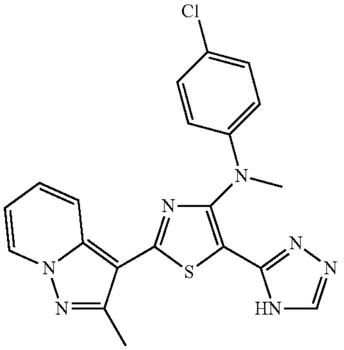

Step 1: Synthesis of N-(4-chlorophenyl)-N-methyl-2-(2-methylpyrazolo[1,5-a]pyridin-3-yl)-5-(1-{[2-(trimethylsilyl)ethoxy]methyl}-1H-1,2,4-triazol-3-yl)-1,3-thiazol-4-amine The mixture of 3-[4-bromo-5-(1-{[2-(trimethylsilyl)ethoxy]methyl}-1H-1,2,4-triazol-3-yl)-1,3-thiazol-2-yl]-2-methylpyrazolo[1,5-a]pyridine (0.0700 g, 0.142 mmol), p-Chloro-N-methylaniline (33.5 mg, 0.236 mmol), Tris(dibenzylideneacetone)dipalladium(0) (4.4 mg, 0.0048 mmol.), racemic 1,1'-binaphthalene-2,2'-diylbis(diphenylphosphine) (8.8 mg, 0.014 mmol) and Sodium tert-butoxide (22.7 mg, 0.236 mmol) in dry Toluene (2.0 mL, 19 mmol) was degassed by vacuum and backfilling with $N_2$ for 5 times, sonicated under $N_2$ for 1 min to dissolve all material, degassed for 5 more times. The resulted brown solution was heated under $N_2$ in a capped vial to 112° C. for 18 hours. The mixture was partitioned in EtOAc (80 mL) and water (30 mL). The EtOAc layer was washed with water, brine, dried over $Na_2SO_4$, filtered, rotavaped to give a crude product. Chromatograph in a 24 g ISCO column using EtOAc/hexane (0/100 to 40/60) afforded a solid product (0.059 g, 75% yield). LCMS: (FA) $ES^+$ 552, 554. $^1H$ NMR (400 MHz, $d_1$-chloroform) δ 8.43 (d, J=6.53 Hz, 1H), 8.32 (d, J=9.04 Hz, 1H), 8.13 (s, 1H), 7.29-7.33 (m, 1H), 7.10-7.12 (d, J=9.04 Hz, 2H), 6.84-6.88 (m, 1H), 6.82-6.84 (d, J=9.04 Hz, 2H), 5.39 (s, 2H), 3.55 (t, J=7.78 Hz, 2H), 3.51 (s, 3H), 2.78 (s, 3H), 0.90 (t, J=7.78 Hz, 2H), 0.00 (s, 9H).

Step 2: Synthesis of N-(4-chlorophenyl)-N-methyl-2-(2-methylpyrazolo[1,5-a]pyridin-3-yl)-5-(4H-1,2,4-triazol-3-yl)-1,3-thiazol-4-amine (156-B)

N-(4-chlorophenyl)-N-methyl-2-(2-methylpyrazolo[1,5-a]pyridin-3-yl)-5-O-{[2-(trimethylsilyl)ethoxy]methyl}-1H-1,2,4-triazol-3-yl)-1,3-thiazol-4-amine (0.0566 g, 0.102 mmol) was treated with 4 M of Hydrochloric acid in 1,4-dioxane (6.0 mL, 24 mmol) and Water (1.0 mL, 56 mmol) at 35° C. to r.t. for 42 hours. The reaction solution was rotavaped, azeotroped with MeOH to give a crude residue. The material was dissolved in small amount of MeOH, diluted with $Et_2O$, filtered to give a solid product. (0.037 g, 84% yield). LCMS: (FA) $ES^+$ 422. $^1H$ NMR (400 MHz, $d_1$-chloroform & d4-methanol) δ 8.89 (s, 1H), 8.41 (d, J=6.78 Hz, 1H), 8.26 (d, J=6.78 Hz, 1H), 7.36 (m, 1H), 7.10-7.12 (d, J=8.78 Hz, 2H), 6.87-6.90 (m, 3H), 3.51 (s, 3H), 2.72 (s, 3H).

Example 129-B

Synthesis of 2-methyl-3-[4-phenyl-5-(1H-1,2,4-triazol-3-yl)-1,3-thiazol-2-yl]-6-(piperazin-1-ylmethyl)imidazo[1,2-a]pyridine (159-B)

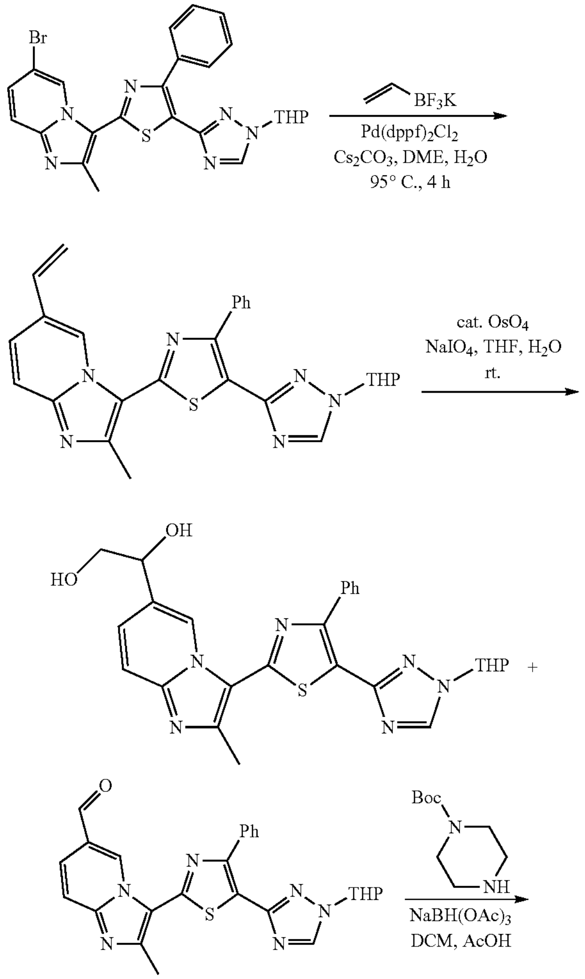

-continued

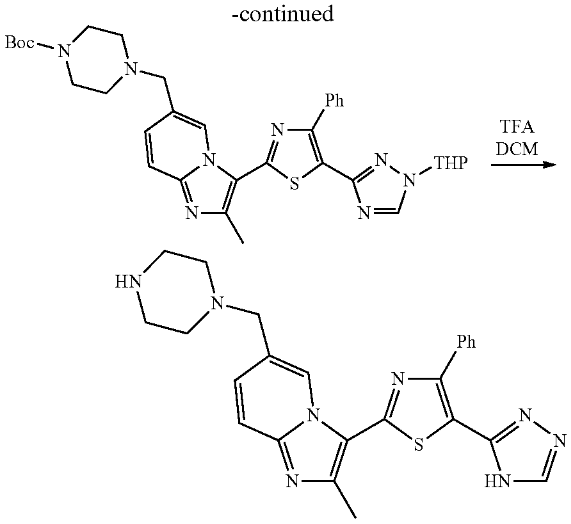

Step 1: Synthesis of 2-methyl-3-{4-phenyl-5-[1-(tetrahydro-2H-pyran-2-yl)-1H-1,2,4-triazol-3-yl]-1,3-thiazol-2-yl}-6-vinylimidazo[1,2-a]pyridine A mixture (suspension) of [A] 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (1.04 g, 2.00 mmol), Potassiumvinyltrifluoroborate (0.402 g, 3.00 mmol), [1,1'-Bis(diphenylphosphino)ferrocene]dichloropalladium (II), complex with dichloromethane (1:1) (0.163 g, 0.200 mmol) and Cesium Carbonate (1.95 g, 6.00 mmol) in 1,2-Dimethoxyethane (70 mL, 700 mmol) and Water (14 mL, 780 mmol) was heated to 95° C. under atmosphere of $N_2$ for 4 hours. The mixture was cooled to r.t., diluted with EtOAc (40 mL), filtered through Celite. The filtrate was diluted further with EtOAc (500 mL), washed with water, brine, dried over $Na_2SO4$, filtered, rotavaped to give a crude product. Chromatograph in a 40 g ISCO column using MeOH/DCM (0/100 to 5/95) gave a solid product (0.747 g, 79.7% yield). LCMS: (FA) $ES^+$ 468. $^1H$ NMR (400 MHz, $d_1$-chloroform) δ 9.97 (s, 1H), 8.29 (s, 1H), 7.95-7.98 (m, 2H), 7.56-7.62 (m, 2H), 7.42-7.46 (m, 3H), 6.71-6.78 (dd, J=17.57, 10.79 Hz, 1H), 5.76-5.81 (d, J=17.57 Hz, 1H), 5.48-5.51 (dd, J=8.53, 3.26 Hz, 1H), 5.33-5.36 (d, J=11.04 Hz, 1H), 4.06-4.10 (m, 1H), 3.70-3.77 (m, 1H), 2.81 (s, 3H), 2.00-2.18 (m, 3H), 1.63-1.74 (m, 3H).

Step 2: Synthesis of 2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine-6-carbaldehyde and 1-(2-methyl-3-{4-phenyl-5-[1-(tetrahydro-2H-pyran-2-yl)-1H-1,2,4-triazol-3-yl]-1,3-thiazol-2-yl}imidazo[1,2-a]pyridin-6-yl)ethane-1,2-diol To the solution of 2-methyl-3-{4-phenyl-5-[1-(tetrahydro-2H-pyran-2-yl)-1H-1,2,4-triazol-3-yl]-1,3-thiazol-2-yl}-6-vinylimidazo[1,2-a]pyridine (0.747 g, 1.59 mmol) in Tetrahydrofuran (55 mL, 680 mmol) and Water (16 mL, 890 mmol) was added Sodium metaperiodate (0.852 g, 3.98 mmol), followed by 0.157 M of Osmium tetraoxide in Water (0.53 mL, 0.083 mmol). The solution was stirred at r.t. for 3 days. The mixture was diluted with ~100 mL of water, filtered to collect the solid product as the first crop of 2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine-6-carbaldehyde (0.255 g, 24% yield). LCMS: (FA) $ES^+$ 471. $^1H$ NMR (400 MHz, $d_1$-chloroform) δ 10.56 (s, 1H), 10.00 (s, 1H), 8.30 (s, 1H), 7.94-7.97 (m, 2H), 7.82-7.85 (m, 1H), 7.69-7.71 (m, 1H), 7.46 (m, 3H), 5.48-5.51 (dd, J=8.78, 2.76 Hz, 1H), 4.06-4.09 (m, 1H), 3.73-3.77 (m, 1H), 2.85 (s, 3H), 2.02-2.15 (m, 3H), 1.59-1.69 (m, 3H). The filtrate was rotavaped to remove THF, extracted with 5% MeOH/DCM (4×60 mL). The combined DCM solution was dried over $Na_2SO_4$, filtered, rotavaped to give a crude material. Chromatograph in a 40 g ISCO column using MeOH/DCM (0/100 to 5/95) gave the second crop of 2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine-6-carbaldehyde (fast fraction, 0.104 g, 14% yield), and 1-(2-methyl-3-[4-phenyl-5-[1-(tetrahydro-2H-pyran-2-yl)-1H-1,2,4-triazol-3-yl]-1,3-thiazol-2-yl]imidazo[1,2-a]pyridin-6-yl)ethane-1,2-diol (slow fraction, 0.243 g, 30.3% yield). LCMS: (FA) $ES^+$ 503. $^1H$ NMR (400 MHz, $d_1$-chloroform & d4-methanol) δ 9.90 (s, 1H), 8.28 (s, 1H), 7.86-7.88 (m, 2H), 7.54-7.57 (d, J=9.29 Hz, 1H), 7.37-7.41 (m, 4H), 5.44-5.47 (m, 1H), 4.80-4.82 (m, 1H), 4.02-4.05 (m, 1H), 3.68-3.80 (m, 3H), 2.73 (s, 3H), 2.00-2.11 (m, 3H), 1.65-1.68 (m, 3H).

Step 3: Synthesis of tert-butyl 4-[(2-methyl-3-{4-phenyl-5-[1-(tetrahydro-2H-pyran-2-yl)-1H-1,2,4-triazol-3-yl]-1,3-thiazol-2-yl}imidazo[1,2-a]pyridin-6-yl)methyl]piperazine-1-carboxylate To the suspension of 2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine-6-carbaldehyde (0.0300 g, 0.0638 mmol), tert-Butyl 1-piperazinecarboxylate (20.8 mg, 0.112 mmol) and Acetic acid (11 mg, 0.18 mmol) in dry Methylene chloride (2.0 mL, 31 mmol) was added Sodium triacetoxyborohydride (27.0 mg, 0.128 mmol). The mixture was stirred at r.t. for 46 hours. The mixture was washed with water (2×2 mL) and brine, dried over $Na_2SO_4$, filtered and the filtrate was chromatographed in an 8 g AnaLogix column using MeOH/DCM (0/100 to 5/95) to give a solid product (0.0253 g, 61.9% yield). LCMS: (FA) $ES^+$ 641. $^1H$ NMR (400 MHz, d-chroloform) δ 9.91 (s, 1H), 8.28 (s, 1H), 7.94-7.97 (m, 2H), 7.58-7.60 (m, 1H), 7.34-7.46 (m, 4H), 5.47-5.51 (m, 1H), 4.05-4.13 (m, 1H), 3.70-3.76 (m, 1H), 3.58 (s, 2H), 3.42 (s, br, 4H), 2.81 (s, 3H), 2.45 (s, br, 4H), 2.00-2.17 (m, 3H), 1.65-1.72 (m, 3H), 1.46 (s, 9H).

Step 4: Synthesis of 2-methyl-3-[4-phenyl-5-(1H-1,2,4-triazol-3-yl)-1,3-thiazol-2-yl]-6-(piperazin-1-ylmethyl)imidazo[1,2-a]pyridine (159-B)

tert-Butyl-4-[(2-methyl-3-{4-phenyl-5-[1-(tetrahydro-2H-pyran-2-yl)-1H-1,2,4-triazol-3-yl]-1,3-thiazol-2-yl}imidazo[1,2-a]pyridin-6-yl)methyl]piperazine-1-carboxylate (0.025 g, 0.039 mmol) was treated with Trifluoroacetic Acid (2.0 mL, 26 mmol) in Methylene chloride (2.0 mL, 31 mmol) at r.t. for 18 hours. The mixture was rotavaped. The residue was triturated with hexane (3×5 mL). The solid residue was suspended in water and neutralized with saturated aqueous $NaHCO_3$ to pH ~9, extracted with 10% MeOH in DCM (3×10 mL). The combined organic layer was dried over $Na_2SO_4$, filtered, rotavaped and dried in hi-vac to give a solid product (0.0085 g, 45% yield). LCMS: (FA) $ES^+$ 457, $ES^-$ 455. $^1H$ NMR (400 MHz, d-chroloform & d4-methanol) δ 9.82 (s, 1H), 8.14 (s, 1H), 7.80-7.82 (m, 2H), 7.55-7.58 (m, 1H), 7.37-7.46 (m, 4H), 3.54 (s, 2H), 2.84 (m, 2H), 2.76 (s, 3H), 2.47 (s, br, 2H), 2.32 (m, 4H).

Compounds in the following table were prepared from the appropriate starting materials in a method analogous to that of Example 129-B:

| | |
|---|---|
| 127-B | LCMS: (FA) ES+ 521. |
| 139-B | LCMS: (FA) ES+ 457. |
| 161-B | LCMS: (FA) ES+ 445. |
| 162-B | LCMS: (FA) ES+ 431. |

Example 130-B

Synthesis of N-methyl-N-({2-methyl-3-[4-phenyl-5-(4H-1,2,4-triazol-3-yl)-1,3-thiazol-2-yl]imidazo[1,2-a]pyridin-6-yl}methyl)ethane-1,2-diamine (147-B)

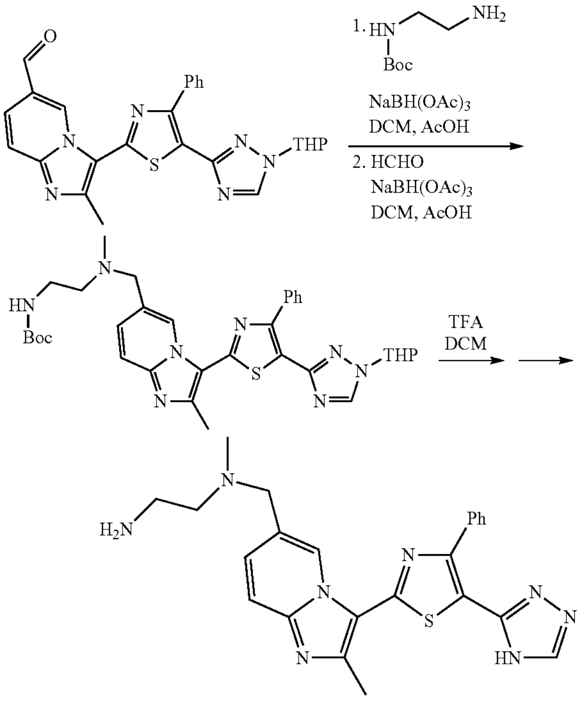

The mixture of 2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine-6-carbaldehyde (0.0300 g, 0.0638 mmol) and N-(2-aminoethyl)(tert-butoxy)carboxamide (15.3 mg, 0.0956 mmol) in dry Methylene chloride (2.0 mL, 31 mmol) and Acetic acid (50 mg, 0.8 mmol) was stirred at r.t. for 20 min. Sodium triacetoxyborohydride (23.3 mg, 0.110 mmol) was added and the mixture was stirred at r.t. for 21 hours. Paraformaldehyde (25 mg, 0.28 mmol) was added, followed by Acetic acid (100 mg, 2 mmol). The mixture was stirred at r.t. for 10 min. Sodium triacetoxyborohydride (172 mg, 0.812 mmol) was added and the mixture was stirred at r.t. for 17 hours. The mixture was quenched with saturated $NaHCO_3$, extracted with DCM. The DCM solution was washed with water, brine, dried over $Na_2SO_4$, filtered. The filtrate was chromatographed in a 24 g ISCO column using MeOH/DCM (0/100 to 5/95) to give a solid. LCMS: (FA) $ES^+$ 629. This solid was treated with Trifluoroacetic Acid (1.0 mL, 13 mmol) in Methylene chloride (1.0 mL, 16 mmol) at r.t. for 18 hours. The mixture was rotavaped, azeotroped with DCM. The residue was triturated with $Et_2O$ and decanted to give a solid residue, dried in hi-vac to give 30 mg of crude product. HPLC purification gave a solid product (0.0040 g, 13.8% yield). LCMS: (FA) $ES^+$ 445, $ES^-$ 443. $^1H$ NMR (400 MHz, d4-methanol) δ 9.88 (s, 1H), 8.47 (s, 1H), 7.78-7.81 (m, 2H), 7.61 (s, 2H), 7.41-7.43 (m, 3H), 3.68 (s, 2H), 3.00-3.03 (m, 2H), 2.75 (s, 3H), 2.66-2.69 (m, 2H), 2.32 (s, 3H).

Example 131-B

Synthesis of 2-methyl-3-[4-phenyl-5-(4H-1,2,4-triazol-3-yl)-1,3-thiazol-2-yl]imidazo[1,2-a]pyridine-6-carbaldehyde (132-B)

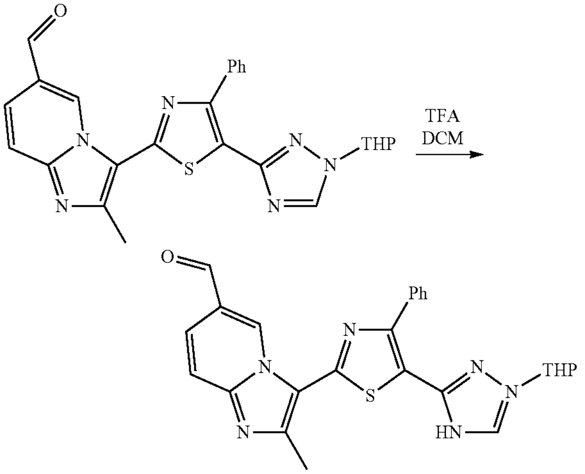

2-Methyl-3-{4-phenyl-5-[1-(tetrahydro-2H-pyran-2-yl)-1H-1,2,4-triazol-3-yl]-1,3-thiazol-2-yl}imidazo[1,2-a]pyridine-6-carbaldehyde (0.0300 g, 0.0638 mmol), obtained in Example 129-B was treated with Trifluoroacetic Acid (0.30 mL, 3.9 mmol) in Methylene chloride (1.5 mL, 23 mmol) at r.t. for 16 hours. The solvent and TFA were removed by purging with $N_2$. The residue was treated with Potassium carbonate (82 mg, 0.59 mmol) in Methanol (2.0 mL, 49 mmol) at r.t. for 3 hours. The solvent was removed and the residue was suspended in 5% MeOH/DCM, filtered. The filtrate was purified by chromatograph in a 8 g AnaLogix column using MeOH/DCM (0/100 to 10/90) to afford a solid product (0.012 g, 48.7% yield). LCMS: (FA) $ES^+$ 387, $ES^-$ 385. $^1H$ NMR (400 MHz, $d_6$-DMSO) δ 10.39 (s, 1H), 10.03 (s, 1H), 8.71 (s, 1H), 7.99-8.01 (m, 2H), 7.82 (s, 1H), 7.43-7.50 (m, 4H), 2.75 (s, 3H).

Compound in the following table was prepared from the appropriate starting material in a method analogous to that of Example 131-B:

| | |
|---|---|
| 157-B | LCMS: (FA) ES+ 468. |

Example 132-B

Synthesis of 2-{2-methyl-3-[4-phenyl-5-(4H-1,2,4-triazol-3-yl)-1,3-thiazol-2-yl]imidazo[1,2-a]pyridin-6-yl}ethanamine (138-B)

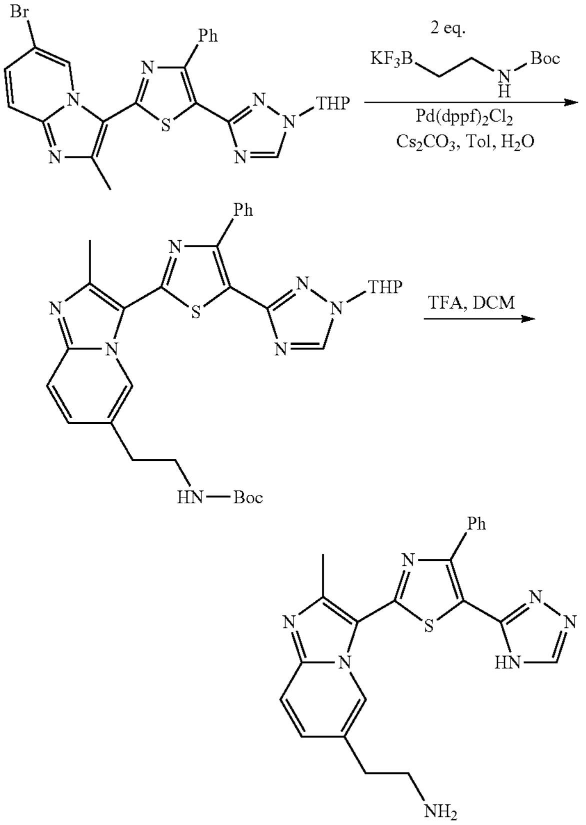

The mixture of [A] 6-bromo-2-methyl-3-[4-phenyl-5-[1-(tetrahydro-2H-pyran-2-yl)-1H-1,2,4-triazol-3-yl]-1,3-thiazol-2-yl]imidazo[1,2-a]pyridine (0.0500 g, 0.0959 mmol), potassium [2-(tert-butoxycarbonylamino)ethyl]trifluorborate (48.2 mg, 0.192 mmol), [1,1'-Bis(diphenylphosphino) ferrocene]dichloropalladium(II), complex with dichloromethane (1:1) (7.83 mg, 0.00959 mmol) and Cesium Carbonate (125 mg, 0.384 mmol) in Toluene (2.0 mL, 19 mmol) and Water (0.3 mL, 20 mmol) in a 4 mL vial was degassed with house vacuum and backfilled with $N_2$ back and forth for 6 times. The mixture was heated under $N_2$ atmosphere to 100° C. (heating block) for 3 hours. The mixture was partitioned between EtOAc/water (100 mL/50 mL). The organic layer was washed with water, brine, dried over $Na_2SO_4$, filtered, rotavaped to give solid crude. Chromatograph in a 24 g ISCO column using MeOH/DCM (0/100 to 5/95) gave 0.014 g of solid. This solid was treated with Trifluoroacetic Acid (1.0 mL, 13 mmol) in Methylene chloride (1.0 mL, 16 mmol) at r.t. for 3 hours. The mixture was rotavaped and the residue was dissolved in small amount of MeOH, diluted with $Et_2O$ (~10 mL) to form precipitate. After 10 min the $Et_2O$ was decanted out and the residue was dried with $N_2$ flow then in hi-vac to give a solid product (0.0098 g, 19.5% yield). LCMS: (FA) $ES^+$ 402, $ES^-$ 400. $^1H$ NMR (400 MHz, $d_6$-DMSO) δ 9.65 (s), 8.67 (m), 7.93 (m, 1H), 7.71-7.78 (m, 2H), 7.43-7.51 (m, 4H), 3.11-3.17 (m, 2H), 2.94-2.97 (m, 2H), 2.72 (s, 3H).

Example 133-B

Synthesis of 3-{2-methyl-3-[4-phenyl-5-(4H-1,2,4-triazol-3-yl)-1,3-thiazol-2-yl]imidazo[1,2-a]pyridin-6-yl}propan-1-amine (128-B)

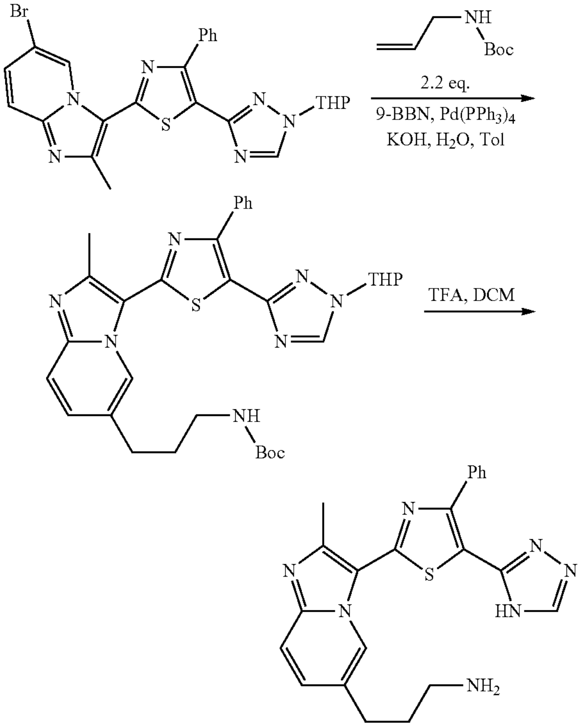

A solution of 3-N-t-Butoxycarbonylamino-1-propene (33.2 mg, 0.211 mmol) in dry Toluene (1.0 mL, 9.4 mmol) was degassed by vacuum and backfill with $N_2$ for 4 times, cooled with ice bath. 0.5 M of 9-BBN in Tetrahydrofuran (0.460 mL, 0.230 mmol) was added and the mixture was stirred at r.t. for 20 hours. The solution was added to a mixture of 6-bromo-2-methyl-3-{4-phenyl-5-[1-(tetrahydro-2H-pyran-2-yl)-1H-1,2,4-triazol-3-yl]-1,3-thiazol-2-yl}imidazo[1,2-a]pyridine (0.0500 g, 0.0959 mmol) and 1.0 M of Potassium hydroxide in Water (0.30 mL, 0.30 mmol) in Toluene (0.5 mL, 5 mmol). The mixture was degassed by vacuum and backfill with $N_2$ for 4 times. Tetrakis(triphenylphosphine) palladium(0) (5.54 mg, 0.00479 mmol) was added and the mixture was then heated under $N_2$ atmosphere to 80° C. for 22 hours. The mixture was cooled to r.t., diluted with EtOAc (50 mL), washed with water (2×), brine, dried over $Na_2SO_4$, filtered. The filtrate was rotavaped to give a crude product. Chromatograph in a 24 g AnaLogix column using MeOH/DCM (0/100 to 5/95) gave 0.0336 g of solid. This solid was treated with Trifluoroacetic Acid (1.0 mL, 13 mmol) in Methylene chloride (1.0 mL, 16 mmol) for 15 hours. The mixture was rotavaped. The residue was diluted with Et2O (10 mL) to give an off-white precipitate. The solvent was decanted. The precipitate was dissolved in water, washed with $Et_2O$, basified with $NaHCO_3$ solution to pH ~9, extracted with DCM for 4 times. The combined DCM solution was washed with brine, dried over $Na_2SO_4$, filtered, rotavaped and dried over hi-vac to give a solid product. The solid product was dissolved in small amount of DCM, acidified with 2 drops of TFA, rotavaped, diluted with $Et_2O$, decanted and triturated with $Et_2O$ one more time to give a powder product as TFA salt (0.0102 g, 19% yield). LCMS: (FA) $ES^+$ 416. NMR (400 MHz, $d_4$-Methanol) δ 9.90 (s, 1H), 8.54 (s, 1H), 7.79-7.84 (m, 4H), 7.43-7.45 (m, 3H), 3.00-3.04 (m, 2H), 2.88-2.93 (m, 2H), 2.85 (s, 3H), 2.04-2.10 (m, 2H).

Example 1-C

Synthesis of N-{4-[4-(2,4-Dichlorophenyl)-5-(1H-imidazol-2-yl)-1,3-thiazol-2-yl]pyridin-2-yl}acetamide (5-C)

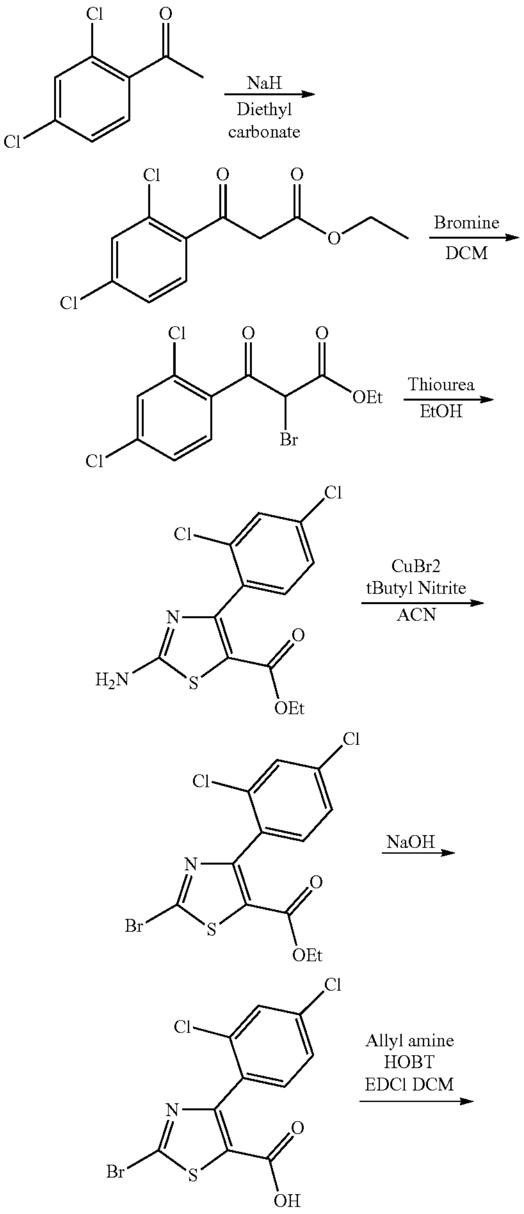

-continued

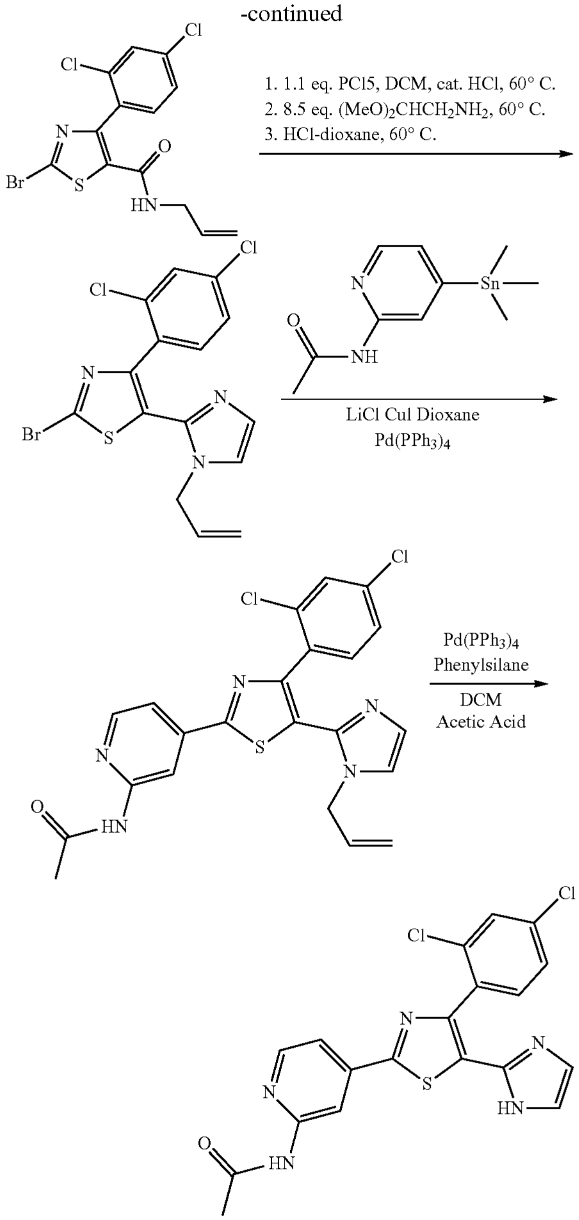

Step 1: Ethyl 3-(2,4-dichlorophenyl)-3-oxopropanoate

To a solution of 2',4'-Dichloroacetophenone (1.50 g, 7.93 mmol) in diethyl carbonate (24.0 mL, 198 mmol) at 0° C. was slowly added NaH (60% suspension in mineral oil, 0.657 g, 16.4 mmol). The mixture was then stirred at 80° C. for 90 minutes. The mixture was cooled to room temperature and then poured into an ice cold solution of 2.0 mL acetic acid in 56 mL water. The layers were separated and the aqueous phase was extracted with ether 3 times. The organic extracts were washed with brine, dried over anhydrous sodium sulfate, filtered and concentrated in vacuo. Column chromatography was performed to yield the title compound (1.16 g, 56%). LCMS: (FA) $ES^+$, 262. $^1H$ NMR (400 MHz, $d_1$-chloroform) δ (2 sets of signals, keto and enol): 12.49 (s, 1H), 7.61-7.29 (m, 2 sets of 3H), 5.57 (s, 1H), 4.28 (q, J=7.28 Hz, 2H), 4.19 (q, J=7.28 Hz, 2H), 4.02 (s, 2H), 1.34 (t, J=7.03 Hz, 3H), 1.25 (t, J=7.03 Hz, 3H).

Step 2: Ethyl 2-bromo-3-(2,4-dichlorophenyl)-3-oxopropanoate

To a solution of ethyl 3-(2,4-dichlorophenyl)-3-oxopropanoate (3.95 g, 15.1 mmol) in dichloromethane (150 mL) was added solution of bromine (0.935 mL, 18.2 mmol) in dichloromethane (20.0 mL) dropwise at 0° C. The solution was then stirred at room temperature for 1 hour. The reaction was quenched with 10% aqueous potassium carbonate solution, and then the layers were separated. The organic extracts were washed with brine, dried over anhydrous sodium sulfate, filtered and concentrated in vacuo. The crude oil was used directly in the next step (5.27 g, quantitative). LCMS: (AA) ES+, 341. $^1$H NMR (400 MHz, $d_1$-chloroform) § (2 sets of signals, keto and enol): 12.78 (s, 1H), 7.73-7.28 (m, 2 sets of 3H), 5.73 (s, 1H), 4.37 (q, J=7.28 Hz, 2H), 4.29 (q, J=7.28 Hz, 2H), 1.41 (t, J=7.03 Hz, 3H), 1.29 (t, J=7.03 Hz, 3H).

Step 3: Ethyl 2-amino-4-(2,4-dichlorophenyl)-1,3-thiazole-5-carboxylate

To a solution of ethyl 2-bromo-3-(2,4-dichlorophenyl)-3-oxopropanoate (5.14 g, 15.1 mmol) in ethanol (90 mL) was added thiourea (1.26 g, 16.6 mmol) and the solution was stirred at reflux for 2 hours. The reaction was allowed to cool to room temperature, then the solvent was evaporated in vacuo. Column chromatography was performed to yield the title compound (4.79 g, 99%). LCMS: (AA) ES$^+$, 319. $^1$H NMR (300 MHz, $d_1$-chloroform) δ: 8.11 (br s, 2H), 7.52-7.33 (m, 3H), 4.24-4.16 (m, 2H), 1.23-1.17 (m, 3H).

Step 4: Ethyl 2-bromo-4-(2,4-dichlorophenyl)-1,3-thiazole-5-carboxylate

To a suspension of ethyl 2-amino-4-(2,4-dichlorophenyl)-1,3-thiazole-5-carboxylate (4.89 g, 15.4 mmol) in acetonitrile (102 mL) at 0° C. was added copper (II) bromide (4.13 g, 18.5 mmol) and tert-butyl nitrite (2.80 mL, 23.6 mmol). The mixture was stirred at 0° C. 2 hours then concentrated in vacuo. Column chromatography was performed to yield the title compound (4.52 g, 77%). LCMS: (AA) ES$^+$, 382. $^1$H NMR (400 MHz, $d_1$-chloroform) δ: 7.49-7.48 (m, 1H), 7.36-7.31 (m, 2H), 4.23 (q, J=7.03 Hz, 2H), 1.21 (t, J=7.03 Hz, 3H).

Step 5: 2-Bromo-4-(2,4-dichlorophenyl)-1,3-thiazole-5-carboxylic acid

To a solution of Ethyl 2-bromo-4-(2,4-dichlorophenyl)-1,3-thiazole-5-carboxylate (4.05 g, 10.6 mmol) in THF (50 mL) and water (20 mL) was added solution of sodium hydroxide in water (1.0M, 31.9 mL, 31.9 mmol). The solution was stirred at room temperature for 16 hours. The reaction was quenched by the addition of aqueous HCl solution (1N, 38 mL), and then extracted five times with ethyl acetate. The organic extracts were washed with brine, dried over anhydrous sodium sulfate, filtered and concentrated in vacuo to give white solid which was dried overnight and then used directly in the next step (3.74 g, 99%). LCMS: (AA) ES$^+$, 354. $^1$H NMR (400 MHz, $d_4$-Methanol) δ: 7.57-7.55 (m, 1H), 7.41-7.39 (m, 2H).

Step 6: N-Allyl-2-bromo-4-(2,4-dichlorophenyl)-1,3-thiazole-5-carboxamide

To a solution of 2-Bromo-4-(2,4-dichlorophenyl)-1,3-thiazole-5-carboxylic acid (3.42 g, 9.69 mmol) in dichloromethane (59 mL) was added HOBT.$H_2O$ (1.48 g, 9.69 mmol) and N-(3-dimethylaminopropyl)-N'-ethylcarbodiimide hydrochloride (2.97 g, 15.5 mmol) followed by 2-propen-1-amine (2.91 mL, 38.8 mmol) and the solution was stirred at room temperature for 16 hours. The solution was then diluted with water and the layers were separated. The organic extracts were washed with brine, dried over anhydrous sodium sulfate, filtered and concentrated in vacuo. Column chromatography was performed to yield the title compound (3.11 g, 82%). LCMS: (AA) ES$^+$, 393. $^1$H NMR (400 MHz, $d_1$-chloroform) δ: 7.57-7.56 (m, 1H), 7.46-7.39 (m, 2H), 5.75-5.65 (m, 1H), 5.43 (br s, 1H), 5.10-5.06 (m, 1H), 5.00-4.94 (m, 1H), 3.88-3.84 (m, 2H).

Step 7: 5-(1-Allyl-1H-imidazol-2-yl)-2-bromo-4-(2,4-dichlorophenyl)-1,3-thiazole To a solution of N-Allyl-2-bromo-4-(2,4-dichlorophenyl)-1,3-thiazole-5-carboxamide (8.40 g, 21.4 mmol) in dichloromethane (200 mL) was added phosphorus pentachloride (5.05 g, 24.2 mmol) and 4M hydrochloric acid in dioxane (0.833 mL, 3.26 mmol), and the reaction was heated to 60° C. for 90 minutes under an atmosphere on nitrogen. The reaction was allowed to cool to room temperature and then aminoacetaldehyde dimethyl acetal (25.7 mL, 236 mmol) was added slowly through the condenser. The mixture was heated to 60° C. for 2 hours under an atmosphere on nitrogen. The mixture was cooled to room temperature, and water was added (200 mL). The layers were separated and the organic phase was washed with water again (2×200 mL). The organic extracts were washed with brine, dried over anhydrous sodium sulfate, filtered and washed with dichloromethane (200 mL). To this dichloromethane solution of the intermediate was added 4M hydrochloric acid in dioxane (17 mL, 65 mmol) and the solution was stirred at reflux for 16 hours. The solution was decanted (leaving behind an oily black residue on the flask) and then evaporated and diluted with ethyl acetate and saturated sodium bicarbonate solution. The layers were separated and the aqueous phase was extracted 3 more times with ethyl acetate. The organic extracts were washed with brine, dried over anhydrous sodium sulfate, filtered and concentrated in vacuo. Column chromatography was performed to yield the title compound (5.93 g, 67%). LCMS: (FA) ES$^+$, 416. $^1$H NMR (400 MHz, $d_1$-chloroform) δ: 7.45-7.42 (m, 1H), 7.25-7.19 (m, 2H), 7.16-7.14 (m, 1H), 6.93-6.90 (m, 1H), 5.55-5.44 (m, 1H), 5.13-5.08 (m, 1H), 5.95-4.88 (m, 1H), 4.19-4.15 (m, 2H).

Step 8: N-{4-[5-(1-Allyl-1H-imidazol-2-yl)-4-(2,4-dichlorophenyl)-1,3-thiazol-2-yl]pyridin-2-yl}acetamide To a solution of 5-(1-Allyl-1H-imidazol-2-yl)-2-bromo-4-(2,4-dichlorophenyl)-1,3-thiazole (0.133 g, 0.320 mmol) in 1,4-dioxane (8 mL) was added N-[4-(trimethylstannyl)pyridine-2-yl]acetamide (0.115 g, 0.384 mmol), lithium chloride (0.0407 g, 0.961 mmol), copper (I) iodide (0.0183 g, 0.0961 mmol) and tetrakis(triphenylphosphine)palladium(0) (0.0185 g, 0.0160 mmol). The flask was purged with argon and then the mixture was heated at 115° C. for 3 hours. The reaction was allowed to cool to room temperature, and then the solvent was evaporated in vacuo. Column chromatography was performed to yield the title compound (0.0650 g, 43%). LCMS: (FA) ES$^+$, 472, 474. $^1$H NMR (400 MHz, $d_4$-Methanol) δ: 8.75-8.72 (m, 1H), 8.45-8.41 (m, 1H), 7.71-7.68 (m, 1H), 7.58-7.55 (m, 1H), 7.43-7.35 (m, 2H), 7.20 (d, J=1.51 Hz, 1H), 7.14 (d, J=1.51 Hz, 1H), 5.69-5.58 (m, 1H), 5.13-5.08 (m, 1H), 4.94-4.88 (m, 1H), 4.38-4.33 (m, 2H), 2.20 (s, 3H).

Step 9: N-{4-[4-(2,4-Dichlorophenyl)-5-(1H-imidazol-2-yl)-1,3-thiazol-2-yl]pyridin-2-yl}acetamide (5-C)

To a solution of N-{4-[5-(1-Allyl-1H-imidazol-2-yl)-4-(2,4-dichlorophenyl)-1,3-thiazol-2-yl]pyridin-2-yl}acetamide (0.0650 g, 0.138 mmol) in dichloromethane (1.0 mL) and acetic acid (0.34 mL) was added tetrakis(triphenylphosphine) palladium(0) (0.00798 g, 0.00691 mmol) followed by phenylsilane (0.0870 mL, 0.706 mmol). The solution was stirred at 40° C. for 90 minutes. The solution was cooled to room temperature then concentrated in vacuo and diluted with ethyl acetate and saturated sodium bicarbonate solution. The layers were separated and the aqueous phase was extracted 3 more times with ethyl acetate. The organic extracts were washed with brine, dried over anhydrous sodium sulfate, filtered and concentrated in vacuo. Column chromatography was performed to yield the title compound (0.0380 g, 64%). LCMS: (FA) $ES^+$, 431, 433. $^1H$ NMR (400 MHz, $d_4$-Methanol) δ: 8.75-8.70 (m, 1H), 8.44-8.39 (m, 1H), 7.70-7.44 (m, 4H), 7.13-7.07 (m, 2H), 2.20 (s, 3H).

Compounds in the following table were prepared from the appropriate starting materials in a method analogous to that of Example 1-C:

| | |
|---|---|
| 11-C | LCMS: (FA) ES+ 444, 446. |
| 12-C | LCMS: (FA) ES+ 389, 391. |
| 15-C | LCMS: (FA) ES+ 446, 448. |
| 18-C | LCMS: (AA) ES+ 460, 462. |
| 30-C | LCMS: (FA) ES+ 410, 412. |
| 31-C | LCMS: (FA) ES+ 456, 458. |
| 32-C | LCMS: (FA) ES+ 388, 390. |
| 36-C | LCMS: (FA) ES+ 376. |
| 43-C | LCMS: (FA) ES+ 431, 433. |
| 66-C | LCMS: (FA) ES+ 444, 446. |

Example 2-C

Synthesis of N-{4-[5-(1H-imidazol-2-yl)-4-phenyl-1,3-thiazol-2-yl]pyridin-2-yl}acetamide (67-C)

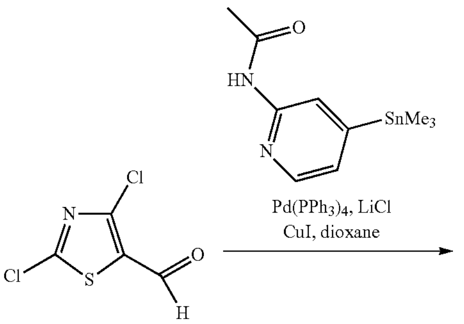

-continued

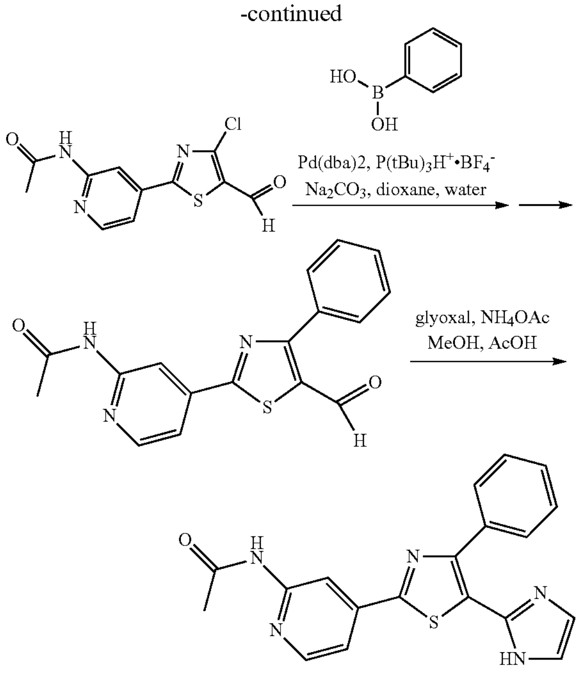

Step 1: Synthesis of N-[4-(4-chloro-5-formyl-1,3-thiazol-2-yl)pyridin-2-yl]acetamide 2,4-Dichloro-5-thiazolecarboxaldehyde (2.50 g, 0.0137 mol), N-[4-(trimethylstannyl)pyridin-2-yl]acetamide (4.93 g, 0.0165 mol), lithium chloride (1.75 g, 0.0412 mol), copper (I) iodide (0.785 g, 0.00412 mol), tetrakis(triphenylphosphine)palladium(0) (0.794 g, 0.000687 mol) were combined in dioxane (200 mL) under an atmosphere of Argon. The solution was heated at 110° C. for 2 hr. TLC indicated complete conversion. Mixture was cooled to rt and MeOH (100 mL) was added until almost all solids dissolved. Suspension was filtered through celite and the filtrate was evaporated. Water (100 mL) was added and the solids were collected by filtration, washed with water and hexane and dried in vacuum at 40° C. to give 1.76 g of amorphous solid (46%). LCMS: (FA) ES+ 282, 284. $^1H$ NMR (400 MHz, $d_6$-DMSO) δ 10.83 (s, 1H), 10.02 (s, 1H), 8.70 (s, 1H), 8.51 (dd, J=5.20, 0.67 Hz, 1H), 7.68 (dd, J=5.20, 1.67 Hz, 1H), 2.13 (s, 3H).

Step 2: Synthesis of N-[4-(5-formyl-4-phenyl-1,3-thiazol-2-yl)pyridin-2-yl]acetamide Tris(dibenzylideneacetone)dipalladium(0) (0.0162 g, 0.0177 mmol) and tri-t-butylphosphonium tetrafluoroborate (0.0103 g, 0.0355 mmol) were weighed into a round bottom flask and dissolved in DME (3 mL). The mixture was sonicated for 15 min under atmosphere of Argon. After addition of water (1 mL), sodium carbonate (0.226 g, 2.13 mmol) was added to the dark purple solution followed by phenylboronic acid (0.173 g, 1.42 mmol) and N-[4-(4-chloro-5-formyl-1,3-thiazol-2-yl)pyridin-2-yl]acetamide (0.200 g, 0.710 mmol). The resulting mixture was stirred for 10 h at 80° C., cooled to room temperature, diluted with water and extracted with DCM (3x5 mL). The organics were washed with brine, dried over anhydrous sodium sulfate, filtered and concentrated. The result mixture was purified by ISCO column with 0-5% MeOH in DCM in 10 min. Fractions containing product were combined and solvent was removed under reduced pressure to give crude material (0.099 g, 43%), which was used in the next step without further purification. LCMS: (FA) ES+ 324.

Step 3: Synthesis of N-{4-[5-(1H-imidazol-2-yl)-4-phenyl-1,3-thiazol-2-yl]pyridin-2-yl}acetamide (67-C)

N-[4-(5-formyl-4-phenyl-1,3-thiazol-2-yl)pyridin-2-yl]acetamide (0.0900 g, 0.278 mmol was weighed into a round bottom flask and dissolved in methanol (5 mL). Acetic acid (0.158 mL, 2.78 mmol) and ammonium acetate (0.257 g, 3.34 mmol) were added followed by glyoxal trimer dihydrate (351 mg, 1.67 mmol). The mixture was stirred at room temperature overnight. At that time LCMS indicated formation of product. The mixture was evaporated to dryness and the residue was purified using preparative HPLC to give the 0.024 mg of the product (22%). LCMS: (FA) ES+ 362. $^1$H NMR (400 MHz, $d_6$-DMSO) δ 10.46 (s, 1H), 8.37 (s, 1H), 8.14 (d, J=5.16 Hz, 1H), 7.45 (s, 2H), 7.34 (dd, J=5.18, 1.60 Hz, 1H), 7.12-7.07 (m, 5H), 1.76 (s, 3H)

Compounds in the following table were prepared from the appropriate starting materials in a method analogous to that of Example 2-C:

| | |
|---|---|
| 7-C | LCMS: (FA) ES+ 396, 398. |
| 34-C | LCMS: (FA) ES+ 396, 398. |
| 42-C | LCMS: (FA) ES+ 458, 460. |
| 55-C | LCMS: (FA) ES+ 396, 398. |

Example 3-C

Synthesis of N-{4-[5-(1H-imidazol-2-yl)-4-phenyl-1,3-thiazol-2-yl]pyridin-2-yl}acetamide (59-C)

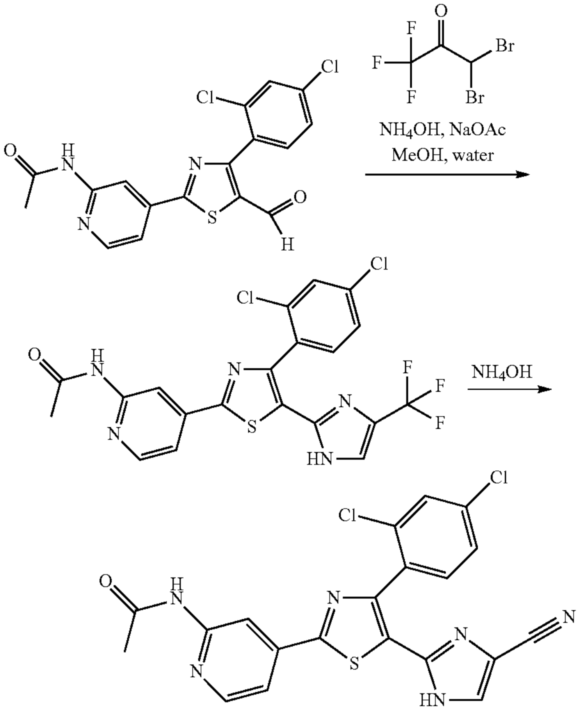

Step 1: Synthesis N-(4-{4-(2,4-dichlorophenyl)-5-[4-(trifluoromethyl)-1H-imidazol-2-yl]-1,3-thiazol-2-yl}pyridin-2-yl)acetamide To a solution of Sodium acetate (104.6 mg, 1.275 mmol) in water (400 uL, 20 mmol) was added 1,1-dibromo-3,3,3-trifluoroacetone (89.73 uL, 0.7648 mmol) and the mixture was stirred at 100° C. for 30 min. N-{4-[4-(2,4-dichlorophenyl)-5-formyl-1,3-thiazol-2-yl]pyridin-2-yl}acetamide (100 mg, 0.2 mmol; prepared as described in Example 2-C) in methanol (5 mL) was added to the above mixture followed by ammonium hydroxide (0.5956 mL, 15.30 mmol). The mixture was stirred at rt for 48 hours, at which time LCMS indicated formation of the product. Mixture was extracted with ethyl acetate (3×10 mL), washed with brine, dried with MgSO4, filtered and evaporated. The crude mixture was purified by ISCO chromatography, eluted with EtOAc in hexanes, 0-45% to give pure product 0.020 g of amorphous solid (20%). LCMS: (FA) ES+ 498, 500. $^1$H NMR (400 MHz, $d_4$-Methanol) δ 8.75 (s, 1H), 8.43 (d, J=5.24 Hz, 1H), 7.69 (dd, J=5.22, 1.57 Hz, 1H), 7.63-7.55 (m, 3H), 7.49 (dd, J=8.36, 2.01 Hz, 1H), 2.22 (s, 3H).

Step 2: Synthesis of N-{4-[5-(4-cyano-1H-imidazol-2-yl)-4-(2,4-dichlorophenyl)-1,3-thiazol-2-yl]pyridin-2-yl}acetamide (59-C)

N-(4-{4-(2,4-dichlorophenyl)-5-[4-(trifluoromethyl)-1H-imidazol-2-yl]-1,3-thiazol-2-yl}pyridin-2-yl)acetamide (20 mg, 0.04 mmol) was taken up in 1 M of Ammonium hydroxide in water (2 mL, 3 mmol) and the mixture was stirred at 60° C. for 6 h. At that time, LCMS indicated complete conversion. Reaction mixture was evaporated under reduced pressure and was purified using preparative HPLC to give 0.004 g of the title compound (20%). LCMS: (FA) ES+ 455, 457. $^1$H NMR (400 MHz, $d_6$-DMSO) δ 8.70 (s, 1H), 8.34 (dd, J=5.26, 0.71 Hz, 1H), 7.65 (dd, J=5.26, 1.60 Hz, 1H), 7.55-7.46 (m, 3H), 7.39 (dd, J=8.28, 2.06 Hz, 1H), 2.24 (s, 3H).

Example 4-C

Synthesis of N-{4-[4-(2,4-dichlorophenyl)-5-(4-methyl-1H-imidazol-2-yl)-1,3-thiazol-2-yl]pyridin-2-yl}acetamide (49-C)

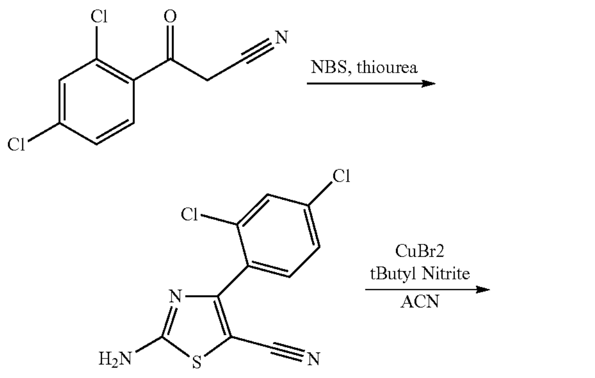

-continued

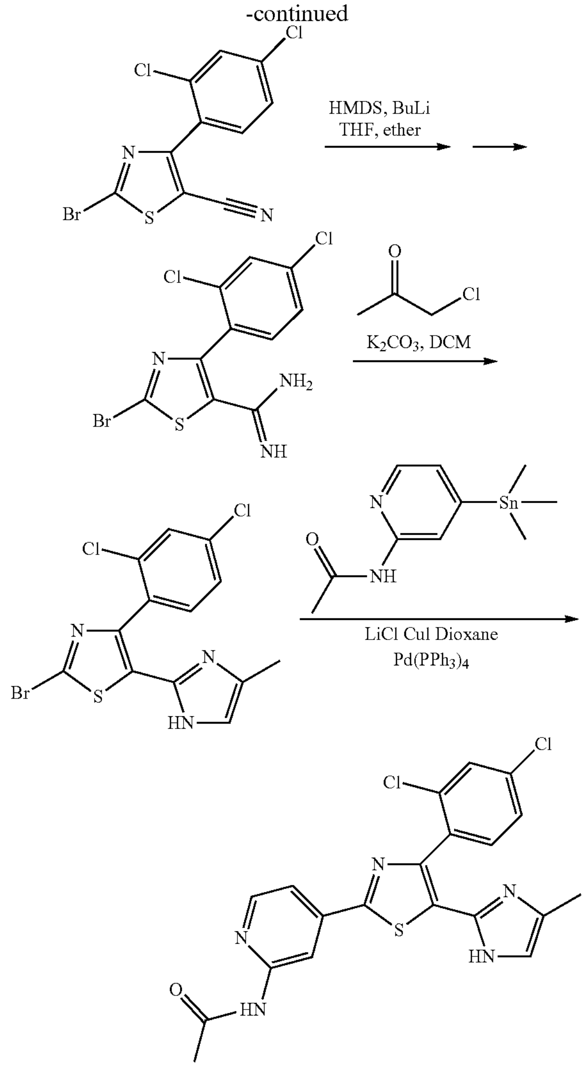

Step 1: 2-amino-4-(2,4-dichlorophenyl)-1,3-thiazole-5-carbonitrile beta-Cyclodextrin (4.29 g, 3.78 mmol) was dissolved in water (75 mL) at 50° C. and a solution of 3-(2,4-dichlorophenyl)-3-oxopropanenitrile (810 mg, 3.8 mmol) in Acetone (3.80 mL) was added dropwise, followed by NBS (0.808 g, 4.54 mmol) and thiourea (0.346 g, 4.54 mmol). Reaction mixture was stirred at 50° C. 1 hr. LCMS indicated complete conversion. Reaction mixture was cooled to rt, extracted with ethyl acetate (3×50 mL), dried with $MgSO_4$, filtered and concentrated under reduced pressure. The residue was purified by ISCO with 5-30% ethyl acetate in hexanes to give 0.43 g of the title compound (42%). LCMS: (FA) $ES^+$, 270, 272. $^1H$ NMR (400 MHz, $d_1$-chloroform) δ 7.49 (d, J=1.84 Hz, 1H), 7.41 (d, J=8.30 Hz, 1H), 7.31 (dd, J=8.16, 1.74 Hz, 1H).

Step 2: 2-bromo-4-(2,4-dichlorophenyl)-1,3-thiazole-5-carbonitrile

To a suspension of 2-amino-4-(2,4-dichlorophenyl)-1,3-thiazole-5-carbonitrile (423 mg, 1.57 mmol) in acetonitrile (10 mL) at 0° C. was added copper (II) bromide (420 mg, 1.9 mmol) and tert-butyl nitrite (0.285 mL, 2.40 mmol). The mixture was stirred at 0° C. for 2 hours, then concentrated in vacuo. Column chromatography was performed to yield the title compound (0.400 g, 80%). LCMS: (FA) $ES^+$, 333, 335, 337. $^1H$ NMR (400 MHz, $d_1$-chloroform) δ: 7.57 (t, J=2.07, 2.07 Hz, 1H), 7.49 (d, J=8.32 Hz, 1H), 7.39 (dd, J=8.33, 2.02 Hz, 1H)

Step 3: 2-bromo-4-(2,4-dichlorophenyl)-1,3-thiazole-5-carboximidamide 2.5 M n-Butyllithium in hexanes (1.20 mL, 2.99 mmol) was added dropwise to a solution of hexamethyldisilazane (0.61 mL, 2.9 mmol) in diethylether (5 mL) at 0° C. The mixture was stirred for 30 mins at 0° C. and 2-bromo-4-(2,4-dichlorophenyl)-1,3-thiazole-5-carbonitrile (400 mg, 1.0 mmol) in THF (50 mL) was added. After stirring at rt for 2 hours LCMS indicated complete conversion. The reaction mixture was poured to a cold 2N HCl (10 ml) and was extracted with diethylether (2×20 mL). The aqueous phase was adjusted to pH~10 with $NH_4OH$ and was extracted with DCM (3×30 mL). Combined DCM extracts were dried over $Na_2SO_4$, filtered and evaporated under reduced pressure to afford the title compound which was used directly in the next step (0.360 g, 80%). LCMS: (FA) $ES^+$, 350, 352, 354.

Step 4: 2-bromo-4-(2,4-dichlorophenyl)-5-(4-methyl-1H-imidazol-2-yl)-1,3-thiazol To a solution of 2-bromo-4-(2,4-dichlorophenyl)-1,3-thiazole-5-carboximidamide (70 mg, 0.2 mmol) in DCM (4 mL) was added potassium carbonate (82.7 mg, 0.598 mmol) followed by solution of chloroacetone (50 uL, 0.6 mmol) in DCM (0.4 mL). The mixture was heated to reflux for 3 hours, at which time LCMS indicated ~50% conversion. Additional cloroacetone (11 ul) and $K_2CO_3$ (19 mg) were added and heating was continued for additional 4 hours. LCMS showed complete conversion. Solvent was removed under reduced pressure and the residue was purified using ISCO chromatography, 20%-60% ethyl acetate in hexane to afford the title compound (56 mg, 70%). LCMS: (FA) $ES^+$, 388, 390, 392. $^1H$ NMR (400 MHz, $d_1$-chloroform) δ: 7.60 (dd, J=5.37, 1.71 Hz, 1H), 7.45-7.40 (m, 3H), 2.23 (s, 3H).

Step 5: N-{4-[4-(2,4-dichlorophenyl)-5-(4-methyl-1H-imidazol-2-yl)-1,3-thiazol-2-yl]pyridin-2-yl}acetamide (49-C)

2-bromo-4-(2,4-dichlorophenyl)-5-(4-methyl-1H-imidazol-2-yl)-1,3-thiazole (55 mg, 0.141 mmol), N-[4-(trimethylstannyl)pyridin-2-yl]acetamide (64 mg, 0.214 mmol) were dissolved in 1,4-dioxane (3.4 mL). Lithium chloride (18.1 mg, 0.427 mmol), copper(I) iodide (8.14 mg, 0.0427 mmol) and tetrakis(triphenylphosphine)palladium(0) (8.23 mg, 0.00712 mmol) were added under atmosphere of argon. The reaction mixture was heated at 90° C. for 7 hours. LCMS indicated complete conversion. Solvent was evaporated and the residue was purified using preparative HPLC to afford 15 mg of the title compound (24%). LCMS: (AA) $ES^+$ 444, 446. $^1H$ NMR (400 MHz, $d_1$-chloroform) δ: 8.79-8.70 (m, 1H), 8.43 (s, 1H), 8.35-8.28 (m, 1H), 7.62-7.59 (m, 2H), 7.50 (d, J=8.25 Hz, 1H), 7.43 (dd, J=8.23, 2.01 Hz, 1H), 2.24 (s, 3H), 2.20 (s, 3H).

Example 5-C

Synthesis of N-(4-(4-(1-methyl-3-(trifluoromethyl)-1H-pyrazol-4-yl)-5-(1-((2-(trimethylsilyl)ethoxy)methyl)-1H-imidazol-2-yl)thiazol-2-yl)pyridin-2-yl)acetamide (6-C)

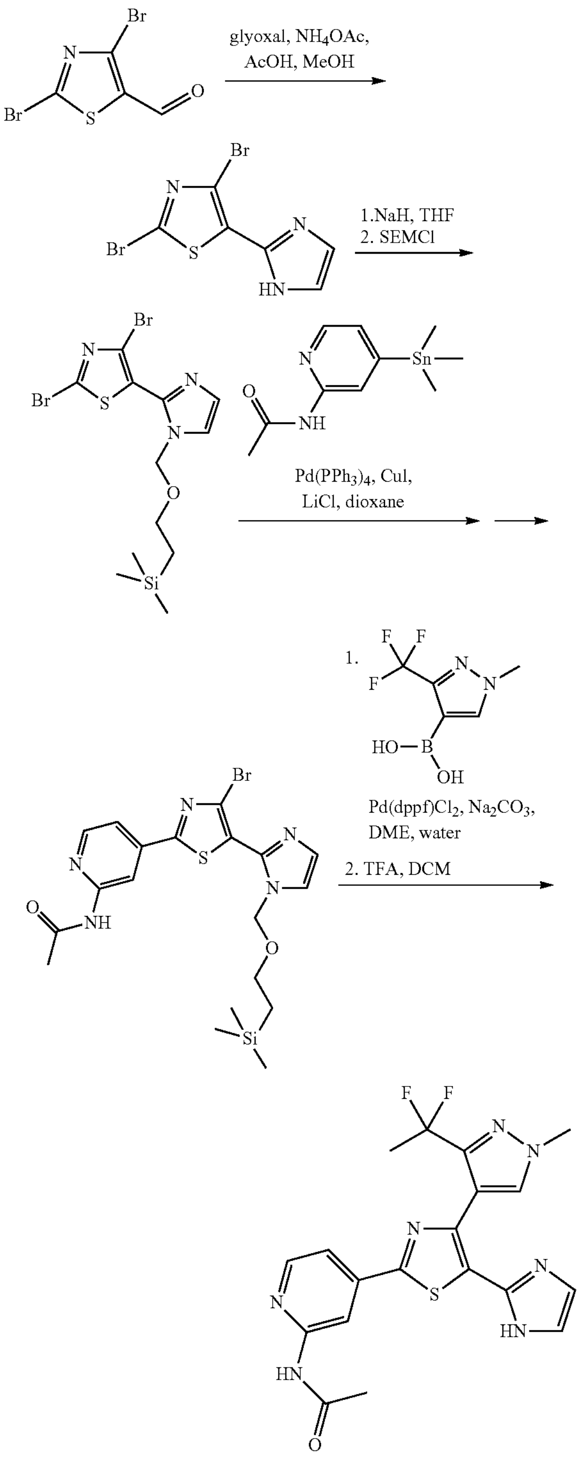

Step 1: 2,4-dibromo-5-(1H-imidazol-2-yl)thiazole

A mixture of 2,4-Dibromo-thiazole-5-carbaldehyde (14.8 g, 54.6 mmol), glyoxal trimer dihydrate (22.96 g, 109.2 mmol) and ammonium acetate (25.26 g, 327.8 mmol) in MeOH (450 mL) and AcOH (31.06 mL) was stirred at RT overnight. The reaction mixture was concentrated in vacuo to a thick liquid mixture. Remaining acetic acid was removed by azeotroping with toluene (3×100 mL) to afford a dark brown solid. The mixture was purified by ISCO chromatography, eluted with EtOAc in hexanes, 0-25% to give pure product (9.12 g, 54%). LCMS: (AA) $ES^+$, 310, 312. NMR (400 MHz, $d_6$-DMSO) δ: 12.50 (br, 1H) 7.21 (br, 2H).

Step 2: 2,4-dibromo-5-(1-((2-(trimethylsilyl)ethoxy)methyl)-1H-imidazol-2-yl)thiazole To a mixture of sodium hydride (2.89 g, 72.2 mmol) in THF (431 mL) was added 2,4-dibromo-5-(1H-imidazol-2-yl)thiazole (18.81 g, 60.88 mmol) in THF (60 mL) at 0° C. After stirring 30 min, [β-(Trimethylsilyl)ethoxy]methyl chloride (11.85 mL, 66.96 mmol) in THF (24 mL) was slowly added at 0° C. After 30 min at this temperature, the reaction was quenched by addition of MeOH (20 mL). The solvent was evaporated and the residue was purified by ISCO chromatography, eluted with EtOAc in hexanes, 0-25%. Product was obtained as colorless oil (21.84 g, 81.6%). LCMS: (AA) $ES^+$, 440, 442. $^1H$ NMR (300 MHz, $d_1$-chloroform) δ: 7.24 (dd, 2H) 5.27 (s, 2H) 3.39 (t, 2H) 0.85 (t, 2H) −0.03 (s, 9H).

Step 3: N-(4-(4-bromo-5-(1-((2-(trimethylsilyl)ethoxy)methyl)-1H-imidazol-2-yl)thiazol-2-yl)pyridin-2-yl)acetamide A mixture of 2,4-dibromo-5-(1-((2-(trimethylsilyl)ethoxy)methyl)-1H-imidazol-2-yl)thiazole (13.62 g, 31.01 mmol), N-[4-(trimethylstannyl)pyridin-2-yl]acetamide (11.1 g, 37.2 mmol), tetrakis(triphenylphosphine)palladium(0) (1.792 g, 1.550 mmol), copper(I) iodide (1.772 g, 9.302 mmol) and lithium chloride (3.944 g, 93.02 mmol) in 1,4-dioxane (569 mL) was degassed with argon. The mixture was sonicated for 20 min and then heated at 120° C. for 5 hrs. Solvent was evaporated and the crude reaction mixture was purified by ISCO chromatography, eluted with MeOH in DCM, 0-3%. Product was obtained as an orange solid (10.13 g, 66.0%). LCMS: (AA) $ES^+$, 494, 496. NMR (300 MHz, $d_1$-chloroform) δ: 8.65 (s, 1H) 8.44 (br, 1H) 8.34 (d, 1H) 7.60 (dd, 1H) 7.30 (d, 2H) 5.30 (s, 2H) 3.40 (t, 2H) 2.25 (s, 3H) 0.86 (t, 2H) −0.05 (s, 9H).

Step 4 and Step 5: N-(4-(4-(1-methyl-3-(trifluoromethyl)-1H-pyrazol-4-yl)-5-(1-((2-(trimethylsilyl)ethoxy)methyl)-1H-imidazol-2-yl)thiazol-2-yl)pyridin-2-yl)acetamide (6-C)

N-(4-(4-bromo-5-(1-((2-(trimethylsilyl)ethoxy)methyl)-1H-imidazol-2-yl)thiazol-2-yl)pyridin-2-yl)acetamide (70.0 mg, 0.120 mmol), 1-methyl-3-trifluoromethyl-1H-pyrazole-4-boronic acid pinacol ester (0.0708 g, 0.241 mmol), [1,1'-bis(diphenylphosphino)ferrocene] palladium(II) dichloride (4.95 mg, 0.00602 mmol) and sodium carbonate (38.3 mg, 0.361 mmol) in DME (1.2 mL) was degassed with argon. Water (0.5 mL) was added to the above mixture. The mixture was irradiated in microwave at 125° C. for 30 min. At that time, LCMS showed the desired product. Reaction mixture was filtered, the filtrate was evaporated to dryness, dissolved in DCM (1.20 mL) and treated with TFA (1.20 mL). This mixture was stirred at room temperature overnight. At that time, LCMS indicated formation of the desired product. The mixture was evaporated to dryness in vacuo, the residue was taken up by DMSO and purified using preparative HPLC to give product as yellow powder (16.3 mg, 31.2%). LCMS: (AA) $ES^+$, 434, 435. $^1H$ NMR (400 MHz, $d_4$-methanol) δ: 8.67 (br, 1H) 8.38 (dd, 1H) 7.87 (s, 1H) 7.63 (dd, 1H) 7.14 (d, 2H) 3.98 (s, 3H) 2.19 (s 3H).

Compounds in the following table were prepared from the appropriate starting materials in a method analogous to that of Example 5-C:

| | |
|---|---|
| 2-C | LCMS: (FA) ES+ 447 |
| 3-C | LCMS: (FA) ES+ 430 |
| 8-C | LCMS: (FA) ES+ 445 |
| 9-C | LCMS: (FA) ES+ 407 |
| 10-C | LCMS: (FA) ES+ 414 |
| 13-C | LCMS: (FA) ES+ 425, 427. |
| 14-C | LCMS: (FA) ES+ 429 |
| 16-C | LCMS: (FA) ES+ 423 |
| 17-C | LCMS: (FA) ES+ 430 |
| 19-C | LCMS: (FA) ES+ 475. |
| 21-C | LCMS: (FA) ES+ 393 |
| 22-C | LCMS: (FA) ES+ 431 |
| 23-C | LCMS: (FA) ES+ 426 |
| 24-C | LCMS: (FA) ES+ 378. |
| 25-C | LCMS: (FA) ES+ 407 |
| 26-C | LCMS: (FA) ES+ 430 |
| 27-C | LCMS: (FA) ES+ 363 |
| 28-C | LCMS: (FA) ES+ 366 |
| 29-C | LCMS: (FA) ES+ 393 |
| 33-C | LCMS: (FA) ES+ 379 |
| 35-C | LCMS: (FA) ES+ 393 |
| 37-C | LCMS: (FA) ES+ 419 |
| 38-C | LCMS: (FA) ES+ 376. |
| 39-C | LCMS: (FA) ES+ 431 |
| 40-C | LCMS: (FA) ES+ 426, 428. |
| 41-C | LCMS: (FA) ES+ 376 |
| 45-C | LCMS: (FA) ES+ 421 |
| 46-C | LCMS: (FA) ES+ 421 |
| 47-C | LCMS: (FA) ES+ 411 |
| 50-C | LCMS: (FA) ES+ 419 |
| 51-C | LCMS: (FA) ES+ 368 |
| 52-C | LCMS: (FA) ES+ 405 |
| 54-C | LCMS: (FA) ES+ 426 |
| 57-C | LCMS: (FA) ES+ 376 |
| 58-C | LCMS: (FA) ES+ 364, 366. |
| 60-C | LCMS: (FA) ES+ 455 |
| 61-C | LCMS: (FA) ES+ 420 |
| 62-C | LCMS: (FA) ES+ 394 |
| 63-C | LCMS: (FA) ES+ 398 |
| 68-C | LCMS: (FA) ES+ 406 |
| 69-C | LCMS: (FA) ES+ 478 |
| 72-C | LCMS: (FA) ES+ 420 |
| 73-C | LCMS: (FA) ES+ 378 |

Example 6-C

Synthesis of N-(4-(4-acetamido-5-(1H-imidazol-2-yl)thiazol-2-yl)pyridin-2-yl)acetamide (20-C)

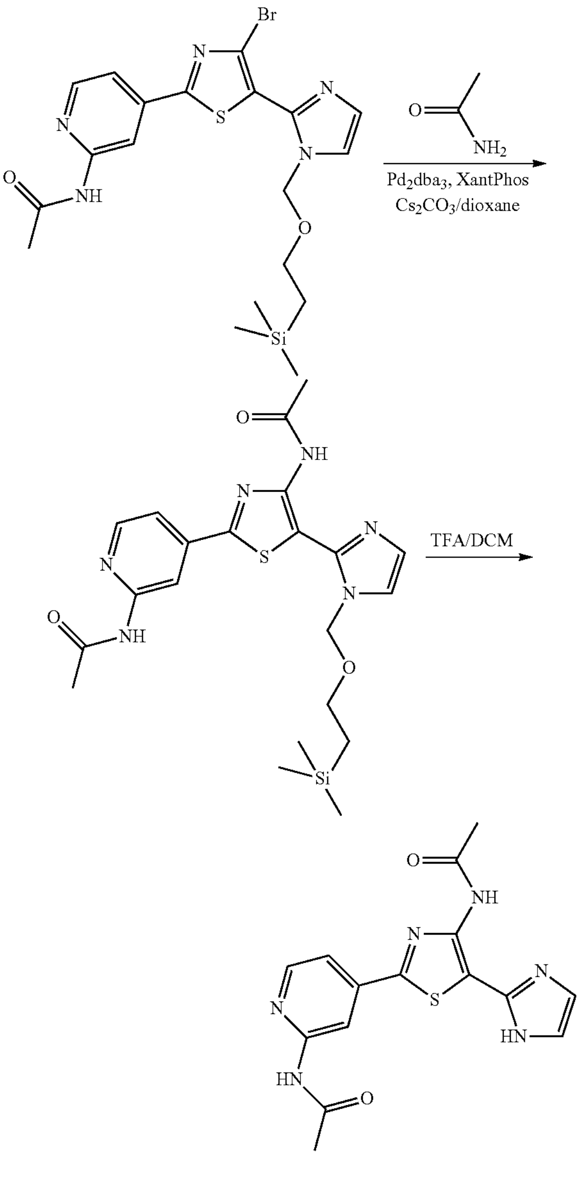

Step 1, Preparation of N-(4-(4-acetamido-5-(1H-imidazol-2-yl)thiazol-2-yl)pyridin-2-yl)acetamide A mixture of N-(4-(4-bromo-5-(1-((2-(trimethylsilyl)ethoxy)methyl)-1H-imidazol-2-yl)thiazol-2-yl)pyridin-2-yl)acetamide (100.0 mg, 0.2022 mmol), Tris(dibenzylideneacetone)dipalladium(0) (21.1 mg, 0.0230 mmol), 4,5-Bis(diphenylphosphino)-9,9-dimethylxanthene (44.2 mg, 0.0764 mmol) and Cesium Carbonate (299 mg, 0.918 mmol) in 1,4-Dioxane (5.0 mL, 64 mmol) was filled with argon and irradiated in microwave at 130° C. for 2 h. The reaction mixture was filtered. The filtration was evaporated to a residue which was purified by column chromatography. Desired title intermediate was obtained LCMS ES+ 473.5, ES− 471.5.

Step 2, Preparation of N-(4-(4-acetamido-5-(1H-imidazol-2-yl)thiazol-2-yl)pyridin-2-yl)acetamide The above intermediate was dissolved in DCM (1.5 mL, 23 mmol) and to this solution was added TFA (2.2 mL, 29 mmol). The mixture was stirred at RT for 2 h. The mixture was evaporated and the residue was purified by column chromatography. The title compound was obtained as white powder. (21.9 mg, 31.6% in 2 steps). LC/MS (AA) ES+ 343.4; ES− 341.5. $^1$H NMR (400 MHz, $d_6$-DMSO) δ ppm 10.78-10.66 (m, 1H), 8.64 (s, 1H), 8.43 (d, J=5.02 Hz, 1H), 7.58-7.52 (m, 1H), 7.26-7.11 (m, 1H), 2.21-2.14 (m, 3H), 2.13 (s, 3H).

Example 7-C

Synthesis of N-{4-[4-(2,6-dimethylphenyl)-5-(4H-1,2,4-triazol-3-yl)-1,3-thiazol-2-yl]pyridin-2-yl}acetamide (56-C)

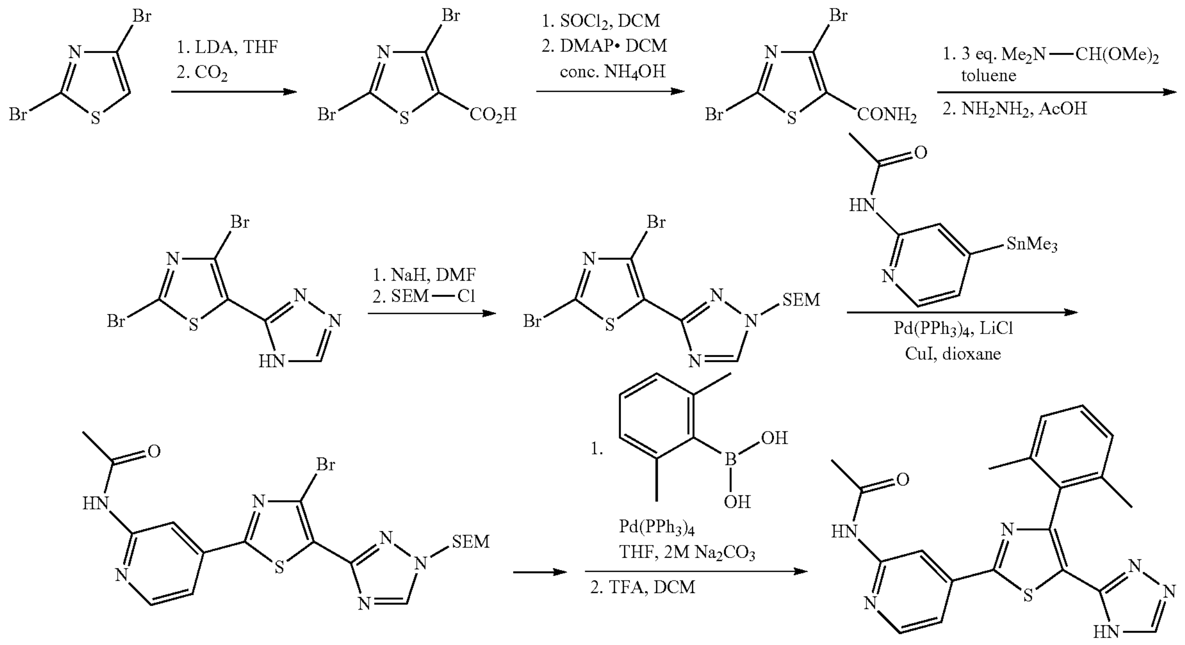

Step 1: Synthesis of 2,4-dibromo-1,3-thiazole-5-carboxylic acid

To a 500 mL 3-neck round bottom flask equipped with dropping funnel and internal temperature monitor was added THF (200 mL) and N,N-Diisopropylamine (14.7 mL, 105 mmol) under atmosphere of Argon. After cooling at −75° C., 2.50 M of n-Butyllithium in Hexane (41.1 mL, 103 mmol) was added dropwise into the solution over 30 min. The internal temperature was kept below −70° C. and the resulting solution was stirred for 15 min at −75° C. To this LDA solution was added a solution of 2,4-dibromothiazole (25.0 g, 99.8 mmol) in THF (60 mL) via dropping funnel over 40 min and the internal temperature was kept below −70° C., then this solution was stirred for 20 min at −75° C. To this solution was added crushed dry ice at −75° C. and the mixture was stirred for 15 min. At that time, 10 mL water was added dropwise. Cooling bath was removed and the mixture was brought to r.t. over 1 hour with a water bath. The solvent was evaporated under reduced pressure to give a solid residue. The residue was suspended in 100 mL water, basified with 1.00 M of Sodium hydroxide in water (110 mL) and extracted with 100 mL ether. The ether layer was washed with 0.5 N NaOH (2×30 mL). The combined aqueous solution was acidified with conc. HCl with ice to pH~2, extracted with ether (5×100 mL, adjusting pH~2 each time after separation). The combined ether solution was washed with brine, dried over $Na_2SO_4$, filtered, evaporated to give a solid product (28.04 g, 98%). LCMS: (FA) ES+ 288, ES− 286.

Step 2: Synthesis of 2,4-dibromo-1,3-thiazole-5-carboxamide

A suspension of 2,4-dibromo-1,3-thiazole-5-carboxylic acid (16.33 g, 56.91 mmol) in dry DCM (250 mL) and DMF (0.400 mL) was cooled with ice bath. Thionyl chloride (40.0 mL, 548 mmol) was added dropwise. The cooling bath was removed and the suspension was stirred at r.t. for 2.5 hours. Toluene (80 mL, 800 mmol) was added and the suspension was heated to reflux for 1 hour. The mixture was cooled to room temperature, solvent was removed and the residue was azeotroped with toluene (2×100 mL) to give a crude intermediate. This material was suspended in DCM (230 mL) and cooled with ice bath. N,N-dimethylaminopyridine (0.70 g, 5.7 mmol) was added, followed by slow addition of 8.5 M of Ammonium hydroxide in Water (100.0 mL, 850.0 mmol). The mixture was stirred at room temperature overnight. The mixture was filtered, aqueous layer was separated and extracted with DCM (3×100 mL). The combined DCM layers were washed with water, brine, dried over $Na_2SO_4$, filtered, and evaporated to give a solid product (11.2 g, 69%). LCMS: (FA) ES+ 287 and ES− 285.

Step 3: Synthesis of 3-(2,4-dibromo-1,3-thiazol-5-yl)-4H-1,2,4-triazole

To the suspension of 2,4-dibromo-1,3-thiazole-5-carboxamide (0.110 g, 0.385 mmol) in dry Toluene (8.0 mL, 75 mmol) was added DMFDMA (0.204 mL, 1.54 mmol). The mixture was stirred at 60° C. under N2 atmosphere for 3 hours. The solvent was removed and to the intermediate was added acetic acid (2.0 mL, 35 mmol), followed by hydrazine (0.0604 mL, 1.92 mmol). The mixture was heated to 120° C. for 30 min. The mixture was cooled to room temperature, solvent was removed and the residual acetic acid was azeotroped with toluene (2×5 mL) to give an oily material, which was basified with saturated aqueous $NaHCO_3$ to pH~8 and extracted with EtOAc (3×30 mL). The EtOAc layer was washed with water, brine, dried over $Na_2SO_4$, filtered, and evaporated to give a crude product. Chromatography on a silica column using EtOAc/hexane (0/100 to 50/50) gave a solid product (0.073 g, 61%). LCMS: (FA) ES+ 311 and ES− 309.111 NMR (400 MHz, $d_4$-Methanol) δ 8.53 (s, 1H).

Step 4: Synthesis of 3-(2,4-dibromo-1,3-thiazol-5-yl)-1-{[2-(trimethylsilyl)ethoxy]methyl}-1H-1,2,4-triazole To the solution of 3-(2,4-dibromo-1,3-thiazol-5-yl)-4H-1,2,4-triazole (1.16 g, 3.74 mmol) in dry DMF (5.0 mL) at 0° C. was added portionwise sodium hydride (60%, 0.180 g, 4.49 mmol). The ice bath was removed, mixture was stirred for 5 min. at ambient temperature and cooled with ice bath. SEM chloride (0.795 mL, 4.49 mmol) in dry DMF (2.0 mL) was added dropwise and the mixture was stirred at room temperature for 2 hours. The mixture was quenched with ice-water, extracted with EtOAc, washed with brine, dried over $Na_2SO_4$, filtered, evaporated to give a crude oil. Chromatograph in a silica column using EtOAc/hexane (0/100 to 20/80) afforded white solid product (1.10 g, 67%). LCMS: (FA) ES+ 441. $^1H$ NMR (400 MHz, $d_1$-chloroform) δ 8.29 (s, 1H), 5.54 (s, 2H), 3.71 (t, J=8.28 Hz, 2H), 0.95 (t, J=8.28 Hz, 2H), 50.00 (s, 9H).

Step 5: Synthesis of N-{4-[4-bromo-5-(1-{[2-(trimethylsilyl)ethoxy]methyl}-1H-1,2,4-triazol-3-yl)-1,3-thiazol-2-yl]pyridin-2-yl}acetamide The mixture of 3-(2,4-dibromo-1,3-thiazol-5-yl)-1-{[2-(trimethylsilyl)ethoxy]methyl}-1H-1,2,4-triazole (1.10 g, 2.50 mmol), N-[4-(trimethylstannyl)pyridin-2-yl]acetamide (0.896 g, 3.00 mmol), tetrakis(triphenylphosphine)palladium (0) (0.155 g, 0.125 mmol), copper(I) iodide (0.143 g, 0.750 mmol) and lithium chloride (0.318 g, 7.50 mmol) in dry 1,4-Dioxane (100 mL) was sonicated for 2 min, degassed and backfilled with nitrogen for 5 times. The mixture was heated under nitrogen atmosphere to reflux for 90 min, cooled to room temperature, filtered thought celite and washed with dioxane/DCM. The filtrate was evaporated under reduced pressure to give a crude residue, which was purified using chromatography on a silica column using MeOH/DCM (0/100 to 5/95) to give a product, which was further purified on a silica column using MeOH/EtOAc/hexane (0/0/100 to 5/45/50) to give pure product (0.150 g, 13%). LCMS: (FA) ES+ 495, 497. $^1H$ NMR (400 MHz, $d_1$-chloroform) δ 8.72 (s, 1H), 8.37 (m, 1H), 8.33 (s, 1H), 8.26 (s, 1H), 7.68 (m, 1H), 5.57 (s, 2H), 3.73 (t, J=8.28 Hz, 2H), 2.25 (s, 3H), 0.97 (t, J=8.28 Hz, 2H), 0.00 (s, 9H).

Step 6: Synthesis of N-{4-[4-(2,6-dimethylphenyl)-5-(4H-1,2,4-triazol-3-yl)-1,3-thiazol-2-yl]pyridin-2-yl}acetamide (56-C)

The mixture of N-{4-[4-bromo-5-(1-{[2-(trimethylsilyl)ethoxy]methyl}-1H-1,2,4-triazol-3-yl)-1,3-thiazol-2-yl]pyridin-2-yl}acetamide (0.0340 g, 0.0686 mmol), 2,6-dimethylphenylboronic acid (20.6 mg, 0.137 mmol), tetrakis(triphenylphosphine)palladium (0) (9.1 mg, 0.0073 mmol), and 2 M sodium carbonate in water (0.0850 mL, 0.170 mmol) in 1,4-dioxane (2.0 mL) in capped vial was heated to 140° C. for 19 hours. Additional tetrakis(triphenylphosphine)palladium(0) (7.1 mg, 0.0057 mmol) was added and the mixture was heated to 140° C. for 1 additional day. The mixture was filtered through celite/$Na_2SO_4$, washed with EtOAc, and evaporated under reduced pressure to give a crude intermediate. The material was treated with TFA (2.0 mL, 26 mmol) in dry DCM (2.0 mL) for 5 hours. The solvent was evaporated under reduced pressure and azeotroped with toluene to give a crude product. HPLC purification gave 0.002 g of pure product as a white powder (7.5%). LCMS: (FA) ES+ 391 and ES− 389. $^1H$ NMR (400 MHz, $d_4$-Methanol) δ 8.73 (s, 1H), 8.40 (d, J=5.84 Hz, 1H), 8.35 (s, 1H), 7.68 (d, J=5.84 Hz, 1H), 7.20 (m, 1H), 7.11 (s, 1H), 7.09 (d, J=7.35 Hz, 1H), 2.21 (s, 3H), 2.03 (s, 6H).

Compounds in the following table were prepared from the appropriate starting materials in a method analogous to that of Example 7-C:

| | |
|---|---|
| 53-C | LCMS: (FA) ES+ 431, 433. |
| 65-C | LCMS: (FA) ES+ 411, 413. |
| 70-C | LCMS: (FA) ES+ 394. |
| 71-C | LCMS: (FA) ES+ 431, 433. |

Example 8-C

Synthesis of N-{4-[5-(acetylamino)-4-(2-chlorophenyl)-1,3-thiazol-2-yl]pyridin-2-yl}acetamide (1-C)

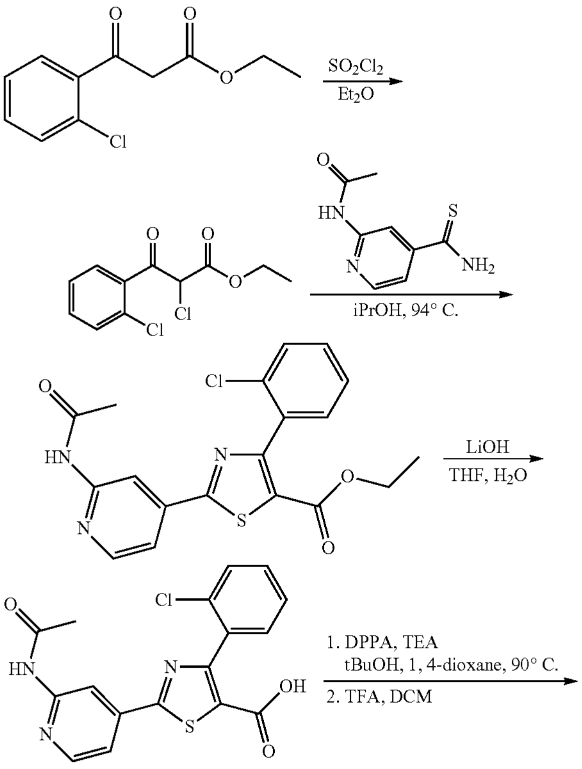

-continued

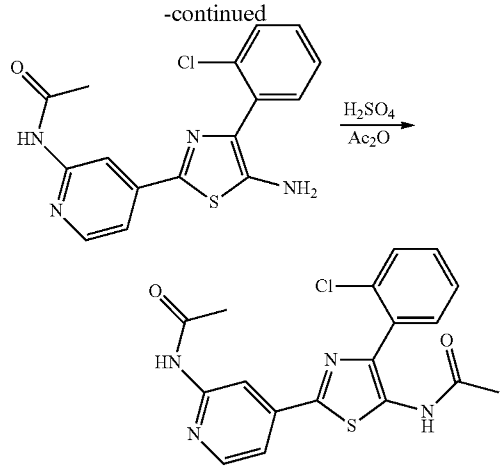

Step 1, Preparation of ethyl 2-chloro-3-(2-chlorophenyl)-3-oxopropanoate

To a stirred solution of 3-(2-chloro-phenyl)-3-oxo-propionicacidethylester (5.000 mL, 26.600 mmol) in ether (75.00 mL) was added dropwise sulfuryl chloride (2.800 mL, 34.600 mmol) and the resulting solution was stirred for 4 h. The reaction mixture was diluted with ether (50.0 mL) and quenched by the slow addition of a saturated aqueous solution of sodium bicarbonate (50.0 mL) and the mixture was vigorously stirred for 30 min. The organic phase was separated and dried over anhydrous $MgSO_4$, filtered, and concentrated in vacuo to provide 6.500 g of crude product as a clear colorless oil (100%). The crude residue was used without further purification. LC/MS (AA) ES+ 261, 263. $^1$H NMR (400 MHz, d, $CDCl_3$) δ: 12.47 (s, 1H), 7.49-7.32 (m, 4H), 4.39 (q, J=7.2 Hz, 2H), 1.41 (t, J=7.2 Hz, 3H).

Step 2, Preparation of ethyl 2-[2-(acetylamino)pyridin-4-yl]-4-(2-chlorophenyl)-1,3-thiazole-5-carboxylate To a stirred solution of crude ethyl 2-chloro-3-(2-chlorophenyl)-3-oxopropanoate (1.390 g, 5.320 mmol) in absolute isopropyl alcohol (50.00 mL) was added N-[4-(aminocarbonothioyl)pyridin-2-yl]acetamide (1.140 g, 5.860 mmol) and the resulting solution was fitted with a condenser and stirred for 23 h at 94° C. The mixture was cooled to ambient temperature and half the solvent was removed in vacuo. Diethyl ether (30.0 mL) was added to allow the formation of the thioamide by-product. The by-product was separated by filtration and the solvent was removed in vacuo. The residue was purified by column chromatography ($SiO_2$, elution with 0-100% EtOAc in hexanes) to provide 0.457 g of product as a yellow oil (21% 2 steps). LC/MS (AA) ES+ 402. NMR (400 MHz, $d_1$ $CDCl_3$) δ: 8.77 (br s, 1H), 8.37-8.35 (m, 1H), 7.71-7.70 (m, 1H), 7.50-7.46 (m, 2H), 7.41-7.46 (m, 3H), 4.24 (q, J=7.2 Hz, 2H), 2.24 (s, 3H), 1.26 (t, J=7.2 Hz, 3H).

Step 3, Preparation of 2-[2-(acetylamino)pyridin-4-yl]-4-(2-chlorophenyl)-1,3-thiazole-5-carboxylic acid To a stirred solution of ethyl 2-[2-(acetylamino)pyridin-4-yl]-4-(2-chlorophenyl)-1,3-thiazole-5-carboxylate (0.249 g, 0.620 mmol) in tetrahydrofuran (1.670 mL) and water (0.100 mL) was added lithium hydroxide, monohydrate (0.037 g, 0.891 mmol) and stirred for 18 h. The mixture was acidified to pH 6 with aqueous 1N HCl (1.20 mL, 1.20 mmol) and extracted with EtOAc (10.0 mL×3). The combined organic layers were dried over anhydrous $Na_2SO_4$, filtered and concentrated in vacuo to afford the crude product (0.232 g) as a yellow solid and used without further purification. LC/MS (AA) ES+ 374, 376. $^1$H NMR (400 MHz, $d_6$ DMSO) δ: 10.75 (br s, 1H), 8.69 (br s, 1H), 8.47-8.46 (m, 0.5H), 8.06-8.04 (m, 0.5H), 7.65-7.64 (m, 0.5H), 7.58-7.44 (m, 5H), 7.06-7.99 (m, 0.5H), 2.12 (s, 3H).

Step 4, Preparation of N-{4-[5-amino-4-(2-chlorophenyl)-1,3-thiazol-2-yl]pyridin-2-yl}acetamide To a stirred solution of 2-[2-(acetylamino)pyridin-4-yl]-4-(2-chlorophenyl)-1,3-thiazole-5-carboxylic acid (0.232 g, 0.621 mmol) in tert-butyl alcohol (29.70 mL) and 1,4-dioxane (9.69 mL) was added dropwise triethylamine (0.432 mL, 3.100 mmol) and stirred for 15 min. Diphenylphosphonic azide (0.345 mL, 1.550 mmol) was added and the reaction mixture was heated to 77° C. and allowed to stir for 2 h. The mixture was cooled to rt and diluted with EtOAc (50.0 mL). The mixture was washed successively with saturated aqueous solution of sodium bicarbonate (10.0 mL), water (10.0 mL), and brine (100.0 mL). The organic layer was dried over anhydrous $Na_2SO_4$, filtered, and concentrated in vacuo to afford the crude product and used without further purification. LC/MS (AA) ES+ 376.

The crude material was dissolved in methylene chloride (8.120 mL) and cooled to 0° C. Trifluoroacetic Acid (0.478 mL, 6.210 mmol) was added and the reaction mixture was allowed to warm to rt and stir for 4 h. The mixture was cooled to 0° C. and the reaction was quenched by the addition of a saturated aqueous solution of sodium bicarbonate (10.0 mL) and warmed to rt. The mixture was extracted with EtOAc (10.0 mL×3) and the combined organic layers were dried over anhydrous $Na_2SO_4$, filtered, and concentrated in vacuo. The residue was purified by column chromatography ($SiO_2$, elution with 0-75% EtOAc in hexanes) to provide 0.074 g of product as a yellow oil (35% 3 steps). LC/MS (AA) ES+ 345, 347. $^1$H NMR (400 MHz, d, $CDCl_3$) δ: 8.47 (br s, 1H), 8.19-7.98 (m, 1H), 7.56-7.04 (m, 6H), 4.67 (br s, 2H), 2.21 (s, 3H).

Step 5, Preparation of N-{4-[5-(acetylamino)-4-(2-chlorophenyl)-1,3-thiazol-2-yl]pyridin-2-yl}acetamide (1-C)

To a stirred solution of N-{4-[5-amino-4-(2-chlorophenyl)-1,3-thiazol-2-yl]pyridin-2-yl}acetamide (0.020 g, 0.058 mmol) in anhydrous acetic anhydride (1.00 mL, 10.60 mmol) was added dropwise concentrated sulfuric acid (0.002 mL, 0.030 mmol) and stirred for 18 h. The reaction was quenched by the dropwise addition of a triethylamine (0.200 mL) and concentrated in vacuo. The residue was purified by column chromatography ($SiO_2$, elution with 0-100% EtOAc in hexanes) to provide 0.014 g of product as a yellow oil (62%). LC/MS (AA) ES+ 387, 389. $^1$H NMR (400 MHz, $d_1$ $CDCl_3$) δ: 9.10 (br s, 1H), 8.63 (br s, 1H), 8.31-8.30 (m, 0.5H), 7.64-7.24 (m, 6.5H), 2.18 (s, 3H), 2.14 (s, 3H).

Example 9-C

Synthesis of 2-[2-(acetylamino)pyridin-4-yl]-4-(2-chlorophenyl)-N-(2-hydroxyethyl)-1,3-thiazole-5-carboxamide (48-C)

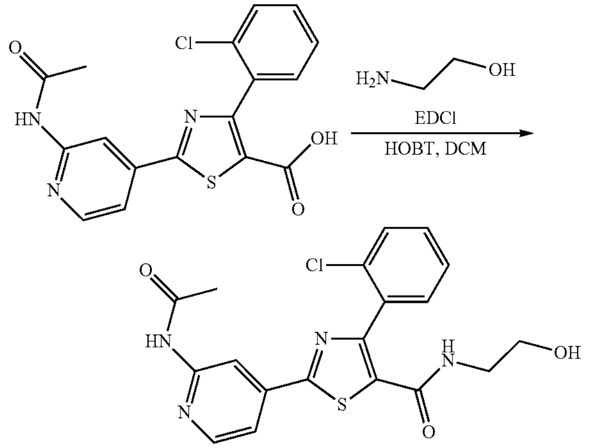

Step 1, Preparation of 2-[2-(acetylamino)pyridin-4-yl]-4-(2-chlorophenyl)-N-(2-hydroxyethyl)-1,3-thiazole-5-carboxamide (48-C)

To a stirred solution of 2-[2-(acetylamino)pyridin-4-yl]-4-(2-chlorophenyl)-1,3-thiazole-5-carboxylic acid (0.050 g, 0.130 mmol) in methylene chloride (3.00 mL, 46.80 mmol) was added N-(3-dimethylaminopropyl)-N'-ethylcarbodiimide hydrochloride (0.056 g, 0.294 mmol) followed by 1-hydroxybenzotriazole (0.040 g, 0.294 mmol) and the resulting solution was stirred for 1 h. Ethanolamine (0.081 mL, 1.340 mmol) was added and the reaction mixture was continued to stir for 18 h. The mixture was quenched by the addition of water (5.0 mL) and extracted with EtOAc (10.0 mL×3). The combined organic layers were dried over anhydrous $Na_2SO_4$, filtered, and concentrated in vacuo. The residue was purified by column chromatography ($SiO_2$, elution with 0-75% EtOAc in hexanes) to provide 0.0300 g of product as a clear colorless oil (54% 2 steps). LC/MS (AA) $ES_+$417, 419. $^1H$ NMR (400 MHz, $d_1$ $CDCl_3$) δ: 8.06-7.98 (m, 1H), 7.72-7.54 (m, 3H), 7.49-7.44 (m, 2H), 7.02-6.96 (m, 1H), 6.28 (br s, 1H), 4.72 (br t, J=5.6 Hz, 1H), 4.66 (br t, J=5.4 Hz, 1H), 3.37 (q, J=6.0 Hz, 2H), 3.18 (q, J=6.4 Hz, 2H), 2.12 (s, 3H).

Compounds in the following table were prepared from the appropriate starting materials in a method analogous to that of Example 9-C:

| | |
|---|---|
| 4-C | LC/MS (AA) ES+ 431, 433. |
| 64-C | LCMS: (AA) ES+ 431, 433. |

Example 10-C

Synthesis of methyl {4-[5-(5-amino-4H-1,2,4-triazol-3-yl)-4-(2,4-dichlorophenyl)-1,3-thiazol-2-yl]pyridin-2-yl}carbamate (44-C)

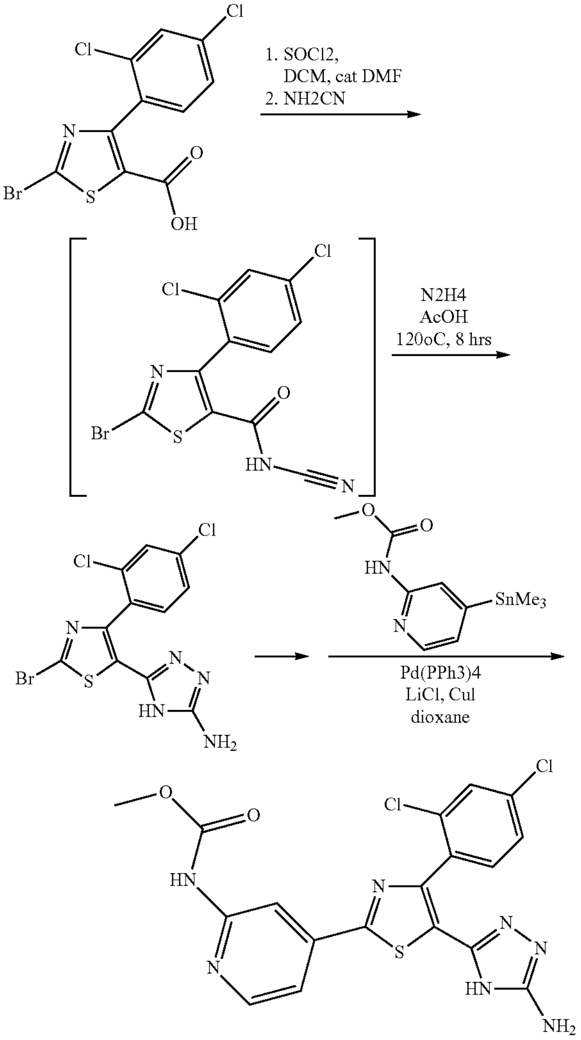

Step 1: Synthesis of 5-[2-bromo-4-(2,4-dichlorophenyl)-1,3-thiazol-5-yl]-4H-1,2,4-triazol-3-amine To the suspension of 2-bromo-4-(2,4-dichlorophenyl)-1,3-thiazole-5-carboxylic acid (0.512 g, 1.45 mmol) in Methylene chloride (10 mL, 200 mmol) and N,N-Dimethylformamide (0.020 mL, 0.26 mmol) was added Thionyl chloride (1.0 mL, 14 mmol), heated to reflux for 2 hours. The mixture was rotavaped, azeotroped with toluene to give the syrup intermediate. The intermediate was dissolved in dry Methylene chloride (10 mL, 200 mmol). N,N-dimethylaminopyridine (17.3 mg, 0.142 mmol) was added followed by N,N-Diisopropylethylamine (0.62 mL, 3.6 mmol). Cyanamide (69.0 mg, 1.64 mmol) was added and the mixture was stirred at r.t. for 1 hour. The mixture was rotavaped to give a crude residue. To the residue was added Acetic acid (10 mL, 200 mmol), followed by Hydrazine (0.200 mL, 6.37 mmol). The solution was heated to 120° C. for 8 hours. The mixture was cooled to r.t., rotavaped to give an oily residue. The residue was neutralized with saturated aqueous $NaHCO_3$ solution to pH~8, extracted with 10% MeOH/DCM (3×50 mL). The DCM solution was dried over $Na_2SO_4$, filtered and rotavaped to give a crude product. Chromatograph in an 80 g ISOC column using MeOH/DCM (0/100 to 5/95) afforded a solid product (0.144 g, 25.4% yield). LCMS: (FA) $ES^+$392, 394, $ES^-$ 390, 392. $^1H$ NMR (400 MHz, d-chloroform & $d_4$-Methanol) δ 7.29-7.39 (m, 2H), 7.19-7.22 (m, 1H).

Step 2: Synthesis of methyl {4-[5-(5-amino-4H-1,2,4-triazol-3-yl)-4-(2,4-dichlorophenyl)-1,3-thiazol-2-yl]pyridin-2-yl}carbamate (44-C)

The mixture of 5-[2-bromo-4-(2,4-dichlorophenyl)-1,3-thiazol-5-yl]-4H-1,2,4-triazol-3-amine (0.0300 g, 0.0767 mmol), methyl [4-(trimethylstannyl)pyridin-2-yl]carbamate (0.0362 g, 0.115 mmol), Lithium chloride (9.76 mg, 0.230 mmol), Copper(I) iodide (7.0 mg, 0.037 mmol) and Tetrakis (triphenylphosphine)palladium(0) (7.0 mg, 0.0060 mmol) in dry 1,4-Dioxane (4.0 mL, 51 mmol) was purged with $N_2$ for 5 min, heated to reflux (120° C.) under $N_2$ atmosphere for 3 hours, cooled to r.t. . . . . The mixture was diluted with 10% MeOH-DCM (10 mL), filtered through a short column of Celite/$Na_2SO_4$. The filtrate was rotavaped and the residue was chromatographed in a 8 g AnaLogix column using MeOH/DCM (0/100 to 5/95) to give a solid product (0.0084 g, 24% yield). LCMS: (FA) $ES^+$ 462, 464, $ES^-$ 460, 462. $^1H$ NMR (400 MHz, d-chloroform & $d_4$-Methanol) δ 8.21 (s, 1H), 8.05 (s, 1H), 7.30-7.32 (m, 1H), 7.19-7.24 (m, 2H), 7.06-7.09 (m, 1H), 3.54 (s, 3H).

Example 1-D

Synthesis of 5-[4-(2,4-dichlorophenyl)-5-(1H-imidazol-2-yl)-1,3-thiazol-2-yl]-3,4-dihydro-1,8-naphthyridin-2(1H)-one (1-D)

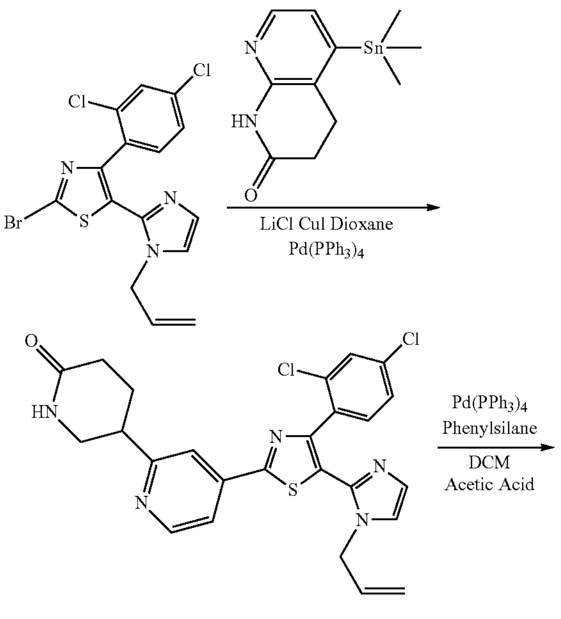

-continued

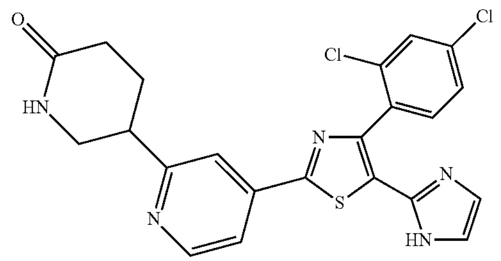

The title compound was prepared from 5-(1-Allyl-1H-imidazol-2-yl)-2-bromo-4-(2,4-dichlorophenyl)-1,3-thiazole and 5-(trimethylstannyl)-3,4-dihydro-1,8-naphthyridin-2(1H)-one using procedures analogous to those described in Example 1-C, Steps 8 and 9. LCMS: (FA) $ES^+$ 442, 444. $^1H$ NMR (300 MHz, $d_6$-DMSO) δ: 12.10-11.89 (bs, 1H), 10.64 (s, 1H), 8.25 (d, J=5.28 Hz, 1H), 7.74 (d, J=1.72 Hz, 1H), 7.60-7.46 (m, 2H), 7.39 (d, J=5.29 Hz, 1H), 7.23-6.94 (m, 2H), 4.11-4.06 (m, 1H), 3.38-3.30 (m, 1H), 3.16 (d, J=5.21 Hz, 2H).

Compounds in the following table were prepared from the appropriate starting materials in a method analogous to that of Example 1-D:

| | |
|---|---|
| 2-D | LCMS: (FA) ES+ 412, 414. |
| 3-D | LCMS: (FA) ES+ 440, 442. |

Example 1-E

Synthesis of 4-[4-(2,4-dichlorophenyl)-5-(1H-imidazol-2-yl)-2-thienyl]thieno[2,3-b]pyridine (4-E)

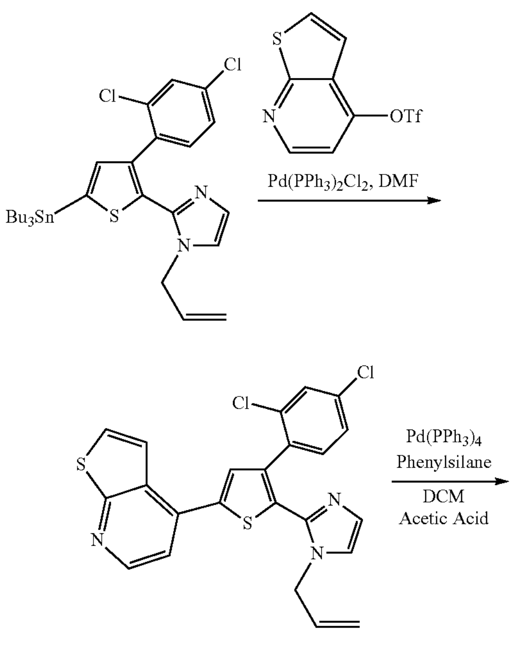

-continued

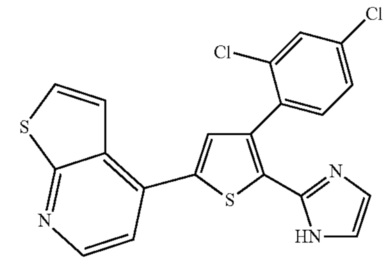

The title compound was prepared from 1-allyl-2-[3-(2,4-dichlorophenyl)-5-(tributylstannyl)-2-thienyl]-1H-imidazole and thieno[2,3-b]pyridin-4-yl trifluoromethanesulfonate using procedures analogous to those described in Example 8-A, Steps 2 and 3. LC/MS (AA) ES+ 428, 430. $^1$H NMR (400 MHz, $d_6$ DMSO) δ: 11.97-11.69 (m, 1H), 8.73 (d, J=4.97 Hz, 1H), 8.27 (d, J=5.56 Hz, 1H), 7.88 (s, 1H), 7.77-7.73 (m, 2H), 7.68 (d, J=5.56 Hz, 1H), 7.52-7.43 (m, 2H), 7.22-6.89 (m, 2H).

Compound in the following table was prepared from the appropriate starting materials in a method analogous to that of Example 1-E:

| | |
|---|---|
| 5-E | LCMS: (FA) ES+ 422, 424. |

Example 2-E

Synthesis of 3-[4-(2,4-dichlorophenyl)-5-(1H-imidazol-2-yl)-2-thienyl]-2-methylpyrazolo[1,5-a]pyridine (2-E)

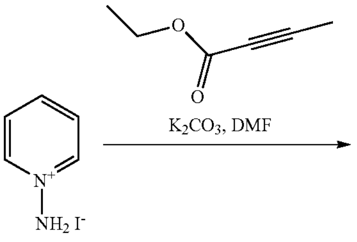

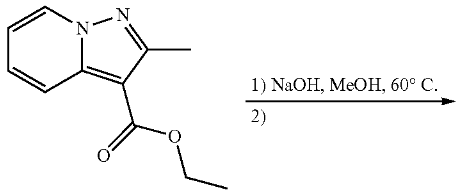

-continued

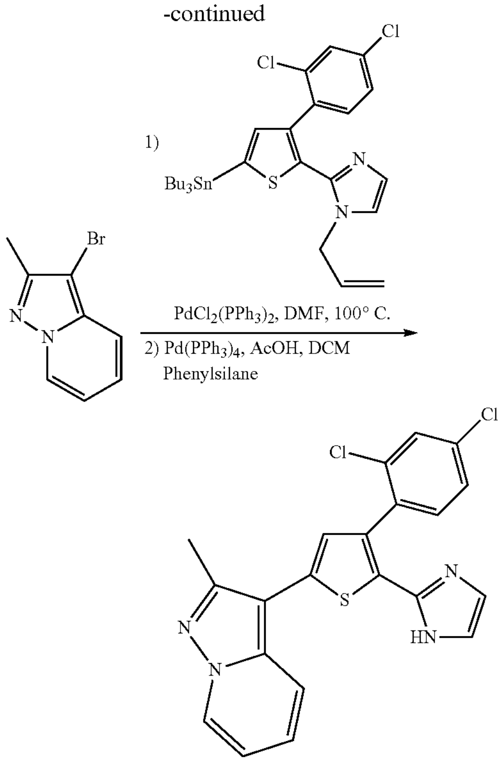

Step 1: Preparation of ethyl 2-methylpyrazolo[1,5-a]pyridine-3-carboxylate

To a mixture of 1-aminopyridinium iodide (19 g, 86 mmol) and potassium carbonate (12 g, 86 mmol) in DMF (100 mL) was added ethyl 2-butynoate (8.0 g, 71 mmol) and the reaction stirred overnight. The DMF was removed by rotary evaporation and the resulting solid was taken up in EtOAc (200 ml) and water (200 ml), partitioned and the aqueous phase extracted with 2×150 ml EtOAc. The combined organics were washed with brine, dried over $MgSO_4$ and concentrated.

The product was purified by column chromatography on silica gel eluting with 25% EtOAc in hexanes. The title compound was isolated as an off white solid, 8.7 g. LC/MS (FA) ES+ 205.0.

Step 2: Preparation of 3-bromo-2-methylpyrazolo[1,5-a]pyridine

To a solution of ethyl 2-methylpyrazolo[1,5-a]pyridine-3-carboxylate (5.6 g, 24 mmol) in methanol (40 mL, 1000 mmol) was added aqueous sodium hydroxide solution (5.0 mL, 8 M) and the mixture heated to 4° C. for 60 h. The reaction was allowed to cool, hydrochloric acid (5.0 mL, 12 M) and water (150 mL) was added to give a colorless precipitate. The solid was filtered, washed with water and dried in a vacuum oven to give crude 2-methylpyrazolo[1,5-a]pyridine-3-carboxylic acid, 2.63 g. A suspension of 2-methylpyrazolo[1,5-a]pyridine-3-carboxylic acid (2.0 g, 11 mmol), in Acetonitrile (120 mL) and water (60 mL) was degassed and [I,I-Bis(trifluoroacetoxy)iodo]benzene (2.90 g, 6.74 mmol) was added and the reaction heated under argon to 60 C for 15 min. Gave a clear solution. N-Bromosuccinimide (2.40 g, 13.5 mmol) was added and the solution was stirred at 60° C. for 30 minutes under an atmosphere of argon. The color turned dark. The reaction was heated for a further 30 min, allowed to cool, concentrated to remove acetonitrile and the aqueous extracted with EtOAc (3×50 ml). The organics were combined, washed with ascorbic acid solution, water, dried (MgSO4) and concentrated. The product was purified by column chromatography on silica gel eluting with DCM to 0.5% MeOH in DCM. The title compound was isolated as an off white solid, 0.56 g. LC/MS (FA) ES+ 210.9, 212.9.

Step 3, Synthesis of 3-[4-(2,4-dichlorophenyl)-5-(1H-imidazol-2-yl)-2-thienyl]-2-methylpyrazolo[1,5-a]pyridine (2-E)

To a solution of 1-allyl-2-[3-(2,4-dichlorophenyl)-5-(tributylstannyl)-2-thienyl]-1H-imidazole (180 mg, 0.29 mmol) in DMF (4.0 mL) was added [3-bromo-2-methylpyrazolo[1,5-a]pyridine (50 mg, 0.2 mmol) (azeotroped from toluene) and Bis(triphenylphosphine)palladium(II) chloride (8.5 mg, 0.012 mmol). The resulting mixture was degassed and stirred for 1 h at 100° C. under an atmosphere of argon. The reaction mixture was allowed to cool, concentrated and the residue was partially purified by silica gel column chromatography (40 g, eluting with 30% EtOAc in hexanes to EtOAc to give 3-[5-(1-allyl-1H-imidazol-2-yl)-4-(2,4-dichlorophenyl)-2-thienyl]-2-methylpyrazolo[1,5-a]pyridine, 82 mg. To a solution of [A] 3-[5-(1-allyl-1H-imidazol-2-yl)-4-(2,4-dichlorophenyl)-2-thienyl]-2-methylpyrazolo [1,5-a]pyridine (70 mg, 0.2 mmol), tetrakis (triphenylphosphine)palladium(0) (8.5 mg, 0.0074 mmol) and acetic acid (0.4 mL, 7 mmol) in DCM (1.5 mL) was added slowly phenylsilane (0.1 mL, 0.8 mmol) and the reaction mixture stirred at 40° C. for 2 h. The reaction mixture was concentrated and the product was purified by column chromatography on silica gel eluting with 1-3% MeOH in DCM. The product was further purified by preparative hplc, formic acid gradient. The title compound was isolated as a colorless lyophilized solid, 25 mg. LC/MS (FA) ES+ 425.0, 427.6, 428.4, 429.3. $^1$H NMR (400 MHz, d4-MeOH) δ: 8.48 (d, J=8.3 Hz, 1H), 7.85-7.87 (m, 1H), 7.50-7.60 (m, 1H), 7.31-7.39 (m, 3H), 7.18 (s, 1H), 7.04 (s, 2H), 6.90-6.95 (m, 1H), 2.62 (s, 3H).

Example 3-E

Synthesis of 2-methyl-3-[4-phenyl-5-(4H-1,2,4-triazol-3-yl)-2-thienyl]pyrazolo[1,5-a]pyridine (3-E)

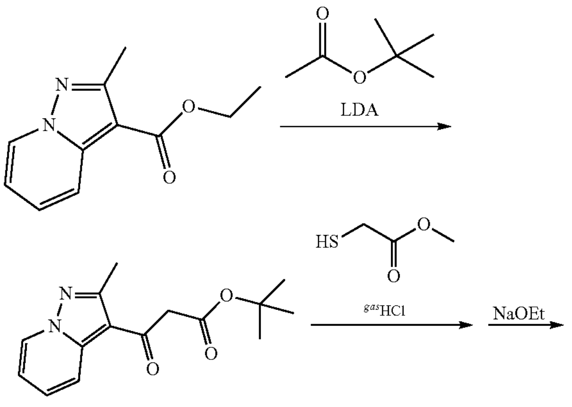

-continued

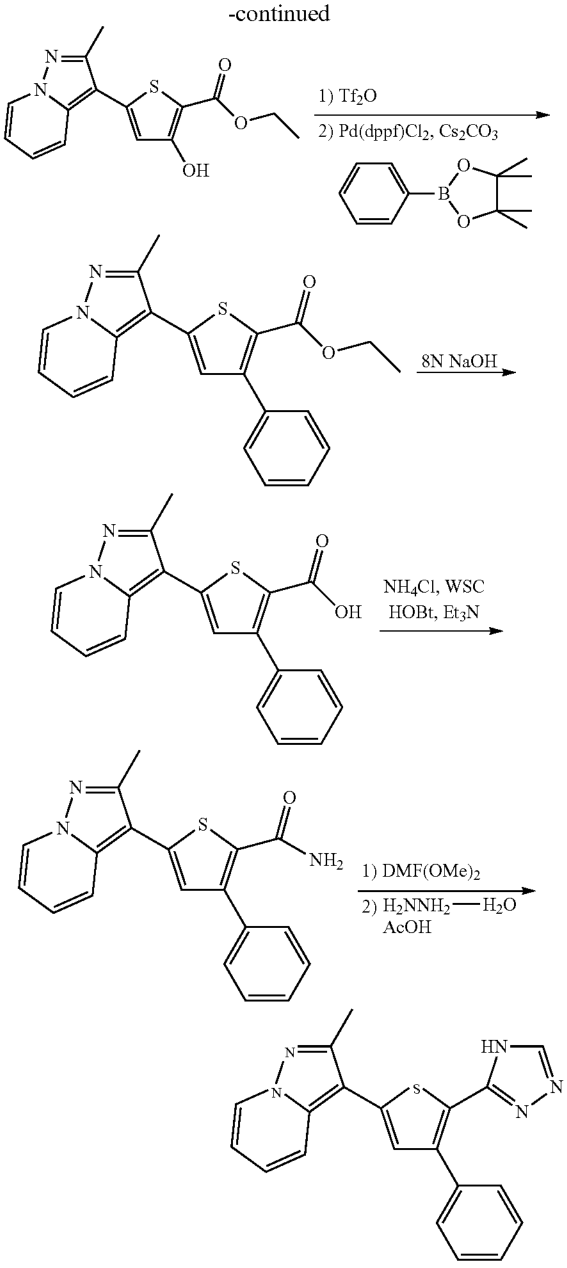

Step 1: tert-Butyl 3-(2-methylpyrazolo[1,5-a]pyridin-3-yl)-3-oxopropanoate

To a solution of N,N-diisopropylethylamine (6.6 mL, 38 mmol) in THF (50 mL), n-butyllithium (1.6 mol/L in hexane solution: 24 mL, 38 mmol) was added at −40° C. After being stirred for 30 min, the mixture was cooled to −78° C. To the mixture, was added 1,1-dimethylethyl acetate (5.28 mL, 62.8 mmol) and the mixture was stirred for 40 min at −78° C. To the mixture, was added ethyl 2-methylpyrazolo[1,5-a]pyridine-3-carboxylate (3.64 g, 17.8 mmol) and the mixture was stirred for 1 h at rt. To the mixture, were added a saturated aqueous solution of ammonium chloride (300 mL) and EtOAc (300 mL) and the resulting biphasic mixture was vigorously stirred for 30 min. The organic phase was washed with brine and then dried over anhydrous magnesium sulfate.

Insoluble materials were removed by filtration and the filtrate was concentrated under reduced pressure. Column chromatography was performed to yield the title compound (1.58 g, 32%) as a pale yellow syrup. $^1$H NMR (300 MHz, $d_6$-DMSO) δ: 8.78 (d, J=7.0 Hz, 1H), 8.19-8.10 (m, 1H), 7.61 (ddd, J=8.7, 7.2 and 1.1 Hz, 1H), 7.15 (td, J=7.0, 1.1 Hz, 1H), 3.91 (s, 2H), 2.61 (s, 3H), 1.42 (s, 9H).

Step 2: Ethyl 3-hydroxy-5-(2-methylpyrazolo[1,5-a]pyridin-3-yl)thiophene-2-carboxylate To a stirred solution of tert-butyl 3-(2-methylpyrazolo[1,5-a]pyridin-3-yl)-3-oxopropanoate (1.5 g, 5.47 mmol) prepared above and methyl 2-mercaptoacetate (4 mL, 40 mmol) in EtOH (4 mL), a stream of hydrogen chloride gas was bubbled at 0° C. for 2 h. After bubbling of hydrogen chloride gas was stopped, the mixture was stirred for 24 h at rt. The solvent was removed by evaporation. To the residue, were added a saturated aqueous solution of $NaHCO_3$ (100 mL) and EtOAc (300 mL). The resulting biphasic mixture was vigorously stirred for 30 min and then aqueous phase was discarded. The organic phase was washed with brine and then dried over anhydrous magnesium sulfate. Insoluble materials were removed by filtration and the filtrate was concentrated under reduced pressure. To the residue was added a 20% solution of sodium ethylate in ethanol (50 mL) and the mixture was stirred for 16 h at rt. To the mixture, were added EtOAc (400 mL), a saturated aqueous solution of ammonium chloride and a 1N aqueous solution of hydrogen chloride to adjust ca pH 4-5. After being stirred for 30 min, the organic phase was washed with brine and then dried over anhydrous magnesium sulfate. Insoluble materials were removed by filtration and the filtrate was concentrated under reduced pressure. Column chromatography was performed to yield the title compound (381 mg, 23%) as a pale yellow solid. $^1$H NMR (300 MHz, $d_6$-DMSO) δ: 10.31 (br s, 1H), 8.69 (d, J=6.8 Hz, 1H), 7.88 (d, J=9.1 Hz, 1H), 7.48-7.38 (m, 1H), 7.04-6.92 (m, 2H), 4.32-4.21 (m, 2H), 2.56 (s, 3H), 1.38-1.18 (m, 3H).

Step 3: Ethyl 5-(2-methylpyrazolo[1,5-a]pyridin-3-yl)-3-phenylthiophene-2-carboxylate A mixture of ethyl 3-hydroxy-5-(2-methylpyrazolo[1,5-a]pyridin-3-yl)thiophene-2-carboxylate (350 mg, 1.16 mmol) prepared above in pyridine (25 mL) was stirred for 10 min at 0° C. To the mixture, trifluoromethanesulfonic anhydride (653 mg, 2.31 mmol) was added at the same temperature and the mixture was stirred for 2 h. To the mixture, were added EtOAc (200 mL) and a saturated aqueous solution of ammonium chloride (200 mL) and the mixture was vigorously stirred for 30 min. The organic phase was washed with brine and then dried over anhydrous magnesium sulfate. Insoluble materials were removed by filtration and the filtrate was concentrated under reduced pressure. Column chromatography was performed to give a pale yellow syrup (370 mg, 0.852 mmol). The above syrup (198 mg, 0.456 mmol), phenylboronic acid pinacol ester (515 mg, 2.51 mmol), cesium carbonate (760 mg, 0.924 mmol) and water (2 mL) were suspended in 1,2-dimethoxyethane (20 mL) and the mixture was stirred for 30 min at rt. The mixture was degassed under vacuum and then the atmosphere was replaced with nitrogen. To the mixture, [1,1'-bis(diphenylphosphino)ferrocene]dichloropalladium(II), complex with dichloromethane (1:1) (70 mg, 0.08 mmol) was added and the mixture was stirred for 2 h at 80° C. Phenylboronic acid pinacol ester (515 mg, 2.51 mmol) and [1,1'-bis(diphenylphosphino)ferrocene]dichloropalladium (II), complex with dichloromethane (1:1) (70 mg, 0.08 mmol) were again added and the mixture was stirred for 3 h at 80° C. The mixture was allowed to cool to 0° C., and then were added EtOAc (200 mL) and a saturated aqueous solution of ammonium chloride (100 mL). The resulting biphasic mixture was vigorously stirred for 30 min. The organic phase was washed with brine and then dried over anhydrous magnesium sulfate. Insoluble materials were removed by filtration and the filtrate was concentrated under reduced pressure. Column chromatography was performed to yield the title compound (119 mg, 53%) as a pale yellow solid. $^1$H NMR (300 MHz, $d_6$-DMSO) δ: 8.83-8.61 (m, 1H), 8.11-7.90 (m, 1H), 7.63-7.52 (m, 2H), 7.50-7.37 (m, 4H), 7.32 (s, 1H), 7.05-6.92 (m, 1H), 4.18 (q, J=7.2 Hz, 2H), 2.59 (s, 3H), 1.17 (t, J=7.2 Hz, 3H).

Step 4: 5-(2-Methylpyrazolo[1,5-a]pyridin-3-yl)-3-phenylthiophene-2-carboxylic acid A mixture of ethyl 5-(2-methylpyrazolo[1,5-a]pyridin-3-yl)-3-phenylthiophene-2-carboxylate (119 mg, 0.327 mmol), a 8N aqueous solution of sodium hydroxide (5 mL), THF (5 mL) and ethanol (10 mL) and water (1 mL) was stirred for 1 h at 70° C. The mixture was allowed to cool to 0° C. To the mixture, was added a 6N aqueous solution of hydrogen chloride to adjust ca pH 3-4. The mixture was extracted with EtOAc-THF mixed solvent and the organic phase was washed with brine and dried over anhydrous magnesium sulfate. Insoluble materials were removed by filtration and the filtrate was concentrated under reduced pressure. The residue was washed with diisopropyl ether and dried under vacuum to yield the title compound (112 mg, over yield) as a pale yellow solid. $^1$H NMR (300 MHz, $d_6$-DMSO) δ: 12.83 (br s, 1H), 8.80-8.65 (m, 1H), 8.00-7.93 (m, 1H), 7.61-7.53 (m, 2H), 7.44-7.36 (m, 4H), 7.28 (s, 1H), 7.02-6.95 (m, 1H), 2.60 (s, 3H).

Step 5: 5-(2-Methylpyrazolo[1,5-a]pyridin-3-yl)-3-phenylthiophene-2-carboxamide

A mixture of 5-(2-methylpyrazolo[1,5-a]pyridin-3-yl)-3-phenylthiophene-2-carboxylic acid (100 mg, 0.299 mmol), EDCI (450 mg, 2.35 mmol), HOBt (95 mg, 0.703 mmol), triethylamine (2.5 mL), ammonium chloride (870 mg, 16.3 mmol) and DMF (35 mL) was stirred for 16 h at rt. To the mixture, were added water and EtOAc and the resulting biphasic mixture was vigorously stirred for 30 min. The organic phase was washed with water and brine and then dried over anhydrous magnesium sulfate. Insoluble materials were removed by filtration and the filtrate was concentrated under reduced pressure. The residue was washed with EtOAc and diisopropyl ether to yield the title compound (72 mg, 71%) as a pale yellow solid. $^1$H NMR (300 MHz, $d_6$-DMSO) δ: 8.68 (d, J=7.0 Hz, 1H), 7.92 (d, J=9.1 Hz, 1H), 7.70-7.53 (m, 2H), 7.53-7.31 (m, 4H), 7.26 (s, 1H), 7.11-6.71 (m, 3H), 2.59 (s, 3H).

Step 6: 2-Methyl-3-[4-phenyl-5-(4H-1,2,4-triazol-3-yl)-2-thienyl]pyrazolo[1,5-a]pyridine (3-E)

A mixture of 5-(2-methylpyrazolo[1,5-a]pyridin-3-yl)-3-phenylthiophene-2-carboxamide (70 mg, 0.210 mmol) and 1,1-dimethoxy-N,N-dimethylmethanamine (10 mL) was stirred for 2 h at 90° C. The mixture was concentrated by evaporation and then the residue was washed with diisopropyl ether.

The residue was dissolved in acetic acid (10 mL) and then was added hydrazine monohydrate (1 mL, 20.6 mmol). The resulting mixture was stirred for 1 h at 90° C. The mixture was allowed to cool to rt. The volatiles were removed under reduced pressure. To the residue, were added a saturated aqueous solution of $NaHCO_3$ and EtOAc and the resulting biphasic mixture was vigorously stirred for 30 min. The organic phase was washed with brine and then dried over anhydrous magnesium sulfate. Insoluble materials were removed by filtration and the filtrate was concentrated under reduced pressure. The residue was washed with EtOAc and diisopropyl ether to yield the title compound (37 mg, 49%) as a pale yellow solid. NMR (300 MHz, $d_6$-DMSO) δ: 14.04 (br s, 1H), 8.67 (d, J=6.8 Hz, 1H), 8.57-8.29 (m, 1H), 7.93 (d, J=8.9 Hz, 1H), 7.55 (d, J=6.6 Hz, 2H), 7.45-7.25 (m, 5H), 6.95 (td, J=6.9, 1.2 Hz, 1H), 2.61 (s, 3H).

Example 4-E

Synthesis of N-(tert-butyl)-7-[4-(2,4-dichlorophenyl)-5-(1H-imidazol-2-yl)-2-thienyl][1,3]thiazolo[5,4-d]pyrimidin-2-amine (6-E)

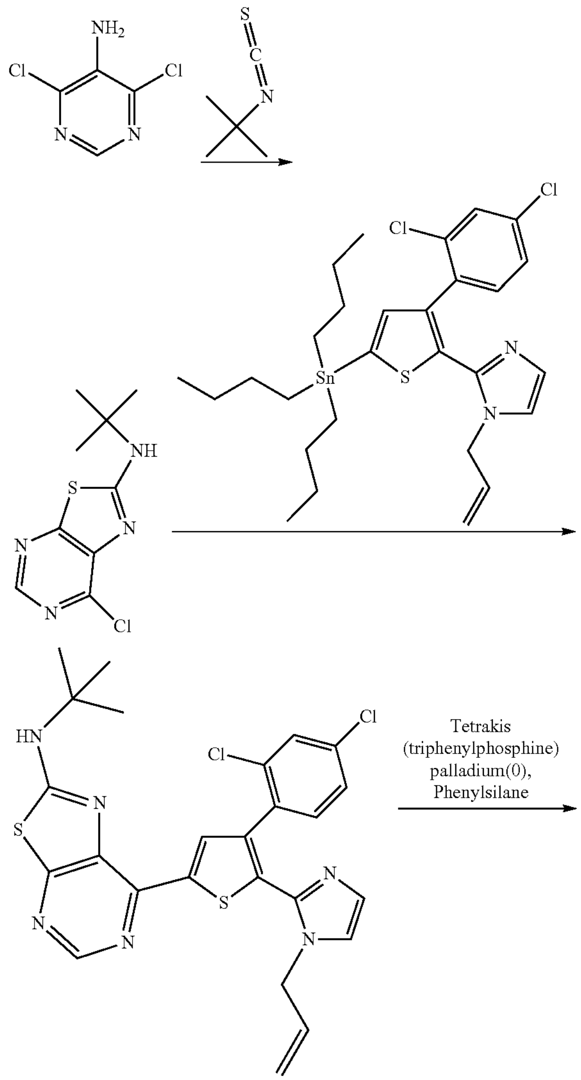

-continued

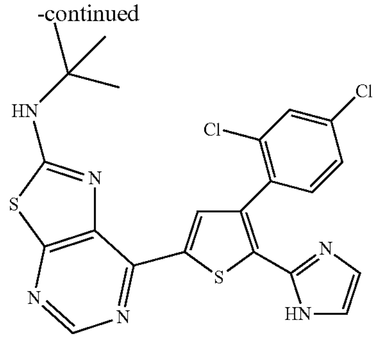

Step 1: tert-Butyl-(7-chlorothiazolo[5,4-d]pyrimidin-2-yl)-amine

A mixture of 5-Amino-4,6-dichloropyrimidine (9.0 g, 55 mmol), tert-butylisothiocyanate (7.02 g, 61.0 mmol), Cesium Carbonate (39.7 g, 122 mmol) and acetonitrile (200 mL) was stirred at 50° C. for 16 hours. The mixture was allowed to cool to rt. To the mixture, were added water and EtOAc. After being stirred for 30 min, the organic layer was washed with brine, dried over anhydrous magnesium sulfate, filtered and concentrated in vacuo. Column chromatography was performed to yield the title compound (6.45 g, 48%) as a white solid. LCMS: (AA) $ES^+$ 243, 245. $^1H$ NMR (400 MHz, $d_6$-DMSO) δ: 8.71 (bs, 1H), 8.49 (s, 1H), 1.45 (s, 9H).

Step 2: 7-[5-(1-allyl-1H-imidazol-2-yl)-4-(2,4-dichlorophenyl)-2-thienyl]-N-(tert-butyl)[1,3]thiazolo[5,4-d]pyrimidin-2-amine A mixture of tert-Butyl-(7-chlorothiazolo[5,4-d]pyrimidin-2-yl)-amine (1.00 g, 4.12 mmol), 1-allyl-2-[3-(2,4-dichlorophenyl)-5-(tributylstannyl)-2-thienyl]-1H-imidazole (1.71 g, 2.75 mmol) and DMF (23 mL) was stirred and degassed with vacuum. The atmosphere was replaced with nitrogen and then bis(triphenylphosphine)palladium(II) chloride (96.4 mg, 0.137 mmol) was added to the mixture. The orange solution was heated at 100° C. for 3 hours and the mixture was allowed to cool to rt. Column chromatography was performed to yield the title compound (1.12 g, 75%) as a pale yellow solid. LCMS: (FA) $ES^+$ 541, 543. $^1H$ NMR (400 MHz, $d_6$-DMSO) δ; 8.73 (bs, 1H), 8.65 (bs, 1H), 8.56 (bs, 1H), 7.75 (d, J=2.5 Hz, 1H), 7.38 (dd, J=8.5, 2.5 Hz, 1H), 7.21 (d, J=1.3 Hz, 1H), 7.12 (d, J=8.5 Hz, 1H), 7.05 (d, J=1.3 Hz, 1H), 5.64-5.55 (m, 1H), 5.06-5.03 (m, 1H), 4.84-4.79 (m, 1H), 4.31-4.27 (m, 2H), 1.49 (s, 9H).

Step 3: N-(tert-butyl)-7-[4-(2,4-dichlorophenyl)-5-(1H-imidazol-2-yl)-2-thienyl][1,3]thiazolo[5,4-d]pyrimidin-2-amine (6-E)

A solution of 7-[5-(1-allyl-1H-imidazol-2-yl)-4-(2,4-dichlorophenyl)-2-thienyl]-N-(tert-butyl)[1,3]thiazolo[5,4-d]pyrimidin-2-amine (100 mg, 0.185 mmol) and acetic acid (2 mL, 40 mmol) in DCM (6 mL) was degassed with vacuum and then the atmosphere was replaced with nitrogen. To the mixture, tetrakis(triphenylphosphine)palladium(0) (10.7 mg, 0.00923 mmol) and phenylsilane (0.136 mL, 1.11 mmol) were added. The resulting mixture was stirred at 40° C. for 30 min. The solution was allowed to cool to rt, followed by adding water and DCM. After being stirred for 10 min, the organic layer was washed with brine, dried over anhydrous magnesium sulfate, filtered and concentrated in vacuo. Column chromatography was performed to yield the title compound (46.0 mg, 50%) as a pale yellow solid. LCMS: (AA) $ES^+$ 501, 503. $^1H$ NMR (400 MHz, $d_6$-DMSO) δ: 11.84 (bs, 1H), 8.69 (bs, 1H), 8.63 (s, 1H), 8.43 (s, 1H), 7.73 (d, J=2.0 Hz, 1H), 7.46-7.43 (m, 1H), 7.34 (d, J=8.3 Hz, 1H), 7.14 (bs, 1H), 6.98 (bs, 1H), 1.47 (s, 9H).

Example 5-E

Synthesis of N-{7-[4-(2,4-dichlorophenyl)-5-(1H-imidazol-2-yl)-2-thienyl][1,3]thiazolo[5,4-d]pyrimidin-2-yl}acetamide (1-E)

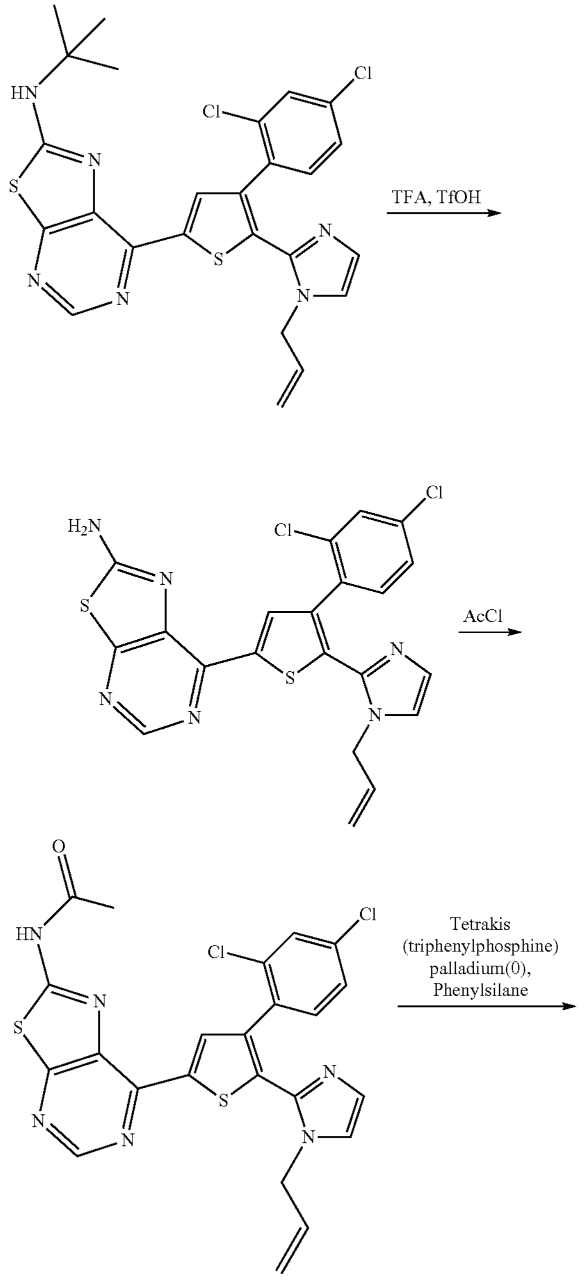

-continued

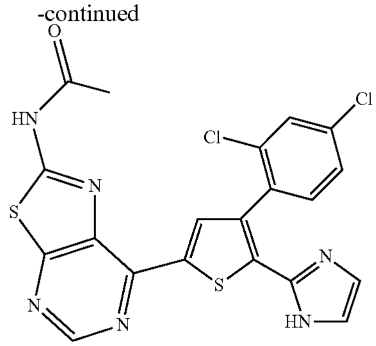

Step 1: 7-[5-(1-allyl-1H-imidazol-2-yl)-4-(2,4-dichlorophenyl)-2-thienyl][1,3]thiazolo[5,4-d]pyrimidin-2-amine A mixture of 7-[5-(1-allyl-1H-imidazol-2-yl)-4-(2,4-dichlorophenyl)-2-thienyl]-N-(tert-butyl)[1,3]thiazolo[5,4-d]pyrimidin-2-amine (480 mg, 0.886 mmol), trifluoroacetic Acid (2.0 mL) and DCM (6.0 mL) was stirred at rt. After being stirred for 30 min, trifluoromethanesulfonic acid (0.118 mL, 1.33 mmol) was added to the mixture. The mixture was stirred at rt for 49 hours and then the solvent was removed in vacuo. To the residue, sat. $NaHCO_3$ and EtOAc were added. After being stirred for 30 min, the organic layer was washed with brine, dried over anhydrous magnesium sulfate, filtered and concentrated in vacuo. The residue was crystallized from EtOAc and Hexane to yield the title compound (352.9 mg, 82%) as a pale yellow solid. LCMS: (AA) $ES^+$ 485, 487. NMR (400 MHz, $d_6$-DMSO) δ: 8.66 (s, 1H), 8.55 (s, 1H), 8.43 (bs, 2H), 7.74 (d, J=2.0 Hz, 1H), 7.41 (dd, J=8.3, 2.3 Hz, 1H), 7.23-7.20 (m, 2H), 7.02 (d, J=1.3 Hz, 1H), 5.68-5.59 (m, 1H), 5.08-5.05 (m, 1H), 4.85-4.80 (m, 1H), 4.35 (d, J=5.5 Hz, 2H).

Step 2: N-{7-[5-(1-allyl-1H-imidazol-2-yl)-4-(2,4-dichlorophenyl)-2-thienyl][1,3]thiazolo[5,4-d]pyrimidin-2-yl}acetamide To a mixture of 7-[5-(1-allyl-1H-imidazol-2-yl)-4-(2,4-dichlorophenyl)-2-thienyl][1,3]thiazolo[5,4-d]pyrimidin-2-amine (200 mg, 0.41 mmol) and pyridine (20 mL), was added acetyl chloride (0.30 mL, 4.2 mmol) at rt. After being stirred for 1 hour, acetyl chloride (0.30 mL, 4.2 mmol) was added at rt. After being stirred for 2 hours, the mixture was concentrated in vacuo. To the residue, were added sat. $NaHCO_3$ and EtOAc. After being stirred for 30 min, the organic layer was washed with brine, dried over anhydrous magnesium sulfate, filtered and concentrated in vacuo. The residue was washed with ether to yield the title compound (204 mg, 90%) as a pale yellow solid. LCMS: (AA) $ES^+$527, 529. $^1H$ NMR (400 MHz, $d_6$-DMSO) δ: 12.76 (s, 1H), 8.97 (s, 1H), 8.68 (s, 1H), 7.77 (d, J=2.3 Hz, 1H), 7.44 (dd, J=8.3, 2.3 Hz, 1H), 7.26-7.23 (m, 2H), 7.04 (d, J=1.3 Hz, 1H), 5.70-5.62 (m, 1H), 5.09-5.06 (m, 1H), 4.85-4.80 (m, 1H), 4.38 (d, J=5.3 Hz, 2H), 2.25 (s, 3H).

Step 3: N-{7-[4-(2,4-dichlorophenyl)-5-(1H-imidazol-2-yl)-2-thienyl][1,3]thiazolo[5,4-d]pyrimidin-2-yl}acetamide (1-E)

A mixture of N-{7-[5-(1-allyl-1H-imidazol-2-yl)-4-(2,4-dichlorophenyl)-2-thienyl][1,3]thiazolo[5,4-d]pyrimidin-2-yl}acetamide (200.0 mg, 0.3792 mmol), acetic acid (5 mL, 90 mmol) and DCM (25 mL) was degassed with vacuum and then the atmosphere was replaced with nitrogen. To the mixture, tetrakis(triphenylphosphine)palladium(0) (10.7 mg, 0.00923 mmol) and phenylsilane (0.187 mL, 1.517 mmol) were added. The resulting mixture was stirred at 40° C. for 30 min. The mixture was allowed to cool to rt followed by adding water and DCM. After being stirred for 10 min, the organic layer was washed with brine, dried over anhydrous magnesium sulfate, filtered and concentrated in vacuo. Column chromatography was performed to yield the title compound (57.3 mg, 31%) as a pale yellow solid. LCMS: (AA) $ES^+$ 487, 489. $^1$H NMR (400 MHz, $d_6$-DMSO) δ: 12.74 (bs, 1H), 11.88 (bs, 1H), 8.95 (s, 1H), 8.52 (s, 1H), 7.77 (d, J=2.3 Hz, 1H), 7.53-7.45 (m, 2H), 7.16 (bs, 1H), 6.98 (bs, 1H), 2.24 (s, 3H).

Example 6-E

Synthesis of 7-[4-(2,4-dichlorophenyl)-5-(1H-imidazol-2-yl)-2-thienyl][1,3]thiazolo[5,4-d]pyrimidin-2-amine (7-E)

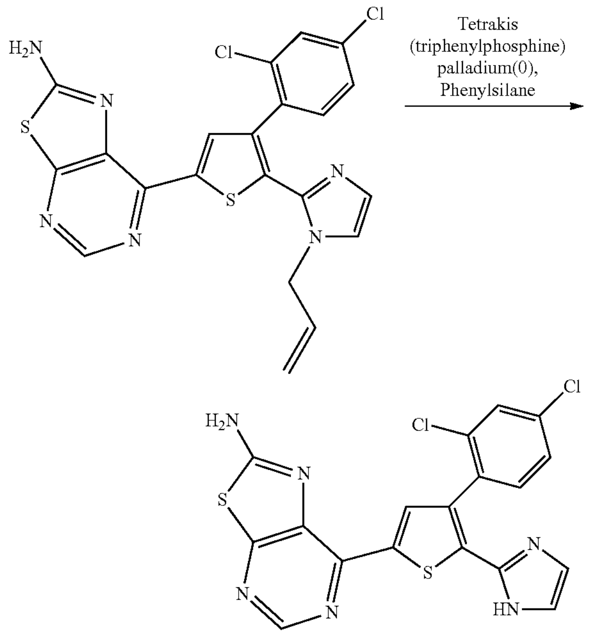

A mixture of 7-[5-(1-allyl-1H-imidazol-2-yl)-4-(2,4-dichlorophenyl)-2-thienyl][1,3]thiazolo[5,4-d]pyrimidin-2-amine (28.0 mg, 0.058 mmol), acetic acid (2.0 mL) and DCM (6.0 mL) was degassed with vacuum and then the atmosphere was replaced with nitrogen. To the mixture, were added tetrakis(triphenylphosphine)palladium(0) (7.03 mg, 0.00608 mmol) and phenylsilane (0.10 mL, 0.81 mmol). The resulting mixture was stirred at 40° C. for 30 min. The mixture was allowed to cool to rt followed by adding sat. $NaHCO_3$ and DCM. After being stirred for 10 min, the organic layer was washed with brine, dried over anhydrous sodium sulfate, filtered and concentrated in vacuo. Column chromatography was performed to yield the title compound (15.1 mg, 59%) as a pale yellow solid. LCMS: (AA) $ES^+$445, 447. $^1$H NMR (400 MHz, $d_6$-DMSO) δ: 11.82 (bs, 1H), 8.64 (s, 1H), 8.39-8.37 (m, 2H), 7.73 (d, J=2.0 Hz, 1H), 7.64-7.42 (m, 3H), 7.12 (bs, 1H), 6.95 (bs, 1H).

Example 1-F

Synthesis of 7-[4-(2,4-dichlorophenyl)-5-(1H-imidazol-2-yl)-2-thienyl][1,3]oxazolo[4,5-b]pyridin-2(3H)-one (1-F)

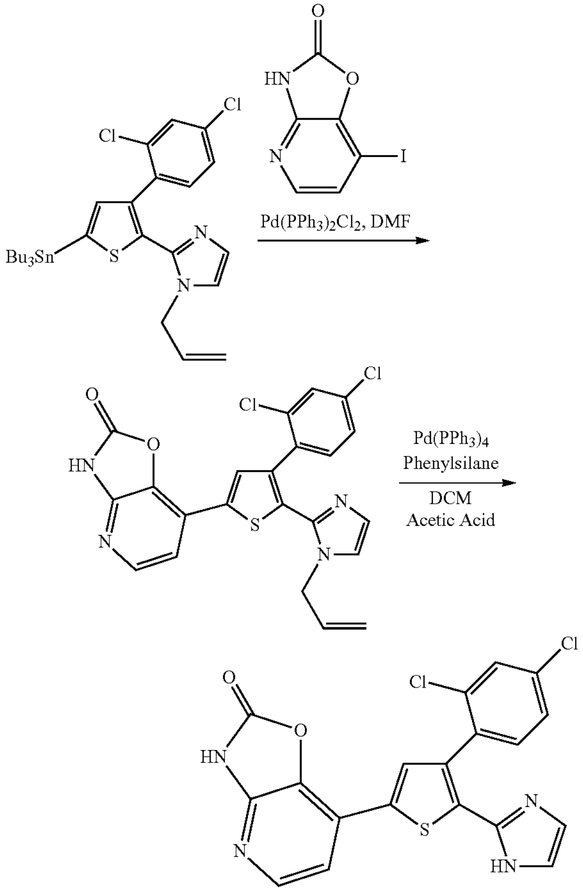

The title compound was prepared from 1-allyl-2-[3-(2,4-dichlorophenyl)-5-(tributylstannyl)-2-thienyl]-1H-imidazole and 7-iodo[1,3]oxazolo[4,5-b]pyridin-2(3H)-one using procedures analogous to those described in Example 8-A, Steps 2 and 3. LC/MS (AA) ES+ 429, 431. $^1$H NMR (400 MHz, $d_6$ DMSO) δ: 8.03 (d, J=5.77 Hz, 1H), 7.83 (s, 1H), 7.59 (d, J=2.01 Hz, 1H), 7.43-7.39 (m, 2H), 7.36 (d, J=8.29 Hz, 1H), 7.06 (s, 2H).

Compounds in the following table were prepared from the appropriate starting materials in a method analogous to that of Example 1-F:

| | |
|---|---|
| 2-F | LCMS: (FA) ES+ 441, 443. |
| 3-F | LCMS: (FA) ES+ 412, 414. |
| 4-F | LCMS: (FA) ES+ 411, 413. |
| 5-F | LCMS: (AA) ES+ 412, 414. |
| 6-F | LCMS: (AA) ES+ 413, 415. |

Biological Data:

PI3K Enzyme Assay

Expression and Purification of PI3K Enzyme

Active phosphatidylinositol 3' kinase (PI3K) enzyme is purified at Millennium Pharmaceuticals from SF9 insect cells (Invitrogen) co-infected with baculovirus containing amino-terminal His-tagged p110α and p85α expression constructs.

PI3K Enzyme Homogenous Time Resolved Fluorescence (HTRF®) Assay

The PI3K enzyme HTRF® assay makes use of an energy transfer complex comprised of biotin-PI(3,4,5)$P_3$, Europhium labeled anti-GST monoclonal antibody, a GST-tagged GRP1 pleckstrin homology (PH) domain, and Streptavidin-APC (allophycocyanin). Excitation of the Europium in the complex results in a stable time-resolved fluorescence resonance energy transfer (FRET) signal. Phosphatidylinositol 3,4,5 triphosphate (PI(3,4,5)$P_3$, the product of PI3K, disrupts the energy transfer complex by competing with biotin-PI(3,4,5)$P_3$ for binding to the GRP1 PH domain, resulting in a decreased fluorescent signal. Inhibitors of PI3K in the reaction prevent a decrease in the fluorescent signal.

PI3K enzyme (325 pM) is incubated with di-C8 PI(4,5)$P_2$ substrate (3.5 μM, CellSignals, Inc.) in assay buffer (50 mM HEPES pH 7.0, 5 mM DTT, 150 mM NaCl, 10 mM β-glycerophosphate, 5 mM $MgCl_2$, 0.25 mM sodium cholate, 0.001% CHAPS) containing 25 μM ATP and 0.5 μL of test compound (in 100% DMSO) at multiple concentrations in a final volume of 20.5 μL in 384 well plates for 30 min at 22-23° C. The reaction is terminated by adding 5 μL of detection buffer (50 mM HEPES pH7.0, 5 mM DTT, 1 mM NaCl, 10% Tween-20) containing EDTA (90 mM) and biotin-PI(3,4,5)$P_3$ (150 nM, Echelon Bioscience) to each well. 5 μL of detection buffer containing GST-fused GRP1 PH domain protein (210 nM, Millennium Pharmaceuticals), anti-GST-Europium tagged cryptate antibody (2.25 nM, CisBio), Streptavidin-XL (90 nM, CisBio) and potassium fluoride (240 mM) are then added to each well and incubated for 1 hour. Fluorescent signal for each well is then measured on an LJL_Analyst (Molecular Devices). Concentration response curves are generated by calculating the fluorescent signal in test compound-treated samples relative to DMSO-treated (0% inhibition) and EDTA-treated (100% inhibition) controls, and concentrations producing 50% inhibition ($IC_{50}$ values) were determined from those curves.

PI3K Cell Assays

Forkhead Redistribution Assay

Inhibition of PI3K in cells can be assessed using the Forkhead Redistribution Assay (BioImage). Foxo1A fused to EGFP (Foxo1A-EGFP) expressed in U2OS osteosarcoma cells localizes to the cytoplasm when the PI3K pathway is actively signaling. Inactivation of pathway signaling leads to a translocation of the protein from the cytoplasm to the nucleus. Therefore, pathway inhibition can be measured by quantifying the fluorescent intensity of Foxo1A-EGFP within the nucleus.

U2OS cells constitutively expressing Foxo1A-EGFP (6500 cells/well) are plated onto the inner 60 wells of 96 well dishes (BD Falcon OPTILUX black clear bottom) in 100 μL of cell culture media (DMEM (Invitrogen) containing 10% Fetal Bovine Serum (HyClone) and 1% Penicillin-Streptavidin (Invitrogen) and grown overnight in a humidified chamber at 37° C. The cell culture media is removed and the cells were rinsed with 100 μL of low serum media (DMEM containing 0.933% Fetal Bovine Serum and 1% Penicillin-Streptavadin) and incubated in 75 μL of low serum media for 1 hour in a humidified chamber at 37° C. Test compounds (25 μL) at multiple concentrations suspended in DMEM containing 1% Penicillin-Streptavadin are added to cells and incubated in a humidified chamber at 37° C. for 1 hour. The media is removed and the cells are fixed in 100 μL of 4% paraformaldehyde in phosphate buffered saline (PBS) for 10 min and then washed with 100 μL of PBS. DRAQ5 mix (100 μL, Alexis Biochemicals) diluted 1:5000 in PBS containing RNAase (1:10,000, Sigma) was added to cells for 30 minutes. The plates are then imaged (16 fields per well) using an Opera Imager (Evotec) and Foxo1A-EGFP fluorescent intensity within the nucleus (DRAQ5-positive) is quantified using Acapella Software (Evotec). Concentration response curves are generated by calculating the nuclear fluorescent intensity of Foxo-1A EGFP in test compound-treated samples and concentrations producing 50% inhibition ($IC_{50}$ values) relative to the positive control were determined from those curves.

Anti-Proliferation Assay

ATPlite Assay

The ATPLite™ (Perkin-Elmer) Assay measures cellular adenosine-triphosphate (ATP) through the generation of a luminescent signal formed from the ATP dependent enzyme firefly luciferase. The luminescent signal intensity can be used as a measure of cellular proliferation, and therefore the anti-proliferative effects of PI3K inhibitors.

Test compounds (4 μL in 100% DMSO) are diluted in 75 μL of Hanks Buffered Saline Solution (Invitrogen). The diluted test compounds (8 μL) are then added to 384-well TC-treated Black/Clear plates (Falcon). HCT-116 cells (American Type Culture Collection) maintained in McCoy's 5a modified media (Invitrogen) containing 10% Fetal Bovine Serum and 1% Penicillin-Streptavadin are added at 1000 cells per well. H460 cells (American Type Culture Collection) maintained in RPMI 1640 containing 10% Fetal Bovine Serum and 1% Penicillin-Streptavadin were added at 1500 cells per well. The cells are then incubated with compound in a humidified chamber at 37° C. for 72 hours. The plates are then removed from the cell culture chambers and allowed to equilibrate to room temperature for 30 min. All but 25 μL of cell culture media is removed from each well, and 25 μl of ATPlite reagent (Perkin Elmer) is added to each well. Luminescence is measured within 5 minutes of adding the ATPlite reagent on a LEADSeeker Luminescence Counter (GE Healthcare Life Sciences). Concentration response curves are generated by calculating the luminescence decrease in test compound-treated samples relative to DMSO-treated controls, and growth inhibition ($IC_{50}$) values are determined from those curves.

Formulation Example 1

Amount Per Tablet

| | |
|---|---|
| (1) Compound obtained in Example 1 | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 1, 60.0 mg of lactose and 35.0 mg of corn starch is granulated through a 1 mm-mesh sieve using 0.03 ml of a 10% by weight aqueous solution of gelatin (3.0 mg of gelatin), after which the granules are dried at 40° C. and filtered again. The granules obtained are mixed with 2.0 mg of magnesium stearate and compressed. The core tablets obtained are coated with a sugar coat comprising a suspension of sucrose, titanium dioxide, talc and gum arabic and polished with beeswax to yield sugar-coated tablets.

Formulation Example 2

Dose Per Tablet

| | |
|---|---|
| (1) Compound obtained in Example 1 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 1 and 3.0 mg of magnesium stearate are granulated using 0.07 ml of an aqueous solution of soluble starch (7.0 mg of soluble starch), after which these granules are dried and mixed with 70.0 mg of lactose and 50.0 mg of corn starch. This mixture is compressed to yield tablets.

Gene Cloning hPIK3CA; p110alpha catalytic subunit (GenBank ACCESSION# NM_006218) and hPIK3R1; p85alpha regulatory subunit (GenBank ACCESSION# NM_181523) were cloned from human cDNA library (Clonetec).

Purification of Human PI3Kα Enzyme

Human p110alpha catalytic subunit gene and human p85alpha regulatory subunit gene were respectively inserted into pFASTBacHT (Invitrogen), and each gene was introduced into a baculovirus vector using a Bac-to-Bac system (Invitrogen). Both viruses were injected to insect cultured cells Sf21 to allow coexpression of proteins. p110alpha catalytic subunit and human p85alpha regulatory subunit complex (hPI3Kα) were purified from the cell extract using a Ni chelate column.

Human PI3Kα Enzyme Assay Method

L-alpha-Phosphatidyl-D-myo-inositol 4,5-Diphosphate (diC16) [PI(4,5)P2, Wako Pure Chemical Industries, Ltd.] is suspended in Phospholipid FlashPlate Coating Buffer (PerkinElmer) and applied onto Phospholipid FlashPlate PLUS. PI3K reaction buffer (50 mM Tris-HCl, pH 7.4, 5 mM $MgCl_2$, 1 mM DTT, 0.005% BSA) containing hPI3Kα, γ-[$^{33}P$] ATP (PerkinElmer) and cold 500 nM ATP is added to the wells on this plate and the mixture was reacted at room temperature for 1 hr. 50 mM EDTA solution is added to quench the reaction, and the wells were washed with PBS. The radioactivity remaining in the well is measured as enzyme activity by TopCount (PerkinElmer).

The obtained results are shown in Table 3. From the results, the compounds of the present invention are shown to strongly inhibit the activity of PI3Kα.

TABLE 3

| Example | Inhibitory rate at 1.0 μm (%) |
|---|---|
| 27-B | 100 |
| 32-B | 100 |
| 35-B | 101 |

Human mTUR Enzyme Assay Method mTOR reaction buffer (50 mM HEPES, pH 7.5, 5 mM $MgCl_2$, 5 mM $MnCl_2$, 1 mM EGTA, 1 mM DTT, 0.01% BRU-35, 0.01% $NaN_3$) containing human mTOR (Invitrogen), 10 μM ATP and 2 μM Z'-lyte 11Ser/Thr peptide (Invitrogen) is added to the well and the mixture is reacted at room temperature for 1 hr.

Development Buffer containing Development Reagent B (for Z'-lyte peptide, Invitrogen) is added, and the mixture was reacted at room temperature for 30 min. The fluorescence at 520 nm and fluorescence at 445 nm are measured with excitation at 400 nm using SpectraMax M5e (Molecular Device). The ratio of the obtained 445 nm fluorescence value/520 nm fluorescence value is calculated, and changes in the fluorescence resonance energy transfer (FRET) of Z'-lyte peptide are detected as the enzyme activity.

The obtained results are shown in Table 4. From the results, the compounds of the present invention are shown to strongly inhibit the activity of mTOR.

TABLE 4

| Example | Inhibitory rate at 1.0 μm (%) |
|---|---|
| 31-B | 93 |
| 33-B | 91 |

PI3K and VPS34 Enzyme Assays

Cloning, Expression, and Purification of PI3Ks and VPS34

The catalytic subunits of PI3Ks are cloned into either pDEST8(p110 alpha) or pDEST10(p110beta, p110delta, and p110gamma) as N-terminal His tagged fusion proteins using the Gateway system (Invitrogen, catalog#11804-010 for pDEST8 and 11806-015 for pDEST10). The sequences are verified before recombinant protein expression using the Baculovirus Expression System with Gateway® Technology. The accession numbers for the subunits are as follows:

p110 alpha (GB:U79143)

p110beta (GB:S67334)

p110delta (GB: U86453)

p110gamma (GB: X83368)

The regulatory subunits of PI3Ks are cloned into pDEST8 as un-tagged protein using the Gateway system (Catalog#11804-010). The sequences are verified before recombinant protein expression using the Baculovirus Expression System with Gateway® Technology. The accession numbers for the subunits are as following:

p85 alpha (GB: BC030815)

p101 (GB: AB028925)

VPS34 (accession number GB:$BCO_{33004}$) is cloned into pDEST20-Thombin as N-terminal GST tagged fusion proteins using the Gateway system (Invitrogen, catalog#11804-013). The sequences are verified before recombinant protein expression using the Baculovirus Expression System with Gateway® Technology.

For expression of the p110 complexes, the p85 (MOI of 4) is co-infected with p110 alpha, beta, and delta respectively (1MOI) in SF9 cells and harvested at 60 hours post co-infection. P110 gamma was infected at 1 MOI and harvested at 60 hours post infection.

VPS34 is infected at 1MOI in SF9 cells and harvested 72 hours post infection.

For purification, PI3Ks are purified by Ni-NTA Agarose (Qiagen #30250) followed by Mono Q 10/100 GL (Ge Healthcare #17-5167-01). VPS34 is purified by Glutathione Sepharose 4 Fast Flow (GE Healthcare #17-5132-03) followed by HiTrap Q (GE Healthcare #17-1153-01).

PI3K Assay Conditions

1) Human PI3Kα Enzyme Assay Method 0.5 uL compounds in DMSO are added to wells of a 384 well microtitre plate (Corning 3575). At room temperature: 10 ul PI3K reaction buffer (50 mM Hepes, 5 mM DTT, 150 mM NaCl, 10 mM beta-glycerophosphate, 10 mM MgCl2, 0.25 mM sodium cholate and 0.001% CHAPS, pH 7.00)

containing ATP (25 uM, Promega) is added followed immediately by 10 ul PI3K reaction buffer containing di-C8 PI(4,5)P2 (3.5 uM, CellSignals) and PI3Kalpha (0.4875 nM, Millennium Protein Sciences Group) and the mixture is incubated with shaking at room temperature for 30 minutes. Then 5 ul PI3K stop mix (50 mM Hepes, 5 mM DTT, 150 mM NaCl, 0.01% Tween-20, 15 mM EDTA and 25 nM biotin-PI (3,4,5)P3 (Echelon) is added to quench the reaction followed immediately by addition of 5 ul HTRF detection mix (50 mM Hepes, 5 mM DTT, 150 mM NaCl, 0.01% Tween-20, 40 mM KF, 10 nM GST:GRP-1 PH domain (Millennium Protein Sciences Group), 15 nM Streptavidin-XL (CisBio) and 0.375 nM anti-GST Eu++ antibody (CisBio) at pH 7.00). The plates are then incubated for 1 hour at room temperature with shaking and then read on a BMG PheraStar Plus reader.

2) Human PI3K beta, delta and gamma isoforms are tested using the procedure described for PI3K alpha above but with the following changes: PI3K beta (5.25 nM), PI3K delta (0.75 nM) and PI3K gamma (5 nM). All isoforms supplied by Millennium Protein Science Group.

3) VPS34 is assayed using Adapta™ Universal Kinase Assay Kit (Invitrogen).

Example 2

PI3K Cell Assays

Forkhead Redistribution Assay

Inhibition of PI3K in cells can be assessed using the Forkhead Redistribution Assay (BioImage). Foxo1A fused to EGFP (Foxo1A-EGFP) expressed in U2OS osteosarcoma cells localizes to the cytoplasm when the PI3K pathway is actively signaling. Inactivation of pathway signaling leads to a translocation of the protein from the cytoplasm to the nucleus. Therefore, pathway inhibition can be measured by quantifying the fluorescent intensity of Foxo1A-EGFP within the nucleus.

U2OS cells constitutively expressing Foxo1A-EGFP (6500 cells/well) are plated onto the inner 60 wells of 96 well dishes (BD Falcon OPTILUX black clear bottom) in 100 μL of cell culture media (DMEM (Invitrogen) containing 10% Fetal Bovine Serum (HyClone) and 1% Penicillin-Streptavidin (Invitrogen) and grown overnight in a humidified chamber at 37° C. The cell culture media is removed and the cells are rinsed with 100 μL of low serum media (DMEM containing 0.933% Fetal Bovine Serum and 1% Penicillin-Streptavadin) and incubated in 75 μL of low serum media for 1 hour in a humidified chamber at 37° C. Test compounds (25 μL) at multiple concentrations suspended in DMEM containing 1% Penicillin-Streptavadin are added to cells and incubated in a humidified chamber at 37° C. for 1 hour. The media is removed and the cells are fixed in 100 μL of 4% paraformaldehyde in phosphate buffered saline (PBS) for 10 min and then washed with 100 μL of PBS. DRAQ5 mix (100 μL, Alexis Biochemicals) diluted 1:5000 in PBS containing RNAase (1:10,000, Sigma) is added to cells for 30 minutes. The plates are then imaged (16 fields per well) using an Opera Imager (Evotec) and Foxo1A-EGFP fluorescent intensity within the nucleus (DRAQ5-positive) is quantified using Acapella Software (Evotec). Concentration response curves are generated by calculating the nuclear fluorescent intensity of Foxo-1A EGFP in test compound-treated samples and concentrations producing 50% inhibition ($IC_{50}$ values) relative to the positive control are determined from those curves.

Example 3

Anti-Proliferation Assay

ATPlite Assay

The ATPLite™ (Perkin-Elmer) Assay measures cellular adenosine-triphosphate (ATP) through the generation of a luminescent signal formed from the ATP dependent enzyme firefly luciferase. The luminescent signal intensity can be used as a measure of cellular proliferation, and therefore the anti-proliferative effects of PI3K inhibitors.

Test compounds (4 μL in 100% DMSO) are diluted in 75 μL of Hanks Buffered Saline Solution (Invitrogen). The diluted test compounds (8 μL) are then added to 384-well TC-treated Black/Clear plates (Falcon). HCT-116 cells (American Type Culture Collection) maintained in McCoy's 5a modified media (Invitrogen) containing 10% Fetal Bovine Serum and 1% Penicillin-Streptavadin are added at 1000 cells per well. H460 cells (American Type Culture Collection) maintained in RPMI 1640 containing 10% Fetal Bovine Serum and 1% Penicillin-Streptavadin are added at 1500 cells per well. The cells are then incubated with compound in a humidified chamber at 37° C. for 72 hours. The plates are then removed from the cell culture chambers and allowed to equilibrate to room temperature for 30 min. All but 25 μL of cell culture media is removed from each well, and 25 μl of ATPlite reagent (Perkin Elmer) is added to each well. Luminescence is measured within 5 minutes of adding the ATPlite reagent on a LEADSeeker Luminescence Counter (GE Healthcare Life Sciences). Concentration response curves are generated by calculating the luminescence decrease in test compound-treated samples relative to DMSO-treated controls, and growth inhibition ($IC_{50}$) values are determined from those curves.

As detailed above, compounds of the invention inhibit PI3K. In certain embodiments, compounds inhibit one or more isoforms of PI3K. In other embodiments, compounds of the invention inhibit PI3Kalpha and have an IC50>1.0 μM. For example, these compounds include compounds A-1, A-4, A-8, A-24, A-33, A-44, A-84, B-19, B-41, B-49, B-50, B-52, B-54, B-66, B-67, B-68, B-71, B-102, C-1, C-4, C-8, C-14, C-16, C-18, C-27, C-30, C-36, C-46, C-47, C-48, C-56, C-57, C-58, C-60, C-61, C-62, C-64, C-65, C-72, and C-73. In other embodiments, compounds of the invention have an IC50<1.0 μM but >0.1 μM. For example, these compounds include compounds A-3, A-7, A-9, A-10, A-14, A-17, A-18, A-21, A-25, A-26, A-28, A-29, A-30, A-35, A-38, A-40, A-42, A-43, A-46 through A-48, A-50, A-56, A-59, A-65, A-67, A-70 through A-72, A-75, A-78, A-79, A-83, B-2, B-4, B-5, B-7, B-9, B-10, B-12, B-16, B-B-37, B-47, B-48, B-53, B-55 through B-64, B-69, B-84, B-105, B-113, B-115, B-116, B-119, B-122, B-123, B-124, B-126, B-129, B-140, B-142, B-148, B-149, B-150, B-152 through B-155, B-164, C-2, C-7, C-9, C-10, C-12, C-13, C-19 through C-22, C-24, C-26, C-29, C-33, C-34, C-35, C-37, C-41, C-42, C-45, C-51, C-52, C-56, C-58, C-59, C-60, C-66 through C-71, E-1, E-5, E-8, and F-6. In still other embodiments, compounds of the invention have an IC50<0.1 μM. For example, these compounds include compounds A-2, A-5, A-6, A-11, A-12, A-13, A-15, A-19, A-20, A-22, A-23, A-27, A-31, A-32, A-34, A-36, A-37, A-39, A-41, A-45, A-49, A-51 through A-55, A-57, A-58, A-60 through A-64, A-66, A-68, A-69, A-73, A-74, A-76, A-77, A-81, A-82, A-85, A-86, A-87, B-1, B-3, B-6, B-8, B-11, B-13, B-14, B-15, B-17, B-18, B-20 through B-36, B-38, B-39, B-42, B-43, B-44, B-46, B-51, B-65, B-70, B-72 through B-79, B-81, B-82, B-83, B-85 through B-101, B-103, B-104, B-106 through B-112, B-114, B-117, B-118, B-120, B-121, B-125, B-127, B-128, B-130 through B-139, B-141, B-147, B-151, B-156 through B-163, C-3, C-5, C-6, C-11, C-15, C-17, C-23, C-25, C-31, C-32, C-38, C-39, C-40, C-43, C-44, C-49, C-50, C-53, C-54, C-55, C-57, C-63, D-1, D-2, D-3, E-2, E-3, E-4, E-6, E-7, and F-2 through F-5.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

The invention claimed is:

1. A compound of formula IA or IB:

IA

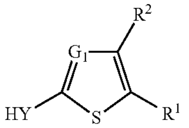

IB

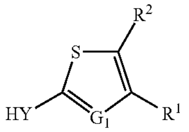

or a pharmaceutically acceptable salt thereof, wherein:

$G_1$ is $CR^3$, wherein $R^3$ is H, —CN, halogen, —Z—$R^5$, $C_{1-6}$ aliphatic, or 3-10-membered cycloaliphatic, wherein:

Z is selected from an optionally substituted $C_{1-3}$ alkylene chain, —O—, —N($R^{3a}$)—, —S—, —S(O)—, —S(O)$_2$—, —C(O)—, —CO$_2$—, —C(O)N$R^{3a}$—, —N($R^{3a}$)C(O)—, —N($R^{3a}$)CO$_2$—, —S(O)$_2$N$R^{3a}$—, —N($R^{3a}$)S(O)$_2$—, —OC(O)N($R^{3a}$)—, —N($R^{3a}$)C(O)N$R^{3a}$—, —N($R^{3a}$)S(O)$_2$N($R^{3a}$)—, and —OC(O)—;

$R^{3a}$ is hydrogen or an optionally substituted $C_{1-4}$ aliphatic, and $R^5$ is an optionally substituted group selected from $C_{1-6}$ aliphatic; 3-10-membered cycloaliphatic; 4-10-membered heterocyclyl having 1-5 heteroatoms independently selected from nitrogen, oxygen, and sulfur; 6-10-membered aryl; and 5-10-membered heteroaryl having 1-5 heteroatoms independently selected from nitrogen, oxygen, and sulfur;

$R^1$ is CY, wherein:

CY is

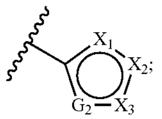

wherein:

$X_1$, $X_2$, and $X_3$, are each independently N, O, S, or $CR^7$, provided that only one of $X_1$, $X_2$, or $X_3$ may be O or S, $G_2$ is —N═ or —$N^{4'}$—, wherein:

each occurrence of $R^{4'}$ is independently H, —$Z_2$—$R^6$, optionally substituted $C_{1-6}$ aliphatic, or optionally substituted 3-10-membered cycloaliphatic, wherein:

$Z_2$ is selected from an optionally substituted $C_{1-3}$ alkylene chain, —S(O)—, —S(O)$_2$—, —C(O)—, —CO$_2$—, —C(O)N$R^{4a}$—, and —S(O)$_2$N$R^{4a}$—, $R^{4a}$ is hydrogen or an optionally substituted $C_{1-4}$ aliphatic, and $R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^7$ is independently hydrogen, —CN, halogen, —$Z_3$—$R^8$, $C_{1-6}$ aliphatic, or 3-10-membered cycloaliphatic, wherein:

$Z_3$ is selected from an optionally substituted $C_{1-3}$ alkylene chain, —O—, —N($R^{7a}$)—, —S—, —S(O)—, —S(O)$_2$—, —C(O)—, —CO$_2$—, —C(O)N$R^{7a}$—, —N($R^{7a}$)C(O)—, —N($R^{7a}$)CO$_2$—, —S(O)$_2$N$R^{7a}$—, —N($R^{7a}$)S(O)$_2$—, —OC(O)N($R^{7a}$)—, —N($R^{7a}$)C(O)N$R^{7a}$—, —N($R^{7a}$)S(O)$_2$N($R^{7a}$)—, and —OC(O)—, $R^{7a}$ is hydrogen or an optionally substituted $C_{1-4}$ aliphatic, and $R^8$ is an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur, $R^2$ is a 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur, optionally substituted with 1-4 independent occurrences of $R^{12}$, wherein $R^{12}$ is —$R^{12a}$, -$T_2$-$R^{12d}$, or —$V_2$-$T_2$- $R^{12d}$, and:

each occurrence of $R^{12a}$ is independently halogen, —CN, —NO$_2$, —$R^{12c}$, —N($R^{12b}$)$_2$, —O$R^{12b}$, —S$R^{12c}$, —S(O)$_2$$R^{12c}$, —C(O)$R^{12b}$, —C(O)O$R^{12b}$, —C(O)N($R^{12b}$)$_2$, —S(O)$_2$N($R^{12b}$)$_2$, —OC(O)N($R^{12b}$)$_2$, —N($R^{12e}$)C(O)$R^{12b}$, —N($R^{12e}$)SO$_2$$R^{12c}$, —N($R^{12e}$)C(O)O$R^{12b}$), —N($R^{12e}$)C(O)N($R^{12b}$)$_2$, or —N($R^{12e}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, and sulfur;

each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{12e}$ is independently hydrogen or an optionally substituted $C_{1-6}$ aliphatic group;

each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —NR$^{12e}$C(O)N($R^{12e}$)—, —N($R^{12e}$)SO$_2$N($R^{12e}$)—, —OC(O)—, or —C(O)N($R^{12e}$)—O—; and $T_2$ is an optionally substituted $C_1$-$C_6$ alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)SO$_2$—, —N($R^{13}$)C(O)O—, —NR$^{13}$C(O)N($R^{13}$)—, —N($R^{13}$)S(O)$_2$N($R^{13}$)—, —OC(O)—, or —C(O)N($R^{13}$)—O— or wherein $T_3$ or a portion thereof optionally forms part of an optionally substituted 3-7 membered cycloaliphatic or heterocyclyl ring, wherein $R^{13}$ is hydrogen or an optionally substituted $C_{1-4}$aliphatic group;

and

HY is i

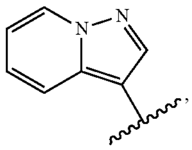, ii

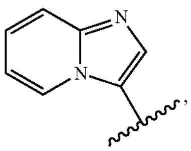, iv

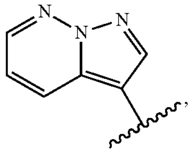,

-continued v

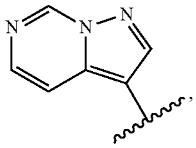, vi

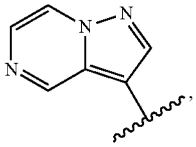, vii

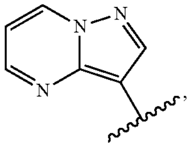, viii

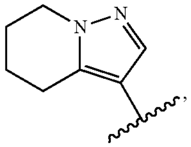, ix

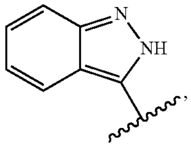, x

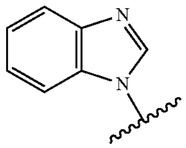

xi

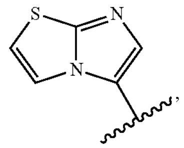, xii

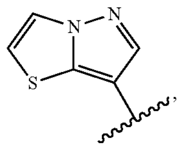, xiii

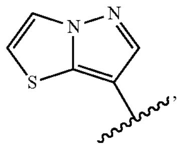, xiv

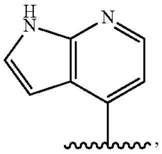,

-continued
xv
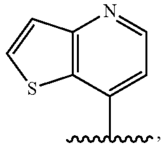
,
xvi
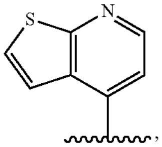
,
xvii
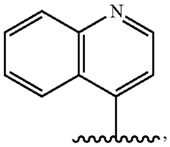
,
xxiii
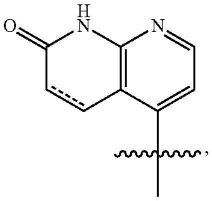
,
xxiv
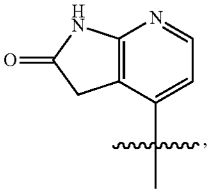
,
xxv
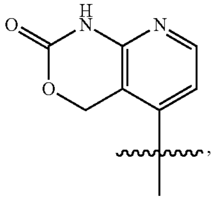
,
xxvi
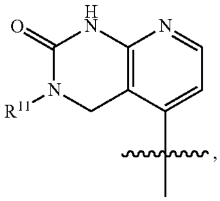
,
xxvii
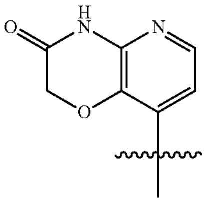
-continued
xxviii
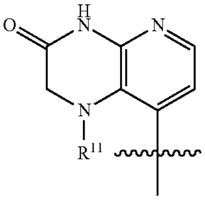
xxvix
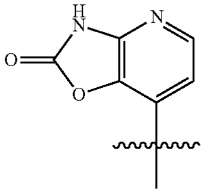
xxx
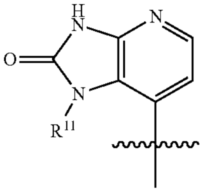
xxxi
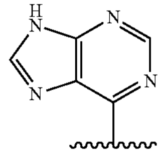
xxxii
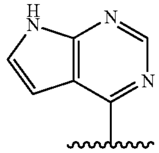
xxxiii
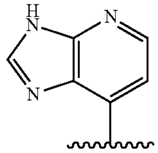
xxxiv
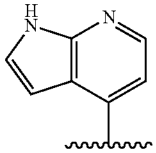
xxxv
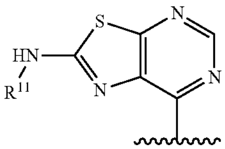
or
xxxvi
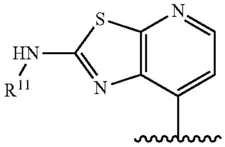

wherein each HY group is optionally additionally substituted with one or more occurrences of $R^{10}$;

wherein $R^{10}$ is —$R^{10b}$, or —$V_1$—$^{10c}$, -$T_1$-$R^{10b}$, or —$V_1$-$T_1$-$R^{10b}$ wherein:

$V_1$ is —$NR^{10a}$—, —$NR^{10a}$—C(O)—, —$NR^{10a}$—C(S)—, —$NR^{10a}$—C($NR^{10a}$)—, —$NR^{10a}$C(O)$OR^{10a}$—, —$NR^{10a}$C(O)$NR^{10a}$—, —$NR^{10a}$C(O)$SR^{10a}$—, —$NR^{10a}$C(S)$OR^{10a}$—, —$NR^{10a}$C(S)$NR^{10a}$—, —$NR^{10a}$C(S)$SR^{10a}$—, —$NR^{10a}$C($NR^{10a}$)$OR^{10a}$—, —$NR^{10a}$C($NR^{10a}$)$NR^{10a}$—, —$NR^{10a}$$S(O)_2$—, —$NR^{10a}$$S(O)_2$$NR^{10a}$—, —C(O)—, —$CO_2$—, —C(O)$NR^{10a}$—, —C(O)$NR^{10a}$O—, —$SO_2$—, or —$SO_2$$NR^{10a}$—;

each occurrence of $R^{10a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;

$T_1$ is an optionally substituted $C_1$-$C_6$ alkylene chain wherein the alkylene chain optionally is interrupted by —N($R^{10a}$)—, —O—, —S—, —S(O)—, —$S(O)_2$—, —C(O)—, —C(O)O—, —C(O)N($R^{10a}$)—, —$S(O)_2$N($R^{10a}$)—, —OC(O)N($R^{10a}$)—, —N($R^{10a}$)C(O)—, —N($R^{10a}$)$SO_2$—, —N($R^{10a}$)C(O)O—, —$NR^{10a}$C(O)N($R^{10a}$)—, —N($R^{10a}$)$S(O)_2$N($R^{10a}$)—, —OC(O)—, or —C(O)N($R^{10a}$)—O— or wherein $T_1$ forms part of an optionally substituted 3-7 membered cycloaliphatic or heterocyclyl ring;

each occurrence of $R^{10b}$ is independently hydrogen, halogen, —CN, —$NO_2$, —N($R^{10a}$)$_2$, —$OR^{10a}$, —$SR^{10a}$, —$S(O)_2R^{10a}$, —C(O)$R^{10a}$, —C(O)$OR^{10a}$, —C(O)N($R^{10a}$)$_2$, —$S(O)_2$N($R^{10a}$)$_2$, —OC(O)N($R^{10a}$)$_2$, —N($R^{10a}$)C(O)$R^{10a}$, —N($R^{10a}$)$SO_2R^{10a}$, —N($R^{10a}$)C(O)$OR^{10a}$, —N($R^{10a}$)C(O)N($R^{10a}$)$_2$, or —N($R^{10a}$)$SO_2$N($R^{10a}$)$_2$, or an optionally substituted group selected from 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;

and wherein each occurrence of $R^{11}$ is independently hydrogen, —C(O)$R^{11a}$—, —$CO_2R^{11a}$—, —C(O)$NR^{11a}$—, C(O)$NR^{11a}$O—, —$SO_2R^{11a}$—, —$SO_2NR^{11a}$—, or an optionally substituted group selected from $C_{1-6}$aliphatic, 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;

wherein each occurrence of $R^{11a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur.

2. The compound of claim 1, wherein $G_1$ is CH.

3. The compound of claim 1, wherein $R^2$ is an optionally substituted 6-10-membered aryl or 5-10-membered heteroaryl having 1-5 heteroatoms independently selected from nitrogen, oxygen, and sulfur.

4. The compound of claim 3, wherein:

$R^2$ is a phenyl group substituted with 1-3 independent occurrences of halogen, $C_{1-3}$ alkyl, CN, $C_{1-3}$haloalkyl, —$OC_{1-3}$ alkyl, —$OC_{1-3}$ haloalkyl, —NHC(O)$C_{1-3}$ alkyl, —NHC(O)NH$C_{1-3}$ alkyl, NHS(O)$_2$$C_{1-3}$ alkyl, or —C(O)H.

5. The compound of claim 1, wherein $X_1$ is N, $G_2$ is $NR^{4'}$, and $X_2$ and $X_3$ are $CR^7$.

6. The compound of claim 5, wherein $X_3$ is CH.

7. The compound of claim 1, wherein HY is selected from:

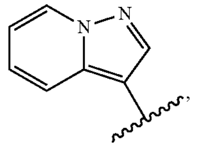

i

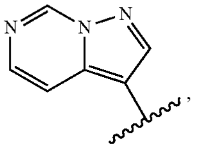

v

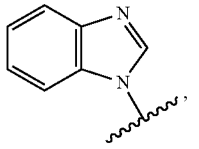

x

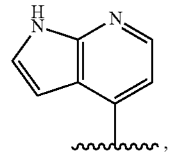

xiv

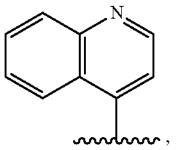

xvii

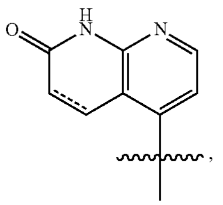

xxiii

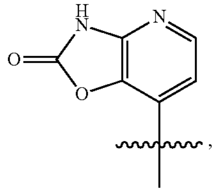

xxix

-continued
xxxi
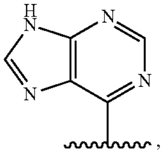,
xxxii
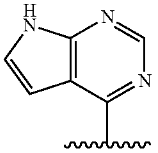 and
xxxv
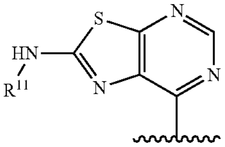
wherein each HY group is optionally additionally substituted with one or more occurrences of $R^{10}$.
8. The compound of claim 1, wherein HY is selected from:
i
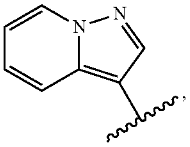,
ii
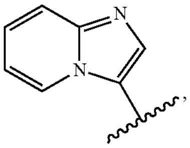,
iv
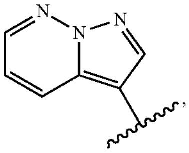,
v
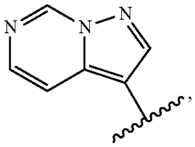,
vi
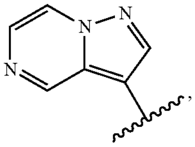,
vii
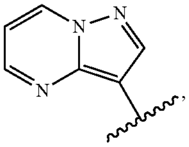,
-continued
viii
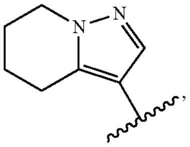,
ix
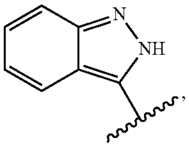,
x
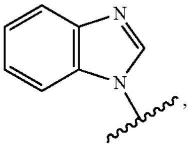,
xi
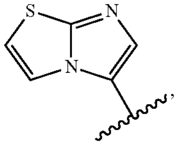,
xii
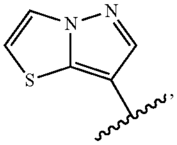,
xiii
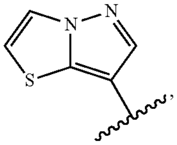,
xiv
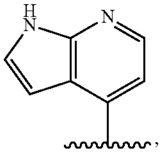,
xv
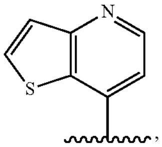,
xvi
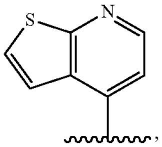,
xvii
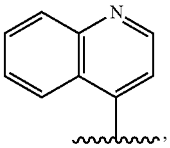, -continued
xxiii
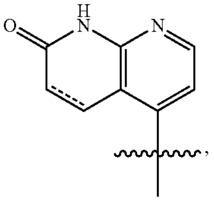
xxiv
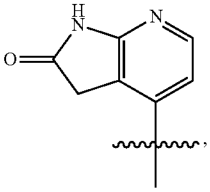
xxv
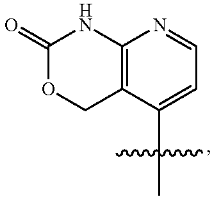
xxvi
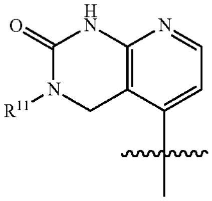
xxvii
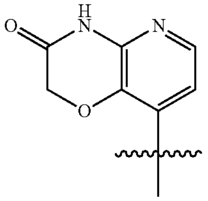
xxviii
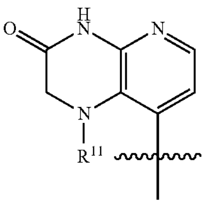
xxix
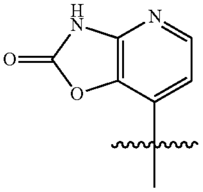
-continued
xxx
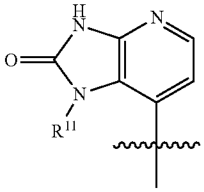
xxxi
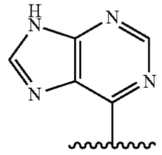
xxxii
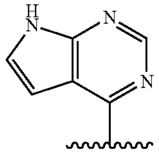
xxxiii
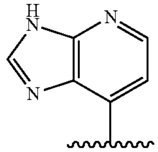
xxxiv
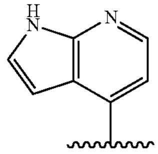
xxxv
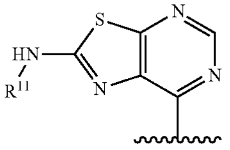
and
xxxvi
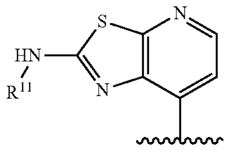
wherein each HY group is optionally additionally substituted with one or more occurrences of $R^{10}$.
9. The compound of claim 1, wherein HY is selected from:
i
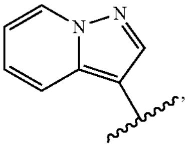

-continued v

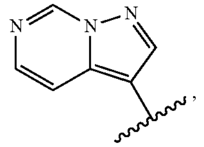

x

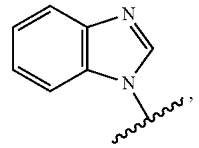

xiv

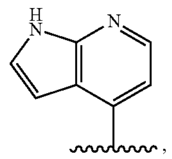

xvii

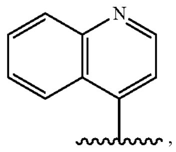

xxiii

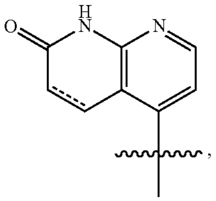

xxix

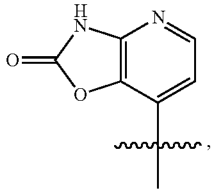

xxxi

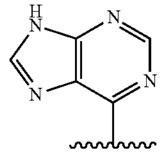

xxxii

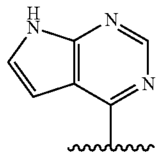

and xxxv

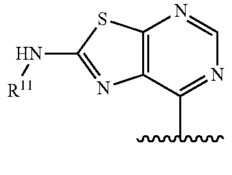

wherein each HY group is optionally additionally substituted with one or more occurrences of $R^{10}$.

10. The compound of any one of claims 7 to 9, wherein $R^2$ is an optionally substituted 6-10-membered aryl or 5-10-membered heteroaryl having 1-5 heteroatoms independently selected from nitrogen, oxygen, and sulfur.

11. The compound of any one claims 7 to 9, wherein:

$R^2$ is a phenyl group substituted with 1-3 independent occurrences of halo, $C_{1-3}$ alkyl, —CN, $C_{1-3}$haloalkyl, —$OC_{1-3}$ alkyl, —$OC_{1-3}$ haloalkyl, —NHC(O)$C_{1-3}$ alkyl, —NHC(O)NH$C_{1-3}$ alkyl, —NHS$(O)_2C_{1-3}$ alkyl, or —C(O)H.

12. The compound of claim 1, wherein HY is selected from:

i

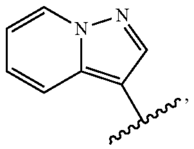

ii

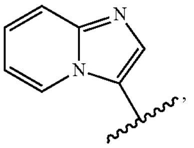

iv

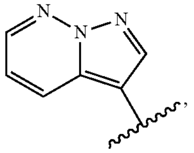

v

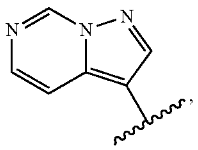

vi

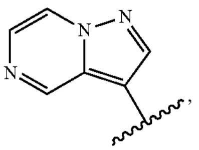

vii

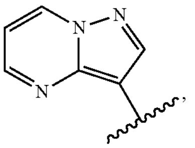

viii

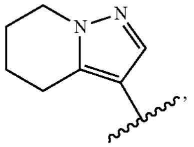

ix

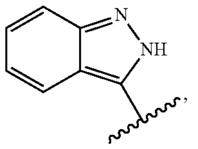

-continued
x
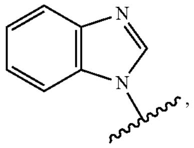
xi
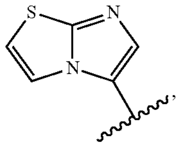
xii
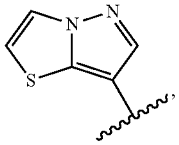
xiii
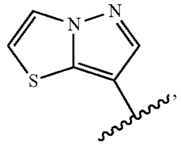
xiv
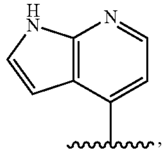
xv
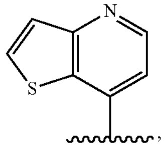
xvi
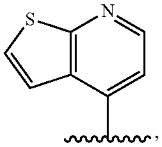
xvii
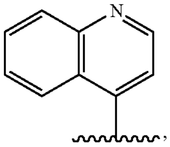
xxiii
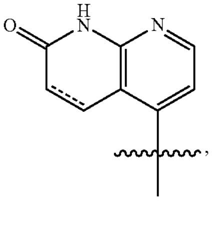
-continued
xxiv
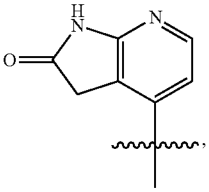
xxv
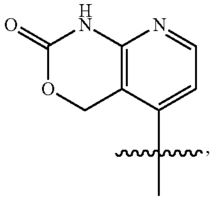
xxvi
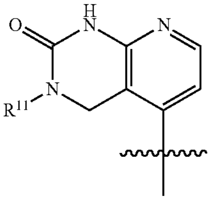
xxvii
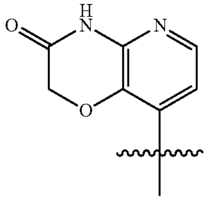
xxviii
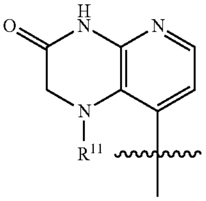
xxvix
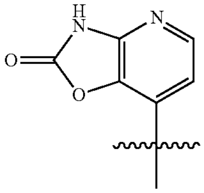
xxx
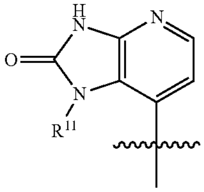
xxxi
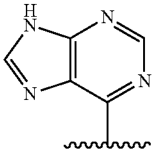

-continued xxxii

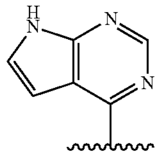

xxxiii

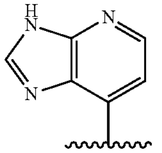

xxxiv

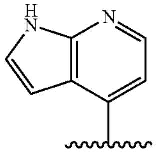

xxxv

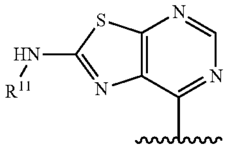

and xxxvi

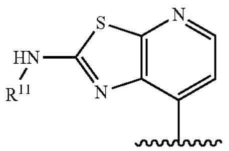

wherein each HY group is optionally additionally substituted with one or more occurrences of $R^{10}$.

13. The compound of claim 1, wherein HY is selected from:

i

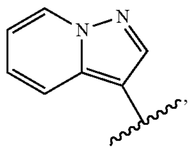

v

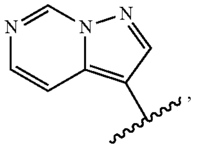

x

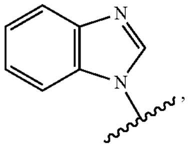

-continued xiv

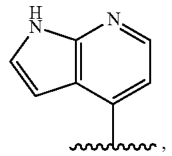

xvii

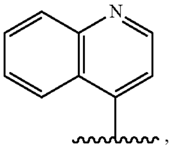

xxiii

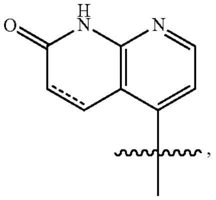

xxix

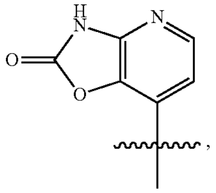

xxxi

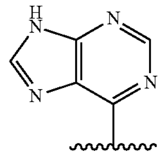

xxxv

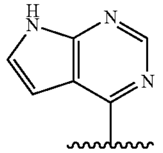

and xxxvi

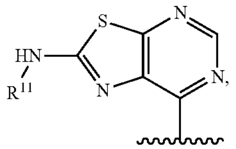

wherein each HY group is optionally additionally substituted with one or more occurrences of $R^{10}$; and wherein $R^2$ is an optionally substituted 6-10-membered aryl or 5-10-membered heteroaryl having 1-5 heteroatoms independently selected from nitrogen, oxygen, and sulfur.

14. The compound of claim 13, wherein $R^2$ is a phenyl group substituted with 1-3 independent occurrences of halo, $C_{1-3}$ alkyl, —CN, $C_{1-3}$haloalkyl, —$OC_{1-3}$ alkyl, —$OC_{1-3}$ haloalkyl, —NHC(O)$C_{1-3}$ alkyl, —NHC(O)NH$C_{1-3}$ alkyl, —NHS$(O)_2C_{1-3}$ alkyl, or —C(O)H.

15. The compound of claim 13, wherein X1 is N and X2 and 13 are CH.

16. The compound of claim 1, wherein $R^2$ is a phenyl group substituted with 1-3 independent occurrences of halo, $C_{1-3}$ alkyl, —CN, $C_{1-3}$haloalkyl, —$OC_{1-3}$ alkyl, —$OC_{1-3}$haloalkyl, —NHC(O)$C_{1-3}$ alkyl, —NHC(O)NH$C_{1-3}$ alkyl, —NHS$(O)_2C_{1-3}$ alkyl, or —C(O)H.

17. The compound of claim 16, wherein $X_1$ is N and $X_2$ and $X_3$ are CH.

18. The compound of claim 16, wherein $X_1$ and $X_2$ are N, and $X_3$ is CH.

19. The compound of claim 1 having formula III:

III

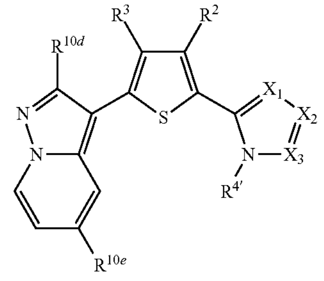

wherein $R^{10d}$ is hydrogen or optionally substituted $C_{1-4}$alkyl, and $R^{10e}$ is $R^{10}$.

20. The compound of claim 19, wherein $R^{10e}$ is —$V_1$—$R^{10c}$, or halogen.

21. The compound of claim 19, wherein $R^{10d}$ is hydrogen or $C_{1-4}$ alkyl, $R^{10e}$ is H, hydroxy, $C_{1-6}$alkyl, $C_{1-6}$ alkoxy optionally substituted by a group selected from hydroxy, $C_{1-6}$ alkyl-carbonylamino and amino-$C_{1-6}$ alkyl-carbonylamino, $C_{6-18}$ aryl-$C_{1-4}$alkyl-oxy, 4- to 7-membered monocyclic aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom optionally substituted by $C_{1-6}$ alkyl optionally substituted by halogen and 4- to 7-membered monocyclic non-aromatic heterocyclyl-$C_{1-4}$ alkyl-oxy containing, as a ring constituting atom besides carbon atom, 1 to 4 heteroatoms selected from an oxygen atom, a sulfur atom and a nitrogen atom optionally substituted by a group selected from halogen, $C_{1-6}$ alkyl, $C_{1-6}$ alkylsulfonyloxy and $C_{1-6}$ alkyl-carbonyl optionally substituted by hydroxyl, $R^3$ is H, and $R^{4'}$ is H.

22. The compound of claim 19, 20, or 21, wherein $X_1$ is N and $X_2$ and $X_3$ are H.

23. The compound of claim 19, 20, or 21, wherein $X_1$ and $X_2$ are N, and $X_3$ is H.

24. The compound of claim 19, 20, or 21, wherein $R^2$ is an optionally substituted 6-10-membered aryl or 5-10-membered heteroaryl having 1-5 heteroatoms independently selected from nitrogen, oxygen, and sulfur.

25. The compound of claim 19, 20, or 21, wherein:

$R^2$ is a phenyl group substituted with 1-3 independent occurrences of halo, $C_{1-3}$ alkyl, —CN, $C_{1-3}$haloalkyl, —O$C_{1-3}$ alkyl, —O$C_{1-3}$ haloalkyl, —NHC(O)$C_{1-3}$ alkyl, —NHC(O)NH$C_{1-3}$ alkyl, —NHS$(O)_2C_{1-3}$ alkyl, or —C(O)H.

26. A composition comprising a compound of claim 1, 17, or 19, and a pharmaceutically acceptable carrier.

27. A compound selected from the group consisting of

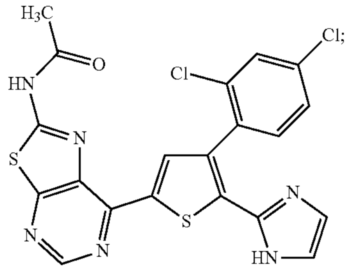 [SMILES: CC(=O)Nc1nc2c(-c3cc(-c4ccc(Cl)cc4Cl)c(-c4ncc[nH]4)s3)ncnc2s1]

1-E

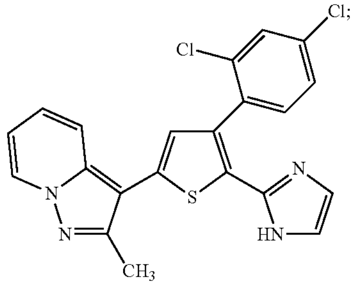 [SMILES: Cc1nn2ccccc2c1-c1cc(-c2ccc(Cl)cc2Cl)c(-c2ncc[nH]2)s1]

2-E

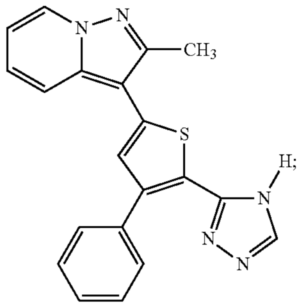

3-E

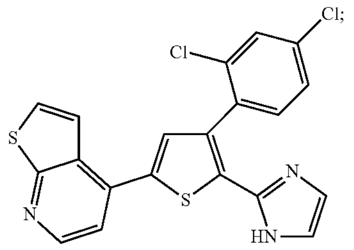 [SMILES: Clc1ccc(-c2cc(-c3ccnc4sccc34)sc2-c2ncc[nH]2)c(Cl)c1]

4-E

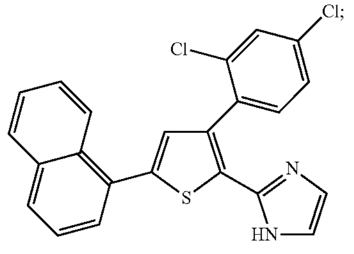 [SMILES: Clc1ccc(-c2cc(-c3cccc4ccccc34)sc2-c2ncc[nH]2)c(Cl)c1]

5-E

-continued
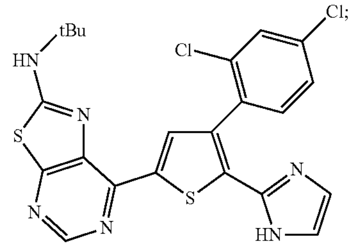 [SMILES: CC(C)(C)Nc1nc2c(-c3cc(-c4ccc(Cl)cc4Cl)c(-c4ncc[nH]4)s3)ncnc2s1]
6-E
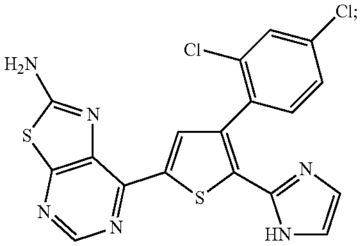 [SMILES: Nc1nc2c(-c3cc(-c4ccc(Cl)cc4Cl)c(-c4ncc[nH]4)s3)ncnc2s1]
7-E
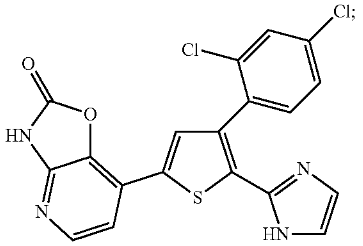 [SMILES: O=c1[nH]c2nccc(-c3cc(-c4ccc(Cl)cc4Cl)c(-c4ncc[nH]4)s3)c2o1]
1-F
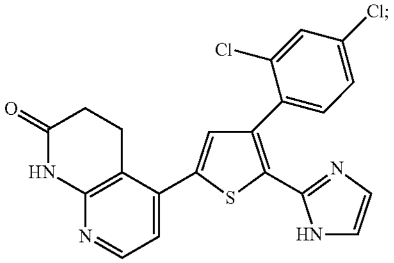 [SMILES: O=C1CCc2c(-c3cc(-c4ccc(Cl)cc4Cl)c(-c4ncc[nH]4)s3)ccnc2N1]
2-F
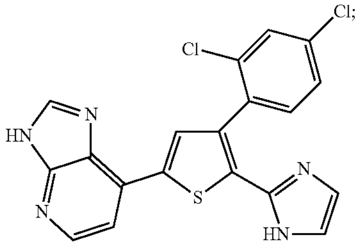 [SMILES: Clc1ccc(-c2cc(-c3ccnc4[nH]cnc34)sc2-c2ncc[nH]2)c(Cl)c1]
-continued
3-F
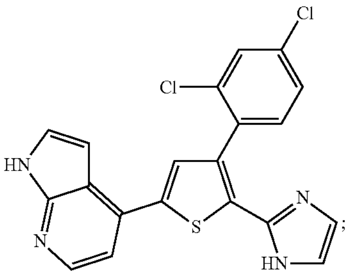 [SMILES: Clc1ccc(-c2cc(-c3ccnc4[nH]ccc34)sc2-c2ncc[nH]2)c(Cl)c1]
4-F
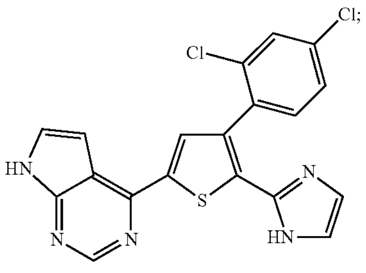
and
5-F
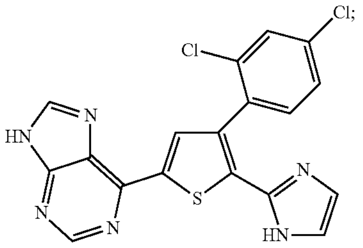 [SMILES: Clc1ccc(-c2cc(-c3ncnc4[nH]cnc34)sc2-c2ncc[nH]2)c(Cl)c1]
6-F
or a pharmaceutically acceptable salt thereof.
28. A composition comprising a compound of claim 27, or a pharmaceutically acceptable salt thereof, and a pharmaceutically acceptable carrier.
* * * * *